United States Patent
Freier et al.

(10) Patent No.: US 11,339,393 B2
(45) Date of Patent: May 24, 2022

(54) COMPOSITIONS FOR MODULATING C9ORF72 EXPRESSION

(71) Applicant: Ionis Pharmaceuticals, Inc., Carlsbad, CA (US)

(72) Inventors: Susan M. Freier, San Diego, CA (US); Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/248,612

(22) Filed: Jan. 15, 2019

(65) Prior Publication Data

US 2019/0367916 A1 Dec. 5, 2019

Related U.S. Application Data

(62) Division of application No. 15/028,626, filed as application No. PCT/US2014/060194 on Oct. 11, 2014, now Pat. No. 10,221,414.

(60) Provisional application No. 61/980,502, filed on Apr. 16, 2014, provisional application No. 61/927,903, filed on Jan. 15, 2014, provisional application No. 61/919,540, filed on Dec. 20, 2013, provisional application No. 61/891,313, filed on Oct. 15, 2013, provisional application No. 61/890,108, filed on Oct. 11, 2013.

(51) Int. Cl.
*C12N 15/113* (2010.01)
*G01N 33/68* (2006.01)

(52) U.S. Cl.
CPC ....... *C12N 15/113* (2013.01); *G01N 33/6896* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/343* (2013.01)

(58) Field of Classification Search
None
See application file for complete search history.

(56) References Cited

U.S. PATENT DOCUMENTS

| | | |
|---|---|---|
| 5,801,154 A | 9/1998 | Baracchini et al. |
| 5,998,148 A | 12/1999 | Bennett et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,759,478 B1 | 7/2010 | Bentwich et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,927,513 B2 | 1/2015 | Manoharan et al. |
| 9,012,421 B2 | 4/2015 | Migawa et al. |
| 9,605,263 B2 | 3/2017 | Rigo |
| 9,896,729 B2 | 2/2018 | Pickering-Brown et al. |
| 9,963,699 B2 | 5/2018 | Bennett et al. |
| 10,066,288 B2 | 9/2018 | Hsiao |
| 10,221,414 B2 | 3/2019 | Freier et al. |
| 10,443,052 B2 | 10/2019 | Freier |
| 10,577,604 B2 | 3/2020 | Bennett et al. |
| 2001/0053519 A1 | 12/2001 | Fodor et al. |
| 2003/0228597 A1 | 12/2003 | Cowsert et al. |
| 2004/0038274 A1 | 2/2004 | Cook et al. |
| 2004/0171570 A1 | 9/2004 | Allerson et al. |
| 2004/0181048 A1 | 9/2004 | Wang |
| 2005/0130923 A1 | 6/2005 | Bhat et al. |
| 2006/0003322 A1 | 1/2006 | Bentwich et al. |
| 2007/0031844 A1 | 2/2007 | Khvorova et al. |
| 2008/0039618 A1 | 2/2008 | Allerson et al. |
| 2009/0012281 A1 | 1/2009 | Swayze et al. |
| 2010/0216864 A1 | 8/2010 | Staarup et al. |
| 2012/0149757 A1 | 6/2012 | Krainer et al. |
| 2012/0214865 A1 | 8/2012 | Bennett et al. |

(Continued)

FOREIGN PATENT DOCUMENTS

| | | |
|---|---|---|
| EP | 1752536 | 2/2007 |
| WO | WO 1996/014329 | 5/1996 |

(Continued)

OTHER PUBLICATIONS

Kurreck "Antisense technologies. Improvement through novel chemical modifications" Eur J Biochem (2003) 270: 1628-1644.

(Continued)

*Primary Examiner* — Tracy Vivlemore
(74) *Attorney, Agent, or Firm* — McNeill Baur PLLC

(57) ABSTRACT

Disclosed herein are compositions and methods for reducing expression of C9ORF72 mRNA and protein in an animal with C9ORF72 specific inhibitors. Also disclosed herein are compositions and methods of selectively inhibiting a C9ORF72 pathogenic associated mRNA variant by administering an antisense compound targeting the region beginning at the start site of exon 1A to the start site of exon 1B of a C9ORF72 pre-mRNA. Such methods are useful to treat, prevent, or ameliorate neurodegenerative diseases in an individual in need thereof. Such C9ORF72 specific inhibitors include antisense compounds.

33 Claims, No Drawings

Specification includes a Sequence Listing.

(56) References Cited

U.S. PATENT DOCUMENTS

| | | |
|---|---|---|
| 2013/0035366 A1 | 2/2013 | Swayze et al. |
| 2014/0255936 A1 | 9/2014 | Rademakers |
| 2014/0303238 A1 | 10/2014 | Linsley et al. |
| 2015/0148404 A1 | 5/2015 | de Visser et al. |
| 2015/0259679 A1 | 9/2015 | Bennett et al. |
| 2015/0267197 A1 | 9/2015 | Bennett et al. |
| 2016/0024496 A1 | 1/2016 | Bennett et al. |
| 2016/0108396 A1 | 4/2016 | Jensen et al. |
| 2016/0251655 A1 | 9/2016 | Freier et al. |
| 2016/0304871 A1 | 10/2016 | Rigo |
| 2017/0349897 A1 | 12/2017 | Rigo |
| 2018/0318330 A1 | 11/2018 | Prakash et al. |
| 2019/0142856 A1 | 5/2019 | Bennett et al. |
| 2019/0264204 A1 | 8/2019 | Rigo |
| 2021/0169916 A1 | 6/2021 | Bennett et al. |

FOREIGN PATENT DOCUMENTS

| | | |
|---|---|---|
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/113016 | 12/2005 |
| WO | WO 2005/121368 | 12/2005 |
| WO | WO 2007/056113 | 5/2007 |
| WO | WO 2007/089584 | 8/2007 |
| WO | WO 2007/131237 | 11/2007 |
| WO | WO 2007/134181 | 11/2007 |
| WO | 2007146511 | 12/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/007855 | 1/2009 |
| WO | WO 2009/049166 | 4/2009 |
| WO | WO 2009/060124 | 5/2009 |
| WO | 2010019270 | 2/2010 |
| WO | WO 2010/148013 | 12/2010 |
| WO | WO 2011/005793 | 1/2011 |
| WO | WO 2011/135396 | 11/2011 |
| WO | WO 2012/005898 | 1/2012 |
| WO | WO 2012/012443 | 1/2012 |
| WO | WO 2012/012467 | 1/2012 |
| WO | WO 2012/087983 | 6/2012 |
| WO | WO 2012/092367 | 7/2012 |
| WO | WO 2012/135736 | 10/2012 |
| WO | WO 2013/030588 | 3/2013 |
| WO | WO 2013/036833 | 3/2013 |
| WO | WO 2013/075079 | 5/2013 |
| WO | WO 2013/082548 | 6/2013 |
| WO | WO 2013/086207 | 6/2013 |
| WO | WO 2013/173608 | 11/2013 |
| WO | WO 2014/062686 | 4/2014 |
| WO | WO 2014/062691 | 4/2014 |
| WO | WO 2014/062952 | 4/2014 |
| WO | WO 2014/114660 | 7/2014 |
| WO | WO 2015/054676 | 4/2015 |
| WO | WO 2016/024205 | 2/2016 |
| WO | WO 2016/050822 | 4/2016 |
| WO | WO 2016/060919 | 4/2016 |
| WO | WO 2016/168592 | 10/2016 |
| WO | WO 2017/079291 | 5/2017 |
| WO | WO 2017/180835 | 10/2017 |
| WO | WO 2018/064600 | 4/2018 |

OTHER PUBLICATIONS

"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides-Inhibition of PKC-αand c-raf Kinase Expression by Chimeric Oligonucleotides Incorporating 6"-Substituted Carbocyclic Nucleosides and 2"-O-Ethylene Glycol Substituted Ribonucleosides" Nucleosides & Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.

Ash et al., "Unconventional Translation of C9ORF72 GGGGCC Expansion Generates Insoluble Ploypeptides Specific to c9FTD/ALS" Neuron (2013) 77(4): 639-646.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.

Baloh, R.H., "Targeting RNA foci shows a therapeutic effect in iPSC-derived motor neurons from C9orf72 repeat patients" ALSMND meeting, Milan, Dec. 6, 2013.

Baloh, R.H., "Induced Pluripotent stem cell models from C9orf72 patients." Oral presentation, California ALS PAC10 Research Summit, Los Angeles, CA, Nov. 11, 2012.

Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.

Baughn et al., "Sense and Anti-Sense RNA Foci in c9ALS/FTD: More Light in a House of Mirrors" Annals of Neurology (Oct. 14, 2013) 74(17): p. S60.

Bennett et al., "Antisense oligonucleotides as a tool for gene functionalization and target validation," Biochimica et Biophysica Acta (1999) 1489: 19-30.

Bieniek et al., "Tau pathology in frontotemporal lobar degeneration with C9ORF72 hexancleotide repeat expansion" Acta Neuropathol (2013) 125(2):289-302.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001)8:1-7.

Branch et al., "A good antisense molecule is hard to find," TIBS (1998) 23:45-50.

Brettschneider et al., "Microglial activation correlates with disease progression and upper motor neuron clinical symptoms in Amyotrophic Lateral Sclerosis", PLOS One (2012) 7:e39216.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chio et al., "Prevalence of SOD1 mutations in the Italian ALS population" Neurology (2008) 70:533-537.

Crooke et al., "Basic Principles of Antisense Therapeutics" Antisense Research and Application (1998) Chapter 1:1-50.

(56) References Cited

OTHER PUBLICATIONS

Dejesus-Hernandez et al., "Expanded GGGGCC Hexanucleotide Repeat in Noncoding Region of C9ORF72 Causes Chromosome 9p-Linked FTP and ALS" Neuron (2011) 72:245-256.

Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4d1e-9569-9a1b1eb21d80&cKey=c5c69155-5d2b-467c-8d1f-87299c514c7f&mKey=%7b70007181-01C9-4DE9-A0A2-EEBFA14CD9F1%7d.

Donnelly et al., "Development of C9ORF72 ALS Biomarkers and Therapeutics" American Neurological Association 2012 Annual Meeting, Poster Presentation, Boston, MA Oct. 10, 2012.

Donnelly et al., "Development of C9orf72 ALS Biomarkers and Therapeutics" Annals of Neurology (Oct. 10, 2012) 72(16):S67-S68.

Donnelly et al., "Limited availability of ZBP1 restricts axonal mRNA localization and nerve regeneration capacity" EMBO J. (2011) 30:4665-4677.

Donnelly et al., "RNA toxicity from the ALS/FTD C9ORF72 expansion is mitigated by antisense intervention" Neuron (2013) 80(2):415-428 [with Supplemental Information].

Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.

Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.

Elayadi et al., "Application of PNA and LNA oligomers to chemotherapy" Curr. Opinion Invens. Drugs (2001) 2:558-561.

European Search Report for application No. 13847957.1 dated Jul. 13, 2016.

European Search Report for application No. 13846313.8 dated May 11, 2016.

European Search Report for application No. 13847099.2 dated May 25, 2016.

Extended European Search Report for application No. 14852924.1 dated Jun. 20, 2017.

Fernandes et al., "Oligonucleotide-Based Therapy for FTD/ALS Caused by the C9orf72 Repeat Expansion: A Perspective" Journal of Nucleic Acids (2013) :1-11.

File History of U.S. Appl. No. 14/436,024, filed Apr. 15, 2015.
File History of U.S. Appl. No. 14/436,030, filed Apr. 15, 2015.
File History of U.S. Appl. No. 14/436,039, filed Apr. 15, 2015.
File History of U.S. Appl. No. 15/130,818, filed Apr. 15, 2016.

Freer et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Ganesalingam et al., "Combination of neurofiliment heavy chain and complement C3 as CSF biomarkers for ALS" Journal of Neurochemistry (2011) 117: 528-537.

Gautschi et al., "Activity of a novel bcl-2/bcl-xLbispecific antisense oligonucleotide against tumors of diverse histologic origins" J. Natl. Cancer Inst. (2001) 93:463-471.

GenBank: Accession No. NT 008413 Jul. 24, 2012.

GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=18&satkey=24474174).

Gendron et al., "Poly(GP) proteins are a useful pharmacodynamic marker for C9ORF72-associated amyotrophic lateral sclerosis" Sci Tran Med (2017) 9(383):1-12.

Hirtz et al., "How common are the "common" neurologic disorders?" Neurology (2007) 68:326-337.

Ince et al., "Molecular pathology and genetic advances in amyotrophic lateral sclerosis: an emerging molecular pathway and the significance of glial pathology," Acta Neuro. (2011) 122:657-671.

International Search Report for application No. PCT/US2013/065073 dated Apr. 22, 2014.

International Search Report for application No. PCT/US2013/065067 dated Jan. 24, 2014.

International Search Report for application No. PCT/US2013/065131 dated Feb. 14, 2014.

International Search Report for application on. PCT/US2014/060194 dated Apr. 14, 2015.

International Search Report for application on. PCT/US2016/027747 dated Sep. 30, 2016.

International Search Report for application No. PCT/US17/27355 dated Jul. 26, 2017.

International Search Report for application No. PCT/US2016/060106 dated Feb. 1, 2017.

Jiang et al., "Anti sense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.

Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.

Jeong et al., "Rapid Identification of Monospecific Monoclonal Antibodies Using a Human Proteome Microarray." Mol. Cell. Proteomics (2012) 11(6): O111.016253-1 to O111.016253-10.

Johnson et al., "Exome sequencing reveals VCP mutations as a cause of familial ALS" Neuron (2010) 68:857-864.

Jones et al., "RNA quantitation by fluorescence-based solution assay: RiboGreen reagent characterization" Analytical Biochemistry (1998) 265(2):368-374.

Klein et al., "Gain of RNA function in pathological cases: Focus on myotonic dystrophy" Biochimie (2011) 93(11):2006-2012.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Kwiatkowski et al., "Mutations in the FUS/TLS gene on chromosome 16 cause familial amyotrophic lateral sclerosis" Science (2009) 323:1205-1208.

Laaksovirta et al, "Chromosome 9p21 in amyotrophic lateral sclerosis in Finland: a genome-wide association study" Lancet Neurol. (2010) 9:978-985.

Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.

Lagier-Tourenne, C., "Targeted degradation of sense and antisense C9orf72 nuclear foci as therapy for ALS and FTP" Oral Presentation, 24th International Symposium on ALS/MND, Milan, Dec. 6, 2013.

Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.

Lagier-Tourenne, C. "Therapy Development for ALS/MND and Frontotemporal Dementia with C9orf72 Expansion: Antisense Oligonucleotide Mediated Reduction in Nuclear RNA Foci." ALS FD (Nov. 4, 2013) 14(sup2): p. 17.

Lagier-Tourenne et al., "Targeted Degradation of Sense and Antisense C9ORF72 RNA Foci as Therapy for ALS and Frontotemporal Degeneration" PNAS (2013) 110(47):E4530-E4539.

(56) References Cited

OTHER PUBLICATIONS

Lee et al., "Antisense Therapy in Neurology" Journal of Personalized Medicine (2013) 3(3): 144-176.
Leumann et al., "DNA Analogues: From Supramolecular Principles to Biological Properties" Bioorganic & Medicinal Chemistry (2002) 10:841-854.
Lelo et al., "Frontotemporal dementia and motor neurone disease: overlapping clinic-pathological disorders" J. Clin. Neurosci. (2009) 16:1131-1135.
Lindquist et al, "Corticobasal and ataxia syndromes widen the spectrum of C9ORF72 hexanucleotide expansion disease." Clin Genet (2013) 83:279-283.
Madson, "Antisense Against C9ORF72", http://alsn.mda.org/article/antisense-against-c9orf72 Jul. 1, 2012 (printed Oct. 28, 2015).
Maher et al., "Comparative hybrid arrest by tandem antisense oligodeoxy ribonucleotides or oligodeoxyribonucleoside methylpbosphonates in a cell-free system" Nucl. Acid. Res. (1998) 16(8):3341-3358.
Mahoney et al., "Frontotemporal dementia with the C9ORF72 hexanucleotide repeat expansion: clinical, neuroanatomical and neuropathological features" BRAIN (2012) 135: 736-750.
Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Helv. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Mulders et al., "Triplet-repeat oligonucleotide-mediated reversal of RNA toxicity in myotonic dystrophy" PNAS (2009) 106(33):13915-13920.
Nelson et al., "The unstable repeats—three evolving faces of neurological disease." Neuron (2013) 77(5):825-43.
Neumann et al., "Ubiquitinated TDP-43 in frontotemporal lobar degeneration and amyotrophic lateral sclerosis" Science (2006) 314:130-133.
New England Biolabs 1998/99 Catalog (cover page and pp. 121 and 284).
O'Rourke et al., "C9orf72 BAC Transgenic Mice Display Typical Pathologic Features of ALS/FTD." Neuron (2015) 88(5):892-901.
Orum et al., "Locked nucleic acids: A promising molecular family for gene-function analysis and antisense drug development" Curr. Opinion Mol. Ther. (2001) 3:239-243.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Pearson et al., "Familial frontotemporal dementia with amyotrophic lateral sclerosis and a shared haplotype on chromosome 9p" J. Nerol. (2011) 258:647-655.
Rabin et al., "Sporadic ALS has compartment-specific aberrant exon splicing and altered cell-matrix adhesion biology" Hum Mol Genet. (2010) 19(2):313-328.
Ravits, J., "Expanding Neurodegenerations: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Renton et al., "A Hexanucleotide Repeat Expansion in C9ORF72 Is the Cause of Chromosome 9p21-Linked ALS-FTD" Neuron (2011) 72:257-268.
Reynolds et al., "Rational siRNA design for RNA interference" Nature Biotechnology (2004) 22(3):326-330.
Riboldi et al., "Antisense Oligonucleotide Therapy for the Treatment of C9ORF72 ALS/FTD Diseases." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sareen et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion," Sci Tran Med (2013) 5(208): 1-13.
Sanghvi et al., "Heterocyclic Base Modifications in Nucleic Acids and Their Applications in Antisense Oligonucleotides" Antisense Research and Applications (1993) pp. 273-288.
Sha et al., "Treatment implications of C9ORF72" Alzheimers Res Ther (2012) 4(6): 46.
Shao et al., "Rational design and rapid screening of antisense oligonucleotides for prokaryotic gene modulation" Nucleic Acids Res (2006) 34: 5660-5669.
Singh et al., "LNA (locked nucleic acids): synthesis and high-affinity nucleic acid recognition" Chem. Commun. (1998) 4:455-456.
Singh et al., "Synthesis of 2'-amino-LNA: A novel conformationally restricted high-affinity oligonucleotide analogue with a handle" J. Org. Chem. (1998) 63: 10035-10039.
Simon-Sanchez et al., "The clinical and pathological phenotype of C9OFR72 hexanucleotide repeat expansions", Brain: Journal of Neurology (2012) 135:723-735.
Smith et al., "Comparison of biosequences" Adv. Appl. Math. (1981) 2(4):482-489.
Sohail et al., "Selecting optimal antisense reagents" Adv Drug Deliv Rev (2000) 44: 23-34.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Thomsen, "Dramatically improved RNA in 1-15 situ hybridization signals using LNA-modified probes" RNA (2005) 11(11): 1745-1748.
Todd et al. "RNA mediated neurodegeneration in repeat expansion disorders," Annals of Neurology (2009) 67(3):291-300.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Natl. Acad. Sci. USA (2000) 97: 5633-5638.
Watts et al., "Silencing disease genes in the laboratory and the clinic" J Pathol (2012) 226(2): 365-379.
Wojciechowska et al., "Cellular toxicity of expanded RNA repeats: focus on RNA foci" Human Molecular Genetics (2011) 1-11.
Woolf et al., "Specificity of antisense oligonucleotides in vivo" PNAS (1992) 89: 7305-7309.
Zhang et al., "PowerBLAST: A New Network BLAST Application for Interactive or Automated Sequence Analysis and Annotation" Genome Res. (1997) 7:649-656.
Zhang et al., "The C9orf72 repeat expansion disrupts nucleocytoplasmic transport." Nature (2015) 525(7567):56-61.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Boeve et al., "Characterization of frontotemporal dementia and/or amyotrophic lateral sclerosis associated with the GGGGCC repeat expansion in C9ORF72" Brain (2012) 135: 765-783.

(56) References Cited

OTHER PUBLICATIONS

Cook "Medicinal Chemistry of Antisense Oligonucleotides" Chapter 2—Medicinal Chemistry of Antisense Oligonucleotides, Antisense Drug Technology, 1st Edition (2001); 28 pages.
Lee et al., "Rnase H-mediated degradation of toxic RNA in myotonic dystrophy type 1" PNAS (2012) 109:4221-4226.
Mori et al., "Bidirectional transcripts of the expanded C9orf72 hexanucleotide repeat are translated into aggregating dipeptide repeat proteins" Acata Neuropathol (2013) 126: 881-893.
Wheeler et al., "Targeting nuclear RNA for in vivo correction of myotonic dystrophy" Nature (2012) 488: 111-117.

SEQUENCE LISTING

```
<160> NUMBER OF SEQ ID NOS: 1548

<210> SEQ ID NO 1
<211> LENGTH: 3339
<212> TYPE: DNA
<213> ORGANISM: Homo sapiens

<400> SEQUENCE: 1
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata     180
atgtgacagt tggaatgcag tgatgtcgac tctttgccca ccgccatctc cagctgttgc     240
caagacagag attgctttaa gtggcaaatc acctttatta gcagctactt ttgcttactg     300
ggacaatatt cttggtccta gagtaaggca catttgggct ccaaagacag aacaggtact     360
tctcagtgat ggagaaataa cttttcttgc caaccacact ctaaatggag aaatccttcg     420
aaatgcagag agtggtgcta tagatgtaaa gttttttgtc ttgtctgaaa agggagtgat     480
tattgtttca ttaatctttg atggaaactg gaatggggat cgcagcacat atggactatc     540
aattatactt ccacagacag aacttagttt ctacctccca cttcatagag tgtgtgttga     600
tagattaaca catataatcc ggaaaggaag aatatgatg cataaggaaa gacaagaaaa     660
tgtccagaag attatcttag aaggcacaga gagaatggaa gatcagggtc agagtattat     720
tccaatgctt actggagaag tgattcctgt aatggaactg ctttcatcta tgaaatcaca     780
cagtgttcct gaagaaatag atatagctga tacagtactc aatgatgatg atattggtga     840
cagctgtcat gaaggctttc ttctcaatgc catcagctca cacttgcaaa cctgtggctg     900
ttccgttgta gtaggtagca gtgcagagaa agtaaataag atagtcagaa cattatgcct     960
ttttctgact ccagcagaga gaaatgctc caggttatgt gaagcagaat catcatttaa    1020
atatgagtca gggctctttg tacaaggcct gctaaaggat tcaactggaa gctttgtgct    1080
gcctttccgg caagtcatgt atgctccata tcccaccaca cacatagatg tggatgtcaa    1140
tactgtgaag cagatgccac cctgtcatga acatatttat aatcagcgta gatacatgag    1200
atccgagctg acagccttct ggagagccac ttcagaagaa gacatggctc aggatacgat    1260
catctacact gacgaaagct ttactcctga tttgaatatt tttcaagatg tcttacacag    1320
agacactcta gtgaaagcct tcctggatca ggtctttcag ctgaaacctg gcttatctct    1380
cagaagtact ttccttgcac agtttctact tgtccttcac agaaaagcct tgacactaat    1440
aaaatatata gaagacgata cgcagaaggg aaaaaagccc tttaaatctc ttcggaacct    1500
gaagatagac cttgatttaa cagcagaggg cgatcttaac ataataatgg ctctggctga    1560
gaaaattaaa ccaggcctac actcttttat ctttggaaga cctttctaca ctagtgtgca    1620
agaacgagat gttctaatga ctttttaaat gtgtaactta ataagcctat tccatcacaa    1680
tcatgatcgc tggtaaagta gctcagtggt gtgggaaac gttcccctgg atcatactcc    1740
agaattctgc tctcagcaat tgcagttaag taagttacac tacagttctc acaagagcct    1800 gtgagggat gtcaggtgca tcattacatt gggtgtctct tttcctagat ttatgctttt    1860
```

```
gggatacaga cctatgttta caatataata aatattattg ctatctttta aagatataat    1920
aataggatgt aaacttgacc acaactactg ttttttgaa atacatgatt catggtttac    1980
atgtgtcaag gtgaaatctg agttggcttt tacagatagt tgactttcta tcttttggca    2040
ttctttggtg tgtagaatta ctgtaatact tctgcaatca actgaaaact agagccttta    2100
aatgatttca attccacaga aagaaagtga gcttgaacat aggatgagct ttagaaagaa    2160
aattgatcaa gcagatgttt aattggaatt gattattaga tcctactttg tggatttagt    2220
ccctgggatt cagtctgtag aaatgtctaa tagttctcta tagtccttgt tcctggtgaa    2280
ccacagttag ggtgttttgt ttattttatt gttcttgcta ttgttgatat tctatgtagt    2340
tgagctctgt aaaaggaaat tgtatttat gttttagtaa ttgttgccaa cttttttaaat   2400 taattttcat tattttttgag ccaaattgaa atgtgcacct cctgtgcctt ttttctcctt   2460
agaaaatcta attacttgga acaagttcag atttcactgg tcagtcattt tcatcttgtt   2520
ttcttcttgc taagtcttac catgtacctg ctttggcaat cattgcaact ctgagattat    2580
aaaatgcctt agagaatata ctaactaata agatcttttt ttcagaaaca gaaaatagtt    2640
ccttgagtac ttccttcttg catttctgcc tatgttttg aagttgttgc tgtttgcctg     2700
caataggcta taaggaatag caggagaaat tttactgaag tgctgttttc ctaggtgcta    2760
ctttggcaga gctaagttat cttttgtttt cttaatgcgt tggaccatt ttgctggcta     2820 taaaataact gattaatata attctaacac aatgttgaca ttgtagttac acaaacacaa    2880
ataaatattt tatttaaaat tctggaagta atataaaagg gaaaatatat ttataagaaa    2940
gggataaagg taatagagcc cttctgcccc ccacccacca aatttacaca acaaaatgac    3000
atgttcgaat gtgaaaggtc ataatagctt tcccatcatg aatcagaaag atgtggacag    3060
cttgatgttt tagacaacca ctgaactaga tgactgttgt actgtagctc agtcatttaa    3120
aaaatatata aatactacct tgtagtgtcc catactgtgt tttttacatg gtagattctt    3180
atttaagtgc taactggtta ttttctttgg ctggtttatt gtactgttat acagaatgta    3240
agttgtacag tgaaataagt tattaaagca tgtgtaaaca ttgttatata tcttttctcc    3300
taaatggaga attttgaata aaatatattt gaaattttg                           3339
```

<210> SEQ ID NO 2  
<211> LENGTH: 30001  
<212> TYPE: DNA  
<213> ORGANISM: Homo sapiens

<400> SEQUENCE: 2

```
caaagaaaag ggggaggttt tgttaaaaaa gagaaatgtt acatagtgct ctttgagaaa      60
attcattggc actattaagg atctgaggag ctggtgagtt caactggtg agtgatggtg     120 gtagataaaa ttagagctgc agcaggtcat tttagcaact attagataaa actggtctca    180
ggtcacaacg ggcagttgca gcagctggac ttggagagaa ttacactgtg ggagcagtgt    240
catttgtcct aagtgctttt ctaccccta ccccactat tttagttggg tataaaaaga      300
atgacccaat ttgtatgatc aactttcaca aagcatagaa cagtaggaaa agggtctgtt    360
tctgcagaag gtgtagacgt tgagagccat tttgtgtatt tattcctccc tttcttcctc    420
ggtgaatgat taaaacgttc tgtgtgattt ttagtgatga aaaagattaa atgctactca    480
ctgtagtaag tgccatctca cacttgcaga tcaaaaggca cacagtttaa aaaacctttg    540
tttttttaca catctgagtg gtgtaaatgc tactcatctg tagtaagtgg aatctataca    600
cctgcagacc aaaagacgca aggtttcaaa aatctttgtg ttttttacac atcaaacaga    660
```

```
atggtacgtt tttcaaaagt taaaaaaaaa caactcatcc acatattgca actagcaaaa      720
atgacattcc ccagtgtgaa aatcatgctt gagagaattc ttacatgtaa aggcaaaatt      780
gcgatgactt tgcaggggac cgtgggattc ccgcccgcag tgccggagct gtcccctacc      840
agggtttgca gtggagtttt gaatgcactt aacagtgtct tacggtaaaa acaaaatttc      900
atccaccaat tatgtgttga gcgcccactg cctaccaagc acaaacaaaa ccattcaaaa      960
ccacgaaatc gtcttcactt tctccagatc cagcagcctc ccctattaag gttcgcacac     1020
gctattgcgc caacgctcct ccagagcggg tcttaagata aagaacagg acaagttgcc      1080 ccgccccatt tcgctagcct cgtgagaaaa cgtcatcgca catagaaaac agacagacgt     1140
aacctacggt gtcccgctag aaagagagg tgcgtcaaac agcgacaagt tccgcccacg      1200
taaaagatga cgcttggtgt gtcagccgtc cctgctgccc ggttgcttct cttttggggg     1260
cggggtctag caagagcagg tgtgggttta ggaggtgtgt gtttttgttt ttcccaccct     1320
ctctccccac tacttgctct cacagtactc gctgagggtg aacaagaaaa gacctgataa     1380
agattaacca gaagaaaaca aggagggaaa caaccgcagc ctgtagcaag ctctggaact     1440
caggagtcgc gcgctagggg ccggggccgg ggcggggcg tggtcggggc gggcccgggg      1500
gcgggcccgg ggcggggctg cggttgcggt gcctgcgccc gcggcggcgg aggcgcaggc     1560
ggtggcgagt gggtgagtga ggaggcggca tcctggcggg tggctgtttg gggttcggct     1620
gccgggaaga ggcgcgggta gaagcggggg ctctcctcag agctcgacgc attttttactt    1680 tccctctcat ttctctgacc gaagctgggg gtcgggcttt cgcctctagc gactggtgga     1740
attgcctgca tccgggcccc gggcttcccg gcggcggcgc cggcggcggc ggcgcaggga     1800
caagggatgg ggatctggcc tcttccttgc tttcccgccc tcagtacccg agctgtctcc     1860
ttcccgggga cccgctggga gcgctgccgc tgcgggctcg agaaagggga gcctcgggta     1920
ctgagaggcc tcgcctgggg gaaggccgga gggtgggcgg cgcgcggctt ctgcggacca     1980
agtcggggtt cgctaggaac ccgagacggt ccctgccggc gaggagatca tgcgggatga     2040
gatgggggtg tggagacgcc tgcacaattt cagcccaagc ttctagagag tggtgatgac     2100
ttgcatatga gggcagcaat gcaagtcggt gtgctcccca ttctgtggga catgacctgg     2160
ttgcttcaca gctccgagat gacacagact tgcttaaagg aagtgactat tgtgacttgg     2220
gcatcacttg actgatggta atcagttgtc taaagaagtg cacagattac atgtccgtgt     2280
gctcattggg tctatctggc cgcgttgaac accaccaggc tttgtattca gaaacaggag     2340
ggaggtcctg cactttccca ggaggggtgg ccctttcaga tgcaatcgag attgttaggc     2400
tctgggagag tagttgcctg gttgtggcag ttggtaaatt tctattcaaa cagttgccat     2460
gcaccagttt tcacaacaa gggtacgtaa tctgtctggc attacttcta cttttgtaca     2520
aaggatcaaa aaaaaaaag atactgttaa gatatgattt ttctcagact ttgggaaact     2580
tttaacataa tctgtgaata tcacagaaac aagactatca tatagggat attaataacc      2640 tggagtcaga atacttgaaa tacggtgtca tttgacacgg gcattgttgt caccacctct     2700
gccaaggcct gccactttag gaaaaccctg aatcagttgg aaactgctac atgctgatag     2760
tacatctgaa acaagaacga gagtaattac cacattccag attgttcact aagccagcat     2820
ttacctgctc caggaaaaaa ttacaagcac cttatgaagt tgataaaata ttttgtttgg     2880
ctatgttggc actccacaat ttgctttcag agaaacaaag taaaccaagg aggacttctg     2940
tttttcaagt ctgccctcgg gttctattct acgttaatta gatagttccc aggaggacta     3000
```

-continued

```
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctctttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat tttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga ttttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg gctaattttt tgtatttttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc attttttttt tcttattctg    4440
ttaggagtga gagtgtaact agcagtataa tagttcaatt ttcacaacgt ggtaaaagtt    4500
tccctataat tcaatcagat tttgctccag ggttcagttc tgttttagga aatacttttta    4560
ttttcagttt aatgatgaaa tattagagtt gtaatattgc ctttatgatt atccacctttt    4620
ttaacctaaa agaatgaaag aaaaatatgt ttgcaatata attttatggt tgtatgttaa    4680
cttaattcat tatgttggcc tccagttttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920
attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgctttccat cagactgaac tctcttgaca agatgtggat    5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatatgac aatcacacat tgcttaggaa    5340
tgcatcatta ggcgattttg tcattatgca aacatcatag agtgtactta cacaaaccta    5400
```

```
gatagtatag cctttatgta cctaggccgt atggtatagt ctgttgctcc taggccacaa    5460
acctgtacaa ctgttactgt actgaatact atagacagtt gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac ttttaacctt tgtaaacttt ttaattttt aactttttaaa atacttagct     5820 tgaaacacaa atacattgta tagctataca aaaatatttt ttctttgtat ccttattcta    5880
gaagcttttt tctatttct attttaaatt tttttttta cttgttagtc gttttttgtta      5940 aaaactaaaa cacacacact ttcacctagg catagacagg attaggatca tcagtatcac    6000
tcccttccac ctcactgcct tccacctcca catcttgtcc cactggaagg tttttagggg    6060
caataacaca catgtagctg tcacctatga taacagtgct ttctgttgaa tacctcctga    6120
aggacttgcc tgaggctgtt ttacatttaa cttaaaaaaa aaaaagtag aaggagtgca     6180 ctctaaaata acaataaaag gcatagtata gtgaatacat aaaccagcaa tgtagtagtt    6240
tattatcaag tgttgtacac tgtaataatt gtatgtgcta tactttaaat aacttgcaaa    6300
atagtactaa gaccttatga tggttacagt gtcactaagg caatagcata ttttcaggtc    6360
cattgtaatc taatgggact accatcatat atgcagtcta ccattgactg aaacgttaca    6420
tggcacataa ctgtatttgc aagaatgatt tgttttacat taatatcaca taggatgtac    6480 cttttagag tggtatgttt atgtggatta agatgtacaa gttgagcaag gggaccaaga     6540
gccctgggtt ctgtcttgga tgtgagcgtt tatgttcttc tcctcatgtc tgttttctca    6600
ttaaattcaa aggcttgaac gggccctatt tagcccttct gttttctacg tgttctaaat    6660
aactaaagct tttaaattct agccatttag tgtagaactc tctttgcagt gatgaaatgc    6720
tgtattggtt tcttggctag catattaaat attttttatct ttgtcttgat acttcaatgt    6780
cgttttaaac atcaggatcg ggcttcagta ttctcataac cagagagttc actgaggata    6840
caggactgtt tgcccatttt ttgttatggc tccagacttg tggtatttcc atgtcttttt    6900
tttttttttt tttttttgacc ttttagcggc tttaaagtat ttctgttgtt aggtgttgta    6960
ttacttttct aagattactt aacaaagcac cacaaactga gtggctttaa acaacagcaa    7020
tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgaccccatt ttaacatgat tacacttatt    7320
tctagataag gtcacattca cgtacaccaa gggttaggaa ttgaacatat cttttttgggg    7380 gacacaattc aacccacaag tgtcagtctc tagctgagcc tttcccttcc tgttttctc     7440 cttttagtt gctatgggtt aggggccaaa tctccagtca tactagaatt gcacatggac     7500
tggatatttg ggaatactgc gggtctattc tatgagcttt agtatgtaac atttaatatc    7560
agtgtaaaga agccctttt taagttattt ctttgaattt ctaaatgtat gccctgaata    7620
taagtaacaa gttaccatgt cttgtaaaat gatcatatca acaaacattt aatgtgcacc    7680
tactgtgcta gttgaatgtc tttatcctga taggagataa caggattcca catctttgac    7740
```

-continued

```
ttaagaggac aaaccaaata tgtctaaatc atttggggtt ttgatggata tcttaaatt    7800
gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgattttc    8340
agcttattaa tcatgttaac ctatctgttg aaagcttatt ttctggtaca tataaatctt    8400
atttttttaa ttatatgcag tgaacatcaa acaataaatg ttatttattt tgcatttacc    8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata cctttgtttt ccctttcatt    8640
gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat ttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc tttttgaaac tatgcagatg ttacattgac tgttttctgt    9180
gaagttatct tttttcact gcagaataaa ggttgttttg atttatttt gtattgttta    9240
tgagaacatg catttgttgg gttaatttcc taccctgcc cccattttt ccctaaagta    9300
gaaagtattt tcttgtgaa ctaaattact acacaagaac atgtctattg aaaataagc    9360
aagtatcaaa atgttgtggg ttgtttttt aaataaattt tctcttgctc aggaaagaca    9420
agaaaatgtc cagaagatta tcttagaagg cacagagaga atggaagatc aggtatatgc    9480
aaattgcata ctgtcaaatg ttttctcac agcatgtatc tgtataaggt tgatggctac    9540
atttgtcaag gccttggaga catacgaata agcctttaat ggagcttta tggaggtgta    9600
cagaataaac tggaggaaga tttccatatc ttaaacccaa agagttaaat cagtaaacaa    9660
aggaaaatag taattgcatc tacaaattaa tatttgctcc ctttttttt ctgtttgccc    9720
agaataaatt ttgataact tgttcatagt aaaaataaaa aaaattgtct ctgatatgtt    9780
ctttaaggta ctacttctcg aacctttccc tagaagtagc tgtaacagaa ggagagcata    9840
tgtacccctg aggtatctgt ctggggtgta ggcccaggtc cacacaatat ttcttctaag    9900
tcttatgttg tatcgttaag actcatgcaa tttacatttt attccataac tatttagta    9960
ttaaaatttg tcagtgatat ttcttaccct ctcctctagg aaaatgtgcc atgtttatcc   10020
cttggctttg aatgccctc aggaacagac actaagagtt tgagaagcat ggttacaagg   10080
gtgtggcttc cctgcggaa actaagtaca gactatttca ctgtaaagca gagaagttct   10140
```

```
tttgaaggag aatctccagt gaagaaagag ttcttcactt ttacttccat ttcctcttgt    10200
gggtgaccct caatgctcct tgtaaaactc aatattttta aacatggctg ttttgccttt    10260
ctttgcttct ttttagcatg aatgagacag atgatacttt aaaaaagtaa ttaaaaaaaa    10320
aaacttgtga aaatacatgg ccataataca gaacccaata caatgatctc ctttaccaaa    10380
ttgttatgtt tgtactttg tagatagctt tccaattcag agacagttat tctgtgtaaa    10440
ggtctgactt aacaagaaaa gatttccctt tacccaaaga atcccagtcc ttatttgctg    10500
gtcaataagc agggtcccca ggaatggggt aactttcagc accctctaac ccactagtta    10560
ttagtagact aattaagtaa acttatcgca agttgaggaa acttagaacc aactaaaatt    10620
ctgcttttac tgggattttg ttttttcaaa ccagaaacct ttacttaagt tgactactat    10680
taatgaattt tggtctctct tttaagtgct cttcttaaaa atgttatctt actgctgaga    10740
agttcaagtt tgggaagtac aaggaggaat agaaacttaa gagattttct tttagagcct    10800
cttctgtatt tagccctgta ggattttttt tttttttttt tttttggtg ttgttgagct    10860 tcagtgaggc tattcattca cttatactga taatgtctga gatactgtga atgaaatact    10920
atgtatgctt aaacctaaga ggaaatattt tcccaaaatt attcttcccg aaaaggagga    10980 gttgccttt gattgagttc ttgcaaatct cacaacgact ttattttgaa caatactgtt    11040
tggggatgat gcattagttt gaaacaactt cagttgtagc tgtcatctga taaaattgct    11100
tcacagggaa ggaaatttaa cacggatcta gtcattattc ttgttagatt gaatgtgtga    11160
attgtaattg taaacaggca tgataattat tactttaaaa actaaaaaca gtgaatagtt    11220
agttgtggag gttactaaag gatggttttt tttaaataa aactttcagc attatgcaaa    11280
tgggcatatg gcttaggata aaacttccag aagtagcatc acatttaaat tctcaagcaa    11340
cttaataata tggggctctg aaaaactggt taaggttact ccaaaaatgg ccctgggtct    11400
gacaaagatt ctaacttaaa gatgcttatg aagactttga gtaaaatcat ttcataaaat    11460
aagtgaggaa aaacaactag tattaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc    11640
catatttgag acactttaca tttgtgatgt gttatactga attttcagtt tgattctata    11700
gactacaaat ttcaaaatta caatttcaag atgtaataag tagtaatatc ttgaaatagc    11760
tctaaaggga atttttctgt tttattgatt cttaaaatat atgtgctgat tttgatttgc    11820
atttgggtag attatacttt tatgagtatg gaggttaggg attgattcaa gttttcctta    11880
cctatttggt aaggatttca aagtcttttt gtgcttggtt ttcctcattt ttaaatatga    11940
aatatattga tgacctttaa caaattttttt tatctcaaa ttttaaagga gatcttttct    12000
aaaagaggca tgatgactta atcattgcat gtaacagtaa acgataaacc aatgattcca    12060
tactctctaa agaataaaag tgagcttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aagtgagct tggattgca    12360 tataaatcct ttagacatgt agtagacttg tttgatactg tgtttgaaca aattacgaag    12420
tattttcatc aaagaatgtt attgtttgat gttattttta ttttttattg cccagcttct    12480
```

```
ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660
ttttggggtt atagtattat tatgtatatt attaatattc taattttaat agtaaggact    12720
ttgtcataca tactattcac atacagtatt agccacttta gcaataagc acacacaaaa    12780 tcctggattt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtcttttga aacaaaactg tgtgccaaag tagtaaccat    12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
gcacagagat tgttttttgg ggagtcttga ttctcggaaa tgaaggcagt gtgttatatt    13260
gaatccagac ttccgaaaac ttgtatatta aaagtgttat ttcaacacta tgttacagcc    13320
agactaattt ttttattttt tgatgcattt tagatagctg atacagtact caatgatgat    13380
gatattggtg acagctgtca tgaaggcttt cttctcaagt aagaattttt cttttcataa    13440
aagctggatg aagcagatac catcttatgc tcacctatga caagatttgg aagaaagaaa    13500
ataacagact gtctacttag attgttctag ggacattacg tatttgaact gttgcttaaa    13560
tttgtgttat ttttcactca ttatatttct atatatattt ggtgttattc catttgctat    13620
ttaaagaaac cgagtttcca tcccagacaa gaaatcatgg ccccttgctt gattctggtt    13680
tcttgtttta cttctcatta aagctaacag aatcctttca tattaagttg tactgtagat    13740
gaacttaagt tatttaggcg tagaacaaaa ttattcatat ttatactgat ctttttccat    13800
ccagcagtgg agtttagtac ttaagagttt gtgcccttaa accagactcc ctggattaat    13860
gctgtgtacc cgtgggcaag gtgcctgaat tctctataca cctatttcct catctgtaaa    13920
atggcaataa tagtaatagt acctaatgtg tagggttgtt ataagcattg agtaagataa    13980
ataatataaa gcacttagaa cagtgcctgg aacataaaaa cacttaataa tagctcatag    14040
ctaacatttc ctatttacat ttcttctaga aatagccagt atttgttgag tgcctacatg    14100
ttagttcctt tactagttgc tttacatgta ttatcttata ttctgtttta agtttcttc     14160 acagttacag atttttcatga aatttttactt ttaataaaag agaagtaaaa gtataaagta   14220
ttcactttta tgttcacagt cttttccttt aggctcatga tggagtatca gaggcatgag    14280
tgtgtttaac ctaagagcct taatggcttg aatcagaagc actttagtcc tgtatctgtt    14340
cagtgtcagc ctttcataca tcattttaaa tcccatttga ctttaagtaa gtcacttaat    14400
ctctctacat gtcaatttct tcagctataa aatgatggta tttcaataaa taatacatt    14460 aattaaatga tattatactg actaattggg ctgtttaag gctcaataag aaaatttctg    14520
tgaaaggtct ctagaaaatg taggttccta tacaaataaa agataacatt gtgcttatag    14580
cttcggtgtt tatcatataa agctattctg agttatttga agagctcacc tactttttt     14640 tgttttagt ttgttaaatt gttttatagg caatgttttt aatctgtttt ctttaactta    14700
cagtgccatc agctcacact tgcaaacctg tggctgttcc gttgtagtag gtagcagtgc    14760
agagaaagta aataaggtag tttatttat aatctagcaa atgatttgac tctttaagac    14820
tgatgatata tcatggattg tcatttaaat ggtaggttgc aattaaaatg atctagtagt    14880
```

```
ataaggaggc aatgtaatct catcaaattg ctaagacacc ttgtggcaac agtgagtttg   14940
aaataaactg agtaagaatc atttatcagt ttatttgat agctcggaaa taccagtgtc    15000
agtagtgtat aaatggtttt gagaatatat taaaatcaga tatataaaaa aaattactct   15060
tctatttccc aatgttatct ttaacaaatc tgaagatagt catgtacttt tggtagtagt   15120
tccaaagaaa tgttatttgt ttattcatct tgatttcatt gtcttcgctt tccttctaaa   15180 tctgtcccett ctagggagct attgggatta agtggtcatt gattattata ctttattcag   15240
taatgtttct gaccctttcc ttcagtgcta cttgagttaa ttaaggatta atgaacagtt   15300
acatttccaa gcattagcta ataaactaaa ggattttgca cttttcttca ctgaccatta   15360
gttagaaaga gttcagagat aagtatgtgt atctttcaat ttcagcaaac ctaatttttt   15420
aaaaaaagtt ttacatagga aatatgttgg aaatgatact ttacaaagat attcataatt   15480 ttttttttgta atcagctact ttgtatattt acatgagcct taatttatat ttctcatata   15540
accatttatg agagcttagt atacctgtgt cattatattg catctacgaa ctagtgacct   15600
tattccttct gttacctcaa acaggtggct ttccatctgt gatctccaaa gccttaggtt   15660
gcacagagtg actgccgagc tgctttatga agggagaaag gctccatagt tggagtgttt   15720 ttttttttt ttttaaacat ttttcccatc ctccatcctc ttgagggaga atagcttacc    15780
ttttatcttg ttttaatttg agaaagaagt tgccaccact ctaggttgaa aaccactcct   15840
ttaacataat aactgtggat atggtttgaa tttcaagata gttacatgcc tttttatttt   15900
tcctaataga gctgtaggtc aaatattatt agaatcagat ttctaaatcc cacccaatga   15960
cctgcttatt ttaaatcaaa ttcaataatt aattctcttc tttttggagg atctggacat   16020
tctttgatat ttcttacaac gaatttcatg tgtagaccca ctaaacagaa gctataaaag   16080
ttgcatggtc aaataagtct gagaaagtct gcagatgata taattcacct gaagagtcac   16140
agtatgtagc caaatgttaa aggttttgag atgccataca gtaaatttac caagcatttt   16200
ctaaatttat ttgaccacag aatccctatt ttaagcaaca actgttacat cccatggatt   16260
ccaggtgact aaagaatact tatttcttag gatatgtttt attgataata acaattaaaa   16320
tttcagatat ctttcataag caaatcagtg gtctttttac ttcatgtttt aatgctaaaa   16380
tattttcttt tatagatagt cagaacatta tgccttttc tgactccagc agagagaaaa    16440
tgctccaggt tatgtgaagc agaatcatca tttaaatatg agtcagggct ctttgtacaa   16500
ggcctgctaa aggtatagtt tctagttatc acaagtgaaa ccacttttct aaaatcattt   16560
ttgagactct ttatagacaa atcttaaata ttagcattta atgtatctca tattgacatg   16620
cccagagact gacttccttt acacagttct gcacatagac tatatgtctt atggatttat   16680
agttagtatc atcagtgaaa caccatagaa tacccttttgt gttccaggtg ggtccctgtt   16740
cctacatgtc tagcctcagg actttttttt ttttaacaca tgcttaaatc aggttgcaca   16800
tcaaaaataa gatcatttct ttttaactaa atagatttga attttattga aaaaaaattt   16860
taaacatctt taagaagctt ataggattta agcaattcct atgtatgtgt actaaaatat   16920
atatatttct atatataata tatattagaa aaaaattgta ttttttcttt atttgagtct   16980
actgtcaagg agcaaaacag agaaatgtaa attagcaatt atttataata cttaaaggga   17040
agaaagttgt tcaccttgtt gaatctatta ttgttatttc aattatagtc ccaagacgtg   17100
aagaaatagc tttcctaatg gttatgtgat tgtctcatag tgactacttt cttgaggatg   17160
tagccacggc aaaatgaaat aaaaaaattt aaaaattgtt gcaaatacaa gttatattag   17220
```

```
gcttttgtgc attttcaata atgtgctgct atgaactcag aatgatagta tttaaatata    17280
gaaactagtt aaaggaaacg tagtttctat ttgagttata catatctgta aattagaact    17340
tctcctgtta aaggcataat aaagtgctta atacttttgt ttcctcagca ccctctcatt    17400
taattatata attttagttc tgaaagggac ctataccaga tgcctagagg aaatttcaaa    17460
actatgatct aatgaaaaaa tatttaatag ttctccatgc aaatacaaat catatagttt    17520
tccagaaaat acctttgaca ttatacaaag atgattatca cagcattata atagtaaaaa    17580
aatggaaata gcctctttct tctgttctgt tcatagcaca gtgcctcata cgcagtaggt    17640
tattattaca tggtaactgg ctaccccaac tgattaggaa agaagtaaat ttgttttata    17700
aaaatacata ctcattgagg tgcatagaat aattaagaaa ttaaaagaca cttgtaatttt   17760 tgaatccagt gaatacccac tgttaatatt tggtatatct ctttctagtc tttttttccc    17820
ttttgcatgt attttctttta agactcccac ccccactgga tcatctctgc atgttctaat   17880 ctgcttttt cacagcagat tctaagcctc tttgaatatc aacacaaact tcaacaactt     17940
catctataga tgccaaataa taaattcatt tttatttact taaccacttc ctttggatgc    18000
ttaggtcatt ctgatgtttt gctattgaaa ccaatgctat actgaacact tctgtcacta    18060
aaactttgca cacactcatg aatagcttct taggataaat ttttagagat ggatttgcta    18120
aatcagagac catttttttaa aattaaaaaa caattattca tatcgtttgg catgtaagac   18180
agtaaatttt cctttttattt tgacaggatt caactggaag ctttgtgctg cctttccggc   18240
aagtcatgta tgctccatat cccaccacac acatagatgt ggatgtcaat actgtgaagc    18300
agatgccacc ctgtcatgaa catatttata atcagcgtag atacatgaga tccgagctga    18360
cagccttctg gagagccact tcagaagaag acatggctca ggatacgatc atctacactg    18420
acgaaagctt tactcctgat ttgtacgtaa tgctctgcct gctggtactg tagtcaagca    18480
atatgaaatt gtgtctttta cgaataaaaa caaaacagaa gttgcattta aaagaaaga    18540 aatattacca gcagaattat gcttgaagaa acatttaatc aagcatttt ttcttaaatg     18600 ttcttctttt tccatacaat tgtgtttacc ctaaaatagg taagattaac ccttaaagta    18660
aatatttaac tatttgttta ataaatatat attgagctcc taggcactgt tctaggtacc    18720
gggcttaata gtggccaacc agacagcccc agccccagcc cctacattgt gtatagtcta    18780
ttatgtaaca gttattgaat ggacttatta acaaaaccaa agaagtaatt ctaagtctttt   18840 tttttcttga catatgaata taaaatacag caaaactgtt aaaatatatt aatggaacat    18900 tttttactt tgcattttat attgttattc acttcttatt tttttttaaa aaaaaagcc      18960 tgaacagtaa attcaaaagg aaaagtaatg ataattaatt gttgagcatg gacccaactt    19020
gaaaaaaaaa atgatgatga taatctctata atcctaaaac cctaagtaaa cacttaaaag   19080
atgttctgaa atcaggaaaa gaattatagt atactttgt gtttctcttt tatcagttga     19140
aaaaaggcac agtagctcat gcctgtaaga acagagcttt gggagtgcaa ggcaggcgga    19200
tcacttgagg ccaggagttc cagaccagcc tgggcaacat agtgaaaccc catctctaca    19260
aaaaataaaa aagaattatt ggaatgtgtt tctgtgtgcc tgtaatccta gctattccga    19320
aagctgaggc aggaggatct tttgagccca ggagtttgag gttacaggga ttatgatgt     19380 gccagtgtac tccagcctgg ggaacaccga gactctgtct tatttaaaaa aaaaaaaaaa    19440
aaaatgcttg caataatgcc tggcacatag aaggtaacag taagtgttaa ctgtaataac    19500
ccaggtctaa gtgtgtaagg caatagaaaa attggggcaa ataagcctga cctatgtatc    19560
tacagaatca gtttgagctt aggtaacaga cctgtggagc accagtaatt acacagtaag    19620
```

```
tgttaaccaa aagcatagaa taggaatatc ttgttcaagg gaccccagc cttatacatc   19680 tcaaggtgca gaaagatgac ttaatatagg acccatttt tcctagttct ccagagtttt   19740
tattggttct tgagaaagta gtagggaat gttttagaaa atgaattggt ccaactgaaa   19800
ttacatgtca gtaagttttt atatattggt aaatttagt agacatgtag aagttttcta   19860
attaatctgt gccttgaaac attttctttt ttcctaaagt gcttagtatt ttttccgttt   19920
tttgattggt tacttgggag cttttttgag gaaatttagt gaactgcaga atgggtttgc   19980
aaccatttgg tatttttgtt ttgttttta gaggatgtat gtgtatttta acatttctta   20040 atcatttta gccagctatg tttgttttgc tgatttgaca aactacagtt agacagctat   20100
tctcattttg ctgatcatga caaaataata tcctgaattt ttaaattttg catccagctc   20160
taaattttct aaacataaaa ttgtccaaaa aatagtattt tcagccacta gattgtgtgt   20220
taagtctatt gtcacagagt catttactt ttaagtatat gttttacat gttaattatg   20280 tttgttattt ttaattttaa ctttttaaaa taattccagt cactgccaat acatgaaaaa   20340
ttggtcactg gaatttttttt tttgactttt attttaggtt catgtgtaca tgtgcaggtg   20400
tgttatacag gtaaattgcg tgtcatgagg gtttggtgta caggtgattt cattacccag   20460
gtaataagca tagtacccaa taggtagttt tttgatcctc accttctcc caccctcaag   20520 taggccctgg tgttgctgtt tccttctttg tgtccatgta tactcagtgt ttagctccca   20580
cttagaagtg agaacatgcg gtagttggtt ttctgttcct ggattagttc acttaggata   20640
atgacctcta gctccatctg gttttttatgg ctgcatagta ttccatggtg tatatgtatc   20700 acatttctt tatccagtct accattgata ggcatttagg ttgattccct gtctttgtta   20760
tcatgaatag tgctgtgatg aacatacaca tgcatgtgtc tttatggtag aaaaatttgt   20820
attcctttag gtacatatag aataatgggg ttgctagggt gaatggtagt tctatttca   20880 gttatttgag aaatcttcaa actgcttttc ataatagcta aactaattta cagtcccgcc   20940
agcagtgtat aagtgttccc tttctccac aaccttgcca acatctgtga tttttttgact   21000 ttttaataat agccattcct agagaattga tttgcaattc tctattagtg atattaagca   21060
ttttttcata tgctttttag ctgtctgtat atattcttct gaaaaatttt catgtccttt   21120
gcccagtttg tagtggggtg ggttgttttt tgcttgttaa ttagttttaa gttccttcca   21180
gattctgcat atcccttgt tggatacatg gtttgcagat attttctcc cattgtgtag   21240 gttgtctttt actctgttga tagtttctt tgccatgcag gagctcgtta ggtcccattt   21300
gtgtttgttt ttgttgcagt tgcttttggc gtcttcatca taaaatctgt gccagggcct   21360
atgtccagaa tggtatttcc taggttgtct tccagggttt ttacaatttt agattttacg   21420
tttatgtctt taatccatct tgagttgatt tttgtatatg gcacaaggaa ggggtccagt   21480
ttcactccaa ttcctatggc tagcaattat cccagcacca tttattgaat acggagtcct   21540
ttccccattg cttgtttttt gtcaactttg ttgaagatca gatggttgta agtgtgtggc   21600
tttatttctt ggctctctat tctccattgg tctatgtgtc tgttttata acagtaccct   21660 gctgttcagg ttcctatagc ctttagtat aaaatcggct aatgtgatgc ctccagcttt   21720 gttcttttg cttaggattg ctttggctat ttgggctcct ttttgggtcc atattaattt   21780
taaaacagtt ttttctggtt ttgtgaagga tatcattggt agtttatagg aatagcattg   21840
aatctgtaga ttgctttggg cagtatggcc attttaacaa tattaattct tcctatctat   21900
gaatatggaa tgttttccca tgtgtttgtg tcatctcttt atacctgatg tataaagaaa   21960
```

```
agctggtatt attcctactc aatctgttcc aaaaaattga ggaggaggaa ctcttccta    22020 atgaggccag catcattctg ataccaaaac ctggcagaga cacaacagaa aaagaaaac    22080 ttcaggccaa tatccttgat gaatatagat gcaaaaatcc tcaacaaaat actagcaaac   22140
caaatccagc agcacatcaa aaagctgatc tactttgatc aagtaggctt tatccctggg   22200
atgcaaggtt ggttcaacat acacaaatca ataagtgtga ttcatcacat aaacagagct   22260
aaaaacaaaa accacaagat tatctcaata ggtagagaaa aggttgtcaa taaaattaa    22320 catcctccat gttaaaaacc ttcagtaggt caggtgtagt gactcacacc tgtaatccca   22380
gcactttggg aggccaaggc gggcatatct cttaagccca ggagttcaag acgagcctag   22440
gcagcatggt gaaaccccat ctctacaaaa aaaaaaaaa aaaaaatta gcttggtatg    22500 gtgacatgca cctatagtcc cagctattca ggaggttgag gtgggaggat tgtttgagcc   22560
cgggaggcag aggttggcag cgagctgaga tcatgccacc gcactccagc ctgggcaacg   22620
gagtgagacc ctgtctcaaa aaagaaaaat cacaaacaat cctaaacaaa ctaggcattg   22680
aaggaacatg cctcaaaaaa ataagaacca tctatgacag acccatagcc aatatcttac   22740
caaatgggca aaagctggaa gtattctcct tgagaaccgt aacaagacaa ggatgtccac   22800
tctcaccact ccttttcagc atagttctgg aagtcctagc cagagcaatc aggaaagaga   22860 aagaagaaa gacattcaga taggaagaga agaagtcaaa ctatttctgt ttgcaggcag   22920
tataattctg tacctagaaa atctcatagt ctctgcccag aaactcctaa atctgttaaa   22980
aatttcagca aagttttggc attctctata ctccaacacc ttccaaagtg agagcaaaat   23040
caagaacaca gtcccattca caatagccgc aaaacgaata aaatacctag gaatccagct   23100
aaccagggag gtgaaagatc tctatgagaa ttacaaaaca ctgctgaaag aaatcagaga   23160
tgacacaaac aaatggaaat gttcttttt aacaccttgc tttatctaat tcacttatga    23220
tgaagatact cattcagtgg aacaggtata ataagtccac tcgattaaat ataagcctta   23280 ttctcttttcc agagcccaag aagggggcact atcagtgccc agtcaataat gacgaaatgc   23340
taatattttt ccccttttacg gtttcttttct tctgtagtgt ggtacactcg tttcttaaga   23400
taaggaaact tgaactacct tcctgtttgc ttctacacat acccattctc ttttttttgcc   23460 actctggtca ggtataggat gatccctacc actttcagtt aaaaactcct cctcttacta   23520
aatgttctct taccctctgg cctgagtaga acctagggaa aatggaagag aaaaagatga   23580
aagggaggtg gggcctggga agggaataag tagtcctgtt tgtttgtgtg tttgctttag   23640
cacctgctat atcctaggtg ctgtgttagg cacacattat tttaagtggc cattatatta   23700
ctactactca ctctggtcgt tgccaaggta ggtagtactt tcttggatag ttggttcatg   23760
ttacttacag atggtgggct tgttgaggca aacccagtgg ataatcatcg gagtgtgttc   23820
tctaatctca ctcaaattt tcttcacatt tttggtttg ttttggtttt tgatggtagt     23880
ggcttatttt tgttgctggt ttgttttttg tttttttg agatggcaag aattggtagt    23940
tttatttatt aattgcctaa gggtctctac tttttttaaa agatgagagt agtaaaatag   24000
attgatagat acatacatac ccttactggg gactgcttat attctttaga gaaaaaatta   24060
catattagcc tgacaaacac cagtaaaatg taaatatatc cttgagtaaa taatgaatag   24120
tatattttgt gtctccaaat atatatatct atattcttac aaatgtgttt atatgtaata   24180
tcaatttata agaacttaaa atgttggctc aagtgaggga ttgtggaagg tagcattata   24240
tggccatttc aacatttgaa cttttttctt ttcttcattt tcttctttc ttcaggaata    24300 ttttttcaaga tgtcttacac agagacactc tagtgaaagc cttcctggat caggtaaatg   24360
```

```
ttgaacttga gattgtcaga gtgaatgata tgacatgttt tctttttaa tatatcctac    24420
aatgcctgtt ctatatattt atattcccct ggatcatgcc ccagagttct gctcagcaat    24480
tgcagttaag ttagttacac tacagttctc agaagagtct gtgagggcat gtcaagtgca    24540
tcattacatt ggttgcctct tgtcctagat ttatgcttcg ggaattcaga cctttgttta    24600
caatataata aatattattg ctatctttta aagatataat aataagatat aaagttgacc    24660
acaactactg ttttttgaaa catagaattc ctggtttaca tgtatcaaag tgaaatctga    24720
cttagctttt acagatataa tatatacata tatatatcct gcaatgcttg tactatatat    24780
gtagtacaag tatatatata tgtttgtgtg tgtatatata tatagtacga gcatatatac    24840
atattaccag cattgtagga tatatatatg tttatatatt aaaaaaaagt tataaactta    24900
aaaccctatt atgttatgta gagtatatgt tatatatgat atgtaaaata tataacatat    24960
actctatgat agagtgtaat atatttttta tatatatttt aacatttata aaatgataga    25020
attaagaatt gagtcctaat ctgtttatt aggtgctttt tgtagtgtct ggtctttcta    25080
aagtgtctaa atgattttc cttttgactt attaatgggg aagagcctgt atattaacaa    25140
ttaagagtgc agcattccat acgtcaaaca acaaacattt taattcaagc attaacctat    25200
aacaagtaag tttttttttt tttttgaga aagggaggtt gtttatttgc ctgaaatgac    25260
tcaaaaatat ttttgaaaca tagtgtactt attaaataa catctttatt gtttcattct    25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt tgggagtccg aggtgggtgg    25920
atcacaaggt caggagatcg agaccatcct gccaacatgg tgaaacccg tctctactaa    25980
gtatacaaaa attagctggg cgtggcagcg tgtgcctgta atcccagcta cctgggaggc    26040
tgaggcagga gaatcgcttg aacccaggag gtgtaggttg cagtgagtca agatcgcgcc    26100
actgcacttt agcctggtga cagagctaga ctccgtctca aaaaaaaaa aaaatatcag    26160
attgttccta cacctagtgc ttctatacca cactcctgtt aggggcatc agtggaaatg    26220
gttaaggaga tgtttagtgt gtattgtctg ccaagcactg tcaacactgt catagaaact    26280
tctgtacgag tagaatgtga gcaaattatg tgttgaaatg gttcctctcc ctgcaggtct    26340
ttcagctgaa acctggctta tctctcagaa gtactttcct tgcacagttt ctacttgtcc    26400
ttcacagaaa agccttgaca ctaataaat atatagaaga cgatacgtga gtaaaactcc    26460
tacacggaag aaaaaccttt gtacattgtt ttttgttt gtttcctttg tacatttct    26520
atatcataat ttttgcgctt cttttttttt ttttttttt ttttttcca ttattttag    26580
gcagaaggga aaaagccct ttaaatctct tcggaacctg aagatagacc ttgatttaac    26640
agcagagggc gatcttaaca taataatggc tctggctgag aaaattaaac caggcctaca    26700
```

```
ctcttttatc tttggaagac ctttctacac tagtgtgcaa gaacgagatg ttctaatgac    26760
tttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatcttttaa agatataata ataggatgta aacttgacca    27060
caactactgt ttttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctactttgt ggatttagtc cctgggattc agtctgtaga    27360
aatgtctaat agttctctat agtccttgtt cctggtgaac cacagttagg gtgttttgtt    27420 tatttattg ttcttgctat tgttgatatt ctatgtagtt gagctctgta aaaggaaatt    27480 gtatttatg ttttagtaat tgttgccaac ttttaaatt aattttcatt atttttgagc      27540
caaattgaaa tgtgcacctc ctgtgccttt tttctcctta gaaaatctaa ttacttggaa    27600
caagttcaga tttcactggt cagtcatttt catcttgttt tcttcttgct aagtcttacc    27660
atgtacctgc tttggcaatc attgcaactc tgagattata aaatgcctta gagaatatac    27720
taactaataa gatcttttt tcagaaacag aaaatagttc cttgagtact tccttcttgc     27780
atttctgcct atgtttttga agttgttgct gtttgcctgc aataggctat aaggaatagc    27840
aggagaaatt ttactgaagt gctgttttcc taggtgctac tttggcagag ctaagttatc    27900
ttttgttttc ttaatgcgtt tggaccattt tgctggctat aaaataactg attaatataa    27960
ttctaacaca atgttgacat tgtagttaca caaacacaaa taaatatttt atttaaaatt    28020
ctggaagtaa tataaaaggg aaaatatatt tataagaaag ggataaaggt aatagagccc    28080
ttctgccccc cacccaccaa atttacacaa caaaatgaca tgttcgaatg tgaaaggtca    28140
taatagcttt cccatcatga atcagaaaga tgtggacagc ttgatgtttt agacaaccac    28200
tgaactagat gactgttgta ctgtagctca gtcatttaaa aaatatataa atactacctt    28260
gtagtgtccc atactgtgtt ttttacatgg tagattctta tttaagtgct aactggttat    28320
tttctttggc tggtttattg tactgttata cagaatgtaa gttgtacagt gaaataagtt    28380
attaaagcat gtgtaaacat tgttatatat cttttctcct aaatggagaa ttttgaataa    28440
aatatatttg aaattttgcc tctttcagtt gttcattcag aaaaaaatac tatgatattt    28500
gaagactgat cagcttctgt tcagctgaca gtcatgctgg atctaaactt ttttaaaat    28560 taattttgtc ttttcaaaga aaaatatttt aaagaagctt tataatataa tcttatgtta    28620
aaaaaacttt ctgcttaact ctctggattt cattttgatt tttcaaatta tatattaata   28680
tttcaaatgt aaaatactat ttagataaat tgttttttaaa cattcttatt attataatat   28740
taatataacc taaactgaag ttattcatcc caggtatcta atacatgtat ccaaagtaaa   28800
aatccaagga atctgaacac tttcatctgc aaagctagga ataggtttga cattttcact   28860
ccaagaaaaa gttttttttt gaaaatagaa tagttgggat gagaggtttc tttaaaagaa   28920
gactaactga tcacattact atgattctca aagaagaaac caaaacttca tataatacta   28980
taaagtaaat ataaaatagt tccttctata gtatatttct ataatgctac agtttaaaca   29040
gatcactctt atataatact attttgattt tgatgtagaa ttgcacaaat tgatatttct   29100
```

```
cctatgatct gcagggtata gcttaaagta acaaaaacag tcaaccacct ccatttaaca    29160
cacagtaaca ctatgggact agtttttatta cttccatttt acaaatgagg aaactaaagc   29220
ttaaagatgt gtaatacacc gcccaaggtc acacagctgg taaaggtgga tttcatccca   29280
gacagttaca gtcattgcca tgggcacagc tcctaactta gtaactccat gtaactggta   29340
ctcagtgtag ctgaattgaa aggagagtaa ggaagcaggt tttacaggtc tacttgcact   29400
attcagagcc cgagtgtgaa tccctgctgt gctgcttgga gaagttactt aacctatgca   29460
aggttcattt tgtaaatatt ggaaatggag tgataatacg tacttcacca gaggatttaa   29520 tgagaccttta tacgatcctt agttcagtac ctgactagtg cttcataaat gcttttttcat   29580 ccaatctgac aatctccagc ttgtaattgg ggcatttaga acatttaata tgattattgg   29640
catggtaggt taaagctgtc atcttgctgt tttctatttg ttctttttgt tttctccttta   29700 cttttggatt ttttttattct actatgtctt ttctattgtc ttattaacta tactctttga   29760
tttattttag tggttgtttt aggggtttatac ctctttctaa tttaccagtt tataaccagt   29820
ttatatacta cttgacatat agcttaagaa acttactgtt gttgtctttt tgctgttatg    29880
gtcttaacgt ttttatttct acaaacatta taaactccac actttattgt tttttaattt    29940
tacttataca gtcaattatc ttttaaagat atttaaatat aaacattcaa aacaccccaa    30000
t                                                                    30001
```

<210> SEQ ID NO 3
<211> LENGTH: 1031
<212> TYPE: DNA
<213> ORGANISM: Homo sapiens

<400> SEQUENCE: 3

```
attcccggga tacgtaacct acggtgtccc gctaggaaag agaggtgcgt caaacagcga     60
caagttccgc ccacgtaaaa gatgacgctt ggtgtgtcag ccgtccctgc tgcccggttg    120
cttctctttt gggggcgggg tctagcaaga gcaggtgtgg gtttaggaga tatctccgga    180
gcatttggat aatgtgacag ttggaatgca gtgatgtcga ctctttgccc accgccatct    240
ccagctgttg ccaagacaga gattgcttta agtggcaaat cacctttatt agcagctact    300
tttgcttact gggacaatat tcttggtcct agagtaaggc acatttgggc tccaaagaca    360
gaacaggtac ttctcagtga tggagaaata acttttcttg ccaaccacac tctaaatgga    420
gaaatccttc gaaatgcaga gagtggtgct atagatgtaa agttttttgt cttgtctgaa    480
aagggagtga ttattgtttc attaatcttt gatggaaact ggaatgggga tcgcagcaca    540
tatggactat caattatact tccacagaca gaacttagtt tctacctccc acttcataga    600
gtgtgtgttg atagattaac acatataatc cggaaaggaa gaatatggat gcataaggaa    660
agacaagaaa aatgtccaga agattatctt agaaggcaca gagagaatgg aagatcaggg   720
tcagagtatt attccaatgc ttactggaga agtgattcct gtaatggaaa ctgctttcct    780
ctatgaaatt cccccggggtt cctggaggaa atagatatag gctgatacag ttacccaatg    840
atggatgaat attgggggac cgcctggtca ttgaaaggct ttcttttctc caggaaagaa    900
atttttttcc ttttccataa aaagcttggg aatggaagac aacaattccc attctttttt    960
tgcgttccac ccctatgtga aacagaaat ttttggggaa acaacaacga aaaaatttta  1020
tcccgcgcgc a                                                       1031
```

<210> SEQ ID NO 4

<211> LENGTH: 3244
<212> TYPE: DNA
<213> ORGANISM: Homo sapiens

<400> SEQUENCE: 4

| | | | | | |
|---|---|---|---|---|---:|
| gggcggggct | gcggttgcgg | tgcctgcgcc | cgcggcggcg | gaggcgcagg | cggtggcgag | 60 |
| tggatatctc | cggagcattt | ggataatgtg | acagttggaa | tgcagtgatg | tcgactcttt | 120 |
| gcccaccgcc | atctccagct | gttgccaaga | cagagattgc | tttaagtggc | aaatcacctt | 180 |
| tattagcagc | tacttttgct | tactgggaca | atattcttgg | tcctagagta | aggcacattt | 240 |
| gggctccaaa | gacagaacag | gtacttctca | gtgatggaga | ataactttt | cttgccaacc | 300 |
| acactctaaa | tggagaaatc | cttcgaaatg | cagagagtgg | tgctatagat | gtaaagtttt | 360 |
| ttgtcttgtc | tgaaaaggga | gtgattattg | tttcattaat | ctttgatgga | aactggaatg | 420 |
| gggatcgcag | cacatatgga | ctatcaatta | tacttccaca | gacagaactt | agtttctacc | 480 |
| tcccacttca | tagagtgtgt | gttgatagat | aacacatat | aatccggaaa | ggaagaatat | 540 |
| ggatgcataa | ggaaagacaa | gaaaatgtcc | agaagattat | cttagaaggc | acagagagaa | 600 |
| tggaagatca | gggtcagagt | attattccaa | tgcttactgg | agaagtgatt | cctgtaatgg | 660 |
| aactgctttc | atctatgaaa | tcacacagtg | ttcctgaaga | aatagatata | gctgatacag | 720 |
| tactcaatga | tgatgatatt | ggtgacagct | gtcatgaagg | ctttcttctc | aatgccatca | 780 |
| gctcacactt | gcaaacctgt | ggctgttccg | ttgtagtagg | tagcagtgca | gagaaagtaa | 840 |
| ataagatagt | cagaacatta | tgccttttc | tgactccagc | agagagaaaa | tgctccaggt | 900 |
| tatgtgaagc | agaatcatca | tttaaatatg | agtcagggct | ctttgtacaa | ggcctgctaa | 960 |
| aggattcaac | tggaagcttt | gtgctgcctt | tccggcaagt | catgtatgct | ccatatccca | 1020 |
| ccacacacat | agatgtggat | gtcaatactg | tgaagcagat | gccaccctgt | catgaacata | 1080 |
| tttataatca | gcgtagatac | atgagatccg | agctgacagc | cttctggaga | gccacttcag | 1140 |
| aagaagacat | ggctcaggat | acgatcatct | acactgacga | aagctttact | cctgatttga | 1200 |
| atattttca | agatgtctta | cacagagaca | ctctagtgaa | agccttcctg | gatcaggtct | 1260 |
| ttcagctgaa | acctggctta | tctctcagaa | gtactttcct | tgcacagttt | ctacttgtcc | 1320 |
| ttcacagaaa | agccttgaca | ctaataaaat | atatagaaga | cgatacgcag | aagggaaaaa | 1380 |
| agcccttaa | atctcttcgg | aacctgaaga | tagaccttga | tttaacagca | gagggcgatc | 1440 |
| ttaacataat | aatggctctg | gctgagaaaa | ttaaaccagg | cctacactct | tttatctttg | 1500 |
| gaagaccttt | ctacactagt | gtgcaagaac | gagatgttct | aatgactttt | taaatgtgta | 1560 |
| acttaataag | cctattccat | cacaatcatg | atcgctggta | aagtagctca | gtggtgtggg | 1620 |
| gaaacgttcc | cctggatcat | actccagaat | tctgctctca | gcaattgcag | ttaagtaagt | 1680 |
| tacactacag | ttctcacaag | agcctgtgag | gggatgtcag | gtgcatcatt | acattgggtg | 1740 |
| tctcttttcc | tagatttatg | cttttgggat | acagacctat | gtttacaata | taataaatat | 1800 |
| tattgctatc | ttttaaagat | ataataatag | gatgtaaact | tgaccacaac | tactgttttt | 1860 |
| ttgaaataca | tgattcatgg | tttacatgtg | tcaaggtgaa | atctgagttg | gctttttacag | 1920 |
| atagttgact | ttctatcttt | tggcattctt | tggtgtgtag | aattactgta | atacttctgc | 1980 |
| aatcaactga | aaactagagc | ctttaaatga | tttcaattcc | acagaaagaa | agtgagcttg | 2040 |
| aacataggat | gagctttaga | aagaaaattg | atcaagcaga | tgtttaattg | gaattgatta | 2100 |
| ttagatccta | ctttgtggat | ttagtccctg | ggattcagtc | tgtagaaatg | tctaatagtt | 2160 |
| ctctatagtc | cttgttcctg | gtgaaccaca | gttagggtgt | tttgtttatt | ttattgttct | 2220 |

```
tgctattgtt gatattctat gtagttgagc tctgtaaaag gaaattgtat tttatgtttt      2280
agtaattgtt gccaactttt taaattaatt ttcattattt ttgagccaaa ttgaaatgtg      2340
cacctcctgt gcctttttc tccttagaaa atctaattac ttggaacaag ttcagatttc      2400
actggtcagt cattttcatc ttgttttctt cttgctaagt cttaccatgt acctgctttg      2460
gcaatcattg caactctgag attataaaat gccttagaga atatactaac taataagatc      2520 ttttttttcag aaacagaaaa tagttccttg agtacttcct tcttgcattt ctgcctatgt      2580
ttttgaagtt gttgctgttt gcctgcaata ggctataagg aatagcagga gaaattttac      2640
tgaagtgctg ttttcctagg tgctactttg gcagagctaa gttatctttt gttttcttaa      2700
tgcgtttgga ccattttgct ggctataaaa taactgatta atataattct aacacaatgt      2760
tgacattgta gttacacaaa cacaaataaa tattttattt aaaattctgg aagtaatata      2820
aaagggaaaa tatatttata agaaagggat aaaggtaata gagcccttct gcccccacc      2880 caccaaattt acacaacaaa atgacatgtt cgaatgtgaa aggtcataat agctttccca      2940
tcatgaatca gaaagatgtg acagcttga tgttttagac aaccactgaa ctagatgact      3000
gttgtactgt agctcagtca tttaaaaaat atataaatac taccttgtag tgtcccatac      3060
tgtgtttttt acatggtaga ttcttattta agtgctaact ggttatttc tttggctggt      3120 ttattgtact gttatacaga atgtaagttg tacagtgaaa taagttatta aagcatgtgt      3180
aaacattgtt atatatcttt tctcctaaat ggagaatttt gaataaaata tatttgaaat      3240
tttg                                                                   3244

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5
cacgaggctt tgatatttct tacaacgaat ttcatgtgta gacccactaa acagaagcta        60
taaaagttgc atggtcaaat aagtctgaga aagtctgcag atgatataat tcacctgaag       120
agtcacagta tgtagccaaa tgttaaaggt tttgagatgc catacagtaa atttaccaag       180
cattttctaa atttatttga ccacagaatc cctatttaa gcaacaactg ttacatccca        240
tggattccag gtgactaaag aatacttatt tcttaggata tgttttattg ataataacaa       300
ttaaaatttc agatatcttt cataagcaaa tcagtggtct ttttacttca tgttttaatg       360
ctaaaatatt ttcttttata gatagtcaga acattatgcc ttttctgac tccagcagag        420 agaaaatgct ccaggttatg tgaagcagaa tcatcattta aatatgagtc agggctcttt       480
gtacaaggcc tgctaaagga ttcaactgga agctttgtgc tgcctttccg gcaagtcatg       540
tatgctccat atcccaccac acacatagat gtggatgtca atactgtgaa gcagatgcca       600
ccctgtcatg aacatattta taatcagcgt agatacatga gatccgagct gacagccttc       660
tggagagcca cttcagaaga agacatggct cangatacga tcatctacac tgacgaaagc       720
tntactcctg atttgaatat ttttcaagat gtcttacaca g                           761
```

<210> SEQ ID NO 6
<211> LENGTH: 1901
<212> TYPE: DNA
<213> ORGANISM: Homo sapiens

<400> SEQUENCE: 6

| | | | | | |
|---|---|---|---|---|---|
| acgtaaccta | cggtgtcccg | ctaggaaaga | gaggtgcgtc | aaacagcgac | aagttccgcc | 60 |
| cacgtaaaag | atgacgcttg | atatctccgg | agcatttgga | taatgtgaca | gttggaatgc | 120 |
| agtgatgtcg | actctttgcc | caccgccatc | tccagctgtt | gccaagacag | agattgcttt | 180 |
| aagtggcaaa | tcacctttat | tagcagctac | ttttgcttac | tgggacaata | ttcttggtcc | 240 |
| tagagtaagg | cacatttggg | ctccaaagac | agaacaggta | cttctcagtg | atggagaaat | 300 |
| aacttttctt | gccaaccaca | ctctaaatgg | agaaatcctt | cgaaatgcag | agagtggtgc | 360 |
| tatagatgta | aagttttttg | tcttgtctga | aaagggagtg | attattgttt | cattaatctt | 420 |
| tgatggaaac | tggaatgggg | atcgcagcac | atatggacta | tcaattatac | ttccacagac | 480 |
| agaacttagt | ttctacctcc | cacttcatag | agtgtgtgtt | gatagattaa | cacatataat | 540 |
| ccggaaagga | agaatatgga | tgcataagga | aagacaagaa | aatgtccaga | agattatctt | 600 |
| agaaggcaca | gagagaatgg | aagatcaggg | tcagagtatt | attccaatgc | ttactggaga | 660 |
| agtgattcct | gtaatggaac | tgctttcatc | tatgaaatca | cacagtgttc | ctgaagaaat | 720 |
| agatatagct | gatacagtac | tcaatgatga | tgatattggt | gacagctgtc | atgaaggctt | 780 |
| tcttctcaag | taagaatttt | tcttttcata | aaagctggat | gaagcagata | ccatcttatg | 840 |
| ctcacctatg | acaagatttg | gaagaaagaa | aataacagac | tgtctactta | gattgttcta | 900 |
| gggacattac | gtatttgaac | tgttgcttaa | atttgtgtta | ttttcactc | attatatttc | 960 |
| tatatatatt | tggtgttatt | ccatttgcta | tttaaagaaa | ccgagtttcc | atcccagaca | 1020 |
| agaaatcatg | gccccttgct | tgattctggt | ttcttgtttt | acttctcatt | aaagctaaca | 1080 |
| gaatcctttc | atattaagtt | gtactgtaga | tgaacttaag | ttatttaggc | gtagaacaaa | 1140 |
| attattcata | tttatactga | tctttttcca | tccagcagtg | gagtttagta | cttaagagtt | 1200 |
| tgtgccctta | aaccagactc | cctggattaa | tgctgtgtac | ccgtgggcaa | ggtgcctgaa | 1260 |
| ttctctatac | acctatttcc | tcatctgtaa | aatggcaata | atagtaatag | tacctaatgt | 1320 |
| gtagggttgt | tataagcatt | gagtaagata | aataatataa | agcacttaga | acagtgcctg | 1380 |
| gaacataaaa | acacttaata | atagctcata | gctaacattt | cctatttaca | tttcttctag | 1440 |
| aaatagccag | tatttgttga | gtgcctacat | gttagttcct | ttactagttg | ctttacatgt | 1500 |
| attatcttat | attctgtttt | aaagtttctt | cacagttaca | gatttcatg | aaattttact | 1560 |
| tttaataaaa | gagaagtaaa | agtataaagt | attcacttt | atgttcacag | tcttttcctt | 1620 |
| taggctcatg | atggagtatc | agaggcatga | gtgtgtttaa | cctaagagcc | ttaatggctt | 1680 |
| gaatcagaag | cacttagtc | ctgtatctgt | tcagtgtcag | cctttcatac | atcatttaa | 1740 |
| atcccatttg | acttaagta | agtcacttaa | tctctctaca | tgtcaatttc | ttcagctata | 1800 |
| aaatgatggt | atttcaataa | ataaatacat | taattaaatg | atattatact | gactaattgg | 1860 |
| gctgttttaa | ggcaaaaaaa | aaaaaaaaaa | aaaaaaaaaa | a | | 1901 |

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

```
agacgtaacc tacggtgtcc cgctaggaaa gagagatatc tccggagcat ttggataatg    60
tgacagttgg aatgcagtga tgtcgactct ttgcccaccg ccatctccag ctgttgccaa   120
gacagagatt gctttaagtg gcaaatcacc tttattagca gctacntttt gcttactggg   180
acaatattct tggtcctaga gtaaggcaca tttgggctcc aaagacagaa caggtacttc   240
tcagtgatgg agaaataact tttcttgcca accacactct aaatggagaa atccttcgaa   300
atgcagagag tggtgctata gatgtaaagt ttttttgtctt gtctgaaaag ggagtgatta   360
ttgtttcatt aatctttgat ggaaactgga atggggatcg cagcacatat ggactatcaa   420
ttatacttcc acagacagaa cttagtttct acctcccact tcatagagtg tgtgttgata   480
gattaacaca tataatccgg aaaggaagaa tatggatgca taaggaaaga caagaaaatg   540
tccagaagat tatcttagaa gg                                            562
```

<210> SEQ ID NO 8
<211> LENGTH: 798
<212> TYPE: DNA
<213> ORGANISM: Homo sapiens

<400> SEQUENCE: 8

```
gggctctctt ttgggggcgg ggtctagcaa gagcagatat ctccggagca tttggataat    60
gtgacagttg gaatgcagtg atgtcgactc tttgcccacc gccatctcca gctgttgcca   120
agacagagat tgctttaagt ggcaaatcac ctttattagc agctactttt gcttactggg   180
acaatattct tggtcctaga gtaaggcaca tttgggctcc aaagacagaa caggtacttc   240
tcagtgatgg agaaataact tttcttgcca accacactct aaatggagaa atccttcgaa   300
atgcagagag tggtgctata gatgtaaagt ttttttgtctt gtctgaaaag ggagtgatta   360
ttgtttcatt aatctttgat ggaaactgga atggggatcg cagcacatat ggactatcaa   420
ttatacttcc acagacagaa cttagtttct acctcccact tcatagagtg tgtgttgata   480
gattaacaca tataatccgg aaaggaagaa tatggatgca taaggaaaga caagaaaatg   540
tccagaagat tatcttagaa ggcacagaga gaatggaaga tcagggtcag agtattattc   600
caatgcttac tggagaagtg attcctgtaa tgggactgct ttcatctatg aaatcacaca   660
gtgttcctga agaaatagat atagctgata cagtactcca tgatgatgat atttggtgac   720
agctgtcatg aaaggctttc ttctcaagta ggaattttt cttttcataa aagctgggat   780
gaagccagat tcccatct                                                 798
```

<210> SEQ ID NO 9
<211> LENGTH: 169
<212> TYPE: DNA
<213> ORGANISM: Homo sapiens

<400> SEQUENCE: 9

```
aaacagcgac aagttccgcc cacgtaaaag atgatgcttg gtgtgtcagc cgtccctgct    60
gcccggttgc ttctcttttg ggggcggggt ctagcaagag cagatatctc cggagcattt   120
ggataatgtg acagttggaa tgcggtgatg tcgactcttt gcccaccgc                169
```

<210> SEQ ID NO 10
<211> LENGTH: 176
<212> TYPE: DNA

<213> ORGANISM: Homo sapiens

<400> SEQUENCE: 10

| | | | | | |
|---|---|---|---|---|---|
| aaaacgtcat | cgcacataga | aaacagacag | acgtaaccta | cggtgtcccg | ctaggaaaga | 60 |
| gaggtgcgtc | aaacagcgac | aagttccgcc | cacgtaaaag | atgacgcttg | atatctccgg | 120 |
| agcatttgga | taatgtgaca | gttggaatgc | agtgatgtcg | actctttgcc | caccgc | 176 |

<210> SEQ ID NO 11
<211> LENGTH: 38001
<212> TYPE: DNA
<213> ORGANISM: Mus musculus

<400> SEQUENCE: 11

| | | | | | |
|---|---|---|---|---|---|
| tgtctctagg | taaaattttg | aaggaaaaaa | aaaacactaa | gaaggtatat | tccttcaaag | 60 |
| ttccagtctt | attctgaagt | gtaatgttat | gttagtttga | ctcacagaca | ggttttaaag | 120 |
| aagggcttac | ttcaagagga | caccaaacaa | atacctccta | ttcctagtgg | gctctggaat | 180 |
| cacagaaaac | tgacccaatc | aattacattg | atagctctgg | cttactacag | acaagcaaat | 240 |
| tatcttaagt | gtgcatgcat | gcgcgtgtat | gtgtgttagt | acctaacacc | cacctgggaa | 300 |
| cttttcagct | tttcagtgtg | ggatatagta | taaacgtcta | ttcctcgtgt | tgtggattag | 360 |
| ctgactggcc | tcactcagct | gccttcctta | cctgcaaact | cacccacttt | gactacagca | 420 |
| tcgcactctt | aaccctagcc | ttccaaacat | ggtcctatgc | tatttctgtg | tgtctggatg | 480 |
| tatttttaac | tctcagatgt | atacttcatt | tatgagatat | acatctgaag | accacggtac | 540 |
| aaaacactgt | aagaacttga | tagaatgaca | actgctaggt | aaaaaaaaaa | aaaaaaaaaa | 600 |
| aaaaaaaaaa | aaaaaaagc | atacaatacc | tggtgagagt | tctattttta | ccgaaggtgg | 660 |
| tattgatagg | tattctgtta | ttaatgcctt | tcttttccct | ataaatgatg | aaaagttgct | 720 |
| ggaaaataat | aaacactact | catctgtagt | gaaaagccac | aatacagtta | caaaccaatc | 780 |
| aatcaatcaa | taaatcagac | gtcatggtgt | tcttttccca | aaggttaaaa | aacaaagtgc | 840 |
| actgtgctat | ttggcaaaaa | tgacgtttag | aagaaaacac | ggtgactacg | cacagagggt | 900 |
| gggggaatca | ttgtgcttgt | tgcggagtga | acacgtacag | tgtgcacgca | gacttacggc | 960 |
| atttaaccgt | gtcataggga | ccaaaggaaa | tccactcact | cactaaatat | ttgttgagca | 1020 |
| cccactacct | gccaactccc | aaacaaaaca | aagcaaaact | acttacaacc | acaaactacg | 1080 |
| cttcgtaacc | tagatagata | acgcaggtga | cactatctat | ctaggttgag | ctcagctctg | 1140 |
| cccatgcttt | tcctgagcgg | ctcttggaag | aaaagctaca | aagcccatga | cagcctccgc | 1200 |
| ctggccagct | gccactggca | tctcaaggct | ggcaaagcaa | agtgaaagcg | ccaacccgga | 1260 |
| acttacggag | tcccacgagg | gaaccgcggc | gcgtcaagca | gagacgagtt | ccgcccacgt | 1320 |
| gaaagatggc | gtttgtagtg | acagccatcc | caattgccct | ttccttctag | gtggaaagtg | 1380 |
| gtgtctagac | agtccaggga | gggtgtgcga | gggaggtgcg | ttttggttgc | ctcagctcgc | 1440 |
| aacttaactc | cacaacggtg | accaaggaca | aaagaaggaa | acaagactgc | agagatccgc | 1500 |
| accggggagc | cctgcagatt | ctgggtctgc | tgtggactgg | gggcgggact | gcgactgggc | 1560 |
| gggcctgggg | gcgtgtccgg | ggcggggcgg | tcccggggcg | gggcccggag | cgggctgcgg | 1620 |
| ttgcggtccc | tgcgccggcg | gtgaaggcgc | agcagcggcg | agtgggtgag | tgagacgcgc | 1680 |
| gggcggaggg | gggctgctgc | cacggtcggc | tcgcgggccg | gccggctccg | ggtaccagcg | 1740 |
| gggtttttt | ctccttcgag | gtgaactcct | ccctgtcccc | cggcgaaag | agcccttggc | 1800 |
| cttgcaggag | ttgcgggggc | cgcggcggtg | cggaggggat | ggggatgggc | ctcatctttg | 1860 |

```
ctgtccgccc gcgctcccog atcccgaccc ggagcgtctc ccgggcccct gagggaaccc    1920
tccgggagta cggcgagcgc ggcccccacc gccacaagcc tgggcccag  gggcctggcc    1980 cggcgacagc tggtgggtcc tgcgacccag tcaggtctcc cgagggtccc cgcccgggag    2040
gagaaagcgc cggtgggatg gagtaaggac ggacagaaca acacgcaggc aggatttcgc    2100
agaagtttgc aaggagtgcg gatgcccact tacatgggct gctactctta ccaggttgtt    2160
ccccagttct gtgggacgtg acctggttgc ctcacagctc cgcggttgta cagacttatt    2220
aaaggaagtg accattgtga cttgggcatc acttgactga tggtaatcag ttgcagagag    2280
agaagtgcac tgattaagtc tgtccacaca gggtctgtct ggccaggagt gcatttgcct    2340
gggagggatt ggttgcgctt tctggtgtgg ggactattag gctcttgtag agttttgtcc    2400
cggcagatgg ataaatttct tgttacactg ttcccgttcg tcaccagttg agaaaaacgg    2460
gtacacagtc tgtctcagta gtacttttac tttatattaa gggcccaaaa gggactggaa    2520
aatactttaa gatagaatcg ttagtccact tggaaaactt aaaatatgag agagagaggg    2580 ggggggaga  gagagagaga gagagagaga gaaaggaagg aagaaggagg aagaggagga    2640
ggaaagagat tgagattatg ttaataatat ggaatcagaa tatttgaaat atagtaagcg    2700
tccactcagt taaagaggac attccaggag gcccccagta tagcctgaaa tctcaggaaa    2760
cgcctacata cacccatcgt gtggatatag gtgttttccc ttcattacat ttcatacaca    2820
gatgttaaag tttagaaagt aggcacaata agagattaca aataactgat aataaagtcg    2880
agccattgca gctgctctgt aaaagtcctg tgaatgtgat cgctttgtgt ttcaaagtaa    2940
cttactgtac ttcacccctg ttaagcaaaa caagattcac ctgaacgcag gcaccttggt    3000
accttggcag acaccagatc tgataaccaa gaggatggag aagtagtggc agacagtgtg    3060
gagagcatga atatgctaga caaaagggtg aatcataacc taggagcaga aagcaggtat    3120
ttcatcatcc tccacagtaa aaacctatgt cacgtaaaaa acctacaagt agttttttctt   3180 ttactctttt tgaatgaaag cttgctacag gcactgaaag ttaaaataat ctgtggatca    3240
ggaggaacag gggttttctg tctgagtcac tgctgactag cacctcagtg accattggca    3300
ctgtgggaaa cccagagtc  agttggaaac ttcgaaacta aaggtgacgg tgttcttatt    3360
tcatagaaca caaaaaataa gaggggttac agcctgcgct gcagactgga cattcaacaa    3420
gcatttaaat ttctgggaga caaatgtaaa tataacttta aaagttggta aaatactctg    3480
tttggctatg ttggccatcc aatgtttgct tttagaaaat gactgaatgg ataaaacgtc    3540
tatcttttga gcctgcccta gaccccatg  ttgagtgaat actgtccaag tgttaggtta    3600
gccggcctga gaaacttgga tctaggcaag atggcacagt cctggtgtca tgagtatgca    3660
tgtgagtttt ggctgaaatt gaacatttgt agagaatgac aaaggctggt ctgcaagta     3720 gtccactgtc tttacagtgg tcttggttag ttcctgtttg gctgagaggg ctggttgatg    3780
gctgtcctgc ccctcttccc acaagtggaa gccttatggt ataattcttg atcacagtag    3840
cagtaggcaa atgaacttcc tcaaagcagc ctggaaagct gatttttttt tctttctttc    3900 tcttttttt  ttttttttca caaggttaaa gaaaaaacaa agggcttcaa atgtgccagt    3960
ctgctaacag tgttaacatg tttattaaca taaataaact ttattagttt ttggaagtat    4020
tggttaagcc ctcgtgaccc ctgaactcgg tttatagagt gatgagtcgt agcctcactc    4080
tggtttggac tctggcttct ctcagaagac tctgtggcta atgttaacct tctgaagtag    4140
ccagaaaaca tataagcaaa agtctgtgag gttgaaatga atttttggc  cacatttgta    4200
```

```
tatgggttcc caccaatgct aacttcaggt gttagtaata tcagactcac agcttccctg   4260
attacacttc gctataagac tttatttttt aggtcatagg aatttcccct ttttcatgat   4320
tcctaaatca tgaaataaca tagtctaaaa atacggtatt cctgaaataa acaatttcta   4380
agttttaagc tgcgtgctat tctgaacagt ctgatgccct cttgtagctt ttactgtgtc   4440
ctaccccggg catggttgat tcctttgtcc aaacatctgt ctgttgtatc cacactggat   4500
tgcaccacct gcgtgctagt cagtcactca gacattttag ttataaggta gcttatatt    4560 actccttatt ttatttaata atggcctcat agcaaggcgg taatgatact ggtaatttgg   4620
gtttgcttaa gaggagccat gaagtagttt taaatgaaaa ggtgaaaatt cccactatag   4680
tttggagggg gaggctatac tggtactact acgattcacg gtaagactaa atcttctgtg   4740
aaattatgaa ggagaaaaag ttacactggt ctggtcttgc tgttggatta attttatagt   4800
tataaccact gtacatgata aataaccta aaacaatgaa tttgtaggtg gatggcataa    4860
tctgaaaacc atgttctgag cagttgatgg cagcaggctg tgctggaagt gttaggcata   4920
tttatagatt tcagcccaag ttctgaagag gctggagaga tggctcagtg gttaagagtg   4980
cttgctattg cagaggacct aggttcctct acaggcacca ggcaagcgtg ggacacactg   5040
agatacatac agacaaaaca taaaattaaa taaattgtgc ataataatac tagtaatata   5100
tgagtaaaat aaggataaat acacatcata attaaataaa taattgtaa agttccctag    5160 aagtgagggt caccaagcca ttcacaagat ggctgcgctg atgcagggat atatgtgaac   5220
tagaaaaagg tcaaacttaa cagagaagtt ccaaggcatg ctactgcagg cttggctagc   5280
atgcttgacc tgcagaaatg ctgacggcca ctgggaggtt ttcacaaatg aggaattaga   5340
agaacttttt ttactaatct ccagaaaaaa aaagggaag aagaaactga agcagcctgt    5400
gatgtggacc agaaacgcag tgacagtaac atgtgtgaca ttgcaaaggc atgaaaggac   5460
agagctgtgg aatacagacc tcaggtggag ctcagcatag agtcattcgg ggattatgcc   5520
tgctgcagca acaaaaggat gagctcaaaa gagacaccga cttctgaatg cagtgggtgt   5580
ttgttttgtt ttgtttcaaa tgaattgggc agaaaacttt ccagctgtgg aagcttctga   5640
accgtccctt gctgctgaca tctaagcgtc cgctgtgtcc cagctcagtg atctagggtc   5700
ttccaaacag atggtccggt gctgagcact ttgaatctca atcctgagtt tctaccacgc   5760
ctttggccat ttaattccca gataaaagac acatacaacc tttatattta taataaacct   5820
tagtcagcac aagagctgag caaatatctg tcctctatgc tattatatct attacccagc   5880
caataacccc attctataat ttgctgtgct tcatctgggc tgctcttaac ttcagtcagc   5940
cagcccacgt ggccattatt ttaagatttt tttacccat agtgtcttct cactttactt    6000
tacatttttc tctctctcct catggttctc ctctgacccc aagcctagga accctaaacc   6060
ccacccatgt ctcttctgcc catctattgg ctgtaggcat ctttattcac caatcaggat   6120
aacttggagg caaggttaag tagtctcctg ggtctaggtg ctgtctctgg gagcaaccag   6180
tatttagcat agcaaaagac cagacctcca caatgatcac tctgaccatc ggggcagaag   6240
gcacctacta gcctgtgcca ctcacctcac tttgttgaat cacatcttat cctgtagtgt   6300
gtatcactgc ctgttatcac aggaaaaagt gagtcccatc aaataagatg tttcagaaag   6360
agaccatgtt catataatta tcattctggt aagcttttaa tggttatatt tgttattaa    6420 tctctttgtt cctattttgc aaattatacc ttacagtaaa tatatatgca tccaatgggg   6480
tctttgaatt cctccccggg gagtaggagg actcttgag gatgggctgc atttaaagct    6540
aaacaacgca acatgacctt tagtccttat agatagccta gagatgagac taaataaaag   6600
```

```
aaatggtata taatgctttta agtttcccaa tcagcttaaa agcttttcct ataaatcttt    6660
aagattatgc tctggggctc aatactgctt caagaagggc ttttcttttg tatttagaat    6720
tattcacctt tttaaacaaa aggagaaaat ggaatagaaa tatgtttgca acataatttt    6780
atgactatgt gtttatttcg cgtgttctgt gggcctgcag tttgctgctg ttaatgagga    6840
caacagtggc accaatacag tttccactca gattacattc tctgttccct ttctgaaagc    6900
tgccctctcc actgggccca aaagagtcag tatcttaaac aagctgtaca acttagataa    6960
ccatggtctc ttcagactag ttaattgaca tatattaaaa agtaaatagt accaaagtga    7020
atttctgaaa ttaaaaatga acatttaaaa actctaggta aactattcct tagagttaag    7080
tgttttgcca agttctgtaa tcataatatg atagaaacgc tcactcagca ttctaaatat    7140
agaagttact ccttcgcatg acactctaat tcttgataag gtggagaaag agagagagag    7200 aggggagag acagaaaata tggtggttca aggaccattt gagggaatta gttatgttct    7260
tccgtcctct gtggatctta ggggttgaat acagtcattg agctcggtgg atggctgtcc    7320
tgttgaaagg tctgcccagc agagcaaata gactttttta tttacatgga catccgtttg    7380
tgactaatct aatgttcact cccaaagtaa tcacacagac agagaggtag cttccttcag    7440
tactcttacc ttacatgaat cctaccattt tgttatttt tttccacttt aaatctttga    7500
ttatgtgttt ttaattagaa aatttgcata caaatttcca tacagtatgt agaattgact    7560
gtgtttgaat gggtgaagat ccacatgtgt aaccctagct ctggactggc tctgagcttg    7620
tttgctcttc tcttttgtgt tctgagtaac tgaaactctt tcattttagc agcttagtat    7680
gcgcccttca cattgctgtg ctgcctgctg cactaacatt actcctttgc ttatgttccc    7740
cttcctgatt cagtgtcatt ttaagcagta gtactggacc tcagtacctt agccggagct    7800
cactgaggtg acagggctga ggctctgctg ctgtcttttg agcttacctc tttttaatgt    7860
tttatggtat ttctgctgcc aggtttgggg gttttgtttt gttttgtttt ttgttttttg    7920
ttttttttaa ttttctagga acacctagaa aacacaaact aggaaactta aaagagcagc    7980
gtcttgttcc ctgcgttcta gaaagtccaa gcctaatgcc agtgtcatgg ttgtcaggaa    8040
catgagcctc tgaaggcttc ttgggaaacc tttcttgtct caacacctct ggtggcaagc    8100
agtagtccat ggtactctct ctgtccacgg tcagcatccc agtccctgcc ctttatcttt    8160
gtgcagccga ccagctttgc tttagtctgt ctccttctca ggtctccttc cccgctcctc    8220
ttaagcacag cagtcattgg attagagccc atccttccct cggatggccc atttgaccta    8280
attttacgta tttgtaacta aggtcccatt tacttacaca gggccctccc cttcctgttt    8340
tgttctttag ctgaaatggt ttggagacca aatatccaat cattacaatt gtgcacaagc    8400
tatgttcatt tggaggtaat aaaggctcat tctttgcttc tattggtatg tgacattttt    8460
ctaagtcact tgggggtttga tagatatctt taaatggctg aacctgatca ctgttctttt    8520
gtatgtccct gtttagctat tgcaagcgtt cggataatgt gagacctgga atgcagtgag    8580
acctgggatg cagggatgtc gactatctgc cccccaccat ctcctgctgt tgccaagaca    8640
gagattgctt taagtggtga atcacccttg ttggcggcta cctttgctta ctgggataat    8700
attcttggtc ctagagtaag gcatatttgg gctccaaaga cagaccaagt gcttctcagt    8760
gatggagaaa taacttttct tgccaaccac actctaaatg gagaaattct tcgaaatgca    8820
gagagtgggg ctatagatgt aaaatttttt gtcttatctg aaaaagggggt aattattgtt    8880 tcattaatct tcgacggaaa ctggaatgga gatcggagca cttatggact atcaattata    8940
```

```
ctgccgcaga cagagctgag cttctacctc ccacttcaca gagtgtgtgt tgacaggcta    9000
acacacatta ttcgaaaagg aagaatatgg atgcataagg taaggggctt ttgagcttga    9060
tcatggtagc ctggccaatg aaagtttttt tctggtacag ttacacttaa gttttggaaa    9120
ttatatgctg ctaacaccag acagctgtta tgttgtgtct cctgggcaca gaaagccctg    9180
ctctcatgcc tggggtcttc acagtcctaa tggaaagtaa gatcttataa acattgtgtc    9240
tgagtttgtt ctggaagctg tgactctacc ttcttgtttt cctttccctg tgtgactttg    9300
tcctttgctt acaacagtgc aaaagtataa atattctcag attttgataa gctgtcagcc    9360
acacagcctt agtaactaag ctgctgtccc acgctcccag ttctgtataa cgaggatgga    9420
ccaattagat tctaaggagt tattccttc aatttgcaaa tttagctaaa ggaaatattg    9480
tttctcctg atatttacat tgcttttcat tttcagcata tctaaagaac aaacctaatt    9540
ctccttccta ctttctagtt taatataatc ctaaaaatcc attaaaacat gactaattct    9600
ataaggcctc taacctacaa agggaagtag cattttgaaa agaatagttt tctctattat    9660
acctattcat gcagacttcc ttccttattt ctgacatact taacaaaaat catttagatt    9720
caaacagttt agctgcaggt gatattacag acaagtaatc ccagtgctct atctagtctg    9780
aggcaaaagg atttgagctc agtgccagcc tgttctatct acctggtgag ttccagtccc    9840
ataaataaac aaactaaaac aaccgttcct ctgttcctca gatgcgagtc gatcttgttt    9900
gatttaaata gtgtgtaatt attttctttt gaagctgcag gtgttatgtg ggctgtttta    9960
gactaaattc tctctttact gtggagtaaa gggtgctgtg attgtatttc atgttctctg   10020
cgagagcttg aacttgttgg gctaatcgct tgtctccatc ctgtctcccc acctgcgtaa   10080
aaagtatttt cctgtgagct gtacatgata gagcatatct acattgaaaa atgaacgagc   10140
atcaaaatgg atttgttaaa gtaaattttc tttttcttag gaaagacaag aaaatgtcca   10200
gaaaattgtc ttggaaggca cagagaggat ggaagatcag gtacagtgca tatcacatgc   10260
tgcctgtggc aggtcctctt tgcttatgtc ggtataaagt tggtgggtac ttctggtaag   10320
gacctgagga tacattcatt tgacggaagg agcctgaaaa tgagtattct tgttaagctg   10380
tatagaatga actgaataaa aatttctgca gcctaagttt gaattttaaa aaaatttaat   10440
tacatctaca aattagtatt tggccaccct ttttcaatca gcaagaatat gtttgaggtc   10500
atttatttgt agtaaaattg catgcagttt atttatttta ttgaaaatag gtttttttaaa   10560
ctatattttc tgattatggt tttccctcct ctgaatcctc ctagaacctc cacctaccca   10620
aatctatatc tgttctttct ctctctcatt aggatacaat caggcatgta aaataatagt   10680
agtagtagta gtaataataa tgtaaaataa gttaaagtaa aaacaaacca gagtaggaca   10740
acataaatag aagtagaaaa gagccaaata agaaattcaa gaaacacata tagacacaga   10800
cacaatattt gcatacacag aaattgcata aaaccgcaag actggaaacc ataatatgta   10860
tgtaaggtgg agtgggaagc cctgacagca cagtgagtaa agcactttca aaaacaccac   10920
tgactttgtg ttgtgttgcc tgtctgctgg gcatgaggcc tggccttaga gagtggtgtg   10980
tatacccagg aagacttaca taaacactta gcttttcatt tgtgacctga tagcaattgg   11040
aaatagtgtc tgggctaggc attccggctt attgccactt cccctcagca ctgaggcccc   11100
atctgaatcg gatccgtgca accttgtgc atatgcagtt ttaaaagtta tcccttctgc   11160
aactatgctc acaggagttg ccgtcttaag ggagtgagca cacccctgag gcatggctcc   11220
aggggtgcag agccagccat aggcacagtt tttttttaaa ggtttatgtt gtagttttga   11280
aactcaaatt tatgtgtatt tgtggcagat tgtttgaatg ttgaaatttg ccagtaacat   11340
```

```
cttttatctt cttcccttta gcctggcatg ccacccaccc tcatttgtcc ttgtcaaact   11400
ccagtaatta aacatggcta tgtggccttt tctctcattt tccttagcat ggctaaggag   11460
aatgggactt aaaaaataat aatcatcatt ttaagtatgt ctgagggttt gaggatatag   11520
tggtagaata tctgcctagc ttccatagct tgatcctaca tttgatccct ggcaaaacac   11580
acacacacac acatatacac acacataaaa tgactttttat aaagttagtg tgctgtgctg   11640
tgatgaacag tgccatagga aatattcttg gaaaagacct gaaactaaat gctctaaaag   11700
gtctaatctt tacttgcttg ctgatcgtta agcagagtct ccaagtataa agtcactttc   11760
accaacctct gcactggatt tctggagtaa ttagggagag tcatttcaat ataagaaaat   11820
ttagtaccaa ataaaatttt cattcagtga aattttgttt ttgaaagtaa gagcccactg   11880
tggtggtttg aatatgcttg gcccagggag tgtcctgtaa gattttttgtt gttgttgaac   11940 tccattgaga cttatgttga caataaatgc ctgagagtcc atgtctaaaa tgctgtacct   12000
gtctgaaccc aacggagata aaacttacca tttctgaaaa ggatgaggtg ttttatttac   12060
atagctgatg taatgtgctt gcaacagctc tattatgaat cttaatacta cttcagtata   12120
tcacagcact tcaggaaatt taacatacat tgtttaattc catgtcttaa ttgtatttgt   12180
aaacagacat ttcagcagtt actctaaaaa gtagaaataa tgagtggttg cttctggtca   12240
ttaggatgaa atattgaaat gataaaattt tctgggctgg agagatggct cagaggttaa   12300
gagcactgac tgctcttcca gagatcctga gttcaattcc cagcaaccac atggtagctc   12360
acaaccatct gtaatgggga tctgatgccc tcttctggtg tgtctgaaga caactacagt   12420
gaactcatac aaataaaaat aaataaatct tttttttaaaa atctatatct gcataggcat   12480
ttctagatta ggataaattt tccaaaggaa ataagcacct ccatgataag ggcattggaa   12540
atgaagcccc cgcccccacc cccggtctgc acgtgtgttg aggatgagat ctagggcctc   12600
cttatacatg ccaggcagct gttctgtcac caagtggaat ataatcctca acccttaatt   12660
tgaggttcta actttaaaat agatgtgagg ggtttaaata atcatttcat gaaacttaaa   12720
tgagcaagtt tattactgag gtgagtataa gtaattgata attttaaata tatttagctg   12780
agattgatag acacttggca atgtcagcat cttatttagg tgatcataaa ctgatgggag   12840
aaatggtaaa tgttaggggg tgtcgctcat gtcacacacc gcagttatgc tgcaaacaag   12900
atgccgggaa atagaaattc aaggtcttgt tttgcgggtg cagactcttc tgtctcactg   12960
attctatgtg gtaacttcag tatgcatttg gatagattat gtcccatttt gaatgtggaa   13020
gctggctgtt gagaggagac ttcctggtga attccttttt ctaagcatta ccatctgtct   13080
tagtcagggt ttctattcct gcacaaacat tatgaccaag aagcacttgg ggaggaaagg   13140
gtttattcag cttacacttc cacactgctg ttcatcacca aggaagtcag gactggaact   13200
taagcaggtc aggaagcagg agctgatgca gaggccacgg agggatgttc tttactggct   13260
tgcttccctg gcttgctcag cctgctgtct tatagaaccc aagactacta gcctagggat   13320
ggcaccaccc acaatgggcc ctcccccctt gatcactaat tgagaaaatg ccccacagct   13380
ggatctcatg gaggcatttc ctcaactgaa actcctttct ctgtgataac tccagcctgt   13440
gtcaagttga cacacaaaac cagccagtac aacatctttt cacatttaat ttttctcact   13500
ttaaacgtgg cctttaacaa gcgcttataa aaatgcttaa gcttaaatgt tatttaagct   13560
taatatactt aatatacagc actgtagctt aaatgttgca tgtgagagta tatgataagc   13620
catgctcacc aaggaaaaga agcttaaaga gcataaaaac cctgacagcg gtttctgagt   13680
```

```
gggaggctcg gggactgtgc tgagcaattc caaccaaggg tgttttactc tctgcctcca    13740
tttgaaatgt ttttcctgca caacctaccc accctgtgat ttcgttcact cgattatgtt    13800
tgatctaggg tcagagtatc attcccatgc ttactgggga agtcattcct gtaatggagc    13860
tgcttgcatc tatgaaatcc cacagtgttc ctgaagacat tgatgtaagt gtcatgtatc    13920
ttttatgggt tcccttgagt ggtgagtggg tggatgtgtg gtgcatgtgc gtgtgtgtgc    13980
ttgcatactg ggaattgaac ccaagtcctc aggaagagca gccggtgctc ttaagcactg    14040
agccatctct tcagaacctc ttccaccagt ttctttgacc atttgttgag aatattccag    14100
tcacacattt tccgtgagta aatctctcta atgctgattt gtcattaagc tcagtctcct    14160
aattctgata gctaagaagg gtaaattatt aaaaagtgcc ctttactctt cctggccaat    14220
tcccctttgt tcttctgaaa agtgcataga cagcatcact ttatagatca ccttgatgct    14280
cgtgagaggg ctggctcgtg ctggctctag acttcggcac acttattaag agttctccca    14340
acactgtaaa cagactaatt tttatattgt gcattttaga tagctgatac agtgctcaat    14400
gatgatgaca ttggtgacag ctgtcacgaa ggctttcttc tcaagtaaga attttacttc    14460
tttttctgaa tgctaagtaa agcagattaa aaatcttaat gctcacccat gacaagattt    14520
acagggaaaa gatggtagaa aacctacttc ctccaattat ttagggtcaa catggcacat    14580
ttgagcttac acgtgttgtt ctcacccata caacagtggc atatctgaca ttactcttcc    14640
cacagtctaa aaaggcagag tttccgtagt acccagggaa gttctggtct gtgtttgggt    14700
ctggtttctt ctttcaattc tcactaagta taaccettag gaatctatca agttgagttg    14760 catttaaat tcctgtgaat tcttcaggtc tagaaatgga aatcattcat attttagact    14820 gacattttc atcttcttgt gtaatttaac atttaagaac ttgagctcta atatcagact    14880
gtctaggtta caactgggaa aacttggtga agctacccaa agctgaacct ccatttttctt    14940 acctgtgaaa tgtgaacagt gataacagct agtttcttgg gtccttgtag gcaccaaatg    15000
acaggataat ataaagcacc taggacagtg gagccaatga gccaggagcc agtgtgcccct    15060 attatatctg ctctaagaaa gacagtaagt ggaatagcca atactgactg tcttagtcag    15120
gctttctatt cctgaacaaa aaacatcatg accaagaagc aagctgggga ggaaagggtt    15180
tattcagctt acacttccac gttgctgttc ctcaccaaag gaagtcagga ctggaactca    15240
gatcaggaaa caggagcaga tgcagaggcc atggaggaat gttacttact agcttgcttt    15300
cttatagacc ccaagactac cagcccagag atggtcccac ccacaaggga ccctgccccc    15360
ttgatcacta attgagaaaa tgccccacag ctggatctca tggaggcatt tccccaactg    15420
aaactccttt ctctatgata actccagcct gtttcaagtt gacacaaaac cagccagtac    15480
gctgaccgag cagctgtgtg ttcctctgca gggctgtgtt ctctgtttgt ccctcatctc    15540
ctgttgtagt ctcctttaca gttacagact gtcatcagta acgagagaga agtgaatagg    15600
attttgttaa agtgtttact tctatgtcac attcccttcc tataataagc tcacagtgaa    15660
ataccaggtg accgtgctta acggcatcta ttacctaact ggggtatctt tttccttaaa    15720
atggatttaa ttttatgtgt gtttgaatac ctgcatatgt gtatgtacac catatttatg    15780
tatgcctggg acctgaaaaa gggaaaagag ggctttggct tcttgaaaac tagatggttg    15840
tgagtctcca tgtgggttct ggattgtctc tgcaagagcg gcaggcacac tttagcagtg    15900
agccgctcct gtcccgagtt gtcttaagac ctgtgaaagg tccctaaaaa atgcagggtt    15960
ttacccgaat aaaagatgac atcatgcaga tggcttggt gttcatcaag ctcttgtgtg    16020
ttgtcctaac cttgctgggc tttgtcgttg tgaagctgta actccgtcaa tgttttcctt    16080
```

```
acctacagtg ccatcagctc acacctgcag acctgtggct gttccgttgt agttggcagc    16140
agtgcagaga aagtaaataa ggtaattcgt tctacagttg aacatgatct gactttatc     16200 atcactagca tatcatacat tatcatctaa acagtaggct gcaattgaaa taacccata     16260 gtataaggaa gcaatgtaat tttaccaaat ttctctgaca ccctctagca gaactgactc    16320
taatagaatg agtaagaatt caattaccaa attaattttg atactctttt ttattttgt     16380 tattactttt ttattttatt ttaattaggt attttcttca tttacatttc caatgctatc    16440
ccaaaagttt cccatacccct cccacccact cccactcccc tatccaccca ctcccctttg   16500
gccttggcgt tcacctgtac tgagacatat aaaatttgca agaccaatgg gcctctcttt    16560
ccaatgatgg ccaactagac catcttctga tacatatgca gctagagaca cgagctccag    16620
ggggtactgg ttagttcata ttgttgttcc acctaaaggg ttgcagaccc ctttagctcc    16680
ttaggtactt tctctagctc ctccattggg ggccctgtga tccatccaat agctgactgt    16740
gagcatccac ttctctgttt gctaggcccc agcatagcct cacaagagac agctatatca    16800
gggtcctttt agcaaaatct tgctagtgtg tgcaatggtg tcagcgtttg gaagctgatt    16860
atgagatgga tccccaggat ggcagtatct agatcgtcca tcctttcgtc tcagttccaa    16920
actttgtctc tgtaactcct tccatggtg ttttgttccc aattctaaga agggacaaag     16980
tgtccacact ttggttttca ttcttcttga atttcatgtg ttttgcaaat tgtatcttat    17040
atcttgggta tcctaagttt ctgggctaat atccacttat cagtgagtac atattgtgtg    17100
agttcctttg tgattgggtt acctcactca ggatgatgcc ctccaagtcc atccatttgc    17160
ctaggaattt cataaattca ttcttttttaa tagctgagta gtactccatt gtataaatgt    17220
accacatttt ctgtatccat tcctctgttg aaggacatct gggttctttc cagcttctgg    17280
ctattataaa taaggctgct atgaacatag tggagcatgt gaccttctta ccggttggaa    17340
catcttctgg atatatgccc aggagaggta ttgtgggatc ctccggtagt actatgtcca    17400
attttctgag gaacggccag actgatttcc agagtggttg tacaagcttg caattccacg    17460
aacaatggag gagtattcct atttctccac atcctcgcca gcatctgctg tcacctgaat    17520
ttttcatcgt agccattctg actggtgtga ggtggaatct cagggttgtt ttgatttgca    17580
tttacctgat gattaaggat gctgagtttt ttttcaggt gcttctctgc cattcggtat     17640
tcctcaggtg agaattcttg gtttagctct gagccccatt tttaatgggg ttatttgatt    17700
ttctggagtc caccttcttg agttctttat atatattgga tattagtccc ctatctgatt    17760
taggataggt aaagatcctt tccaaatctg ttggtgacct ttttgtctta ttgatggtgt    17820
cttttgcctt acagaagctt tgcaatttta tgaggtacca tttgtcgatt ctcgctctta    17880
cagcacaagc cattgatgtt ctattcagga atttttcccc tgagccaata tcttcgaggc    17940
tgttccccac tctctcctct ataagcttca ctgtctctgg ttttatgtgg agttccttga    18000
tccacatgga tttgacatta gtacaaggaa ataggaatgg attaatttgc attcttctac    18060
atgatatccg ccagttgtgc tagcaccatt tgttgaaaat gcttttttcc actggatggt    18120
tttagctccc ttgtcaaaga tcaagtgacc ataggtgtgt gggttcattt ctgggtcttc    18180
aattctattc cattggtcta cttgtctgta tataccacta ccatgcagtt tttatcacaa    18240
ttgccctgta gtacagcttt aggtcaggca tggtgattcc accagaggat cttttatcct    18300
tgagaagagt ttttgctatc ctaggttttt tgttattcca gatgaatttg catattgccc    18360
tttctaattc gttgaagaat tgagttggaa ttttgatggg gattgcattg aatctgtaga    18420
```

```
ttgcttttgg caagatagcc attttttacaa tgttgatcct gccaatccat gagcatggga   18480
gatctttcca tcttctgaga tcttctttaa tttctttctt cagagacttt aagttcttgt   18540
catacagatc tttcacttcc ttagagtcac gccaaggtat tttatattat tgtgactat    18600 tgagaagggt gttgttttcc taatttcttt ctcagcctgt ttatcctttg tatagagaaa   18660
ggccattact tgtttgagtt aattttatat ccagctactt cattgaagct gtttatcaga   18720
tttaggagtt ctctggtgga attcttaggg tcacttatat atactaccat atcatctgca   18780
aaaagtgata ttttgacttc ttcctttcca atttgtatcc ccttgatctc ctcttgttat   18840
cgaattgctc tggctaagac ttcaagtaca gtgttgaata gggaggaaga aagtggacag   18900
ccttgtctag tccctgattt tagtggggtt gcttccagct tctcaccatt tactttgatg   18960
ttggctactg gtttgctgta gattgctttt atcatgttta ggtatgggcc ttgaattcct   19020
gatctttcca agactttat catgaatggg tgttggattt tgacaaatgc tttctcctca    19080
tctaacgaga tgatcatgtg gttttttgtct ttgagtttat ataatggatt acattgatgg   19140
atttccgtat attgaaccat ctctgcatcc ctggaataaa acctacttgg tcaggatgga   19200
tgattgtttt gatgagttct tggattcagt tagtgagaat tttactgagt attttttgcat  19260 caatattcat aagggaaatt ggtctgaagt tctctatctt tgttggttct ttctgtggtt   19320
taggtatcag agtaattgtg gcttcataga atgagttggg tagagtacct tctgcttctg   19380
ttttgtggaa tagtttgtga agaactggaa ttagatcttc tttgaaggtc tgatagaact   19440
ctgcactaaa cccatctggt cctgggattt ttttttggttg ggagactatt aatgactgct    19500
tctatttctt taggggatat aggactgttt agatcattaa cctgatcttg atttaacttt   19560
ggtacctggt atctgtctag aaacttgtcc atttcatcca ggttctccag ttttgttgag   19620
tatagccttt tgtagaagga tctgatggtg ttttggattt cttcaggatc tgttgttatg   19680
tctccctttt catttctgat tttgttaatt agaatacttt ccctgtggcc tctagtgagt   19740
ctggctaagg gttatctat cttgttgatt ttctctaaga accagctcct tgattggttg    19800
attctttgaa tagttcttct tgtttccact tggttgattt caccccctgag tttgattgtt   19860 tcctgccgtc tactcctctt gggtgaattt gcttctttttt gttctagagc ttttaggtgt   19920
gttgtcaagc tgctaatgtg tgctctctct agtttccttt tggaggcact cagagctatg   19980
agttttcccc ttagaaatgc tatcattgtg tcccataagt ttgggtatgt agtggcttca   20040
ttttcattaa actccaaaaa gtccttaatt tctttcttca ttccttcctt gaccaaggta   20100
tcattgagaa gactgttgtt cagtttccac gtgaatgttg gctttctatt atttattttg   20160
ttattgaaga tcagccttag tccatggtga tctgatagga tgcatgggac aatttcaata   20220
tttttgtata tgttgaggct tgtttttctg accaattatg tggtcaattt tggagaaggt   20280
accatgaggt gctgagaaga aggtatatcc ttttgttta ggataaaatg ttctgtagat     20340
atctgtcaga tccatttgtt tcattacttc tgttagtttc actgtgtccc tgtttagttt   20400
ctgtttccac gatctgtcca ttggtgaaag tggccatctt tatagtcact gaagacatac   20460
aaatacatat tcatatcaac tggaacaaac ctaatttctt tttaaatgtt ttacatggaa   20520
ataagttagg ggttgttatt tgcattacaa agttactcat cccttccctt cttttctttt   20580
tttttttttt tttttttttg agaacaagcc tgtgtactta tatgaacttt aatttgccaa   20640
attcataatt cttattcaat catttatgac agaatgctaa aactctcatt atattttagc   20700
taggcattta gagctgttat gtgtaacccc aaaaagtagc tttccacttg agatgctgaa   20760
ggccttgggt tccgtgggct gtcatcatgg ttggctgtat gaaaagagaa aggctccatt   20820
```

```
gtttgggcat cacttaaata ttttttcacc tttcatcttc ttttaggtta agtagcttgt    20880
ccttgatcat ttcattttg agagacaact tgccactact ctagttgaaa agtgctgtct    20940
tgacgctgtc tctggctgtg gtcagagtcc agcagagctg cacagctggt tacctttctc   21000
tgtacagctc taggccaact cttcttactg gcgaccattt ctaaatccac cattcacttg   21060
ttccccatga aagtgagtag ggtttttttct gtggaagatt tgggcagtc ctgttgccac    21120 tttgcatcag acaatagttc cctcattgaa acacgcagtt tattctccag agcggtctgc   21180
ccactccaaa ggcagtaggt gctgggtaga gatatgccaa gtatcacact aggctatgac   21240
tgctcactca gatcactcgg atgaagcttt catggccaaa tacagttgag aaagaacaaa   21300
tattcttcac ttagagagca acaagagtta ttcaagtgta acaagttctg agattccatg   21360
cagttgattt accagctact tcctaaactt aactggccac aaaatcccctt tgtaagcagt   21420 atgttgtttt gacccatgcc ctgtcaaagg atactcctta cttgggaact gttttaatga   21480
tggcaacaaa aatttctatt taaatttatt tcataagcaa gcaaagatct ttttacttca   21540
cattccaatg ttgactcttt tcctctagat agtaagaacg ctgtgccttt ttctgacacc   21600
agcagagagg aaatgctcca ggctgtgtga agcagaatcg tcctttaagt acgaatcggg   21660
actctttgtg caaggcttgc taaaggtaca cttgccgatc atttatcatg tgtgacgcaa   21720
caagtagaga tggagggtac aaataatcac tgagaggctt tggaaagtat attgttagca   21780
tttaatgtct catagtttta gttgtctggg tactggtttg ttttcatcat tctgagcatg   21840
aagtgtatgt cttagggatt tatagttcgt atcatgtatg aaacaccatg gggtaatatt   21900
tatatttcac ttggttccct ctagctatgt gtctggcccc agtgctttcc ttgtaaatgc   21960
atgcttgaat cagactgagc tgatatgata atgttgatgc tccttttgct tactgagtgg   22020
ctatgaatat gcaccatact tactcattgt aagaaattaa aatgtctctt aaggatgtaa   22080
acatagcaaa atgaagcaaa acaaaagcga tgctgtttta ggtaccctaa ctgaccttgt   22140
gtattcaagg agcattccta cttctgtgat gcaaaagctg tctacactgg gcagatctac   22200
aaccagcatt aaaccaaata gggaatcact gaaatcacgt tatcaaagat gagaaacaag   22260
ataataatgt ctactttcac ggcttttatt caggtctagt gctataagtt tttgccaaaa   22320
caaaaatgaa aacatagact ctgggctgag gctttccctt agcagaaaag tgcttacttg   22380
ttgtgtccgg ccagcagatc acagcctggg ttctagcctg gaaaggcatt ttggaaacct   22440
ggaagagaag aggggctagg taacgagaga aagaacggag ccaagtcaaa agcaactctg   22500
atcaaagctc aattttacta tatcagcacg cagttataaa ggaggggaag ggggggccaa   22560
tagcaaggcg gcaggttcca gcagtgggcg tggcagaccg attgagccgg caagctcctt   22620
ccaggtgtaa acagtggagc cctaaggctg ggggagggga ggctacactt agcatgcctg   22680
atgccctaga tgccacctaa atgacaaatc cagtccagta caggatgtag agcaccccccc  22740 cccaaaaaat tatttttttt gtataccaga aatgaaattg ctgagaaaaa aaatgaaga    22800 ccataattat actcccagta gctacaaact aaacagcccc atagatgaag tgagtgatgt   22860
ctgctgtgac aattatgaaa tgaaagaagt aaagatgaac aaatgaaggg aagacatcca   22920
gtactcagga ctgaaagact gctgctaaaa tgcctatcca acccagagct ctctgcagac   22980
tctggacaga tccgctctag atgtgaagat ggtctttttt ttttttttt tttttggtt    23040 tttcgagaca gggtttctct gtgtagccct ggctgtccag gaactcactc tgtagaccag   23100
gctggcctcg aactcagaaa tccgcctgcc tctgcctccc gagtgctggg attaaaggcg   23160
```

```
tgcaccacca tacctggctt tttgtgaaga tgttcttaac agaactagaa agaagtaccc   23220
cttggtttgc tgcccttctg atgcagtatc cccaaaggct cgcatgcact gaacatttca   23280
tcttacctgg tgccactgtt gggaagtgat ggaaatgcga ggaattgtag cctcgttgag   23340
atgtttctca ttaaggcact gggggcatac ctatggagca tacagtagga acctggtttg   23400
caacctctcc cctctccatc caggctctcc cctgtgcacc tggccttggt gttctgccac   23460
tccatgaacc caaagtaaag tggactatgc ccttagactg taacagtgag tcagaagaaa   23520
catttcctct ttaaagctga gttttctggg tgctttgtca tgttaatgga gtctgattag   23580
tacagaccct gagtaggcag ggcaatctta tgcagaaaca tcaaagctgg tagcatagac   23640
atacctaatt tcacaataga cactgatgga ctcagtctgg agtacttaca gtaagaatat   23700
acagcagaga tacggagctc tcttacagtg gtgctctggg agaactggcc gtcctgtgaa   23760
gaaaagccag agtggctcat tctcaccaga cacaaactga gctcataaga cgcttgaacc   23820
tgagatcctg gtcagcagcc actagaagaa aacttaggag aaaccattca acacgtcagt   23880
ctggggaaaa gggtggtttt ggttttggtt ttggtttttt agtatattcc ccaaatcaaa   23940
aacaacaaaa cccaaacttg acagatgaca tcacactgca aagcttttgc acaaccaaga   24000
aagcaacctg cagagtgcag taataaccca cagaaggaga ggagatactt gtgggcagtt   24060
catcacacag gtcaatataa gcaagtactg atagtgtggc catctccaaa gaagatatga   24120
aaataactgg tatatatgaa gtagtactta gcattgctgc gtatatggta aattcaaaac   24180
catgatgaga tattgcccca cttagatgga tattatcaaa acaacatcaa aaagtgacaa   24240
atgctttcaa ggatatgggg aaagtgtact tgcaggaatt taaattatta atttgccatt   24300
caagaggata ggatggcagt ttaaattaaa aaactagaag tggtagagca gtcgcctaga   24360
acatacaagg ttcagcacta taataaatga gcaattagac atttgaagca acaatctcac   24420
cactaggcaa gtcctaaaag aaatggactc gcttcttctt cttcgggaaa acaccaaatg   24480
gcagatgacg ccggtgcagc gggagggccc agaggacctg ggggctcagg attaggaggc   24540
cgcggcggct tccacggagg attcggcagc ggtcttaggg gccgtggtcg tggccgaggc   24600 cgtgccgtg gtcgaggccg cggggctcgt ggaggtaaag ctgaagacaa ggagtggatc   24660
cccgtcacca agctgggccg cctggttaag gacatgaaga tcaagtcctt ggaggagatc   24720
tacctgttct ccctgcgcat taaggagtct gagatcattg atttcttcct gggtgcgtcc   24780
ctaaaggatg aggttctgaa aatcatgcca gtgcagaagc agactcgggc tggccagcgg   24840
accaggttca aggctttcgt cgctattggg gactacaatg gtcacgttgg tcttggtgtt   24900
aagtgctcca aggaggttgc tactgccatc cgaggggcca tcatcttggc caagctttcc   24960
atcgtccctg tgcggagagg ctactggggg aacaagattg gcaagcccca cactgttcca   25020
tgcaaggtga caggccgctg tggctctgtg ctggtgcgtc tcatccctgc ccccagaggc   25080
actggcattg tctctgctcc tgaagctcct gatgatggcc ggtatagatg actgctacac   25140
ttcagccaga ggctgcactg ccaccctggg caactttgct aaggccacct ttgatgccat   25200
ctccaagact tacagctacc tgacccccga cctctggaaa gagactgtct tcaccaagtc   25260
tccttatcag gaattcacgg atcatcttgt gaaacccac accagagtct ctgttcagag   25320
gacccaggct ccagctgtgg ctaccacata agggttttta tatgagaaaa ataaaagaat   25380
taagtctgct gaaaaaaaaa aaaaagaaa gaaagaaaga aagaaatgg actcggtatg   25440 tggatgaagc ccaggcacct tcatctgtgt tgcagcacga gtcaccatgc aggatcagtc   25500
taaacgccca tgcacaaatg aatggtacat agccacagtg aagtgtttga ccacaaaaag   25560
```

```
gaaagtcagt tgtgataagt gaaacaagcc aggcacagaa agataaatgc tgcatgttat   25620
cattatgtgt aaaggctaaa acgtttatct catacaagta gaaggtaaat acggagacta   25680
ccagaactta taaagagttc taggaaaaag ctatagagag gctcagggtt gaataactaa   25740
aattatacct aaaataacta aaaggatagc ttacaatatt ctgtagcact gtagaataat   25800
tgtgacagtt tgttgtattt ttctggtttg tgtatgtggg agagaaagta tgtggacaga   25860
ggttgatatc aagtgtctga ctctgcactg cattatttta ggcagggtct ctctctaacc   25920
attgaatgga ctggctaggc agtggtgccc taacatctac ctgtccgtac atctcccaat   25980
actaggttat aagtacactg ggttttaagt acaggctata ggtatagata taggctacag   26040
gtatagatat aggctgctgc aactgattac atgggtgctg ggaacctaac ataggttggg   26100
tcctcatgtt tacacagaaa tcagtactgt gcctactgag tcatttcccc agttctagta   26160
tttgtttttt aaatagctag taattggaat tgtgaatgtt cctaacaaaa gaaaatgata   26220
actatctgag atgctagtta tgatacccct agtgaatcac actttgtgtg catgtactga   26280
aattcattgt accctgaaaa tacaaaaatt gctctgtgtt gattggctag atgcatgtgt   26340
attagtcagc aatctctaga gtaataaaac ttagatatat gggatgtatt agacttttgg   26400
ccttacaggc caagatccag ctaatccatc agtggcaggc tgtgaacagt aagtctaaga   26460
atccaatagt tgttcagtcc acaaggccgg gtggctcagc tgccttctgt atacagtgga   26520
atcccaaaga aataggcgcc aaagctagtg aggaatggtc ttgctagcaa agcgaaggtg   26580
aaggtaatca ggcagaagac aagaccttcc ttttttccgtg tccttatata ggctcctagc   26640
agaacaagtg gcccagacta gatgtggatt aaatgttttg ggtttggttt ggtttgattt   26700
ggtttggttt ggtttggttt ggtttggttt ggtttggttt ggtttggctt ttcgagacag   26760
ggtttctctg tatagccctg gctgtcctgg gttgtagacc aggctggcct caaactcaga   26820
aatctcttgc ctctgcttcc caagtgctgg gattaaaggc gtgcacacca ctacgcccgg   26880
ctcaatagca ttaaatggca tgtcttttcc tatctcaaat gatctggatt aaaagagtgt   26940
cttcctacct caaggtctg gattagaagt ggatctttct acttcagatt aagttaaact   27000
ctctcacagg tgtgccctct acttttggat ttttggttct agatggagtc aacatgacaa   27060
ccaaaagtaa ctattacaag tccacccaat atcaacttga tacacaatca tatctcctta   27120
tgtcataatt aatttccaaa tgaaacaat aaccatgtca taaaaacacc taaacatgaa   27180
taactattcc acatacaatc agaaatgcat tcattatata tttaaccaag tcctaattat   27240
gcctaacgtg atataactat tcttcataca acagcaaaca tgataaattt acaataggtg   27300
gcaatgtctt attcttttaa tatctcaaac ttaaatatga taaccattga tgttatctta   27360
attgatgtta tatcatatga taaagaaatt gatgaaagaa agcacaaatg tctgtataaa   27420
tgctttctta agaaaatagg acagaaactc tgtcaattat aatcatcttt tctgcaacta   27480
gtcatgtggc cttagtattt ataactacct tcctctgcta aaccattttg tattttctcc   27540
acccttggca agaacctcag caggtcttgg ctcttttcct ggaggagtga cccataccct   27600
cattccttac atgtatgtgc cctttgtcat cctgcctgga ccaggttgtt gtaacattga   27660
ctttaatcac aggacatcgt agcaccaaca catgccccaa aggatctcct gccctataga   27720
cataaccttt cttacctcca tagtggggag gcagtcccag tcctccttgg tagtctgcat   27780
cagtcacgcc tcctaacact gttattcctt tcttagccgg ttgacttaag ggcatcagaa   27840
ggccaaagtt gccagaggaa aatctgagct tccagttcaa tgaatgtaat gttgttctag   27900
```

```
gcaagcagaa ctgaaggtct caggaatagg aagcaaacac ttcccatgga tcactacagg   27960
gtgagagtga gtagaattat tctcttttct accacttgac tcctggacct atggatcctg   28020
gtatcaaaga aaatgtctca tatattgtac actgattcag agcatgcctt ctggaaaacc   28080
ctgccccagc ccttcatact gctgccatca aattgtcacc tgtgtcttcc tggtaccaac   28140
ttttgtcctg gttagggtta ctattgctgt gaggaaacac catgagcacc aaagcaactt   28200
ggggagaaat gggtttattc agcttatgcg tctacatcac agctcatcat caaaggaagt   28260
cagaacagga gctcaagcag ggcaggaatc tggaggccgt ggaggaaagc tgctgactgg   28320
ctcgctccct aggcttgctc agactgctta tagaactcag gaccaccagc tccagggtgg   28380
ccccaccccg caatggattg ggcctccct caggaatcac aattgcccca cagacttacc   28440
tacagcctag gcattttgga ggctttgagt ctgcctcctc tctgatgatt ctagcttttg   28500
tcaagttgaa gcaaaagtag acaggcctta aactcacaac aacccacctg cctcaatttt   28560
ctgagtgcta atattatatc aatttaaaat ttaaatataa catataaagg gcaatagaaa   28620
ggactagatt catgtaatgg atacaagtta tggaagatgt gtgtgtgtgt gtctgtctgt   28680
ctgtgtgtgt gtttctagtt taattctgtc atgattttt tcttgtaggt ggtaggtgag   28740
tgcatggaat acatttgata ctgaaagggt aaattgaatg tggagcctca cagcttctgt   28800
tccacatgcc tatgataacc gtagaaattc atggattagt atagacgttg agtctggtta   28860
attttggtgt gtgatattta tatatatatg tatatatata tgtgtgtgta tgtatgtatg   28920
tatgtatata tatatgta tatgtgtata tatatata tatatatata tatgcaagat   28980
ttcttataat taagtttaca aaattaaaaa ctatcttaaa aattgaattc ttgcaaataa   29040
aaatttagct tttggtgatt ggattcttaa tatggttgat gtttacctag aaagttaaaa   29100
gccctgagtt cagtctccac tttcaccccc aaaatgaaaa tcagcttttg ggtttcagat   29160
catgagctca gaattaaaga aaacacattt ctaactttgc ttttacaaat cttaattta   29220 ccaatttcct ttaaagtcac aatgagatac acagtacttc ctagcacccc ttgttcaatt   29280
agataatgtg atttctgaaa gagctccctc tacacagggc acagggcagg tgcaaaactg   29340
tgattgggtg aaataccctgc gagctctcca agcaaagcca ggcctatttg ctttagctgc   29400
cacatcgggt tcttagaccc gacatccctt cccacctgta tcctccctaa ttccttccaa   29460
ccccacaaca ctaggtagga gagaaagaag gttagtggtg gaagtttgca cacatctttt   29520
tagactattt cctactgatt agggtgttta ggtccttgag acaagtccag tcttcattgt   29580
caggatatct ccaacttctt cttctcatct ctttgctcac aaagttttatc acaagttgat   29640 aaactacaac aacaggaacc agcagtagca aggacatcag agttgtatag ctttccagaa   29700
aatactttga tatacagtaa ttatcctagc ctttaagagt gaaagatttg gcagcctctg   29760
tgttctacac tcagcataat accttgtata ctgcaggtat ttgctgcatg gtaagtggct   29820
gcccagctac ctagaaagag gtaaatactt ttctattaac atacatattc atttagatat   29880
aggaagaaga taaacaatg gagaaaggca gtcataattt tacagaccag caagtaaacg   29940
cattaacttg gcataggtct ttgtagtctt tttctgcagt gcgtatttcc tgcagtgccc   30000 acccctaca gttggattgc acgtggcatg ttctgaccca cttttttatgg tatactgtgt   30060 actgtcactg tcaacacaaa tggtagtggc tggattttta tacagtatca gcttgaaggt   30120
tatttctgaa caagccctgt accagattca caggaatatg catctcttat cattactata   30180
ttcttttaac aattgcttct ctcagttggc atgtggtcag tgagttctct cttccttctg   30240
acaggatgca acaggcagtt ttgtcctacc cttccggcaa gttatgtatg cccgtaccc    30300
```

```
caccacgcac attgatgtgg atgtcaacac tgtcaagcag atgccaccgt gtcatgaaca    30360
tatttataat caacgcagat acatgaggtc agagctgaca gccttctgga gggcaacttc    30420
agaagaggac atggcgcagg acaccatcat ctacacagat gagagcttca ctcctgattt    30480
gtatgtgacg cttggcctta ggtgtcattg ttaaacaaca taaaacttct catttatgag    30540
taaaaacagt gcaagttgta tttaaaagaa aagaaatatg acaagcacat actcaggcac    30600
tttttcttta ttttcttaac tttaaggttt ttttttttt aagatttatt tattattata    30660
tctaagtaca ctgtagctgt cttcagacac accagaagag ggcgtcagat ctcattacaa    30720
atggttgtga gccaccatgt ggttgctggg atttgaactc aggacctttg gaagagcagt    30780
cagtgctctt acctgctgag ccatcttgcc acccccaact ttaaattttt tatactatta    30840
tttttagaca gtctcactgg gcctaatgac ttacataggg ggcctggaac tcactatata    30900
gatcaggcta gccttcaact cccagatatc cacctgcctc tgccacccaa atacttggat    30960
taaaggcgtg tgcctccata cctagcctaa atcttcattt cttaaaatac tgttttgcta    31020
agataggtaa agatttcctc ttaaaaataa atacttagca aatatatacc gatctcctaa    31080
ttacttaatg aagggccagc ttaatagtta tcagtcagtt atcagtgcca gcccctactg    31140
ctgggaattt agtgtataac gttcattgta tggtagactg aagtaattct aagtattttt    31200
ttcttgggtg tgactatcaa acacagaaaa gtatttgaaa tttataaaga gaacaggttt    31260
tttctttgca ttttatattt tgctatttat ttcttaccag aagatgcgag cagcaaagta    31320
aaaggcagta agtgctgatg ggtttggagg aacttgggat tttaattata aaacttcaag    31380
aaagcatttc aatggtgttc tagagtctaa aaaagaatag tgagaccccta ttcctgttct    31440 ctccgatcaa ccaagagctt gaaatggtgc tagtccttag tatacactga aaagacgcta    31500
agtgtggtca tcccggttgg agggctttag gaagcagtga ccctggacca atgggtgtca    31560
ccgtgtgtct gaagaagaaa gcagagctga acaagaggc gcatggtagg gacaccagca    31620
gccacagtaa actgctgccc agaggtccct gtgtggggct gcagaattaa aagaacccat    31680
tctacacagc tctgctgtgc tctgttagtg ctgagaaagg ttgagaggaa ttgtttcaga    31740
agaggaatcg ttcaaattga actcttatgt cactagttca catactggca atcttggaaa    31800
acatagaaat tttctcactg agtctgcgtg cctgcgtctt cctcgtgact aatatacttg    31860
aagtcctgtt tatttttta gttgattgtt tagaatctct tctcaggaaa tgaggtaaac    31920
ttgaatggat ttgcaccatg ttagtgtttt tgttttgaat atgtttgttt ggaagatttg    31980
aagaaaaagc aattgttcag ctattctggc atgacaaaat catgtcatga attttagaat    32040
tttatttcca gttctaagta aatgttttga atataaaatt gtcagaaata ttttcagcca    32100
caagattata tcttctatta ttgtgggctc atgatagtat cagtgtggtt taaataatat    32160
tcacttttga gtctgggagg tttgaggttt cagattcagg gactcacaca ctgggcaatt    32220
actgtaccac tatgcagttg cttattagta ccacagagta attcccagtt aagttacttt    32280
taattttaac ctttttaaga taaaagcagt ctgatgatac attaaagtcg acatttcct    32340 tgaagatagt ctttccttt ccagcttttg tgatccagat ctcattcagt aaagcagaaa    32400
ttgggaaata gtggacttaa gttctaaggg acccacaaac cccgtgactg tgctgtccgt    32460
tttcagccag taaccatgaa gtgctggcgt cccttccagc gccccttct ccatttggtg    32520 cactcatccc tcaaggctga gaggcgtgct gctctcctgt ctatttccct cttccccatg    32580
gttcctgggc agtgatgttg tgatctctac catctgagtc ttgctttgca tttatcttac    32640
```

```
tgtgaaaaat gttatatttt ccctctgaca tgaatataat agcctaggga aagacagaag   32700
taaaacactg aaagggaatg ggggctgaga aaaaaacagt cattagcttc tgtctggcca   32760
gcatgctgaa gtgggtcacc tcagttggcc attttgtctg aacgttacat gccagccaac   32820
cttagctgcg gtagtaataa gttatgctgc tggctcatac ttacagatgg taagtctctt   32880
gacctgaggc aaacgtgtaa ggtgacggtt ctaaacacac tgatggacag gcacatgccc   32940
tgcctggata gcctcaaaac acaaacagtg tacaaatgta cccttgcgtt aaagtggatc   33000
tatgtgcgtt tgtgtttatt ttctgtgcat taagtatgta tatgtatgtg tgtttatatt   33060
gtgcacattg agtatatgca tgtgtgttta cactgaatac tgaacccacg gcctcctgca   33120
aactaagtat gcattccaaa tgcacacatc tgtcttctta cacatctgtt tataaaactt   33180 caacttttt actagagcaa gaagttgtgg aatgtaactc tgtaaaaccg tttaatatct   33240
gaaccttttt cttcttagga atattttcca agatgtctta cacagagaca ctctagtgaa   33300
agccttcctg gatcaggtaa atatgatgcc acccattgcc agacaaaaga acatcatata   33360
ttttctttta aaatatgtcc cacagtgcct acagaatata taaaaagcac caagaattaa   33420
aagtgctaga ggccttttcta aagtctgtaa acggattcct ctttgaatta ttaatgggaa   33480
atagcctgta tattaaccgt taaagcagca ttctccatcc tagtggctgc ttcaggtcca   33540
accctctgcc tttagaattt ttgtggttgg tgaagacagg ggtgtgcttt catttgtgtt   33600
aattgaattg aaaatattct taaaacttag gttgcttctg cttaaatggt agcatcctta   33660
ttgtctctgt ttttaaaagt atctgatgag taaacatctg gagatggtac tggattctat   33720
gcgacttgtt tctatacgta agcagagctt tgtcataata gcatgctggg aatcaggcca   33780
agatcctgtg ccatagacat agagttgaga tgaggagaac ctcgtgttca ctgggacttg   33840
tgggtctggg tctgtgtgag gtgaggacag cctgtaatcc caagtctctg aagctgaaaa   33900
gtcccctcct ctactccaca caacctgaag tcattgactt agttatttcc ataataaaat   33960
aaggagatat tttaaggtag aatacaagat ctaagtgcat taaactaggg aatctgaaaa   34020
ggggacagtg ggtttccaga catttgccgc taccagagtc ttgccctttg gaaatcggaa   34080
gaaatggctg taatgggtgt tgtgtgtcag atcctgtcaa caatgtcgcg gaagctgcac   34140
tgtcttgtgt ccctgcaggt cttccatttg aagcctggcc tgtctctcag gagtactttc   34200
cttgcacagt tcctcctcat tcttcacaga aaagccttga cactaatcaa gtacatcgag   34260
gatgatacgt gagtcctgct cctctagagg aaagccttta tgcattgaca gttgctgttc   34320
gttccctttg aacattgtct gtattataat gcggggtttt ttgtctcttt tgttttgttt   34380
ataggcagaa ggggaaaaag ccctttaagt ctcttcggaa cctgaagata gatcttgatt   34440
taacagcaga gggcgatctt aacataataa tggctctagc tgagaaaatt aagccaggcc   34500
tacactcttt catctttggg agaccttttct acactagtgt acaagaacgt gatgttctaa   34560
tgaccttttg accgtgtggt ttgctgtgtc tgtctcttca cagtcacacc tgctgttaca   34620
gtgtctcagc agtgtgtggg cacatccttc ctcccgagtc ctgctgcagg acagggtaca   34680
ctacacttgt cagtagaagt ctgtacctga tgtcaggtgc atcgttacag tgaatgactc   34740
ttcctagaat agatgtactc ttttagggcc ttatgtttac aattatccta agtactattg   34800
ctgtctttta aagatatgaa tgatggaata tacacttgac cataactgct gattggtttt   34860
ttgttttgtt ttgtttgttt tcttggaaac ttatgattcc tggtttacat gtaccacact   34920
gaaaccctcg ttagctttac agataaagtg tgagttgact tcctgcccct ctgtgttctg   34980
tggtatgtcc gattacttct gccacagcta aacattagag catttaaagt ttgcagttcc   35040
```

```
tcagaaagga acttagtctg actacagatt agttcttgag agaagacact gatagggcag   35100
agctgtaggt gaaatcagtt gttagccctt cctttataga cgtagtcctt cagattcggt   35160
ctgtacagaa atgccgaggg gtcatgcatg ggccctgagt atcgtgacct gtgacaagtt   35220
ttttgttggt ttattgtagt tctgtcaaag aaagtggcat ttgttttat aattgttgcc    35280 aacttttaag gttaattttc attatttttg agccgaatta aaatgcgcac ctcctgtgcc   35340
tttcccaatc ttggaaaata taatttcttg gcagagggtc agatttcagg gcccagtcac   35400
tttcatctga ccacccttg cacggctgcc gtgtgcctgg cttagattag aagtccttgt    35460
taagtatgtc agagtacatt cgctgataag atctttgaag agcagggaag cgtcttgcct   35520
ctttcctttg gtttctgcct gtactctggt gtttcccgtg tcacctgcat cataggaaca   35580
gcagagaaat ctgacccagt gctattttc taggtgctac tatggcaaac tcaagtggtc    35640
tgtttctgtt cctgtaacgt tcgactatct cgctagctgt gaagtactga ttagtggagt   35700
tctgtgcaac agcagtgtag gagtatacac aaacacaaat atgtgtttct atttaaaact   35760
gtggacttag cataaaaagg gagaatatat ttattttta caaagggat aaaaatgggc     35820 cccgttcctc acccaccaga tttagcgaga aaaagctttc tattctgaaa ggtcacggtg   35880
gctttggcat tacaaatcag aacaacacac actgaccatg atggcttgtg aactaactgc   35940
aaggcactcc gtcatggtaa gcgagtaggt cccacctcct agtgtgccgc tcattgcttt   36000
acacagtaga atcttatttg agtgctaatt gttgtctttg ctgctttact gtgttgttat   36060
agaaaatgta agctgtacag tgaataagtt attgaagcat gtgtaaacac tgttatatat   36120 ctttctcct agatggggaa ttttgaataa aataccttg aaattctgtg tatgttttag     36180
ttcattattt agggaaaacg ctgctgtgaa aggggcgtg atcagcttcc tattctgcga    36240
cagtcgtgtt gaacggaacc cattggtttt catcttcgct cccccccct tggttttcg     36300 agacagggt tctctgtata gccctggctg tcctggacct cactctgtag accaggctgg    36360
cctcgaactc agaaatctac ctgcctctgc ctcccaagtg ctgggaggca gttgcccac    36420 caactagtct tctttttca aagaagatat ttaaagctaa cgaataatgc tagactctta    36480
catcttaaaa aaaaagaag agaaaagaaa agaaaggta atcacactgc ccagtgtgta    36540
gtgcatgctt ctacttccgg tccttgggag atggggcag gatgagacgc tccagaccgg    36600
cttccaatac agagttcaag acccactgag ctacgtgagg ctacacgagc ctgcctttaa   36660
aaacataaag ctaaagcttt cttcttaact tccagtattg caccttgatt ccccttcaa    36720 atttcacata caaaataatt cttaaattct cttttgaaaa atgttctact gaggccagag   36780
agacagttcg cttggtaaag gtgcctgttg ccaaacgtga taacctgagt taaatcatag   36840
ccccacatgg gggaggaaga aaccccgca gcttgccctc tgatgccatg tatgcactaa    36900
aacacgcacg tgtgtgcgca cactttttt aagttcctat tacattgata gtaatataat    36960
ttaaactgat ttattctccc caagtcattg atacgggtgt ccaacgtaaa atccagcggc   37020
tgaacaaagc acttttaggc gctttaagtt ggaaagcaag aaacggagat tgacactgtc   37080
actccaagag aaaactcttc gtagtagcga gatcggctgt ggagtgaaga tgctcagagg   37140
ctgggaacgc acacagctca ggagtggata gcatccccca gcctcaactc ctaacactgg   37200
gaaagcgtag ggctctcaga tgaggaaaca aaaccataca aagctgctgc aagctaaaca   37260 gaaaatagt ggcattacac taactgttgt ggaattgtac agaccgattc tcctcccaat    37320
ctgccgagtg tgggcggctt gagagaatga agagagctac tggcctcagg taacagtgct   37380
```

```
tcccacagga ctgtctcagg ctgccaccac cataaatagc attttagacg tgacagagct   37440
aaggcttgac acacagccaa aagctactca cattccattt catccccagc tgttctgtca   37500
tcgctaagca cagagcattc agcacagctc ttccctgtgg tgggtactca gcactgttga   37560
gttgaaagga ttgaaaaaac tcaagactat gttctcaaac attttttttaa gctcttttta   37620 aaaccacctt agaatgaaag cttttgactt cttattaaca tgcactaact tcatatacac   37680
atttagtgtt attgtacagg cacgaagcat actctggtca gaacctgtct cctttggtcc   37740
accctcccca ccgttttcag cttctattcc accttccata cgtctcaaga tccacatgtg   37800
agagggaaca ctcagagcct tgtctttctg tatctgggat atctcactta acatgatatt   37860
ctccagttct gttccatcca tttcattgca aagagcaaga tttcactcta cagccaaata   37920
acacatttgt ccatgtatat ccgtattttt ccttattcat ctgttgaatg gcacaagact   37980
gatatcatgg gtaatatcta t                                             38001

<210> SEQ ID NO 12
<211> LENGTH: 3435
<212> TYPE: DNA
<213> ORGANISM: Rattus norvegicus

<400> SEQUENCE: 12
cgtttgtagt gtcagccatc ccaattgcct gttccttctc tgtgggagtg gtgtctagac     60
agtccaggca gggtatgcta ggcaggtgcg tttggttgc ctcagatcgc aacttgactc    120
cataacggtg accaaagaca aagaaggaa accagattaa aaagaaccgg acacagaccc    180
ctgcagaatc tggagcggcc gtggttgggg gcggggctac gacggggcgg actcgggggc    240
gtgggagggc ggggccgggg cggggcccgg agccggctgc ggttgcggtc cctgcgccgg    300
cggtgaaggc gcagcggcgg cgagtggcta ttgcaagcgt ttggataatg tgagacctgg    360
gatgcaggga tgtcgactat ctgccccca ccatctcctg ctgttgccaa gacagagatt    420
gctttaagtg gtgaatcacc cttgttgcg gctacctttg cttactggga taatattctt    480
ggtcctagag taaggcacat ttgggctcca aagacagacc aagtactcct cagtgatgga    540
gaaatcactt tcttgccaa ccacactctg aatggagaaa ttcttcggaa tgcggagagt    600
ggggcaatag atgtaaagtt ttttgtctta tctgaaaagg gcgtcattat tgtttcatta    660
atcttcgacg ggaactggaa cggagatcgg agcacttacg gactatcaat tatactgccg    720
cagacggagc tgagtttcta cctcccactg cacagagtgt gtgttgacag gctaacgcac    780
atcattcgaa aaggaaggat atggatgcac aaggaaagac aagaaaatgt ccagaaaatt    840
gtcttggaag gcaccgagag gatggaagat cagggtcaga gtatcatccc tatgcttact    900
ggggaggtca tccctgtgat ggagctgctt gcgtctatga gatcacacag tgttcctgaa    960
gacctcgata tagctgatac agtactcaat gatgatgaca ttggtgacag ctgtcatgaa   1020
ggctttcttc tcaatgccat cagctcacat ctgcagacct cggctgttc tgtggtggta   1080 ggcagcagtg cagagaaagt aaataagata gtaagaacac tgtgccttt tctgacacca   1140 gcagagagga agtgctccag gctgtgtgaa gccgaatcgt cctttaaata cgaatctgga   1200
ctctttgtac aaggcttgct aaaggatgcg actggcagtt ttgtactacc tttccggcaa   1260
gttatgtatg ccccttatcc caccacacac atcgatgtgg atgtcaacac tgtcaagcag   1320
atgccaccgt gtcatgaaca tatttataat caacgcagat acatgaggtc agagctgaca   1380
gccttctgga gggcaacttc agaagaggac atggctcagg acaccatcat ctacacagat   1440
gagagcttca ctcctgattt gaatattttc caagatgtct tacacagaga cactctagtg   1500
```

| | |
|---|---|
| aaagcctttc tggatcaggt cttccatttg aagcctggcc tgtctctcag gagtactttc | 1560 |
| cttgcacagt tcctcctcat tcttcacaga aaagccttga cactaatcaa gtacatagag | 1620 |
| gatgacacgc agaaggggaa aaagcccttt aagtctcttc ggaacctgaa gatagatctt | 1680 |
| gatttaacag cagagggcga ccttaacata ataatggctc tagctgagaa aattaagcca | 1740 |
| ggcctacact ctttcatctt cgggagacct ttctacacta gtgtccaaga acgtgatgtt | 1800 |
| ctaatgactt tttaaacatg tggtttgctc cgtgtgtctc atgacagtca cacttgctgt | 1860 |
| tacagtgtct cagcgctttg gacacatcct tcctccaggg tcctgccgca ggacacgtta | 1920 |
| cactacactt gtcagtagag gtctgtacca gatgtcaggt acatcgttgt agtgaatgtc | 1980 |
| tcttttccta gactagatgt accctcgtag ggacttatgt ttacaaccct cctaagtact | 2040 |
| agtgctgtct tgtaaggata cgaatgaagg gatgtaaact tcaccacaac tgctggttgg | 2100 |
| ttttgttgtt tttgtttttt gaaacttata attcatggtt tacatgcatc acactgaaac | 2160 |
| cctagttagc tttttacagg taagctgtga gttgactgcc tgtccctgtg ttctctggcc | 2220 |
| tgtacgatct gtggcgtgta ggatcacttt tgcaacaact aaaaactaaa gcactttgtt | 2280 |
| tgcagttcta cagaaagcaa cttagtctgt ctgcagattc gttttgaaa gaagacatga | 2340 |
| gaaagcggag ttttaggtga agtcagttgt tggatcttcc tttatagact tagtcccttta | 2400 |
| gatgtggtct gtatagacat gcccaaccat catgcatggg cactgaatat cgtgaactgt | 2460 |
| ggtatgcttt ttgttggttt attgtacttc tgtcaaagaa agtggcattg gttttataa | 2520 |
| ttgttgccaa gttttaaggt taattttcat tattttgag ccaaattaaa atgtgcacct | 2580 |
| cctgtgcctt tcccaatctt ggaaaatata atttcttggc agaaggtcag atttcagggc | 2640 |
| ccagtcactt tcgtctgact tcccctttgca cagtccgcca tgggcctggc ttagaagttc | 2700 |
| ttgtaaacta tgccagagag tacattcgct gataaaatct tctttgcaga gcaggagagc | 2760 |
| ttcttgcctc tttccttcca tttctgcctg gactttggtg ttctccacgt tccctgcatc | 2820 |
| ctaaggacag caggagaact ctgaccccag tgctatttct ctaggtgcta ttgtggcaaa | 2880 |
| ctcaagcggt ccgtctctgt ccctgtaacg ttcgtacctt gctggctgtg aagtactgac | 2940 |
| tggtaaagct ccgtgctaca gcagtgtagg gtatacacaa acacaagtaa gtgttttatt | 3000 |
| taaaactgtg gacttagcat aaaaagggag actatattta ttttttacaa aagggataaa | 3060 |
| aatggaaccc tttcctcacc caccagattt agtcagaaaa aaacattcta ttctgaaagg | 3120 |
| tcacagtggt tttgacatga cacatcagaa caacgcacac tgtccatgat ggcttatgaa | 3180 |
| ctccaagtca ctccatcatg gtaaatgggt agatccctcc ttctagtgtg ccacaccatt | 3240 |
| gcttcccaca gtagaatctt atttaagtgc taagtgttgt ctctgctggt ttactctgtt | 3300 |
| gttttagaga atgtaagttg tatagtgaat aagttattga agcatgtgta aacactgtta | 3360 |
| tacatctttt ctcctagatg gggaattttgg aataaaatac ctttaaaatt caaaaaaaaa | 3420 |
| aaaaaaaaaa aaaaa | 3435 |

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13

| | |
|---|---|
| gggtctagca agagcaggtg | 20 |

```
<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
gtcttggcaa cagctggaga t                                              21

<210> SEQ ID NO 15
<211> LENGTH: 24
<212> TYPE: DNA
<213> ORGANISM: Artificial sequence
<220> FEATURE:
<223> OTHER INFORMATION: Probe

<400> SEQUENCE: 15
tgatgtcgac tctttgccca ccgc                                           24

<210> SEQ ID NO 16
<211> LENGTH: 22
<212> TYPE: DNA
<213> ORGANISM: Artificial sequence
<220> FEATURE:
<223> OTHER INFORMATION: Primer

<400> SEQUENCE: 16
tgtgacagtt ggaatgcagt ga                                             22

<210> SEQ ID NO 17
<211> LENGTH: 25
<212> TYPE: DNA
<213> ORGANISM: Artificial sequence
<220> FEATURE:
<223> OTHER INFORMATION: Primer

<400> SEQUENCE: 17
gccacttaaa gcaatctctg tcttg                                          25

<210> SEQ ID NO 18
<211> LENGTH: 21
<212> TYPE: DNA
<213> ORGANISM: Artificial sequence
<220> FEATURE:
<223> OTHER INFORMATION: Probe

<400> SEQUENCE: 18
tcgactcttt gcccaccgcc a                                              21

<210> SEQ ID NO 19
<211> LENGTH: 30001
<212> TYPE: DNA
<213> ORGANISM: Macaca mulatta
<220> FEATURE:
<221> NAME/KEY: misc_feature
<222> LOCATION: (26113)..(26155)
<223> OTHER INFORMATION: n is a, c, g, or t
<220> FEATURE:
<221> NAME/KEY: misc_feature
<222> LOCATION: (28797)..(29186)
<223> OTHER INFORMATION: n is a, c, g, or t

<400> SEQUENCE: 19
aatctctaag caattttttg gggaagaaag aattgcaatt agggcatacg tgtagatcag     60
atggtcttcg gtatatccaa cgacaaagaa aaggtgggag gtttcgttaa aaaagagaaa    120
```

-continued

```
tgttacatag tacttttaga gaaaattcac tggcactatt aagggtctga ggagctggta        180
agtttcaatt ggtgagtgat ggtggtagat aaaattagag ctgcagcagg tcatttcagc        240
aactatcaga taaaactggt ctcaggtcac aacgggcagt ttcagcagct agacttgaaa        300
gaattacact gcgggagcaa tgtcatttgt cctgcatgct tttctacccc ctaccccac         360 tttttagtt gggtataaca agaacgaccc aaattgtatg atcaactttc acaaagcata         420
gaacagtagg aaaagggtct gtttctgcag aagatgtaga cgttgagagc cattttatgt        480
atttatttct ccctttcttc atcggtgaat gattaaaatg ttctgtatga tttttagtga        540
tgagaaaggt taaacgccac tcatctgtag taagtgtaat ctacacactt gcagaccaaa        600
aggcataagg tttaaaaaac ctttgttttt ttacacatca aacagagtgg tataaatgct        660
actcatctgt agtaagtgaa atctatacac ctgcagacca acgacgcaag gtttcaaaaa        720
tctttgtgtt ttttacacat caaacagaat ggtacatttt tcaaaagttt aaaaaaaaaa        780
aaaatccaca tatcacaact agcaaaaatg acattcccca gtgtgaaaat catgcttgag        840
agaattctta catgtaaagg caaaattgca gtgactttac aagggacctg ggattcccg         900 cccacagtgt ggagctgtcc cctaccaggg tttgcggcgg agttttgaat gtacttaaca        960
gtgtctcacg gtaaaaacaa aacttcatcc accaaatatt tgttgagcgc ccactgcctg       1020
ccaagcacaa acaaaaccat tcaaaaccac gaaatcgtct gcactttctc cggatccagc       1080
agcctctgcg attaaggttt gcacacgcta ttgcgccaac gctcctccag agcgcgtctt       1140
aagataaaag aatgggacaa gttgcccctc cccctttcac gggcctcgtg cgtcaacgtc       1200
atcgcatata gaaaacacac agacgtaacc tacggtgtcc cgctaggaaa gagaggcgcg       1260
tcaaacagcg acaagttccg cccacgtaaa agatgacgct tggtgcgtca gccgtccctg       1320
ctgcccggtt ccttctctct gggggcgggg cctggctaga gcaggtgtgg gtttaggagg       1380
tgtgtgtttt tgttttttcct accctctccc ctctacttgc tctcacagta ctcgctgagg      1440
gtgaacaaga aaagacctga taaagattaa ccagaagaaa acaaagaggg aaacaactgc       1500
agcctgtagc gggctctgga gcttaagaga ggcgcgctag gcgccgggcc gtgggcgtgg       1560 tcgggcggg gtcgggccag gggcggggct gcggttgcgg tccctgcgcc cgcggcggcg        1620
gcggcggcgg cagcggaggc gcaggcggtg gcgagtgggt gagtgaagag gcggcgtcct       1680
ggcgggtgtc tgtttggcgt ccggttgccg ggaagagacg cgggtagcag ccggggctct       1740
cctcagagct cgacacattt ttactttccc tctcgtttct ctgaccgaag tcgggtgtcc       1800
ggctttcgcc tctagcgact ggtggaattg cctgcatctg gccccgggc ttcgcggcgg        1860 cgcagggacg agggatggga atctggcctc ttcctcgctt tcccgcccgc agtgcgctgc       1920
cccagctgtc tccttcccgg ggacctgctg ggagcgctgc cgctacagac tcgagagaaa       1980
ggagcctcgg gcactgagag gcctcgcccg ggggaaggcc ggagggcggg cggcgggcgg       2040
cgagcggctc ctgcggacca agtctgggtt ctctgggaac ccgagacggt ccctgatggc       2100
gaggagatca tgcggggtgc tatggggtg tggagacgtc tgcagaattt tagcccaagc        2160
ttctaaggag tgctgatgac ttgcatatga gggcagcaat gccagtcggt gtactcccta       2220
ttctgtggga catgatgtgg ttgcttcaca gctccgagat gacacagact tgcttaaagg       2280
aagtgaccat tgtgacttgg gcatcacttg actgatggta atcagttgca gacagaagtg       2340
cacagattac atgtctgtgt ccacactgga tcagtctggc cacgaggaac accacaggct       2400
ttgtattgag aaacaggagg gaggtcctgc actttcccag gaggggtggc cctttcagat       2460
```

```
gcaatcgaga ttgttaggct ctggtagagt ggttgcctgg ttgtggcagt tggcaaattc    2520
ctattcaaac tgttgccgtg cgtcaccagt taacaacaag ggtacacgat ctgtctggca    2580
ttacttctac tttgtacaaa ggatcaaaaa tactgttaga tatgattttt ctcagacttt    2640
gggaaacttt taacgtaatc tgtgaatatc acagaagcaa gactgtcata tagaggatat    2700
taataacctg gagtcagaat acttgaaata tggtgtcatt tgacacgggc tctgttatca    2760
ccacctttgc caagcccttt cacttgagga aaccctcaa tcagttggaa actgcctcat     2820
gctgacagta catctgaaac aaaaacgaga gtagttacca cattccagat tgttcactaa    2880
ggcagcattt atctgctcca ggaaaacatt acaagcaact tatgaagttg ataaatatt     2940 ttgtttggct atgttggtac tccaaaagtt gctttcagag aaacaaagta aaccaaggag    3000
gacttctgtt gttcacgtct gcccttgggc tctattctac gttaattagg tagttcccag    3060
gaggactaga ttagcctacc tattgtctga gaaacttgga tctgtgagaa atggccagat    3120
agtgatacga acttcacctc ccagtctttc ctgatgttta agattgagaa gtgttgtga    3180 actttctggt gctgtaagca gttcactgtc cttaaagtgg tcctgggcag ctcctgttgt    3240
ggaaagtgga ccgatttagg attctgcttg gctttggact gggagaaaat aaactgcatg    3300
gttacaagta ttgagagcca agttggagaa ggtggcttac acctataatg ccagagcctt    3360
aggaggcagg ggcaagagga tcactggaag tcaggagttc aagcccaacc tgggcagcct    3420
agaccctgtc tctacaaaaa attaaaaact tagccgggcg cggtggtgtg cacctgtagt    3480
cctagctact ggggaggctg aggcaggagg gtcttttgag cccaggagtt tgaagttaca    3540
gggagctatg atcctgccag tgcactccag cctggatggc aaaacgagac cctgtctcta    3600
aaaaacaaga agtgagggct ttatgatcgt agaaattttg cttacaatag cagtggacca    3660
accacctttc taaataccaa tcagggaaga catagttgat tttaacaaa catttaaga     3720 aaaagcaaaa cctcaaactt agcactctac taacagtttt agccgatgct aattaaggta    3780
atcatgtctg catatatggg attactttca gaaagtgtat tgggaaacct tcatgaacc     3840 ctgtgcaacc ctgagcaagc caccgtctca ctcagtttga atcttggctt ccctcaaaag    3900
actctgtggc taatgtttgg taactctctg gagtagccag cactgcatgt acataggata    3960
ggtacataaa acaattattg gttttgagct gattttttc agctgcattt gcgtgtatgg     4020 attttctca ccaaagacaa tgacttcaag tgttaataaa ataattgtac agctctccta     4080
attatacttc tctgtaacat ttcatttctc agactatttc ttttggtagg atttaaaact    4140
aaacaattca gtatgatctt tgttcttcat tttcttctt attctttttt ttttcgagac     4200
agagtctccc tctgttgtgc catctcagcc cattgcaacc tccgccacct gggttcaagt    4260
gattctcctg cctcagcctc ctgagtagct gggattacag gtgcccgcca ccacacctac    4320 ctaattttt gtatttttag tagaggcggg gtttcaccat gttggctagg ctggtcttaa    4380
actcctgacc tcagatgatc cacctgcctc ggcctcccaa agagctggga tgataggcgt    4440
gacccaccat gcccgcccca tttttttct tattctgtta ggagtgagag tgtaactagc     4500
agtctataat agttcaattt tcacaacgtg gtaaaattt tccctgtaat tcaacgagat     4560
tttgcttcag ggctcagttc tgttttagga aatactttta ttttcagttt gatgatgaaa    4620
tattagagtt gtgatattgc ctttatgatt acctaccttt ttaacctaaa agaatgaaag    4680
aaaaatatgt ttacagtata attgtatggt tgcgtgttaa cttaattcat tatgttggcc    4740
tccagtttgc tgttgttcgt tatgacagca gtagtgtcat taccatttca attcagatta    4800
cattcctgta tttgatcatt gtaaactgat tgcttaaatt gtattaaaaa cagtggatat    4860
```

```
tttaaacaag ctgtactgct tatatccagt gctgtctcct aagactatta aattgatata    4920
acatatttaa aagtaaatat ttcctaaatg aatttttgaa attaaaaata cacgtgttaa    4980
aactgtcttt gtgttcaacc atttctgtac gtacttagag ttaactgttt tgccaggctc    5040
tgtatgccta ctcataatgt gataaaagca ctcatctaat gctctataaa tagaagtcag    5100
tgctttccat cagactgaac actcttggca agatgtggat aaaattattt aagtaaaatt    5160
gtttactttg tcatacattt acagatcaaa tgttagctcc caaagcaatc atatggcaaa    5220
gataggcata tcataatttg cctattagct gctttgtatt gctattatga tagatttcac    5280
agttttagat ctgcttagat gaaaatgtaa ttccttttac tgtcagtctt agatataagt    5340
cttcaattat agtacagtca cacattgctt aggaatgcat cattaggcga ttttgtcatt    5400
atgcaaacat catagagtat acttacataa acctatatag tacagccttt acgtacgtag    5460
gccatatggt atagtctatt gctcctaggc tacaaatctg tacagctgtt actgtactga    5520
atactataga cagttgtaac acagtggtat ttatttatct aaatatatcc aaacatagaa    5580
aaggtacagt taaagtatgg tataaaaaat aatgatatac ctatataggc cacttaccgt    5640
gaatggagct tgcaggacta gaagttgctc tgggtgagtc agtaagtaag tggtgaatga    5700
atgtgaaggc ctagaacatt actgtacaca ctgtagactt tataaacaca gtatgcttaa    5760
gctacaccaa atttatcttt acagttttc ttcaataaaa aattaatgtg aacctactat    5820 aacttttaa ctttgtaaac ttttaatt tttaactttt aaaatactta gcttgaaaca    5880
caaacacgca tagctataca aaaatatttt ttctttatat ccttattcta gaagcttttt    5940 cctatttta actttttttt ttttacttgt tagtcgtttt tgttaaaaac taaaacacac    6000
acactttcac ctaagcatag acaggattag gatcatcagt ttcactccct tccacctcac    6060
tgccttccac ctccacatct tgtcccactg gaacgttttt aggggaata acacacatgt    6120 agctgtcacc tgctatgata acagtgcttt ctgttgaata cctcctgaag gacctgcctg    6180
aggctgtttt acatttaact taaaaaaaaa aataagtaga aggagtacac tctaaaataa    6240
caataaaagg tatagtctag tgaatacata aaccagcaac atagtagttt attatcaagt    6300
gttgtatact gtaataattg tatgtgctat actttaaatg acttgaaaaa ttgtactaag    6360
accttatgat ggttacagtg tcactaaggc gatagcatat tttcaggtcc attgtaatct    6420
aatgggacca ccatcatata tgcagtccac cattgactga aatgttacat ggtacgtaac    6480
tgtatttgca agaatgattt gttttacatt aatatcacat aggatgtacc tttttagagt    6540
gatatgttta tgtggattaa gatgtacaag tggagcaagg ggacaagagc ccttggttct    6600
gtcttggatg tgagctttta tgctcttctc atcatgtctg ttttcttatt aaattcaaag    6660
gcttggacag gccctattta gcccttgttt tctatgtgtt ctaaataact aaagcttttta    6720 aattctagcc atttagtgga gaactctctt tgcaatggta aaatgctgta ttggtttctt    6780
gactagcata ttaaatatat ttatctttgt cttgatattt caatgtcatt ttaaacatca    6840
ggattgggct ttagtattct catacccaga gagttcactg aggatacagg actgtttgcc    6900 catttttgt tatggctcca gacttgtggt atttcgatgt cttttttttt tttttttttt    6960
tttaaccttt tagcagcttt aaagtatttc tgttgttagg tgttgtatta cttttctaag    7020
attactgtaa caaagcacca caaactgagt ggctttaaac aacagcaatt tattctctca    7080
caattctaga agctagaagt ccgaaatgga agtgttgatg gggcatgatc ctcaaaagag    7140
agaagactct ttccttgcct cttcctggct tctggtggtt accagcaatc ctgagcgttc    7200
```

```
ctttcttgct tcgtagtttc agcagtccag tatctgcctt ttgtcttcac atggatgtct    7260
accccttgtc tctgtgtctc cagatctctc tccttataaa cacagaagtt actggattag    7320
gccccactct aatccagtat gacccccattt taacacgatt acacctattt ctaaataagg   7380
tcacattcac ataccaag ggttaggaat tgagcatatc ttttgcaggg acacaattca      7440
acccacaagt gtcagtctct agctgagcct ttcccttcct ggttttctcc ttttagttg     7500
ctgtgggtta ggggccaaat ctccagtcat actagacttg cacatggact ggagatttgg    7560
gaatactgcg ggtctattct atgagcttta gtatgtaaca tttaatatca gtgtaaagaa    7620
gccatttttt cagttcacta tttctttgaa tttcttaatg tatgccctga ataagtaa     7680
caagttacta tgtctcataa aatgatcata tcaacaaaca tttaatgtgc acctactgtg    7740
ctagttgaat gtctttatcc tgataggaga taacaggctt ccgcatcttt gacttaagag    7800
gacaaaccaa gtatgtctga atcatttggg gttttgatgg atatctttaa attgctgaac    7860
ctaatcattg gttttatatg tcattgttta gatatctcag gagcatttgg ataatgtgac    7920
agttggaatg cagtgatgtc gactctttgc ccaccgccat ctccagctgt tgccaagaca    7980
gagattgctt taagtggtga atcacccttta ttagcagcta cttttgctta ctgggacaat   8040
attcttggtc ctagagtaag gcacatttgg gctccaaaga cagaacaggt acttctcagt    8100
gatggagaaa taacttttct tgccaaccac actctaaatg gagaaatcct tcgaaatgca    8160
gagagtggtg ctatagatgt aaagtttttt gtcttgtctg aaaagggagt gattattgtt    8220
tcattaatct ttgatggaaa ctggaatggg gatcgcagca catacggact atcaattata    8280
cttccacaga cagaacttag tttctacctc ccacttcata gagtgtgtgt tgatagatta    8340
acacatataa tccggaaagg aagaatatgg atgcataagg taagtgattt ttcagcttat    8400
taatcatgtt aacctatctt ttgaaagctt attttctgat acatataaat cttatttta    8460
aattatatgc agtgaacatc aaacaataga tattatttat tttgcattta tcctgttaga    8520
tacaaataca tctggtctga tgcctgtcat cttcatatta actgtggaag gtaggaaatg    8580
gtagctccac attacagatg aaaagctaaa gcttaaacaa atgcagaaac ttttagatcc    8640
tggattcttc ttgggagcct ttgactctaa taccttttgt ttcccttca ttgcacaatc     8700
ctgtctttcg cttactacta tgtgtaagta taacagttca aaaaaatagt ttcataagct    8760
gttggttatg tagcctttgg tctctttaac ctctttgcca agttcccagg ttcataaaat    8820
gaggaggttg aaccgcatgg ttcccaagag aattccttt aatttttacag aaattattgt    8880
tttccccgaa gtcctatagt tcaatatata atgatattta catttcagta tagttttggc    8940
atatctaaag aacacattaa gttctccttc ctgtgttcca gtttgatact aacctggaag    9000
tccattaagc attaccaatt ttaaaaggct tttgcccaat agtaaggaaa aataatatct    9060
tttaaaagaa taatttttta ctatgtttgc aggcttactt cctttttct cacattatga     9120
aactcttaaa atcaggagaa tcttttaaac atcataatgt ttaatttgaa aagtgcaagt    9180
cattcttttc cttttgaaaa ctatgcagat gttacattga ctatttctg tgaagttatc     9240
ttttttttcc ctgcagaata aagggtgttt tgatttttatt ttgtgttgtt tataagaaca    9300
tacattcgtt gggttaattt cctgcccctg cccccgtttt ttccctaaag tagaaagtat    9360
ttttcttgtg aactaaatta ctacacaaga acatgtctat tgaaaaataa gtatcaaaat    9420
gttgtgggtt gtttttttaa ataaattctt tcttgctcag gaaagacaag aaaatgtcca    9480
gaagattatc ttagaaggca cagagagaat ggaagatcag gtatatgcag attgcatact    9540
gtcaaatatt attctcatgg catgtatctg tgtaaagttg atggctacat ttgtgaaggc    9600
```

```
cttggggaca tacagagtaa gccttaatgg agcttttatg gaggtgtaca gaataaacta   9660
gaggaagatt tccatatctt agacctgaag agttaaatca gtaaacaaag gaaaatagta   9720
attgcatcta caaattaata tttgctccct ttttttttct gtttgaacag aataaatttt   9780
ggataacttg ttactagtaa aaaatttaaa aattgtctgt gatatgttct ttaaggtact   9840
acttctcgaa cttttttccta gaagtagctg taacaggagg agagcatatg taccectaag  9900 gtatctgggg tataggccca tgtccaaaca atatttcttt taagtcttgt gttgtatctt   9960
taagactcat gcaatttaca ttttattcca tgatataact attttaatat taaaatttgt  10020
cagtgatatt tcttaccctc tcctctagga aaatgtgcca tgtttatact ttggctttga  10080 gtgccctga ggaacagaca ctagagtttg agaagcatgg ttacacaggc gtggcttccc   10140
ctgcagaaat taagtacaga ctatttcagt gtaaagcaga gaagttcttt tgaaggggaa  10200
tctccagtga agaaagggtt cttcactttt acttccattt cctcttgagg gtgaccctca  10260
ttgctccttg taaaactccg atattttaaa catggctgtt ttgctttcct ctggttcttt  10320
ttaacatgag tgagacagat gatactttaa aaagtaattt taaaaaaaag tgttaaaata  10380
tatggccata atgcagaacc ctatgctgtg atctccttta ccaaattgtt gtgtttgtac  10440
ttttgtagat agctttccag tccagagaca gttattctgt gtaaaggtct gactcaacaa  10500
gaaaagattt ccctttaccc aaagaatgcc agtctttatt tgctggtcaa taagcagggt  10560
ccccaggaaa ggggtaactt tcaccaccct ctaacccact ggttattagt aaactaatta  10620
agtagactta tctcaagatg aggaaactta aaaccaagta aaattctgct tttactggga  10680 ttttatttt tgaaaccaga aacgtttact taagttgact actattaatg aattttggtc    10740
tctcttttaa gtactcttct taaaaatgtt atcctactgc tgagaagttc aagtttgaga  10800
agtacaagga ggaatagaaa cttgagagat tttctttttc ttttagagcc tcttctgtat  10860
ttagccctgt aggaattttt ttttttccccc aagattcttc ttcgtgaaaa ggaggagttg  10920 cctttttgatt gagttcttgc aaatctcaca acgactttat tttgaacaat actgtttggg  10980
gatgatgcat gagtctgaaa caacttcagt tgtagctgtc atctgataaa attgcttcac  11040
agggaaggaa atttagcacg gatctagtca ttattcttgt tagattgaat gtgttaatca  11100
taattgtaaa caggcatgat aattattact ttaaaaactg aaaacagtga atagttagtt  11160
gtggaggtta ctaaagcatg attttttttaa aataaaactt tcagcatttt gcaaatatgc  11220
atatggttta ggatagaact tccagaggta gcatcacatt taaattctca agcaacttag  11280
taatacgagg ctctgaaaaa ctggttaaag ttactccaga aatggccctg ggtctgacag  11340
acattctaac ttaaagatgc atatgaagac tttgaataaa atcatttcat atgaagacat  11400
tgaataaaat catttcataa aataagtgag gaaaacaac tactattgaa ttcatcttaa   11460
tgtatgattt taaaaatatg tttagctaaa aattcataga catttgacaa tttcgtttat  11520
atctcaaaaa gttgacttac ccaagttgat cacaaaactg atgagactgg tggtggtagt  11580
gaataaatga gggaccaccc atatttgaga cactttacat ttgtgatgtg ttatactgaa  11640
ttttcagttt gattctataa actaccaatt tcaaaattac aatttcaagg tgtaataagt  11700
agtggtatta tcttgaaata ggtctaaagg gaactttct gttttaaaat attcttaaac   11760
tatatgtgct gattttgatt tgcatttggg tagattatac tcttatgaat cgggggggctg  11820 ggtattgatt caggttttcc ttacctattt ggtaaggatt tcaaagtctt tttgtgcttg  11880
attttcctcg tttttaaata tgaaacatat tgatgacttt taattaacaa atgttttat    11940
```

-continued

```
ctcgaataaa ttttaaagga gatcttttct aaaagaggta tgatgactta attattgcat    12000
ataacaataa atgagaaacc agtgattcca tactctctaa agaataaaag tgagctttag    12060
gcccaggcat ggtggctcat gcctgtaatc ccagcacttt ggaaggccga ggcaggcgga    12120
tcacctgagg tcaggaattc gacaccagcc tggccaaatg gcaaaccct gtctctacta     12180 caaatacaaa aattagctgg gcatggtggc agccctata gtcccagcta cttggaagac     12240
tgagacagga gagtcactcg aacccgagag gcagaggttg cagtaagctg aaatcacacc    12300
attgcactcc agcctgggca acaagagcaa aactccgtct caaaaaaaa aaaaaaaaa      12360 aaaaagaata aaagtgagct ttggattgcg tataaatcct ttagacaagt agtgacttg     12420 tttgatactg tgtttgaaca aattacaaag tattttcatc aaagaatgtt attgtttgct    12480 gttatttta ttttttattg cccagcttct ctcatattca ttatgtgatt ttcttcactt     12540
catgttactt tattgtgcag ggtcagagta ttattccaat gcttactgga gaagtgattc    12600
ctgtaatgga actgctttca tctatgaaat cacacagtgt tcctgaagaa atagatgtaa    12660 gttttatat ttttaaatga gagcaattat accctttatc agttttttgg ggttatatta    12720
ttattatgta tattattaat attctaattt taatactaag cacttcgtcg tacgtactat    12780
ccacatgcag tattagccac ttgaacagat aagcacacac aaaatcctgg attttatggc    12840
ataacagagg catttttgat cagtgatgac aaaactaaat ttattttgtt tatttcacta    12900
cttttataat tcctaaaagt gggaggatcc cagctcttat aggagcaatt aatatttaat    12960
gcagtacctt ttgaaacaaa actgtgtgcc aaagcagtaa ccattaatgg aagttgactt    13020
atagtcacaa atttagttc cttaatcatt tgttgaggat gttttgaatc acacactatg     13080
agtgttaaga gatatcttta ggacactatt cttgttgttt tattgtcatt taggttagtc    13140
tcctgtctga cagctcagaa gaggaagttg ttcttgtaaa aattgtttac acaacctgat    13200
tgaccagctt tcacatttgt tcttctgaaa gctgatggta gtgcacagat tgttttatgg    13260
ggagtcttga ttctcagaaa tgaaggcagt gtgttatatt gaatccagac ttcagaaaac    13320
ttgtatatta aaagtgtttt ttcaacacta tgttatagcc agactaattt ttttattttt    13380
ttgatgcatt ttagatagct gatacagtac tcaatgatga tgatattggt gacagttgtc    13440
atgaaggctt tcttctcaag taagaatttt tcttttcata aaacctggat gaagcatatg    13500
ttcacctatg acaagatttg gaaggaagaa aataacagac tgtctactta gattgttcta    13560
gggacaacat tgcatatttg aattgttgct taaatttgtg ttatttttca ttcgttatat    13620
ttctataata tatttgatgt tattccattt gctatttaaa gaaactgagt ttccatattt    13680
cccagacaag aaatcatggc cccttgcttg attctggttt cttgttttac ttctcattaa    13740
agctaaaaga acccttttcaa attaagttgt actgtagatg aacttaagtt atttaggcct   13800
agaaaaaaaa aattcatatt tatactgatc tttttccatc cagcagtgga gtttagtact    13860
taagagtttg tgcccttaaa ccagactccc tgggttaatg ctgtgtacct gtgggcaagg    13920
tccctgaatt ctctatacac ctatttcctc atctgtaaaa tggcaataat aataatagta    13980
cctaatgtat agagttgtta taagcattga gtaagataaa taatataaag cacttagaac    14040
agtgcctgga acataagaac acttaataat agctaacatt ttctatttac atttcttcta    14100
aggaaaaggt taacagaaat agccaatatt tgttcagtgc ctacatgtta gttcctatac    14160
taagtgcttt acatgtatta tcttatattc tattttaatg tttcttcaca gttgcagatt    14220
atcatgaaat tttattttt aaaaagaga agtaaaagga taaagtattc acttttatgt      14280
ccacagtctt ttcctttagg ctcatgatgg agtatcagag gcatgaatgt gtttaaccta    14340
```

```
agagccttaa tggcttgaat cagaagcact ttagtcctgt atctgttcag tgtcagcctt   14400
tcaaacatca ttttaaatcc catttgactt taagtaaatc acttaatctc tctacatgtc   14460
aatttcttca gctataaaat gatggtattt caataaataa atacattaat taaatgatat   14520
tttacaaact aattgggctg ttttaaggct caataagaaa atttctgtga aaggtctcta   14580
gcaaatgtag ggttctatac aaataaaaga taacattatg cttatatctt cggtgtttat   14640
catgcaaagc tcttctgagt ttttgaaga gctcacctac tattttttgt ttttagtttg   14700
ttaaattgtt ttataggcaa tgttttaat ctgttttctt taacttacag tgccatcagc    14760
tcacacttgc aaacctgtgg ctgttccgtt gtagtaggta gcagtgcaga gaaagtaaat   14820
aaggtagttt attttataat ctagcaaatg atttgactct ttaagactga tgatatatca   14880
tggattgtca tttaaatggt aggttgcaat taaaatgatc taatagtata aggaggcaat   14940
gtaatctcat cgaattgctg agacaacttg tggcaacagt gagtttgaaa taaagtgaat   15000
aggagtcatt tatcagttta ttttgataac ttgtaaatac cagtgtcaga tgtgtataaa   15060
tggttttgag aatatattaa aatcaggtat ttaaaaaaac actattcttc tatttcccaa   15120
tgtaatcttt aacaaatctg aaggtagtca tgtactttcg gtactagttc tgaagaaatg   15180
ttatttgttt attcatcttg atttcattgt cttggctttc cttctaaatc tatcccttct   15240
tgggagctat tgggattaag tggtcattga tgattatact ttattcagta atgtttctga   15300
ccctttcctt cagtgctact tgagttaata aaggattaat gaacagttac atttccaagc   15360
attagctaat aaactaaagg attttgcact tttcttcact gaccattagt taaaaacagt   15420
tcagagataa gtacatgtat ctttcaattc tagcaaacct aatttttaa aagaagttt    15480 acataggaaa tatgttggaa atgattattt actttacaaa gatattcata atttattttt   15540
tctgtaacta gctactttgt atatttacat gagccttaat ttatcaaaat tatatttctc   15600
atataaccat ttatgagagc ttagtattcc tctgtcatta tattgcgtct acggactagt   15660
gatcttacta cttctgttac ctcgaacaag tggcttcccg tctgtgacct ccaaagccgt   15720
aggttccaca gagtgactgc tgagctgctt tatgaaggga gaaaggctcc atagttgggt   15780
ttttggtttt gcttttgttt ttgttttaa cattttcct atcctccatc ctcttgaggc    15840
agagtagctt acctttatc ttgttttaat ttgagaaaga agttgccact gctctagatt    15900 gaaaccact gctttaacat aataactctg aatatggttt gaattcaag atagtgacat    15960 gcctttttat ttttactaat agagctgtag gtcgaatatt attagatttc taaaccccac   16020
ccaatgacct ccttatttta aatcaaattt aataattaat tatcttctta ttggaggatc   16080
tggacattct ttgatgtttc ttacaatgaa tttcacatgt agacccacta aacagaagtt   16140 ataaggttc catggtcaaa taagtctgag aaagtctgca tattatataa ttcacctaaa    16200
gagtcacagt atgtacccaa atgttaaagg ttttgagatg ccatacagta aatttaccaa   16260
gcattttcta aatttatttg accacagaat ccctattta agcaacaact gttatatccc    16320
ataggttcca ggtgactaaa gaatacttat tgcttaggat atgttttatt gataataaca   16380
attaaaatgt cagatatctt tcataagcag atcagtggtc ttttaaaac tttgtatttt    16440 aatgctaaaa tcttttcttt tgtagatagt cagaacatta tgccttttc tgactgcagc    16500 agagagaaaa tgctccaggt tatgtgaagc agaatcatca tttaaatatg agtcagggct   16560
ctttgtacag ggcctgctaa aggtatagtt tctacttatc acaagggaaa ccaattttct   16620
aaaatcattt ttgagactct ttgtagacaa atattaaata ttagcattta atgtatctca   16680
```

```
tattgacatg cccagtgact gacttccttt gcacagttct gcgcatagac tatatgtctt    16740
atggatttat agttagtatc atcagtgtaa caccatagaa tacccttttgt tttccaggtg   16800 ggtccctgta cctacatgtc tagcatcagg tgttgttttt tttttttttt tttaaaacat   16860
atgcttaaat caggttgcac atctaaaata agatcatttc ttttaacta aatagatttg    16920 aattttattg aaaaaaattt taaaacatct ttaagaagca tataggatt aagcagttac    16980 tatgtatgtg tactaaaata tatatatatt cctaaatata tattcctata tataatatat   17040
gtatttctat atataatata tattagaaaa aacttagagt tttctttcat ttgagtctac   17100
tgttcaagga gcaaaacaga gaaatgtaaa ttagcaatta tttacaataa ttaaagggaa   17160
gaaagttgtt caccttgttg gatctattat tgttgtttta attatagtcc caagacgtga   17220
agaaatagct ttcctaatgg ttatgtgatt gtctcatagt gactactttc ttgaggatgt   17280
agccacagca aaatgaaatt taaaaaattt aaaaattgtt gcaaataaaa gttatattag   17340
gcttttgtgc aatttcaata atgtgctgct atgaactcag aatgatagta tttaaatata   17400
gaaactagtt aaaggaaaca cagtttctat ttgagttata caaatctgta aattagaact   17460
tctcctgtta aggcattata aagtgcttaa tacttttgtt tcctcagcac cctctcattt   17520
aattatataa ttttagctct gaaagggacc tataccagat gtgtagagga aatttcaaaa   17580
ctatgatcta atgaaaaaat atttaatagt tctccatgca aatacaaatt atatagtttt   17640
ctggaaaata cctttgacat tatacaaaga tgattatcac agcattataa tagtgaaaaa   17700
atggaaatag cctctttctt ctgttctgtt cacagcatat ggcacagtac ctcatatgca   17760
gtaggttatt atgacctggt aactggctcc cccaactgat taggaaagaa gtaaatttgt   17820
tatttataaa aatacgtgtt cattgagatg catagaataa ttaagaaatt aaaagacact   17880
tgtaatttca aatccagtga ataccactg ttaatatttg gcatatctct ttctagtctt    17940
tttttccctt ttgcatgtat tttctttaag actcccaccc ccactggatc atctctgcat   18000
attctaatct gctttttca cagcagattc taagcctttt tgcatatcaa cacaaacttc    18060
aacaacttca tctttagatg ctaaataatg aattcatttt tatttactta accactttct   18120
ttggatgctc aggttattct gatgttttgc cattaaaacc aatgctatac tgaacacttc   18180
tgtcactaaa acttgaacac actcatgaat aatttcttag gataaatttt tagagatgga   18240
tttgctaaat caaagaccat ttttttaaaaa ttgaaaaaca attatatcgt ttggcatgta   18300
agacagtaca ttttccttt attttgacag gattcaactg gaagctttgt gctgcctttc    18360
cggcaagtca tgtatgctcc atatcccacc acacacatag atgtggatgt caatactgtg   18420
aagcagatgc caccctgtca tgaacatatt tataatcagc gtagatacat gagatccgag   18480
ctgacagcct tctggagagc cacttcagaa gaagacatgg ctcaggatac gatcatctac   18540
actgacgaaa gctttactcc tgatttgtac gtaatgctct gcgtgctggt actgtagtca   18600
agcaatatga aactgtgtct tttatgaata aaaacaaaac agaagttgca ttcaaaaaga   18660
aagaaatatt actagcagaa ttatgcttga agaaacattt aatcaagcat ttttttctta   18720
aatgttcttc ttttttccata cgattgtgtt taccctaaaa taagtaagat taaccccttaa 18780 agtgaatatt taactatttg tttaataaat atatattgag ctcctaagca ctgttctagg   18840
tactgggctt aatagtggct aaccacacag ctccagcccc tacattgcat atagtctatt   18900
gtataagtta ctgaatggac ttactaacaa aaccagagaa gtaattctaa gtcttttttt   18960
tcttgacata tgaatataaa atacaacaaa actggtaaaa tatattaata gagcattctt   19020
ttactttgca ttttatattg ttactcactt cgtatttaag aaaaacagtc tgatcaggaa   19080
```

```
attcaaaagg aaaagtaatg ataattaatt gagcatagac ccaacttgaa aagaaaaaaa   19140
aggatgatga taaatctata atcctaaaac cctaagtaaa cacttaaatg atgttctgaa   19200
atcaggaaaa gaattatagt atattttgt ggttctcttt tattagttga aaaaaggcac    19260
agtagctcat gcctataaga acagagcttt gggattccaa ggcaggcaga tcacttgagg   19320
ccaggagttc cagaccagcc tgggcaacat agtgaaaccc catctctaca aaaataaaaa   19380
agaattagtt gaatgtgttt ctgtgtgcct ataatcctag ctattcagaa agctgaggca   19440
ggaggatctc ttgagcccag gagtttgagg ttacatggag ttatgatgtg ccagtgtact   19500
ccagcctgcg ggacaatgag actctgtctt gttaaaaaaa aaagtgcttg gaataatgtt   19560
tggcatatag aaggtaacaa cagtaaatgt taactgtaat aacccaggta taagtgtgta   19620
aggtgataga aaaattgggg caaacaaccc tgacctgtgt ctctacagaa taagtttgag   19680
ttgaggcaac agacatgtgg agcaccagta attacacact aaatgttaac caaaagcgtt   19740
gaatagtaac atcttattca agggacccc agccttatat atctcaaggt gcagaaagat    19800
gacttaatat aggacccatt ttttccgagt tctccagagt ttttattggt tcttgagaaa   19860
gtagtggggg aattgtttta gaaaatgaat tggtcaaact gaaattccat gtcagtaagt   19920
ttttacatat tggtaaattt tgatagacat gtagaagttt tctaattaat ctgcgccttg   19980
aaacattttc cttttccta aagtgcttag tattttttcc cttttgat tggttgcttg     20040 ggagcttttt tgaggaaatt tagtgaactg cagaatgagt ttgcaaccat ttagtatttt   20100
tgttttgtgt tttagaggag gtatgtgtat tttaacattt cttaatcatt tttagccagc   20160
tatgtttgtt ttgctgattg acaaactata attaaacagc tattctcatt ttgctgatca   20220
tgacaaagta atatcctgaa tttttaaatt ttgcatccag ctctaaattt tctaaatttt   20280
ctaaacataa aattgttcaa aaaatagtat ttttagccac tagattgtgt gttgttaagt   20340
ctgttgtcac agactcattt tacttttcag tgtgtgtttt tacatgttaa ttatgtttgt   20400 cattttaat tttaactttt taaaataatt ccagtcactg ccaaaacatg aaaaattggt    20460
cactggaaat tttttttta acttttattt taggttcatg tgtacatgtg caggtttgtt   20520
atacaggtaa attgcgtgtc gtgagggttt ggtgtaccca ggtaataagg gtagtaccca   20580
ataggtagtt ttttgatcct taccctttctc ccaccccttct ttcaccctcg agtaggcctt 20640
ggtgttgctg tttccttctt tgtgtccatg tgtactcaat ggttagctcc tacttagaag   20700
tgagaacatg cggtatttgg ttttctgttc ctggattagt tcactcagga taatggcctc   20760
tagctccatc tgttttttat ggctgcatag tattccatgg tgtatatgta tcatgttttc   20820
tttatccagt ctaccattga tagacattta ggttgattct ctgtctttac tatcatgaat   20880
agcgctgtga tgaacatata cacatgcatg tgtccttatg gtggaacaat ttgtattcct   20940
ttaagtatat acagaataat ggggttgcta gggtgaatgg tagttctatt gtaagttatt   21000
tgtgaaatct tcaaactgct tttcacaata gctaaactaa tttacagtcc caccagcagt   21060
gtataagtgt tcccttttct ccacaacctt gccaacatgt tattttttta cttttcaata   21120
ataggcattc ctagagaatt gatttgcaat tctctaatga ttagtgatat tgagcatttt   21180
ttcgtatgct ttttagctgt gtgtatatat tcttttgaaa aatgttaatg tcctttgccc   21240
agtttgtaat gggttgttt gtttttgctt gttaattaaa gttccttcca gattctggat   21300 atcccttgt cagatgcgtg gtttgcagat attttctcc ccttgtgtag gttgtctttt     21360
tactctgttg atagtttctt ttgccgggca ggagctcatt aggtctcatt tgtgtttgtt   21420
```

```
tttgttgcag ttgcttttgg cgtcttcatc ataaaatctg tgccagggcc tatgtccaga   21480
atggtatttc ctagtttgtc ttccagggtt tttacaattt tagattttac gtttatgtct   21540
ttaatccgtc ttgagttgat taaggaaggg gtccagtttc actctaattc ctatggctaa   21600
caattatccc agcaccattt attgaatacg gagtcctttc cccattgctt gttttgtca   21660
attttgttga agatctgatg gttgtaggtg ctatgtggct ttatttcttg gctctctatt   21720
ctccactggt ctgtctgttt ttataccagt accctgctgt taaggttcct atagccttt   21780
agtataaggt cggctaatgt gatgcctcca gctttgttct ttttgcttag gattgctttg   21840
gctatttggg ctccttttg gttccatatt aattttaaaa tagttttttc tagttttgtg   21900
aagaatgtca ttgatagttt agaggaatag cgttgaatct gtagattgct ttgggcaaat   21960
ggccattta acaatattga ttcttcctat ctatgaacat ggaatgtttt tccatgtgtt   22020
tgtgtcatct ctttataccct gatgtataaa gaaaaaccag tattattgct actcaatctg   22080
ttccaaaaaa ttgaggagga ggaactcttc cctaatgaga ccggcttcct tctgatacca   22140
aaacctggca gagatacaac agaaaaaaga aaacttcagg ccaatatcct tgatgaatat   22200
agatgcaaaa atcctcaaca aaatactagc aaccaaatcc agcagtacgt caaaaagcta   22260
atctactta agtaggctt atccctggga tgcaaggttg gttcaacata cacaaatcaa   22320
taagtgtgat tcatcacata aacagagcta aaaacaaaaa ccacaagatt atctcaatag   22380
gtgcagaaaa ggctttcaat acaatttaac atccttcatg ttaaaaacct tcagtaggtc   22440
aggtgcagtg actcacacct gtaatcccag cactttggga ggccaaggcg gacgtatatc   22500
ttaagcccag gagttcaaga ccagcctagg cagcatggtg aaaccccatc tctacaggaa   22560
aaaaaaaaaa aaaaaaaaaa aaaaaaaaaaa agcttaatat ggcggcatgc acctatagtc   22620
ccagctactc aggaggttga ggtgggagga ttgcttgagc ccaggaggca gaggttgcag   22680
cgagctgaga tcgtgccact gcactccaac ctgggcaata aagtgagacc ctgtctcaaa   22740
aagaaaaaca aaaataatcc taaaccaact aggcattgaa ggaatatgcc tcaaaaaaat   22800
aagaaccatc tatgacagac ccacagccaa tatcttacca aatgggcaaa agctggaagt   22860
attctccttg agaaccgtaa caagacaagg atacacactc tcatccctcc ttttcagcat   22920
agttctggaa gtcctcgcca gagcagtcag gaaagagaaa gaaagaaaag gcattcagat   22980
aggaagagaa gaagtcaaac tatttctgtt tgcaggcagt ataattctat acctagaaaa   23040
tgccatagtt tctgcccaga agctcctaca tctgttaaaa atttcagcaa gttttagca   23100
ttgtctgtat tccaacagct tccagggtga gagtgaaatc aggaacacag tcccgttcac   23160
aatagccgca aaaagaataa aataccttgg aatccagcta accagggagg tgaaacatct   23220
ctacgagaat tacaaaacgc tgctgaaaga aatcagagat gacacaaaca aatggaaatg   23280
ttgttttaa caccttgctt tatctaattc acttataact aagatattca ttcagtggaa   23340
caggtataat aagaccactc gacttaaata taagccttat tctcttcca gagcccaaga   23400
aggggcacta tcagtgccca gtcaataatg ataaaatgct gatattttc ccctttactg   23460
tttctttctt ctgtagtgtg gtacactcat ttcttaagat tagaaaactt gacctacctt   23520
cctgtttgct tctacacacc cccattctct ttttttgcca ctccggtcag gtataggatg   23580
atccctacca cttttagtta aaacctcctt cccttattaa atgttctctt accactctgg   23640
cctgagtaga acctagggaa aatggaagag aaaagatgaa agggaggtgg gggctgggaa   23700
gggaatagtc ttgtttgtgt gtttgcttta gcacctacta tatcctaggt gctgtgttag   23760
gcacacatta ttttaagtgg ccattatatt gctacatctc actctggtca ttgccaaggt   23820
```

```
aggtagtact ttcttggata gttggttcat gttacttata ggtggtggac ttgttgaggc   23880
aaccccaatg gataatcatc tgagtgtgtt ctctaatctc agattttcct tcatatttt    23940 tggtttgttt tggttttga tggtggtggt tgtgtgctta ttttgttgc tggcttgttt     24000 ttttgttttg tttttgatat ggcaagaatt ggtagtttta tttattaatt gcctaagggg   24060
ctctactttt tttaaaagat gagagtacta aatagattg ataggtacat acaccttt      24120 atgggggact gcttatattc cttagagaaa aaaattactt attagcctga caaacaccag   24180
taaaatgtaa atatatccgt gagtaaataa atgaatgtat gctttgtatc tccaaatata   24240
tacatctata ttcttacaaa tatgttttta tgtaatacca atttataaga acttaaaatg   24300
ttggctcaag tgagggatgg tggaaagtag cattatatag ccatttcaac atttgaactt   24360
ttttcttcat tttcttcttt tcttcaggaa tatttttcaa gatgtcttac acagagacac   24420
tctagtgaaa gccttcctgg atcaggtaaa tgttgaactt gagattgtca gagtgaatga   24480
tatgacatgt tttcttttt aatatatctt acaatgcctg ttctctctct ctatatatat    24540
atatttatat atttccctgg atcatgcccc agagttctgc tgagcaattg cagttaagtt   24600
agttacacta cagttctcac aagagtctgt gaggggatgt caggtgcatc attacattgg   24660
atgcctcttg tcctagattt atgtttcggg aattcagacc tatgtttaca atataataaa   24720
tattgttgct gccttttaca gataaaataa taagatataa acttgaccac aactactgtt   24780
ttttgaaaca tagagttcat ggtttacatg tatcaaagtg aaatctgagt tagcttttac   24840
agatataata tatacatata tatatcctac aatgcttgta ctatatatgt agtacaagta   24900
tatatatgtg tgtgtgtgtg tgtatatata ttatggcact gtagtatata tatgtttata   24960
tgttaaaaaa tatataaata tatgttacat atttaacata aacatatata catatatgtt   25020
aaatatataa catatactct atatatgaca aatagagtat aatatatatt tttatttttt   25080
atatatatat aaaacatgat agaattaaga attagtcct aatctgtttt attaggtgct    25140
ttttgtagtg ttcagtcttt ctaaagtgtc taaatgattt ttcctttga cttattaatg    25200 gggaagagcc tctatattaa caattaaggc tgcagcattg attacttcaa acaacaaaca   25260
ttttaattca agcattaacc tataactcaa gtaagttttt tttttttttt ttttgagaaa   25320
gggaggttgt ttatttgcct gaattgagtc aaaaatattt ttgaaacatc atgtactcat   25380
ttaaatgata acatctttat tgtttcattc ttttaaaaaa tatctactta attacacagt   25440
tgaaggaaat tgtagattat atggaactta tttcttaata tattacagtt ttgttataat   25500
aacattctgg ggatcaggcc aggaaactgt gtcatagata aagctttgaa ataatgagat   25560
ccttatgttt actagaaatt ttggattgag atctatgtgg tctgtgacat attgcaaagt   25620
tcaaggaaaa ttcgtaggca tggaatttct caaactgaaa atccctccca ctgtccacct   25680
catcacatgc acacattcta ctcttaccca cccactccac cccttgcaaa agtacagata   25740
tatgaatgtc tcaaaccat gggctcatct tctagaagct tcaatgttat ttgaagattt    25800
gggcagagga agttaagaaa tatgaaatag cttacatatg agttttaata gtgaaacaaa   25860
catggatgta ttctgaagta gaatgcaaaa tttgagtgca ttttttttt tttgagactg     25920 agtctggctc tgtcgcccag gctggagtgc agtggccgga tctcagctca ctgcaagctc   25980
cacctcccgg gttacgcca ttctcctgcc tcagcctccc gagtagctgg gaccacaggc     26040
gcccgccact tcgcccggct agtttgtttg tattttttag tagagatggg gtttcaccgt   26100
gttagccagg gannnnnnn nnnnnnnnn nnnnnnnnn nnnnnnnnn nnnnccatt         26160
```

```
gagtgcattt ttaaagataa atcagaaaac ttcgaaaaac tatcagattg gccggacatg   26220
gtggcttatg cctgtaatcc tagcactttg ggaggctgag gtgggtggat cacgaggtca   26280
ggagatcgag accatcctgc caacatggtg aaacccatc tctactaagt atacaaaaat   26340
tagctgggcg tgacagcacg tgcctgtaat cccagctact tgggaggctg aggcaggaga   26400
atcgcttgaa cccgggaggt ggaggttgca gtgagtcaag atcacaccac tgcacttcag   26460
cttggtgaca gagctagact ccatatcaaa aaaaaaaaa aaaaaagaa gtcagattgt   26520 tcctacaccc agtgcttcta taccacactc ctactagggg gcatcagtgg aaatggttaa   26580
ggagatgttt agtgtgtatt gtctgccaag cactgttaac actgtcctag aaacattgct   26640
gtacaagtag aatgtgagca aattatgtat tgaaatggtt cctctccctg caggtctttc   26700
agctgaaacc tggcttatct ctcaggagta cttttccttgc acagttttta cttgtccttc   26760
acagaaaagc cttgacacta ataaaatata tagaagatga tacgtgagta caactcctac   26820
atggaggaaa aaccttttgt acgttgtttt ttgttttatt tcctttgtac attttctgta   26880
tcataatttt tgcttttttt tttttttttt ttttctccat tactttcagg cagaagggaa   26940
aaaagccctt taaatctctt cggaacctga agatagacct tgatttaaca gcagagggcg   27000
atcttaacat aataatggct ctggctgaga aaattaaacc aggcctacac tcttttatct   27060
ttggaagacc tttctacact agtgtacaag aacgagatgt tctaatgact ttttaaatgt   27120
gtaacttaat aagcctattc catcacaatc gtgatcgctg ctaaagtagc tcggtggtgt   27180
ggggaaacat tcccctggat catactccag agctctgctc ggcagttgca gttaagttag   27240
ttacactaca gttctcacaa gagtctgtga ggggatgtca ggtgcatcat tacattggat   27300
gtctcttttc ctagatttat gcttttggga tacagaccta tgtttacaat ataataggta   27360
ttattgctgt cttttaaata tataataata ggatataaac ttgaccacaa ctgctgtttt   27420
tttgaaatat atgattcatg gtttacatgt attaaggtga aatccgagtt cgcttttaca   27480
gatattagtt gactttctat cttttggcat tctttggtgt gtggaattac tgtaatactt   27540
ctgcaatcaa ctgaaaatta gagcctttaa atgatttcag ttccacagaa agaaagtgag   27600
cttcaacata ggataagctt tagaaagaga attgatcaag cagatgttta attggaattg   27660
attattagat cctgctttgt ggatttagcc ctcgggattc agtctgtaga aatgtctgat   27720
agttctctat agtccctgct catggtgaac cacagttagg atgttttgtt tgttttattg   27780
ttgttgctat tgttgatgtt ctatatagtt gagctctata aaaggaaatt gtattttatg   27840
ttttagtagt tgttgccaac ttttaaatt aattttcatt attttgagc caaattgaaa    27900 tgtgcacctc ctgtgccttt ttttttccttg gaaaatcgaa ttacttggaa gaagttcaga   27960
tttcactggt cagtcgtttt catcttgttt tcttcttgca gagtcttacc atgtacctgc   28020
tttggcaatc attgtaactc tgagattata aaatgcatta gagaatatat taactaataa   28080
gatctttttt ttcaggaaca gaaaatagtt ccttgagtac ttccttctta catttctgcc   28140 catgttttg aagttgttgc catttgcctg caataggcta taaggaatag caggagaaat    28200
tttactgaag tgctattttt ctaggtgcta ctttggcaga gctaagtggt ctgtttcttt   28260 tgtttccttta atgcgtttgg accattttgc tggctgtaaa ataactgatt aatataattc   28320
taacacaata ttgacattgt agtgtacaca aacacaaata ttttatttaa aactggaagt   28380
aacataaaag ggaaaatata tttataagaa aggaataaag gtaatagagc tcttctgtcc   28440
cccagccacc aaatttacac aacaaaatca tatgttctaa tgtgaaaggt cataatagct   28500
ttcccatcat taatcagaaa gatgtggcag cttgatttt tagacaaccc ctgaactaga    28560
```

```
tgactgttgt actgtagctc agtcatttaa aaaatatata aatactatct cgtagtgtcc    28620
catactatgt tttttacatg atagattctt atttaagtgc taactggtta ttttctttgg    28680
ctggtttatt gtactgttat atagaatgta agttgtacag tgaaataagt tattaaagca    28740
tgtgtaaaca ttgttatata tcttttctcc tagatggaga attttgaata aaatatnnnn    28800
nnnnnnnnnn nnnnnnnnnn nnnnnnnnnn nnnnnnnnnn nnnnnnnnnn nnnnnnnnnn    28860
nnnnnnnnnn nnnnnnnnnn nnnnnnnnnn nnnnnnnnnn nnnnnnnnnn nnnnnnnnnn    28920
nnnnnnnnnn nnnnnnnnnn nnnnnnnnnn nnnnnnnnnn nnnnnnnnnn nnnnnnnnnn    28980
nnnnnnnnnn nnnnnnnnnn nnnnnnnnnn nnnnnnnnnn nnnnnnnnnn nnnnnnnnnn    29040
nnnnnnnnnn nnnnnnnnnn nnnnnnnnnn nnnnnnnnnn nnnnnnnnnn nnnnnnnnnn    29100
nnnnnnnnnn nnnnnnnnnn nnnnnnnnnn nnnnnnnnnn nnnnnnnnnn nnnnnnnnnn    29160
nnnnnnnnnn nnnnnnnnnn nnnnnnagaa gactaattga tcatatcact atgattctca    29220
aagaagaacc aaaacttcat ataatactac aaatatgaga tagttacttc tgtagtatat    29280
ttctgtaatg ctacaggtta aacaggtcac tcttatataa cactattttg attttgatgt    29340
agaattgcac aaattgatat ttcttctatg atctgtaggg tatagcttaa agtagcaaaa    29400
acagtccacc acctccagtt aacacacagt aacactatgg gactagtatt attatttcca    29460
ttttacaaag gaggaaacta aagcttaaag atgtgtaata tacagcccaa ggtcacacag    29520
ctggtaaagg tagatttcat cccagacagt tacagtcatt gccgtgggca cagctcctaa    29580
cttattaact ccatgtaact ggtactcagt ttagttgaat tgaaaggaga gtagggaagc    29640
aggtctgttt gcactattca gagcccaagt gtgaatccct gctgtgctgc ttggagaagt    29700
tacttaacct atgcaaggtt cattttttaa atatttgaaa cggaatgata atacatactt    29760
caccagtggg tttaatgaga ccttataaga tcgttagttc agtacctgac cagtgcttca    29820
taaatgcttt ttcatccaat ctgacaatct ctagcttgta attggggcat ttagaacatt    29880
taatatgatt attggcatgg taggttaaag ttgtcatctt gctgttttct ctttgttctt    29940
ttttctcctt tcttttggat tttttttttaa ttttactgtg tcttctctgt tgtcttatta    30000
a                                                                   30001
```

<210> SEQ ID NO 20  
<211> LENGTH: 20  
<212> TYPE: DNA  
<213> ORGANISM: Artificial sequence  
<220> FEATURE:  
<223> OTHER INFORMATION: Synthetic oligonucleotide
<400> SEQUENCE: 20
gccttactct aggaccaaga                                                20

<210> SEQ ID NO 21  
<211> LENGTH: 20  
<212> TYPE: DNA  
<213> ORGANISM: Artificial sequence  
<220> FEATURE:  
<223> OTHER INFORMATION: Synthetic oligonucleotide
<400> SEQUENCE: 21
ctttcctagc gggacaccgt                                                20

<210> SEQ ID NO 22  
<211> LENGTH: 20  
<212> TYPE: DNA

```
<213> ORGANISM: Artificial sequence
<220> FEATURE:
<223> OTHER INFORMATION: Synthetic oligonucleotide

<400> SEQUENCE: 22
aaaagagaag caaccgggca                                                20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
caaaagagaa gcaaccgggc                                                20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccaaaagaga agcaaccggg                                                20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cccaaaagag aagcaaccgg                                                20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tctttcctag cgggacaccg                                                20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ctctttccta gcgggacacc                                                20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tctctttcct agcgggacac                                                20
```

```
<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ctctctttcc tagcgggaca                                                     20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cctctctttc ctagcgggac                                                     20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
acctctcttt cctagcggga                                                     20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
atccaaatgc tccggagata                                                     20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cacctctctt tcctagcggg                                                     20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcacctctct ttcctagcgg                                                     20

<210> SEQ ID NO 35
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 35
cgcacctctc tttcctagcg                                                  20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gcgggacacc gtaggttacg                                                  20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
acgcacctct ctttcctagc                                                  20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gacgcacctc tctttcctag                                                  20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tgacgcacct ctctttccta                                                  20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ttgacgcacc tctctttcct                                                  20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tttgacgcac ctctctttcc                                                  20

```
<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
gtttgacgca cctctctttc                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tgtttgacgc acctctcttt                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgtttgacg cacctctctt                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gctgtttgac gcacctctct                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cgctgtttga cgcacctctc                                               20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
agcgggacac cgtaggttac                                               20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 48
tcgctgtttg acgcacctct                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gtcgctgttt gacgcacctc                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tgtcgctgtt tgacgcacct                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
tggagcccaa atgtgcctta                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
ttgtcgctgt ttgacgcacc                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tctgtctttg gagcccaaat                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
cttgtcgctg tttgacgcac                                               20

<210> SEQ ID NO 55
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 55
acttgtcgct gtttgacgca                                            20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
aacttgtcgc tgtttgacgc                                            20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
gaacttgtcg ctgtttgacg                                            20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggaacttgtc gctgtttgac                                            20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cggaacttgt cgctgtttga                                            20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tagcgggaca ccgtaggtta                                            20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
```
gcggaacttg tcgctgtttg                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
ggcggaactt gtcgctgttt                                               20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gggcggaact tgtcgctgtt                                               20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
tgggcggaac ttgtcgctgt                                               20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
gtgggcggaa cttgtcgctg                                               20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
cgtgggcgga acttgtcgct                                               20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ctagcgggac accgtaggtt                                               20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
cctagcggga caccgtaggt                                          20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
tcctagcggg acaccgtagg                                          20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
gacggctgac acaccaagcg                                          20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ggacggctga cacaccaagc                                          20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gggacggctg acacaccaag                                          20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
agggacggct gacacaccaa                                          20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
cagggacggc tgacacacca                                          20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ttcctagcgg gacaccgtag                                                   20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gcagggacgg ctgacacacc                                                   20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
agcagggacg gctgacacac                                                   20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
cagcagggac ggctgacaca                                                   20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
gcagcaggga cggctgacac                                                   20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
ggcagcaggg acggctgaca                                                   20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 81
tttcctagcg ggacaccgta                                              20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
agaagcaacc gggcagcagg                                              20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
gagaagcaac cgggcagcag                                              20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
agagaagcaa ccgggcagca                                              20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
aagagaagca accgggcagc                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
aaagagaagc aaccgggcag                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
gttttctatg tgcgatgacg                                              20

<210> SEQ ID NO 88
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
tgttttctat gtgcgatgac                                               20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ctgttttcta tgtgcgatga                                               20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
tctgttttct atgtgcgatg                                               20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gtctgttttc tatgtgcgat                                               20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
tgtctgtttt ctatgtgcga                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
ctgtctgttt tctatgtgcg                                               20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
```
tctgtctgtt ttctatgtgc    20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
gtctgtctgt tttctatgtg    20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
cgtctgtctg ttttctatgt    20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
tacaggctgc ggttgtttcc    20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
cccggcccct agcgcgcgac    20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
ccccaaaaga gaagcaaccg    20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
cccccaaaag agaagcaacc    20

<210> SEQ ID NO 101
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 101
gcccccaaaa gagaagcaac					20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102 cgccccaaa agagaagcaa					20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103 ccgccccaa aagagaagca					20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
cccgccccca aaagagaagc					20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
ccccgccccc aaaagagaag					20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
accccgcccc caaaagagaa					20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gaccccgccc ccaaaagaga					20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
agaccccgcc cccaaaagag                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
tagaccccgc ccccaaaaga                                               20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
ctagaccccg cccccaaaag                                               20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
gctagacccc gcccccaaaa                                               20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tgctagaccc cgcccccaaa                                               20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
ttgctagacc ccgcccccaa                                               20

<210> SEQ ID NO 114
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 114
cttgctagac cccgccccca                                                  20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
tcttgctaga ccccgccccc                                                  20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ctcttgctag accccgcccc                                                  20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
gctcttgcta gaccccgccc                                                  20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
tgctcttgct agaccccgcc                                                  20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
ctgctcttgc tagaccccgc                                                  20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
cctgctcttg ctagaccccg                                                  20

```
<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
acctgctctt gctagacccc                                              20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
cacctgctct tgctagaccc                                              20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
acacctgctc ttgctagacc                                              20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
cacacctgct cttgctagac                                              20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
ccacacctgc tcttgctaga                                              20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
cccacacctg ctcttgctag                                              20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 127
acccacacct gctcttgcta                                                  20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
aacccacacc tgctcttgct                                                  20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
aaacccacac ctgctcttgc                                                  20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
taaacccaca cctgctcttg                                                  20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
ctaaacccac acctgctctt                                                  20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
cctaaaccca cacctgctct                                                  20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
tcctaaaccc acacctgctc                                                  20

<210> SEQ ID NO 134
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 134
ctcctaaacc cacacctgct                                                   20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gtacctgttc tgtctttgga                                                   20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
ccatcactga gaagtacctg                                                   20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
ggcataatgt tctgactatc                                                   20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
cctcctaaac ccacacctgc                                                   20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
acctcctaaa cccacacctg                                                   20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
```
cacctcctaa acccacacct                                                    20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
acacctccta aacccacacc                                                    20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
cacacctcct aaacccacac                                                    20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
acacacctcc taaacccaca                                                    20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
cacacacctc ctaaacccac                                                    20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
acacacacct cctaaaccca                                                    20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
aacacacacc tcctaaaccc                                                    20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
aaacacacac ctcctaaacc          20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
aaaacacaca cctcctaaac          20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
aaaaacacac acctcctaaa          20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
caaaaacaca cacctcctaa          20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
acaaaaacac acacctccta          20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
aacaaaaaca cacacctcct          20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
aaacaaaaac acacacctcc          20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aaaacaaaaa cacacacctc                                               20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
gaaaaacaaa aacacacacc                                               20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
ggaaaaacaa aaacacacac                                               20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
tgggaaaaac aaaaacacac                                               20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
gtgggaaaaa caaaaacaca                                               20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
ggtgggaaaa acaaaaacac                                               20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 160
ctgtgagagc aagtagtggg                                           20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
actgtgagag caagtagtgg                                           20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
tactgtgaga gcaagtagtg                                           20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
gtactgtgag agcaagtagt                                           20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
agtactgtga gagcaagtag                                           20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
gagtactgtg agagcaagta                                           20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
cgagtactgt gagagcaagt                                           20

<210> SEQ ID NO 167
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
gcgagtactg tgagagcaag                                              20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
agcgagtact gtgagagcaa                                              20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
cagcgagtac tgtgagagca                                              20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
tcagcgagta ctgtgagagc                                              20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
ctcagcgagt actgtgagag                                              20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
cctcagcgag tactgtgaga                                              20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
```
ccctcagcga gtactgtgag                                          20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
accctcagcg agtactgtga                                          20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
caccctcagc gagtactgtg                                          20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
tcaccctcag cgagtactgt                                          20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
ttcaccctca gcgagtactg                                          20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
gttcaccctc agcgagtact                                          20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
tgttcaccct cagcgagtac                                          20

<210> SEQ ID NO 180
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 180
ttgttcaccc tcagcgagta                                              20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
cttgttcacc ctcagcgagt                                              20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
tcttgttcac cctcagcgag                                              20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
ttcttgttca ccctcagcga                                              20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
tttcttgttc accctcagcg                                              20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
ttttcttgtt caccctcagc                                              20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
cttttcttgt tcaccctcag                                              20
```

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
tcttttcttg ttcaccctca                                        20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
gtcttttctt gttcaccctc                                        20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
ggtcttttct tgttcaccct                                        20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
aggtcttttc ttgttcaccc                                        20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
caggtctttt cttgttcacc                                        20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
tcaggtcttt tcttgttcac                                        20

<210> SEQ ID NO 193
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 193
atcaggtctt ttcttgttca                                          20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
tatcaggtct tttcttgttc                                          20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
ttatcaggtc ttttcttgtt                                          20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
tttatcaggt cttttcttgt                                          20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
ctttatcagg tcttttcttg                                          20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
tctttatcag gtcttttctt                                          20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
atctttatca ggtcttttct                                          20

```
<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
aatctttatc aggtcttttc                                              20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
taatctttat caggtctttt                                              20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
ttaatcttta tcaggtcttt                                              20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
gttaatcttt atcaggtctt                                              20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
ggttaatctt tatcaggtct                                              20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
tggttaatct ttatcaggtc                                              20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 206
ctggttaatc tttatcaggt                                        20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
tctggttaat ctttatcagg                                        20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
ttctggttaa tctttatcag                                        20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
cttctggtta atctttatca                                        20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
tcttctggtt aatctttatc                                        20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
ttcttctggt taatctttat                                        20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
tttcttctgg ttaatcttta                                        20

<210> SEQ ID NO 213
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 213
ttttcttctg gttaatcttt                                              20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
gttttcttct ggttaatctt                                              20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
tgttttcttc tggttaatct                                              20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
ttgttttctt ctggttaatc                                              20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
cttgttttct tctggttaat                                              20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
ccttgttttc ttctggttaa                                              20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
```
tccttgtttt cttctggtta                                               20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
ctccttgttt tcttctggtt                                               20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
cctccttgtt ttcttctggt                                               20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
ccctccttgt tttcttctgg                                               20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
tccctccttg ttttcttctg                                               20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
ttccctcctt gttttcttct                                               20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
tttccctcct tgttttcttc                                               20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
gtttccctcc ttgttttctt					20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
tgtttccctc cttgttttct					20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
ttgtttccct ccttgttttc					20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
gttgtttccc tccttgtttt					20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
ggttgtttcc ctccttgttt					20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
cggttgtttc cctccttgtt					20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
gcggttgttt ccctccttgt					20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
tgcggttgtt tccctccttg                                            20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
ctgcggttgt ttccctcctt                                            20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
gctgcggttg tttccctcct                                            20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
ggctgcggtt gtttccctcc                                            20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
aggctgcggt tgtttccctc                                            20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
caggctgcgg ttgtttccct                                            20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
acaggctgcg gttgtttccc					20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
ctacaggctg cggttgtttc					20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
gctacaggct gcggttgttt					20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
tgctacaggc tgcggttgtt					20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
ttgctacagg ctgcggttgt					20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
cttgctacag gctgcggttg					20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
gcttgctaca ggctgcggtt					20

<210> SEQ ID NO 246

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
agcttgctac aggctgcggt                                          20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
gagcttgcta caggctgcgg                                          20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
agagcttgct acaggctgcg                                          20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
aaaaaacagt agttgtggtc                                          20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
gccaactcag atttcacctt                                          20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
ccagagcttg ctacaggctg                                          20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
```
tccagagctt gctacaggct                                               20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
ttccagagct tgctacaggc                                               20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
gttccagagc ttgctacagg                                               20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
agttccagag cttgctacag                                               20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
gagttccaga gcttgctaca                                               20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
tgagttccag agcttgctac                                               20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
ctgagttcca gagcttgcta                                               20

<210> SEQ ID NO 259
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 259
cctgagttcc agagcttgct                                              20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
tcctgagttc cagagcttgc                                              20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
ctcctgagtt ccagagcttg                                              20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
actcctgagt tccagagctt                                              20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
gactcctgag ttccagagct                                              20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
cgactcctga gttccagagc                                              20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
gcgactcctg agttccagag                                              20
```

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
cgcgactcct gagttccaga                                               20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
gcgcgactcc tgagttccag                                               20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cgcgcgactc ctgagttcca                                               20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
gcgcgcgact cctgagttcc                                               20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
agcgcgcgac tcctgagttc                                               20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
tagcgcgcga ctcctgagtt                                               20

<210> SEQ ID NO 272
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 272
ctagcgcgcg actcctgagt                                          20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
cctagcgcgc gactcctgag                                          20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ccctagcgcg cgactcctga                                          20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
cccctagcgc gcgactcctg                                          20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
gcccctagcg cgcgactcct                                          20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
ggcccctagc gcgcgactcc                                          20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278 cggccccctag cgcgcgactc                                         20

```
<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
ccggccccta gcgcgcgact                                              20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
ccccggcccc tagcgcgcga                                              20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
gccccggccc ctagcgcgcg                                              20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
ggccccggcc cctagcgcgc                                              20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
cggccccggc cctagcgcg                                               20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
ccggccccgg ccctagcgc                                               20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 285
cccggccccg gccctagcg                                                    20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
ccccggcccc ggccctagc                                                    20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
gccccggccc cggccctag                                                    20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
ggccccggcc ccggcccta                                                    20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
acgccccggc cccggccccg                                                   20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
cacgccccgg ccccggcccc                                                   20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
ccacgccccg gccccggccc                                                   20

<210> SEQ ID NO 292
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 292
accacgcccc ggccccggcc                                               20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
gaccacgccc cggccccggc                                               20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
cgaccacgcc ccggccccgg                                               20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
ccgaccacgc cccggccccg                                               20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
cccgaccacg ccccggcccc                                               20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
ccccgaccac gccccggccc                                               20

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
```
gccccgacca cgccccggcc                                                20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
cgccccgacc acgccccggc                                                20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
ccgccccgac cacgccccgg                                                20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
cccgccccga ccacgccccg                                                20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
gcccgccccg accacgcccc                                                20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
ggcccgcccc gaccacgccc                                                20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
gggcccgccc cgaccacgcc                                                20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
cgggcccgcc ccgaccacgc                                          20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
ccgggcccgc cccgaccacg                                          20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
cccgggcccg ccccgaccac                                          20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
ccccgggccc gccccgacca                                          20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
cccccgggcc cgccccgacc                                          20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
gcccccgggc ccgccccgac                                          20

<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
cgcccccggg cccgccccga                                          20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
cccgcccccg ggcccgcccc                                         20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
gcccgccccc gggcccgccc                                         20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
ggcccgcccc cgggcccgcc                                         20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
cgccccgggc ccgcccccgg                                         20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
cccgccccgg gcccgccccc                                         20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
ccccgccccg ggcccgcccc                                         20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 318
gccccgcccc gggcccgccc                                            20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
agccccgccc cgggcccgcc                                            20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
cagccccgcc ccgggcccgc                                            20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
gcagccccgc cccgggcccg                                            20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
cgcagccccg ccccgggccc                                            20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
ctacacacca aagaatgcca                                            20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 324
ggaataaggt cactagttcg                                            20

<210> SEQ ID NO 325
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
cagagcttgc tacaggctgc                                          20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
ccgcagcccc gccccgggcc                                          20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
accgcagccc cgccccgggc                                          20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
aaccgcagcc ccgccccggg                                          20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
caaccgcagc cccgccccgg                                          20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
gcaaccgcag ccccgccccg                                          20

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
```
cgcaaccgca gccccgcccc                                                    20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
ccgcaaccgc agccccgccc                                                    20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
accgcaaccg cagccccgcc                                                    20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
caccgcaacc gcagccccgc                                                    20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
gcaccgcaac cgcagccccg                                                    20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
ggcaccgcaa ccgcagcccc                                                    20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
aggcaccgca accgcagccc                                                    20

<210> SEQ ID NO 338
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 338
caggcaccgc aaccgcagcc                                               20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
gcaggcaccg caaccgcagc                                               20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
cgcaggcacc gcaaccgcag                                               20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
gcgcaggcac cgcaaccgca                                               20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
ggcgcaggca ccgcaaccgc                                               20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
gggcgcaggc accgcaaccg                                               20

<210> SEQ ID NO 344
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 344
tctctctttc ctagcgggac                                               20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
atctctcttt cctagcggga                                            20

<210> SEQ ID NO 346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 346
tatctctctt tcctagcggg                                            20

<210> SEQ ID NO 347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 347
atatctctct ttcctagcgg                                            20

<210> SEQ ID NO 348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 348
gatatctctc tttcctagcg                                            20

<210> SEQ ID NO 349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 349
agatatctct ctttcctagc                                            20

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 350
gagatatctc tctttcctag                                            20

<210> SEQ ID NO 351
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 351
ggagatatct ctctttccta                                           20

<210> SEQ ID NO 352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 352
cggagatatc tctctttcct                                           20

<210> SEQ ID NO 353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 353
ccggagatat ctctctttcc                                           20

<210> SEQ ID NO 354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 354
tccggagata tctctctttc                                           20

<210> SEQ ID NO 355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 355
ctccggagat atctctcttt                                           20

<210> SEQ ID NO 356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 356
gctccggaga tatctctctt                                           20

<210> SEQ ID NO 357
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 357
tgctccggag atatctctct                                           20

```
<210> SEQ ID NO 358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 358
atgctccgga gatatctctc                                                   20

<210> SEQ ID NO 359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 359
aatgctccgg agatatctct                                                   20

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 360
tctgctcttg ctagaccccg                                                   20

<210> SEQ ID NO 361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 361
atctgctctt gctagacccc                                                   20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 362
tatctgctct tgctagaccc                                                   20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 363
atatctgctc ttgctagacc                                                   20

<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 364
gatatctgct cttgctagac                                               20

<210> SEQ ID NO 365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 365
agatatctgc tcttgctaga                                               20

<210> SEQ ID NO 366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 366
gagatatctg ctcttgctag                                               20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 367
ggagatatct gctcttgcta                                               20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 368
cggagatatc tgctcttgct                                               20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 369
ccggagatat ctgctcttgc                                               20

<210> SEQ ID NO 370
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 370
tccggagata tctgctcttg                                               20

<210> SEQ ID NO 371
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 371
ctccggagat atctgctctt                                        20

<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 372
gctccggaga tatctgctct                                        20

<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 373
tgctccggag atatctgctc                                        20

<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 374
atgctccgga gatatctgct                                        20

<210> SEQ ID NO 375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 375
aatgctccgg agatatctgc                                        20

<210> SEQ ID NO 376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 376
aaatgctccg gagatatctg                                        20

<210> SEQ ID NO 377
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 377
```

-continued tgctccggag atatcaagcg                                    20

<210> SEQ ID NO 378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 378
atgctccgga gatatcaagc                                    20

<210> SEQ ID NO 379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 379
aatgctccgg agatatcaag                                    20

<210> SEQ ID NO 380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 380
aaatgctccg gagatatcaa                                    20

<210> SEQ ID NO 381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 381
caaatgctcc ggagatatca                                    20

<210> SEQ ID NO 382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 382
ggtaacttca aactcttggg                                    20

<210> SEQ ID NO 383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 383
gccatgattt cttgtctggg                                    20

<210> SEQ ID NO 384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 384
tctcctaaac ccacacctgc                                              20

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 385
atctcctaaa cccacacctg                                              20

<210> SEQ ID NO 386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 386
tatctcctaa acccacacct                                              20

<210> SEQ ID NO 387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 387
atatctccta aacccacacc                                              20

<210> SEQ ID NO 388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 388
gatatctcct aaacccacac                                              20

<210> SEQ ID NO 389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 389
agatatctcc taaacccaca                                              20

<210> SEQ ID NO 390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 390
gagatatctc ctaaacccac                                              20

```
<210> SEQ ID NO 391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 391
ggagatatct cctaaaccca                                                 20

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 392
cggagatatc tcctaaaccc                                                 20

<210> SEQ ID NO 393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 393
ccggagatat ctcctaaacc                                                 20

<210> SEQ ID NO 394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 394
tccggagata tctcctaaac                                                 20

<210> SEQ ID NO 395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 395
ctccggagat atctcctaaa                                                 20

<210> SEQ ID NO 396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 396
gctccggaga tatctcctaa                                                 20

<210> SEQ ID NO 397
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 397
tgctccggag atatctccta					20

<210> SEQ ID NO 398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 398
atgctccgga gatatctcct					20

<210> SEQ ID NO 399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 399
aatgctccgg agatatctcc					20

<210> SEQ ID NO 400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 400
aaatgctccg gagatatctc					20

<210> SEQ ID NO 401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 401
gggacactac aaggtagtat					20

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409
<400> SEQUENCE: 409
000

<210> SEQ ID NO 410
<400> SEQUENCE: 410
000

<210> SEQ ID NO 411
<400> SEQUENCE: 411
000

<210> SEQ ID NO 412
<400> SEQUENCE: 412
000

<210> SEQ ID NO 413
<400> SEQUENCE: 413
000

<210> SEQ ID NO 414
<400> SEQUENCE: 414
000

<210> SEQ ID NO 415
<400> SEQUENCE: 415
000

<210> SEQ ID NO 416
<400> SEQUENCE: 416
000

<210> SEQ ID NO 417
<400> SEQUENCE: 417
000

<210> SEQ ID NO 418
<400> SEQUENCE: 418
000

<210> SEQ ID NO 419
<400> SEQUENCE: 419
000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428

```
<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439
```

000

<210> SEQ ID NO 440

<400> SEQUENCE: 440

000

<210> SEQ ID NO 441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 441
tcacattatc caaatgctcc                                            20

<210> SEQ ID NO 442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 442
ctgtcacatt atccaaatgc                                            20

<210> SEQ ID NO 443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 443
caactgtcac attatccaaa                                            20

<210> SEQ ID NO 444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 444
ttccaactgt cacattatcc                                            20

<210> SEQ ID NO 445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 445
tgcattccaa ctgtcacatt                                            20

<210> SEQ ID NO 446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 446

```
cactgcattc caactgtcac                                                        20

<210> SEQ ID NO 447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 447
catcactgca ttccaactgt                                                        20

<210> SEQ ID NO 448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 448
cgacatcact gcattccaac                                                        20

<210> SEQ ID NO 449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 449
agtcgacatc actgcattcc                                                        20

<210> SEQ ID NO 450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 450
aagagtcgac atcactgcat                                                        20

<210> SEQ ID NO 451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 451
gcaaagagtc gacatcactg                                                        20

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 452
tgggcaaaga gtcgacatca                                                        20

<210> SEQ ID NO 453
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 453
cggtgggcaa agagtcgaca                                                    20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 454
tggcggtggg caaagagtcg                                                    20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 455
gagatggcgg tgggcaaaga                                                    20

<210> SEQ ID NO 456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 456
ctggagatgg cggtgggcaa                                                    20

<210> SEQ ID NO 457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 457
acagctggag atggcggtgg                                                    20

<210> SEQ ID NO 458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 458
gcaacagctg gagatggcgg                                                    20

<210> SEQ ID NO 459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 459
ttggcaacag ctggagatgg                                                    20
```

<210> SEQ ID NO 460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 460
gtcttggcaa cagctggaga                                               20

<210> SEQ ID NO 461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 461
tctgtcttgg caacagctgg                                               20

<210> SEQ ID NO 462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 462
tctctgtctt ggcaacagct                                               20

<210> SEQ ID NO 463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 463
gcaatctctg tcttggcaac                                               20

<210> SEQ ID NO 464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 464
agcaatctct gtcttggcaa                                               20

<210> SEQ ID NO 465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 465
aaagcaatct ctgtcttggc                                               20

<210> SEQ ID NO 466
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 466
cttaaagcaa tctctgtctt                                    20

<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 467
ccacttaaag caatctctgt                                    20

<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 468
agctgctaat aaaggtgatt                                    20

<210> SEQ ID NO 469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 469
agtagctgct aataaaggtg                                    20

<210> SEQ ID NO 470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 470
aaaagtagct gctaataaag                                    20

<210> SEQ ID NO 471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 471
agcaaaagta gctgctaata                                    20

<210> SEQ ID NO 472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 472
gtaagcaaaa gtagctgcta                                    20

```
<210> SEQ ID NO 473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 473
ccagtaagca aaagtagctg                                                  20

<210> SEQ ID NO 474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 474
gtcccagtaa gcaaaagtag                                                  20

<210> SEQ ID NO 475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 475
tgtcccagta agcaaaagta                                                  20

<210> SEQ ID NO 476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 476
attgtcccag taagcaaaag                                                  20

<210> SEQ ID NO 477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 477
atattgtccc agtaagcaaa                                                  20

<210> SEQ ID NO 478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 478
aatattgtcc cagtaagcaa                                                  20

<210> SEQ ID NO 479
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 479
aagaatattg tcccagtaag                                           20

<210> SEQ ID NO 480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 480
accaagaata ttgtcccagt                                           20

<210> SEQ ID NO 481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 481
aggaccaaga atattgtccc                                           20

<210> SEQ ID NO 482
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 482
tctaggacca agaatattgt                                           20

<210> SEQ ID NO 483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 483
tactctagga ccaagaatat                                           20

<210> SEQ ID NO 484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 484
ccttactcta ggaccaagaa                                           20

<210> SEQ ID NO 485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 485
gtgccttact ctaggaccaa                                           20

<210> SEQ ID NO 486
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 486
aatgtgcctt actctaggac                                            20

<210> SEQ ID NO 487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 487
agcccaaatg tgccttactc                                            20

<210> SEQ ID NO 488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 488
ctttggagcc caaatgtgcc                                            20

<210> SEQ ID NO 489
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 489
tgtctttgga gcccaaatgt                                            20

<210> SEQ ID NO 490
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 490
ttctgtcttt ggagcccaaa                                            20

<210> SEQ ID NO 491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 491
gttctgtctt tggagcccaa                                            20

<210> SEQ ID NO 492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 492
```
ctgttctgtc tttggagccc                                          20

<210> SEQ ID NO 493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 493
tacctgttct gtctttggag                                          20

<210> SEQ ID NO 494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 494
aagtacctgt tctgtctttg                                          20

<210> SEQ ID NO 495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 495
gagaagtacc tgttctgtct                                          20

<210> SEQ ID NO 496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 496
actgagaagt acctgttctg                                          20

<210> SEQ ID NO 497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 497
tcactgagaa gtacctgttc                                          20

<210> SEQ ID NO 498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 498
atcactgaga agtacctgtt                                          20

<210> SEQ ID NO 499
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 499
tccatcactg agaagtacct                                              20

<210> SEQ ID NO 500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 500
tttctccatc actgagaagt                                              20

<210> SEQ ID NO 501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 501
ttatttctcc atcactgaga                                              20

<210> SEQ ID NO 502
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 502
aagttatttc tccatcactg                                              20

<210> SEQ ID NO 503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 503
gaaaagttat ttctccatca                                              20

<210> SEQ ID NO 504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 504
ggttggcaag aaaagttatt                                              20

<210> SEQ ID NO 505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 505
tgtggttggc aagaaaagtt                                              20
```

<210> SEQ ID NO 506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 506
gagtgtggtt ggcaagaaaa                                               20

<210> SEQ ID NO 507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 507
ttagagtgtg gttggcaaga                                               20

<210> SEQ ID NO 508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 508
catttagagt gtggttggca                                               20

<210> SEQ ID NO 509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 509
ccatttagag tgtggttggc                                               20

<210> SEQ ID NO 510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 510
tttctccatt tagagtgtgg                                               20

<210> SEQ ID NO 511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 511
ggatttctcc atttagagtg                                               20

<210> SEQ ID NO 512
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 512
cgccaccgcc tgcgcctccg                                           20

<210> SEQ ID NO 513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 513
actcgccacc gcctgcgcct                                           20

<210> SEQ ID NO 514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 514
tccactcgcc accgcctgcg                                           20

<210> SEQ ID NO 515
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 515
atatccactc gccaccgcct                                           20

<210> SEQ ID NO 516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 516
gagatatcca ctcgccaccg                                           20

<210> SEQ ID NO 517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 517
ttcgaaggat ttctccattt                                           20

<210> SEQ ID NO 518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 518
catttcgaag gatttctcca                                           20

<210> SEQ ID NO 519
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 519
ctgcatttcg aaggatttct                                           20

<210> SEQ ID NO 520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 520
tctctgcatt tcgaaggatt                                           20

<210> SEQ ID NO 521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 521
cactctctgc atttcgaagg                                           20

<210> SEQ ID NO 522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 522
caccactctc tgcatttcga                                           20

<210> SEQ ID NO 523
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 523
agcaccactc tctgcatttc                                           20

<210> SEQ ID NO 524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 524
tagcaccact ctctgcattt                                           20

<210> SEQ ID NO 525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 525
```
ctatagcacc actctctgca                                          20

<210> SEQ ID NO 526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 526
catctatagc accactctct                                          20

<210> SEQ ID NO 527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 527
actttacatc tatagcacca                                          20

<210> SEQ ID NO 528
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 528
aaaactttac atctatagca                                          20

<210> SEQ ID NO 529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 529
aagacaaaaa actttacatc                                          20

<210> SEQ ID NO 530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 530
caagacaaaa aactttacat                                          20

<210> SEQ ID NO 531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 531
gacaagacaa aaactttac                                           20

<210> SEQ ID NO 532
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 532
tcagacaaga caaaaaactt                                                    20

<210> SEQ ID NO 533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 533
tttcagacaa gacaaaaaac                                                    20

<210> SEQ ID NO 534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 534
cttttcagac aagacaaaaa                                                    20

<210> SEQ ID NO 535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 535
tcccttttca gacaagacaa                                                    20

<210> SEQ ID NO 536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 536
cactcccttt tcagacaaga                                                    20

<210> SEQ ID NO 537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 537
aatcactccc ttttcagaca                                                    20

<210> SEQ ID NO 538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 538
aataatcact cccttttcag                                                    20
```

<210> SEQ ID NO 539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 539
acaataatca ctcccttttc                                               20

<210> SEQ ID NO 540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 540
aacaataatc actcccthtt                                               20

<210> SEQ ID NO 541
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 541
tgaaacaata atcactccct                                               20

<210> SEQ ID NO 542
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 542
taatgaaaca ataatcactc                                               20

<210> SEQ ID NO 543
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 543
gattaatgaa acaataatca                                               20

<210> SEQ ID NO 544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 544
tcaaagatta atgaaacaat                                               20

<210> SEQ ID NO 545
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 545
ccatcaaaga ttaatgaaac    20

<210> SEQ ID NO 546
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 546
tttccatcaa agattaatga    20

<210> SEQ ID NO 547
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 547
cagtttccat caaagattaa    20

<210> SEQ ID NO 548
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 548
ttccagtttc catcaaagat    20

<210> SEQ ID NO 549
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 549
ccattccagt ttccatcaaa    20

<210> SEQ ID NO 550
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 550
tccccattcc agtttccatc    20

<210> SEQ ID NO 551
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 551
cgatccccat tccagtttcc    20

```
<210> SEQ ID NO 552
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 552
ctgcgatccc cattccagtt                                               20

<210> SEQ ID NO 553
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 553
gtgctgcgat ccccattcca                                               20

<210> SEQ ID NO 554
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 554
tatgtgctgc gatccccatt                                               20

<210> SEQ ID NO 555
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 555
ggaagtataa ttgatagtcc                                               20

<210> SEQ ID NO 556
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 556
tgtggaagta taattgatag                                               20

<210> SEQ ID NO 557
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 557
gtctgtggaa gtataattga                                               20

<210> SEQ ID NO 558
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 558
tctgtctgtg gaagtataat                                           20

<210> SEQ ID NO 559
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 559
agttctgtct gtggaagtat                                           20

<210> SEQ ID NO 560
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 560
ctaagttctg tctgtggaag                                           20

<210> SEQ ID NO 561
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 561
aaactaagtt ctgtctgtgg                                           20

<210> SEQ ID NO 562
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 562
tagaaactaa gttctgtctg                                           20

<210> SEQ ID NO 563
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 563
aggtagaaac taagttctgt                                           20

<210> SEQ ID NO 564
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 564
gggaggtaga aactaagttc                                           20

<210> SEQ ID NO 565
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 565
agtgggaggt agaaactaag                                               20

<210> SEQ ID NO 566
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 566
tgaagtggga ggtagaaact                                               20

<210> SEQ ID NO 567
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 567
ctatgaagtg ggaggtagaa                                               20

<210> SEQ ID NO 568
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 568
actctatgaa gtgggaggta                                               20

<210> SEQ ID NO 569
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 569
acactctatg aagtgggagg                                               20

<210> SEQ ID NO 570
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 570
cacactctat gaagtgggag                                               20

<210> SEQ ID NO 571
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 571
```

-continued acacactcta tgaagtggga                                           20

<210> SEQ ID NO 572
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 572
acacacactc tatgaagtgg                                           20

<210> SEQ ID NO 573
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 573
tcaacacaca ctctatgaag                                           20

<210> SEQ ID NO 574
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 574
ctatcaacac acactctatg                                           20

<210> SEQ ID NO 575
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 575
aatctatcaa cacacactct                                           20

<210> SEQ ID NO 576
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 576
gttaatctat caacacacac                                           20

<210> SEQ ID NO 577
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 577
gtgttaatct atcaacacac                                           20

<210> SEQ ID NO 578
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 578
tgtgttaatc tatcaacaca                                                 20

<210> SEQ ID NO 579
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 579
tatgtgttaa tctatcaaca                                                 20

<210> SEQ ID NO 580
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 580
atatgtgtta atctatcaac                                                 20

<210> SEQ ID NO 581
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 581
attatatgtg ttaatctatc                                                 20

<210> SEQ ID NO 582
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 582
cggattatat gtgttaatct                                                 20

<210> SEQ ID NO 583
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 583
ttccggatta tatgtgttaa                                                 20

<210> SEQ ID NO 584
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 584
cctttccgga ttatatgtgt                                                 20
```

<210> SEQ ID NO 585
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 585
cttcctttcc ggattatatg                                               20

<210> SEQ ID NO 586
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 586
attcttcctt tccggattat                                               20

<210> SEQ ID NO 587
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 587
catattcttc ctttccggat                                               20

<210> SEQ ID NO 588
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 588
atccatattc ttcctttccg                                               20

<210> SEQ ID NO 589
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 589
atgcatccat attcttcctt                                               20

<210> SEQ ID NO 590
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 590
ttatgcatcc atattcttcc                                               20

<210> SEQ ID NO 591
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 591
tccttatgca tccatattct                                           20

<210> SEQ ID NO 592
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 592
ctttccttat gcatccatat                                           20

<210> SEQ ID NO 593
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 593
tgtctttcct tatgcatcca                                           20

<210> SEQ ID NO 594
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 594
aggacctccc tcctgtttct                                           20

<210> SEQ ID NO 595
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 595
agaagtaatg ccagacagat                                           20

<210> SEQ ID NO 596
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 596
ctttgtttct ctgaaagcaa                                           20

<210> SEQ ID NO 597
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 597
gtggttggtc cactgctatt                                           20

<210> SEQ ID NO 598

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 598
ttgagggaag ccaagattca                                           20

<210> SEQ ID NO 599
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 599
agagctgtac aattatttta                                           20

<210> SEQ ID NO 600
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 600
ggtaatgaca ctactgctgt                                           20

<210> SEQ ID NO 601
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 601
gatcctaatc ctgtctatgc                                           20

<210> SEQ ID NO 602
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 602
acttgtgggt tgaattgtgt                                           20

<210> SEQ ID NO 603
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 603
taccttatgc atccatattc                                           20

<210> SEQ ID NO 604
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 604
```
gatgttcact gcatataatt 20

<210> SEQ ID NO 605
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 605
ccagatgtat ttgtatctaa 20

<210> SEQ ID NO 606
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 606
taatgtggag ctaccatttc 20

<210> SEQ ID NO 607
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 607
gctcccaaga agaatccagg 20

<210> SEQ ID NO 608
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 608
acttacacat agtagtaagc 20

<210> SEQ ID NO 609
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 609
aaagagacca aaggctacat 20

<210> SEQ ID NO 610
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 610
ggaattctct tgggaaccat 20

<210> SEQ ID NO 611
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 611
tcttgtcttt ccttatgcat                                               20

<210> SEQ ID NO 612
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 612
ttttcttgtc tttccttatg                                               20

<210> SEQ ID NO 613
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 613
tggacatttt cttgtctttc                                               20

<210> SEQ ID NO 614
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 614
ttctggacat tttcttgtct                                               20

<210> SEQ ID NO 615
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 615
atcttctgga cattttcttg                                               20

<210> SEQ ID NO 616
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 616
taatcttctg gacattttct                                               20

<210> SEQ ID NO 617
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 617
aagataatct tctggacatt                                               20
```

```
<210> SEQ ID NO 618
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 618
tctaagataa tcttctggac                                           20

<210> SEQ ID NO 619
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 619
ccttctaaga taatcttctg                                           20

<210> SEQ ID NO 620
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 620
gtgccttcta agataatctt                                           20

<210> SEQ ID NO 621
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 621
tctgtgcctt ctaagataat                                           20

<210> SEQ ID NO 622
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 622
ctctctgtgc cttctaagat                                           20

<210> SEQ ID NO 623
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 623
attctctctg tgccttctaa                                           20

<210> SEQ ID NO 624
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 624
tccattctct ctgtgccttc                                        20

<210> SEQ ID NO 625
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 625
tcttccattc tctctgtgcc                                        20

<210> SEQ ID NO 626
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 626
tgatcttcca ttctctctgt                                        20

<210> SEQ ID NO 627
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 627
gaccctgatc ttccattctc                                        20

<210> SEQ ID NO 628
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 628
tctgaccctg atcttccatt                                        20

<210> SEQ ID NO 629
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 629
tactctgacc ctgatcttcc                                        20

<210> SEQ ID NO 630
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 630
taatactctg accctgatct                                        20

```
<210> SEQ ID NO 631
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 631
gaataatact ctgaccctga                                               20

<210> SEQ ID NO 632
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 632
gcattggaat aatactctga                                               20

<210> SEQ ID NO 633
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 633
taagcattgg aataatactc                                               20

<210> SEQ ID NO 634
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 634
cagtaagcat tggaataata                                               20

<210> SEQ ID NO 635
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 635
ctccagtaag cattggaata                                               20

<210> SEQ ID NO 636
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 636
cttctccagt aagcattgga                                               20

<210> SEQ ID NO 637
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 637
tcacttctcc agtaagcatt                                               20

<210> SEQ ID NO 638
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 638
gaatcacttc tccagtaagc                                               20

<210> SEQ ID NO 639
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 639
caggaatcac ttctccagta                                               20

<210> SEQ ID NO 640
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 640
ttacaggaat cacttctcca                                               20

<210> SEQ ID NO 641
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 641
ccattacagg aatcacttct                                               20

<210> SEQ ID NO 642
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 642
aagcagttcc attacaggaa                                               20

<210> SEQ ID NO 643
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 643
tgaaagcagt tccattacag                                               20

<210> SEQ ID NO 644
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 644
agatgaaagc agttccatta                                               20

<210> SEQ ID NO 645
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 645
catagatgaa agcagttcca                                               20

<210> SEQ ID NO 646
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 646
tttcatagat gaaagcagtt                                               20

<210> SEQ ID NO 647
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 647
gtgtgatttc atagatgaaa                                               20

<210> SEQ ID NO 648
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 648
cactgtgtga tttcatagat                                               20

<210> SEQ ID NO 649
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 649
gaacactgtg tgatttcata                                               20

<210> SEQ ID NO 650
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 650
```
caggaacact gtgtgatttc                                        20

<210> SEQ ID NO 651
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 651
tttcttcagg aacactgtgt                                        20

<210> SEQ ID NO 652
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 652
ctatttcttc aggaacactg                                        20

<210> SEQ ID NO 653
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 653
tatctatttc ttcaggaaca                                        20

<210> SEQ ID NO 654
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 654
ctatatctat ttcttcagga                                        20

<210> SEQ ID NO 655
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 655
cagctatatc tatttcttca                                        20

<210> SEQ ID NO 656
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 656
tatcagctat atctatttct                                        20

<210> SEQ ID NO 657
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 657
ctgtatcagc tatatctatt                                          20

<210> SEQ ID NO 658
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 658
gtactgtatc agctatatct                                          20

<210> SEQ ID NO 659
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 659
tgagtactgt atcagctata                                          20

<210> SEQ ID NO 660
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 660
cattgagtac tgtatcagct                                          20

<210> SEQ ID NO 661
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 661
catcattgag tactgtatca                                          20

<210> SEQ ID NO 662
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 662
catcatcatt gagtactgta                                          20

<210> SEQ ID NO 663
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 663
tatcatcatc attgagtact                                          20
```

```
<210> SEQ ID NO 664
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 664
caatatcatc atcattgagt                                               20

<210> SEQ ID NO 665
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 665
gtcaccaata tcatcatcat                                               20

<210> SEQ ID NO 666
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 666
ttgagaagaa agccttcatg                                               20

<210> SEQ ID NO 667
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 667
actatactga aatgtaaata                                               20

<210> SEQ ID NO 668
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 668
tatcaaactg gaacacagga                                               20

<210> SEQ ID NO 669
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 669
tgggcaaaag cctttaaaa                                                20

<210> SEQ ID NO 670
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 670
gcaaacatag taaaaaatta                                          20

<210> SEQ ID NO 671
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 671
ttctcctgat tttaagagtt                                          20

<210> SEQ ID NO 672
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 672
aagaatgact tgcacttttc                                          20

<210> SEQ ID NO 673
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 673
aaagataact tcacagaaaa                                          20

<210> SEQ ID NO 674
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 674
ctttctactt tagggaaaaa                                          20

<210> SEQ ID NO 675
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 675
tttttcaata gacatgttct                                          20

<210> SEQ ID NO 676
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 676
cttgtctttc ctgagcaaga                                          20

<210> SEQ ID NO 677

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 677
acctgatctt ccattctctc                                               20

<210> SEQ ID NO 678
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 678
ctccataaaa gctccattaa                                               20

<210> SEQ ID NO 679
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 679
tgtttactga tttaactctt                                               20

<210> SEQ ID NO 680
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 680
aacagaaaaa aaaagggagc                                               20

<210> SEQ ID NO 681
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 681
gtaccttaaa gaacatatca                                               20

<210> SEQ ID NO 682
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 682
aaatgtaaat tgcatgagtc                                               20

<210> SEQ ID NO 683
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 683
```
gggtaagaaa tatcactgac                                                      20

<210> SEQ ID NO 684
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 684
aaccatgctt ctcaaactct                                                      20

<210> SEQ ID NO 685
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 685
aagaacttct ctgctttaca                                                      20

<210> SEQ ID NO 686
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 686
aatggaagta aaagtgaaga                                                      20

<210> SEQ ID NO 687
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 687
aacagccatg tttaaaatat                                                      20

<210> SEQ ID NO 688
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 688
ttaaagtatc atctgtctca                                                      20

<210> SEQ ID NO 689
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 689
caatttggta aaggagatca                                                      20

<210> SEQ ID NO 690
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 690
acacagaata actgtctctg         20

<210> SEQ ID NO 691
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 691
gcttattgac cagcaaataa         20

<210> SEQ ID NO 692
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 692
cccagtaaaa gcagaatttt         20

<210> SEQ ID NO 693
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 693
attaatagta gtcaacttaa         20

<210> SEQ ID NO 694
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 694
acttgaactt ctcagcagta         20

<210> SEQ ID NO 695
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 695
agaagaggct ctaaaagaaa         20

<210> SEQ ID NO 696
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 696
aaaggcaact cctccttttc         20

<210> SEQ ID NO 697
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 697
acagtattgt tcaaaataaa                                                   20

<210> SEQ ID NO 698
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 698
cagatgacag ctacaactga                                                   20

<210> SEQ ID NO 699
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 699
gaataatgac tagatccgtg                                                   20

<210> SEQ ID NO 700
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 700
ataattatca tgcctgttta                                                   20

<210> SEQ ID NO 701
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 701
ctttagtaac ctccacaact                                                   20

<210> SEQ ID NO 702
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 702
gaatttaaat gtgatgctac                                                   20

<210> SEQ ID NO 703
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 703
tgtcagaccc agggccattt                                              20

<210> SEQ ID NO 704
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 704
acttatttta tgaaatgatt                                              20

<210> SEQ ID NO 705
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 705
ttttagctaa acatattttt                                              20

<210> SEQ ID NO 706
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 706
cagtctcatc agttttgtga                                              20

<210> SEQ ID NO 707
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 707
tgtaaagtgt ctcaaatatg                                              20

<210> SEQ ID NO 708
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 708
cttgaaattg taattttgaa                                              20

<210> SEQ ID NO 709
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 709
aatcaaaatc agcacatata                                              20

<210> SEQ ID NO 710
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 710
accaaatagg taaggaaaac                                              20

<210> SEQ ID NO 711
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 711
aaagatctcc tttaaaattt                                              20

<210> SEQ ID NO 712
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 712
ctttagagag tatggaatca                                              20

<210> SEQ ID NO 713
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 713
caaagctcac ttttattctt                                              20

<210> SEQ ID NO 714
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 714
acacagtatc aaacaagtct                                              20

<210> SEQ ID NO 715
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 715
aagctgggca ataaaaaata                                              20

<210> SEQ ID NO 716
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 716
ctgaccctgc acaataaagt					20

<210> SEQ ID NO 717
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 717
catctatttc ttcaggaaca					20

<210> SEQ ID NO 718
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 718
gaatattaat aatatacata					20

<210> SEQ ID NO 719
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 719
aggattttgt gtgtgcttat					20

<210> SEQ ID NO 720
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 720
ttttaggaat tataaaagta					20

<210> SEQ ID NO 721
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 721
acacagtttt gtttcaaaag					20

<210> SEQ ID NO 722
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 722
ggaaactaaa tttgtgacta					20

<210> SEQ ID NO 723
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 723
ctcttaacac tcatagtgtg                                          20

<210> SEQ ID NO 724
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 724
gagactaacc taaatgacaa                                          20

<210> SEQ ID NO 725
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 725
caaatgtgaa agctggtcaa                                          20

<210> SEQ ID NO 726
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 726
taacacactg ccttcatttc                                          20

<210> SEQ ID NO 727
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 727
tatctaaaat gcatcaaaaa                                          20

<210> SEQ ID NO 728
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 728
cttgagaaga aagccttcat                                          20

<210> SEQ ID NO 729
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 729
```
ccaaatcttg tcataggtga                                               20

<210> SEQ ID NO 730
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 730
taacacaaat ttaagcaaca                                               20

<210> SEQ ID NO 731
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 731
aaatagcaaa tggaataaca                                               20

<210> SEQ ID NO 732
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 732
aaaccagaat caagcaaggg                                               20

<210> SEQ ID NO 733
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 733
catctacagt acaacttaat                                               20

<210> SEQ ID NO 734
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 734
agatcagtat aaatatgaat                                               20

<210> SEQ ID NO 735
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 735
gtttaagggc acaaactctt                                               20

<210> SEQ ID NO 736
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 736
aggtgtatag agaattcagg                                               20

<210> SEQ ID NO 737
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 737
tactcaatgc ttataacaac                                               20

<210> SEQ ID NO 738
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 738
ggaactaaca tgtaggcact                                               20

<210> SEQ ID NO 739
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 739
cataaaagtg aatactttat                                               20

<210> SEQ ID NO 740
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 740
aggctcttag gttaaacaca                                               20

<210> SEQ ID NO 741
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 741
gctgacactg aacagataca                                               20

<210> SEQ ID NO 742
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 742
catgtagaga gattaagtga                                               20
```

<210> SEQ ID NO 743
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 743
atcatttaat taatgtattt                                              20

<210> SEQ ID NO 744
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 744
gtgagagcaa gtagtggg                                                18

<210> SEQ ID NO 745
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 745
tgtgagagca agtagtgg                                                18

<210> SEQ ID NO 746
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 746
ctgtgagagc aagtagtg                                                18

<210> SEQ ID NO 747
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 747
actgtgagag caagtagt                                                18

<210> SEQ ID NO 748
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 748
tactgtgaga gcaagtag                                                18

<210> SEQ ID NO 749
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 749
gtactgtgag agcaagta                                                   18

<210> SEQ ID NO 750
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 750
agtactgtga gagcaagt                                                   18

<210> SEQ ID NO 751
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 751
gagtactgtg agagcaag                                                   18

<210> SEQ ID NO 752
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 752
cgagtactgt gagagcaa                                                   18

<210> SEQ ID NO 753
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 753
gcgagtactg tgagagca                                                   18

<210> SEQ ID NO 754
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 754
agcgagtact gtgagagc                                                   18

<210> SEQ ID NO 755
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 755
cagcgagtac tgtgagag                                                   18

<210> SEQ ID NO 756
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 756
tcagcgagta ctgtgaga                                              18

<210> SEQ ID NO 757
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 757
ctcagcgagt actgtgag                                              18

<210> SEQ ID NO 758
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 758
cctcagcgag tactgtga                                              18

<210> SEQ ID NO 759
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 759
ccctcagcga gtactgtg                                              18

<210> SEQ ID NO 760
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 760
accctcagcg agtactgt                                              18

<210> SEQ ID NO 761
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 761
caccctcagc gagtactg                                              18

<210> SEQ ID NO 762
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 762
```
tcaccctcag cgagtact                                                 18

<210> SEQ ID NO 763
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 763
ttcaccctca gcgagtac                                                 18

<210> SEQ ID NO 764
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 764
gttcaccctc agcgagta                                                 18

<210> SEQ ID NO 765
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 765
tgttcaccct cagcgagt                                                 18

<210> SEQ ID NO 766
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 766
ttgttcaccc tcagcgag                                                 18

<210> SEQ ID NO 767
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 767
cttgttcacc ctcagcga                                                 18

<210> SEQ ID NO 768
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 768
tcttgttcac cctcagcg                                                 18

<210> SEQ ID NO 769
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 769
ttcttgttca ccctcagc                                                 18

<210> SEQ ID NO 770
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 770
tttcttgttc accctcag                                                 18

<210> SEQ ID NO 771
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 771
ttttcttgtt caccctca                                                 18

<210> SEQ ID NO 772
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 772
cttttcttgt tcaccctc                                                 18

<210> SEQ ID NO 773
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 773
tcttttcttg ttcaccct                                                 18

<210> SEQ ID NO 774
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 774
gtcttttctt gttcaccc                                                 18

<210> SEQ ID NO 775
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 775
ggtcttttct tgttcacc                                                 18
```

<210> SEQ ID NO 776
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 776
aggtcttttc ttgttcac            18

<210> SEQ ID NO 777
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 777
caggtctttt cttgttca            18

<210> SEQ ID NO 778
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 778
tcaggtcttt tcttgttc            18

<210> SEQ ID NO 779
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 779
atcaggtctt tcttgtt             18

<210> SEQ ID NO 780
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 780
tatcaggtct tttcttgt            18

<210> SEQ ID NO 781
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 781
ttatcaggtc ttttcttg            18

<210> SEQ ID NO 782
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 782
tttatcaggt cttttctt                                                          18

<210> SEQ ID NO 783
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 783
aatctttatc aggtcttt                                                          18

<210> SEQ ID NO 784
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 784
taatctttat caggtctt                                                          18

<210> SEQ ID NO 785
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 785
ttaatcttta tcaggtct                                                          18

<210> SEQ ID NO 786
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 786
gttaatcttt atcaggtc                                                          18

<210> SEQ ID NO 787
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 787
ggttaatctt tatcaggt                                                          18

<210> SEQ ID NO 788
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 788
tggttaatct ttatcagg                                                          18

```
<210> SEQ ID NO 789
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 789
ctggttaatc tttatcag                                                  18

<210> SEQ ID NO 790
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 790
tctggttaat ctttatca                                                  18

<210> SEQ ID NO 791
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 791
ttctggttaa tctttatc                                                  18

<210> SEQ ID NO 792
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 792
tccctccttg ttttcttc                                                  18

<210> SEQ ID NO 793
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 793
tttccctcct tgttttct                                                  18

<210> SEQ ID NO 794
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 794
gtttccctcc ttgttttc                                                  18

<210> SEQ ID NO 795
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 795
tgtttccctc cttgtttt                                                   18

<210> SEQ ID NO 796
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 796
ttgtttccct ccttgttt                                                   18

<210> SEQ ID NO 797
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 797
gttgtttccc tccttgtt                                                   18

<210> SEQ ID NO 798
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 798
ggttgtttcc ctccttgt                                                   18

<210> SEQ ID NO 799
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 799
cggttgtttc cctccttg                                                   18

<210> SEQ ID NO 800
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 800
gcggttgttt ccctcctt                                                   18

<210> SEQ ID NO 801
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 801
tgcggttgtt tccctcct                                                   18

<210> SEQ ID NO 802
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 802
ctgcggttgt ttccctcc                                              18

<210> SEQ ID NO 803
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 803
gctgcggttg tttccctc                                              18

<210> SEQ ID NO 804
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 804
ggctgcggtt gtttccct                                              18

<210> SEQ ID NO 805
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 805
aggctgcggt tgtttccc                                              18

<210> SEQ ID NO 806
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 806
caggctgcgg ttgtttcc                                              18

<210> SEQ ID NO 807
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 807
acaggctgcg gttgtttc                                              18

<210> SEQ ID NO 808
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 808
```

-continued tacaggctgc ggttgttt                                        18

<210> SEQ ID NO 809
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 809
ctacaggctg cggttgtt                                        18

<210> SEQ ID NO 810
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 810
gctacaggct gcggttgt                                        18

<210> SEQ ID NO 811
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 811
tgctacaggc tgcggttg                                        18

<210> SEQ ID NO 812
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 812
ttgctacagg ctgcggtt                                        18

<210> SEQ ID NO 813
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 813
cttgctacag gctgcggt                                        18

<210> SEQ ID NO 814
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 814
gcttgctaca ggctgcgg                                        18

<210> SEQ ID NO 815
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 815
agcttgctac aggctgcg                                                     18

<210> SEQ ID NO 816
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 816
gagcttgcta caggctgc                                                     18

<210> SEQ ID NO 817
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 817
agagcttgct acaggctg                                                     18

<210> SEQ ID NO 818
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 818
cagagcttgc tacaggct                                                     18

<210> SEQ ID NO 819
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 819
ccagagcttg ctacaggc                                                     18

<210> SEQ ID NO 820
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 820
tccagagctt gctacagg                                                     18

<210> SEQ ID NO 821
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 821
ttccagagct tgctacag                                                     18
```

```
<210> SEQ ID NO 822
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 822
gttccagagc ttgctaca                                                 18

<210> SEQ ID NO 823
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 823
agttccagag cttgctac                                                 18

<210> SEQ ID NO 824
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 824
gagttccaga gcttgcta                                                 18

<210> SEQ ID NO 825
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 825
tgagttccag agcttgct                                                 18

<210> SEQ ID NO 826
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 826
ctgagttcca gagcttgc                                                 18

<210> SEQ ID NO 827
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 827
cctgagttcc agagcttg                                                 18

<210> SEQ ID NO 828
<211> LENGTH: 18
<212> TYPE: DNA
<213> ORGANISM: Artificial sequence
<220> FEATURE:
<223> OTHER INFORMATION: Synthetic oligonucleotide
```

-continued

<400> SEQUENCE: 828
tcctgagttc cagagctt                                                    18

<210> SEQ ID NO 829
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 829
ctcctgagtt ccagagct                                                    18

<210> SEQ ID NO 830
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 830
actcctgagt tccagagc                                                    18

<210> SEQ ID NO 831
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 831
gactcctgag ttccagag                                                    18

<210> SEQ ID NO 832
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 832
cgactcctga gttccaga                                                    18

<210> SEQ ID NO 833
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 833
gcgactcctg agttccag                                                    18

<210> SEQ ID NO 834
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 834
cgcgactcct gagttcca                                                    18

<210> SEQ ID NO 835

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 835
gcgcgactcc tgagttcc                                              18

<210> SEQ ID NO 836
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 836
cgcgcgactc ctgagttc                                              18

<210> SEQ ID NO 837
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 837
gcgcgcgact cctgagtt                                              18

<210> SEQ ID NO 838
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 838
agcgcgcgac tcctgagt                                              18

<210> SEQ ID NO 839
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 839
tagcgcgcga ctcctgag                                              18

<210> SEQ ID NO 840
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 840
ctagcgcgcg actcctga                                              18

<210> SEQ ID NO 841
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 841
```
cctagcgcgc gactcctg                                                  18

<210> SEQ ID NO 842
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 842
ccctagcgcg cgactcct                                                  18

<210> SEQ ID NO 843
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 843 ccctagcgc gcgactcc                                                   18

<210> SEQ ID NO 844
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 844 gccctagcg cgcgactc                                                   18

<210> SEQ ID NO 845
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 845 ggccctagc gcgcgact                                                   18

<210> SEQ ID NO 846
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 846 cggccctag cgcgcgac                                                   18

<210> SEQ ID NO 847
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 847 ccggcccta gcgcgcga                                                   18

<210> SEQ ID NO 848
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 848
cccggcccct agcgcgcg                                                 18

<210> SEQ ID NO 849
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 849
ccccggcccc tagcgcgc                                                 18

<210> SEQ ID NO 850
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 850
gccccggccc ctagcgcg                                                 18

<210> SEQ ID NO 851
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 851
ggccccggcc cctagcgc                                                 18

<210> SEQ ID NO 852
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 852
cggccccggc ccctagcg                                                 18

<210> SEQ ID NO 853
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 853
ccggccccgg ccctagc                                                  18

<210> SEQ ID NO 854
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 854
cccggccccg gccctag                                                  18
```

<210> SEQ ID NO 855
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 855
ccccggcccc ggccccta                          18

<210> SEQ ID NO 856
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 856
acgccccggc cccggccc                          18

<210> SEQ ID NO 857
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 857
cacgccccgg ccccggcc                          18

<210> SEQ ID NO 858
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 858
ccacgccccg gccccggc                          18

<210> SEQ ID NO 859
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 859
accacgcccc ggccccgg                          18

<210> SEQ ID NO 860
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 860
gaccacgccc cggccccg                          18

<210> SEQ ID NO 861
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 861
cgaccacgcc ccggcccc                                                    18

<210> SEQ ID NO 862
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 862
ccgaccacgc cccggccc                                                    18

<210> SEQ ID NO 863
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 863
cccgaccacg ccccggcc                                                    18

<210> SEQ ID NO 864
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 864
ccccgaccac gccccggc                                                    18

<210> SEQ ID NO 865
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 865
gccccgacca cgccccgg                                                    18

<210> SEQ ID NO 866
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 866
cgccccgacc acgccccg                                                    18

<210> SEQ ID NO 867
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 867
ccgccccgac cacgcccc                                                    18

```
<210> SEQ ID NO 868
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 868
cccgccccga ccacgccc                                                 18

<210> SEQ ID NO 869
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 869
gcccgccccg accacgcc                                                 18

<210> SEQ ID NO 870
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 870
ggcccgcccc gaccacgc                                                 18

<210> SEQ ID NO 871
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 871
gggcccgccc cgaccacg                                                 18

<210> SEQ ID NO 872
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 872
cgggcccgcc ccgaccac                                                 18

<210> SEQ ID NO 873
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 873
ccgggcccgc cccgacca                                                 18

<210> SEQ ID NO 874
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 874
cccgggcccg ccccgacc                                                18

<210> SEQ ID NO 875
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 875
ccccgggccc gccccgac                                                18

<210> SEQ ID NO 876
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 876
agccccgccc cgggcccg                                                18

<210> SEQ ID NO 877
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 877
cagccccgcc ccgggccc                                                18

<210> SEQ ID NO 878
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 878
gcagccccgc ccgggcc                                                 18

<210> SEQ ID NO 879
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 879
cgcagccccg ccccgggc                                                18

<210> SEQ ID NO 880
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 880
ccgcagcccc gccccggg                                                18

<210> SEQ ID NO 881
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 881
accgcagccc cgccccgg                                                   18

<210> SEQ ID NO 882
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 882
aaccgcagcc ccgccccg                                                   18

<210> SEQ ID NO 883
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 883
caaccgcagc cccgcccc                                                   18

<210> SEQ ID NO 884
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 884
gcaaccgcag ccccgccc                                                   18

<210> SEQ ID NO 885
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 885
cgcaaccgca gccccgcc                                                   18

<210> SEQ ID NO 886
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 886
ccgcaaccgc agccccgc                                                   18

<210> SEQ ID NO 887
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 887
```
accgcaaccg cagccccg                          18

<210> SEQ ID NO 888
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 888
caccgcaacc gcagcccc                          18

<210> SEQ ID NO 889
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 889
gcaccgcaac cgcagccc                          18

<210> SEQ ID NO 890
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 890
ggcaccgcaa ccgcagcc                          18

<210> SEQ ID NO 891
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 891
aggcaccgca accgcagc                          18

<210> SEQ ID NO 892
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 892
caggcaccgc aaccgcag                          18

<210> SEQ ID NO 893
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 893
gcaggcaccg caaccgca                          18

<210> SEQ ID NO 894
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 894
cgcaggcacc gcaaccgc                                                    18

<210> SEQ ID NO 895
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 895
gcgcaggcac cgcaaccg                                                    18

<210> SEQ ID NO 896
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 896
ggcgcaggca ccgcaacc                                                    18

<210> SEQ ID NO 897
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 897
gggcgcaggc accgcaac                                                    18

<210> SEQ ID NO 898
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 898
tgagagcaag tagtggg                                                     17

<210> SEQ ID NO 899
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 899
gtgagagcaa gtagtgg                                                     17

<210> SEQ ID NO 900
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 900
tgtgagagca agtagtg                                                     17

<210> SEQ ID NO 901
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 901
ctgtgagagc aagtagt                                                    17

<210> SEQ ID NO 902
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 902
actgtgagag caagtag                                                    17

<210> SEQ ID NO 903
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 903
tactgtgaga gcaagta                                                    17

<210> SEQ ID NO 904
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 904
gtactgtgag agcaagt                                                    17

<210> SEQ ID NO 905
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 905
agtactgtga gagcaag                                                    17

<210> SEQ ID NO 906
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 906
gagtactgtg agagcaa                                                    17

<210> SEQ ID NO 907
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 907
cgagtactgt gagagca                                                      17

<210> SEQ ID NO 908
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 908
gcgagtactg tgagagc                                                      17

<210> SEQ ID NO 909
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 909
agcgagtact gtgagag                                                      17

<210> SEQ ID NO 910
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 910
cagcgagtac tgtgaga                                                      17

<210> SEQ ID NO 911
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 911
tcagcgagta ctgtgag                                                      17

<210> SEQ ID NO 912
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 912
ctcagcgagt actgtga                                                      17

<210> SEQ ID NO 913
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 913
cctcagcgag tactgtg                                                      17

<210> SEQ ID NO 914

-continued

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 914
ccctcagcga gtactgt                                                  17

<210> SEQ ID NO 915
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 915
accctcagcg agtactg                                                  17

<210> SEQ ID NO 916
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 916
caccctcagc gagtact                                                  17

<210> SEQ ID NO 917
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 917
tcaccctcag cgagtac                                                  17

<210> SEQ ID NO 918
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 918
ttcaccctca gcgagta                                                  17

<210> SEQ ID NO 919
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 919
gttcaccctc agcgagt                                                  17

<210> SEQ ID NO 920
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 920
```
tgttcaccct cagcgag                                                  17

<210> SEQ ID NO 921
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 921
ttgttcaccc tcagcga                                                  17

<210> SEQ ID NO 922
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 922
cttgttcacc ctcagcg                                                  17

<210> SEQ ID NO 923
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 923
tcttgttcac cctcagc                                                  17

<210> SEQ ID NO 924
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 924
ttcttgttca ccctcag                                                  17

<210> SEQ ID NO 925
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 925
tttcttgttc accctca                                                  17

<210> SEQ ID NO 926
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 926
ttttcttgtt caccctc                                                  17

<210> SEQ ID NO 927
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 927
cttttcttgt tcaccct                                                    17

<210> SEQ ID NO 928
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 928
tcttttcttg ttcaccc                                                    17

<210> SEQ ID NO 929
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 929
gtcttttctt gttcacc                                                    17

<210> SEQ ID NO 930
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 930
ggtcttttct tgttcac                                                    17

<210> SEQ ID NO 931
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 931
aggtcttttc ttgttca                                                    17

<210> SEQ ID NO 932
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 932
caggtctttt cttgttc                                                    17

<210> SEQ ID NO 933
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 933
tcaggtcttt tcttgtt                                                    17
```

<210> SEQ ID NO 934
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 934
atcaggtctt ttcttgt                                                17

<210> SEQ ID NO 935
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 935
tatcaggtct tttcttg                                                17

<210> SEQ ID NO 936
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 936
ttatcaggtc ttttctt                                                17

<210> SEQ ID NO 937
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 937
atctttatca ggtcttt                                                17

<210> SEQ ID NO 938
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 938
aatctttatc aggtctt                                                17

<210> SEQ ID NO 939
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 939
taatctttat caggtct                                                17

<210> SEQ ID NO 940
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 940 ttaatctttatcaggtc                                               17

<210> SEQ ID NO 941
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 941 gttaatctttatcaggt                                               17

<210> SEQ ID NO 942
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 942 ggttaatctttatcagg                                               17

<210> SEQ ID NO 943
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 943 tggttaatctttatcag                                               17

<210> SEQ ID NO 944
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 944 ctggttaatctttatca                                               17

<210> SEQ ID NO 945
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 945 tctggttaatctttatc                                               17

<210> SEQ ID NO 946
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 946 ccctccttgttttcttc                                               17

```
<210> SEQ ID NO 947
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 947
tccctccttg ttttctt                                                17

<210> SEQ ID NO 948
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 948
ttccctcctt gttttct                                                17

<210> SEQ ID NO 949
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 949
tttccctcct tgttttc                                                17

<210> SEQ ID NO 950
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 950
gtttccctcc ttgtttt                                                17

<210> SEQ ID NO 951
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 951
tgtttccctc cttgttt                                                17

<210> SEQ ID NO 952
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 952
ttgtttccct ccttgtt                                                17

<210> SEQ ID NO 953
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 953
ggttgtttcc ctccttg                                                    17

<210> SEQ ID NO 954
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 954
cggttgtttc cctcctt                                                    17

<210> SEQ ID NO 955
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 955
gcggttgttt ccctcct                                                    17

<210> SEQ ID NO 956
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 956
tgcggttgtt tccctcc                                                    17

<210> SEQ ID NO 957
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 957
ctgcggttgt ttccctc                                                    17

<210> SEQ ID NO 958
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 958
gctgcggttg tttccct                                                    17

<210> SEQ ID NO 959
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 959
ggctgcggtt gtttccc                                                    17

<210> SEQ ID NO 960
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 960
aggctgcggt tgtttcc                                                    17

<210> SEQ ID NO 961
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 961
caggctgcgg ttgtttc                                                    17

<210> SEQ ID NO 962
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 962
acaggctgcg gttgttt                                                    17

<210> SEQ ID NO 963
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 963
tacaggctgc ggttgtt                                                    17

<210> SEQ ID NO 964
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 964
ctacaggctg cggttgt                                                    17

<210> SEQ ID NO 965
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 965
gctacaggct gcggttg                                                    17

<210> SEQ ID NO 966
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 966
```
tgctacaggc tgcggtt                                                    17

<210> SEQ ID NO 967
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 967
ttgctacagg ctgcggt                                                    17

<210> SEQ ID NO 968
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 968
cttgctacag gctgcgg                                                    17

<210> SEQ ID NO 969
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 969
gcttgctaca ggctgcg                                                    17

<210> SEQ ID NO 970
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 970
agcttgctac aggctgc                                                    17

<210> SEQ ID NO 971
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 971
gagcttgcta caggctg                                                    17

<210> SEQ ID NO 972
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 972
agagcttgct acaggct                                                    17

<210> SEQ ID NO 973
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 973
cagagcttgc tacaggc                                                    17

<210> SEQ ID NO 974
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 974
ccagagcttg ctacagg                                                    17

<210> SEQ ID NO 975
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 975
tccagagctt gctacag                                                    17

<210> SEQ ID NO 976
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 976
ttccagagct tgctaca                                                    17

<210> SEQ ID NO 977
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 977
gttccagagc ttgctac                                                    17

<210> SEQ ID NO 978
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 978
agttccagag cttgcta                                                    17

<210> SEQ ID NO 979
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 979
gagttccaga gcttgct                                                    17
```

<210> SEQ ID NO 980
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 980
tgagttccag agcttgc                                                  17

<210> SEQ ID NO 981
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 981
ctgagttcca gagcttg                                                  17

<210> SEQ ID NO 982
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 982
cctgagttcc agagctt                                                  17

<210> SEQ ID NO 983
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 983
tcctgagttc cagagct                                                  17

<210> SEQ ID NO 984
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 984
ctcctgagtt ccagagc                                                  17

<210> SEQ ID NO 985
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 985
actcctgagt tccagag                                                  17

<210> SEQ ID NO 986
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 986
gactcctgag ttccaga                                                17

<210> SEQ ID NO 987
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 987
cgactcctga gttccag                                                17

<210> SEQ ID NO 988
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 988
gcgactcctg agttcca                                                17

<210> SEQ ID NO 989
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 989
cgcgactcct gagttcc                                                17

<210> SEQ ID NO 990
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 990
gcgcgactcc tgagttc                                                17

<210> SEQ ID NO 991
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 991
cgcgcgactc ctgagtt                                                17

<210> SEQ ID NO 992
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 992
gcgcgcgact cctgagt                                                17

<210> SEQ ID NO 993

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 993
agcgcgcgac tcctgag                                                    17

<210> SEQ ID NO 994
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 994
tagcgcgcga ctcctga                                                    17

<210> SEQ ID NO 995
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 995
ctagcgcgcg actcctg                                                    17

<210> SEQ ID NO 996
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 996
cctagcgcgc gactcct                                                    17

<210> SEQ ID NO 997
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 997
ccctagcgcg cgactcc                                                    17

<210> SEQ ID NO 998
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 998
cccctagcgc gcgactc                                                    17

<210> SEQ ID NO 999
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 999
``` gccccctagcg cgcgact 17

<210> SEQ ID NO 1000
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1000
ggcccctagc gcgcgac 17

<210> SEQ ID NO 1001
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1001
cggcccctag cgcgcga 17

<210> SEQ ID NO 1002
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1002 ccggcccta gcgcgcg 17

<210> SEQ ID NO 1003
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1003
cccggcccct agcgcgc 17

<210> SEQ ID NO 1004
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1004
ccccggcccc tagcgcg 17

<210> SEQ ID NO 1005
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1005
gccccggccc ctagcgc 17

<210> SEQ ID NO 1006
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1006 ggcccccggcc cctagcg                                              17

<210> SEQ ID NO 1007
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1007
cggccccggc ccctagc                                               17

<210> SEQ ID NO 1008
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1008
ccggccccgg cccctag                                               17

<210> SEQ ID NO 1009
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1009
cccggccccg gcccta                                                17

<210> SEQ ID NO 1010
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1010
acgccccggc cccggcc                                               17

<210> SEQ ID NO 1011
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1011
cacgccccgg ccccggc                                               17

<210> SEQ ID NO 1012
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1012
ccacgccccg gccccgg                                               17
```

<210> SEQ ID NO 1013
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1013
accacgcccc ggccccg                                                    17

<210> SEQ ID NO 1014
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1014
gaccacgccc cggcccc                                                    17

<210> SEQ ID NO 1015
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1015
cgaccacgcc ccggccc                                                    17

<210> SEQ ID NO 1016
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1016
ccgaccacgc cccggcc                                                    17

<210> SEQ ID NO 1017
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1017
cccgaccacg ccccggc                                                    17

<210> SEQ ID NO 1018
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1018
ccccgaccac gccccgg                                                    17

<210> SEQ ID NO 1019
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1019
gccccgacca cgccccg                                                        17

<210> SEQ ID NO 1020
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1020
cgccccgacc acgcccc                                                        17

<210> SEQ ID NO 1021
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1021
ccgccccgac cacgccc                                                        17

<210> SEQ ID NO 1022
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1022
cccgccccga ccacgcc                                                        17

<210> SEQ ID NO 1023
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1023
gcccgccccg accacgc                                                        17

<210> SEQ ID NO 1024
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1024
ggcccgcccc gaccacg                                                        17

<210> SEQ ID NO 1025
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1025
gggcccgccc cgaccac                                                        17

```
<210> SEQ ID NO 1026
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1026
cgggcccgcc ccgacca                                                    17

<210> SEQ ID NO 1027
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1027
ccgggcccgc cccgacc                                                    17

<210> SEQ ID NO 1028
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1028
cccgggcccg ccccgac                                                    17

<210> SEQ ID NO 1029
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1029
gcagccccgc cccgggc                                                    17

<210> SEQ ID NO 1030
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1030
cgcagccccg ccccggg                                                    17

<210> SEQ ID NO 1031
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1031
ccgcagcccc gccccgg                                                    17

<210> SEQ ID NO 1032
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 1032
accgcagccc cgccccg                                              17

<210> SEQ ID NO 1033
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1033
aaccgcagcc ccgcccc                                              17

<210> SEQ ID NO 1034
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1034
caaccgcagc cccgccc                                              17

<210> SEQ ID NO 1035
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1035
gcaaccgcag ccccgcc                                              17

<210> SEQ ID NO 1036
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1036
cgcaaccgca gccccgc                                              17

<210> SEQ ID NO 1037
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1037
ccgcaaccgc agccccg                                              17

<210> SEQ ID NO 1038
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1038
accgcaaccg cagcccc                                              17

<210> SEQ ID NO 1039
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 1039
caccgcaacc gcagccc                                                  17

<210> SEQ ID NO 1040
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1040
gcaccgcaac cgcagcc                                                  17

<210> SEQ ID NO 1041
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1041
ggcaccgcaa ccgcagc                                                  17

<210> SEQ ID NO 1042
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1042
aggcaccgca accgcag                                                  17

<210> SEQ ID NO 1043
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1043
caggcaccgc aaccgca                                                  17

<210> SEQ ID NO 1044
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1044
gcaggcaccg caaccgc                                                  17

<210> SEQ ID NO 1045
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1045
```
cgcaggcacc gcaaccg                                                    17

<210> SEQ ID NO 1046
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1046
gcgcaggcac cgcaacc                                                    17

<210> SEQ ID NO 1047
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1047
ggcgcaggca ccgcaac                                                    17

<210> SEQ ID NO 1048
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1048
ccactcgcca ccgcctgcgc                                                 20

<210> SEQ ID NO 1049
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1049
tgcattccta agcaatgtgt                                                 20

<210> SEQ ID NO 1050
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1050
cccggccccg gccccggccc                                                 20

<210> SEQ ID NO 1051
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1051
ccccggcccc ggccccggcc                                                 20

<210> SEQ ID NO 1052
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1052
ttacatctat agcaccactc                                                 20

<210> SEQ ID NO 1053
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1053
tcactccctt ttcagacaag                                                 20

<210> SEQ ID NO 1054
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1054
aactaagttc tgtctgtgga                                                 20

<210> SEQ ID NO 1055
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1055
atacaggact aaagtgcttc                                                 20

<210> SEQ ID NO 1056
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1056
ctctgaccct gatcttccat                                                 20

<210> SEQ ID NO 1057
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1057
aacagctgga gatggcgg                                                   18

<210> SEQ ID NO 1058
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1058
caacagctgg agatggcg                                                   18

-continued

<210> SEQ ID NO 1059
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1059
gcaacagctg gagatggc                                                 18

<210> SEQ ID NO 1060
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1060
ggcaacagct ggagatgg                                                 18

<210> SEQ ID NO 1061
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1061
tggcaacagc tggagatg                                                 18

<210> SEQ ID NO 1062
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1062
ttggcaacag ctggagat                                                 18

<210> SEQ ID NO 1063
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1063
cttggcaaca gctggaga                                                 18

<210> SEQ ID NO 1064
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1064
tcttggcaac agctggag                                                 18

<210> SEQ ID NO 1065
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 1065
gtcttggcaa cagctgga                                          18

<210> SEQ ID NO 1066
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1066
tgtcttggca acagctgg                                          18

<210> SEQ ID NO 1067
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1067
ctgtcttggc aacagctg                                          18

<210> SEQ ID NO 1068
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1068
tctgtcttgg caacagct                                          18

<210> SEQ ID NO 1069
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1069
ctctgtcttg gcaacagc                                          18

<210> SEQ ID NO 1070
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1070
tctctgtctt ggcaacag                                          18

<210> SEQ ID NO 1071
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1071
atctctgtct tggcaaca                                          18

<210> SEQ ID NO 1072
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1072
aatctctgtc ttggcaac                                                   18

<210> SEQ ID NO 1073
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1073
caatctctgt cttggcaa                                                   18

<210> SEQ ID NO 1074
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1074
gcaatctctg tcttggca                                                   18

<210> SEQ ID NO 1075
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1075
agcaatctct gtcttggc                                                   18

<210> SEQ ID NO 1076
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1076
aagcaatctc tgtcttgg                                                   18

<210> SEQ ID NO 1077
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1077
aaagcaatct ctgtcttg                                                   18

<210> SEQ ID NO 1078
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1078
```
taaagcaatc tctgtctt					18

<210> SEQ ID NO 1079
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1079
ttaaagcaat ctctgtct					18

<210> SEQ ID NO 1080
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1080
cttaaagcaa tctctgtc					18

<210> SEQ ID NO 1081
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1081
acttaaagca atctctgt					18

<210> SEQ ID NO 1082
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1082
cacttaaagc aatctctg					18

<210> SEQ ID NO 1083
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1083
ccacttaaag caatctct					18

<210> SEQ ID NO 1084
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1084
ctgctaataa aggtgatt					18

<210> SEQ ID NO 1085
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 1085
gctgctaata aaggtgat                                                 18

<210> SEQ ID NO 1086
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1086
agctgctaat aaaggtga                                                 18

<210> SEQ ID NO 1087
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1087
tagctgctaa taaaggtg                                                 18

<210> SEQ ID NO 1088
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1088
gtagctgcta ataaaggt                                                 18

<210> SEQ ID NO 1089
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1089
agtagctgct aataaagg                                                 18

<210> SEQ ID NO 1090
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1090
aagtagctgc taataaag                                                 18

<210> SEQ ID NO 1091
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1091
aaagtagctg ctaataaa                                                 18
```

<210> SEQ ID NO 1092
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1092
aaaagtagct gctaataa                                                 18

<210> SEQ ID NO 1093
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1093
caaaagtagc tgctaata                                                 18

<210> SEQ ID NO 1094
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1094
gcaaaagtag ctgctaat                                                 18

<210> SEQ ID NO 1095
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1095
agcaaaagta gctgctaa                                                 18

<210> SEQ ID NO 1096
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1096
aagcaaaagt agctgcta                                                 18

<210> SEQ ID NO 1097
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1097
taagcaaaag tagctgct                                                 18

<210> SEQ ID NO 1098
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 1098
gtaagcaaaa gtagctgc                                            18

<210> SEQ ID NO 1099
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1099
agtaagcaaa agtagctg                                            18

<210> SEQ ID NO 1100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1100
cagtaagcaa aagtagct                                            18

<210> SEQ ID NO 1101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1101
ccagtaagca aaagtagc                                            18

<210> SEQ ID NO 1102
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1102
cccagtaagc aaaagtag                                            18

<210> SEQ ID NO 1103
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1103
tcccagtaag caaaagta                                            18

<210> SEQ ID NO 1104
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1104
gtcccagtaa gcaaaagt                                            18

```
<210> SEQ ID NO 1105
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1105
tgtcccagta agcaaaag                                                   18

<210> SEQ ID NO 1106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1106
ttgtcccagt aagcaaaa                                                   18

<210> SEQ ID NO 1107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1107
attgtcccag taagcaaa                                                   18

<210> SEQ ID NO 1108
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1108
tattgtccca gtaagcaa                                                   18

<210> SEQ ID NO 1109
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1109
atattgtccc agtaagca                                                   18

<210> SEQ ID NO 1110
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1110
aatattgtcc cagtaagc                                                   18

<210> SEQ ID NO 1111
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 1111
gaatattgtc ccagtaag                                                18

<210> SEQ ID NO 1112
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1112
agaatattgt cccagtaa                                                18

<210> SEQ ID NO 1113
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1113
aagaatattg tcccagta                                                18

<210> SEQ ID NO 1114
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1114
caagaatatt gtcccagt                                                18

<210> SEQ ID NO 1115
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1115
ccaagaatat tgtcccag                                                18

<210> SEQ ID NO 1116
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1116
accaagaata ttgtccca                                                18

<210> SEQ ID NO 1117
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1117
gaccaagaat attgtccc                                                18

<210> SEQ ID NO 1118
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 1118
ggaccaagaa tattgtcc                                                18

<210> SEQ ID NO 1119
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1119
aggaccaaga atattgtc                                                18

<210> SEQ ID NO 1120
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1120
taggaccaag aatattgt                                                18

<210> SEQ ID NO 1121
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1121
ctaggaccaa gaatattg                                                18

<210> SEQ ID NO 1122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1122
tctaggacca agaatatt                                                18

<210> SEQ ID NO 1123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1123
ctctaggacc aagaatat                                                18

<210> SEQ ID NO 1124
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1124
```
actctaggac caagaata                                           18

<210> SEQ ID NO 1125
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1125
tactctagga ccaagaat                                           18

<210> SEQ ID NO 1126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1126
ttactctagg accaagaa                                           18

<210> SEQ ID NO 1127
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1127
cttactctag gaccaaga                                           18

<210> SEQ ID NO 1128
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1128
ccttactcta ggaccaag                                           18

<210> SEQ ID NO 1129
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1129
gccttactct aggaccaa                                           18

<210> SEQ ID NO 1130
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1130
tgccttactc taggacca                                           18

<210> SEQ ID NO 1131
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 1131
gtgccttact ctaggacc                                                 18

<210> SEQ ID NO 1132
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1132
tgtgccttac tctaggac                                                 18

<210> SEQ ID NO 1133
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1133 atgtgccttas ctctagga                                                18

<210> SEQ ID NO 1134
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1134
aatgtgcctt actctagg                                                 18

<210> SEQ ID NO 1135
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1135
aaatgtgcct tactctag                                                 18

<210> SEQ ID NO 1136
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1136
caaatgtgcc ttactcta                                                 18

<210> SEQ ID NO 1137
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1137
ccaaatgtgc cttactct                                                 18
```

<210> SEQ ID NO 1138
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1138
cccaaatgtg ccttactc                                                 18

<210> SEQ ID NO 1139
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1139
gcccaaatgt gccttact                                                 18

<210> SEQ ID NO 1140
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1140
agcccaaatg tgccttac                                                 18

<210> SEQ ID NO 1141
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1141
gagcccaaat gtgcctta                                                 18

<210> SEQ ID NO 1142
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1142
ggagcccaaa tgtgcctt                                                 18

<210> SEQ ID NO 1143
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1143
tggagcccaa atgtgcct                                                 18

<210> SEQ ID NO 1144
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 1144
ttggagccca aatgtgcc                                              18

<210> SEQ ID NO 1145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1145
tttggagccc aaatgtgc                                              18

<210> SEQ ID NO 1146
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1146
ctttggagcc caaatgtg                                              18

<210> SEQ ID NO 1147
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1147
tctttggagc ccaaatgt                                              18

<210> SEQ ID NO 1148
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1148
gtctttggag cccaaatg                                              18

<210> SEQ ID NO 1149
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1149
tgtctttgga gcccaaat                                              18

<210> SEQ ID NO 1150
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1150
ctgtctttgg agcccaaa                                              18

<210> SEQ ID NO 1151
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1151
tctgtctttg gagcccaa                                                 18

<210> SEQ ID NO 1152
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1152
ttctgtcttt ggagccca                                                 18

<210> SEQ ID NO 1153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1153
gttctgtctt tggagccc                                                 18

<210> SEQ ID NO 1154
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1154
tgttctgtct ttggagcc                                                 18

<210> SEQ ID NO 1155
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1155
ctgttctgtc tttggagc                                                 18

<210> SEQ ID NO 1156
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1156
cctgttctgt ctttggag                                                 18

<210> SEQ ID NO 1157
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1157
```
acctgttctg tctttgga                                    18

<210> SEQ ID NO 1158
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1158
tacctgttct gtctttgg                                    18

<210> SEQ ID NO 1159
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1159
gtacctgttc tgtctttg                                    18

<210> SEQ ID NO 1160
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1160
agtacctgtt ctgtcttt                                    18

<210> SEQ ID NO 1161
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1161
aagtacctgt tctgtctt                                    18

<210> SEQ ID NO 1162
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1162
gaagtacctg ttctgtct                                    18

<210> SEQ ID NO 1163
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1163
agaagtacct gttctgtc                                    18

<210> SEQ ID NO 1164
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 1164
gagaagtacc tgttctgt                                                 18

<210> SEQ ID NO 1165
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1165
tgagaagtac ctgttctg                                                 18

<210> SEQ ID NO 1166
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1166
ctgagaagta cctgttct                                                 18

<210> SEQ ID NO 1167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1167
actgagaagt acctgttc                                                 18

<210> SEQ ID NO 1168
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1168
cactgagaag tacctgtt                                                 18

<210> SEQ ID NO 1169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1169
tcactgagaa gtacctgt                                                 18

<210> SEQ ID NO 1170
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1170
atcactgaga agtacctg                                                 18

<210> SEQ ID NO 1171
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1171
catcactgag aagtacct                                                 18

<210> SEQ ID NO 1172
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1172
ccatcactga gaagtacc                                                 18

<210> SEQ ID NO 1173
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1173
tccatcactg agaagtac                                                 18

<210> SEQ ID NO 1174
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1174
ctccatcact gagaagta                                                 18

<210> SEQ ID NO 1175
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1175
tctccatcac tgagaagt                                                 18

<210> SEQ ID NO 1176
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1176
ttctccatca ctgagaag                                                 18

<210> SEQ ID NO 1177
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 1177
tttctccatc actgagaa                                                     18

<210> SEQ ID NO 1178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1178
atttctccat cactgaga                                                     18

<210> SEQ ID NO 1179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1179
tatttctcca tcactgag                                                     18

<210> SEQ ID NO 1180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1180
gttatttctc catcactg                                                     18

<210> SEQ ID NO 1181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1181
agttatttct ccatcact                                                     18

<210> SEQ ID NO 1182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1182
aagttatttc tccatcac                                                     18

<210> SEQ ID NO 1183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1183
aaagttattt ctccatca                                                     18

```
<210> SEQ ID NO 1184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1184
aaaagttatt tctccatc                                                 18

<210> SEQ ID NO 1185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1185
gaaaagttat ttctccat                                                 18

<210> SEQ ID NO 1186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1186
aagaaaagtt atttctcc                                                 18

<210> SEQ ID NO 1187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1187
caagaaaagt tatttctc                                                 18

<210> SEQ ID NO 1188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1188
gcaagaaaag ttatttct                                                 18

<210> SEQ ID NO 1189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1189
ggcaagaaaa gttatttc                                                 18

<210> SEQ ID NO 1190
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 1190
tggcaagaaa agttattt						18

<210> SEQ ID NO 1191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1191
ttggcaagaa aagttatt						18

<210> SEQ ID NO 1192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1192
gttggcaaga aaagttat						18

<210> SEQ ID NO 1193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1193
ggttggcaag aaaagtta						18

<210> SEQ ID NO 1194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1194
tggttggcaa gaaaagtt						18

<210> SEQ ID NO 1195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1195
gtggttggca agaaaagt						18

<210> SEQ ID NO 1196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1196
tgtggttggc aagaaaag						18

<210> SEQ ID NO 1197
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 1197
gtgtggttgg caagaaaa                                                    18

<210> SEQ ID NO 1198
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1198
agtgtggttg gcaagaaa                                                    18

<210> SEQ ID NO 1199
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1199
gagtgtggtt ggcaagaa                                                    18

<210> SEQ ID NO 1200
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1200
agagtgtggt tggcaaga                                                    18

<210> SEQ ID NO 1201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1201
tagagtgtgg ttggcaag                                                    18

<210> SEQ ID NO 1202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1202
ttagagtgtg gttggcaa                                                    18

<210> SEQ ID NO 1203
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1203
```
tttagagtgt ggttggca                                           18

<210> SEQ ID NO 1204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1204
atttagagtg tggttggc                                           18

<210> SEQ ID NO 1205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1205
catttagagt gtggttgg                                           18

<210> SEQ ID NO 1206
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1206
ccatttagag tgtggttg                                           18

<210> SEQ ID NO 1207
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1207
tccatttaga gtgtggtt                                           18

<210> SEQ ID NO 1208
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1208
ctccatttag agtgtggt                                           18

<210> SEQ ID NO 1209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1209
tctccattta gagtgtgg                                           18

<210> SEQ ID NO 1210
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 1210
ttctccattt agagtgtg                                                18

<210> SEQ ID NO 1211
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1211
tttctccatt tagagtgt                                                18

<210> SEQ ID NO 1212
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1212
atttctccat ttagagtg                                                18

<210> SEQ ID NO 1213
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1213
gatttctcca tttagagt                                                18

<210> SEQ ID NO 1214
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1214
ggatttctcc atttagag                                                18

<210> SEQ ID NO 1215
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1215
aggatttctc catttaga                                                18

<210> SEQ ID NO 1216
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1216
aaggatttct ccatttag                                                18
```

<210> SEQ ID NO 1217
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1217
gaaggatttc tccattta                                              18

<210> SEQ ID NO 1218
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1218
cgaaggattt ctccattt                                              18

<210> SEQ ID NO 1219
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1219
tcgaaggatt tctccatt                                              18

<210> SEQ ID NO 1220
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1220
ttcgaaggat ttctccat                                              18

<210> SEQ ID NO 1221
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1221
tttcgaagga tttctcca                                              18

<210> SEQ ID NO 1222
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1222
atttcgaagg atttctcc                                              18

<210> SEQ ID NO 1223
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 1223
catttcgaag gatttctc                                         18

<210> SEQ ID NO 1224
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1224
gcatttcgaa ggatttct                                         18

<210> SEQ ID NO 1225
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1225
tgcatttcga aggatttc                                         18

<210> SEQ ID NO 1226
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1226
ctgcatttcg aaggattt                                         18

<210> SEQ ID NO 1227
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1227
tctgcatttc gaaggatt                                         18

<210> SEQ ID NO 1228
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1228
ctctgcattt cgaaggat                                         18

<210> SEQ ID NO 1229
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1229
tctctgcatt tcgaagga                                         18

<210> SEQ ID NO 1230
```

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1230
ctctctgcat ttcgaagg                                         18

<210> SEQ ID NO 1231
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1231
actctctgca tttcgaag                                         18

<210> SEQ ID NO 1232
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1232
cactctctgc atttcgaa                                         18

<210> SEQ ID NO 1233
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1233
ccactctctg catttcga                                         18

<210> SEQ ID NO 1234
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1234
accactctct gcatttcg                                         18

<210> SEQ ID NO 1235
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1235
caccactctc tgcatttc                                         18

<210> SEQ ID NO 1236
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1236

-continued gcaccactct ctgcattt                                        18

<210> SEQ ID NO 1237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1237
agcaccactc tctgcatt                                        18

<210> SEQ ID NO 1238
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1238
tagcaccact ctctgcat                                        18

<210> SEQ ID NO 1239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1239
atagcaccac tctctgca                                        18

<210> SEQ ID NO 1240
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1240
tatagcacca ctctctgc                                        18

<210> SEQ ID NO 1241
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1241
ctatagcacc actctctg                                        18

<210> SEQ ID NO 1242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1242
tctatagcac cactctct                                        18

<210> SEQ ID NO 1243
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 1243
atctatagca ccactctc                                                18

<210> SEQ ID NO 1244
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1244
catctatagc accactct                                                18

<210> SEQ ID NO 1245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1245
acatctatag caccactc                                                18

<210> SEQ ID NO 1246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1246
tacatctata gcaccact                                                18

<210> SEQ ID NO 1247
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1247
ttacatctat agcaccac                                                18

<210> SEQ ID NO 1248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1248
tttacatcta tagcacca                                                18

<210> SEQ ID NO 1249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1249
ctttacatct atagcacc                                                18
```

-continued

<210> SEQ ID NO 1250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1250
actttacatc tatagcac                                                 18

<210> SEQ ID NO 1251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1251
aactttacat ctatagca                                                 18

<210> SEQ ID NO 1252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1252
aaactttaca tctatagc                                                 18

<210> SEQ ID NO 1253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1253
aaaactttac atctatag                                                 18

<210> SEQ ID NO 1254
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1254
aaaaaacttt acatctat                                                 18

<210> SEQ ID NO 1255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1255
caaaaaactt tacatcta                                                 18

<210> SEQ ID NO 1256
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 1256
acaaaaaact ttacatct                                                    18

<210> SEQ ID NO 1257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1257
gacaaaaaac tttacatc                                                    18

<210> SEQ ID NO 1258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1258
caagacaaaa aactttac                                                    18

<210> SEQ ID NO 1259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1259
gacaagacaa aaaacttt                                                    18

<210> SEQ ID NO 1260
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1260
agacaagaca aaaaactt                                                    18

<210> SEQ ID NO 1261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1261
cagacaagac aaaaaact                                                    18

<210> SEQ ID NO 1262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1262
tcagacaaga caaaaaac                                                    18

```
<210> SEQ ID NO 1263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1263
ttcagacaag acaaaaaa                                                 18

<210> SEQ ID NO 1264
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1264
ttttcagaca agacaaaa                                                 18

<210> SEQ ID NO 1265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1265
cttttcagac aagacaaa                                                 18

<210> SEQ ID NO 1266
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1266
ccttttcaga caagacaa                                                 18

<210> SEQ ID NO 1267
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1267
cccttttcag acaagaca                                                 18

<210> SEQ ID NO 1268
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1268
tcccttttca gacaagac                                                 18

<210> SEQ ID NO 1269
<211> LENGTH: 18
<212> TYPE: DNA
<213> ORGANISM: Artificial sequence
<220> FEATURE:
<223> OTHER INFORMATION: Synthetic oligonucleotide
```

-continued

<400> SEQUENCE: 1269 ctccctttc agacaaga                                                  18

<210> SEQ ID NO 1270
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1270
actccctttt cagacaag                                                 18

<210> SEQ ID NO 1271
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1271
cactcccttt tcagacaa                                                 18

<210> SEQ ID NO 1272
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1272
tcactccctt ttcagaca                                                 18

<210> SEQ ID NO 1273
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1273
atcactccct tttcagac                                                 18

<210> SEQ ID NO 1274
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1274
aatcactccc ttttcaga                                                 18

<210> SEQ ID NO 1275
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1275
taatcactcc cttttcag                                                 18

<210> SEQ ID NO 1276
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 1276
ataatcactc cctttca                                                    18

<210> SEQ ID NO 1277
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1277
aataatcact ccctttc                                                    18

<210> SEQ ID NO 1278
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1278
caataatcac tccctttt                                                   18

<210> SEQ ID NO 1279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1279
acaataatca ctcccttt                                                   18

<210> SEQ ID NO 1280
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1280
aacaataatc actccctt                                                   18

<210> SEQ ID NO 1281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1281
aaacaataat cactccct                                                   18

<210> SEQ ID NO 1282
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1282
```

```
gaaacaataa tcactccc                                            18

<210> SEQ ID NO 1283
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1283
tgaaacaata atcactcc                                            18

<210> SEQ ID NO 1284
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1284
atgaaacaat aatcactc                                            18

<210> SEQ ID NO 1285
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1285
aatgaaacaa taatcact                                            18

<210> SEQ ID NO 1286
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1286
taatgaaaca ataatcac                                            18

<210> SEQ ID NO 1287
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1287
ttaatgaaac aataatca                                            18

<210> SEQ ID NO 1288
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1288
attaatgaaa caataatc                                            18

<210> SEQ ID NO 1289
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 1289
atcaaagatt aatgaaac                                                        18

<210> SEQ ID NO 1290
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1290
catcaaagat taatgaaa                                                        18

<210> SEQ ID NO 1291
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1291
ccatcaaaga ttaatgaa                                                        18

<210> SEQ ID NO 1292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1292
tccatcaaag attaatga                                                        18

<210> SEQ ID NO 1293
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1293
ttccatcaaa gattaatg                                                        18

<210> SEQ ID NO 1294
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1294
tttccatcaa agattaat                                                        18

<210> SEQ ID NO 1295
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1295
gtttccatca aagattaa                                                        18
```

<210> SEQ ID NO 1296
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1296
agtttccatc aaagatta                                                     18

<210> SEQ ID NO 1297
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1297
cagtttccat caaagatt                                                     18

<210> SEQ ID NO 1298
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1298
ccagtttcca tcaaagat                                                     18

<210> SEQ ID NO 1299
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1299
tccagtttcc atcaaaga                                                     18

<210> SEQ ID NO 1300
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1300
ttccagtttc catcaaag                                                     18

<210> SEQ ID NO 1301
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1301
attccagttt ccatcaaa                                                     18

<210> SEQ ID NO 1302
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1302
cattccagtt tccatcaa                                          18

<210> SEQ ID NO 1303
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1303
ccattccagt ttccatca                                          18

<210> SEQ ID NO 1304
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1304
cccattccag tttccatc                                          18

<210> SEQ ID NO 1305
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1305
ccccattcca gtttccat                                          18

<210> SEQ ID NO 1306
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1306
tccccattcc agtttcca                                          18

<210> SEQ ID NO 1307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1307
atccccattc cagtttcc                                          18

<210> SEQ ID NO 1308
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1308
gatccccatt ccagtttc                                          18

<210> SEQ ID NO 1309

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1309
cgatccccat tccagttt                                                    18

<210> SEQ ID NO 1310
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1310
gcgatcccca ttccagtt                                                    18

<210> SEQ ID NO 1311
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1311
tgcgatcccc attccagt                                                    18

<210> SEQ ID NO 1312
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1312
ctgcgatccc cattccag                                                    18

<210> SEQ ID NO 1313
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1313
gctgcgatcc ccattcca                                                    18

<210> SEQ ID NO 1314
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1314
tgctgcgatc cccattcc                                                    18

<210> SEQ ID NO 1315
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1315
gtgctgcgat ccccattc                                                    18

<210> SEQ ID NO 1316
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1316
tgtgctgcga tccccatt                                                    18

<210> SEQ ID NO 1317
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1317
atgtgctgcg atccccat                                                    18

<210> SEQ ID NO 1318
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1318
tatgtgctgc gatcccca                                                    18

<210> SEQ ID NO 1319
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1319
aagtataatt gatagtcc                                                    18

<210> SEQ ID NO 1320
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1320
gaagtataat tgatagtc                                                    18

<210> SEQ ID NO 1321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1321
ggaagtataa ttgatagt                                                    18

<210> SEQ ID NO 1322
<211> LENGTH: 18
<212> TYPE: DNA

-continued

<213> ORGANISM: Artificial sequence
<220> FEATURE:
<223> OTHER INFORMATION: Synthetic oligonucleotide

<400> SEQUENCE: 1322
tggaagtata attgatag                                                 18

<210> SEQ ID NO 1323
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1323
gtggaagtat aattgata                                                 18

<210> SEQ ID NO 1324
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1324
tgtggaagta taattgat                                                 18

<210> SEQ ID NO 1325
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1325
ctgtggaagt ataattga                                                 18

<210> SEQ ID NO 1326
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1326
tctgtggaag tataattg                                                 18

<210> SEQ ID NO 1327
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1327
gtctgtggaa gtataatt                                                 18

<210> SEQ ID NO 1328
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1328
tgtctgtgga agtataat                                                 18

<210> SEQ ID NO 1329
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1329
ctgtctgtgg aagtataa                                                 18

<210> SEQ ID NO 1330
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1330
tctgtctgtg gaagtata                                                 18

<210> SEQ ID NO 1331
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1331
ttctgtctgt ggaagtat                                                 18

<210> SEQ ID NO 1332
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1332
gttctgtctg tggaagta                                                 18

<210> SEQ ID NO 1333
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1333
agttctgtct gtggaagt                                                 18

<210> SEQ ID NO 1334
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1334
aagttctgtc tgtggaag                                                 18

<210> SEQ ID NO 1335
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 1335
taagttctgt ctgtggaa                                              18

<210> SEQ ID NO 1336
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1336
ctaagttctg tctgtgga                                              18

<210> SEQ ID NO 1337
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1337
actaagttct gtctgtgg                                              18

<210> SEQ ID NO 1338
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1338
aactaagttc tgtctgtg                                              18

<210> SEQ ID NO 1339
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1339
aaactaagtt ctgtctgt                                              18

<210> SEQ ID NO 1340
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1340
gaaactaagt tctgtctg                                              18

<210> SEQ ID NO 1341
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1341
agaaactaag ttctgtct                                              18

```
<210> SEQ ID NO 1342
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1342
tagaaactaa gttctgtc                                                 18

<210> SEQ ID NO 1343
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1343
gtagaaacta agttctgt                                                 18

<210> SEQ ID NO 1344
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1344
ggtagaaact aagttctg                                                 18

<210> SEQ ID NO 1345
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1345
aggtagaaac taagttct                                                 18

<210> SEQ ID NO 1346
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1346
gaggtagaaa ctaagttc                                                 18

<210> SEQ ID NO 1347
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1347
ggaggtagaa actaagtt                                                 18

<210> SEQ ID NO 1348
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 1348
gggaggtaga aactaagt                                                 18

<210> SEQ ID NO 1349
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1349
tgggaggtag aaactaag                                                 18

<210> SEQ ID NO 1350
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1350
gtgggaggta gaaactaa                                                 18

<210> SEQ ID NO 1351
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1351
agtgggaggt agaaacta                                                 18

<210> SEQ ID NO 1352
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1352
aagtgggagg tagaaact                                                 18

<210> SEQ ID NO 1353
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1353
gaagtgggag gtagaaac                                                 18

<210> SEQ ID NO 1354
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1354
tgaagtggga ggtagaaa                                                 18

<210> SEQ ID NO 1355
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 1355
atgaagtggg aggtagaa                                                 18

<210> SEQ ID NO 1356
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1356
tatgaagtgg gaggtaga                                                 18

<210> SEQ ID NO 1357
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1357
ctatgaagtg ggaggtag                                                 18

<210> SEQ ID NO 1358
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1358
tctatgaagt gggaggta                                                 18

<210> SEQ ID NO 1359
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1359
ctctatgaag tgggaggt                                                 18

<210> SEQ ID NO 1360
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1360
actctatgaa gtgggagg                                                 18

<210> SEQ ID NO 1361
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1361
```
cactctatga agtgggag                                                   18

<210> SEQ ID NO 1362
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1362
acactctatg aagtggga                                                   18

<210> SEQ ID NO 1363
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1363
cacactctat gaagtggg                                                   18

<210> SEQ ID NO 1364
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1364
acacactcta tgaagtgg                                                   18

<210> SEQ ID NO 1365
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1365
cacacactct atgaagtg                                                   18

<210> SEQ ID NO 1366
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1366
acacacactc tatgaagt                                                   18

<210> SEQ ID NO 1367
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1367
ccctgatctt ccattctc                                                   18

<210> SEQ ID NO 1368
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1368
accctgatct tccattct                                                18

<210> SEQ ID NO 1369
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1369
gaccctgatc ttccattc                                                18

<210> SEQ ID NO 1370
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1370
tgaccctgat cttccatt                                                18

<210> SEQ ID NO 1371
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1371
ctgaccctga tcttccat                                                18

<210> SEQ ID NO 1372
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1372
tctgaccctg atcttcca                                                18

<210> SEQ ID NO 1373
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1373
ctctgaccct gatcttcc                                                18

<210> SEQ ID NO 1374
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1374
actctgaccc tgatcttc                                                18

<210> SEQ ID NO 1375
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1375
tactctgacc ctgatctt                                                 18

<210> SEQ ID NO 1376
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1376
atactctgac cctgatct                                                 18

<210> SEQ ID NO 1377
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1377
aatactctga ccctgatc                                                 18

<210> SEQ ID NO 1378
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1378
atgatttctt gtctggga                                                 18

<210> SEQ ID NO 1379
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1379
catgatttct tgtctggg                                                 18

<210> SEQ ID NO 1380
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1380
ccatgatttc ttgtctgg                                                 18

<210> SEQ ID NO 1381
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1381
gccatgattt cttgtctg                                                    18

<210> SEQ ID NO 1382
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1382
ggccatgatt tcttgtct                                                    18

<210> SEQ ID NO 1383
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1383
gggccatgat ttcttgtc                                                    18

<210> SEQ ID NO 1384
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1384
aactaacatg taggcact                                                    18

<210> SEQ ID NO 1385
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1385
gaactaacat gtaggcac                                                    18

<210> SEQ ID NO 1386
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1386
ggaactaaca tgtaggca                                                    18

<210> SEQ ID NO 1387
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1387
aggaactaac atgtaggc                                                    18

<210> SEQ ID NO 1388

-continued

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1388
cttctgattc aagccatt                                           18

<210> SEQ ID NO 1389
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1389
gcttctgatt caagccat                                           18

<210> SEQ ID NO 1390
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1390
tgcttctgat tcaagcca                                           18

<210> SEQ ID NO 1391
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1391
gtgcttctga ttcaagcc                                           18

<210> SEQ ID NO 1392
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1392
agtgcttctg attcaagc                                           18

<210> SEQ ID NO 1393
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1393
aagtgcttct gattcaag                                           18

<210> SEQ ID NO 1394
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1394
aaagtgcttc tgattcaa                                          18

<210> SEQ ID NO 1395
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1395
taaagtgctt ctgattca                                          18

<210> SEQ ID NO 1396
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1396
ctaaagtgct tctgattc                                          18

<210> SEQ ID NO 1397
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1397
actaaagtgc ttctgatt                                          18

<210> SEQ ID NO 1398
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1398
gactaaagtg cttctgat                                          18

<210> SEQ ID NO 1399
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1399
ggactaaagt gcttctga                                          18

<210> SEQ ID NO 1400
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1400
aggactaaag tgcttctg                                          18

<210> SEQ ID NO 1401
<211> LENGTH: 18
<212> TYPE: DNA

-continued

```
<213> ORGANISM: Artificial sequence
<220> FEATURE:
<223> OTHER INFORMATION: Synthetic oligonucleotide

<400> SEQUENCE: 1401
caggactaaa gtgcttct                                                 18

<210> SEQ ID NO 1402
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1402
acaggactaa agtgcttc                                                 18

<210> SEQ ID NO 1403
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1403
tacaggacta aagtgctt                                                 18

<210> SEQ ID NO 1404
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1404
atacaggact aaagtgct                                                 18

<210> SEQ ID NO 1405
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1405
gatacaggac taaagtgc                                                 18

<210> SEQ ID NO 1406
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1406
agatacagga ctaaagtg                                                 18

<210> SEQ ID NO 1407
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1407
cagatacagg actaaagt                                                 18
```

<210> SEQ ID NO 1408
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1408
acagatacag gactaaag                                                 18

<210> SEQ ID NO 1409
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1409
aacagataca ggactaaa                                                 18

<210> SEQ ID NO 1410
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1410
gaacagatac aggactaa                                                 18

<210> SEQ ID NO 1411
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1411
tgaacagata caggacta                                                 18

<210> SEQ ID NO 1412
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1412
ctgaacagat acaggact                                                 18

<210> SEQ ID NO 1413
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1413
actgaacaga tacaggac                                                 18

<210> SEQ ID NO 1414
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 1414
cactgaacag atacagga                                                 18

<210> SEQ ID NO 1415
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1415
acactgaaca gatacagg                                                 18

<210> SEQ ID NO 1416
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1416
gacactgaac agatacag                                                 18

<210> SEQ ID NO 1417
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1417
tgacactgaa cagataca                                                 18

<210> SEQ ID NO 1418
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1418
ctgacactga acagatac                                                 18

<210> SEQ ID NO 1419
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1419
gctgacactg aacagata                                                 18

<210> SEQ ID NO 1420
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1420
ggctgacact gaacagat                                                 18

```
<210> SEQ ID NO 1421
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1421
aggctgacac tgaacaga                                                 18

<210> SEQ ID NO 1422
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1422
aaggctgaca ctgaacag                                                 18

<210> SEQ ID NO 1423
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1423
aaaggctgac actgaaca                                                 18

<210> SEQ ID NO 1424
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1424
gaaaggctga cactgaac                                                 18

<210> SEQ ID NO 1425
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1425
tgaaaggctg acactgaa                                                 18

<210> SEQ ID NO 1426
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1426
tgggatttaa aatgatgt                                                 18

<210> SEQ ID NO 1427
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 1427
atgggattta aaatgatg                                                 18

<210> SEQ ID NO 1428
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1428
cttgagaaga aagccttc                                                 18

<210> SEQ ID NO 1429
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1429
attaaggctc ttaggtta                                                 18

<210> SEQ ID NO 1430
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1430
gtagacagtc tgttattt                                                 18

<210> SEQ ID NO 1431
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1431
tgacatgtag agagatta                                                 18

<210> SEQ ID NO 1432
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1432
tggtttaagg gcacaaac                                                 18

<210> SEQ ID NO 1433
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1433
acttgagaag aaagcctt                                                 18

<210> SEQ ID NO 1434
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 1434
cctctgatac tccatcat                                                 18

<210> SEQ ID NO 1435
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1435
aaatcttgtc ataggtga                                                 18

<210> SEQ ID NO 1436
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1436
aattcttact tgagaaga                                                 18

<210> SEQ ID NO 1437
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1437
ggtgtataga gaattcag                                                 18

<210> SEQ ID NO 1438
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1438
tactccatca tgagccta                                                 18

<210> SEQ ID NO 1439
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1439
gctggatgga aaaagatc                                                 18

<210> SEQ ID NO 1440
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1440
```

```
gtccctagaa caatctaa                                                       18

<210> SEQ ID NO 1441
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1441
gaagaaattg acatgtag                                                       18

<210> SEQ ID NO 1442
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1442
catctacagt acaactta                                                       18

<210> SEQ ID NO 1443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1443
atctctgtct tggcaacagc                                                     20

<210> SEQ ID NO 1444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1444
aatctctgtc ttggcaacag                                                     20

<210> SEQ ID NO 1445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1445
caatctctgt cttggcaaca                                                     20

<210> SEQ ID NO 1446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1446
aagcaatctc tgtcttggca                                                     20

<210> SEQ ID NO 1447
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 1447
ttactctagg accaagaata                                               20

<210> SEQ ID NO 1448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1448
cttactctag gaccaagaat                                               20

<210> SEQ ID NO 1449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1449
tgccttactc taggaccaag                                               20

<210> SEQ ID NO 1450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1450
tgtgccttac tctaggacca                                               20

<210> SEQ ID NO 1451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1451
atgtgcctta ctctaggacc                                               20

<210> SEQ ID NO 1452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1452
cccaaatgtg ccttactcta                                               20

<210> SEQ ID NO 1453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1453
gcccaaatgt gccttactct                                               20
```

<210> SEQ ID NO 1454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1454
gagcccaaat gtgccttact                                                 20

<210> SEQ ID NO 1455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1455
ggagcccaaa tgtgccttac                                                 20

<210> SEQ ID NO 1456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1456
ttggagccca aatgtgcctt                                                 20

<210> SEQ ID NO 1457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1457
tttggagccc aaatgtgcct                                                 20

<210> SEQ ID NO 1458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1458
ctgtctttgg agcccaaatg                                                 20

<210> SEQ ID NO 1459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1459
tgttctgtct tggagccca                                                  20

<210> SEQ ID NO 1460
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 1460
cctgttctgt ctttggagcc                                                    20

<210> SEQ ID NO 1461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1461
acctgttctg tctttggagc                                                    20

<210> SEQ ID NO 1462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1462
agtacctgtt ctgtctttgg                                                    20

<210> SEQ ID NO 1463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1463
catcactgag aagtacctgt                                                    20

<210> SEQ ID NO 1464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1464
ctccatcact gagaagtacc                                                    20

<210> SEQ ID NO 1465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1465
ccactctctg catttcgaag                                                    20

<210> SEQ ID NO 1466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1466
accactctct gcatttcgaa                                                    20

<210> SEQ ID NO 1467
```

-continued

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1467
gcaccactct ctgcatttcg                                        20

<210> SEQ ID NO 1468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1468
atagcaccac tctctgcatt                                        20

<210> SEQ ID NO 1469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1469
tatagcacca ctctctgcat                                        20

<210> SEQ ID NO 1470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1470
acatctatag caccactctc                                        20

<210> SEQ ID NO 1471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1471
tacatctata gcaccactct                                        20

<210> SEQ ID NO 1472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1472
tttacatcta tagcaccact                                        20

<210> SEQ ID NO 1473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1473
ctttacatct atagcaccac					20

<210> SEQ ID NO 1474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1474
aactttacat ctatagcacc					20

<210> SEQ ID NO 1475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1475
aaactttaca tctatagcac					20

<210> SEQ ID NO 1476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1476
ctcccttttc agacaagaca					20

<210> SEQ ID NO 1477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1477 actcccttttt cagacaagac					20

<210> SEQ ID NO 1478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1478
atcactccct tttcagacaa					20

<210> SEQ ID NO 1479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1479
taatcactcc cttttcagac					20

<210> SEQ ID NO 1480
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1480
ataatcactc cctttcaga                                            20

<210> SEQ ID NO 1481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1481
atccccattc cagtttccat                                           20

<210> SEQ ID NO 1482
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1482
gatccccatt ccagtttcca                                           20

<210> SEQ ID NO 1483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1483
gcgatcccca ttccagtttc                                           20

<210> SEQ ID NO 1484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1484
tgcgatcccc attccagttt                                           20

<210> SEQ ID NO 1485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1485
gctgcgatcc ccattccagt                                           20

<210> SEQ ID NO 1486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1486
tgctgcgatc cccattccag                                           20
```

<210> SEQ ID NO 1487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1487
tgtgctgcga tccccattcc                                               20

<210> SEQ ID NO 1488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1488
atgtgctgcg atccccattc                                               20

<210> SEQ ID NO 1489
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1489
actaagttct gtctgtggaa                                               20

<210> SEQ ID NO 1490
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1490
gaaactaagt tctgtctgtg                                               20

<210> SEQ ID NO 1491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1491
agaaactaag ttctgtctgt                                               20

<210> SEQ ID NO 1492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1492
tgaccctgat cttccattct                                               20

<210> SEQ ID NO 1493
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 1493
ctgaccctga tcttccattc                                               20

<210> SEQ ID NO 1494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1494
actctgaccc tgatcttcca                                               20

<210> SEQ ID NO 1495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1495
atactctgac cctgatcttc                                               20

<210> SEQ ID NO 1496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1496
aatactctga ccctgatctt                                               20

<210> SEQ ID NO 1497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1497
ccatgatttc ttgtctggga                                               20

<210> SEQ ID NO 1498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1498
ggccatgatt tcttgtctgg                                               20

<210> SEQ ID NO 1499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1499
gggccatgat tcttgtctg                                                20

```
<210> SEQ ID NO 1500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1500
acttaagttc atctacagta                                               20

<210> SEQ ID NO 1501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1501
tccactgctg gatggaaaaa                                               20

<210> SEQ ID NO 1502
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1502
atattattta tcttactcaa                                               20

<210> SEQ ID NO 1503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1503
gttctaagtg ctttatatta                                               20

<210> SEQ ID NO 1504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1504
aggaactaac atgtaggcac                                               20

<210> SEQ ID NO 1505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1505
atataagata atacatgtaa                                               20

<210> SEQ ID NO 1506
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1506
catcatgagc ctaaaggaaa                                           20

<210> SEQ ID NO 1507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1507
ccatcatgag cctaaaggaa                                           20

<210> SEQ ID NO 1508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1508
cttctgattc aagccattaa                                           20

<210> SEQ ID NO 1509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1509
tgcttctgat tcaagccatt                                           20

<210> SEQ ID NO 1510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1510
gtgcttctga ttcaagccat                                           20

<210> SEQ ID NO 1511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1511
agtgcttctg attcaagcca                                           20

<210> SEQ ID NO 1512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1512
aagtgcttct gattcaagcc                                           20

<210> SEQ ID NO 1513
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1513
aaagtgcttc tgattcaagc                                               20

<210> SEQ ID NO 1514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1514
taaagtgctt ctgattcaag                                               20

<210> SEQ ID NO 1515
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1515
ctaaagtgct tctgattcaa                                               20

<210> SEQ ID NO 1516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1516
actaaagtgc ttctgattca                                               20

<210> SEQ ID NO 1517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1517
gactaaagtg cttctgattc                                               20

<210> SEQ ID NO 1518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1518
ggactaaagt gcttctgatt                                               20

<210> SEQ ID NO 1519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1519
```
aggactaaag tgcttctgat                                           20

<210> SEQ ID NO 1520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1520
caggactaaa gtgcttctga                                           20

<210> SEQ ID NO 1521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1521
acaggactaa agtgcttctg                                           20

<210> SEQ ID NO 1522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1522
tacaggacta aagtgcttct                                           20

<210> SEQ ID NO 1523
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1523
gatacaggac taaagtgctt                                           20

<210> SEQ ID NO 1524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1524
agatacagga ctaaagtgct                                           20

<210> SEQ ID NO 1525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1525
cagatacagg actaaagtgc                                           20

<210> SEQ ID NO 1526
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1526
acagatacag gactaaagtg                                                 20

<210> SEQ ID NO 1527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1527
aacagataca ggactaaagt                                                 20

<210> SEQ ID NO 1528
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1528
gaacagatac aggactaaag                                                 20

<210> SEQ ID NO 1529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1529
tgaacagata caggactaaa                                                 20

<210> SEQ ID NO 1530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1530
ctgaacagat acaggactaa                                                 20

<210> SEQ ID NO 1531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1531
actgaacaga tacaggacta                                                 20

<210> SEQ ID NO 1532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1532
cactgaacag atacaggact                                                 20
```

<210> SEQ ID NO 1533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1533
acactgaaca gatacaggac                                               20

<210> SEQ ID NO 1534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1534
gacactgaac agatacagga                                               20

<210> SEQ ID NO 1535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1535
tgacactgaa cagatacagg                                               20

<210> SEQ ID NO 1536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1536
ctgacactga acagatacag                                               20

<210> SEQ ID NO 1537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1537
ggctgacact gaacagatac                                               20

<210> SEQ ID NO 1538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1538
aggctgacac tgaacagata                                               20

<210> SEQ ID NO 1539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1539
aaggctgaca ctgaacagat                                          20

<210> SEQ ID NO 1540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1540
aaaggctgac actgaacaga                                          20

<210> SEQ ID NO 1541
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1541
gaaaggctga cactgaacag                                          20

<210> SEQ ID NO 1542
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1542
tgaaaggctg acactgaaca                                          20

<210> SEQ ID NO 1543
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1543
aatgggattt aaaatgatgt                                          20

<210> SEQ ID NO 1544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1544
aaatgggatt taaaatgatg                                          20

<210> SEQ ID NO 1545
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1545
caaatgggat ttaaaatgat                                          20

<210> SEQ ID NO 1546

```
<211> LENGTH: 24
<212> TYPE: DNA
<213> ORGANISM: Artificial sequence
<220> FEATURE:
<223> OTHER INFORMATION: Primer

<400> SEQUENCE: 1546
ttccaatgct tactggagaa gtga                                    24

<210> SEQ ID NO 1547
<211> LENGTH: 26
<212> TYPE: DNA
<213> ORGANISM: Artificial sequence
<220> FEATURE:
<223> OTHER INFORMATION: Primer

<400> SEQUENCE: 1547
ggaacactgt gtgatttcat agatga                                  26

<210> SEQ ID NO 1548
<211> LENGTH: 17
<212> TYPE: DNA
<213> ORGANISM: Artificial sequence
<220> FEATURE:
<223> OTHER INFORMATION: Probe

<400> SEQUENCE: 1548
tcctgtaatg gaactgc                                            17
```

COMPOSITIONS FOR MODULATING C9ORF72 EXPRESSION

SEQUENCE LISTING

The present application is being filed along with a Sequence Listing in electronic format. The Sequence Listing is provided as a file entitled BIOL0235USC1SEQ_ST25.txt created Jan. 15, 2019, which is 444 Kb in size. The information in the electronic format of the sequence listing is incorporated herein by reference in its entirety.

FIELD

Provided are compositions and methods for reducing expression of C9ORF72 mRNA and protein in an animal. Such methods are useful to treat, prevent, or ameliorate neurodegenerative diseases, including amyotrophic lateral sclerosis (ALS), frontotemporal dementia (FTD), corticalbasal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The mutation in the C9ORF72 gene is the most common genetic cause of ALS and FTD. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Provided herein are compositions and methods for modulating levels of C9ORF72 mRNA and protein in cells, tissues, and animals. In certain embodiments, C9ORF72 specific inhibitors modulate expression of C9ORF72 mRNA and protein. In certain embodiments, C9ORF72 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 mRNA levels are reduced. In certain embodiments, C9ORF72 protein levels are reduced. In certain embodiments, C9ORF72 associated Repeat Associated Non-ATG Translation (RAN translation) products are reduced. In certain embodiments, the C9ORF72 associated RAN translation products are poly-(glycine-proline), poly-(glycine-alanine), and poly-(glycine-arginine). In certain embodiments, certain C9ORF72 mRNA variants are preferentially reduced. In certain embodiments, the C9ORF72 mRNA variants preferentially reduced are variants processed from a pre-mRNA containing intron 1. In certain embodiments, intron 1 contains a hexanucleotide repeat expansion. In certain embodiments, the C9ORF72 mRNA variant preferentially reduced is a C9ORF72 pathogenic associated mRNA variant. In certain embodiments, the C9ORF72 pathogenic associated mRNA variant is NM_001256054.1 (SEQ ID NO: 1). In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 24 GGGGCC repeats. In certain embodiments, the hexanucleotide repeat expansion is associated with nuclear foci. In certain embodiments, C9ORF72 associated RAN translation products are associated with nuclear foci. In certain embodiments, the C9ORF72 associated RAN translation products are poly-(glycine-proline), poly-(glycine-alanine), and poly-(glycine-arginine). In certain embodiments, the compositions and methods described herein are useful for reducing C9ORF72 mRNA levels, C9ORF72 protein levels, C9ORF72 RAN translation products, and nuclear foci. In certain embodiments, the compositions and methods described herein are useful for selectively reducing C9ORF72 pathogenic associated mRNA variants. Such reduction can occur in a time-dependent manner or in a dose-dependent manner.

Also provided are methods useful for preventing, treating, and ameliorating diseases, disorders, and conditions associated with C9ORF72. In certain embodiments, such diseases, disorders, and conditions associated with C9ORF72 are neurodegenerative diseases. In certain embodiments, the neurodegenerative disease is amyotrophic lateral sclerosis (ALS), frontotemporal dementia (FTD), corticalbasal degeneration syndrome (CBD), atypical Parkinsonian syndrome, and olivopontocerellar degeneration (OPCD).

Such diseases, disorders, and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 specific inhibitor to an individual in need thereof. In certain embodiments, the C9ORF72 specific inhibitor is a nucleic acid. In certain embodiments, the nucleic acid is an antisense compound. In certain embodiments, the antisense compound is a single-stranded antisense oligonucleotide. In certain embodiments, the single-stranded antisense oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"About" means within +7% of a value. For example, if it is stated, "the compounds affected at least about 70% inhibition of C9ORF72", it is implied that the C9ORF72 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson- Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 associated disease" means any disease associated with any C9ORF72 nucleic acid or expression product thereof. Such diseases may include a neurodegenerative disease. Such neurodegenerative diseases may include ALS and FTD.

"C9ORF72 associated RAN translation products" means aberrant peptide or di-peptide polymers translated through RAN translation (i.e., repeat-associated, and non-ATG-dependent translation). In certain embodiments, the C9ORF72 associated RAN translation products are any of poly-(glycine-proline), poly-(glycine-alanine), and poly-(glycine-arginine).

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise GGGGCC, GGGGGG, GGGGGC, or GGGGCG repeated at least 24 times. Such diseases may include a neurodegenerative disease. Such neurodegenerative diseases may include ALS and FTD.

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Foci" means a nuclear foci comprising a C9ORF72 transcript. In certain embodiments, a foci comprises at least one C9ORF72 transcript. In certain embodiments, C9ORF72 foci comprise transcripts comprising any of the following hexanucleotide repeats: GGGGCC, GGGGGG, GGGGGC, and/or GGGGCG.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 24 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing the level or expression of a C9ORF72 mRNA and/or protein. In certain embodiments, C9ORF72 mRNA and/or protein levels are inhibited in the presence of an antisense compound targeting C9ORF72, including an antisense oligonucleotide targeting C9ORF72, as compared to expression of C9ORF72 mRNA and/or protein levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

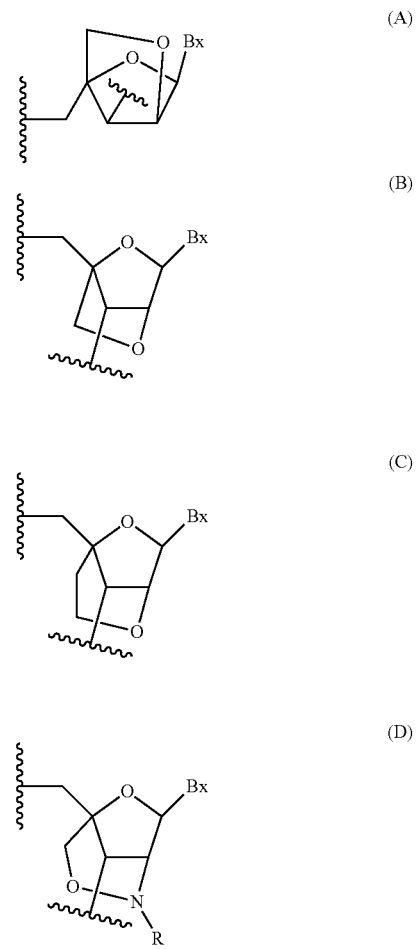

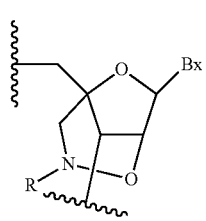

(E)

As used herein, LNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —[C($R_1$)($R_2$)]$_n$—, —[C($R_1$)($R_2$)]$_n$—O—, —C($R_1R_2$)—N($R_1$)—O— or —C($R_1R_2$)—O—N($R_1$)—. Furthermore, other bridging groups encompassed with the definition of LNA are 4'-$CH_2$-2', 4'-($CH_2$)$_2$-2', 4'-($CH_2$)$_3$-2', 4'—$CH_2$—O-2', 4'-($CH_2$)$_2$—O-2', 4'—$CH_2$—O—N($R_1$)-2' and 4'-$CH_2$—N($R_1$)—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicylic sugar moiety having an ethylene bridging group in this position, the term ethyleneoxy (4'-$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to C9ORF72 is a pharmaceutical agent.

"Pharmaceutical composition" means a mixture of substances suitable for administering to as subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

CERTAIN EMBODIMENTS

Certain embodiments provide compositions and methods for decreasing total C9ORF72 mRNA and protein expression.

Certain embodiments provide compositions and methods for decreasing C9ORF72 pathogenic associated mRNA variants.

Certain embodiments provide methods for the treatment, prevention, or amelioration of diseases, disorders, and conditions associated with C9ORF72 in an individual in need thereof. Also contemplated are methods for the preparation of a medicament for the treatment, prevention, or amelioration of a disease, disorder, or condition associated with C9ORF72. C9ORF72 associated diseases, disorders, and conditions include neurodegenerative diseases. In certain embodiments, the neurodegenerative disease may be ALS or FTD. In certain embodiments, the neurodegenerative disease may be familial or sporadic.

Certain embodiments provide compositions and methods for the treatment, prevention, or amelioration of a C9ORF72 hexanucleotide repeat expansion associated disease. In certain embodiments, the hexanucleotide repeat expansion may comprise GGGGCC, GGGGGG, GGGGGC, or GGGGCG.

Provided herein are compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: SEQ ID NOs: 20-401 and 441-1545.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1107-1520 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1111-1200 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1211-1318 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1326-1540 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1331-1375 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1368-1391 of SEQ ID NO: 2

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1398-1424 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1411-1440 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1429-1481 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1502-1539 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 1508-1539 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 7860-7906 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 7907-9744 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 7989-8038 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 8020-8135 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 8136-8161 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 8174-8211 of SEQ ID NO: 2.

Provided herein are compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 8213-8325 of SEQ ID NO: 2.

In certain embodiments, the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1.

In certain embodiments, the modified oligonucleotide is a single-stranded modified oligonucleotide.

In certain embodiments at least one internucleoside linkage of the modified oligonucleotide is a modified internucleoside linkage.

In certain embodiments, at least one modified internucleoside linkage is a phosphorothioate internucleoside linkage.

In certain embodiments, each modified internucleoside linkage is a phosphorothioate internucleoside linkage.

In certain embodiments, at least one internucleoside linkage is a phosphodiester internucleoside linkage.

In certain embodiments, at least one internucleoside linkage is a phosphorothioate linkage and at least one internucleoside linkage is a phosphodiester linkage.

In certain embodiments, at least one nucleoside comprises a modified nucleobase.

In certain embodiments, the modified nucleobase is a 5-methylcytosine.

In certain embodiments, at least one nucleoside of the modified oligonucleotide comprises a modified sugar.

In certain embodiments, the at least one modified sugar is a bicyclic sugar.

In certain embodiments, the bicyclic sugar comprises a chemical link between the 2' and 4' position of the sugar 4'-CH2-N(R)—O-2' bridge wherein R is, independently, H, C1-C12 alkyl, or a protecting group.

In certain embodiments, the bicyclic sugar comprises a 4'-CH2-N(R)—O-2' bridge wherein R is, independently, H, C1-C12 alkyl, or a protecting group.

In certain embodiments, at least one modified sugar comprises a 2'-O-methoxyethyl group.

In certain embodiments, the modified sugar comprises a 2'-O(CH$_2$)$_2$—OCH$_3$ group.

In certain embodiments, the modified oligonucleotide comprises:
 a gap segment consisting of 10 linked deoxynucleosides;
 a 5' wing segment consisting of 5 linked nucleosides; and
 a 3' wing segment consisting of 5 linked nucleosides;
 wherein the gap segment is positioned between the 5' wing segment and the 3' wing segment and wherein each nucleoside of each wing segment comprises a modified sugar.

In certain embodiments, the modified oligonucleotide comprises:
 a gap segment consisting of 8 linked deoxynucleosides;
 a 5' wing segment consisting of 5 linked nucleosides; and
 a 3' wing segment consisting of 5 linked nucleosides;
 wherein the gap segment is positioned between the 5' wing segment and the 3' wing segment and wherein each nucleoside of each wing segment comprises a modified sugar.

In certain embodiments, the modified oligonucleotide comprises sugar modifications in any of the following patterns: eeekkddddddddkkeee, eekkddddddddkkeee, ekdddddddddekekeee, kekedddddddddekeke, and ekekddddddddkekee; wherein,
 e=a 2'-O-methoxyethyl modified nucleoside
 d=a 2'-deoxynucleoside, and
 k=a cEt nucleoside.

In certain embodiments, the modified oligonucleotide comprises internucleoside linkages in any of the following patterns: soooossssssssssooss, sooosssssssssooss, soossssssssssooss, and sosssssssssoooss; wherein,
 s=a phosphorothioate linkage, and
 o=a phosphodiester linkage.

In certain embodiments, the modified oligonucleotide consists of 20 linked nucleosides.

In certain embodiments, the modified oligonucleotide consists of 19 linked nucleosides.

In certain embodiments, the modified oligonucleotide consists of 18 linked nucleosides.

In certain embodiments, the modified oligonucleotide consists of 17 linked nucleosides.

Provided herein are compositions comprising the compound of any preceding claim or salt thereof and at least one of a pharmaceutically acceptable carrier or diluent.

Provided herein are methods comprising administering to an animal the compound or composition of any preceding claim.

In certain embodiments, the animal is a human.

In certain embodiments, administering the compound prevents, treats, ameliorates, or slows progression of a C9ORF72 associated disease, disorder or condition.

In certain embodiments, administering the compound prevents, treats, ameliorates, or slows progression of a C9ORF72 hexanucleotide repeat expansion associated disease, disorder or condition.

In certain embodiments, the disease, disorder or condition is amyotrophic lateral sclerosis (ALS), frontotemporal dementia (FTD), corticalbasal degeneration syndrome (CBD), atypical Parkinsonian syndrome, and olivopontocerellar degeneration (OPCD).

In certain embodiments, the administering reduces nuclear foci.

In certain embodiments, the administering reduces expression of C9ORF72 associated RAN translation products.

In certain embodiments, the C9ORF72 associated RAN translation products are any of poly-(glycine-proline), poly-(glycine-alanine), and poly-(glycine-arginine).

Provided herein are uses of the compound or composition of any preceding claim for the manufacture of a medicament for treating a neurodegenerative disorder.

Provided herein are methods of selectively inhibiting a C9ORF72 pathogenic associated mRNA variant by administering an antisense compound targeting the region beginning at the start site of exon 1A to the start site of exon 1B of a C9ORF72 pre-mRNA.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-8-5 gapmer motif.

In certain embodiments, antisense compounds targeted to a C9ORF72 nucleic acid possess sugar modifications in any of the following patterns: eeekkdddddddkkeee, eekkdddddddddkkeee, ekddddddddddekekeee, kekedddddddde-keke, and ekekdddddddddkekee; wherein,
    e=a 2'-O-methoxyethyl modified nucleoside
    d=a 2'-deoxynucleoside, and
    k=a cEt nucleoside.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$-O-2' bridge, wherein n is 1 or 2; and 4'-CH$_2$—O—CH$_2$-2'. In certain embodiments, the bicyclic sugar is comprises a 4'-CH(CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to U.S. Pat. No. 27,565,000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10), and GENBANK Accession No. NW_001101662.1 truncated from nucleosides 8522000 to U.S. Pat. No. 8,552,000 (incorporated herein as SEQ ID NO: 19).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage.

In certain embodiments, antisense compounds targeted to a C9ORF72 nucleic acid possess internucleoside linkages in any of the following patterns: soooosssssssssooss, sooosssssssssooss, soosssssssssooss, and sosssssssssoooss; wherein,
s=a phosphorothioate linkage, and
o=a phosphodiester linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)-O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Serial Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)C(R$_b$)—, —C(R$_a$)=N—, —C(O)—, —C(=NR$_a$)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_a R_b$)—N(R)—O— or —C($R_a R_b$)—O—N(R)—. In certain embodiments, the bridge is 4'-CH$_2$-2', 4'-(CH$_2$)$_2$-2', 4'-(CH$_2$)$_3$-2', 4'—CH$_2$—O-2', 4'-(CH$_2$)$_2$—O-2', 4'—CH$_2$—O—N(R)-2' and 4'-CH$_2$—N(R)—O-2'— wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-CH$_2$—O-2') BNA, (B) 3-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

(A)

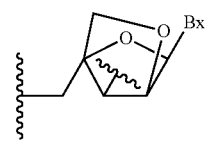

(B)

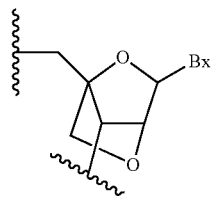

(C)

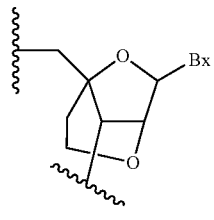

(D)

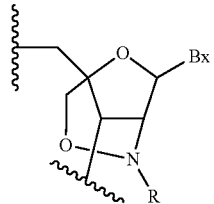

(E)

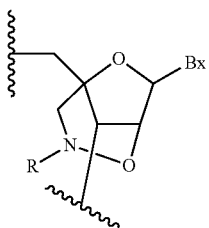

(F)

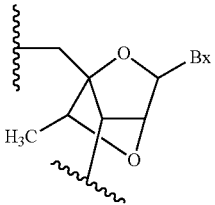

(G)

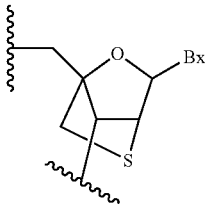

(H)

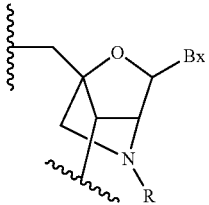

(I)

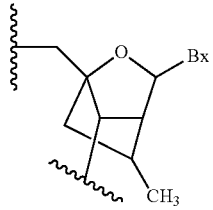

(J)

wherein Bx is the base moiety and R is independently H, a protecting group or $C_1$-$C_{12}$ alkyl.

In certain embodiments, bicyclic nucleosides are provided having Formula I:

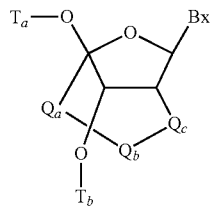

wherein:

Bx is a heterocyclic base moiety;

$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1-C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

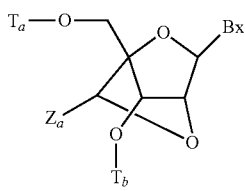

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1-C_6$ alkyl, or substituted $C_1-C_6$ alkyl and X is O or $NJ_c$.

In certain embodiments, bicyclic nucleosides are provided having Formula III:

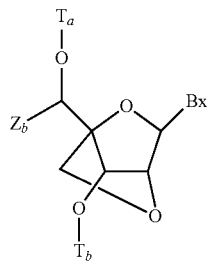

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl or substituted acyl (C(=O)—).

In certain embodiments, bicyclic nucleosides are provided having Formula IV:

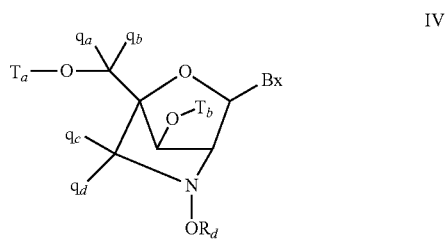

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl;

each $q_a$, $q_b$, $q_c$ and $q_d$ is, independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl, $C_1-C_6$ alkoxyl, substituted $C_1-C_6$ alkoxyl, acyl, substituted acyl, $C_1-C_6$ aminoalkyl or substituted $C_1-C_6$ aminoalkyl;

In certain embodiments, bicyclic nucleosides are provided having Formula V:

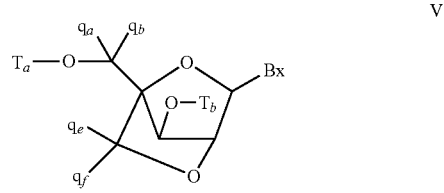

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl, $C_1-C_{12}$ alkoxy, substituted $C_1-C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1-C_{12}$ alkyl or substituted $C_1-C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

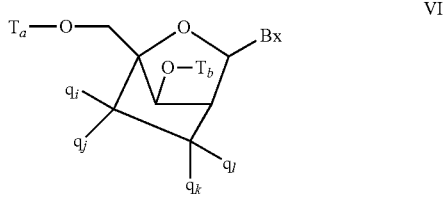

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxyl, substituted C$_1$-C$_{12}$ alkoxyl, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$; and $q_i$ and $q_j$ or $q_l$ and $q_k$ together are =C($q_g$)($q_h$), wherein $q_g$ and $q_h$ are each, independently, H, halogen, C$_1$-C$_{12}$ alkyl or substituted C$_1$-C$_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

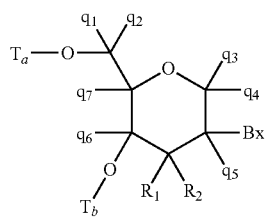

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline (PBS) or artificial cerebrospinal fluid (aCSF). Administration includes parenteral routes of administration, such as intraperitoneal, intravenous, and subcutaneous, as well as central routes of administration such as intracerebroventricular or intrathecal. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, the antisense oligonucleotides described herein selectively hybridize to pre-mRNA variants containing the hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of one or more variants of C9ORF72. In certain embodiments, the antisense oligonucleotides described herein preferentially inhibit expression of variants of C9ORF72 containing a hexanucleotide repeat expansion. In certain embodiments, the antisense oligonucleotides described herein selectively inhibit expression of pre-mRNA variants containing the hexanucleotide repeat. In certain embodiments, the antisense oligonucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Selective Inhibition of Certain Pathogenic Associated Variants

In certain examples herein, primer probe set RTS3905 detects an mRNA variant (e.g. NM_001256054.1) processed from a pre-mRNA variant containing the hexanucleotide repeat. The mRNA variant processed from a pre-mRNA variant containing the hexanucleotide repeat (i.e., the "C9ORF72 pathogenic associated mRNA variant"). A pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). Oligonucleotides were designed in this region to selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat.

C9ORF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

| Functional Segments for NM_001256054.1 (SEQ ID NO: 1) | | | | |
|---|---|---|---|---|
| Exon Number | mRNA start site | mRNA stop site | Start site in reference to SEQ ID NO: 2 | Stop site in reference to SEQ ID NO: 2 |
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Amplicon Regions

Certain antisense oligonucleotides described herein may target the amplicon region of the primer probe set. Additional assays may be used to measure the potency and efficacy of these compounds.

Certain Human Therapeutics

The human C9ORF72 antisense oligonucleotides described herein are being evaluated as possible human therapeutics. Various parameters of potency, efficacy, and/or tolerability are being examined. Such parameters include in vitro inhibition of total C9ORF72 RNA expression, in vitro inhibition of C9ORF72 pathogenic associated RNA variant expression, in vitro dose response (IC50), in vivo inhibition of total or pathogenic RNA and/or protein in a transgenic animal containing a human C9ORF72 transgene in relevant tissues (e.g., brain and/or spinal cord), tolerability in mouse, tolerability in rat, and/or tolerability in a primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

Certain Hotspot Regions

1. Nucleobases 1107-1520 of SEQ ID NO: 2

In certain embodiments, antisense oligonucleotides are designed to target nucleobases 1107-1520 of SEQ ID NO: 2 (the complement of GENBANK Accession No. NT_008413.18 truncated from nucleosides 27535000 to 27565000). In certain embodiments, nucleobases 1107-1520 are a hotspot region. In certain embodiments, nucleobases 1107-1520 are targeted by antisense oligonucleotides. In certain embodiments, the antisense oligonucleotides are 17, 18, or 20 nucleobases in length. In certain embodiments, the antisense oligonucleotides are gapmers. In certain embodiments, the gapmers are 5-10-5 MOE gapmers or 5-8-5 MOE gapmers. In certain embodiments, the antisense oligonucleotides are 17-mer Deoxy, MOE and cEt oligonucleotides. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 1107-1520 are targeted by the following ISIS numbers: 619042-619333, 672581-672714, 672735-672865, 672885-673015, 673035-673165, 673185-673315, and 673335-673465.

In certain embodiments, nucleobases 1107-1520 are targeted by the following SEQ ID NOs: 21-31, 33-50, 52, 54-134, 138-248, 251-319, 325, 744-877, and 898-1028.

In certain embodiments, nucleobases 1107-1520 are targeted by the following ISIS numbers: 619042-619333.

In certain embodiments, nucleobases 1107-1520 are targeted by the following SEQ ID NOs: 21-31, 33-50, 52, 54-134, 138-248, 251-319, and 325.

In certain embodiments, antisense oligonucleotides targeting nucleobases 1107-1520 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of total C9ORF72 mRNA and/or protein levels in vitro and/or in vivo.

In certain embodiments, antisense oligonucleotides targeting nucleobases 1107-1520 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

2. Nucleobases 1111-1200 of SEQ ID NO: 2

In certain embodiments, antisense oligonucleotides are designed to target nucleobases 1111-1200 of SEQ ID NO: 2 (the complement of GENBANK Accession No. NT_008413.18 truncated from nucleosides 27535000 to 27565000). In certain embodiments, nucleobases 1111-1200 are a hotspot region. In certain embodiments, nucleobases 1111-1200 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 1111-1200 are targeted by the following ISIS numbers: 619042-619095.

In certain embodiments, nucleobases 1111-1200 are targeted by the following SEQ ID NOs: 21, 26-31, 33-50, 52, 54-60, 75, 81, and 87-96.

In certain embodiments, antisense oligonucleotides targeting nucleobases 1111-1200 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of total C9ORF72 mRNA and/or protein levels in vitro and/or in vivo.

In certain embodiments, antisense oligonucleotides targeting nucleobases 1111-1200 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

3. Nucleobases 1211-1318 of SEQ ID NO: 2

In certain embodiments, antisense oligonucleotides are designed to target nucleobases 1211-1318 of SEQ ID NO: 2 (the complement of GENBANK Accession No. NT_008413.18 truncated from nucleosides 27535000 to 27565000). In certain embodiments, nucleobases 1211-1318 are a hotspot region. In certain embodiments, nucleobases 1211-1318 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 1211-1318 are targeted by the following ISIS numbers: 619096-619172.

In certain embodiments, nucleobases 1211-1318 are targeted by the following SEQ ID NOs: 22-25, 70-74, 76-80, 82-86, 99-134, and 138-159.

In certain embodiments, antisense oligonucleotides targeting nucleobases 1211-1318 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of total C9ORF72 mRNA and/or protein levels in vitro and/or in vivo.

In certain embodiments, antisense oligonucleotides targeting nucleobases 1211-1318 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

4. Nucleobases 1326-1540 of SEQ ID NO: 2

In certain embodiments, antisense oligonucleotides are designed to target nucleobases 1326-1540 of SEQ ID NO: 2 (the complement of GENBANK Accession No. NT_008413.18 truncated from nucleosides 27535000 to 27565000). In certain embodiments, nucleobases 1326-1540 are a hotspot region. In certain embodiments, nucleobases 1326-1540 are targeted by antisense oligonucleotides. In certain embodiments, the antisense oligonucleotides are 17, 18, or 20 nucleobases in length. In certain embodiments, the antisense oligonucleotides are gapmers. In certain embodiments, the gapmers are 5-10-5 MOE gapmers or 5-8-5 MOE gapmers. In certain embodiments, the antisense oligonucleotides are 17-mer Deoxy, MOE and cEt oligonucleotides. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 1326-1540 are targeted by the following ISIS numbers: 619173-619354, and 672581-673484.

In certain embodiments, nucleobases 1326-1540 are targeted by the following SEQ ID NOs: 97, 98, 160-248, 251-322, 325-343, and 744-1047.

In certain embodiments, nucleobases 1326-1540 are targeted by the following ISIS numbers: 619173-619354.

In certain embodiments, nucleobases 1326-1540 are targeted by the following SEQ ID NOs: 97, 98, 160-248, 251-322, and 325-343.

In certain embodiments, antisense oligonucleotides targeting nucleobases 1326-1540 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of total C9ORF72 mRNA and/or protein levels in vitro and/or in vivo.

In certain embodiments, antisense oligonucleotides targeting nucleobases 1326-1540 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

5. Nucleobases 1331-1375 of SEQ ID NO: 2

In certain embodiments, antisense oligonucleotides are designed to target nucleobases 1331-1375 of SEQ ID NO: 2 (the complement of GENBANK Accession No. NT_008413.18 truncated from nucleosides 27535000 to 27565000). In certain embodiments, nucleobases 1331-1375 are a hotspot region. In certain embodiments, nucleobases 1331-1375 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssssooss.

In certain embodiments, nucleobases 1331-1375 are targeted by the following ISIS numbers: 619178-619203.

In certain embodiments, nucleobases 1331-1375 are targeted by the following SEQ ID NOs: 165-190.

In certain embodiments, antisense oligonucleotides targeting nucleobases 1331-1375 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

6. Nucleobases 1368-1391 of SEQ ID NO: 2

In certain embodiments, antisense oligonucleotides are designed to target nucleobases 1368-1391 of SEQ ID NO: 2 (the complement of GENBANK Accession No. NT_008413.18 truncated from nucleosides 27535000 to 27565000). In certain embodiments, nucleobases 1368-1391 are a hotspot region. In certain embodiments, nucleobases 1368-1391 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssssooss.

In certain embodiments, nucleobases 1368-1391 are targeted by the following ISIS numbers: 619215-619219.

In certain embodiments, nucleobases 1368-1391 are targeted by the following SEQ ID NOs: 202-206.

In certain embodiments, antisense oligonucleotides targeting nucleobases 1368-1391 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

7. Nucleobases 1398-1424 of SEQ ID NO: 2

In certain embodiments, antisense oligonucleotides are designed to target nucleobases 1398-1424 of SEQ ID NO: 2 (the complement of GENBANK Accession No. NT_008413.18 truncated from nucleosides 27535000 to 27565000). In certain embodiments, nucleobases 1398-1424 are a hotspot region. In certain embodiments, nucleobases 1398-1424 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssssooss.

In certain embodiments, nucleobases 1398-1424 are targeted by the following ISIS numbers: 619245-619252.

In certain embodiments, nucleobases 1398-1424 are targeted by the following SEQ ID NOs: 232-239.

In certain embodiments, antisense oligonucleotides targeting nucleobases 1398-1424 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

8. Nucleobases 1411-1440 of SEQ ID NO: 2

In certain embodiments, antisense oligonucleotides are designed to target nucleobases 1411-1440 of SEQ ID NO: 2 (the complement of GENBANK Accession No. NT_008413.18 truncated from nucleosides 27535000 to 27565000). In certain embodiments, nucleobases 1411-1440 are a hotspot region. In certain embodiments, nucleobases 1411-1440 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssooss.

In certain embodiments, nucleobases 1411-1440 are targeted by the following ISIS numbers: 619258-619268.

In certain embodiments, nucleobases 1411-1440 are targeted by the following SEQ ID NOs: 244-248, 251-255, and 325.

In certain embodiments, antisense oligonucleotides targeting nucleobases 1411-1440 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

9. Nucleobases 1429-1481 of SEQ ID NO: 2

In certain embodiments, antisense oligonucleotides are designed to target nucleobases 1429-1481 of SEQ ID NO: 2 (the complement of GENBANK Accession No. NT_008413.18 truncated from nucleosides 27535000 to 27565000). In certain embodiments, nucleobases 1429-1481 are a hotspot region. In certain embodiments, nucleobases 1429-1481 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssooss.

In certain embodiments, nucleobases 1429-1481 are targeted by the following ISIS numbers: 619276-619303.

In certain embodiments, nucleobases 1429-1481 are targeted by the following SEQ ID NOs: 98 and 263-289.

In certain embodiments, antisense oligonucleotides targeting nucleobases 1429-1481 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

10. Nucleobases 1502-1539 of SEQ ID NO: 2

In certain embodiments, antisense oligonucleotides are designed to target nucleobases 1502-1539 of SEQ ID NO: 2 (the complement of GENBANK Accession No. NT_008413.18 truncated from nucleosides 27535000 to 27565000). In certain embodiments, nucleobases 1502-1539 are a hotspot region. In certain embodiments, nucleobases 1502-1539 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssssooss.

In certain embodiments, nucleobases 1502-1539 are targeted by the following ISIS numbers: 619335-619353.

In certain embodiments, nucleobases 1502-1539 are targeted by the following SEQ ID NOs: 321, 322, and 326-342.

In certain embodiments, antisense oligonucleotides targeting nucleobases 1502-1539 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

11. Nucleobases 1508-1539 of SEQ ID NO: 2

In certain embodiments, antisense oligonucleotides are designed to target nucleobases 1508-1539 of SEQ ID NO: 2 (the complement of GENBANK Accession No. NT_008413.18 truncated from nucleosides 27535000 to 27565000). In certain embodiments, nucleobases 1508-1539 are a hotspot region. In certain embodiments, nucleobases 1508-1539 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense olignonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones"). In certain embodiments, the antisense oligonucleotides comprise the following sugar modification pattern: soooosssssssssssooss.

In certain embodiments, nucleobases 1508-1539 are targeted by the following ISIS numbers: 619341-619353.

In certain embodiments, nucleobases 1508-1539 are targeted by the following SEQ ID NOs: 330-342.

In certain embodiments, antisense oligonucleotides targeting nucleobases 1508-1539 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo 12. Nucleobases 7860-7906 of SEQ ID NO: 2

In certain embodiments, antisense oligonucleotides are designed to target nucleobases 7860-7906 of SEQ ID NO: 2 (the complement of GENBANK Accession No. NT_008413.18 truncated from nucleosides 27535000 to 27565000). In certain embodiments, nucleobases 7860-7906 are a hotspot region. In certain embodiments, nucleobases 7860-7906 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 7860-7906 are targeted by the following ISIS numbers: 655135-655144.

In certain embodiments, nucleobases 7860-7906 are targeted by the following SEQ ID NOs: 445-454.

In certain embodiments, antisense oligonucleotides targeting nucleobases 7860-7906 achieve at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, or at least 89% reduction of total C9ORF72 mRNA and/or protein levels in vitro and/or in vivo.

13. Nucleobases 7907-7944 of SEQ ID NO: 2

In certain embodiments, antisense oligonucleotides are designed to target nucleobases 7907-7944 of SEQ ID NO: 2 (the complement of GENBANK Accession No. NT_008413.18 truncated from nucleosides 27535000 to 27565000). In certain embodiments, nucleobases 7907-7944 are a hotspot region. In certain embodiments, nucleobases 7907-7944 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 7907-7944 are targeted by the following ISIS numbers: 655150-655156.

In certain embodiments, nucleobases 7907-7944 are targeted by the following SEQ ID NOs: 460-467.

In certain embodiments, antisense oligonucleotides targeting nucleobases 7907-7944 achieve at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, or at least 91% reduction of total C9ORF72 mRNA and/or protein levels in vitro and/or in vivo.

14. Nucleobases 7989-8038 of SEQ ID NO: 2

In certain embodiments, antisense oligonucleotides are designed to target nucleobases 7989-8038 of SEQ ID NO: 2 (the complement of GENBANK Accession No. NT_008413.18 truncated from nucleosides 27535000 to 27565000). In certain embodiments, nucleobases 7989-8038 are a hotspot region. In certain embodiments, nucleobases 7989-8038 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester Internucleoside linkages (e.g., the antisense oligonucleotides have "mixed backbones").

In certain embodiments, nucleobases 7989-8038 are targeted by the following ISIS numbers: 619411, 619412, 619420, 625183, 627833, and 655173-655180.

In certain embodiments, nucleobases 7989-8038 are targeted by the following SEQ ID NOs: 20, 51, 53, and 484-493.

In certain embodiments, antisense oligonucleotides targeting nucleobases 7989-8038 achieve at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, or at least 76% reduction of total C9ORF72 mRNA and/or protein levels in vitro and/or in vivo.

In certain embodiments, antisense oligonucleotides targeting nucleobases 7989-8038 achieve at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

15. Nucleobases 8020-8135 of SEQ ID NO: 2

In certain embodiments, antisense oligonucleotides are designed to target nucleobases 8020-8135 of SEQ ID NO: 2 (the complement of GENBANK Accession No. NT_008413.18 truncated from nucleosides 27535000 to 27565000). In certain embodiments, nucleobases 8020-8135 are a hotspot region. In certain embodiments, nucleobases 8020-8135 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 8020-8135 are targeted by the following ISIS numbers: 619413, 619414, 625255, 627834, 655181-655208.

In certain embodiments, nucleobases 8020-8135 are targeted by the following SEQ ID NOs: 135, 136, 494-511, and 517-528.

In certain embodiments, antisense oligonucleotides targeting nucleobases 8020-8135 achieve at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, or at least 54% reduction of total C9ORF72 mRNA and/or protein levels in vitro and/or in vivo.

In certain embodiments, antisense oligonucleotides targeting nucleobases 8020-8135 achieve at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

16. Nucleobases 8136-8161 of SEQ ID NO: 2

In certain embodiments, antisense oligonucleotides are designed to target nucleobases 8136-8161 of SEQ ID NO: 2 (the complement of GENBANK Accession No. NT_008413.18 truncated from nucleosides 27535000 to 27565000). In certain embodiments, nucleobases 8136-8161 are a hotspot region. In certain embodiments, nucleobases 8136-8161 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 8136-8161 are targeted by the following ISIS numbers: 655215-655217.

In certain embodiments, nucleobases 8136-8161 are targeted by the following SEQ ID NOs: 535-537.

In certain embodiments, antisense oligonucleotides targeting nucleobases 8136-8161 achieve at least 32%, at least 33%, at least 34%, at least 35%, at least 36%, at least 37%, at least 38%, at least 39%, at least 40%, or at least 41% reduction of total C9ORF72 mRNA and/or protein levels in vitro and/or in vivo.

In certain embodiments, antisense oligonucleotides targeting nucleobases 8136-8161 achieve at least 91%, at least 92%, at least 93%, at least 94%, or at least 95% reduction of C9ORF72 pathogenic associated mRNA variant levels in vitro and/or in vivo.

17. Nucleobases 8174-8211 of SEQ ID NO: 2

In certain embodiments, antisense oligonucleotides are designed to target nucleobases 8174-8211 of SEQ ID NO: 2 (the complement of GENBANK Accession No. NT_008413.18 truncated from nucleosides 27535000 to 27565000). In certain embodiments, nucleobases 8174-8211 are a hotspot region. In certain embodiments, nucleobases 8174-8211 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 8174-8211 are targeted by the following ISIS numbers: 655228-655234.

In certain embodiments, nucleobases 8174-8211 are targeted by the following SEQ ID NOs: 548-554.

In certain embodiments, antisense oligonucleotides targeting nucleobases 8174-8211 achieve at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, or at least 63% reduction of total C9ORF72 mRNA and/or protein levels in vitro and/or in vivo.

In certain embodiments, antisense oligonucleotides targeting nucleobases 8174-8211 achieve at least 88%, at least 89%, at least 90%, at least 91%, at least 92%, at least 93%, at least 94%, at least 95%, at least 96%, at least 97%, at least 98%, at least 99%, or at least 100% reduction of C9ORF72 pathogenic associated mRNA variant levels in vitro and/or in vivo.

18. Nucleobases 8213-8325 of SEQ ID NO: 2

In certain embodiments, antisense oligonucleotides are designed to target nucleobases 8213-8325 of SEQ ID NO: 2 (the complement of GENBANK Accession No. NT_008413.18 truncated from nucleosides 27535000 to 27565000). In certain embodiments, nucleobases 8213-8325 are a hotspot region. In certain embodiments, nucleobases 8213-8325 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleoside linkages (e.g., the antisense oligonucleotides have "mixed backbones").

In certain embodiments, nucleobases 8213-8325 are targeted by the following ISIS numbers: 655235-655270.

In certain embodiments, nucleobases 8213-8325 are targeted by the following SEQ ID NOs: 555-590.

In certain embodiments, antisense oligonucleotides targeting nucleobases 8213-8325 achieve at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, or at least 51% reduction of total C9ORF72 mRNA and/or protein levels in vitro and/or in vivo.

In certain embodiments, antisense oligonucleotides targeting nucleobases 8213-8325 achieve at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% reduction of C9ORF72 pathogenic associated mRNA variant levels in vitro and/or in vivo.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of a Human C9ORF72 mRNA Variant in HepG2 Cells by MOE Gapmers Antisense oligonucleotides targeting a C9ORF72 nucleic acid were designed and tested for their effects on C9ORF72 mRNA in vitro. ISIS 576816, previously tested in U.S. Application No. 61/714,132, filed Oct. 15, 2012, was used as a benchmark oligonucleotide. ISIS 576816 is a 5-10-5 MOE gapmer with phosphorothioate linkages throughout. Cultured HepG2 cells at a density of 20,000 cells per well were transfected using electroporation with 4,000 nM antisense oligonucleotide. After a treatment period of approximately 24 hours, RNA was isolated from the cells and C9ORF72 mRNA levels were measured by quantitative real-time PCR. Human primer probe set RTS3905 (forward primer sequence GGGTCTAGCAAGAGCAGGTG, designated herein as SEQ ID NO: 13; reverse primer sequence GTCTTGGCAACAGCTGGAGAT, designated herein as SEQ ID NO: 14; probe sequence TGATGTCGACTCTTTGCCCACCGC, designated herein as SEQ ID NO: 15—a TAQ-man primer probe set) was used. RTS3905 detects an mRNA variant (e.g. NM_001256054.1) processed from a pre-mRNA variant containing the hexanucleotide repeat. The mRNA variant processed from a pre-mRNA variant containing the hexanucleotide repeat is herein the "C9ORF72 pathogenic associated mRNA variant." A pre-mRNA contains the hexanucleotide repeat when transcription of the pre-mRNA begins in the region from the start site of exon 1A to the start site of exon 1B (generally nucleotides 1107 to 1520 of the genomic sequence: SEQ ID NO: 2, the complement of GENBANK Accession No. NT_008413.18 truncated from nucleosides 27535000 to 27565000. Therefore, oligonucleotides were designed in this region selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat. The levels of the C9ORF72 pathogenic associated mRNA variant were normalized to the total RNA content of the cell, as measured by RIBOGREEN®. Results are presented as percent inhibition of C9ORF72, relative to untreated control cells. The oligonucleotide marked with an asterisk (*) targets the amplicon region of the primer probe set. Additional assays may be used to measure the potency and efficacy of these oligonucleotides.

The chimeric antisense oligonucleotides in the Tables below were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment comprises a 2'-MOE group. All cytosine residues throughout each oligonucleotide are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

"Start site" indicates the 5'-most nucleoside to which the gapmer is targeted in the human gene sequence. "Stop site" indicates the 3'-most nucleoside to which the gapmer is targeted human gene sequence. Each antisense oligonucleotide listed in the Table below is targeted to either human C9ORF72 mRNA sequence, designated herein as SEQ ID NO: 1 (GENBANK Accession No. NM_001256054.1) or the human C9ORF72 genomic sequence, designated herein as SEQ ID NO: 2 (the complement of GENBANK Accession No. NT_008413.18 truncated from nucleosides 27535000 to 27565000), or both. 'n/a' indicates that the antisense oligonucleotide does not target that particular gene sequence

TABLE 6

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 576816 | 310 | 7990 | GCCTTACTCTAGGACCAAGA | sssssssssssssssssss | 40 | 20 |
| 619060 | 10 | 1146 | CTTTCCTAGCGGGACACCGT | soooosssssssssssooss | 34 | 21 |
| 619111 | 100 | 1236 | AAAAGAGAAGCAACCGGGCA | soooosssssssssssooss | 34 | 22 |
| 619112 | 101 | 1237 | CAAAAGAGAAGCAACCGGGC | soooosssssssssssooss | 38 | 23 |
| 619113 | 102 | 1238 | CCAAAAGAGAAGCAACCGGG | soooosssssssssssooss | 44 | 24 |
| 619114 | 103 | 1239 | CCCAAAAGAGAAGCAACCGG | soooosssssssssssooss | 100 | 25 |
| 619061 | 11 | 1147 | TCTTTCCTAGCGGGACACCG | soooosssssssssssooss | 100 | 26 |

TABLE 6-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619062 | 12 | 1148 | CTCTTTCCTAGCGGGACACC | soooosssssssssssooss | 20 | 27 |
| 619063 | 13 | 1149 | TCTCTTTCCTAGCGGGACAC | soooosssssssssssooss | 14 | 28 |
| 619064 | 14 | 1150 | CTCTCTTTCCTAGCGGGACA | soooosssssssssssooss | 9 | 29 |
| 619065 | 15 | 1151 | CCTCTCTTTCCTAGCGGGAC | soooosssssssssssooss | 12 | 30 |
| 619066 | 16 | 1152 | ACCTCTCTTTCCTAGCGGGA | soooosssssssssssooss | 0 | 31 |
| 619410* | 160 | 7840 | ATCCAAATGCTCCGGAGATA | soooosssssssssssooss | 96 | 32 |
| 619067 | 17 | 1153 | CACCTCTCTTTCCTAGCGGG | soooosssssssssssooss | 0 | 33 |
| 619068 | 18 | 1154 | GCACCTCTCTTTCCTAGCGG | soooosssssssssssooss | 24 | 34 |
| 619069 | 19 | 1155 | CGCACCTCTCTTTCCTAGCG | soooosssssssssssooss | 39 | 35 |
| 619052 | 2 | 1138 | GCGGGACACCGTAGGTTACG | soooosssssssssssooss | 30 | 36 |
| 619070 | 20 | 1156 | ACGCACCTCTCTTTCCTAGC | soooosssssssssssooss | 14 | 37 |
| 619071 | 21 | 1157 | GACGCACCTCTCTTTCCTAG | soooosssssssssssooss | 7 | 38 |
| 619072 | 22 | 1158 | TGACGCACCTCTCTTTCCTA | soooosssssssssssooss | 50 | 39 |
| 619073 | 23 | 1159 | TTGACGCACCTCTCTTTCCT | soooosssssssssssooss | 0 | 40 |
| 619074 | 24 | 1160 | TTTGACGCACCTCTCTTTCC | soooosssssssssssooss | 55 | 41 |
| 619075 | 25 | 1161 | GTTTGACGCACCTCTCTTTC | soooosssssssssssooss | 12 | 42 |
| 619076 | 26 | 1162 | TGTTTGACGCACCTCTCTTT | soooosssssssssssooss | 65 | 43 |
| 619077 | 27 | 1163 | CTGTTTGACGCACCTCTCTT | soooosssssssssssooss | 28 | 44 |
| 619078 | 28 | 1164 | GCTGTTTGACGCACCTCTCT | soooosssssssssssooss | 18 | 45 |
| 619079 | 29 | 1165 | CGCTGTTTGACGCACCTCTC | soooosssssssssssooss | 14 | 46 |
| 619053 | 3 | 1139 | AGCGGGACACCGTAGGTTAC | soooosssssssssssooss | 23 | 47 |
| 619080 | 30 | 1166 | TCGCTGTTTGACGCACCTCT | soooosssssssssssooss | 100 | 48 |
| 619081 | 31 | 1167 | GTCGCTGTTTGACGCACCTC | soooosssssssssssooss | 23 | 49 |
| 619082 | 32 | 1168 | TGTCGCTGTTTGACGCACCT | soooosssssssssssooss | 0 | 50 |
| 619411 | 324 | 8004 | TGGAGCCCAAATGTGCCTTA | soooosssssssssssooss | 99 | 51 |
| 619083 | 33 | 1169 | TTGTCGCTGTTTGACGCACC | soooosssssssssssooss | 36 | 52 |
| 619412 | 332 | 8012 | TCTGTCTTTGGAGCCCAAAT | soooosssssssssssooss | 100 | 53 |
| 619084 | 34 | 1170 | CTTGTCGCTGTTTGACGCAC | soooosssssssssssooss | 28 | 54 |
| 619085 | 35 | 1171 | ACTTGTCGCTGTTTGACGCA | soooosssssssssssooss | 55 | 55 |
| 619086 | 36 | 1172 | AACTTGTCGCTGTTTGACGC | soooosssssssssssooss | 29 | 56 |
| 619087 | 37 | 1173 | GAACTTGTCGCTGTTTGACG | soooosssssssssssooss | 21 | 57 |
| 619088 | 38 | 1174 | GGAACTTGTCGCTGTTTGAC | soooosssssssssssooss | 100 | 58 |
| 619089 | 39 | 1175 | CGGAACTTGTCGCTGTTTGA | soooosssssssssssooss | 67 | 59 |
| 619054 | 4 | 1140 | TAGCGGGACACCGTAGGTTA | soooosssssssssssooss | 59 | 60 |
| 619090 | 40 | 1176 | GCGGAACTTGTCGCTGTTTG | soooosssssssssssooss | 8 | 61 |

TABLE 6-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619091 | 41 | 1177 | GGCGGAACTTGTCGCTGTTT | soooosssssssssssooss | 38 | 62 |
| 619092 | 42 | 1178 | GGGCGGAACTTGTCGCTGTT | soooosssssssssssooss | 16 | 63 |
| 619093 | 43 | 1179 | TGGGCGGAACTTGTCGCTGT | soooosssssssssssooss | 22 | 64 |
| 619094 | 44 | 1180 | GTGGGCGGAACTTGTCGCTG | soooosssssssssssooss | 24 | 65 |
| 619095 | 45 | 1181 | CGTGGGCGGAACTTGTCGCT | soooosssssssssssooss | 100 | 66 |
| 619055 | 5 | 1141 | CTAGCGGGACACCGTAGGTT | soooosssssssssssooss | 100 | 67 |
| 619056 | 6 | 1142 | CCTAGCGGGACACCGTAGGT | soooosssssssssssooss | 11 | 68 |
| 619057 | 7 | 1143 | TCCTAGCGGGACACCGTAGG | soooosssssssssssooss | 22 | 69 |
| 619096 | 75 | 1211 | GACGGCTGACACACCAAGCG | soooosssssssssssooss | 100 | 70 |
| 619097 | 76 | 1212 | GGACGGCTGACACACCAAGC | soooosssssssssssooss | 88 | 71 |
| 619098 | 77 | 1213 | GGGACGGCTGACACACCAAG | soooosssssssssssooss | 29 | 72 |
| 619099 | 78 | 1214 | AGGGACGGCTGACACACCAA | soooosssssssssssooss | 83 | 73 |
| 619100 | 79 | 1215 | CAGGGACGGCTGACACACCA | soooosssssssssssooss | 23 | 74 |
| 619058 | 8 | 1144 | TTCCTAGCGGGACACCGTAG | soooosssssssssssooss | 32 | 75 |
| 619101 | 80 | 1216 | GCAGGGACGGCTGACACACC | soooosssssssssssooss | 18 | 76 |
| 619102 | 81 | 1217 | AGCAGGGACGGCTGACACAC | soooosssssssssssooss | 39 | 77 |
| 619103 | 82 | 1218 | CAGCAGGGACGGCTGACACA | soooosssssssssssooss | 39 | 78 |
| 619104 | 83 | 1219 | GCAGCAGGGACGGCTGACAC | soooosssssssssssooss | 22 | 79 |
| 619105 | 84 | 1220 | GGCAGCAGGGACGGCTGACA | soooosssssssssssooss | 43 | 80 |
| 619059 | 9 | 1145 | TTTCCTAGCGGGACACCGTA | soooosssssssssssooss | 4 | 81 |
| 619106 | 95 | 1231 | AGAAGCAACCGGGCAGCAGG | soooosssssssssssooss | 54 | 82 |
| 619107 | 96 | 1232 | GAGAAGCAACCGGGCAGCAG | soooosssssssssssooss | 100 | 83 |
| 619108 | 97 | 1233 | AGAGAAGCAACCGGGCAGCA | soooosssssssssssooss | 32 | 84 |
| 619109 | 98 | 1234 | AAGAGAAGCAACCGGGCAGC | soooosssssssssssooss | 30 | 85 |
| 619110 | 99 | 1235 | AAAGAGAAGCAACCGGGCAG | soooosssssssssssooss | 44 | 86 |
| 619042 | n/a | 1111 | GTTTTCTATGTGCGATGACG | soooosssssssssssooss | 6 | 87 |
| 619043 | n/a | 1112 | TGTTTTCTATGTGCGATGAC | soooosssssssssssooss | 45 | 88 |
| 619044 | n/a | 1113 | CTGTTTTCTATGTGCGATGA | soooosssssssssssooss | 23 | 89 |
| 619045 | n/a | 1114 | TCTGTTTTCTATGTGCGATG | soooosssssssssssooss | 10 | 90 |
| 619046 | n/a | 1115 | GTCTGTTTTCTATGTGCGAT | soooosssssssssssooss | 11 | 91 |
| 619047 | n/a | 1116 | TGTCTGTTTTCTATGTGCGA | soooosssssssssssooss | 28 | 92 |
| 619048 | n/a | 1117 | CTGTCTGTTTTCTATGTGCG | soooosssssssssssooss | 34 | 93 |
| 619049 | n/a | 1118 | TCTGTCTGTTTTCTATGTGC | soooosssssssssssooss | 72 | 94 |
| 619050 | n/a | 1119 | GTCTGTCTGTTTTCTATGTG | soooosssssssssssooss | 37 | 95 |
| 619051 | n/a | 1120 | CGTCTGTCTGTTTTCTATGT | soooosssssssssssooss | 1 | 96 |

TABLE 6-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619253 | n/a | 1406 | TACAGGCTGCGGTTGTTTCC | soooosssssssssssooss | 100 | 97 |
| 619293 | n/a | 1446 | CCCGGCCCCTAGCGCGCGAC | soooosssssssssssooss | 98 | 98 |

Example 2: Antisense Inhibition of a Human C9ORF72 mRNA Variant in HepG2 Cells by MOE Gapmers Additional antisense oligonucleotides targeting a C9ORF72 nucleic acid were designed and tested for their effects on C9ORF72 mRNA in vitro. ISIS 576816, previously tested in U.S. Application No. 61/714,132, filed Oct. 15, 2012, was used as a benchmark oligonucleotide. The antisense oligonucleotides were tested in a series of experiments that had similar culture conditions. The results for each experiment are presented in separate tables shown below. Cultured HepG2 cells at a density of 20,000 cells per well were transfected using electroporation with 1,000 nM antisense oligonucleotide. After a treatment period of approximately 24 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. The levels of the C9ORF72 pathogenic associated mRNA variant were normalized to the total RNA content of the cell, as measured by RIBOGREEN®. Results are presented as percent inhibition of C9ORF72, relative to untreated control cells. The oligonucleotides marked with as asterisk (*) targets the region of the primer probe set. Additional assays may be used to measure the potency and efficacy of these oligonucleotides. 'n.d.' indicates that there was no signal reading in the assay for that particular oligonucleotide.

The chimeric antisense oligonucleotides in the Tables below were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment comprises a 2'-MOE group. All cytosine residues throughout each oligonucleotide are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

"Start site" indicates the 5'-most nucleoside to which the gapmer is targeted in the human gene sequence. "Stop site" indicates the 3'-most nucleoside to which the gapmer is targeted human gene sequence. The gapmers of the Tables below also target either human C9ORF72 mRNA sequence, designated herein as SEQ ID NO: 1 (GENBANK Accession No. NM_001256054.1) or the human C9ORF72 genomic sequence, designated herein as SEQ ID NO: 2 (the complement of GENBANK Accession No. NT_008413.18 truncated from nucleosides 27535000 to 27565000), or both. Some of the gapmers of Table 10 are targeted to GENBANK Accession No. NM_145005.5 (incorporated herein as SEQ ID NO: 3), GENBANK Accession No. DB079375.1 (incorporated herein as SEQ ID NO: 4), or GENBANK Accession No. BU194591.1 (incorporated herein as SEQ ID NO: 5). 'n/a' indicates that the antisense oligonucleotide does not target that particular gene sequence.

TABLE 7

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 576816 | 310 | 7990 | GCCTTACTCTAGGACCAAGA | ssssssssssssssssssss | 70 | 20 |
| 619115 | 104 | 1240 | CCCCAAAAGAGAAGCAACCG | soooosssssssssssooss | 10 | 99 |
| 619116 | 105 | 1241 | CCCCCAAAAGAGAAGCAACC | soooosssssssssssooss | 19 | 100 |
| 619117 | 106 | 1242 | GCCCCCAAAAGAGAAGCAAC | soooosssssssssssooss | 0 | 101 |
| 619118* | 107 | 1243 | CGCCCCCAAAAGAGAAGCAA | soooosssssssssssooss | 17 | 102 |
| 619119* | 108 | 1244 | CCGCCCCCAAAAGAGAAGCA | soooosssssssssssooss | 14 | 103 |

TABLE 7-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619120* | 109 | 1245 | CCCGCCCCCAAAAGAGAAGC | sooooossssssssssooss | 4 | 104 |
| 619121* | 110 | 1246 | CCCCGCCCCCAAAAGAGAAG | sooooossssssssssooss | 19 | 105 |
| 619122* | 111 | 1247 | ACCCCGCCCCCAAAAGAGAA | sooooossssssssssooss | 47 | 106 |
| 619123* | 112 | 1248 | GACCCCGCCCCCAAAAGAGA | sooooossssssssssooss | 11 | 107 |
| 619124* | 113 | 1249 | AGACCCCGCCCCCAAAAGAG | sooooossssssssssooss | 16 | 108 |
| 619125* | 114 | 1250 | TAGACCCCGCCCCCAAAAGA | sooooossssssssssooss | 15 | 109 |
| 619126* | 115 | 1251 | CTAGACCCCGCCCCCAAAAG | sooooossssssssssooss | 43 | 110 |
| 619127* | 116 | 1252 | GCTAGACCCCGCCCCCAAAA | sooooossssssssssooss | 67 | 111 |
| 619128* | 117 | 1253 | TGCTAGACCCCGCCCCCAAA | sooooossssssssssooss | 85 | 112 |
| 619129* | 118 | 1254 | TTGCTAGACCCCGCCCCCAA | sooooossssssssssooss | 41 | 113 |
| 619130* | 119 | 1255 | CTTGCTAGACCCCGCCCCCA | sooooossssssssssooss | 62 | 114 |
| 619131* | 120 | 1256 | TCTTGCTAGACCCCGCCCCC | sooooossssssssssooss | 95 | 115 |
| 619132* | 121 | 1257 | CTCTTGCTAGACCCCGCCCC | sooooossssssssssooss | 81 | 116 |
| 619133* | 122 | 1258 | GCTCTTGCTAGACCCCGCCC | sooooossssssssssooss | 90 | 117 |
| 619134* | 123 | 1259 | TGCTCTTGCTAGACCCCGCC | sooooossssssssssooss | 85 | 118 |
| 619135* | 124 | 1260 | CTGCTCTTGCTAGACCCCGC | sooooossssssssssooss | 81 | 119 |
| 619136* | 125 | 1261 | CCTGCTCTTGCTAGACCCCG | sooooossssssssssooss | 78 | 120 |
| 619137* | 126 | 1262 | ACCTGCTCTTGCTAGACCCC | sooooossssssssssooss | 85 | 121 |
| 619138* | 127 | 1263 | CACCTGCTCTTGCTAGACCC | sooooossssssssssooss | 81 | 122 |
| 619139* | 128 | 1264 | ACACCTGCTCTTGCTAGACC | sooooossssssssssooss | 77 | 123 |
| 619140* | 129 | 1265 | CACACCTGCTCTTGCTAGAC | sooooossssssssssooss | 86 | 124 |
| 619141* | 130 | 1266 | CCACACCTGCTCTTGCTAGA | sooooossssssssssooss | 90 | 125 |
| 619142* | 131 | 1267 | CCCACACCTGCTCTTGCTAG | sooooossssssssssooss | 98 | 126 |
| 619143* | 132 | 1268 | ACCCACACCTGCTCTTGCTA | sooooossssssssssooss | 94 | 127 |
| 619144* | 133 | 1269 | AACCCACACCTGCTCTTGCT | sooooossssssssssooss | 93 | 128 |
| 619145* | 134 | 1270 | AAACCCACACCTGCTCTTGC | sooooossssssssssooss | 95 | 129 |
| 619146* | 135 | 1271 | TAAACCCACACCTGCTCTTG | sooooossssssssssooss | 78 | 130 |
| 619147* | 136 | 1272 | CTAAACCCACACCTGCTCTT | sooooossssssssssooss | 64 | 131 |
| 619148* | 137 | 1273 | CCTAAACCCACACCTGCTCT | sooooossssssssssooss | 84 | 132 |
| 619149* | 138 | 1274 | TCCTAAACCCACACCTGCTC | sooooossssssssssooss | 87 | 133 |
| 619150* | 139 | 1275 | CTCCTAAACCCACACCTGCT | sooooossssssssssooss | 89 | 134 |
| 619413 | 340 | 8020 | GTACCTGTTCTGTCTTTGGA | sooooossssssssssooss | 70 | 135 |
| 619414 | 353 | 8033 | CCATCACTGAGAAGTACCTG | sooooossssssssssooss | 78 | 136 |
| 619415 | 940 | 16395 | GGCATAATGTTCTGACTATC | sooooossssssssssooss | 67 | 137 |
| 619151* | n/a | 1276 | CCTCCTAAACCCACACCTGC | sooooossssssssssooss | 64 | 138 |

TABLE 7-continued

Percent inhibition of the C9ORF72 pathogenic associated mRNA variant
compared to PBS control by antisense oligonucleotides targeting
SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619152* | n/a | 1277 | ACCTCCTAAACCCACACCTG | soooosssssssssssooss | 45 | 139 |
| 619153* | n/a | 1278 | CACCTCCTAAACCCACACCT | soooosssssssssssooss | 36 | 140 |
| 619154* | n/a | 1279 | ACACCTCCTAAACCCACACC | soooosssssssssssooss | 26 | 141 |
| 619155* | n/a | 1280 | CACACCTCCTAAACCCACAC | soooosssssssssssooss | 50 | 142 |
| 619156* | n/a | 1281 | ACACACCTCCTAAACCCACA | soooosssssssssssooss | 53 | 143 |
| 619157* | n/a | 1282 | CACACACCTCCTAAACCCAC | soooosssssssssssooss | 44 | 144 |
| 619158* | n/a | 1283 | ACACACACCTCCTAAACCCA | soooosssssssssssooss | 65 | 145 |
| 619159* | n/a | 1284 | AACACACACCTCCTAAACCC | soooosssssssssssooss | 9 | 146 |
| 619160* | n/a | 1285 | AAACACACACCTCCTAAACC | soooosssssssssssooss | 0 | 147 |
| 619161* | n/a | 1286 | AAAACACACACCTCCTAAAC | soooosssssssssssooss | 15 | 148 |
| 619162* | n/a | 1287 | AAAAACACACACCTCCTAAA | soooosssssssssssooss | 10 | 149 |
| 619163* | n/a | 1288 | CAAAAACACACACCTCCTAA | soooosssssssssssooss | 7 | 150 |
| 619164* | n/a | 1289 | ACAAAAACACACACCTCCTA | soooosssssssssssooss | 55 | 151 |
| 619165* | n/a | 1290 | AACAAAAACACACACCTCCT | soooosssssssssssooss | 24 | 152 |
| 619166* | n/a | 1291 | AAACAAAAACACACACCTCC | soooosssssssssssooss | 19 | 153 |
| 619167* | n/a | 1292 | AAAACAAAAACACACACCTC | soooosssssssssssooss | 8 | 154 |
| 619168* | n/a | 1294 | GAAAAACAAAAACACACACC | soooosssssssssssooss | 17 | 155 |
| 619169* | n/a | 1295 | GGAAAAACAAAAACACACAC | soooosssssssssssooss | 26 | 156 |
| 619170 | n/a | 1297 | TGGGAAAAACAAAAACACAC | soooosssssssssssooss | 30 | 157 |
| 619171 | n/a | 1298 | GTGGGAAAAACAAAAACACA | soooosssssssssssooss | 23 | 158 |
| 619172 | n/a | 1299 | GGTGGGAAAAACAAAAACAC | soooosssssssssssooss | 22 | 159 |
| 619173 | n/a | 1326 | CTGTGAGAGCAAGTAGTGGG | soooosssssssssssooss | 43 | 160 |
| 619174 | n/a | 1327 | ACTGTGAGAGCAAGTAGTGG | soooosssssssssssooss | 36 | 161 |
| 619175 | n/a | 1328 | TACTGTGAGAGCAAGTAGTG | soooosssssssssssooss | 24 | 162 |
| 619176 | n/a | 1329 | GTACTGTGAGAGCAAGTAGT | soooosssssssssssooss | 58 | 163 |
| 619177 | n/a | 1330 | AGTACTGTGAGAGCAAGTAG | soooosssssssssssooss | 22 | 164 |
| 619178 | n/a | 1331 | GAGTACTGTGAGAGCAAGTA | soooosssssssssssooss | 100 | 165 |
| 619179 | n/a | 1332 | CGAGTACTGTGAGAGCAAGT | soooosssssssssssooss | 62 | 166 |
| 619180 | n/a | 1333 | GCGAGTACTGTGAGAGCAAG | soooosssssssssssooss | 63 | 167 |
| 619181 | n/a | 1334 | AGCGAGTACTGTGAGAGCAA | soooosssssssssssooss | 36 | 168 |
| 619182 | n/a | 1335 | CAGCGAGTACTGTGAGAGCA | soooosssssssssssooss | 41 | 169 |
| 619183 | n/a | 1336 | TCAGCGAGTACTGTGAGAGC | soooosssssssssssooss | 66 | 170 |
| 619184 | n/a | 1337 | CTCAGCGAGTACTGTGAGAG | soooosssssssssssooss | 28 | 171 |
| 619185 | n/a | 1338 | CCTCAGCGAGTACTGTGAGA | soooosssssssssssooss | 37 | 172 |
| 619186 | n/a | 1339 | CCCTCAGCGAGTACTGTGAG | soooosssssssssssooss | 43 | 173 |

TABLE 7-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619187 | n/a | 1340 | ACCCTCAGCGAGTACTGTGA | soooossssssssssooss | 84 | 174 |
| 619253 | n/a | 1406 | TACAGGCTGCGGTTGTTTCC | soooossssssssssooss | 31 | 97 |
| 619293 | n/a | 1446 | CCCGGCCCCTAGCGCGCGAC | soooossssssssssooss | 63 | 98 |

TABLE 8

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 576816 | 310 | 7990 | GCCTTACTCTAGGACCAAGA | ssssssssssssssssssss | 82 | 20 |
| 619188 | n/a | 1341 | CACCCTCAGCGAGTACTGTG | soooossssssssssooss | 56 | 175 |
| 619189 | n/a | 1342 | TCACCCTCAGCGAGTACTGT | soooossssssssssooss | 66 | 176 |
| 619190 | n/a | 1343 | TTCACCCTCAGCGAGTACTG | soooossssssssssooss | 57 | 177 |
| 619191 | n/a | 1344 | GTTCACCCTCAGCGAGTACT | soooossssssssssooss | 83 | 178 |
| 619192 | n/a | 1345 | TGTTCACCCTCAGCGAGTAC | soooossssssssssooss | 66 | 179 |
| 619193 | n/a | 1346 | TTGTTCACCCTCAGCGAGTA | soooossssssssssooss | 57 | 180 |
| 619194 | n/a | 1347 | CTTGTTCACCCTCAGCGAGT | soooossssssssssooss | 48 | 181 |
| 619195 | n/a | 1348 | TCTTGTTCACCCTCAGCGAG | soooossssssssssooss | 46 | 182 |
| 619196 | n/a | 1349 | TTCTTGTTCACCCTCAGCGA | soooossssssssssooss | 66 | 183 |
| 619197 | n/a | 1350 | TTTCTTGTTCACCCTCAGCG | soooossssssssssooss | 31 | 184 |
| 619198 | n/a | 1351 | TTTTCTTGTTCACCCTCAGC | soooossssssssssooss | 47 | 185 |
| 619199 | n/a | 1352 | CTTTTCTTGTTCACCCTCAG | soooossssssssssooss | 53 | 186 |
| 619200 | n/a | 1353 | TCTTTTCTTGTTCACCCTCA | soooossssssssssooss | 46 | 187 |
| 619201 | n/a | 1354 | GTCTTTTCTTGTTCACCCTC | soooossssssssssooss | 71 | 188 |
| 619202 | n/a | 1355 | GGTCTTTTCTTGTTCACCCT | soooossssssssssooss | 73 | 189 |
| 619203 | n/a | 1356 | AGGTCTTTTCTTGTTCACCC | soooossssssssssooss | 79 | 190 |
| 619204 | n/a | 1357 | CAGGTCTTTTCTTGTTCACC | soooossssssssssooss | 0 | 191 |
| 619205 | n/a | 1358 | TCAGGTCTTTTCTTGTTCAC | soooossssssssssooss | 68 | 192 |
| 619206 | n/a | 1359 | ATCAGGTCTTTTCTTGTTCA | soooossssssssssooss | 52 | 193 |
| 619207 | n/a | 1360 | TATCAGGTCTTTTCTTGTTC | soooossssssssssooss | 47 | 194 |
| 619208 | n/a | 1361 | TTATCAGGTCTTTTCTTGTT | soooossssssssssooss | 37 | 195 |
| 619209 | n/a | 1362 | TTTATCAGGTCTTTTCTTGT | soooossssssssssooss | 31 | 196 |
| 619210 | n/a | 1363 | CTTTATCAGGTCTTTTCTTG | soooossssssssssooss | 24 | 197 |
| 619211 | n/a | 1364 | TCTTTATCAGGTCTTTTCTT | soooossssssssssooss | 37 | 198 |

TABLE 8-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619212 | n/a | 1365 | ATCTTTATCAGGTCTTTTCT | sooooosssssssssssooss | 34 | 199 |
| 619213 | n/a | 1366 | AATCTTTATCAGGTCTTTTC | sooooosssssssssssooss | 38 | 200 |
| 619214 | n/a | 1367 | TAATCTTTATCAGGTCTTTT | sooooosssssssssssooss | 32 | 201 |
| 619215 | n/a | 1368 | TTAATCTTTATCAGGTCTTT | sooooosssssssssssooss | 55 | 202 |
| 619216 | n/a | 1369 | GTTAATCTTTATCAGGTCTT | sooooosssssssssssooss | 72 | 203 |
| 619217 | n/a | 1370 | GGTTAATCTTTATCAGGTCT | sooooosssssssssssooss | 85 | 204 |
| 619218 | n/a | 1371 | TGGTTAATCTTTATCAGGTC | sooooosssssssssssooss | 82 | 205 |
| 619219 | n/a | 1372 | CTGGTTAATCTTTATCAGGT | sooooosssssssssssooss | 62 | 206 |
| 619220 | n/a | 1373 | TCTGGTTAATCTTTATCAGG | sooooosssssssssssooss | 19 | 207 |
| 619221 | n/a | 1374 | TTCTGGTTAATCTTTATCAG | sooooosssssssssssooss | 31 | 208 |
| 619222 | n/a | 1375 | CTTCTGGTTAATCTTTATCA | sooooosssssssssssooss | 40 | 209 |
| 619223 | n/a | 1376 | TCTTCTGGTTAATCTTTATC | sooooosssssssssssooss | 41 | 210 |
| 619224 | n/a | 1377 | TTCTTCTGGTTAATCTTTAT | sooooosssssssssssooss | 11 | 211 |
| 619225 | n/a | 1378 | TTTCTTCTGGTTAATCTTTA | sooooosssssssssssooss | 46 | 212 |
| 619226 | n/a | 1379 | TTTTCTTCTGGTTAATCTTT | sooooosssssssssssooss | 14 | 213 |
| 619227 | n/a | 1380 | GTTTTCTTCTGGTTAATCTT | sooooosssssssssssooss | 50 | 214 |
| 619228 | n/a | 1381 | TGTTTTCTTCTGGTTAATCT | sooooosssssssssssooss | 49 | 215 |
| 619229 | n/a | 1382 | TTGTTTTCTTCTGGTTAATC | sooooosssssssssssooss | 31 | 216 |
| 619230 | n/a | 1383 | CTTGTTTTCTTCTGGTTAAT | sooooosssssssssssooss | 16 | 217 |
| 619231 | n/a | 1384 | CCTTGTTTTCTTCTGGTTAA | sooooosssssssssssooss | 23 | 218 |
| 619232 | n/a | 1385 | TCCTTGTTTTCTTCTGGTTA | sooooosssssssssssooss | 52 | 219 |
| 619233 | n/a | 1386 | CTCCTTGTTTTCTTCTGGTT | sooooosssssssssssooss | 32 | 220 |
| 619234 | n/a | 1387 | CCTCCTTGTTTTCTTCTGGT | sooooosssssssssssooss | 59 | 221 |
| 619235 | n/a | 1388 | CCCTCCTTGTTTTCTTCTGG | sooooosssssssssssooss | 48 | 222 |
| 619236 | n/a | 1389 | TCCCTCCTTGTTTTCTTCTG | sooooosssssssssssooss | 31 | 223 |
| 619237 | n/a | 1390 | TTCCCTCCTTGTTTTCTTCT | sooooosssssssssssooss | 24 | 224 |
| 619238 | n/a | 1391 | TTTCCCTCCTTGTTTTCTTC | sooooosssssssssssooss | 42 | 225 |
| 619239 | n/a | 1392 | GTTTCCCTCCTTGTTTTCTT | sooooosssssssssssooss | 46 | 226 |
| 619240 | n/a | 1393 | TGTTTCCCTCCTTGTTTTCT | sooooosssssssssssooss | 81 | 227 |
| 619241 | n/a | 1394 | TTGTTTCCCTCCTTGTTTTC | sooooosssssssssssooss | 53 | 228 |
| 619242 | n/a | 1395 | GTTGTTTCCCTCCTTGTTTT | sooooosssssssssssooss | 28 | 229 |
| 619243 | n/a | 1396 | GGTTGTTTCCCTCCTTGTTT | sooooosssssssssssooss | 40 | 230 |
| 619244 | n/a | 1397 | CGGTTGTTTCCCTCCTTGTT | sooooosssssssssssooss | 31 | 231 |
| 619245 | n/a | 1398 | GCGGTTGTTTCCCTCCTTGT | sooooosssssssssssooss | 69 | 232 |
| 619246 | n/a | 1399 | TGCGGTTGTTTCCCTCCTTG | sooooosssssssssssooss | 73 | 233 |

TABLE 8-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619247 | n/a | 1400 | CTGCGGTTGTTTCCCTCCTT | soooossssssssssooss | 90 | 234 |
| 619248 | n/a | 1401 | GCTGCGGTTGTTTCCCTCCT | soooossssssssssooss | 40 | 235 |
| 619249 | n/a | 1402 | GGCTGCGGTTGTTTCCCTCC | soooossssssssssooss | 50 | 236 |
| 619250 | n/a | 1403 | AGGCTGCGGTTGTTTCCCTC | soooossssssssssooss | 61 | 237 |
| 619251 | n/a | 1404 | CAGGCTGCGGTTGTTTCCCT | soooossssssssssooss | 72 | 238 |
| 619252 | n/a | 1405 | ACAGGCTGCGGTTGTTTCCC | soooossssssssssooss | 69 | 239 |
| 619253 | n/a | 1406 | TACAGGCTGCGGTTGTTTCC | soooossssssssssooss | 67 | 97 |
| 619254 | n/a | 1407 | CTACAGGCTGCGGTTGTTTC | soooossssssssssooss | 43 | 240 |
| 619255 | n/a | 1408 | GCTACAGGCTGCGGTTGTTT | soooossssssssssooss | 54 | 241 |
| 619256 | n/a | 1409 | TGCTACAGGCTGCGGTTGTT | soooossssssssssooss | 36 | 242 |
| 619257 | n/a | 1410 | TTGCTACAGGCTGCGGTTGT | soooossssssssssooss | 29 | 243 |
| 619258 | n/a | 1411 | CTTGCTACAGGCTGCGGTTG | soooossssssssssooss | 50 | 244 |
| 619259 | n/a | 1412 | GCTTGCTACAGGCTGCGGTT | soooossssssssssooss | 76 | 245 |
| 619260 | n/a | 1413 | AGCTTGCTACAGGCTGCGGT | soooossssssssssooss | 80 | 246 |
| 619261 | n/a | 1414 | GAGCTTGCTACAGGCTGCGG | soooossssssssssooss | 54 | 247 |
| 619262 | n/a | 1415 | AGAGCTTGCTACAGGCTGCG | soooossssssssssooss | 62 | 248 |
| 619293 | n/a | 1446 | CCCGGCCCCTAGCGCGCGAC | soooossssssssssooss | 64 | 98 |
| 619416 | 1937 | 24657 27056 | AAAAAACAGTAGTTGTGGTC | soooossssssssssooss | 78 | 249 |
| 619417 | 1988 | 27107 | GCCAACTCAGATTTCACCTT | soooossssssssssooss | 86 | 250 |

TABLE 9

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 576816 | 310 | 7990 | GCCTTACTCTAGGACCAAGA | sssssssssssssssssss | 71 | 20 |
| 619264 | n/a | 1417 | CCAGAGCTTGCTACAGGCTG | soooossssssssssooss | 54 | 251 |
| 619265 | n/a | 1418 | TCCAGAGCTTGCTACAGGCT | soooossssssssssooss | 69 | 252 |
| 619266 | n/a | 1419 | TTCCAGAGCTTGCTACAGGC | soooossssssssssooss | 70 | 253 |
| 619267 | n/a | 1420 | GTTCCAGAGCTTGCTACAGG | soooossssssssssooss | 49 | 254 |
| 619268 | n/a | 1421 | AGTTCCAGAGCTTGCTACAG | soooossssssssssooss | 95 | 255 |
| 619269 | n/a | 1422 | GAGTTCCAGAGCTTGCTACA | soooossssssssssooss | 36 | 256 |
| 619270 | n/a | 1423 | TGAGTTCCAGAGCTTGCTAC | soooossssssssssooss | 15 | 257 |

TABLE 9-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619271 | n/a | 1424 | CTGAGTTCCAGAGCTTGCTA | sooooosssssssssssooss | 31 | 258 |
| 619272 | n/a | 1425 | CCTGAGTTCCAGAGCTTGCT | sooooosssssssssssooss | 41 | 259 |
| 619273 | n/a | 1426 | TCCTGAGTTCCAGAGCTTGC | sooooosssssssssssooss | 36 | 260 |
| 619274 | n/a | 1427 | CTCCTGAGTTCCAGAGCTTG | sooooosssssssssssooss | 25 | 261 |
| 619275 | n/a | 1428 | ACTCCTGAGTTCCAGAGCTT | sooooosssssssssssooss | 50 | 262 |
| 619276 | n/a | 1429 | GACTCCTGAGTTCCAGAGCT | sooooosssssssssssooss | 74 | 263 |
| 619277 | n/a | 1430 | CGACTCCTGAGTTCCAGAGC | sooooosssssssssssooss | 69 | 264 |
| 619278 | n/a | 1431 | GCGACTCCTGAGTTCCAGAG | sooooosssssssssssooss | 98 | 265 |
| 619279 | n/a | 1432 | CGCGACTCCTGAGTTCCAGA | sooooosssssssssssooss | 69 | 266 |
| 619280 | n/a | 1433 | GCGCGACTCCTGAGTTCCAG | sooooosssssssssssooss | 75 | 267 |
| 619281 | n/a | 1434 | CGCGCGACTCCTGAGTTCCA | sooooosssssssssssooss | 67 | 268 |
| 619282 | n/a | 1435 | GCGCGCGACTCCTGAGTTCC | sooooosssssssssssooss | 55 | 269 |
| 619283 | n/a | 1436 | AGCGCGCGACTCCTGAGTTC | sooooosssssssssssooss | 62 | 270 |
| 619284 | n/a | 1437 | TAGCGCGCGACTCCTGAGTT | sooooosssssssssssooss | 100 | 271 |
| 619285 | n/a | 1438 | CTAGCGCGCGACTCCTGAGT | sooooosssssssssssooss | 68 | 272 |
| 619286 | n/a | 1439 | CCTAGCGCGCGACTCCTGAG | sooooosssssssssssooss | 41 | 273 |
| 619287 | n/a | 1440 | CCCTAGCGCGCGACTCCTGA | sooooosssssssssssooss | 70 | 274 |
| 619288 | n/a | 1441 | CCCCTAGCGCGCGACTCCTG | sooooosssssssssssooss | 68 | 275 |
| 619289 | n/a | 1442 | GCCCCTAGCGCGCGACTCCT | sooooosssssssssssooss | 52 | 276 |
| 619290 | n/a | 1443 | GGCCCCTAGCGCGCGACTCC | sooooosssssssssssooss | 49 | 277 |
| 619291 | n/a | 1444 | CGGCCCCTAGCGCGCGACTC | sooooosssssssssssooss | 69 | 278 |
| 619292 | n/a | 1445 | CCGGCCCCTAGCGCGCGACT | sooooosssssssssssooss | 76 | 279 |
| 619293 | n/a | 1446 | CCCGGCCCCTAGCGCGCGAC | sooooosssssssssssooss | 52 | 98 |
| 619294 | n/a | 1447 | CCCCGGCCCCTAGCGCGCGA | sooooosssssssssssooss | 62 | 280 |
| 619295 | n/a | 1448 | GCCCCGGCCCCTAGCGCGCG | sooooosssssssssssooss | 68 | 281 |
| 619296 | n/a | 1449 | GGCCCCGGCCCCTAGCGCGC | sooooosssssssssssooss | 56 | 282 |
| 619297 | n/a | 1450 | CGGCCCCGGCCCCTAGCGCG | sooooosssssssssssooss | 71 | 283 |
| 619298 | n/a | 1451 | CCGGCCCCGGCCCCTAGCGC | sooooosssssssssssooss | 73 | 284 |
| 619299 | n/a | 1452 | CCCGGCCCCGGCCCCTAGCG | sooooosssssssssssooss | 51 | 285 |
| 619300 | n/a | 1453 | CCCCGGCCCCGGCCCCTAGC | sooooosssssssssssooss | 49 | 286 |
| 619301 | n/a | 1454 | GCCCCGGCCCCGGCCCCTAG | sooooosssssssssssooss | 60 | 287 |
| 619302 | n/a | 1455 | GGCCCCGGCCCCGGCCCCTA | sooooosssssssssssooss | 48 | 288 |
| 619303 | n/a | 1462 | ACGCCCCGGCCCCGGCCCCG | sooooosssssssssssooss | 49 | 289 |
| 619304 | n/a | 1463 | CACGCCCCGGCCCCGGCCCC | sooooosssssssssssooss | 25 | 290 |
| 619305 | n/a | 1464 | CCACGCCCCGGCCCCGGCCC | sooooosssssssssssooss | 66 | 291 |

TABLE 9-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619306 | n/a | 1465 | ACCACGCCCCGGCCCCGGCC | soooossssssssssooss | 70 | 292 |
| 619307 | n/a | 1466 | GACCACGCCCCGGCCCCGGC | soooossssssssssooss | 73 | 293 |
| 619308 | n/a | 1467 | CGACCACGCCCCGGCCCCGG | soooossssssssssooss | 55 | 294 |
| 619309 | n/a | 1468 | CCGACCACGCCCCGGCCCCG | soooossssssssssooss | 70 | 295 |
| 619310 | n/a | 1469 | CCCGACCACGCCCCGGCCCC | soooossssssssssooss | 50 | 296 |
| 619311 | n/a | 1470 | CCCCGACCACGCCCCGGCCC | soooossssssssssooss | 45 | 297 |
| 619312 | n/a | 1471 | GCCCCGACCACGCCCCGGCC | soooossssssssssooss | 36 | 298 |
| 619313 | n/a | 1472 | CGCCCCGACCACGCCCCGGC | soooossssssssssooss | 58 | 299 |
| 619314 | n/a | 1473 | CCGCCCCGACCACGCCCCGG | soooossssssssssooss | 100 | 300 |
| 619315 | n/a | 1474 | CCCGCCCCGACCACGCCCCG | soooossssssssssooss | 44 | 301 |
| 619316 | n/a | 1475 | GCCCGCCCCGACCACGCCCC | soooossssssssssooss | 97 | 302 |
| 619317 | n/a | 1476 | GGCCCGCCCCGACCACGCCC | soooossssssssssooss | 76 | 303 |
| 619318 | n/a | 1477 | GGGCCCGCCCCGACCACGCC | soooossssssssssooss | 44 | 304 |
| 619319 | n/a | 1478 | CGGGCCCGCCCCGACCACGC | soooossssssssssooss | 40 | 305 |
| 619320 | n/a | 1479 | CCGGGCCCGCCCCGACCACG | soooossssssssssooss | 50 | 306 |
| 619321 | n/a | 1480 | CCCGGGCCCGCCCCGACCAC | soooossssssssssooss | 22 | 307 |
| 619322 | n/a | 1481 | CCCCGGGCCCGCCCCGACCA | soooossssssssssooss | 56 | 308 |
| 619323 | n/a | 1482 | CCCCCGGGCCCGCCCCGACC | soooossssssssssooss | 40 | 309 |
| 619324 | n/a | 1483 | GCCCCCGGGCCCGCCCCGAC | soooossssssssssooss | 65 | 310 |
| 619325 | n/a | 1484 | CGCCCCCGGGCCCGCCCCGA | soooossssssssssooss | 25 | 311 |
| 619326 | n/a | 1486 | CCCGCCCCCGGGCCCGCCCC | soooossssssssssooss | 41 | 312 |
| 619327 | n/a | 1487 | GCCCGCCCCGGGCCCGCCC | soooossssssssssooss | 36 | 313 |
| 619328 | n/a | 1488 | GGCCCGCCCCCGGGCCCGCC | soooossssssssssooss | 14 | 314 |
| 619329 | n/a | 1495 | CGCCCCGGGCCCGCCCCGG | soooossssssssssooss | 33 | 315 |
| 619330 | n/a | 1497 | CCCGCCCCGGGCCCGCCCCC | soooossssssssssooss | 35 | 316 |
| 619331 | n/a | 1498 | CCCCGCCCCGGGCCCGCCCC | soooossssssssssooss | 42 | 317 |
| 619332 | n/a | 1499 | GCCCCGCCCCGGGCCCGCCC | soooossssssssssooss | 47 | 318 |
| 619333 | n/a | 1500 | AGCCCCGCCCCGGGCCCGCC | soooossssssssssooss | 53 | 319 |
| 619334 | n/a | 1501 | CAGCCCCGCCCCGGGCCCGC | soooossssssssssooss | 32 | 320 |
| 619335 | n/a | 1502 | GCAGCCCCGCCCCGGGCCCG | soooossssssssssooss | 58 | 321 |
| 619336 | n/a | 1503 | CGCAGCCCCGCCCCGGGCCC | soooossssssssssooss | 75 | 322 |
| 619418 | n/a | 27155 | CTACACACCAAAGAATGCCA | soooossssssssssooss | 71 | 323 |
| 619419 | n/a | 15587 | GGAATAAGGTCACTAGTTCG | soooossssssssssooss | 72 | 324 |

TABLE 9-continued

Percent inhibition of the C9ORF72 pathogenic associated mRNA variant compared to PBS control by antisense oligonucleotides targeting SEQ ID NOs: 1 and 2

| ISIS NO | SEQ ID NO: 1 Start Site | SEQ ID NO: 2 Start Site | Sequence | Linkage | % inhibition | SEQ ID NO |
|---|---|---|---|---|---|---|
| 619420 | n/a | 7990 | GCCTTACTCTAGGACCAAGA | soooosssssssssssooss | 100 | 20 |
| 619263 | n/a | 1416 | CAGAGCTTGCTACAGGCTGC | soooosssssssssssooss | 63 | 325 |
| 619253 | n/a | 1406 | TACAGGCTGCGGTTGTTTCC | soooosssssssssssooss | 50 | 97 |

TABLE 10

Percent inhibition of the C9ORF72 pathogenic associated mRNA variant compared to PBS control by antisense oligonucleotides targeting SEQ ID NOs: 1-5

| ISIS NO | SEQ ID NO: 1 Start Site | SEQ ID NO: 2 Start Site | SEQ ID NO: 3 Start Site | SEQ ID NO: 4 Start Site | SEQ ID NO: 5 Start Site | Sequence | Linkage | % inhibition | SEQ ID NO |
|---|---|---|---|---|---|---|---|---|---|
| 576816 | 310 | 7990 | 232 | 188 | 188 | GCCTTACTCTAGGACCAAGA | ssssssssssssssssssss | 69 | 20 |
| 619253 | n/a | 1406 | n/a | n/a | n/a | TACAGGCTGCGGTTGTTTCC | soooosssssssssssooss | 19 | 97 |
| 619293 | n/a | 1446 | n/a | n/a | n/a | CCCGGCCCCTAGCGCGCGAC | soooosssssssssssooss | 56 | 98 |
| 619337 | n/a | 1504 | n/a | n/a | n/a | CCGCAGCCCCGCCCCGGGCC | soooosssssssssssooss | 55 | 326 |
| 619338 | n/a | 1505 | n/a | n/a | n/a | ACCGCAGCCCCGCCCCGGGC | soooosssssssssssooss | 62 | 327 |
| 619339 | n/a | 1506 | n/a | n/a | n/a | AACCGCAGCCCCGCCCCGGG | soooosssssssssssooss | 68 | 328 |
| 619340 | n/a | 1507 | n/a | n/a | n/a | CAACCGCAGCCCCGCCCCGG | soooosssssssssssooss | 14 | 329 |
| 619341 | n/a | 1508 | n/a | n/a | n/a | GCAACCGCAGCCCCGCCCCG | soooosssssssssssooss | 95 | 330 |
| 619342 | n/a | 1509 | n/a | n/a | n/a | CGCAACCGCAGCCCCGCCCC | soooosssssssssssooss | 56 | 331 |
| 619343 | n/a | 1510 | n/a | n/a | n/a | CCGCAACCGCAGCCCCGCCC | soooosssssssssssooss | 58 | 332 |
| 619344 | n/a | 1511 | n/a | n/a | n/a | ACCGCAACCGCAGCCCCGCC | soooosssssssssssooss | 51 | 333 |
| 619345 | n/a | 1512 | n/a | n/a | n/a | CACCGCAACCGCAGCCCCGC | soooosssssssssssooss | 97 | 334 |
| 619346 | n/a | 1513 | n/a | n/a | n/a | GCACCGCAACCGCAGCCCCG | soooosssssssssssooss | 49 | 335 |
| 619347 | n/a | 1514 | n/a | n/a | n/a | GGCACCGCAACCGCAGCCCC | soooosssssssssssooss | 100 | 336 |
| 619348 | n/a | 1515 | n/a | n/a | n/a | AGGCACCGCAACCGCAGCCC | soooosssssssssssooss | 46 | 337 |
| 619349 | n/a | 1516 | n/a | n/a | n/a | CAGGCACCGCAACCGCAGCC | soooosssssssssssooss | 100 | 338 |
| 619350 | n/a | 1517 | n/a | n/a | n/a | GCAGGCACCGCAACCGCAGC | soooosssssssssssooss | 55 | 339 |
| 619351 | n/a | 1518 | n/a | n/a | n/a | CGCAGGCACCGCAACCGCAG | soooosssssssssssooss | 63 | 340 |
| 619352 | n/a | 1519 | n/a | n/a | n/a | GCGCAGGCACCGCAACCGCA | soooosssssssssssooss | 42 | 341 |
| 619353 | n/a | 1520 | n/a | n/a | n/a | GGCGCAGGCACCGCAACCGC | soooosssssssssssooss | 95 | 342 |
| 619354 | n/a | 1521 | n/a | n/a | n/a | GGGCGCAGGCACCGCAACCG | soooosssssssssssooss | 23 | 343 |
| 619355* | 140 | n/a | n/a | n/a | n/a | TCTCCTAAACCCACACCTGC | soooosssssssssssooss | 94 | 384 |
| 619356* | 141 | n/a | n/a | n/a | n/a | ATCTCCTAAACCCACACCTG | soooosssssssssssooss | 69 | 385 |
| 619357 | 142 | n/a | n/a | n/a | n/a | TATCTCCTAAACCCACACCT | soooosssssssssssooss | n.d. | 386 |
| 619358* | 143 | n/a | n/a | n/a | n/a | ATATCTCCTAAACCCACACC | soooosssssssssssooss | 53 | 387 |

TABLE 10-continued

Percent inhibition of the C9ORF72 pathogenic associated mRNA variant compared to PBS control by antisense oligonucleotides targeting SEQ ID NOs: 1-5

| ISIS NO | SEQ ID NO: 1 Start Site | SEQ ID NO: 2 Start Site | SEQ ID NO: 3 Start Site | SEQ ID NO: 4 Start Site | SEQ ID NO: 5 Start Site | Sequence | Linkage | % inhibition | SEQ ID NO |
|---|---|---|---|---|---|---|---|---|---|
| 619359 | 144 | n/a | n/a | n/a | n/a | GATATCTCCTAAACCCACAC | sooooosssssssssssooss | n.d. | 388 |
| 619360* | 145 | n/a | n/a | n/a | n/a | AGATATCTCCTAAACCCACA | sooooosssssssssssooss | 30 | 389 |
| 619361* | 146 | n/a | n/a | n/a | n/a | GAGATATCTCCTAAACCCAC | sooooosssssssssssooss | 48 | 390 |
| 619362* | 147 | n/a | n/a | n/a | n/a | GGAGATATCTCCTAAACCCA | sooooosssssssssssooss | 60 | 391 |
| 619363* | 148 | n/a | n/a | n/a | n/a | CGGAGATATCTCCTAAACCC | sooooosssssssssssooss | 26 | 392 |
| 619364* | 149 | n/a | n/a | n/a | n/a | CCGGAGATATCTCCTAAACC | sooooosssssssssssooss | 97 | 393 |
| 619365* | 150 | n/a | n/a | n/a | n/a | TCCGGAGATATCTCCTAAAC | sooooosssssssssssooss | 60 | 394 |
| 619366* | 151 | n/a | n/a | n/a | n/a | CTCCGGAGATATCTCCTAAA | sooooosssssssssssooss | 34 | 395 |
| 619367 | 152 | n/a | n/a | n/a | n/a | GCTCCGGAGATATCTCCTAA | sooooosssssssssssooss | n.d. | 396 |
| 619368* | 153 | n/a | n/a | n/a | n/a | TGCTCCGGAGATATCTCCTA | sooooosssssssssssooss | 95 | 397 |
| 619369 | 154 | n/a | n/a | n/a | n/a | ATGCTCCGGAGATATCTCCT | sooooosssssssssssooss | n.d. | 398 |
| 619370* | 155 | n/a | n/a | n/a | n/a | AATGCTCCGGAGATATCTCC | sooooosssssssssssooss | 59 | 399 |
| 619371* | n/a | n/a | n/a | 17 | n/a | TCTCTCTTTCCTAGCGGGAC | sooooosssssssssssooss | 0 | 344 |
| 619372* | n/a | n/a | n/a | 18 | n/a | ATCTCTCTTTCCTAGCGGGA | sooooosssssssssssooss | 8 | 345 |
| 619373* | n/a | n/a | n/a | 19 | n/a | TATCTCTCTTTCCTAGCGGG | sooooosssssssssssooss | 6 | 346 |
| 619374* | n/a | n/a | n/a | 20 | n/a | ATATCTCTCTTTCCTAGCGG | sooooosssssssssssooss | 0 | 347 |
| 619375* | n/a | n/a | n/a | 21 | n/a | GATATCTCTCTTTCCTAGCG | sooooosssssssssssooss | 8 | 348 |
| 619376* | n/a | n/a | n/a | 22 | n/a | AGATATCTCTCTTTCCTAGC | sooooosssssssssssooss | 0 | 349 |
| 619377* | n/a | n/a | n/a | 23 | n/a | GAGATATCTCTCTTTCCTAG | sooooosssssssssssooss | 89 | 350 |
| 619378* | n/a | n/a | n/a | 24 | n/a | GGAGATATCTCTCTTTCCTA | sooooosssssssssssooss | 1 | 351 |
| 619379* | n/a | n/a | n/a | 25 | n/a | CGGAGATATCTCTCTTTCCT | sooooosssssssssssooss | 0 | 352 |
| 619380 | n/a | n/a | n/a | 26 | n/a | CCGGAGATATCTCTCTTTCC | sooooosssssssssssooss | n.d. | 353 |
| 619381* | n/a | n/a | n/a | 27 | n/a | TCCGGAGATATCTCTCTTTC | sooooosssssssssssooss | 28 | 354 |
| 619382* | n/a | n/a | n/a | 28 | n/a | CTCCGGAGATATCTCTCTTT | sooooosssssssssssooss | 28 | 355 |
| 619383* | n/a | n/a | n/a | 29 | n/a | GCTCCGGAGATATCTCTCTT | sooooosssssssssssooss | 91 | 356 |
| 619384* | n/a | n/a | n/a | 30 | n/a | TGCTCCGGAGATATCTCTCT | sooooosssssssssssooss | 61 | 357 |
| 619385* | n/a | n/a | n/a | 31 | n/a | ATGCTCCGGAGATATCTCTC | sooooosssssssssssooss | 69 | 358 |
| 619386* | n/a | n/a | n/a | 32 | n/a | AATGCTCCGGAGATATCTCT | sooooosssssssssssooss | 75 | 359 |
| 619387 | 156 | n/a | n/a | 33 | n/a | AAATGCTCCGGAGATATCTC | sooooosssssssssssooss | n.d. | 400 |
| 619388* | n/a | n/a | n/a | n/a | 18 | TCTGCTCTTGCTAGACCCCG | sooooosssssssssssooss | 50 | 360 |
| 619389 | n/a | n/a | n/a | n/a | 19 | ATCTGCTCTTGCTAGACCCC | sooooosssssssssssooss | n.d. | 361 |
| 619390* | n/a | n/a | n/a | n/a | 20 | TATCTGCTCTTGCTAGACCC | sooooosssssssssssooss | 5 | 362 |
| 619391* | n/a | n/a | n/a | n/a | 21 | ATATCTGCTCTTGCTAGACC | sooooosssssssssssooss | 0 | 363 |
| 619392* | n/a | n/a | n/a | n/a | 22 | GATATCTGCTCTTGCTAGAC | sooooosssssssssssooss | 0 | 364 |
| 619393* | n/a | n/a | n/a | n/a | 23 | AGATATCTGCTCTTGCTAGA | sooooosssssssssssooss | 6 | 365 |
| 619394* | n/a | n/a | n/a | n/a | 24 | GAGATATCTGCTCTTGCTAG | sooooosssssssssssooss | 57 | 366 |

TABLE 10-continued

Percent inhibition of the C9ORF72 pathogenic associated mRNA variant compared to PBS control by antisense oligonucleotides targeting SEQ ID NOs: 1-5

| ISIS NO | SEQ ID NO: 1 Start Site | SEQ ID NO: 2 Start Site | SEQ ID NO: 3 Start Site | SEQ ID NO: 4 Start Site | SEQ ID NO: 5 Start Site | Sequence | Linkage | % inhibition | SEQ ID NO |
|---|---|---|---|---|---|---|---|---|---|
| 619395* | n/a | n/a | n/a | n/a | 25 | GGAGATATCTGCTCTTGCTA | sooooossssssssssooss | 6 | 367 |
| 619396* | n/a | n/a | n/a | n/a | 26 | CGGAGATATCTGCTCTTGCT | sooooossssssssssooss | 0 | 368 |
| 619397* | n/a | n/a | n/a | n/a | 27 | CCGGAGATATCTGCTCTTGC | sooooossssssssssooss | 0 | 369 |
| 619398* | n/a | n/a | n/a | n/a | 28 | TCCGGAGATATCTGCTCTTG | sooooossssssssssooss | 22 | 370 |
| 619399* | n/a | n/a | n/a | n/a | 29 | CTCCGGAGATATCTGCTCTT | sooooossssssssssooss | 14 | 371 |
| 619400* | n/a | n/a | n/a | n/a | 30 | GCTCCGGAGATATCTGCTCT | sooooossssssssssooss | 46 | 372 |
| 619401* | n/a | n/a | n/a | n/a | 31 | TGCTCCGGAGATATCTGCTC | sooooossssssssssooss | 40 | 373 |
| 619402* | n/a | n/a | n/a | n/a | 32 | ATGCTCCGGAGATATCTGCT | sooooossssssssssooss | 79 | 374 |
| 619403* | n/a | n/a | n/a | n/a | 33 | AATGCTCCGGAGATATCTGC | sooooossssssssssooss | 65 | 375 |
| 619404* | n/a | n/a | n/a | n/a | 34 | AAATGCTCCGGAGATATCTG | sooooossssssssssooss | 22 | 376 |
| 619405* | n/a | n/a | 75 | n/a | n/a | TGCTCCGGAGATATCAAGCG | sooooossssssssssooss | 18 | 377 |
| 619406* | n/a | n/a | 76 | n/a | n/a | ATGCTCCGGAGATATCAAGC | sooooossssssssssooss | 21 | 378 |
| 619407* | n/a | n/a | 77 | n/a | n/a | AATGCTCCGGAGATATCAAG | sooooossssssssssooss | 98 | 379 |
| 619408 | n/a | n/a | 78 | n/a | n/a | AAATGCTCCGGAGATATCAA | sooooossssssssssooss | n.d. | 380 |
| 619409* | n/a | n/a | 79 | n/a | n/a | CAAATGCTCCGGAGATATCA | sooooossssssssssooss | 98. | 381 |
| 619421 | 3132 | 28251 | n/a | n/a | n/a | GGGACACTACAAGGTAGTAT | sooooossssssssssooss | 80 | 401 |
| 619422* | n/a | 3452 | n/a | n/a | n/a | GGTAACTTCAAACTCTTGGG | sooooossssssssssooss | 85. | 382 |
| 619423 | n/a | 13642 | 1013 | n/a | n/a | GCCATGATTTCTTGTCTGGG | sooooossssssssssooss | 67 | 383 |

Example 3: Dose-Dependent Antisense Inhibition of a Human C9ORF72 mRNA Variant in HepG2 Cells Antisense oligonucleotides from the study described above exhibiting significant in vitro inhibition of C9ORF72 mRNA were selected and tested at various doses in HepG2 cells. ISIS 576816 and ISIS 577061, previously tested in U.S. Application No. 61/714,132, filed Oct. 15, 2012, were used as benchmark oligonucleotides. ISIS 576816 and ISIS 577061 are 5-10-5 MOE gapmers with phosphorothioate linkages throughout. The antisense oligonucleotides were tested in a series of experiments that had similar culture conditions. The results for each experiment are presented in separate tables shown below. Cells were plated at a density of 20,000 cells per well and transfected using electroporation with 78.1 nM, 312.5 nM, 1,250.0 nM, or 5,000.0 nM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3905 was used to measure the C9ORF72 pathogenic associated mRNA variant. The levels of the C9ORF72 pathogenic associated mRNA variant were adjusted according to total RNA content, as measured by RIBOGREEN®. Results are presented as percent inhibition of variant C9ORF72 levels, relative to untreated control cells. 'n.d.' means no data.

The half maximal inhibitory concentration ($IC_{50}$) of each oligonucleotide is also presented in the Tables below. As illustrated, the C9ORF72 pathogenic associated mRNA variant levels were reduced in a dose-dependent manner in some of the antisense oligonucleotide treated cells.

TABLE 11

Dose-dependent inhibition of the C9ORF72 pathogenic associated mRNA variant

| ISIS No | 78.1 nM | 312.5 nM | 1250.0 nM | 5000.0 nM | $IC_{50}$ (µM) |
|---|---|---|---|---|---|
| 576816 | 13 | 47 | 92 | 95 | 0.4 |
| 577061 | 0 | 1 | 23 | 57 | 4.2 |
| 619049 | 11 | 46 | 34 | 18 | >5.0 |
| 619055 | 14 | 13 | 0 | 0 | >5.0 |
| 619061 | 0 | 2 | 0 | 0 | >5.0 |
| 619080 | 7 | 4 | 0 | 0 | >5.0 |
| 619088 | 0 | 7 | 16 | 16 | >5.0 |
| 619089 | 2 | 0 | 0 | 17 | >5.0 |
| 619095 | 10 | 0 | 0 | 27 | >5.0 |
| 619096 | 16 | 0 | 10 | 27 | >5.0 |
| 619097 | 23 | 55 | 41 | 38 | >5.0 |
| 619099 | 10 | 36 | 46 | 23 | >5.0 |
| 619107 | 15 | 0 | 4 | 33 | >5.0 |

TABLE 11-continued

Dose-dependent inhibition of the C9ORF72 pathogenic associated mRNA variant

| ISIS No | 78.1 nM | 312.5 nM | 1250.0 nM | 5000.0 nM | IC$_{50}$ (μM) |
|---|---|---|---|---|---|
| 619114 | 0 | 0 | 8 | 31 | >5.0 |
| 619253 | 26 | 33 | 66 | 86 | 0.5 |
| 619293 | 26 | 71 | n.d. | 95 | 0.2 |
| 619410 | 42 | 63 | 86 | n.d. | 0.1 |
| 619411 | 28 | 20 | 96 | n.d. | 0.3 |
| 619412 | 39 | 66 | 93 | 97 | 0.1 |

TABLE 12

Dose-dependent inhibition of the C9ORF72 pathogenic associated mRNA variant

| ISIS No | 78.1 nM | 312.5 nM | 1250.0 nM | 5000.0 nM | IC$_{50}$ (μM) |
|---|---|---|---|---|---|
| 576816 | 39 | 84 | 96 | 90 | 0.1 |
| 577061 | 29 | 0 | 25 | 71 | 3.7 |
| 619173 | 18 | 46 | 84 | 98 | 0.4 |
| 619174 | 21 | 36 | 77 | n.d. | 0.4 |
| 619176 | 16 | 29 | 57 | 95 | 0.7 |
| 619178 | 5 | 31 | 86 | 97 | 0.5 |
| 619179 | 0 | 16 | 65 | 96 | 0.8 |
| 619180 | 4 | 24 | 66 | 96 | 0.7 |
| 619181 | 10 | 34 | 72 | 95 | 0.6 |
| 619182 | 23 | 32 | 74 | 92 | 0.5 |
| 619183 | 0 | 26 | 44 | 96 | 1.0 |
| 619185 | 14 | 34 | 70 | 93 | 0.5 |
| 619186 | 8 | 32 | 71 | 98 | 0.6 |
| 619187 | 18 | 36 | 81 | 95 | 0.4 |
| 619253 | 17 | 22 | 61 | 97 | 0.7 |
| 619293 | 0 | 49 | 86 | 99 | 0.6 |
| 619413 | 8 | 48 | 84 | 95 | 0.4 |
| 619415 | 26 | 67 | 90 | n.d. | 0.2 |

TABLE 13

Dose-dependent inhibition of the C9ORF72 pathogenic associated mRNA variant

| ISIS No | 78.1 nM | 312.5 nM | 1250.0 nM | 5000.0 nM | IC$_{50}$ (μM) |
|---|---|---|---|---|---|
| 576816 | 0 | 71 | 97 | n.d. | 0.3 |
| 577061 | 0 | 12 | 46 | 82 | 1.4 |
| 619191 | 66 | 84 | 94 | 98 | <0.07 |
| 619201 | 16 | 64 | 95 | 97 | 0.3 |
| 619202 | 35 | 78 | 95 | 95 | 0.1 |
| 619203 | 29 | 55 | 92 | 95 | 0.2 |
| 619216 | 61 | 55 | 92 | 96 | <0.07 |
| 619217 | 44 | 86 | 83 | n.d. | 0.1 |
| 619218 | 35 | 87 | 93 | n.d. | 0.1 |
| 619240 | 0 | 43 | 52 | 78 | 1.0 |
| 619245 | 0 | 39 | 85 | n.d. | 0.5 |
| 619246 | 34 | 74 | 96 | 99 | 0.1 |
| 619247 | 0 | 46 | 92 | 93 | 0.6 |
| 619251 | 40 | 91 | 93 | 96 | <0.07 |
| 619252 | 24 | 67 | 87 | n.d. | 0.2 |
| 619259 | 7 | 76 | 85 | 98 | 0.3 |
| 619260 | 16 | 80 | 92 | 99 | 0.2 |
| 619416 | 13 | 63 | 91 | 92 | 0.3 |
| 619417 | 45 | 88 | 91 | 97 | <0.07 |

TABLE 14

Dose-dependent inhibition of the C9ORF72 pathogenic associated mRNA variant

| ISIS No | 78.1 nM | 312.5 nM | 1250.0 nM | 5000.0 nM | IC$_{50}$ (μM) |
|---|---|---|---|---|---|
| 576816 | 38 | 61 | 95 | 98 | 0.1 |
| 577061 | 0 | 8 | 13 | 77 | 2.5 |
| 619266 | 0 | 23 | 73 | 98 | 0.8 |
| 619268 | 5 | 29 | 77 | 97 | 0.6 |
| 619276 | 31 | 82 | 90 | 91 | 0.1 |
| 619278 | 35 | 83 | 97 | 99 | 0.1 |
| 619280 | 66 | 80 | 97 | 96 | <0.07 |
| 619284 | 22 | 55 | 88 | 98 | 0.3 |
| 619292 | 37 | 79 | 85 | 94 | 0.1 |
| 619297 | 0 | 68 | 82 | 91 | 0.6 |
| 619298 | 47 | 89 | 93 | 91 | <0.07 |
| 619307 | 37 | 71 | 96 | 98 | 0.1 |
| 619314 | 21 | 0 | 61 | 97 | 0.8 |
| 619316 | 13 | 37 | 71 | 91 | 0.5 |
| 619317 | 7 | 17 | 68 | 87 | 0.8 |
| 619336 | 17 | 51 | 64 | 90 | 0.5 |
| 619418 | 43 | 78 | 89 | 95 | 0.1 |
| 619419 | 43 | 68 | 94 | 95 | 0.1 |
| 619420 | 66 | 88 | 100 | n.d. | <0.07 |

TABLE 15

Dose-dependent inhibition of the C9ORF72 pathogenic associated mRNA variant

| ISIS No | 78.1 nM | 312.5 nM | 1250.0 nM | 5000.0 nM | IC$_{50}$ (μM) |
|---|---|---|---|---|---|
| 576816 | 8 | 48 | 91 | 91 | 0.4 |
| 577061 | 0 | 13 | 33 | 64 | 2.6 |
| 619293 | 32 | 77 | 85 | 95 | 0.1 |
| 619337 | 28 | 42 | 79 | 95 | 0.3 |
| 619338 | 11 | 55 | 83 | 91 | 0.4 |
| 619339 | 6 | 42 | 83 | 90 | 0.5 |
| 619341 | 17 | 14 | 66 | 83 | 0.8 |
| 619342 | 37 | 57 | 85 | 97 | 0.2 |
| 619343 | 25 | 51 | 87 | 96 | 0.3 |
| 619344 | 17 | 27 | 75 | 91 | 0.5 |
| 619345 | 0 | 18 | 50 | 88 | 1.2 |
| 619346 | 0 | 22 | 76 | 90 | 0.8 |
| 619347 | 1 | 8 | 41 | 76 | 1.7 |
| 619349 | 10 | 12 | 51 | 78 | 1.3 |
| 619350 | 16 | 46 | 84 | 91 | 0.4 |
| 619351 | 20 | 21 | 69 | 87 | 0.6 |
| 619353 | 0 | 13 | 52 | 76 | 1.4 |
| 619421 | 27 | 78 | 93 | 92 | 0.1 |
| 619423 | 0 | 53 | 87 | 93 | 0.5 |

TABLE 16

Gapmers chosen for further analysis

| Isis No | IC$_{50}$ (µM) | Sequence | SEQ ID NO: 2 Start Site | Location | SEQ ID NO |
|---|---|---|---|---|---|
| 619173 | 0.4 | CTGTGAGAGCAAGTAGTGGG | 1326 | intron | 160 |
| 619174 | 0.4 | ACTGTGAGAGCAAGTAGTGG | 1327 | intron | 161 |
| 619178 | 0.5 | GAGTACTGTGAGAGCAAGTA | 1331 | intron | 165 |
| 619179 | 0.8 | CGAGTACTGTGAGAGCAAGT | 1332 | intron | 166 |
| 619181 | 0.5 | AGCGAGTACTGTGAGAGCAA | 1334 | intron | 168 |
| 619182 | 0.5 | CAGCGAGTACTGTGAGAGCA | 1335 | intron | 169 |
| 619185 | 0.5 | CCTCAGCGAGTACTGTGAGA | 1338 | intron | 172 |
| 619186 | 0.6 | CCCTCAGCGAGTACTGTGAG | 1339 | intron | 173 |
| 619187 | 0.4 | ACCCTCAGCGAGTACTGTGA | 1340 | intron | 174 |
| 619191 | <0.07 | GTTCACCCTCAGCGAGTACT | 1344 | intron | 178 |
| 619201 | 0.3 | GTCTTTTCTTGTTCACCCTC | 1354 | intron | 188 |
| 619202 | 0.1 | GGTCTTTTCTTGTTCACCCT | 1355 | intron | 189 |
| 619203 | 0.2 | AGGTCTTTTCTTGTTCACCC | 1356 | intron | 190 |
| 619216 | <0.07 | GTTAATCTTTATCAGGTCTT | 1369 | intron | 203 |
| 619217 | 0.1 | GGTTAATCTTTATCAGGTCT | 1370 | intron | 204 |
| 619218 | 0.1 | TGGTTAATCTTTATCAGGTC | 1371 | intron | 205 |
| 619245 | 0.5 | GCGGTTGTTTCCCTCCTTGT | 1398 | intron | 232 |
| 619246 | 0.1 | TGCGGTTGTTTCCCTCCTTG | 1399 | intron | 233 |
| 619251 | <0.07 | CAGGCTGCGGTTGTTTCCCT | 1404 | intron | 238 |
| 619252 | 0.2 | ACAGGCTGCGGTTGTTTCCC | 1405 | intron | 239 |
| 619253 | 0.5 | TACAGGCTGCGGTTGTTTCC | 1406 | intron | 97 |
| 619259 | 0.3 | GCTTGCTACAGGCTGCGGTT | 1412 | intron | 245 |
| 619260 | 0.2 | AGCTTGCTACAGGCTGCGGT | 1413 | intron | 246 |
| 619276 | 0.1 | GACTCCTGAGTTCCAGAGCT | 1429 | intron | 263 |
| 619278 | 0.1 | GCGACTCCTGAGTTCCAGAG | 1431 | intron | 265 |
| 619280 | <0.07 | GCGCGACTCCTGAGTTCCAG | 1433 | intron | 267 |
| 619284 | 0.3 | TAGCGCGCGACTCCTGAGTT | 1437 | Intron | 271 |
| 619292 | 0.1 | CCGGCCCCTAGCGCGCGACT | 1445 | intron | 279 |
| 619293 | 0.2 | CCCGGCCCCTAGCGCGCGAC | 1446 | intron | 98 |
| 619298 | <0.07 | CCGGCCCCGGCCCCTAGCGC | 1451 | intron | 284 |
| 619307 | 0.1 | GACCACGCCCCGGCCCCGGC | 1466 | intron | 293 |
| 619337 | 0.3 | CCGCAGCCCCGCCCCGGGCC | 1504 | intron:exon1B junction | 326 |
| 619338 | 0.4 | ACCGCAGCCCCGCCCCGGGC | 1505 | intron:exon1B junction | 327 |

TABLE 16-continued

Gapmers chosen for further analysis

| Isis No | IC$_{50}$ (µM) | Sequence | SEQ ID NO: 2 Start Site | Location | SEQ ID NO |
|---|---|---|---|---|---|
| 619339 | 0.5 | AACCGCAGCCCCGCCCCGGG | 1506 | intron:exon1B junction | 328 |
| 619342 | 0.2 | CGCAACCGCAGCCCCGCCCC | 1509 | intron:exon1B junction | 331 |
| 619343 | 0.3 | CCGCAACCGCAGCCCCGCCC | 1510 | intron:exon1B junction | 332 |
| 619344 | 0.5 | ACCGCAACCGCAGCCCCGCC | 1511 | intron:exon1B junction | 333 |
| 619350 | 0.4 | GCAGGCACCGCAACCGCAGC | 1517 | intron:exon1B junction | 339 |
| 619351 | 0.6 | CGCAGGCACCGCAACCGCAG | 1518 | intron:exon1B junction | 340 |

Example 4: Antisense Inhibition of C9ORF72 by Human-Rhesus Cross-Reactive Antisense Oligonucleotides in LLC-MK2 Cells Antisense oligonucleotides targeting a human C9ORF72 nucleic acid and fully cross-reactive with a rhesus C9ORF72 nucleic acid were designed and were tested for their effects on rhesus C9ORF72 mRNA in vitro. ISIS 576816, previously tested in U.S. Application No. 61/714,132, filed Oct. 15, 2012, was used as a benchmark oligonucleotide. The antisense oligonucleotides were tested in a series of experiments that had similar culture conditions. The results for each experiment are presented in the tables below. Cultured rhesus LLC-MK2 cells at a density of 20,000 cells per well were transfected using electroporation with 4,000 nM antisense oligonucleotide. After a treatment period of approximately 24 hours, RNA was isolated from the cells and C9ORF72 mRNA levels were measured by quantitative real-time PCR. Human primer probe set RTS3750 (forward sequence TGTGACAGTITGGAATGCAGTGA, designated herein as SEQ ID NO: 16; reverse sequence GCCACI-TAAAGCAATCTCTGTCITG, designated herein as SEQ ID NO: 17; probe sequence TCGACTCTITGCC-CACCGCCA, designated herein as SEQ ID NO: 18—a TAQ-man primer probe set) was used to measure total C9ORF72 mRNA levels. RTS3750 targets exon 2 of the mRNA transcripts and, therefore, measures total mRNA transcripts. C9ORF72 mRNA levels were adjusted according to total RNA content, as measured by RIBOGREEN®. Results are presented as percent inhibition of C9ORF72, relative to untreated control cells. The oligonucleotides marked with as asterisk (*) target the amplicon region of the primer probe set. Additional assays may be used to measure the potency and efficacy of these oligonucleotides. 'n.d.' indicates that there was no signal reading in the assay for that particular oligonucleotide. The antisense oligonucleotides were also tested in HepG2 cells in a series of experiments that had similar culture conditions. The results for each experiment are also presented in tables shown below. Cultured HepG2 cells at a density of 20,000 cells per well were transfected using electroporation with 4,000 nM antisense oligonucleotide. After a treatment period of approximately 24 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. The levels of the C9ORF72 pathogenic associated mRNA variant were normalized to the total RNA content of the cell, as measured by RIBOGREEN®. Results are presented as percent inhibition of C9ORF72, relative to untreated control cells. 'n.d.' means no data.

The chimeric antisense oligonucleotides in the Tables below were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment comprises a 2'-MOE group. All cytosine residues throughout each oligonucleotide are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

"Start site" indicates the 5'-most nucleoside to which the gapmer is targeted in the human gene sequence. "Stop site" indicates the 3'-most nucleoside to which the gapmer is targeted human gene sequence. Each antisense oligonucleotide listed in the Tables below is targeted to either human C9ORF72 mRNA sequence, designated herein as SEQ ID NO: 1 (GENBANK Accession No. NM_001256054.1), the human C9ORF72 genomic sequence, designated herein as SEQ ID NO: 2 (the complement of GENBANK Accession No. NT_008413.18 truncated from nucleosides 27535000 to 27565000), GENBANK Accession No. NM_018325.3 (incorporated herein as SEQ ID NO: 6), or all three. 'n/a' indicates that the antisense oligonucleotide does not target that particular gene sequence.

TABLE 17

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 576816 | 310 | 7990 | 215 | GCCTTACTCTAGGACCAAGA | sssssssssssssssssss | 51 | 91 | 20 |
| 619343 | n/a | 1510 | 1 | CCGCAACCGCAGCCCCGCCC | sooosssssssssssooss | 0 | 96 | 332 |
| 619420 | 310 | 7990 | 215 | GCCTTACTCTAGGACCAAGA | sooosssssssssssooss | 59 | 100 | 20 |
| 625183 | 309 | 7989 | 214 | CCTTACTCTAGGACCAAGAA | sooosssssssssssooss | 27 | 92 | 484 |
| 625249 | 239 | 7919 | 144 | AAAGCAATCTCTGTCTTGGC | sooosssssssssssooss | 78 | n.d. | 465 |
| 625255 | 364 | 8044 | 269 | AAGTTATTTCTCCATCACTG | sooosssssssssssooss | 40 | 97 | 502 |
| 627833 | 321 | 8001 | 226 | AGCCCAAATGTGCCTTACTC | sooosssssssssssooss | 52 | n.d. | 487 |
| 627834 | 382 | 8062 | 287 | GAGTGTGGTTGGCAAGAAAA | sooosssssssssssooss | 0 | 61 | 506 |
| 655126 | n/a | 1548 | 39 | CGCCACCGCCTGCGCCTCCG | sooosssssssssssooss | 0 | 96 | 512 |
| 655127 | n/a | 1551 | 42 | ACTCGCCACCGCCTGCGCCT | sooosssssssssssooss | 11 | 93 | 513 |
| 655128 | n/a | n/a | 45 | TCCACTCGCCACCGCCTGCG | sooosssssssssssooss | 0 | 60 | 514 |
| 655129 | n/a | n/a | 48 | ATATCCACTCGCCACCGCCT | sooosssssssssssooss | 1 | 79 | 515 |
| 655130 | n/a | n/a | 51 | GAGATATCCACTCGCCACCG | sooosssssssssssooss | 8 | 45 | 516 |
| 655131* | 167 | 7847 | 72 | TCACATTATCCAAATGCTCC | sooosssssssssssooss | 36 | 88 | 441 |
| 655132* | 170 | 7850 | 75 | CTGTCACATTATCCAAATGC | sooosssssssssssooss | 20 | 79 | 442 |
| 655133* | 173 | 7853 | 78 | CAACTGTCACATTATCCAAA | sooosssssssssssooss | 31 | 82 | 443 |
| 655134* | 176 | 7856 | 81 | TTCCAACTGTCACATTATCC | sooosssssssssssooss | 43 | 90 | 444 |
| 655135* | 180 | 7860 | 85 | TGCATTCCAACTGTCACATT | sooosssssssssssooss | 69 | 94 | 445 |
| 655136* | 183 | 7863 | 88 | CACTGCATTCCAACTGTCAC | sooosssssssssssooss | 75 | 98 | 446 |
| 655137* | 186 | 7866 | 91 | CATCACTGCATTCCAACTGT | sooosssssssssssooss | 71 | 95 | 447 |
| 655138 | 189 | 7869 | 94 | CGACATCACTGCATTCCAAC | sooosssssssssssooss | 85 | n.d. | 448 |
| 655139 | 192 | 7872 | 97 | AGTCGACATCACTGCATTCC | sooosssssssssssooss | 89 | n.d. | 449 |
| 655140* | 195 | 7875 | 100 | AAGAGTCGACATCACTGCAT | sooosssssssssssooss | 81 | 100 | 450 |
| 655141* | 198 | 7878 | 103 | GCAAAGAGTCGACATCACTG | sooosssssssssssooss | 68 | 98 | 451 |
| 655142* | 201 | 7881 | 106 | TGGGCAAAGAGTCGACATCA | sooosssssssssssooss | 60 | 98 | 452 |
| 655143* | 204 | 7884 | 109 | CGGTGGGCAAAGAGTCGACA | sooosssssssssssooss | 69 | 99 | 453 |
| 655144* | 207 | 7887 | 112 | TGGCGGTGGGCAAAGAGTCG | sooosssssssssssooss | 60 | 97 | 454 |
| 655145* | 211 | 7891 | 116 | GAGATGGCGGTGGGCAAAGA | sooosssssssssssooss | 27 | 93 | 455 |
| 655146* | 214 | 7894 | 119 | CTGGAGATGGCGGTGGGCAA | sooosssssssssssooss | 56 | 99 | 456 |
| 655147* | 218 | 7898 | 123 | ACAGCTGGAGATGGCGGTGG | sooosssssssssssooss | 17 | 84 | 457 |
| 655148 | 221 | 7901 | 126 | GCAACAGCTGGAGATGGCGG | sooosssssssssssooss | 34 | n.d. | 458 |
| 655149 | 224 | 7904 | 129 | TTGGCAACAGCTGGAGATGG | sooosssssssssssooss | 27 | n.d. | 459 |
| 655150* | 227 | 7907 | 132 | GTCTTGGCAACAGCTGGAGA | sooosssssssssssooss | 52 | 99 | 460 |
| 655151 | 230 | 7910 | 135 | TCTGTCTTGGCAACAGCTGG | sooosssssssssssooss | 60 | n.d. | 461 |
| 655152* | 232 | 7912 | 137 | TCTCTGTCTTGGCAACAGCT | sooosssssssssssooss | 65 | 98 | 462 |

TABLE 17-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655153* | 236 | 7916 | 141 | GCAATCTCTGTCTTGGCAAC | sooooossssssssssooss | 91 | 99 | 463 |
| 655154* | 237 | 7917 | 142 | AGCAATCTCTGTCTTGGCAA | sooooossssssssssooss | 87 | 99 | 464 |
| 655155* | 242 | 7922 | 147 | CTTAAAGCAATCTCTGTCTT | sooooossssssssssooss | 80 | 76 | 466 |
| 655156* | 245 | 7925 | 150 | CCACTTAAAGCAATCTCTGT | sooooossssssssssooss | 74 | 86 | 467 |
| 655157 | 267 | 7947 | 172 | AGCTGCTAATAAAGGTGATT | sooooossssssssssooss | 27 | 90 | 468 |
| 655158 | 270 | 7950 | 175 | AGTAGCTGCTAATAAAGGTG | sooooossssssssssooss | 17 | 87 | 469 |
| 655159 | 273 | 7953 | 178 | AAAAGTAGCTGCTAATAAAG | sooooossssssssssooss | 6 | 48 | 470 |
| 655160 | 276 | 7956 | 181 | AGCAAAAGTAGCTGCTAATA | sooooossssssssssooss | 3 | 87 | 471 |
| 655161 | 279 | 7959 | 184 | GTAAGCAAAAGTAGCTGCTA | sooooossssssssssooss | 30 | 99 | 472 |
| 655162 | 282 | 7962 | 187 | CCAGTAAGCAAAAGTAGCTG | sooooossssssssssooss | 24 | 85 | 473 |
| 655163 | 285 | 7965 | 190 | GTCCCAGTAAGCAAAAGTAG | sooooossssssssssooss | 15 | 70 | 474 |
| 655164 | 286 | 7966 | 191 | TGTCCCAGTAAGCAAAAGTA | sooooossssssssssooss | 5 | 60 | 475 |
| 655165 | 288 | 7968 | 193 | ATTGTCCCAGTAAGCAAAAG | sooooossssssssssooss | 0 | 46 | 476 |
| 655166 | 290 | 7970 | 195 | ATATTGTCCCAGTAAGCAAA | sooooossssssssssooss | 0 | 54 | 477 |
| 655167 | 291 | 7971 | 196 | AATATTGTCCCAGTAAGCAA | sooooossssssssssooss | 16 | 60 | 478 |
| 655168 | 294 | 7974 | 199 | AAGAATATTGTCCCAGTAAG | sooooossssssssssooss | 0 | 52 | 479 |
| 655169 | 297 | 7977 | 202 | ACCAAGAATATTGTCCCAGT | sooooossssssssssooss | 20 | 82 | 480 |
| 655170 | 300 | 7980 | 205 | AGGACCAAGAATATTGTCCC | sooooossssssssssooss | 17 | 54 | 481 |
| 655171 | 303 | 7983 | 208 | TCTAGGACCAAGAATATTGT | sooooossssssssssooss | 0 | 36 | 482 |
| 655172 | 306 | 7986 | 211 | TACTCTAGGACCAAGAATAT | sooooossssssssssooss | 10 | 43 | 483 |
| 655173 | 312 | 7992 | 217 | GTGCCTTACTCTAGGACCAA | sooooossssssssssooss | 75 | 99 | 485 |
| 655174 | 315 | 7995 | 220 | AATGTGCCTTACTCTAGGAC | sooooossssssssssooss | 47 | 98 | 486 |
| 655175 | 327 | 8007 | 232 | CTTTGGAGCCCAAATGTGCC | sooooossssssssssooss | 21 | 86 | 488 |
| 655176 | 330 | 8010 | 235 | TGTCTTTGGAGCCCAAATGT | sooooossssssssssooss | 21 | 88 | 489 |
| 655177 | 333 | 8013 | 238 | TTCTGTCTTTGGAGCCCAAA | sooooossssssssssooss | 42 | 97 | 490 |
| 655178 | 334 | 8014 | 239 | GTTCTGTCTTTGGAGCCCAA | sooooossssssssssooss | 66 | 99 | 491 |
| 655179 | 336 | 8016 | 241 | CTGTTCTGTCTTTGGAGCCC | sooooossssssssssooss | 68 | 95 | 492 |
| 655180 | 339 | 8019 | 244 | TACCTGTTCTGTCTTTGGAG | sooooossssssssssooss | 29 | 92 | 493 |
| 655181 | 342 | 8022 | 247 | AAGTACCTGTTCTGTCTTTG | sooooossssssssssooss | 26 | 76 | 494 |
| 655182 | 345 | 8025 | 250 | GAGAAGTACCTGTTCTGTCT | sooooossssssssssooss | 38 | 94 | 495 |
| 655183 | 348 | 8028 | 253 | ACTGAGAAGTACCTGTTCTG | sooooossssssssssooss | 23 | 89 | 496 |
| 655184 | 350 | 8030 | 255 | TCACTGAGAAGTACCTGTTC | sooooossssssssssooss | 19 | 83 | 497 |
| 655185 | 351 | 8031 | 256 | ATCACTGAGAAGTACCTGTT | sooooossssssssssooss | 40 | 87 | 498 |
| 655186 | 354 | 8034 | 259 | TCCATCACTGAGAAGTACCT | sooooossssssssssooss | 46 | 97 | 499 |

TABLE 17-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655187 | 358 | 8038 | 263 | TTTCTCCATCACTGAGAAGT | sooooosssssssssssooss | 36 | 94 | 500 |
| 655188 | 361 | 8041 | 266 | TTATTTCTCCATCACTGAGA | sooooosssssssssssooss | 9 | 82 | 501 |
| 655189 | 367 | 8047 | 272 | GAAAAGTTATTTCTCCATCA | sooooosssssssssssooss | 37 | 96 | 503 |
| 655190 | 376 | 8056 | 281 | GGTTGGCAAGAAAAGTTATT | sooooosssssssssssooss | 15 | 74 | 504 |
| 655191 | 379 | 8059 | 284 | TGTGGTTGGCAAGAAAAGTT | sooooosssssssssssooss | 15 | 62 | 505 |
| 655192 | 385 | 8065 | 290 | TTAGAGTGTGGTTGGCAAGA | sooooosssssssssssooss | 12 | 63 | 507 |
| 655193 | 388 | 8068 | 293 | CATTTAGAGTGTGGTTGGCA | sooooosssssssssssooss | 7 | 89 | 508 |
| 655194 | 389 | 8069 | 294 | CCATTTAGAGTGTGGTTGGC | sooooosssssssssssooss | 31 | 93 | 509 |
| 655195 | 394 | 8074 | 299 | TTTCTCCATTTAGAGTGTGG | sooooosssssssssssooss | 19 | 91 | 510 |
| 655196 | 397 | 8077 | 302 | GGATTTCTCCATTTAGAGTG | sooooosssssssssssooss | 8 | 82 | 511 |

TABLE 18

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 576816 | 310 | 7990 | 215 | GCCTTACTCTAGGACCAAGA | sssssssssssssssssss | 55 | 97 | 20 |
| 619420 | 310 | 7990 | 215 | GCCTTACTCTAGGACCAAGA | sooooosssssssssssooss | 74 | 97 | 20 |
| 655197 | 403 | 8083 | 308 | TTCGAAGGATTTCTCCATTT | sooooosssssssssssooss | 14 | 87 | 517 |
| 655198 | 406 | 8086 | 311 | CATTTCGAAGGATTTCTCCA | sooooosssssssssssooss | 23 | 83 | 518 |
| 655199 | 409 | 8089 | 314 | CTGCATTTCGAAGGATTTCT | sooooosssssssssssooss | 42 | 97 | 519 |
| 655200 | 412 | 8092 | 317 | TCTCTGCATTTCGAAGGATT | sooooosssssssssssooss | 21 | 87 | 520 |
| 655201 | 415 | 8095 | 320 | CACTCTCTGCATTTCGAAGG | sooooosssssssssssooss | 25 | 89 | 521 |
| 655202 | 418 | 8098 | 323 | CACCACTCTCTGCATTTCGA | sooooosssssssssssooss | 54 | 96 | 522 |
| 655203 | 420 | 8100 | 325 | AGCACCACTCTCTGCATTTC | sooooosssssssssssooss | 51 | 90 | 523 |
| 655204 | 421 | 8101 | 326 | TAGCACCACTCTCTGCATTT | sooooosssssssssssooss | 28 | 94 | 524 |
| 655205 | 424 | 8104 | 329 | CTATAGCACCACTCTCTGCA | sooooosssssssssssooss | 17 | 90 | 525 |
| 655206 | 427 | 8107 | 332 | CATCTATAGCACCACTCTCT | sooooosssssssssssooss | 15 | 83 | 526 |
| 655207 | 433 | 8113 | 338 | ACTTTACATCTATAGCACCA | sooooosssssssssssooss | 20 | 85 | 527 |
| 655208 | 436 | 8116 | 341 | AAAACTTTACATCTATAGCA | sooooosssssssssssooss | 25 | 72 | 528 |
| 655209 | 443 | 8123 | 348 | AAGACAAAAAACTTTACATC | sooooosssssssssssooss | 10 | 45 | 529 |
| 655210 | 444 | 8124 | 349 | CAAGACAAAAAACTTTACAT | sooooosssssssssssooss | 0 | 56 | 530 |
| 655211 | 446 | 8126 | 351 | GACAAGACAAAAAACTTTAC | sooooosssssssssssooss | 32 | 84 | 531 |

TABLE 18-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655212 | 449 | 8129 | 354 | TCAGACAAGACAAAAAACTT | sooooosssssssssssooss | 10 | 74 | 532 |
| 655213 | 451 | 8131 | 356 | TTTCAGACAAGACAAAAAAC | sooooosssssssssssooss | 7 | 54 | 533 |
| 655214 | 453 | 8133 | 358 | CTTTTCAGACAAGACAAAAA | sooooosssssssssssooss | 7 | 57 | 534 |
| 655215 | 456 | 8136 | 361 | TCCCTTTTCAGACAAGACAA | sooooosssssssssssooss | 32 | 91 | 535 |
| 655216 | 459 | 8139 | 364 | CACTCCCTTTTCAGACAAGA | sooooosssssssssssooss | 39 | 91 | 536 |
| 655217 | 462 | 8142 | 367 | AATCACTCCCTTTTCAGACA | sooooosssssssssssooss | 41 | 95 | 537 |
| 655218 | 465 | 8145 | 370 | AATAATCACTCCCTTTTCAG | sooooosssssssssssooss | 13 | 63 | 538 |
| 655219 | 467 | 8147 | 372 | ACAATAATCACTCCCTTTTC | sooooosssssssssssooss | 2 | 60 | 539 |
| 655220 | 468 | 8148 | 373 | AACAATAATCACTCCCTTTT | sooooosssssssssssooss | 11 | 73 | 540 |
| 655221 | 471 | 8151 | 376 | TGAAACAATAATCACTCCCT | sooooosssssssssssooss | 17 | 83 | 541 |
| 655222 | 474 | 8154 | 379 | TAATGAAACAATAATCACTC | sooooosssssssssssooss | 1 | 79 | 542 |
| 655223 | 477 | 8157 | 382 | GATTAATGAAACAATAATCA | sooooosssssssssssooss | 12 | 59 | 543 |
| 655224 | 482 | 8162 | 387 | TCAAAGATTAATGAAACAAT | sooooosssssssssssooss | 0 | 9 | 544 |
| 655225 | 485 | 8165 | 390 | CCATCAAAGATTAATGAAAC | sooooosssssssssssooss | 17 | 81 | 545 |
| 655226 | 488 | 8168 | 393 | TTTCCATCAAAGATTAATGA | sooooosssssssssssooss | 14 | 87 | 546 |
| 655227 | 491 | 8171 | 396 | CAGTTTCCATCAAAGATTAA | sooooosssssssssssooss | 7 | 69 | 547 |
| 655228 | 494 | 8174 | 399 | TTCCAGTTTCCATCAAAGAT | sooooosssssssssssooss | 25 | 88 | 548 |
| 655229 | 497 | 8177 | 402 | CCATTCCAGTTTCCATCAAA | sooooosssssssssssooss | 44 | 90 | 549 |
| 655230 | 500 | 8180 | 405 | TCCCCATTCCAGTTTCCATC | sooooosssssssssssooss | 48 | 94 | 550 |
| 655231 | 503 | 8183 | 408 | CGATCCCCATTCCAGTTTCC | sooooosssssssssssooss | 54 | 96 | 551 |
| 655232 | 506 | 8186 | 411 | CTGCGATCCCCATTCCAGTT | sooooosssssssssssooss | 61 | 96 | 552 |
| 655233 | 509 | 8189 | 414 | GTGCTGCGATCCCCATTCCA | sooooosssssssssssooss | 63 | 100 | 553 |
| 655234 | 512 | 8192 | 417 | TATGTGCTGCGATCCCCATT | sooooosssssssssssooss | 34 | 94 | 554 |
| 655235 | 533 | 8213 | 438 | GGAAGTATAATTGATAGTCC | sooooosssssssssssooss | 25 | 91 | 555 |
| 655236 | 536 | 8216 | 441 | TGTGGAAGTATAATTGATAG | sooooosssssssssssooss | 13 | 66 | 556 |
| 655237 | 539 | 8219 | 444 | GTCTGTGGAAGTATAATTGA | sooooosssssssssssooss | 24 | 83 | 557 |
| 655238 | 542 | 8222 | 447 | TCTGTCTGTGGAAGTATAAT | sooooosssssssssssooss | 51 | 92 | 558 |
| 655239 | 545 | 8225 | 450 | AGTTCTGTCTGTGGAAGTAT | sooooosssssssssssooss | 42 | 96 | 559 |
| 655240 | 548 | 8228 | 453 | CTAAGTTCTGTCTGTGGAAG | sooooosssssssssssooss | 16 | 88 | 560 |
| 655241 | 551 | 8231 | 456 | AAACTAAGTTCTGTCTGTGG | sooooosssssssssssooss | 25 | 93 | 561 |
| 655242 | 554 | 8234 | 459 | TAGAAACTAAGTTCTGTCTG | sooooosssssssssssooss | 29 | 94 | 562 |
| 655243 | 557 | 8237 | 462 | AGGTAGAAACTAAGTTCTGT | sooooosssssssssssooss | 43 | 85 | 563 |
| 655244 | 560 | 8240 | 465 | GGGAGGTAGAAACTAAGTTC | sooooosssssssssssooss | 27 | 77 | 564 |
| 655245 | 563 | 8243 | 468 | AGTGGGAGGTAGAAACTAAG | sooooosssssssssssooss | 22 | 77 | 565 |

TABLE 18-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655246 | 566 | 8246 | 471 | TGAAGTGGGAGGTAGAAACT | sooooossssssssssooss | 16 | 45 | 566 |
| 655247 | 569 | 8249 | 474 | CTATGAAGTGGGAGGTAGAA | sooooossssssssssooss | 14 | 60 | 567 |
| 655248 | 572 | 8252 | 477 | ACTCTATGAAGTGGGAGGTA | sooooossssssssssooss | 30 | 81 | 568 |
| 655249 | 574 | 8254 | 479 | ACACTCTATGAAGTGGGAGG | sooooossssssssssooss | 34 | 94 | 569 |
| 655250 | 575 | 8255 | 480 | CACACTCTATGAAGTGGGAG | sooooossssssssssooss | 46 | 98 | 570 |
| 655251 | 576 | 8256 | 481 | ACACACTCTATGAAGTGGGA | sooooossssssssssooss | 20 | 94 | 571 |
| 655252 | 578 | 8258 | 483 | ACACACTCTATGAAGTGG | sooooossssssssssooss | 28 | 97 | 572 |
| 655253 | 581 | 8261 | 486 | TCAACACACACTCTATGAAG | sooooossssssssssooss | 12 | 62 | 573 |
| 655254 | 584 | 8264 | 489 | CTATCAACACACACTCTATG | sooooossssssssssooss | 6 | 68 | 574 |
| 655255 | 587 | 8267 | 492 | AATCTATCAACACACACTCT | sooooossssssssssooss | 16 | 87 | 575 |
| 655256 | 590 | 8270 | 495 | GTTAATCTATCAACACAC | sooooossssssssssooss | 28 | 95 | 576 |
| 655257 | 592 | 8272 | 497 | GTGTTAATCTATCAACACAC | sooooossssssssssooss | 15 | 76 | 577 |
| 655258 | 593 | 8273 | 498 | TGTGTTAATCTATCAACACA | sooooossssssssssooss | 14 | 53 | 578 |
| 655259 | 595 | 8275 | 500 | TATGTGTTAATCTATCAACA | sooooossssssssssooss | 11 | 78 | 579 |
| 655260 | 596 | 8276 | 501 | ATATGTGTTAATCTATCAAC | sooooossssssssssooss | 25 | 79 | 580 |
| 655261 | 599 | 8279 | 504 | ATTATATGTGTTAATCTATC | sooooossssssssssooss | 11 | 71 | 581 |
| 655262 | 602 | 8282 | 507 | CGGATTATATGTGTTAATCT | sooooossssssssssooss | 21 | 91 | 582 |
| 655263 | 605 | 8285 | 510 | TTCCGGATTATATGTGTTAA | sooooossssssssssooss | 15 | 88 | 583 |
| 655264 | 608 | 8288 | 513 | CCTTTCCGGATTATATGTGT | sooooossssssssssooss | 12 | 83 | 584 |
| 655265 | 611 | 8291 | 516 | CTTCCTTTCCGGATTATATG | sooooossssssssssooss | 1 | 69 | 585 |
| 655266 | 614 | 8294 | 519 | ATTCTTCCTTTCCGGATTAT | sooooossssssssssooss | 15 | 76 | 586 |
| 655267 | 617 | 8297 | 522 | CATATTCTTCCTTTCCGGAT | sooooossssssssssooss | 17 | 69 | 587 |
| 655268 | 620 | 8300 | 525 | ATCCATATTCTTCCTTTCCG | sooooossssssssssooss | 21 | 67 | 588 |
| 655269 | 624 | 8304 | 529 | ATGCATCCATATTCTTCCTT | sooooossssssssssooss | 5 | 73 | 589 |
| 655270 | 626 | 8306 | 531 | TTATGCATCCATATTCTTCC | sooooossssssssssooss | 23 | 71 | 590 |
| 655271 | 629 | n/a | 534 | TCCTTATGCATCCATATTCT | sooooossssssssssooss | 15 | 64 | 591 |
| 655272 | 632 | n/a | 537 | CTTTCCTTATGCATCCATAT | sooooossssssssssooss | 24 | 66 | 592 |
| 655273 | 635 | n/a | 540 | TGTCTTTCCTTATGCATCCA | sooooossssssssssooss | 37 | 76 | 593 |

TABLE 19

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 576816 | 310 | 7990 | 215 | GCCTTACTCTAGGACCAAGA | sssssssssssssssssss | 53 | 95 | 20 |
| 619253 | n/a | 1406 | n/a | TACAGGCTGCGGTTGTTTCC | sooooosssssssssssooss | 0 | 72 | 97 |
| 619293 | n/a | 1446 | n/a | CCCGGCCCCTAGCGCGCGAC | sooooosssssssssssooss | 0 | 95 | 98 |
| 619422 | n/a | 3452 | n/a | GGTAACTTCAAACTCTTGGG | sooooosssssssssssooss | 0 | 93 | 382 |
| 655329 | n/a | 2330 | n/a | AGGACCTCCCTCCTGTTTCT | sooooosssssssssssooss | 0 | 84 | 594 |
| 655330 | n/a | 2490 | n/a | AGAAGTAATGCCAGACAGAT | sooooosssssssssssooss | 0 | 75 | 595 |
| 655331 | n/a | 2901 | n/a | CTTTGTTTCTCTGAAAGCAA | sooooosssssssssssooss | 16 | 75 | 596 |
| 655332 | n/a | 3576 | n/a | GTGGTTGGTCCACTGCTATT | sooooosssssssssssooss | 28 | 94 | 597 |
| 655333 | n/a | 3801 | n/a | TTGAGGGAAGCCAAGATTCA | sooooosssssssssssooss | 10 | 77 | 598 |
| 655334 | n/a | 3975 | n/a | AGAGCTGTACAATTATTTTA | sooooosssssssssssooss | 13 | 90 | 599 |
| 655335 | n/a | 4725 | n/a | GGTAATGACACTACTGCTGT | sooooosssssssssssooss | 27 | 96 | 600 |
| 655336 | n/a | 5970 | n/a | GATCCTAATCCTGTCTATGC | sooooosssssssssssooss | 0 | 70 | 601 |
| 655337 | n/a | 7382 | n/a | ACTTGTGGGTTGAATTGTGT | sooooosssssssssssooss | 4 | 66 | 602 |
| 655338 | n/a | 8310 | n/a | TACCTTATGCATCCATATTC | sooooosssssssssssooss | 11 | 62 | 603 |
| 655339 | n/a | 8409 | n/a | GATGTTCACTGCATATAATT | sooooosssssssssssooss | 31 | 88 | 604 |
| 655340 | n/a | 8464 | n/a | CCAGATGTATTTGTATCTAA | sooooosssssssssssooss | 41 | 96 | 605 |
| 655341 | n/a | 8523 | n/a | TAATGTGGAGCTACCATTTC | sooooosssssssssssooss | 6 | 72 | 606 |
| 655342 | n/a | 8587 | n/a | GCTCCCAAGAAGAATCCAGG | sooooosssssssssssooss | 44 | 74 | 607 |
| 655343 | n/a | 8658 | n/a | ACTTACACATAGTAGTAAGC | sooooosssssssssssooss | 16 | 88 | 608 |
| 655344 | n/a | 8716 | n/a | AAAGAGACCAAAGGCTACAT | sooooosssssssssssooss | 4 | 82 | 609 |
| 655345 | n/a | 8785 | n/a | GGAATTCTCTTGGGAACCAT | sooooosssssssssssooss | 9 | 80 | 610 |
| 619420 | 310 | 7990 | 215 | GCCTTACTCTAGGACCAAGA | sooooosssssssssssooss | 51 | 98 | 20 |
| 655274 | 638 | n/a | 543 | TCTTGTCTTTCCTTATGCAT | sooooosssssssssssooss | 0 | 73 | 611 |
| 655275 | 641 | n/a | 546 | TTTTCTTGTCTTTCCTTATG | sooooosssssssssssooss | 10 | 61 | 612 |
| 625344 | 647 | 9413 | 552 | TGGACATTTTCTTGTCTTTC | sooooosssssssssssooss | 32 | 94 | 613 |
| 655276 | 650 | 9416 | 555 | TTCTGGACATTTTCTTGTCT | sooooosssssssssssooss | 8 | 79 | 614 |
| 655277 | 653 | 9419 | 558 | ATCTTCTGGACATTTTCTTG | sooooosssssssssssooss | 0 | 60 | 615 |
| 655278 | 655 | 9421 | 560 | TAATCTTCTGGACATTTTCT | sooooosssssssssssooss | 0 | 66 | 616 |
| 655279 | 659 | 9425 | 564 | AAGATAATCTTCTGGACATT | sooooosssssssssssooss | 5 | 72 | 617 |
| 655280 | 662 | 9428 | 567 | TCTAAGATAATCTTCTGGAC | sooooosssssssssssooss | 2 | 81 | 618 |
| 655281 | 665 | 9431 | 570 | CCTTCTAAGATAATCTTCTG | sooooosssssssssssooss | 0 | 19 | 619 |
| 655282 | 668 | 9434 | 573 | GTGCCTTCTAAGATAATCTT | sooooosssssssssssooss | 4 | 20 | 620 |
| 655283 | 671 | 9437 | 576 | TCTGTGCCTTCTAAGATAAT | sooooosssssssssssooss | 9 | 27 | 621 |
| 655284 | 674 | 9440 | 579 | CTCTGTGCCTTCTAAGATAT | sooooosssssssssssooss | 0 | 35 | 622 |
| 655285 | 677 | 9443 | 582 | ATTCTCTGTGCCTTCTAA | sooooosssssssssssooss | 7 | 40 | 623 |

TABLE 19-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655286 | 680 | 9446 | 585 | TCCATTCTCTCTGTGCCTTC | sooooosssssssssssooss | 18 | 65 | 624 |
| 655287 | 683 | 9449 | 588 | TCTTCCATTCTCTCTGTGCC | sooooosssssssssssooss | 14 | 67 | 625 |
| 655288 | 686 | 9452 | 591 | TGATCTTCCATTCTCTCTGT | sooooosssssssssssooss | 7 | 65 | 626 |
| 655289 | 691 | n/a | 596 | GACCCTGATCTTCCATTCTC | sooooosssssssssssooss | 12 | 89 | 627 |
| 655290 | 694 | n/a | 599 | TCTGACCCTGATCTTCCATT | sooooosssssssssssooss | 13 | 81 | 628 |
| 655291 | 697 | n/a | 602 | TACTCTGACCCTGATCTTCC | sooooosssssssssssooss | 0 | 82 | 629 |
| 655292 | 700 | n/a | 605 | TAATACTCTGACCCTGATCT | sooooosssssssssssooss | 0 | 72 | 630 |
| 655293 | 703 | n/a | 608 | GAATAATACTCTGACCCTGA | sooooosssssssssssooss | 0 | 77 | 631 |
| 655294 | 709 | 12529 | 614 | GCATTGGAATAATACTCTGA | sooooosssssssssssooss | 0 | 79 | 632 |
| 655295 | 712 | 12532 | 617 | TAAGCATTGGAATAATACTC | sooooosssssssssssooss | 8 | 79 | 633 |
| 655296 | 715 | 12535 | 620 | CAGTAAGCATTGGAATAATA | sooooosssssssssssooss | 0 | 66 | 634 |
| 655297 | 718 | 12538 | 623 | CTCCAGTAAGCATTGGAATA | sooooosssssssssssooss | 12 | 78 | 635 |
| 655298 | 721 | 12541 | 626 | CTTCTCCAGTAAGCATTGGA | sooooosssssssssssooss | 0 | 81 | 636 |
| 655299 | 724 | 12544 | 629 | TCACTTCTCCAGTAAGCATT | sooooosssssssssssooss | 0 | 70 | 637 |
| 655300 | 727 | 12547 | 632 | GAATCACTTCTCCAGTAAGC | sooooosssssssssssooss | 0 | 75 | 638 |
| 655301 | 730 | 12550 | 635 | CAGGAATCACTTCTCCAGTA | sooooosssssssssssooss | 20 | 85 | 639 |
| 655302 | 733 | 12553 | 638 | TTACAGGAATCACTTCTCCA | sooooosssssssssssooss | 0 | 50 | 640 |
| 655303 | 736 | 12556 | 641 | CCATTACAGGAATCACTTCT | sooooosssssssssssooss | 0 | 57 | 641 |
| 655304 | 744 | 12564 | 649 | AAGCAGTTCCATTACAGGAA | sooooosssssssssssooss | 0 | 83 | 642 |
| 655305 | 747 | 12567 | 652 | TGAAAGCAGTTCCATTACAG | sooooosssssssssssooss | 0 | 55 | 643 |
| 655306 | 750 | 12570 | 655 | AGATGAAAGCAGTTCCATTA | sooooosssssssssssooss | 0 | 82 | 644 |
| 655307 | 753 | 12573 | 658 | CATAGATGAAAGCAGTTCCA | sooooosssssssssssooss | 2 | 83 | 645 |
| 655308 | 756 | 12576 | 661 | TTTCATAGATGAAAGCAGTT | sooooosssssssssssooss | 0 | 59 | 646 |
| 655309 | 762 | 12582 | 667 | GTGTGATTTCATAGATGAAA | sooooosssssssssssooss | 0 | 39 | 647 |
| 655310 | 766 | 12586 | 671 | CACTGTGTGATTTCATAGAT | sooooosssssssssssooss | 10 | 31 | 648 |
| 655311 | 769 | 12589 | 674 | GAACACTGTGTGATTTCATA | sooooosssssssssssooss | 0 | 80 | 649 |
| 655312 | 772 | 12592 | 677 | CAGGAACACTGTGTGATTTC | sooooosssssssssssooss | 0 | 53 | 650 |
| 655313 | 778 | 12598 | 683 | TTTCTTCAGGAACACTGTGT | sooooosssssssssssooss | 0 | 45 | 651 |
| 655314 | 781 | 12601 | 686 | CTATTTCTTCAGGAACACTG | sooooosssssssssssooss | 0 | 56 | 652 |
| 655315 | 784 | n/a | 689 | TATCTATTTCTTCAGGAACA | sooooosssssssssssooss | 0 | 75 | 653 |
| 655316 | 787 | n/a | 692 | CTATATCTATTTCTTCAGGA | sooooosssssssssssooss | 0 | 75 | 654 |
| 655317 | 790 | n/a | 695 | CAGCTATATCTATTTCTTCA | sooooosssssssssssooss | 23 | 89 | 655 |
| 655318 | 793 | n/a | 698 | TATCAGCTATATCTATTTCT | sooooosssssssssssooss | 7 | 80 | 656 |
| 655319 | 796 | n/a | 701 | CTGTATCAGCTATATCTATT | sooooosssssssssssooss | 34 | 86 | 657 |

TABLE 19-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655320 | 799 | n/a | 704 | GTACTGTATCAGCTATATCT | sooooossssssssssooss | 42 | 88 | 658 |
| 655321 | 802 | n/a | 707 | TGAGTACTGTATCAGCTATA | sooooossssssssssooss | 31 | 87 | 659 |
| 655322 | 805 | 13356 | 710 | CATTGAGTACTGTATCAGCT | sooooossssssssssooss | 3 | 84 | 660 |
| 655323 | 808 | 13359 | 713 | CATCATTGAGTACTGTATCA | sooooossssssssssooss | 5 | 88 | 661 |
| 655324 | 811 | 13362 | 716 | CATCATCATTGAGTACTGTA | sooooossssssssssooss | 17 | 90 | 662 |
| 655325 | 814 | 13365 | 719 | TATCATCATCATTGAGTACT | sooooossssssssssooss | 2 | 84 | 663 |
| 655326 | 817 | 13368 | 722 | CAATATCATCATCATTGAGT | sooooossssssssssooss | 0 | 74 | 664 |
| 655327 | 822 | 13373 | 727 | GTCACCAATATCATCATCAT | sooooossssssssssooss | 6 | 78 | 665 |
| 655328 | 848 | 13399 | 753 | TTGAGAAGAAAGCCTTCATG | sooooossssssssssooss | 0 | 42 | 666 |
| 619421 | 3132 | 28251 | 3037 | GGGACACTACAAGGTAGTAT | sooooossssssssssooss | 0 | 94 | 401 |

TABLE 20

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 576816 | 310 | 7990 | 215 | GCCTTACTCTAGGACCAAGA | sssssssssssssssssss | 49 | 97 | 20 |
| 655346 | n/a | 8861 | n/a | ACTATACTGAAATGTAAATA | sooooossssssssssooss | 4 | 7 | 667 |
| 655347 | n/a | 8915 | n/a | TATCAAACTGGAACACAGGA | sooooossssssssssooss | 16 | 53 | 668 |
| 655348 | n/a | 8965 | n/a | TGGGCAAAAGCCTTTTAAAA | sooooossssssssssooss | 13 | 63 | 669 |
| 655349 | n/a | 9017 | n/a | GCAAACATAGTAAAAAATTA | sooooossssssssssooss | 6 | 7 | 670 |
| 655350 | n/a | 9067 | n/a | TTCTCCTGATTTTAAGAGTT | sooooossssssssssooss | 39 | 90 | 671 |
| 655351 | n/a | 9117 | n/a | AAGAATGACTTGCACTTTTC | sooooossssssssssooss | 25 | 100 | 672 |
| 655352 | n/a | 9173 | n/a | AAAGATAACTTCACAGAAAA | sooooossssssssssooss | 13 | 10 | 673 |
| 655353 | n/a | 9286 | n/a | CTTTCTACTTTAGGGAAAAA | sooooossssssssssooss | 16 | 64 | 674 |
| 655354 | n/a | 9336 | n/a | TTTTTCAATAGACATGTTCT | sooooossssssssssooss | 19 | 81 | 675 |
| 655355 | n/a | 9403 | n/a | CTTGTCTTTCCTGAGCAAGA | sooooossssssssssooss | 8 | 54 | 676 |
| 655356 | n/a | 9455 | n/a | ACCTGATCTTCCATTCTCTC | sooooossssssssssooss | 22 | 81 | 677 |
| 655357 | n/a | 9576 | n/a | CTCCATAAAAGCTCCATTAA | sooooossssssssssooss | 34 | 52 | 678 |
| 655358 | n/a | 9640 | n/a | TGTTTACTGATTTAACTCTT | sooooossssssssssooss | 34 | 83 | 679 |
| 655359 | n/a | 9696 | n/a | AACAGAAAAAAAAGGGAGC | sooooossssssssssooss | 18 | 22 | 680 |
| 655360 | n/a | 9772 | n/a | GTACCTTAAAGAACATATCA | sooooossssssssssooss | 34 | 100 | 681 |
| 655361 | n/a | 9920 | n/a | AAATGTAAATTGCATGAGTC | sooooossssssssssooss | 7 | 100 | 682 |

TABLE 20-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655362 | n/a | 9970 | n/a | GGGTAAGAAATATCACTGAC | sooooosssssssssssooss | 43 | 63 | 683 |
| 655363 | n/a | 10055 | n/a | AACCATGCTTCTCAAACTCT | sooooosssssssssssooss | 29 | 75 | 684 |
| 655364 | n/a | 10122 | n/a | AAGAACTTCTCTGCTTTACA | sooooosssssssssssooss | 13 | 68 | 685 |
| 655365 | n/a | 10172 | n/a | AATGGAAGTAAAAGTGAAGA | sooooosssssssssssooss | 7 | 13 | 686 |
| 655366 | n/a | 10233 | n/a | AACAGCCATGTTTAAAATAT | sooooosssssssssssooss | 15 | 37 | 687 |
| 655367 | n/a | 10283 | n/a | TTAAAGTATCATCTGTCTCA | sooooosssssssssssooss | 34 | 74 | 688 |
| 655368 | n/a | 10364 | n/a | CAATTTGGTAAAGGAGATCA | sooooosssssssssssooss | 6 | 48 | 689 |
| 655369 | n/a | 10418 | n/a | ACACAGAATAACTGTCTCTG | sooooosssssssssssooss | 16 | 64 | 690 |
| 655370 | n/a | 10491 | n/a | GCTTATTGACCAGCAAATAA | sooooosssssssssssooss | 22 | 69 | 691 |
| 655371 | n/a | 10615 | n/a | CCCAGTAAAAGCAGAATTTT | sooooosssssssssssooss | 24 | 57 | 692 |
| 655372 | n/a | 10665 | n/a | ATTAATAGTAGTCAACTTAA | sooooosssssssssssooss | 20 | 10 | 693 |
| 655373 | n/a | 10730 | n/a | ACTTGAACTTCTCAGCAGTA | sooooosssssssssssooss | 25 | 62 | 694 |
| 655374 | n/a | 10786 | n/a | AGAAGAGGCTCTAAAAGAAA | sooooosssssssssssooss | 7 | 59 | 695 |
| 655375 | n/a | 10970 | n/a | AAAGGCAACTCCTCCTTTTC | sooooosssssssssssooss | 13 | 78 | 696 |
| 655376 | n/a | 11020 | n/a | ACAGTATTGTTCAAAATAAA | sooooosssssssssssooss | 18 | 100 | 697 |
| 655377 | n/a | 11070 | n/a | CAGATGACAGCTACAACTGA | sooooosssssssssssooss | 16 | 49 | 698 |
| 655378 | n/a | 11121 | n/a | GAATAATGACTAGATCCGTG | sooooosssssssssssooss | 26 | 88 | 699 |
| 655379 | n/a | 11171 | n/a | ATAATTATCATGCCTGTTTA | sooooosssssssssssooss | 22 | 80 | 700 |
| 655380 | n/a | 11221 | n/a | CTTTAGTAACCTCCACAACT | sooooosssssssssssooss | 19 | 26 | 701 |
| 655381 | n/a | 11313 | n/a | GAATTTAAATGTGATGCTAC | sooooosssssssssssooss | 15 | 49 | 702 |
| 655382 | n/a | 11385 | n/a | TGTCAGACCCAGGGCCATTT | sooooosssssssssssooss | 40 | 83 | 703 |
| 655383 | n/a | 11445 | n/a | ACTTATTTTATGAAATGATT | sooooosssssssssssooss | 7 | 3 | 704 |
| 655384 | n/a | 11513 | n/a | TTTTAGCTAAACATATTTTT | sooooosssssssssssooss | 2 | 1 | 705 |
| 655385 | n/a | 11591 | n/a | CAGTCTCATCAGTTTTGTGA | sooooosssssssssssooss | 33 | 83 | 706 |
| 655386 | n/a | 11641 | n/a | TGTAAAGTGTCTCAAATATG | sooooosssssssssssooss | 21 | 39 | 707 |
| 655387 | n/a | 11711 | n/a | CTTGAAATTGTAATTTTGAA | sooooosssssssssssooss | 14 | 42 | 708 |
| 655388 | n/a | 11798 | n/a | AATCAAAATCAGCACATATA | sooooosssssssssssooss | 8 | 46 | 709 |
| 655389 | n/a | 11871 | n/a | ACCAAATAGGTAAGGAAAAC | sooooosssssssssssooss | 9 | 32 | 710 |
| 655390 | n/a | 11978 | n/a | AAAGATCTCCTTTAAAATTT | sooooosssssssssssooss | 11 | 29 | 711 |
| 655391 | n/a | 12053 | n/a | CTTTAGAGAGTATGGAATCA | sooooosssssssssssooss | 22 | 71 | 712 |
| 655392 | n/a | 12334 | n/a | CAAAGCTCACTTTTATTCTT | sooooosssssssssssooss | 25 | 70 | 713 |
| 655393 | n/a | 12384 | n/a | ACACAGTATCAAACAAGTCT | sooooosssssssssssooss | 29 | 45 | 714 |
| 655394 | n/a | 12459 | n/a | AAGCTGGGCAATAAAAAATA | sooooosssssssssssooss | 0 | 24 | 715 |
| 655395 | n/a | 12513 | n/a | CTGACCCTGCACAATAAAGT | sooooosssssssssssooss | 17 | 0 | 716 |

TABLE 20-continued

Percent inhibition of human C9ORF72 compared to PBS control by antisense oligonucleotides targeting SEQ ID NOs: 1, 2, and 6

| ISIS NO | SEQ ID NO: 1 Start Site | SEQ ID NO: 2 Start Site | SEQ ID NO: 6 Start Site | Sequence | Linkage | % inhibition (LLC-MK2) Primer Probe RTS3750 | % inhibition (HepG2) Primer Probe RTS3905 | SEQ ID NO |
|---|---|---|---|---|---|---|---|---|
| 655396 | n/a | 12604 | n/a | CATCTATTTCTTCAGGAACA | soooosssssssssssooss | 21 | 74 | 717 |
| 655397 | n/a | 12681 | n/a | GAATATTAATAATATACATA | soooosssssssssssooss | 0 | 16 | 718 |
| 655398 | n/a | 12765 | n/a | AGGATTTTGTGTGTGCTTAT | soooosssssssssssooss | 30 | 65 | 719 |
| 655399 | n/a | 12855 | n/a | TTTTAGGAATTATAAAAGTA | soooosssssssssssooss | 7 | 61 | 720 |
| 655400 | n/a | 12924 | n/a | ACACAGTTTTGTTTCAAAAG | soooosssssssssssooss | 13 | 61 | 721 |
| 655401 | n/a | 12978 | n/a | GGAAACTAAATTTGTGACTA | soooosssssssssssooss | 21 | 56 | 722 |
| 655402 | n/a | 13028 | n/a | CTCTTAACACTCATAGTGTG | soooosssssssssssooss | 13 | 52 | 723 |
| 655403 | n/a | 13084 | n/a | GAGACTAACCTAAATGACAA | soooosssssssssssooss | 20 | 35 | 724 |
| 655404 | n/a | 13159 | n/a | CAAATGTGAAAGCTGGTCAA | soooosssssssssssooss | 8 | 100 | 725 |
| 655405 | n/a | 13237 | n/a | TAACACACTGCCTTCATTTC | soooosssssssssssooss | 17 | 32 | 726 |
| 655406 | n/a | 13337 | n/a | TATCTAAAATGCATCAAAAA | soooosssssssssssooss | 2 | 6 | 727 |
| 655407 | n/a | 13400 | n/a | CTTGAGAAGAAAGCCTTCAT | soooosssssssssssooss | 23 | 42 | 728 |
| 655408 | n/a | 13471 | n/a | CCAAATCTTGTCATAGGTGA | soooosssssssssssooss | 42 | 95 | 729 |
| 655409 | n/a | 13550 | n/a | TAACACAAATTTAAGCAACA | soooosssssssssssooss | 21 | 55 | 730 |
| 655410 | n/a | 13603 | n/a | AAATAGCAAATGGAATAACA | soooosssssssssssooss | 14 | 55 | 731 |
| 655411 | n/a | 13662 | n/a | AAACCAGAATCAAGCAAGGG | soooosssssssssssooss | 27 | 73 | 732 |
| 655412 | n/a | 13722 | n/a | CATCTACAGTACAACTTAAT | soooosssssssssssooss | 13 | 100 | 733 |
| 655413 | n/a | 13773 | n/a | AGATCAGTATAAATATGAAT | soooosssssssssssooss | 1 | 43 | 734 |
| 655414 | n/a | 13823 | n/a | GTTTAAGGGCACAAACTCTT | soooosssssssssssooss | 27 | 78 | 735 |
| 655415 | n/a | 13884 | n/a | AGGTGTATAGAGAATTCAGG | soooosssssssssssooss | 43 | 89 | 736 |
| 655416 | n/a | 13955 | n/a | TACTCAATGCTTATAACAAC | soooosssssssssssooss | 26 | 84 | 737 |
| 655417 | n/a | 14089 | n/a | GGAACTAACATGTAGGCACT | soooosssssssssssooss | 66 | 100 | 738 |
| 655418 | n/a | 14213 | n/a | CATAAAAGTGAATACTTTAT | soooosssssssssssooss | 13 | 0 | 739 |
| 655419 | n/a | 14281 | n/a | AGGCTCTTAGGTTAAACACA | soooosssssssssssooss | 16 | 79 | 740 |
| 655420 | n/a | 14331 | n/a | GCTGACACTGAACAGATACA | soooosssssssssssooss | 52 | 84 | 741 |
| 655421 | n/a | 14392 | n/a | CATGTAGAGAGATTAAGTGA | soooosssssssssssooss | 27 | 42 | 742 |
| 655422 | n/a | 14452 | n/a | ATCATTTAATTAATGTATTT | soooosssssssssssooss | 13 | 0 | 743 |
| 619420 | 310 | 7990 | 215 | GCCTTACTCTAGGACCAAGA | soooosssssssssssooss | 76 | 98 | 20 |

Example 5: Dose-Dependent Antisense Inhibition of Human C9ORF72 mRNA in LLC-MK2

Antisense oligonucleotides from the study described above exhibiting significant in vitro inhibition of C9ORF72 mRNA were selected and tested at various doses in LLC-MK2 cells. ISIS 576816, previously tested in U.S. Application No. 61/714,132, filed Oct. 15, 2012, was used as a benchmark oligonucleotide. Cells were plated at a density of 20,000 cells per well and transfected using electroporation with 0.33 M, 1.00 µM, 3.00 µM, or 9.00 µM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3750 was used to measure total C9ORF72 mRNA levels. C9ORF72 mRNA levels were adjusted according to total RNA content, as measured by RIBOGREEN®. Results are presented as percent inhibition of C9ORF72 levels, relative to untreated control cells.

As shown in Table 21, total C9ORF72 mRNA levels were reduced in a dose-dependent manner in the antisense oligonucleotide treated cells.

TABLE 21

Dose-dependent inhibition of total C9ORF72 mRNA transcript levels in LLC-MK2 cells

| ISIS No | 0.33 µM | 1.00 µM | 3.00 µM | 9.00 µM |
|---|---|---|---|---|
| 576816 | 0 | 33 | 55 | 66 |
| 619411 | 15 | 43 | 67 | 87 |
| 619412 | 9 | 30 | 55 | 84 |
| 619413 | 17 | 27 | 58 | 79 |
| 619414 | 13 | 49 | 75 | 83 |
| 619415 | 15 | 41 | 62 | 57 |
| 619416 | 29 | 47 | 70 | 81 |
| 619420 | 17 | 49 | 70 | 85 |
| 619423 | 25 | 52 | 71 | 82 |
| 627833 | 4 | 31 | 63 | 82 |
| 655173 | 37 | 72 | 86 | 90 |
| 655178 | 9 | 35 | 71 | 86 |
| 655179 | 30 | 50 | 52 | 84 |
| 655202 | 1 | 12 | 41 | 72 |
| 655231 | 0 | 28 | 43 | 71 |
| 655232 | 17 | 45 | 64 | 76 |
| 655233 | 19 | 30 | 62 | 80 |
| 655420 | 24 | 28 | 49 | 78 |

The antisense oligonucleotides were also selected and tested at various doses in HepG2 cells. ISIS 576816, previously tested in U.S. Application No. 61/714,132, filed Oct. 15, 2012, was used as a benchmark oligonucleotide. Cells were plated at a density of 20,000 cells per well and transfected using electroporation with 0.11 M, 0.33 M, 1.00 µM, or 3.00 µM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3750 was used to measure total C9ORF72 mRNA levels. C9ORF72 mRNA levels were adjusted according to total RNA content, as measured by RIBOGREEN®. Results are presented as percent inhibition of C9ORF72 levels, relative to untreated control cells.

As shown in Table 22, total C9ORF72 mRNA levels were reduced in a dose-dependent manner in the antisense oligonucleotide treated cells.

TABLE 22

Dose-dependent inhibition of total C9ORF72 mRNA transcript levels in HepG2 cells

| ISIS No | 0.11 µM | 0.33 µM | 1.00 µM | 3.00 µM |
|---|---|---|---|---|
| 576816 | 16 | 32 | 71 | 90 |
| 619411 | 11 | 41 | 71 | 91 |
| 619412 | 24 | 44 | 79 | 92 |
| 619413 | 0 | 18 | 59 | 84 |
| 619414 | 16 | 51 | 76 | 92 |
| 619415 | 16 | 38 | 72 | 85 |
| 619416 | 16 | 36 | 47 | 80 |
| 619420 | 15 | 47 | 75 | 91 |
| 619423 | 24 | 50 | 81 | 89 |
| 627833 | 0 | 29 | 69 | 90 |
| 655173 | 24 | 56 | 88 | 96 |
| 655178 | 25 | 48 | 81 | 92 |
| 655179 | 16 | 43 | 79 | 87 |
| 655202 | 17 | 19 | 61 | 84 |
| 655231 | 14 | 45 | 68 | 84 |
| 655232 | 13 | 38 | 69 | 79 |
| 655233 | 17 | 30 | 65 | 86 |
| 655420 | 19 | 35 | 60 | 86 |

Example 6: Design of Mixed Backbone 5-8-5 MOE Gapmers and Deoxy, MOE, and cEt Oligonucleotides Targeting Human C9ORF72

Additional antisense oligonucleotides were designed targeting a C9ORF72 nucleic acid. The newly designed chimeric antisense oligonucleotides in the Tables below were designed as 5-8-5 MOE gapmers, 5-10-5 MOE gapmers, or deoxy, MOE, and cEt gapmers.

The 5-8-5 MOE gapmers are 18 nucleosides in length, wherein the central gap segment comprises of eight 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The linkages between the nucleosides are described in the Linkage column; 'o' indicates a phosphodiester linkage and 's' indicates a phosphorothioate linkage. All cytosine residues throughout each gapmer are 5-methylcytosines.

The 5-10-5 MOE gapmers are 20 nucleosides in length, wherein the central gap segment comprises often 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The linkages between the nucleosides are described in the Linkage column; 'o' indicates a phosphodiester linkage and 's' indicates a phosphorothioate linkage. All cytosine residues throughout each gapmer are 5-methylcytosines.

The deoxy, MOE, and cEt oligonucleotides are 17 nucleosides in length wherein the nucleoside has either a MOE sugar modification, a cEt sugar modification, or a deoxyribose sugar. The 'Chemistry' column describes the sugar modifications of each oligonucleotide; 'k' indicates a cEt nucleoside; d' indicates deoxyribonucleosides, the number indicates the number of deoxyribonucleosides; and 'e' indicates a 2'-MOE nucleoside. The internucleoside linkages throughout each gapmer are either phosphorothioate linkages or phosphodiester linkages. The linkages between the nucleosides are described in the Linkage column; 'o' indicates a phosphodiester linkage and 's' indicates a phosphorothioate linkage. All cytosine residues throughout each gapmer are 5-methylcytosines.

"Start site" indicates the 5'-most nucleoside to which the antisense oligonucleotide is targeted in the human gene sequence. "Stop site" indicates the 3'-most nucleoside to which the antisense oligonucleotide is targeted in the human gene sequence. Each antisense oligonucleotide listed in the Tables 23-29 below is targeted to the human C9ORF72 genomic sequence, designated herein as SEQ ID NO: 2 (the complement of GENBANK Accession No. NT_008413.18 truncated from nucleosides 27535000 to 27565000. Table 30 presents a 5-10-5 gapmer that is targeted to C9ORF72 mRNA sequence, SEQ ID NO: 1 (GENBANK Accession No. NM_001256054.1).

TABLE 23

5-8-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 672581 | GTGAGAGCAAGTAGTGGG | sooossssssssssooss | 1326 | 1343 | 744 |
| 672582 | TGTGAGAGCAAGTAGTGG | sooossssssssssooss | 1327 | 1344 | 745 |
| 672583 | CTGTGAGAGCAAGTAGTG | sooossssssssssooss | 1328 | 1345 | 746 |
| 672584 | ACTGTGAGAGCAAGTAGT | sooossssssssssooss | 1329 | 1346 | 747 |
| 672585 | TACTGTGAGAGCAAGTAG | sooossssssssssooss | 1330 | 1347 | 748 |
| 672586 | GTACTGTGAGAGCAAGTA | sooossssssssssooss | 1331 | 1348 | 749 |
| 672587 | AGTACTGTGAGAGCAAGT | sooossssssssssooss | 1332 | 1349 | 750 |
| 672588 | GAGTACTGTGAGAGCAAG | sooossssssssssooss | 1333 | 1350 | 751 |
| 672589 | CGAGTACTGTGAGAGCAA | sooossssssssssooss | 1334 | 1351 | 752 |
| 672590 | GCGAGTACTGTGAGAGCA | sooossssssssssooss | 1335 | 1352 | 753 |
| 672591 | AGCGAGTACTGTGAGAGC | sooossssssssssooss | 1336 | 1353 | 754 |
| 672592 | CAGCGAGTACTGTGAGAG | sooossssssssssooss | 1337 | 1354 | 755 |
| 672593 | TCAGCGAGTACTGTGAGA | sooossssssssssooss | 1338 | 1355 | 756 |
| 672594 | CTCAGCGAGTACTGTGAG | sooossssssssssooss | 1339 | 1356 | 757 |
| 672595 | CCTCAGCGAGTACTGTGA | sooossssssssssooss | 1340 | 1357 | 758 |
| 672596 | CCCTCAGCGAGTACTGTG | sooossssssssssooss | 1341 | 1358 | 759 |
| 672597 | ACCCTCAGCGAGTACTGT | sooossssssssssooss | 1342 | 1359 | 760 |
| 672598 | CACCCTCAGCGAGTACTG | sooossssssssssooss | 1343 | 1360 | 761 |
| 672599 | TCACCCTCAGCGAGTACT | sooossssssssssooss | 1344 | 1361 | 762 |
| 672600 | TTCACCCTCAGCGAGTAC | sooossssssssssooss | 1345 | 1362 | 763 |
| 672601 | GTTCACCCTCAGCGAGTA | sooossssssssssooss | 1346 | 1363 | 764 |
| 672602 | TGTTCACCCTCAGCGAGT | sooossssssssssooss | 1347 | 1364 | 765 |
| 672603 | TTGTTCACCCTCAGCGAG | sooossssssssssooss | 1348 | 1365 | 766 |
| 672604 | CTTGTTCACCCTCAGCGA | sooossssssssssooss | 1349 | 1366 | 767 |
| 672605 | TCTTGTTCACCCTCAGCG | sooossssssssssooss | 1350 | 1367 | 768 |
| 672606 | TTCTTGTTCACCCTCAGC | sooossssssssssooss | 1351 | 1368 | 769 |
| 672607 | TTTCTTGTTCACCCTCAG | sooossssssssssooss | 1352 | 1369 | 770 |
| 672608 | TTTTCTTGTTCACCCTCA | sooossssssssssooss | 1353 | 1370 | 771 |
| 672609 | CTTTTCTTGTTCACCCTC | sooossssssssssooss | 1354 | 1371 | 772 |
| 672610 | TCTTTTCTTGTTCACCCT | sooossssssssssooss | 1355 | 1372 | 773 |
| 672611 | GTCTTTTCTTGTTCACCC | sooossssssssssooss | 1356 | 1373 | 774 |
| 672612 | GGTCTTTTCTTGTTCACC | sooossssssssssooss | 1357 | 1374 | 775 |
| 672613 | AGGTCTTTTCTTGTTCAC | sooossssssssssooss | 1358 | 1375 | 776 |
| 672614 | CAGGTCTTTTCTTGTTCA | sooossssssssssooss | 1359 | 1376 | 777 |
| 672615 | TCAGGTCTTTTCTTGTTC | sooossssssssssooss | 1360 | 1377 | 778 |
| 672616 | ATCAGGTCTTTTCTTGTT | sooossssssssssooss | 1361 | 1378 | 779 |
| 672617 | TATCAGGTCTTTTCTTGT | sooossssssssssooss | 1362 | 1379 | 780 |

TABLE 23-continued 5-8-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 672618 | TTATCAGGTCTTTTCTTG | sooossssssssssooss | 1363 | 1380 | 781 |
| 672619 | TTTATCAGGTCTTTTCTT | sooossssssssssooss | 1364 | 1381 | 782 |
| 672620 | AATCTTTATCAGGTCTTT | sooossssssssssooss | 1368 | 1385 | 783 |
| 672621 | TAATCTTTATCAGGTCTT | sooossssssssssooss | 1369 | 1386 | 784 |
| 672622 | TTAATCTTTATCAGGTCT | sooossssssssssooss | 1370 | 1387 | 785 |
| 672623 | GTTAATCTTTATCAGGTC | sooossssssssssooss | 1371 | 1388 | 786 |
| 672624 | GGTTAATCTTTATCAGGT | sooossssssssssooss | 1372 | 1389 | 787 |
| 672625 | TGGTTAATCTTTATCAGG | sooossssssssssooss | 1373 | 1390 | 788 |
| 672626 | CTGGTTAATCTTTATCAG | sooossssssssssooss | 1374 | 1391 | 789 |
| 672627 | TCTGGTTAATCTTTATCA | sooossssssssssooss | 1375 | 1392 | 790 |
| 672628 | TTCTGGTTAATCTTTATC | sooossssssssssooss | 1376 | 1393 | 791 |
| 672629 | TCCCTCCTTGTTTTCTTC | sooossssssssssooss | 1391 | 1408 | 792 |
| 672630 | TTTCCCTCCTTGTTTTCT | sooossssssssssooss | 1393 | 1410 | 793 |
| 672631 | GTTTCCCTCCTTGTTTTC | sooossssssssssooss | 1394 | 1411 | 794 |
| 672632 | TGTTTCCCTCCTTGTTTT | sooossssssssssooss | 1395 | 1412 | 795 |
| 672633 | TTGTTTCCCTCCTTGTTT | sooossssssssssooss | 1396 | 1413 | 796 |
| 672634 | GTTGTTTCCCTCCTTGTT | sooossssssssssooss | 1397 | 1414 | 797 |
| 672635 | GGTTGTTTCCCTCCTTGT | sooossssssssssooss | 1398 | 1415 | 798 |
| 672636 | CGGTTGTTTCCCTCCTTG | sooossssssssssooss | 1399 | 1416 | 799 |
| 672637 | GCGGTTGTTTCCCTCCTT | sooossssssssssooss | 1400 | 1417 | 800 |
| 672638 | TGCGGTTGTTTCCCTCCT | sooossssssssssooss | 1401 | 1418 | 801 |
| 672639 | CTGCGGTTGTTTCCCTCC | sooossssssssssooss | 1402 | 1419 | 802 |
| 672640 | GCTGCGGTTGTTTCCCTC | sooossssssssssooss | 1403 | 1420 | 803 |
| 672641 | GGCTGCGGTTGTTTCCCT | sooossssssssssooss | 1404 | 1421 | 804 |
| 672642 | AGGCTGCGGTTGTTTCCC | sooossssssssssooss | 1405 | 1422 | 805 |
| 672643 | CAGGCTGCGGTTGTTTCC | sooossssssssssooss | 1406 | 1423 | 806 |
| 672644 | ACAGGCTGCGGTTGTTTC | sooossssssssssooss | 1407 | 1424 | 807 |
| 672645 | TACAGGCTGCGGTTGTTT | sooossssssssssooss | 1408 | 1425 | 808 |
| 672646 | CTACAGGCTGCGGTTGTT | sooossssssssssooss | 1409 | 1426 | 809 |
| 672647 | GCTACAGGCTGCGGTTGT | sooossssssssssooss | 1410 | 1427 | 810 |
| 672648 | TGCTACAGGCTGCGGTTG | sooossssssssssooss | 1411 | 1428 | 811 |
| 672649 | TTGCTACAGGCTGCGGTT | sooossssssssssooss | 1412 | 1429 | 812 |
| 672650 | CTTGCTACAGGCTGCGGT | sooossssssssssooss | 1413 | 1430 | 813 |
| 672651 | GCTTGCTACAGGCTGCGG | sooossssssssssooss | 1414 | 1431 | 814 |
| 672652 | AGCTTGCTACAGGCTGCG | sooossssssssssooss | 1415 | 1432 | 815 |
| 672653 | GAGCTTGCTACAGGCTGC | sooossssssssssooss | 1416 | 1433 | 816 |
| 672654 | AGAGCTTGCTACAGGCTG | sooossssssssssooss | 1417 | 1434 | 817 |

TABLE 23-continued 5-8-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 672655 | CAGAGCTTGCTACAGGCT | sooosssssssssooss | 1418 | 1435 | 818 |
| 672656 | CCAGAGCTTGCTACAGGC | sooosssssssssooss | 1419 | 1436 | 819 |
| 672657 | TCCAGAGCTTGCTACAGG | sooosssssssssooss | 1420 | 1437 | 820 |
| 672658 | TTCCAGAGCTTGCTACAG | sooosssssssssooss | 1421 | 1438 | 821 |
| 672659 | GTTCCAGAGCTTGCTACA | sooosssssssssooss | 1422 | 1439 | 822 |
| 672660 | AGTTCCAGAGCTTGCTAC | sooosssssssssooss | 1423 | 1440 | 823 |
| 672661 | GAGTTCCAGAGCTTGCTA | sooosssssssssooss | 1424 | 1441 | 824 |
| 672662 | TGAGTTCCAGAGCTTGCT | sooosssssssssooss | 1425 | 1442 | 825 |
| 672663 | CTGAGTTCCAGAGCTTGC | sooosssssssssooss | 1426 | 1443 | 826 |
| 672664 | CCTGAGTTCCAGAGCTTG | sooosssssssssooss | 1427 | 1444 | 827 |
| 672665 | TCCTGAGTTCCAGAGCTT | sooosssssssssooss | 1428 | 1445 | 828 |
| 672666 | CTCCTGAGTTCCAGAGCT | sooosssssssssooss | 1429 | 1446 | 829 |
| 672667 | ACTCCTGAGTTCCAGAGC | sooosssssssssooss | 1430 | 1447 | 830 |
| 672668 | GACTCCTGAGTTCCAGAG | sooosssssssssooss | 1431 | 1448 | 831 |
| 672669 | CGACTCCTGAGTTCCAGA | sooosssssssssooss | 1432 | 1449 | 832 |
| 672670 | GCGACTCCTGAGTTCCAG | sooosssssssssooss | 1433 | 1450 | 833 |
| 672671 | CGCGACTCCTGAGTTCCA | sooosssssssssooss | 1434 | 1451 | 834 |
| 672672 | GCGCGACTCCTGAGTTCC | sooosssssssssooss | 1435 | 1452 | 835 |
| 672673 | CGCGCGACTCCTGAGTTC | sooosssssssssooss | 1436 | 1453 | 836 |
| 672674 | GCGCGCGACTCCTGAGTT | sooosssssssssooss | 1437 | 1454 | 837 |
| 672675 | AGCGCGCGACTCCTGAGT | sooosssssssssooss | 1438 | 1455 | 838 |
| 672676 | TAGCGCGCGACTCCTGAG | sooosssssssssooss | 1439 | 1456 | 839 |
| 672677 | CTAGCGCGCGACTCCTGA | sooosssssssssooss | 1440 | 1457 | 840 |
| 672678 | CCTAGCGCGCGACTCCTG | sooosssssssssooss | 1441 | 1458 | 841 |
| 672679 | CCCTAGCGCGCGACTCCT | sooosssssssssooss | 1442 | 1459 | 842 |
| 672680 | CCCCTAGCGCGCGACTCC | sooosssssssssooss | 1443 | 1460 | 843 |
| 672681 | GCCCCTAGCGCGCGACTC | sooosssssssssooss | 1444 | 1461 | 844 |
| 672682 | GGCCCCTAGCGCGCGACT | sooosssssssssooss | 1445 | 1462 | 845 |
| 672683 | CGGCCCCTAGCGCGCGAC | sooosssssssssooss | 1446 | 1463 | 846 |
| 672684 | CCGGCCCCTAGCGCGCGA | sooosssssssssooss | 1447 | 1464 | 847 |
| 672685 | CCCGGCCCCTAGCGCGCG | sooosssssssssooss | 1448 | 1465 | 848 |
| 672686 | CCCCGGCCCCTAGCGCGC | sooosssssssssooss | 1449 | 1466 | 849 |
| 672687 | GCCCCGGCCCCTAGCGCG | sooosssssssssooss | 1450 | 1467 | 850 |
| 672688 | GGCCCCGGCCCCTAGCGC | sooosssssssssooss | 1451 | 1468 | 851 |
| 672689 | CGGCCCCGGCCCCTAGCG | sooosssssssssooss | 1452 | 1469 | 852 |
| 672690 | CCGGCCCCGGCCCCTAGC | sooosssssssssooss | 1453 | 1470 | 853 |
| 672691 | CCCGGCCCCGGCCCCTAG | sooosssssssssooss | 1454 | 1471 | 854 |

TABLE 23-continued 5-8-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 672692 | CCCCGGCCCCGGCCCCTA | sooossssssssssooss | 1455 | 1472 | 855 |
| 672693 | ACGCCCCGGCCCCGGCCC | sooossssssssssooss | 1464 | 1481 | 856 |
| 672694 | CACGCCCCGGCCCCGGCC | sooossssssssssooss | 1465 | 1482 | 857 |
| 672695 | CCACGCCCCGGCCCCGGC | sooossssssssssooss | 1466 | 1483 | 858 |
| 672696 | ACCACGCCCCGGCCCCGG | sooossssssssssooss | 1467 | 1484 | 859 |
| 672697 | GACCACGCCCCGGCCCCG | sooossssssssssooss | 1468 | 1485 | 860 |
| 672698 | CGACCACGCCCCGGCCCC | sooossssssssssooss | 1469 | 1486 | 861 |
| 672699 | CCGACCACGCCCCGGCCC | sooossssssssssooss | 1470 | 1487 | 862 |
| 672700 | CCCGACCACGCCCCGGCC | sooossssssssssooss | 1471 | 1488 | 863 |
| 672701 | CCCCGACCACGCCCCGGC | sooossssssssssooss | 1472 | 1489 | 864 |
| 672702 | GCCCCGACCACGCCCCGG | sooossssssssssooss | 1473 | 1490 | 865 |
| 672703 | CGCCCCGACCACGCCCCG | sooossssssssssooss | 1474 | 1491 | 866 |
| 672704 | CCGCCCCGACCACGCCCC | sooossssssssssooss | 1475 | 1492 | 867 |
| 672705 | CCCGCCCCGACCACGCCC | sooossssssssssooss | 1476 | 1493 | 868 |
| 672706 | GCCCGCCCCGACCACGCC | sooossssssssssooss | 1477 | 1494 | 869 |
| 672707 | GGCCCGCCCCGACCACGC | sooossssssssssooss | 1478 | 1495 | 870 |
| 672708 | GGGCCCGCCCCGACCACG | sooossssssssssooss | 1479 | 1496 | 871 |
| 672709 | CGGGCCCGCCCCGACCAC | sooossssssssssooss | 1480 | 1497 | 872 |
| 672710 | CCGGGCCCGCCCCGACCA | sooossssssssssooss | 1481 | 1498 | 873 |
| 672711 | CCCGGGCCCGCCCCGACC | sooossssssssssooss | 1482 | 1499 | 874 |
| 672712 | CCCCGGGCCCGCCCCGAC | sooossssssssssooss | 1483 | 1500 | 875 |
| 672713 | AGCCCGCCCCGGGCCCG | sooossssssssssooss | 1502 | 1519 | 876 |
| 672714 | CAGCCCCGCCCCGGGCCC | sooossssssssssooss | 1503 | 1520 | 877 |
| 672715 | GCAGCCCCGCCCCGGGCC | sooossssssssssooss | 1504 | 1521 | 878 |
| 672716 | CGCAGCCCCGCCCCGGGC | sooossssssssssooss | 1505 | 1522 | 879 |
| 672717 | CCGCAGCCCCGCCCCGGG | sooossssssssssooss | 1506 | 1523 | 880 |
| 672718 | ACCGCAGCCCCGCCCCGG | sooossssssssssooss | 1507 | 1524 | 881 |
| 672719 | AACCGCAGCCCCGCCCCG | sooossssssssssooss | 1508 | 1525 | 882 |
| 672720 | CAACCGCAGCCCCGCCCC | sooossssssssssooss | 1509 | 1526 | 883 |
| 672721 | GCAACCGCAGCCCCGCCC | sooossssssssssooss | 1510 | 1527 | 884 |
| 672722 | CGCAACCGCAGCCCCGCC | sooossssssssssooss | 1511 | 1528 | 885 |
| 672723 | CCGCAACCGCAGCCCCGC | sooossssssssssooss | 1512 | 1529 | 886 |
| 672724 | ACCGCAACCGCAGCCCCG | sooossssssssssooss | 1513 | 1530 | 887 |
| 672725 | CACCGCAACCGCAGCCCC | sooossssssssssooss | 1514 | 1531 | 888 |
| 672726 | GCACCGCAACCGCAGCCC | sooossssssssssooss | 1515 | 1532 | 889 |
| 672727 | GGCACCGCAACCGCAGCC | sooossssssssssooss | 1516 | 1533 | 890 |
| 672728 | AGGCACCGCAACCGCAGC | sooossssssssssooss | 1517 | 1534 | 891 |

TABLE 23-continued

5-8-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 672729 | CAGGCACCGCAACCGCAG | sooosssssssssoss | 1518 | 1535 | 892 |
| 672730 | GCAGGCACCGCAACCGCA | sooosssssssssooss | 1519 | 1536 | 893 |
| 672731 | CGCAGGCACCGCAACCGC | sooosssssssssooss | 1520 | 1537 | 894 |
| 672732 | GCGCAGGCACCGCAACCG | sooosssssssssooss | 1521 | 1538 | 895 |
| 672733 | GGCGCAGGCACCGCAACC | sooosssssssssooss | 1522 | 1539 | 896 |
| 672734 | GGGCGCAGGCACCGCAAC | sooosssssssssooss | 1523 | 1540 | 897 |

TABLE 24

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672735 | TGAGAGCAAGTAGTGGG | eeekk-d7-kkeee | sooossssssssooss | 1326 | 1342 | 898 |
| 672736 | GTGAGAGCAAGTAGTGG | eeekk-d7-kkeee | sooossssssssooss | 1327 | 1343 | 899 |
| 672737 | TGTGAGAGCAAGTAGTG | eeekk-d7-kkeee | sooossssssssooss | 1328 | 1344 | 900 |
| 672738 | CTGTGAGAGCAAGTAGT | eeekk-d7-kkeee | sooossssssssooss | 1329 | 1345 | 901 |
| 672739 | ACTGTGAGAGCAAGTAG | eeekk-d7-kkeee | sooossssssssooss | 1330 | 1346 | 902 |
| 672740 | TACTGTGAGAGCAAGTA | eeekk-d7-kkeee | sooossssssssooss | 1331 | 1347 | 903 |
| 672741 | GTACTGTGAGAGCAAGT | eeekk-d7-kkeee | sooossssssssooss | 1332 | 1348 | 904 |
| 672742 | AGTACTGTGAGAGCAAG | eeekk-d7-kkeee | sooossssssssooss | 1333 | 1349 | 905 |
| 672743 | GAGTACTGTGAGAGCAA | eeekk-d7-kkeee | sooossssssssooss | 1334 | 1350 | 906 |
| 672744 | CGAGTACTGTGAGAGCA | eeekk-d7-kkeee | sooossssssssooss | 1335 | 1351 | 907 |
| 672745 | GCGAGTACTGTGAGAGC | eeekk-d7-kkeee | sooossssssssooss | 1336 | 1352 | 908 |
| 672746 | AGCGAGTACTGTGAGAG | eeekk-d7-kkeee | sooossssssssooss | 1337 | 1353 | 909 |
| 672747 | CAGCGAGTACTGTGAGA | eeekk-d7-kkeee | sooossssssssooss | 1338 | 1354 | 910 |
| 672748 | TCAGCGAGTACTGTGAG | eeekk-d7-kkeee | sooossssssssooss | 1339 | 1355 | 911 |
| 672749 | CTCAGCGAGTACTGTGA | eeekk-d7-kkeee | sooossssssssooss | 1340 | 1356 | 912 |
| 672750 | CCTCAGCGAGTACTGTG | eeekk-d7-kkeee | sooossssssssooss | 1341 | 1357 | 913 |
| 672751 | CCCTCAGCGAGTACTGT | eeekk-d7-kkeee | sooossssssssooss | 1342 | 1358 | 914 |
| 672752 | ACCCTCAGCGAGTACTG | eeekk-d7-kkeee | sooossssssssooss | 1343 | 1359 | 915 |
| 672753 | CACCCTCAGCGAGTACT | eeekk-d7-kkeee | sooossssssssooss | 1344 | 1360 | 916 |
| 672754 | TCACCCTCAGCGAGTAC | eeekk-d7-kkeee | sooossssssssooss | 1345 | 1361 | 917 |
| 672755 | TTCACCCTCAGCGAGTA | eeekk-d7-kkeee | sooossssssssooss | 1346 | 1362 | 918 |
| 672756 | GTTCACCCTCAGCGAGT | eeekk-d7-kkeee | sooossssssssooss | 1347 | 1363 | 919 |
| 672757 | TGTTCACCCTCAGCGAG | eeekk-d7-kkeee | sooossssssssooss | 1348 | 1364 | 920 |
| 672758 | TTGTTCACCCTCAGCGA | eeekk-d7-kkeee | sooossssssssooss | 1349 | 1365 | 921 |
| 672759 | CTTGTTCACCCTCAGCG | eeekk-d7-kkeee | sooossssssssooss | 1350 | 1366 | 922 |

TABLE 24-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672760 | TCTTGTTCACCCTCAGC | eeekk-d7-kkeee | sooosssssssssooss | 1351 | 1367 | 923 |
| 672761 | TTCTTGTTCACCCTCAG | eeekk-d7-kkeee | sooosssssssssooss | 1352 | 1368 | 924 |
| 672762 | TTTCTTGTTCACCCTCA | eeekk-d7-kkeee | sooosssssssssooss | 1353 | 1369 | 925 |
| 672763 | TTTTCTTGTTCACCCTC | eeekk-d7-kkeee | sooosssssssssooss | 1354 | 1370 | 926 |
| 672764 | CTTTTCTTGTTCACCCT | eeekk-d7-kkeee | sooosssssssssooss | 1355 | 1371 | 927 |
| 672765 | TCTTTTCTTGTTCACCC | eeekk-d7-kkeee | sooosssssssssooss | 1356 | 1372 | 928 |
| 672766 | GTCTTTTCTTGTTCACC | eeekk-d7-kkeee | sooosssssssssooss | 1357 | 1373 | 929 |
| 672767 | GGTCTTTTCTTGTTCAC | eeekk-d7-kkeee | sooosssssssssooss | 1358 | 1374 | 930 |
| 672768 | AGGTCTTTTCTTGTTCA | eeekk-d7-kkeee | sooosssssssssooss | 1359 | 1375 | 931 |
| 672769 | CAGGTCTTTTCTTGTTC | eeekk-d7-kkeee | sooosssssssssooss | 1360 | 1376 | 932 |
| 672770 | TCAGGTCTTTTCTTGTT | eeekk-d7-kkeee | sooosssssssssooss | 1361 | 1377 | 933 |
| 672771 | ATCAGGTCTTTTCTTGT | eeekk-d7-kkeee | sooosssssssssooss | 1362 | 1378 | 934 |
| 672772 | TATCAGGTCTTTTCTTG | eeekk-d7-kkeee | sooosssssssssooss | 1363 | 1379 | 935 |
| 672773 | TTATCAGGTCTTTTCTT | eeekk-d7-kkeee | sooosssssssssooss | 1364 | 1380 | 936 |
| 672774 | ATCTTTATCAGGTCTTT | eeekk-d7-kkeee | sooosssssssssooss | 1368 | 1384 | 937 |
| 672775 | AATCTTTATCAGGTCTT | eeekk-d7-kkeee | sooosssssssssooss | 1369 | 1385 | 938 |
| 672776 | TAATCTTTATCAGGTCT | eeekk-d7-kkeee | sooosssssssssooss | 1370 | 1386 | 939 |
| 672777 | TTAATCTTTATCAGGTC | eeekk-d7-kkeee | sooosssssssssooss | 1371 | 1387 | 940 |
| 672778 | GTTAATCTTTATCAGGT | eeekk-d7-kkeee | sooosssssssssooss | 1372 | 1388 | 941 |
| 672779 | GGTTAATCTTTATCAGG | eeekk-d7-kkeee | sooosssssssssooss | 1373 | 1389 | 942 |
| 672780 | TGGTTAATCTTTATCAG | eeekk-d7-kkeee | sooosssssssssooss | 1374 | 1390 | 943 |
| 672781 | CTGGTTAATCTTTATCA | eeekk-d7-kkeee | sooosssssssssooss | 1375 | 1391 | 944 |
| 672782 | TCTGGTTAATCTTTATC | eeekk-d7-kkeee | sooosssssssssooss | 1376 | 1392 | 945 |
| 672783 | CCCTCCTTGTTTTCTTC | eeekk-d7-kkeee | sooosssssssssooss | 1391 | 1407 | 946 |
| 672784 | TCCCTCCTTGTTTTCTT | eeekk-d7-kkeee | sooosssssssssooss | 1392 | 1408 | 947 |
| 672785 | TTCCCTCCTTGTTTTCT | eeekk-d7-kkeee | sooosssssssssooss | 1393 | 1409 | 948 |
| 672786 | TTTCCCTCCTTGTTTTC | eeekk-d7-kkeee | sooosssssssssooss | 1394 | 1410 | 949 |
| 672787 | GTTTCCCTCCTTGTTTT | eeekk-d7-kkeee | sooosssssssssooss | 1395 | 1411 | 950 |
| 672788 | TGTTTCCCTCCTTGTTT | eeekk-d7-kkeee | sooosssssssssooss | 1396 | 1412 | 951 |
| 672789 | TTGTTTCCCTCCTTGTT | eeekk-d7-kkeee | sooosssssssssooss | 1397 | 1413 | 952 |
| 672790 | GGTTGTTTCCCTCCTTG | eeekk-d7-kkeee | sooosssssssssooss | 1399 | 1415 | 953 |
| 672791 | CGGTTGTTTCCCTCCTT | eeekk-d7-kkeee | sooosssssssssooss | 1400 | 1416 | 954 |
| 672792 | GCGGTTGTTTCCCTCCT | eeekk-d7-kkeee | sooosssssssssooss | 1401 | 1417 | 955 |
| 672793 | TGCGGTTGTTTCCCTCC | eeekk-d7-kkeee | sooosssssssssooss | 1402 | 1418 | 956 |
| 672794 | CTGCGGTTGTTTCCCTC | eeekk-d7-kkeee | sooosssssssssooss | 1403 | 1419 | 957 |
| 672795 | GCTGCGGTTGTTTCCCT | eeekk-d7-kkeee | sooosssssssssooss | 1404 | 1420 | 958 |
| 672796 | GGCTGCGGTTGTTTCCC | eeekk-d7-kkeee | sooosssssssssooss | 1405 | 1421 | 959 |

TABLE 24-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672797 | AGGCTGCGGTTGTTTCC | eeekk-d7-kkeee | sooosssssssssssooss | 1406 | 1422 | 960 |
| 672798 | CAGGCTGCGGTTGTTTC | eeekk-d7-kkeee | sooosssssssssssooss | 1407 | 1423 | 961 |
| 672799 | ACAGGCTGCGGTTGTTT | eeekk-d7-kkeee | sooosssssssssssooss | 1408 | 1424 | 962 |
| 672800 | TACAGGCTGCGGTTGTT | eeekk-d7-kkeee | sooosssssssssssooss | 1409 | 1425 | 963 |
| 672801 | CTACAGGCTGCGGTTGT | eeekk-d7-kkeee | sooosssssssssssooss | 1410 | 1426 | 964 |
| 672802 | GCTACAGGCTGCGGTTG | eeekk-d7-kkeee | sooosssssssssssooss | 1411 | 1427 | 965 |
| 672803 | TGCTACAGGCTGCGGTT | eeekk-d7-kkeee | sooosssssssssssooss | 1412 | 1428 | 966 |
| 672804 | TTGCTACAGGCTGCGGT | eeekk-d7-kkeee | sooosssssssssssooss | 1413 | 1429 | 967 |
| 672805 | CTTGCTACAGGCTGCGG | eeekk-d7-kkeee | sooosssssssssssooss | 1414 | 1430 | 968 |
| 672806 | GCTTGCTACAGGCTGCG | eeekk-d7-kkeee | sooosssssssssssooss | 1415 | 1431 | 969 |
| 672807 | AGCTTGCTACAGGCTGC | eeekk-d7-kkeee | sooosssssssssssooss | 1416 | 1432 | 970 |
| 672808 | GAGCTTGCTACAGGCTG | eeekk-d7-kkeee | sooosssssssssssooss | 1417 | 1433 | 971 |
| 672809 | AGAGCTTGCTACAGGCT | eeekk-d7-kkeee | sooosssssssssssooss | 1418 | 1434 | 972 |
| 672810 | CAGAGCTTGCTACAGGC | eeekk-d7-kkeee | sooosssssssssssooss | 1419 | 1435 | 973 |
| 672811 | CCAGAGCTTGCTACAGG | eeekk-d7-kkeee | sooosssssssssssooss | 1420 | 1436 | 974 |
| 672812 | TCCAGAGCTTGCTACAG | eeekk-d7-kkeee | sooosssssssssssooss | 1421 | 1437 | 975 |
| 672813 | TTCCAGAGCTTGCTACA | eeekk-d7-kkeee | sooosssssssssssooss | 1422 | 1438 | 976 |
| 672814 | GTTCCAGAGCTTGCTAC | eeekk-d7-kkeee | sooosssssssssssooss | 1423 | 1439 | 977 |
| 672815 | AGTTCCAGAGCTTGCTA | eeekk-d7-kkeee | sooosssssssssssooss | 1424 | 1440 | 978 |
| 672816 | GAGTTCCAGAGCTTGCT | eeekk-d7-kkeee | sooosssssssssssooss | 1425 | 1441 | 979 |
| 672817 | TGAGTTCCAGAGCTTGC | eeekk-d7-kkeee | sooosssssssssssooss | 1426 | 1442 | 980 |
| 672818 | CTGAGTTCCAGAGCTTG | eeekk-d7-kkeee | sooosssssssssssooss | 1427 | 1443 | 981 |
| 672819 | CCTGAGTTCCAGAGCTT | eeekk-d7-kkeee | sooosssssssssssooss | 1428 | 1444 | 982 |
| 672820 | TCCTGAGTTCCAGAGCT | eeekk-d7-kkeee | sooosssssssssssooss | 1429 | 1445 | 983 |
| 672821 | CTCCTGAGTTCCAGAGC | eeekk-d7-kkeee | sooosssssssssssooss | 1430 | 1446 | 984 |
| 672822 | ACTCCTGAGTTCCAGAG | eeekk-d7-kkeee | sooosssssssssssooss | 1431 | 1447 | 985 |
| 672823 | GACTCCTGAGTTCCAGA | eeekk-d7-kkeee | sooosssssssssssooss | 1432 | 1448 | 986 |
| 672824 | CGACTCCTGAGTTCCAG | eeekk-d7-kkeee | sooosssssssssssooss | 1433 | 1449 | 987 |
| 672825 | GCGACTCCTGAGTTCCA | eeekk-d7-kkeee | sooosssssssssssooss | 1434 | 1450 | 988 |
| 672826 | CGCGACTCCTGAGTTCC | eeekk-d7-kkeee | sooosssssssssssooss | 1435 | 1451 | 989 |
| 672827 | GCGCGACTCCTGAGTTC | eeekk-d7-kkeee | sooosssssssssssooss | 1436 | 1452 | 990 |
| 672828 | CGCGCGACTCCTGAGTT | eeekk-d7-kkeee | sooosssssssssssooss | 1437 | 1453 | 991 |
| 672829 | GCGCGCGACTCCTGAGT | eeekk-d7-kkeee | sooosssssssssssooss | 1438 | 1454 | 992 |
| 672830 | AGCGCGCGACTCCTGAG | eeekk-d7-kkeee | sooosssssssssssooss | 1439 | 1455 | 993 |
| 672831 | TAGCGCGCGACTCCTGA | eeekk-d7-kkeee | sooosssssssssssooss | 1440 | 1456 | 994 |
| 672832 | CTAGCGCGCGACTCCTG | eeekk-d7-kkeee | sooosssssssssssooss | 1441 | 1457 | 995 |

TABLE 24-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672833 | CCTAGCGCGCGACTCCT | eeekk-d7-kkeee | soossssssssssooss | 1442 | 1458 | 996 |
| 672834 | CCCTAGCGCGCGACTCC | eeekk-d7-kkeee | soossssssssssooss | 1443 | 1459 | 997 |
| 672835 | CCCCTAGCGCGCGACTC | eeekk-d7-kkeee | soossssssssssooss | 1444 | 1460 | 998 |
| 672836 | GCCCCTAGCGCGCGACT | eeekk-d7-kkeee | soossssssssssooss | 1445 | 1461 | 999 |
| 672837 | GGCCCCTAGCGCGCGAC | eeekk-d7-kkeee | soossssssssssooss | 1446 | 1462 | 1000 |
| 672838 | CGGCCCCTAGCGCGCGA | eeekk-d7-kkeee | soossssssssssooss | 1447 | 1463 | 1001 |
| 672839 | CCGGCCCCTAGCGCGCG | eeekk-d7-kkeee | soossssssssssooss | 1448 | 1464 | 1002 |
| 672840 | CCCGGCCCCTAGCGCGC | eeekk-d7-kkeee | soossssssssssooss | 1449 | 1465 | 1003 |
| 672841 | CCCCGGCCCCTAGCGCG | eeekk-d7-kkeee | soossssssssssooss | 1450 | 1466 | 1004 |
| 672842 | GCCCCGGCCCCTAGCGC | eeekk-d7-kkeee | soossssssssssooss | 1451 | 1467 | 1005 |
| 672843 | GGCCCCGGCCCCTAGCG | eeekk-d7-kkeee | soossssssssssooss | 1452 | 1468 | 1006 |
| 672844 | CGGCCCCGGCCCCTAGC | eeekk-d7-kkeee | soossssssssssooss | 1453 | 1469 | 1007 |
| 672845 | CCGGCCCCGGCCCCTAG | eeekk-d7-kkeee | soossssssssssooss | 1454 | 1470 | 1008 |
| 672846 | CCCGGCCCCGGCCCCTA | eeekk-d7-kkeee | soossssssssssooss | 1455 | 1471 | 1009 |
| 672847 | ACGCCCCGGCCCCGGCC | eeekk-d7-kkeee | soossssssssssooss | 1465 | 1481 | 1010 |
| 672848 | CACGCCCCGGCCCCGGC | eeekk-d7-kkeee | soossssssssssooss | 1466 | 1482 | 1011 |
| 672849 | CCACGCCCCGGCCCCGG | eeekk-d7-kkeee | soossssssssssooss | 1467 | 1483 | 1012 |
| 672850 | ACCACGCCCCGGCCCCG | eeekk-d7-kkeee | soossssssssssooss | 1468 | 1484 | 1013 |
| 672851 | GACCACGCCCCGGCCCC | eeekk-d7-kkeee | soossssssssssooss | 1469 | 1485 | 1014 |
| 672852 | CGACCACGCCCCGGCCC | eeekk-d7-kkeee | soossssssssssooss | 1470 | 1486 | 1015 |
| 672853 | CCGACCACGCCCCGGCC | eeekk-d7-kkeee | soossssssssssooss | 1471 | 1487 | 1016 |
| 672854 | CCCGACCACGCCCCGGC | eeekk-d7-kkeee | soossssssssssooss | 1472 | 1488 | 1017 |
| 672855 | CCCCGACCACGCCCCGG | eeekk-d7-kkeee | soossssssssssooss | 1473 | 1489 | 1018 |
| 672856 | GCCCCGACCACGCCCCG | eeekk-d7-kkeee | soossssssssssooss | 1474 | 1490 | 1019 |
| 672857 | CGCCCCGACCACGCCCC | eeekk-d7-kkeee | soossssssssssooss | 1475 | 1491 | 1020 |
| 672858 | CCGCCCCGACCACGCCC | eeekk-d7-kkeee | soossssssssssooss | 1476 | 1492 | 1021 |
| 672859 | CCCGCCCCGACCACGCC | eeekk-d7-kkeee | soossssssssssooss | 1477 | 1493 | 1022 |
| 672860 | GCCCGCCCCGACCACGC | eeekk-d7-kkeee | soossssssssssooss | 1478 | 1494 | 1023 |
| 672861 | GGCCCGCCCCGACCACG | eeekk-d7-kkeee | soossssssssssooss | 1479 | 1495 | 1024 |
| 672862 | GGGCCCGCCCCGACCAC | eeekk-d7-kkeee | soossssssssssooss | 1480 | 1496 | 1025 |
| 672863 | CGGGCCCGCCCCGACCA | eeekk-d7-kkeee | soossssssssssooss | 1481 | 1497 | 1026 |
| 672864 | CCGGGCCCGCCCCGACC | eeekk-d7-kkeee | soossssssssssooss | 1482 | 1498 | 1027 |
| 672865 | CCCGGGCCCGCCCCGAC | eeekk-d7-kkeee | soossssssssssooss | 1483 | 1499 | 1028 |
| 672866 | GCAGCCCCGCCCCGGGC | eeekk-d7-kkeee | soossssssssssooss | 1505 | 1521 | 1029 |
| 672867 | CGCAGCCCCGCCCCGGG | eeekk-d7-kkeee | soossssssssssooss | 1506 | 1522 | 1030 |
| 672868 | CCGCAGCCCCGCCCCGG | eeekk-d7-kkeee | soossssssssssooss | 1507 | 1523 | 1031 |
| 672869 | ACCGCAGCCCCGCCCCG | eeekk-d7-kkeee | soossssssssssooss | 1508 | 1524 | 1032 |

TABLE 24-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672870 | AACCGCAGCCCCGCCCC | eeekk-d7-kkeee | sooosssssssssooss | 1509 | 1525 | 1033 |
| 672871 | CAACCGCAGCCCCGCCC | eeekk-d7-kkeee | sooosssssssssooss | 1510 | 1526 | 1034 |
| 672872 | GCAACCGCAGCCCCGCC | eeekk-d7-kkeee | sooosssssssssooss | 1511 | 1527 | 1035 |
| 672873 | CGCAACCGCAGCCCCGC | eeekk-d7-kkeee | sooosssssssssooss | 1512 | 1528 | 1036 |
| 672874 | CCGCAACCGCAGCCCCG | eeekk-d7-kkeee | sooosssssssssooss | 1513 | 1529 | 1037 |
| 672875 | ACCGCAACCGCAGCCCC | eeekk-d7-kkeee | sooosssssssssooss | 1514 | 1530 | 1038 |
| 672876 | CACCGCAACCGCAGCCC | eeekk-d7-kkeee | sooosssssssssooss | 1515 | 1531 | 1039 |
| 672877 | GCACCGCAACCGCAGCC | eeekk-d7-kkeee | sooosssssssssooss | 1516 | 1532 | 1040 |
| 672878 | GGCACCGCAACCGCAGC | eeekk-d7-kkeee | sooosssssssssooss | 1517 | 1533 | 1041 |
| 672879 | AGGCACCGCAACCGCAG | eeekk-d7-kkeee | sooosssssssssooss | 1518 | 1534 | 1042 |
| 672880 | CAGGCACCGCAACCGCA | eeekk-d7-kkeee | sooosssssssssooss | 1519 | 1535 | 1043 |
| 672881 | GCAGGCACCGCAACCGC | eeekk-d7-kkeee | sooosssssssssooss | 1520 | 1536 | 1044 |
| 672882 | CGCAGGCACCGCAACCG | eeekk-d7-kkeee | sooosssssssssooss | 1521 | 1537 | 1045 |
| 672883 | GCGCAGGCACCGCAACC | eeekk-d7-kkeee | sooosssssssssooss | 1522 | 1538 | 1046 |
| 672884 | GGCGCAGGCACCGCAAC | eeekk-d7-kkeee | sooosssssssssooss | 1523 | 1539 | 1047 |

TABLE 25

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672885 | TGAGAGCAAGTAGTGGG | eekk-d8-kkeee | soossssssssssooss | 1326 | 1342 | 898 |
| 672886 | GTGAGAGCAAGTAGTGG | eekk-d8-kkeee | soossssssssssooss | 1327 | 1343 | 899 |
| 672887 | TGTGAGAGCAAGTAGTG | eekk-d8-kkeee | soossssssssssooss | 1328 | 1344 | 900 |
| 672888 | CTGTGAGAGCAAGTAGT | eekk-d8-kkeee | soossssssssssooss | 1329 | 1345 | 901 |
| 672889 | ACTGTGAGAGCAAGTAG | eekk-d8-kkeee | soossssssssssooss | 1330 | 1346 | 902 |
| 672890 | TACTGTGAGAGCAAGTA | eekk-d8-kkeee | soossssssssssooss | 1331 | 1347 | 903 |
| 672891 | GTACTGTGAGAGCAAGT | eekk-d8-kkeee | soossssssssssooss | 1332 | 1348 | 904 |
| 672892 | AGTACTGTGAGAGCAAG | eekk-d8-kkeee | soossssssssssooss | 1333 | 1349 | 905 |
| 672893 | GAGTACTGTGAGAGCAA | eekk-d8-kkeee | soossssssssssooss | 1334 | 1350 | 906 |
| 672894 | CGAGTACTGTGAGAGCA | eekk-d8-kkeee | soossssssssssooss | 1335 | 1351 | 907 |
| 672895 | GCGAGTACTGTGAGAGC | eekk-d8-kkeee | soossssssssssooss | 1336 | 1352 | 908 |
| 672896 | AGCGAGTACTGTGAGAG | eekk-d8-kkeee | soossssssssssooss | 1337 | 1353 | 909 |
| 672897 | CAGCGAGTACTGTGAGA | eekk-d8-kkeee | soossssssssssooss | 1338 | 1354 | 910 |
| 672898 | TCAGCGAGTACTGTGAG | eekk-d8-kkeee | soossssssssssooss | 1339 | 1355 | 911 |
| 672899 | CTCAGCGAGTACTGTGA | eekk-d8-kkeee | soossssssssssooss | 1340 | 1356 | 912 |

TABLE 25-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672900 | CCTCAGCGAGTACTGTG | eekk-d8-kkeee | soosssssssssooss | 1341 | 1357 | 913 |
| 672901 | CCCTCAGCGAGTACTGT | eekk-d8-kkeee | soosssssssssooss | 1342 | 1358 | 914 |
| 672902 | ACCCTCAGCGAGTACTG | eekk-d8-kkeee | soosssssssssooss | 1343 | 1359 | 915 |
| 672903 | CACCCTCAGCGAGTACT | eekk-d8-kkeee | soosssssssssooss | 1344 | 1360 | 916 |
| 672904 | TCACCCTCAGCGAGTAC | eekk-d8-kkeee | soosssssssssooss | 1345 | 1361 | 917 |
| 672905 | TTCACCCTCAGCGAGTA | eekk-d8-kkeee | soosssssssssooss | 1346 | 1362 | 918 |
| 672906 | GTTCACCCTCAGCGAGT | eekk-d8-kkeee | soosssssssssooss | 1347 | 1363 | 919 |
| 672907 | TGTTCACCCTCAGCGAG | eekk-d8-kkeee | soosssssssssooss | 1348 | 1364 | 920 |
| 672908 | TTGTTCACCCTCAGCGA | eekk-d8-kkeee | soosssssssssooss | 1349 | 1365 | 921 |
| 672909 | CTTGTTCACCCTCAGCG | eekk-d8-kkeee | soosssssssssooss | 1350 | 1366 | 922 |
| 672910 | TCTTGTTCACCCTCAGC | eekk-d8-kkeee | soosssssssssooss | 1351 | 1367 | 923 |
| 672911 | TTCTTGTTCACCCTCAG | eekk-d8-kkeee | soosssssssssooss | 1352 | 1368 | 924 |
| 672912 | TTTCTTGTTCACCCTCA | eekk-d8-kkeee | soosssssssssooss | 1353 | 1369 | 925 |
| 672913 | TTTTCTTGTTCACCCTC | eekk-d8-kkeee | soosssssssssooss | 1354 | 1370 | 926 |
| 672914 | CTTTTCTTGTTCACCCT | eekk-d8-kkeee | soosssssssssooss | 1355 | 1371 | 927 |
| 672915 | TCTTTTCTTGTTCACCC | eekk-d8-kkeee | soosssssssssooss | 1356 | 1372 | 928 |
| 672916 | GTCTTTTCTTGTTCACC | eekk-d8-kkeee | soosssssssssooss | 1357 | 1373 | 929 |
| 672917 | GGTCTTTTCTTGTTCAC | eekk-d8-kkeee | soosssssssssooss | 1358 | 1374 | 930 |
| 672918 | AGGTCTTTTCTTGTTCA | eekk-d8-kkeee | soosssssssssooss | 1359 | 1375 | 931 |
| 672919 | CAGGTCTTTTCTTGTTC | eekk-d8-kkeee | soosssssssssooss | 1360 | 1376 | 932 |
| 672920 | TCAGGTCTTTTCTTGTT | eekk-d8-kkeee | soosssssssssooss | 1361 | 1377 | 933 |
| 672921 | ATCAGGTCTTTTCTTGT | eekk-d8-kkeee | soosssssssssooss | 1362 | 1378 | 934 |
| 672922 | TATCAGGTCTTTTCTTG | eekk-d8-kkeee | soosssssssssooss | 1363 | 1379 | 935 |
| 672923 | TTATCAGGTCTTTTCTT | eekk-d8-kkeee | soosssssssssooss | 1364 | 1380 | 936 |
| 672924 | ATCTTTATCAGGTCTTT | eekk-d8-kkeee | soosssssssssooss | 1368 | 1384 | 937 |
| 672925 | AATCTTTATCAGGTCTT | eekk-d8-kkeee | soosssssssssooss | 1369 | 1385 | 938 |
| 672926 | TAATCTTTATCAGGTCT | eekk-d8-kkeee | soosssssssssooss | 1370 | 1386 | 939 |
| 672927 | TTAATCTTTATCAGGTC | eekk-d8-kkeee | soosssssssssooss | 1371 | 1387 | 940 |
| 672928 | GTTAATCTTTATCAGGT | eekk-d8-kkeee | soosssssssssooss | 1372 | 1388 | 941 |
| 672929 | GGTTAATCTTTATCAGG | eekk-d8-kkeee | soosssssssssooss | 1373 | 1389 | 942 |
| 672930 | TGGTTAATCTTTATCAG | eekk-d8-kkeee | soosssssssssooss | 1374 | 1390 | 943 |
| 672931 | CTGGTTAATCTTTATCA | eekk-d8-kkeee | soosssssssssooss | 1375 | 1391 | 944 |
| 672932 | TCTGGTTAATCTTTATC | eekk-d8-kkeee | soosssssssssooss | 1376 | 1392 | 945 |
| 672933 | CCCTCCTTGTTTTCTTC | eekk-d8-kkeee | soosssssssssooss | 1391 | 1407 | 946 |
| 672934 | TCCCTCCTTGTTTTCTT | eekk-d8-kkeee | soosssssssssooss | 1392 | 1408 | 947 |
| 672935 | TTCCCTCCTTGTTTTCT | eekk-d8-kkeee | soosssssssssooss | 1393 | 1409 | 948 |

TABLE 25-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672936 | TTTCCCTCCTTGTTTTC | eekk-d8-kkeee | soossssssssssooss | 1394 | 1410 | 949 |
| 672937 | GTTTCCCTCCTTGTTTT | eekk-d8-kkeee | soossssssssssooss | 1395 | 1411 | 950 |
| 672938 | TGTTTCCCTCCTTGTTT | eekk-d8-kkeee | soossssssssssooss | 1396 | 1412 | 951 |
| 672939 | TTGTTTCCCTCCTTGTT | eekk-d8-kkeee | soossssssssssooss | 1397 | 1413 | 952 |
| 672940 | GGTTGTTTCCCTCCTTG | eekk-d8-kkeee | soossssssssssooss | 1399 | 1415 | 953 |
| 672941 | CGGTTGTTTCCCTCCTT | eekk-d8-kkeee | soossssssssssooss | 1400 | 1416 | 954 |
| 672942 | GCGGTTGTTTCCCTCCT | eekk-d8-kkeee | soossssssssssooss | 1401 | 1417 | 955 |
| 672943 | TGCGGTTGTTTCCCTCC | eekk-d8-kkeee | soossssssssssooss | 1402 | 1418 | 956 |
| 672944 | CTGCGGTTGTTTCCCTC | eekk-d8-kkeee | soossssssssssooss | 1403 | 1419 | 957 |
| 672945 | GCTGCGGTTGTTTCCCT | eekk-d8-kkeee | soossssssssssooss | 1404 | 1420 | 958 |
| 672946 | GGCTGCGGTTGTTTCCC | eekk-d8-kkeee | soossssssssssooss | 1405 | 1421 | 959 |
| 672947 | AGGCTGCGGTTGTTTCC | eekk-d8-kkeee | soossssssssssooss | 1406 | 1422 | 960 |
| 672948 | CAGGCTGCGGTTGTTTC | eekk-d8-kkeee | soossssssssssooss | 1407 | 1423 | 961 |
| 672949 | ACAGGCTGCGGTTGTTT | eekk-d8-kkeee | soossssssssssooss | 1408 | 1424 | 962 |
| 672950 | TACAGGCTGCGGTTGTT | eekk-d8-kkeee | soossssssssssooss | 1409 | 1425 | 963 |
| 672951 | CTACAGGCTGCGGTTGT | eekk-d8-kkeee | soossssssssssooss | 1410 | 1426 | 964 |
| 672952 | GCTACAGGCTGCGGTTG | eekk-d8-kkeee | soossssssssssooss | 1411 | 1427 | 965 |
| 672953 | TGCTACAGGCTGCGGTT | eekk-d8-kkeee | soossssssssssooss | 1412 | 1428 | 966 |
| 672954 | TTGCTACAGGCTGCGGT | eekk-d8-kkeee | soossssssssssooss | 1413 | 1429 | 967 |
| 672955 | CTTGCTACAGGCTGCGG | eekk-d8-kkeee | soossssssssssooss | 1414 | 1430 | 968 |
| 672956 | GCTTGCTACAGGCTGCG | eekk-d8-kkeee | soossssssssssooss | 1415 | 1431 | 969 |
| 672957 | AGCTTGCTACAGGCTGC | eekk-d8-kkeee | soossssssssssooss | 1416 | 1432 | 970 |
| 672958 | GAGCTTGCTACAGGCTG | eekk-d8-kkeee | soossssssssssooss | 1417 | 1433 | 971 |
| 672959 | AGAGCTTGCTACAGGCT | eekk-d8-kkeee | soossssssssssooss | 1418 | 1434 | 972 |
| 672960 | CAGAGCTTGCTACAGGC | eekk-d8-kkeee | soossssssssssooss | 1419 | 1435 | 973 |
| 672961 | CCAGAGCTTGCTACAGG | eekk-d8-kkeee | soossssssssssooss | 1420 | 1436 | 974 |
| 672962 | TCCAGAGCTTGCTACAG | eekk-d8-kkeee | soossssssssssooss | 1421 | 1437 | 975 |
| 672963 | TTCCAGAGCTTGCTACA | eekk-d8-kkeee | soossssssssssooss | 1422 | 1438 | 976 |
| 672964 | GTTCCAGAGCTTGCTAC | eekk-d8-kkeee | soossssssssssooss | 1423 | 1439 | 977 |
| 672965 | AGTTCCAGAGCTTGCTA | eekk-d8-kkeee | soossssssssssooss | 1424 | 1440 | 978 |
| 672966 | GAGTTCCAGAGCTTGCT | eekk-d8-kkeee | soossssssssssooss | 1425 | 1441 | 979 |
| 672967 | TGAGTTCCAGAGCTTGC | eekk-d8-kkeee | soossssssssssooss | 1426 | 1442 | 980 |
| 672968 | CTGAGTTCCAGAGCTTG | eekk-d8-kkeee | soossssssssssooss | 1427 | 1443 | 981 |
| 672969 | CCTGAGTTCCAGAGCTT | eekk-d8-kkeee | soossssssssssooss | 1428 | 1444 | 982 |
| 672970 | TCCTGAGTTCCAGAGCT | eekk-d8-kkeee | soossssssssssooss | 1429 | 1445 | 983 |
| 672971 | CTCCTGAGTTCCAGAGC | eekk-d8-kkeee | soossssssssssooss | 1430 | 1446 | 984 |

TABLE 25-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 672972 | ACTCCTGAGTTCCAGAG | eekk-d8-kkeee | soossssssssssooss | 1431 | 1447 | 985 |
| 672973 | GACTCCTGAGTTCCAGA | eekk-d8-kkeee | soossssssssssooss | 1432 | 1448 | 986 |
| 672974 | CGACTCCTGAGTTCCAG | eekk-d8-kkeee | soossssssssssooss | 1433 | 1449 | 987 |
| 672975 | GCGACTCCTGAGTTCCA | eekk-d8-kkeee | soossssssssssooss | 1434 | 1450 | 988 |
| 672976 | CGCGACTCCTGAGTTCC | eekk-d8-kkeee | soossssssssssooss | 1435 | 1451 | 989 |
| 672977 | GCGCGACTCCTGAGTTC | eekk-d8-kkeee | soossssssssssooss | 1436 | 1452 | 990 |
| 672978 | CGCGCGACTCCTGAGTT | eekk-d8-kkeee | soossssssssssooss | 1437 | 1453 | 991 |
| 672979 | GCGCGCGACTCCTGAGT | eekk-d8-kkeee | soossssssssssooss | 1438 | 1454 | 992 |
| 672980 | AGCGCGCGACTCCTGAG | eekk-d8-kkeee | soossssssssssooss | 1439 | 1455 | 993 |
| 672981 | TAGCGCGCGACTCCTGA | eekk-d8-kkeee | soossssssssssooss | 1440 | 1456 | 994 |
| 672982 | CTAGCGCGCGACTCCTG | eekk-d8-kkeee | soossssssssssooss | 1441 | 1457 | 995 |
| 672983 | CCTAGCGCGCGACTCCT | eekk-d8-kkeee | soossssssssssooss | 1442 | 1458 | 996 |
| 672984 | CCCTAGCGCGCGACTCC | eekk-d8-kkeee | soossssssssssooss | 1443 | 1459 | 997 |
| 672985 | CCCCTAGCGCGCGACTC | eekk-d8-kkeee | soossssssssssooss | 1444 | 1460 | 998 |
| 672986 | GCCCCTAGCGCGCGACT | eekk-d8-kkeee | soossssssssssooss | 1445 | 1461 | 999 |
| 672987 | GGCCCCTAGCGCGCGAC | eekk-d8-kkeee | soossssssssssooss | 1446 | 1462 | 1000 |
| 672988 | CGGCCCCTAGCGCGCGA | eekk-d8-kkeee | soossssssssssooss | 1447 | 1463 | 1001 |
| 672989 | CCGGCCCCTAGCGCGCG | eekk-d8-kkeee | soossssssssssooss | 1448 | 1464 | 1002 |
| 672990 | CCCGGCCCCTAGCGCGC | eekk-d8-kkeee | soossssssssssooss | 1449 | 1465 | 1003 |
| 672991 | CCCCGGCCCCTAGCGCG | eekk-d8-kkeee | soossssssssssooss | 1450 | 1466 | 1004 |
| 672992 | GCCCCGGCCCCTAGCGC | eekk-d8-kkeee | soossssssssssooss | 1451 | 1467 | 1005 |
| 672993 | GGCCCCGGCCCCTAGCG | eekk-d8-kkeee | soossssssssssooss | 1452 | 1468 | 1006 |
| 672994 | CGGCCCCGGCCCCTAGC | eekk-d8-kkeee | soossssssssssooss | 1453 | 1469 | 1007 |
| 672995 | CCGGCCCCGGCCCCTAG | eekk-d8-kkeee | soossssssssssooss | 1454 | 1470 | 1008 |
| 672996 | CCCGGCCCCGGCCCCTA | eekk-d8-kkeee | soossssssssssooss | 1455 | 1471 | 1009 |
| 672997 | ACGCCCCGGCCCCGGCC | eekk-d8-kkeee | soossssssssssooss | 1465 | 1481 | 1010 |
| 672998 | CACGCCCCGGCCCCGGC | eekk-d8-kkeee | soossssssssssooss | 1466 | 1482 | 1011 |
| 672999 | CCACGCCCCGGCCCCGG | eekk-d8-kkeee | soossssssssssooss | 1467 | 1483 | 1012 |
| 673000 | ACCACGCCCCGGCCCCG | eekk-d8-kkeee | soossssssssssooss | 1468 | 1484 | 1013 |
| 673001 | GACCACGCCCCGGCCCC | eekk-d8-kkeee | soossssssssssooss | 1469 | 1485 | 1014 |
| 673002 | CGACCACGCCCCGGCCC | eekk-d8-kkeee | soossssssssssooss | 1470 | 1486 | 1015 |
| 673003 | CCGACCACGCCCCGGCC | eekk-d8-kkeee | soossssssssssooss | 1471 | 1487 | 1016 |
| 673004 | CCCGACCACGCCCCGGC | eekk-d8-kkeee | soossssssssssooss | 1472 | 1488 | 1017 |
| 673005 | CCCCGACCACGCCCCGG | eekk-d8-kkeee | soossssssssssooss | 1473 | 1489 | 1018 |
| 673006 | GCCCCGACCACGCCCCG | eekk-d8-kkeee | soossssssssssooss | 1474 | 1490 | 1019 |
| 673007 | CGCCCCGACCACGCCCC | eekk-d8-kkeee | soossssssssssooss | 1475 | 1491 | 1020 |

TABLE 25-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673008 | CCGCCCCGACCACGCCC | eekk-d8-kkeee | sooSssssssssssooss | 1476 | 1492 | 1021 |
| 673009 | CCCGCCCCGACCACGCC | eekk-d8-kkeee | sooSssssssssssooss | 1477 | 1493 | 1022 |
| 673010 | GCCCGCCCCGACCACGC | eekk-d8-kkeee | sooSssssssssssooss | 1478 | 1494 | 1023 |
| 673011 | GGCCCGCCCCGACCACG | eekk-d8-kkeee | sooSssssssssssooss | 1479 | 1495 | 1024 |
| 673012 | GGGCCCGCCCCGACCAC | eekk-d8-kkeee | sooSssssssssssooss | 1480 | 1496 | 1025 |
| 673013 | CGGGCCCGCCCCGACCA | eekk-d8-kkeee | sooSssssssssssooss | 1481 | 1497 | 1026 |
| 673014 | CCGGGCCCGCCCCGACC | eekk-d8-kkeee | sooSssssssssssooss | 1482 | 1498 | 1027 |
| 673015 | CCCGGGCCCGCCCCGAC | eekk-d8-kkeee | sooSssssssssssooss | 1483 | 1499 | 1028 |
| 673016 | GCAGCCCCGCCCCGGGC | eekk-d8-kkeee | sooSssssssssssooss | 1505 | 1521 | 1029 |
| 673017 | CGCAGCCCCGCCCCGGG | eekk-d8-kkeee | sooSssssssssssooss | 1506 | 1522 | 1030 |
| 673018 | CCGCAGCCCCGCCCCGG | eekk-d8-kkeee | sooSssssssssssooss | 1507 | 1523 | 1031 |
| 673019 | ACCGCAGCCCCGCCCCG | eekk-d8-kkeee | sooSssssssssssooss | 1508 | 1524 | 1032 |
| 673020 | AACCGCAGCCCCGCCCC | eekk-d8-kkeee | sooSssssssssssooss | 1509 | 1525 | 1033 |
| 673021 | CAACCGCAGCCCCGCCC | eekk-d8-kkeee | sooSssssssssssooss | 1510 | 1526 | 1034 |
| 673022 | GCAACCGCAGCCCCGCC | eekk-d8-kkeee | sooSssssssssssooss | 1511 | 1527 | 1035 |
| 673023 | CGCAACCGCAGCCCCGC | eekk-d8-kkeee | sooSssssssssssooss | 1512 | 1528 | 1036 |
| 673024 | CCGCAACCGCAGCCCCG | eekk-d8-kkeee | sooSssssssssssooss | 1513 | 1529 | 1037 |
| 673025 | ACCGCAACCGCAGCCCC | eekk-d8-kkeee | sooSssssssssssooss | 1514 | 1530 | 1038 |
| 673026 | CACCGCAACCGCAGCCC | eekk-d8-kkeee | sooSssssssssssooss | 1515 | 1531 | 1039 |
| 673027 | GCACCGCAACCGCAGCC | eekk-d8-kkeee | sooSssssssssssooss | 1516 | 1532 | 1040 |
| 673028 | GGCACCGCAACCGCAGC | eekk-d8-kkeee | sooSssssssssssooss | 1517 | 1533 | 1041 |
| 673029 | AGGCACCGCAACCGCAG | eekk-d8-kkeee | sooSssssssssssooss | 1518 | 1534 | 1042 |
| 673030 | CAGGCACCGCAACCGCA | eekk-d8-kkeee | sooSssssssssssooss | 1519 | 1535 | 1043 |
| 673031 | GCAGGCACCGCAACCGC | eekk-d8-kkeee | sooSssssssssssooss | 1520 | 1536 | 1044 |
| 673032 | CGCAGGCACCGCAACCG | eekk-d8-kkeee | sooSssssssssssooss | 1521 | 1537 | 1045 |
| 673033 | GCGCAGGCACCGCAACC | eekk-d8-kkeee | sooSssssssssssooss | 1522 | 1538 | 1046 |
| 673034 | GGCGCAGGCACCGCAAC | eekk-d8-kkeee | sooSssssssssssooss | 1523 | 1539 | 1047 |

TABLE 26

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673035 | TGAGAGCAAGTAGTGGG | ek-d8-ekekeee | sosssssssssssooss | 1326 | 1342 | 898 |
| 673036 | GTGAGAGCAAGTAGTGG | ek-d8-ekekeee | sosssssssssssooss | 1327 | 1343 | 899 |

TABLE 26-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673037 | TGTGAGAGCAAGTAGTG | ek-d8-ekekeee | sosssssssssooss | 1328 | 1344 | 900 |
| 673038 | CTGTGAGAGCAAGTAGT | ek-d8-ekekeee | sosssssssssooss | 1329 | 1345 | 901 |
| 673039 | ACTGTGAGAGCAAGTAG | ek-d8-ekekeee | sosssssssssooss | 1330 | 1346 | 902 |
| 673040 | TACTGTGAGAGCAAGTA | ek-d8-ekekeee | sosssssssssooss | 1331 | 1347 | 903 |
| 673041 | GTACTGTGAGAGCAAGT | ek-d8-ekekeee | sosssssssssooss | 1332 | 1348 | 904 |
| 673042 | AGTACTGTGAGAGCAAG | ek-d8-ekekeee | sosssssssssooss | 1333 | 1349 | 905 |
| 673043 | GAGTACTGTGAGAGCAA | ek-d8-ekekeee | sosssssssssooss | 1334 | 1350 | 906 |
| 673044 | CGAGTACTGTGAGAGCA | ek-d8-ekekeee | sosssssssssooss | 1335 | 1351 | 907 |
| 673045 | GCGAGTACTGTGAGAGC | ek-d8-ekekeee | sosssssssssooss | 1336 | 1352 | 908 |
| 673046 | AGCGAGTACTGTGAGAG | ek-d8-ekekeee | sosssssssssooss | 1337 | 1353 | 909 |
| 673047 | CAGCGAGTACTGTGAGA | ek-d8-ekekeee | sosssssssssooss | 1338 | 1354 | 910 |
| 673048 | TCAGCGAGTACTGTGAG | ek-d8-ekekeee | sosssssssssooss | 1339 | 1355 | 911 |
| 673049 | CTCAGCGAGTACTGTGA | ek-d8-ekekeee | sosssssssssooss | 1340 | 1356 | 912 |
| 673050 | CCTCAGCGAGTACTGTG | ek-d8-ekekeee | sosssssssssooss | 1341 | 1357 | 913 |
| 673051 | CCCTCAGCGAGTACTGT | ek-d8-ekekeee | sosssssssssooss | 1342 | 1358 | 914 |
| 673052 | ACCCTCAGCGAGTACTG | ek-d8-ekekeee | sosssssssssooss | 1343 | 1359 | 915 |
| 673053 | CACCCTCAGCGAGTACT | ek-d8-ekekeee | sosssssssssooss | 1344 | 1360 | 916 |
| 673054 | TCACCCTCAGCGAGTAC | ek-d8-ekekeee | sosssssssssooss | 1345 | 1361 | 917 |
| 673055 | TTCACCCTCAGCGAGTA | ek-d8-ekekeee | sosssssssssooss | 1346 | 1362 | 918 |
| 673056 | GTTCACCCTCAGCGAGT | ek-d8-ekekeee | sosssssssssooss | 1347 | 1363 | 919 |
| 673057 | TGTTCACCCTCAGCGAG | ek-d8-ekekeee | sosssssssssooss | 1348 | 1364 | 920 |
| 673058 | TTGTTCACCCTCAGCGA | ek-d8-ekekeee | sosssssssssooss | 1349 | 1365 | 921 |
| 673059 | CTTGTTCACCCTCAGCG | ek-d8-ekekeee | sosssssssssooss | 1350 | 1366 | 922 |
| 673060 | TCTTGTTCACCCTCAGC | ek-d8-ekekeee | sosssssssssooss | 1351 | 1367 | 923 |
| 673061 | TTCTTGTTCACCCTCAG | ek-d8-ekekeee | sosssssssssooss | 1352 | 1368 | 924 |
| 673062 | TTTCTTGTTCACCCTCA | ek-d8-ekekeee | sosssssssssooss | 1353 | 1369 | 925 |
| 673063 | TTTTCTTGTTCACCCTC | ek-d8-ekekeee | sosssssssssooss | 1354 | 1370 | 926 |
| 673064 | CTTTTCTTGTTCACCCT | ek-d8-ekekeee | sosssssssssooss | 1355 | 1371 | 927 |
| 673065 | TCTTTTCTTGTTCACCC | ek-d8-ekekeee | sosssssssssooss | 1356 | 1372 | 928 |
| 673066 | GTCTTTTCTTGTTCACC | ek-d8-ekekeee | sosssssssssooss | 1357 | 1373 | 929 |
| 673067 | GGTCTTTTCTTGTTCAC | ek-d8-ekekeee | sosssssssssooss | 1358 | 1374 | 930 |
| 673068 | AGGTCTTTTCTTGTTCA | ek-d8-ekekeee | sosssssssssooss | 1359 | 1375 | 931 |
| 673069 | CAGGTCTTTTCTTGTTC | ek-d8-ekekeee | sosssssssssooss | 1360 | 1376 | 932 |
| 673070 | TCAGGTCTTTTCTTGTT | ek-d8-ekekeee | sosssssssssooss | 1361 | 1377 | 933 |
| 673071 | ATCAGGTCTTTTCTTGT | ek-d8-ekekeee | sosssssssssooss | 1362 | 1378 | 934 |
| 673072 | TATCAGGTCTTTTCTTG | ek-d8-ekekeee | sosssssssssooss | 1363 | 1379 | 935 |

TABLE 26-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673073 | TTATCAGGTCTTTTCTT | ek-d8-ekekeee | sosssssssssssooss | 1364 | 1380 | 936 |
| 673074 | ATCTTTATCAGGTCTTT | ek-d8-ekekeee | sosssssssssssooss | 1368 | 1384 | 937 |
| 673075 | AATCTTTATCAGGTCTT | ek-d8-ekekeee | sosssssssssssooss | 1369 | 1385 | 938 |
| 673076 | TAATCTTTATCAGGTCT | ek-d8-ekekeee | sosssssssssssooss | 1370 | 1386 | 939 |
| 673077 | TTAATCTTTATCAGGTC | ek-d8-ekekeee | sosssssssssssooss | 1371 | 1387 | 940 |
| 673078 | GTTAATCTTTATCAGGT | ek-d8-ekekeee | sosssssssssssooss | 1372 | 1388 | 941 |
| 673079 | GGTTAATCTTTATCAGG | ek-d8-ekekeee | sosssssssssssooss | 1373 | 1389 | 942 |
| 673080 | TGGTTAATCTTTATCAG | ek-d8-ekekeee | sosssssssssssooss | 1374 | 1390 | 943 |
| 673081 | CTGGTTAATCTTTATCA | ek-d8-ekekeee | sosssssssssssooss | 1375 | 1391 | 944 |
| 673082 | TCTGGTTAATCTTTATC | ek-d8-ekekeee | sosssssssssssooss | 1376 | 1392 | 945 |
| 673083 | CCCTCCTTGTTTTCTTC | ek-d8-ekekeee | sosssssssssssooss | 1391 | 1407 | 946 |
| 673084 | TCCCTCCTTGTTTTCTT | ek-d8-ekekeee | sosssssssssssooss | 1392 | 1408 | 947 |
| 673085 | TTCCCTCCTTGTTTTCT | ek-d8-ekekeee | sosssssssssssooss | 1393 | 1409 | 948 |
| 673086 | TTTCCCTCCTTGTTTTC | ek-d8-ekekeee | sosssssssssssooss | 1394 | 1410 | 949 |
| 673087 | GTTTCCCTCCTTGTTTT | ek-d8-ekekeee | sosssssssssssooss | 1395 | 1411 | 950 |
| 673088 | TGTTTCCCTCCTTGTTT | ek-d8-ekekeee | sosssssssssssooss | 1396 | 1412 | 951 |
| 673089 | TTGTTTCCCTCCTTGTT | ek-d8-ekekeee | sosssssssssssooss | 1397 | 1413 | 952 |
| 673090 | GGTTGTTTCCCTCCTTG | ek-d8-ekekeee | sosssssssssssooss | 1399 | 1415 | 953 |
| 673091 | CGGTTGTTTCCCTCCTT | ek-d8-ekekeee | sosssssssssssooss | 1400 | 1416 | 954 |
| 673092 | GCGGTTGTTTCCCTCCT | ek-d8-ekekeee | sosssssssssssooss | 1401 | 1417 | 955 |
| 673093 | TGCGGTTGTTTCCCTCC | ek-d8-ekekeee | sosssssssssssooss | 1402 | 1418 | 956 |
| 673094 | CTGCGGTTGTTTCCCTC | ek-d8-ekekeee | sosssssssssssooss | 1403 | 1419 | 957 |
| 673095 | GCTGCGGTTGTTTCCCT | ek-d8-ekekeee | sosssssssssssooss | 1404 | 1420 | 958 |
| 673096 | GGCTGCGGTTGTTTCCC | ek-d8-ekekeee | sosssssssssssooss | 1405 | 1421 | 959 |
| 673097 | AGGCTGCGGTTGTTTCC | ek-d8-ekekeee | sosssssssssssooss | 1406 | 1422 | 960 |
| 673098 | CAGGCTGCGGTTGTTTC | ek-d8-ekekeee | sosssssssssssooss | 1407 | 1423 | 961 |
| 673099 | ACAGGCTGCGGTTGTTT | ek-d8-ekekeee | sosssssssssssooss | 1408 | 1424 | 962 |
| 673100 | TACAGGCTGCGGTTGTT | ek-d8-ekekeee | sosssssssssssooss | 1409 | 1425 | 963 |
| 673101 | CTACAGGCTGCGGTTGT | ek-d8-ekekeee | sosssssssssssooss | 1410 | 1426 | 964 |
| 673102 | GCTACAGGCTGCGGTTG | ek-d8-ekekeee | sosssssssssssooss | 1411 | 1427 | 965 |
| 673103 | TGCTACAGGCTGCGGTT | ek-d8-ekekeee | sosssssssssssooss | 1412 | 1428 | 966 |
| 673104 | TTGCTACAGGCTGCGGT | ek-d8-ekekeee | sosssssssssssooss | 1413 | 1429 | 967 |
| 673105 | CTTGCTACAGGCTGCGG | ek-d8-ekekeee | sosssssssssssooss | 1414 | 1430 | 968 |
| 673106 | GCTTGCTACAGGCTGCG | ek-d8-ekekeee | sosssssssssssooss | 1415 | 1431 | 969 |
| 673107 | AGCTTGCTACAGGCTGC | ek-d8-ekekeee | sosssssssssssooss | 1416 | 1432 | 970 |
| 673108 | GAGCTTGCTACAGGCTG | ek-d8-ekekeee | sosssssssssssooss | 1417 | 1433 | 971 |

TABLE 26-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673109 | AGAGCTTGCTACAGGCT | ek-d8-ekekeee | sosssssssssoooss | 1418 | 1434 | 972 |
| 673110 | CAGAGCTTGCTACAGGC | ek-d8-ekekeee | sosssssssssoooss | 1419 | 1435 | 973 |
| 673111 | CCAGAGCTTGCTACAGG | ek-d8-ekekeee | sosssssssssoooss | 1420 | 1436 | 974 |
| 673112 | TCCAGAGCTTGCTACAG | ek-d8-ekekeee | sosssssssssoooss | 1421 | 1437 | 975 |
| 673113 | TTCCAGAGCTTGCTACA | ek-d8-ekekeee | sosssssssssoooss | 1422 | 1438 | 976 |
| 673114 | GTTCCAGAGCTTGCTAC | ek-d8-ekekeee | sosssssssssoooss | 1423 | 1439 | 977 |
| 673115 | AGTTCCAGAGCTTGCTA | ek-d8-ekekeee | sosssssssssoooss | 1424 | 1440 | 978 |
| 673116 | GAGTTCCAGAGCTTGCT | ek-d8-ekekeee | sosssssssssoooss | 1425 | 1441 | 979 |
| 673117 | TGAGTTCCAGAGCTTGC | ek-d8-ekekeee | sosssssssssoooss | 1426 | 1442 | 980 |
| 673118 | CTGAGTTCCAGAGCTTG | ek-d8-ekekeee | sosssssssssoooss | 1427 | 1443 | 981 |
| 673119 | CCTGAGTTCCAGAGCTT | ek-d8-ekekeee | sosssssssssoooss | 1428 | 1444 | 982 |
| 673120 | TCCTGAGTTCCAGAGCT | ek-d8-ekekeee | sosssssssssoooss | 1429 | 1445 | 983 |
| 673121 | CTCCTGAGTTCCAGAGC | ek-d8-ekekeee | sosssssssssoooss | 1430 | 1446 | 984 |
| 673122 | ACTCCTGAGTTCCAGAG | ek-d8-ekekeee | sosssssssssoooss | 1431 | 1447 | 985 |
| 673123 | GACTCCTGAGTTCCAGA | ek-d8-ekekeee | sosssssssssoooss | 1432 | 1448 | 986 |
| 673124 | CGACTCCTGAGTTCCAG | ek-d8-ekekeee | sosssssssssoooss | 1433 | 1449 | 987 |
| 673125 | GCGACTCCTGAGTTCCA | ek-d8-ekekeee | sosssssssssoooss | 1434 | 1450 | 988 |
| 673126 | CGCGACTCCTGAGTTCC | ek-d8-ekekeee | sosssssssssoooss | 1435 | 1451 | 989 |
| 673127 | GCGCGACTCCTGAGTTC | ek-d8-ekekeee | sosssssssssoooss | 1436 | 1452 | 990 |
| 673128 | CGCGCGACTCCTGAGTT | ek-d8-ekekeee | sosssssssssoooss | 1437 | 1453 | 991 |
| 673129 | GCGCGCGACTCCTGAGT | ek-d8-ekekeee | sosssssssssoooss | 1438 | 1454 | 992 |
| 673130 | AGCGCGCGACTCCTGAG | ek-d8-ekekeee | sosssssssssoooss | 1439 | 1455 | 993 |
| 673131 | TAGCGCGCGACTCCTGA | ek-d8-ekekeee | sosssssssssoooss | 1440 | 1456 | 994 |
| 673132 | CTAGCGCGCGACTCCTG | ek-d8-ekekeee | sosssssssssoooss | 1441 | 1457 | 995 |
| 673133 | CCTAGCGCGCGACTCCT | ek-d8-ekekeee | sosssssssssoooss | 1442 | 1458 | 996 |
| 673134 | CCCTAGCGCGCGACTCC | ek-d8-ekekeee | sosssssssssoooss | 1443 | 1459 | 997 |
| 673135 | CCCCTAGCGCGCGACTC | ek-d8-ekekeee | sosssssssssoooss | 1444 | 1460 | 998 |
| 673136 | GCCCCTAGCGCGCGACT | ek-d8-ekekeee | sosssssssssoooss | 1445 | 1461 | 999 |
| 673137 | GGCCCCTAGCGCGCGAC | ek-d8-ekekeee | sosssssssssoooss | 1446 | 1462 | 1000 |
| 673138 | CGGCCCCTAGCGCGCGA | ek-d8-ekekeee | sosssssssssoooss | 1447 | 1463 | 1001 |
| 673139 | CCGGCCCCTAGCGCGCG | ek-d8-ekekeee | sosssssssssoooss | 1448 | 1464 | 1002 |
| 673140 | CCCGGCCCCTAGCGCGC | ek-d8-ekekeee | sosssssssssoooss | 1449 | 1465 | 1003 |
| 673141 | CCCCGGCCCCTAGCGCG | ek-d8-ekekeee | sosssssssssoooss | 1450 | 1466 | 1004 |
| 673142 | GCCCCGGCCCCTAGCGC | ek-d8-ekekeee | sosssssssssoooss | 1451 | 1467 | 1005 |
| 673143 | GGCCCCGGCCCCTAGCG | ek-d8-ekekeee | sosssssssssoooss | 1452 | 1468 | 1006 |
| 673144 | CGGCCCCGGCCCCTAGC | ek-d8-ekekeee | sosssssssssoooss | 1453 | 1469 | 1007 |

TABLE 26-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673145 | CCGGCCCCGGCCCCTAG | ek-d8-ekekeee | sossssssssssooosss | 1454 | 1470 | 1008 |
| 673146 | CCCGGCCCCGGCCCCTA | ek-d8-ekekeee | sossssssssssooosss | 1455 | 1471 | 1009 |
| 673147 | ACGCCCCGGCCCCGGCC | ek-d8-ekekeee | sossssssssssooosss | 1465 | 1481 | 1010 |
| 673148 | CACGCCCCGGCCCCGGC | ek-d8-ekekeee | sossssssssssooosss | 1466 | 1482 | 1011 |
| 673149 | CCACGCCCCGGCCCCGG | ek-d8-ekekeee | sossssssssssooosss | 1467 | 1483 | 1012 |
| 673150 | ACCACGCCCCGGCCCCG | ek-d8-ekekeee | sossssssssssooosss | 1468 | 1484 | 1013 |
| 673151 | GACCACGCCCCGGCCCC | ek-d8-ekekeee | sossssssssssooosss | 1469 | 1485 | 1014 |
| 673152 | CGACCACGCCCCGGCCC | ek-d8-ekekeee | sossssssssssooosss | 1470 | 1486 | 1015 |
| 673153 | CCGACCACGCCCCGGCC | ek-d8-ekekeee | sossssssssssooosss | 1471 | 1487 | 1016 |
| 673154 | CCCGACCACGCCCCGGC | ek-d8-ekekeee | sossssssssssooosss | 1472 | 1488 | 1017 |
| 673155 | CCCCGACCACGCCCCGG | ek-d8-ekekeee | sossssssssssooosss | 1473 | 1489 | 1018 |
| 673156 | GCCCCGACCACGCCCCG | ek-d8-ekekeee | sossssssssssooosss | 1474 | 1490 | 1019 |
| 673157 | CGCCCCGACCACGCCCC | ek-d8-ekekeee | sossssssssssooosss | 1475 | 1491 | 1020 |
| 673158 | CCGCCCCGACCACGCCC | ek-d8-ekekeee | sossssssssssooosss | 1476 | 1492 | 1021 |
| 673159 | CCCGCCCCGACCACGCC | ek-d8-ekekeee | sossssssssssooosss | 1477 | 1493 | 1022 |
| 673160 | GCCCGCCCCGACCACGC | ek-d8-ekekeee | sossssssssssooosss | 1478 | 1494 | 1023 |
| 673161 | GGCCCGCCCCGACCACG | ek-d8-ekekeee | sossssssssssooosss | 1479 | 1495 | 1024 |
| 673162 | GGGCCCGCCCCGACCAC | ek-d8-ekekeee | sossssssssssooosss | 1480 | 1496 | 1025 |
| 673163 | CGGGCCCGCCCCGACCA | ek-d8-ekekeee | sossssssssssooosss | 1481 | 1497 | 1026 |
| 673164 | CCGGGCCCGCCCCGACC | ek-d8-ekekeee | sossssssssssooosss | 1482 | 1498 | 1027 |
| 673165 | CCCGGGCCCGCCCCGAC | ek-d8-ekekeee | sossssssssssooosss | 1483 | 1499 | 1028 |
| 673166 | GCAGCCCCGCCCCGGGC | ek-d8-ekekeee | sossssssssssooosss | 1505 | 1521 | 1029 |
| 673167 | CGCAGCCCCGCCCCGGG | ek-d8-ekekeee | sossssssssssooosss | 1506 | 1522 | 1030 |
| 673168 | CCGCAGCCCCGCCCCGG | ek-d8-ekekeee | sossssssssssooosss | 1507 | 1523 | 1031 |
| 673169 | ACCGCAGCCCCGCCCCG | ek-d8-ekekeee | sossssssssssooosss | 1508 | 1524 | 1032 |
| 673170 | AACCGCAGCCCCGCCCC | ek-d8-ekekeee | sossssssssssooosss | 1509 | 1525 | 1033 |
| 673171 | CAACCGCAGCCCCGCCC | ek-d8-ekekeee | sossssssssssooosss | 1510 | 1526 | 1034 |
| 673172 | GCAACCGCAGCCCCGCC | ek-d8-ekekeee | sossssssssssooosss | 1511 | 1527 | 1035 |
| 673173 | CGCAACCGCAGCCCCGC | ek-d8-ekekeee | sossssssssssooosss | 1512 | 1528 | 1036 |
| 673174 | CCGCAACCGCAGCCCCG | ek-d8-ekekeee | sossssssssssooosss | 1513 | 1529 | 1037 |
| 673175 | ACCGCAACCGCAGCCCC | ek-d8-ekekeee | sossssssssssooosss | 1514 | 1530 | 1038 |
| 673176 | CACCGCAACCGCAGCCC | ek-d8-ekekeee | sossssssssssooosss | 1515 | 1531 | 1039 |
| 673177 | GCACCGCAACCGCAGCC | ek-d8-ekekeee | sossssssssssooosss | 1516 | 1532 | 1040 |
| 673178 | GGCACCGCAACCGCAGC | ek-d8-ekekeee | sossssssssssooosss | 1517 | 1533 | 1041 |
| 673179 | AGGCACCGCAACCGCAG | ek-d8-ekekeee | sossssssssssooosss | 1518 | 1534 | 1042 |
| 673180 | CAGGCACCGCAACCGCA | ek-d8-ekekeee | sossssssssssooosss | 1519 | 1535 | 1043 |

TABLE 26-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673181 | GCAGGCACCGCAACCGC | ek-d8-ekekeee | sossssssssooss | 1520 | 1536 | 1044 |
| 673182 | CGCAGGCACCGCAACCG | ek-d8-ekekeee | sossssssssooss | 1521 | 1537 | 1045 |
| 673183 | GCGCAGGCACCGCAACC | ek-d8-ekekeee | sossssssssooss | 1522 | 1538 | 1046 |
| 673184 | GGCGCAGGCACCGCAAC | ek-d8-ekekeee | sossssssssooss | 1523 | 1539 | 1047 |

TABLE 27

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673185 | TGAGAGCAAGTAGTGGG | keke-d8-ekeke | soossssssssooss | 1326 | 1342 | 898 |
| 673186 | GTGAGAGCAAGTAGTGG | keke-d8-ekeke | soossssssssooss | 1327 | 1343 | 899 |
| 673187 | TGTGAGAGCAAGTAGTG | keke-d8-ekeke | soossssssssooss | 1328 | 1344 | 900 |
| 673188 | CTGTGAGAGCAAGTAGT | keke-d8-ekeke | soossssssssooss | 1329 | 1345 | 901 |
| 673189 | ACTGTGAGAGCAAGTAG | keke-d8-ekeke | soossssssssooss | 1330 | 1346 | 902 |
| 673190 | TACTGTGAGAGCAAGTA | keke-d8-ekeke | soossssssssooss | 1331 | 1347 | 903 |
| 673191 | GTACTGTGAGAGCAAGT | keke-d8-ekeke | soossssssssooss | 1332 | 1348 | 904 |
| 673192 | AGTACTGTGAGAGCAAG | keke-d8-ekeke | soossssssssooss | 1333 | 1349 | 905 |
| 673193 | GAGTACTGTGAGAGCAA | keke-d8-ekeke | soossssssssooss | 1334 | 1350 | 906 |
| 673194 | CGAGTACTGTGAGAGCA | keke-d8-ekeke | soossssssssooss | 1335 | 1351 | 907 |
| 673195 | GCGAGTACTGTGAGAGC | keke-d8-ekeke | soossssssssooss | 1336 | 1352 | 908 |
| 673196 | AGCGAGTACTGTGAGAG | keke-d8-ekeke | soossssssssooss | 1337 | 1353 | 909 |
| 673197 | CAGCGAGTACTGTGAGA | keke-d8-ekeke | soossssssssooss | 1338 | 1354 | 910 |
| 673198 | TCAGCGAGTACTGTGAG | keke-d8-ekeke | soossssssssooss | 1339 | 1355 | 911 |
| 673199 | CTCAGCGAGTACTGTGA | keke-d8-ekeke | soossssssssooss | 1340 | 1356 | 912 |
| 673200 | CCTCAGCGAGTACTGTG | keke-d8-ekeke | soossssssssooss | 1341 | 1357 | 913 |
| 673201 | CCCTCAGCGAGTACTGT | keke-d8-ekeke | soossssssssooss | 1342 | 1358 | 914 |
| 673202 | ACCCTCAGCGAGTACTG | keke-d8-ekeke | soossssssssooss | 1343 | 1359 | 915 |
| 673203 | CACCCTCAGCGAGTACT | keke-d8-ekeke | soossssssssooss | 1344 | 1360 | 916 |
| 673204 | TCACCCTCAGCGAGTAC | keke-d8-ekeke | soossssssssooss | 1345 | 1361 | 917 |
| 673205 | TTCACCCTCAGCGAGTA | keke-d8-ekeke | soossssssssooss | 1346 | 1362 | 918 |
| 673206 | GTTCACCCTCAGCGAGT | keke-d8-ekeke | soossssssssooss | 1347 | 1363 | 919 |
| 673207 | TGTTCACCCTCAGCGAG | keke-d8-ekeke | soossssssssooss | 1348 | 1364 | 920 |
| 673208 | TTGTTCACCCTCAGCGA | keke-d8-ekeke | soossssssssooss | 1349 | 1365 | 921 |
| 673209 | CTTGTTCACCCTCAGCG | keke-d8-ekeke | soossssssssooss | 1350 | 1366 | 922 |
| 673210 | TCTTGTTCACCCTCAGC | keke-d8-ekeke | soossssssssooss | 1351 | 1367 | 923 |

TABLE 27-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673211 | TTCTTGTTCACCCTCAG | keke-d8-ekeke | sooossssssssssooss | 1352 | 1368 | 924 |
| 673212 | TTTCTTGTTCACCCTCA | keke-d8-ekeke | sooossssssssssooss | 1353 | 1369 | 925 |
| 673213 | TTTTCTTGTTCACCCTC | keke-d8-ekeke | sooossssssssssooss | 1354 | 1370 | 926 |
| 673214 | CTTTTCTTGTTCACCCT | keke-d8-ekeke | sooossssssssssooss | 1355 | 1371 | 927 |
| 673215 | TCTTTTCTTGTTCACCC | keke-d8-ekeke | sooossssssssssooss | 1356 | 1372 | 928 |
| 673216 | GTCTTTTCTTGTTCACC | keke-d8-ekeke | sooossssssssssooss | 1357 | 1373 | 929 |
| 673217 | GGTCTTTTCTTGTTCAC | keke-d8-ekeke | sooossssssssssooss | 1358 | 1374 | 930 |
| 673218 | AGGTCTTTTCTTGTTCA | keke-d8-ekeke | sooossssssssssooss | 1359 | 1375 | 931 |
| 673219 | CAGGTCTTTTCTTGTTC | keke-d8-ekeke | sooossssssssssooss | 1360 | 1376 | 932 |
| 673220 | TCAGGTCTTTTCTTGTT | keke-d8-ekeke | sooossssssssssooss | 1361 | 1377 | 933 |
| 673221 | ATCAGGTCTTTTCTTGT | keke-d8-ekeke | sooossssssssssooss | 1362 | 1378 | 934 |
| 673222 | TATCAGGTCTTTTCTTG | keke-d8-ekeke | sooossssssssssooss | 1363 | 1379 | 935 |
| 673223 | TTATCAGGTCTTTTCTT | keke-d8-ekeke | sooossssssssssooss | 1364 | 1380 | 936 |
| 673224 | ATCTTTATCAGGTCTTT | keke-d8-ekeke | sooossssssssssooss | 1368 | 1384 | 937 |
| 673225 | AATCTTTATCAGGTCTT | keke-d8-ekeke | sooossssssssssooss | 1369 | 1385 | 938 |
| 673226 | TAATCTTTATCAGGTCT | keke-d8-ekeke | sooossssssssssooss | 1370 | 1386 | 939 |
| 673227 | TTAATCTTTATCAGGTC | keke-d8-ekeke | sooossssssssssooss | 1371 | 1387 | 940 |
| 673228 | GTTAATCTTTATCAGGT | keke-d8-ekeke | sooossssssssssooss | 1372 | 1388 | 941 |
| 673229 | GGTTAATCTTTATCAGG | keke-d8-ekeke | sooossssssssssooss | 1373 | 1389 | 942 |
| 673230 | TGGTTAATCTTTATCAG | keke-d8-ekeke | sooossssssssssooss | 1374 | 1390 | 943 |
| 673231 | CTGGTTAATCTTTATCA | keke-d8-ekeke | sooossssssssssooss | 1375 | 1391 | 944 |
| 673232 | TCTGGTTAATCTTTATC | keke-d8-ekeke | sooossssssssssooss | 1376 | 1392 | 945 |
| 673233 | CCCTCCTTGTTTTCTTC | keke-d8-ekeke | sooossssssssssooss | 1391 | 1407 | 946 |
| 673234 | TCCCTCCTTGTTTTCTT | keke-d8-ekeke | sooossssssssssooss | 1392 | 1408 | 947 |
| 673235 | TTCCCTCCTTGTTTTCT | keke-d8-ekeke | sooossssssssssooss | 1393 | 1409 | 948 |
| 673236 | TTTCCCTCCTTGTTTTC | keke-d8-ekeke | sooossssssssssooss | 1394 | 1410 | 949 |
| 673237 | GTTTCCCTCCTTGTTTT | keke-d8-ekeke | sooossssssssssooss | 1395 | 1411 | 950 |
| 673238 | TGTTTCCCTCCTTGTTT | keke-d8-ekeke | sooossssssssssooss | 1396 | 1412 | 951 |
| 673239 | TTGTTTCCCTCCTTGTT | keke-d8-ekeke | sooossssssssssooss | 1397 | 1413 | 952 |
| 673240 | GGTTGTTTCCCTCCTTG | keke-d8-ekeke | sooossssssssssooss | 1399 | 1415 | 953 |
| 673241 | CGGTTGTTTCCCTCCTT | keke-d8-ekeke | sooossssssssssooss | 1400 | 1416 | 954 |
| 673242 | GCGGTTGTTTCCCTCCT | keke-d8-ekeke | sooossssssssssooss | 1401 | 1417 | 955 |
| 673243 | TGCGGTTGTTTCCCTCC | keke-d8-ekeke | sooossssssssssooss | 1402 | 1418 | 956 |
| 673244 | CTGCGGTTGTTTCCCTC | keke-d8-ekeke | sooossssssssssooss | 1403 | 1419 | 957 |
| 673245 | GCTGCGGTTGTTTCCCT | keke-d8-ekeke | sooossssssssssooss | 1404 | 1420 | 958 |
| 673246 | GGCTGCGGTTGTTTCCC | keke-d8-ekeke | sooossssssssssooss | 1405 | 1421 | 959 |

TABLE 27-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673247 | AGGCTGCGGTTGTTTCC | keke-d8-ekeke | sooosssssssssooss | 1406 | 1422 | 960 |
| 673248 | CAGGCTGCGGTTGTTTC | keke-d8-ekeke | sooosssssssssooss | 1407 | 1423 | 961 |
| 673249 | ACAGGCTGCGGTTGTTT | keke-d8-ekeke | sooosssssssssooss | 1408 | 1424 | 962 |
| 673250 | TACAGGCTGCGGTTGTT | keke-d8-ekeke | sooosssssssssooss | 1409 | 1425 | 963 |
| 673251 | CTACAGGCTGCGGTTGT | keke-d8-ekeke | sooosssssssssooss | 1410 | 1426 | 964 |
| 673252 | GCTACAGGCTGCGGTTG | keke-d8-ekeke | sooosssssssssooss | 1411 | 1427 | 965 |
| 673253 | TGCTACAGGCTGCGGTT | keke-d8-ekeke | sooosssssssssooss | 1412 | 1428 | 966 |
| 673254 | TTGCTACAGGCTGCGGT | keke-d8-ekeke | sooosssssssssooss | 1413 | 1429 | 967 |
| 673255 | CTTGCTACAGGCTGCGG | keke-d8-ekeke | sooosssssssssooss | 1414 | 1430 | 968 |
| 673256 | GCTTGCTACAGGCTGCG | keke-d8-ekeke | sooosssssssssooss | 1415 | 1431 | 969 |
| 673257 | AGCTTGCTACAGGCTGC | keke-d8-ekeke | sooosssssssssooss | 1416 | 1432 | 970 |
| 673258 | GAGCTTGCTACAGGCTG | keke-d8-ekeke | sooosssssssssooss | 1417 | 1433 | 971 |
| 673259 | AGAGCTTGCTACAGGCT | keke-d8-ekeke | sooosssssssssooss | 1418 | 1434 | 972 |
| 673260 | CAGAGCTTGCTACAGGC | keke-d8-ekeke | sooosssssssssooss | 1419 | 1435 | 973 |
| 673261 | CCAGAGCTTGCTACAGG | keke-d8-ekeke | sooosssssssssooss | 1420 | 1436 | 974 |
| 673262 | TCCAGAGCTTGCTACAG | keke-d8-ekeke | sooosssssssssooss | 1421 | 1437 | 975 |
| 673263 | TTCCAGAGCTTGCTACA | keke-d8-ekeke | sooosssssssssooss | 1422 | 1438 | 976 |
| 673264 | GTTCCAGAGCTTGCTAC | keke-d8-ekeke | sooosssssssssooss | 1423 | 1439 | 977 |
| 673265 | AGTTCCAGAGCTTGCTA | keke-d8-ekeke | sooosssssssssooss | 1424 | 1440 | 978 |
| 673266 | GAGTTCCAGAGCTTGCT | keke-d8-ekeke | sooosssssssssooss | 1425 | 1441 | 979 |
| 673267 | TGAGTTCCAGAGCTTGC | keke-d8-ekeke | sooosssssssssooss | 1426 | 1442 | 980 |
| 673268 | CTGAGTTCCAGAGCTTG | keke-d8-ekeke | sooosssssssssooss | 1427 | 1443 | 981 |
| 673269 | CCTGAGTTCCAGAGCTT | keke-d8-ekeke | sooosssssssssooss | 1428 | 1444 | 982 |
| 673270 | TCCTGAGTTCCAGAGCT | keke-d8-ekeke | sooosssssssssooss | 1429 | 1445 | 983 |
| 673271 | CTCCTGAGTTCCAGAGC | keke-d8-ekeke | sooosssssssssooss | 1430 | 1446 | 984 |
| 673272 | ACTCCTGAGTTCCAGAG | keke-d8-ekeke | sooosssssssssooss | 1431 | 1447 | 985 |
| 673273 | GACTCCTGAGTTCCAGA | keke-d8-ekeke | sooosssssssssooss | 1432 | 1448 | 986 |
| 673274 | CGACTCCTGAGTTCCAG | keke-d8-ekeke | sooosssssssssooss | 1433 | 1449 | 987 |
| 673275 | GCGACTCCTGAGTTCCA | keke-d8-ekeke | sooosssssssssooss | 1434 | 1450 | 988 |
| 673276 | CGCGACTCCTGAGTTCC | keke-d8-ekeke | sooosssssssssooss | 1435 | 1451 | 989 |
| 673277 | GCGCGACTCCTGAGTTC | keke-d8-ekeke | sooosssssssssooss | 1436 | 1452 | 990 |
| 673278 | CGCGCGACTCCTGAGTT | keke-d8-ekeke | sooosssssssssooss | 1437 | 1453 | 991 |
| 673279 | GCGCGCGACTCCTGAGT | keke-d8-ekeke | sooosssssssssooss | 1438 | 1454 | 992 |
| 673280 | AGCGCGCGACTCCTGAG | keke-d8-ekeke | sooosssssssssooss | 1439 | 1455 | 993 |
| 673281 | TAGCGCGCGACTCCTGA | keke-d8-ekeke | sooosssssssssooss | 1440 | 1456 | 994 |
| 673282 | CTAGCGCGCGACTCCTG | keke-d8-ekeke | sooosssssssssooss | 1441 | 1457 | 995 |

TABLE 27-continued

| | | | | SEQ ID NO: 2 Start Site | SEQ ID NO: 2 Stop Site | SEQ ID NO |
|---|---|---|---|---|---|---|
| ISIS NO | Sequence | Chemistry | Linkage | | | |
| 673283 | CCTAGCGCGCGACTCCT | keke-d8-ekeke | sooossssssssssooss | 1442 | 1458 | 996 |
| 673284 | CCCTAGCGCGCGACTCC | keke-d8-ekeke | sooossssssssssooss | 1443 | 1459 | 997 |
| 673285 | CCCCTAGCGCGCGACTC | keke-d8-ekeke | sooossssssssssooss | 1444 | 1460 | 998 |
| 673286 | GCCCCTAGCGCGCGACT | keke-d8-ekeke | sooossssssssssooss | 1445 | 1461 | 999 |
| 673287 | GGCCCCTAGCGCGCGAC | keke-d8-ekeke | sooossssssssssooss | 1446 | 1462 | 1000 |
| 673288 | CGGCCCCTAGCGCGCGA | keke-d8-ekeke | sooossssssssssooss | 1447 | 1463 | 1001 |
| 673289 | CCGGCCCCTAGCGCGCG | keke-d8-ekeke | sooossssssssssooss | 1448 | 1464 | 1002 |
| 673290 | CCCGGCCCCTAGCGCGC | keke-d8-ekeke | sooossssssssssooss | 1449 | 1465 | 1003 |
| 673291 | CCCCGGCCCCTAGCGCG | keke-d8-ekeke | sooossssssssssooss | 1450 | 1466 | 1004 |
| 673292 | GCCCCGGCCCCTAGCGC | keke-d8-ekeke | sooossssssssssooss | 1451 | 1467 | 1005 |
| 673293 | GGCCCCGGCCCCTAGCG | keke-d8-ekeke | sooossssssssssooss | 1452 | 1468 | 1006 |
| 673294 | CGGCCCCGGCCCCTAGC | keke-d8-ekeke | sooossssssssssooss | 1453 | 1469 | 1007 |
| 673295 | CCGGCCCCGGCCCCTAG | keke-d8-ekeke | sooossssssssssooss | 1454 | 1470 | 1008 |
| 673296 | CCCGGCCCCGGCCCCTA | keke-d8-ekeke | sooossssssssssooss | 1455 | 1471 | 1009 |
| 673297 | ACGCCCCGGCCCCGGCC | keke-d8-ekeke | sooossssssssssooss | 1465 | 1481 | 1010 |
| 673298 | CACGCCCCGGCCCCGGC | keke-d8-ekeke | sooossssssssssooss | 1466 | 1482 | 1011 |
| 673299 | CCACGCCCCGGCCCCGG | keke-d8-ekeke | sooossssssssssooss | 1467 | 1483 | 1012 |
| 673300 | ACCACGCCCCGGCCCCG | keke-d8-ekeke | sooossssssssssooss | 1468 | 1484 | 1013 |
| 673301 | GACCACGCCCCGGCCCC | keke-d8-ekeke | sooossssssssssooss | 1469 | 1485 | 1014 |
| 673302 | CGACCACGCCCCGGCCC | keke-d8-ekeke | sooossssssssssooss | 1470 | 1486 | 1015 |
| 673303 | CCGACCACGCCCCGGCC | keke-d8-ekeke | sooossssssssssooss | 1471 | 1487 | 1016 |
| 673304 | CCCGACCACGCCCCGGC | keke-d8-ekeke | sooossssssssssooss | 1472 | 1488 | 1017 |
| 673305 | CCCCGACCACGCCCCGG | keke-d8-ekeke | sooossssssssssooss | 1473 | 1489 | 1018 |
| 673306 | GCCCCGACCACGCCCCG | keke-d8-ekeke | sooossssssssssooss | 1474 | 1490 | 1019 |
| 673307 | CGCCCCGACCACGCCCC | keke-d8-ekeke | sooossssssssssooss | 1475 | 1491 | 1020 |
| 673308 | CCGCCCCGACCACGCCC | keke-d8-ekeke | sooossssssssssooss | 1476 | 1492 | 1021 |
| 673309 | CCCGCCCCGACCACGCC | keke-d8-ekeke | sooossssssssssooss | 1477 | 1493 | 1022 |
| 673310 | GCCCGCCCCGACCACGC | keke-d8-ekeke | sooossssssssssooss | 1478 | 1494 | 1023 |
| 673311 | GGCCCGCCCCGACCACG | keke-d8-ekeke | sooossssssssssooss | 1479 | 1495 | 1024 |
| 673312 | GGGCCCGCCCCGACCAC | keke-d8-ekeke | sooossssssssssooss | 1480 | 1496 | 1025 |
| 673313 | CGGGCCCGCCCCGACCA | keke-d8-ekeke | sooossssssssssooss | 1481 | 1497 | 1026 |
| 673314 | CCGGGCCCGCCCCGACC | keke-d8-ekeke | sooossssssssssooss | 1482 | 1498 | 1027 |
| 673315 | CCCGGGCCCGCCCCGAC | keke-d8-ekeke | sooossssssssssooss | 1483 | 1499 | 1028 |
| 673316 | GCAGCCCCGCCCCGGGC | keke-d8-ekeke | sooossssssssssooss | 1505 | 1521 | 1029 |
| 673317 | CGCAGCCCCGCCCCGGG | keke-d8-ekeke | sooossssssssssooss | 1506 | 1522 | 1030 |
| 673318 | CCGCAGCCCCGCCCCGG | keke-d8-ekeke | sooossssssssssooss | 1507 | 1523 | 1031 |

TABLE 27-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673319 | ACCGCAGCCCCGCCCCG | keke-d8-ekeke | soosssssssssssooss | 1508 | 1524 | 1032 |
| 673320 | AACCGCAGCCCCGCCCC | keke-d8-ekeke | soosssssssssssooss | 1509 | 1525 | 1033 |
| 673321 | CAACCGCAGCCCCGCCC | keke-d8-ekeke | soosssssssssssooss | 1510 | 1526 | 1034 |
| 673322 | GCAACCGCAGCCCCGCC | keke-d8-ekeke | soosssssssssssooss | 1511 | 1527 | 1035 |
| 673323 | CGCAACCGCAGCCCCGC | keke-d8-ekeke | soosssssssssssooss | 1512 | 1528 | 1036 |
| 673324 | CCGCAACCGCAGCCCCG | keke-d8-ekeke | soosssssssssssooss | 1513 | 1529 | 1037 |
| 673325 | ACCGCAACCGCAGCCCC | keke-d8-ekeke | soosssssssssssooss | 1514 | 1530 | 1038 |
| 673326 | CACCGCAACCGCAGCCC | keke-d8-ekeke | soosssssssssssooss | 1515 | 1531 | 1039 |
| 673327 | GCACCGCAACCGCAGCC | keke-d8-ekeke | soosssssssssssooss | 1516 | 1532 | 1040 |
| 673328 | GGCACCGCAACCGCAGC | keke-d8-ekeke | soosssssssssssooss | 1517 | 1533 | 1041 |
| 673329 | AGGCACCGCAACCGCAG | keke-d8-ekeke | soosssssssssssooss | 1518 | 1534 | 1042 |
| 673330 | CAGGCACCGCAACCGCA | keke-d8-ekeke | soosssssssssssooss | 1519 | 1535 | 1043 |
| 673331 | GCAGGCACCGCAACCGC | keke-d8-ekeke | soosssssssssssooss | 1520 | 1536 | 1044 |
| 673332 | CGCAGGCACCGCAACCG | keke-d8-ekeke | soosssssssssssooss | 1521 | 1537 | 1045 |
| 673333 | GCGCAGGCACCGCAACC | keke-d8-ekeke | soosssssssssssooss | 1522 | 1538 | 1046 |
| 673334 | GGCGCAGGCACCGCAAC | keke-d8-ekeke | soosssssssssssooss | 1523 | 1539 | 1047 |

TABLE 28

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673335 | TGAGAGCAAGTAGTGGG | ekek-d8-kekee | soosssssssssssooss | 1326 | 1342 | 898 |
| 673336 | GTGAGAGCAAGTAGTGG | ekek-d8-kekee | soosssssssssssooss | 1327 | 1343 | 899 |
| 673337 | TGTGAGAGCAAGTAGTG | ekek-d8-kekee | soosssssssssssooss | 1328 | 1344 | 900 |
| 673338 | CTGTGAGAGCAAGTAGT | ekek-d8-kekee | soosssssssssssooss | 1329 | 1345 | 901 |
| 673339 | ACTGTGAGAGCAAGTAG | ekek-d8-kekee | soosssssssssssooss | 1330 | 1346 | 902 |
| 673340 | TACTGTGAGAGCAAGTA | ekek-d8-kekee | soosssssssssssooss | 1331 | 1347 | 903 |
| 673341 | GTACTGTGAGAGCAAGT | ekek-d8-kekee | soosssssssssssooss | 1332 | 1348 | 904 |
| 673342 | AGTACTGTGAGAGCAAG | ekek-d8-kekee | soosssssssssssooss | 1333 | 1349 | 905 |
| 673343 | GAGTACTGTGAGAGCAA | ekek-d8-kekee | soosssssssssssooss | 1334 | 1350 | 906 |
| 673344 | CGAGTACTGTGAGAGCA | ekek-d8-kekee | soosssssssssssooss | 1335 | 1351 | 907 |
| 673345 | GCGAGTACTGTGAGAGC | ekek-d8-kekee | soosssssssssssooss | 1336 | 1352 | 908 |
| 673346 | AGCGAGTACTGTGAGAG | ekek-d8-kekee | soosssssssssssooss | 1337 | 1353 | 909 |
| 673347 | CAGCGAGTACTGTGAGA | ekek-d8-kekee | soosssssssssssooss | 1338 | 1354 | 910 |

TABLE 28-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673348 | TCAGCGAGTACTGTGAG | ekek-d8-kekee | soosssssssssooss | 1339 | 1355 | 911 |
| 673349 | CTCAGCGAGTACTGTGA | ekek-d8-kekee | soosssssssssooss | 1340 | 1356 | 912 |
| 673350 | CCTCAGCGAGTACTGTG | ekek-d8-kekee | soosssssssssooss | 1341 | 1357 | 913 |
| 673351 | CCCTCAGCGAGTACTGT | ekek-d8-kekee | soosssssssssooss | 1342 | 1358 | 914 |
| 673352 | ACCCTCAGCGAGTACTG | ekek-d8-kekee | soosssssssssooss | 1343 | 1359 | 915 |
| 673353 | CACCCTCAGCGAGTACT | ekek-d8-kekee | soosssssssssooss | 1344 | 1360 | 916 |
| 673354 | TCACCCTCAGCGAGTAC | ekek-d8-kekee | soosssssssssooss | 1345 | 1361 | 917 |
| 673355 | TTCACCCTCAGCGAGTA | ekek-d8-kekee | soosssssssssooss | 1346 | 1362 | 918 |
| 673356 | GTTCACCCTCAGCGAGT | ekek-d8-kekee | soosssssssssooss | 1347 | 1363 | 919 |
| 673357 | TGTTCACCCTCAGCGAG | ekek-d8-kekee | soosssssssssooss | 1348 | 1364 | 920 |
| 673358 | TTGTTCACCCTCAGCGA | ekek-d8-kekee | soosssssssssooss | 1349 | 1365 | 921 |
| 673359 | CTTGTTCACCCTCAGCG | ekek-d8-kekee | soosssssssssooss | 1350 | 1366 | 922 |
| 673360 | TCTTGTTCACCCTCAGC | ekek-d8-kekee | soosssssssssooss | 1351 | 1367 | 923 |
| 673361 | TTCTTGTTCACCCTCAG | ekek-d8-kekee | soosssssssssooss | 1352 | 1368 | 924 |
| 673362 | TTTCTTGTTCACCCTCA | ekek-d8-kekee | soosssssssssooss | 1353 | 1369 | 925 |
| 673363 | TTTTCTTGTTCACCCTC | ekek-d8-kekee | soosssssssssooss | 1354 | 1370 | 926 |
| 673364 | CTTTTCTTGTTCACCCT | ekek-d8-kekee | soosssssssssooss | 1355 | 1371 | 927 |
| 673365 | TCTTTTCTTGTTCACCC | ekek-d8-kekee | soosssssssssooss | 1356 | 1372 | 928 |
| 673366 | GTCTTTTCTTGTTCACC | ekek-d8-kekee | soosssssssssooss | 1357 | 1373 | 929 |
| 673367 | GGTCTTTTCTTGTTCAC | ekek-d8-kekee | soosssssssssooss | 1358 | 1374 | 930 |
| 673368 | AGGTCTTTTCTTGTTCA | ekek-d8-kekee | soosssssssssooss | 1359 | 1375 | 931 |
| 673369 | CAGGTCTTTTCTTGTTC | ekek-d8-kekee | soosssssssssooss | 1360 | 1376 | 932 |
| 673370 | TCAGGTCTTTTCTTGTT | ekek-d8-kekee | soosssssssssooss | 1361 | 1377 | 933 |
| 673371 | ATCAGGTCTTTTCTTGT | ekek-d8-kekee | soosssssssssooss | 1362 | 1378 | 934 |
| 673372 | TATCAGGTCTTTTCTTG | ekek-d8-kekee | soosssssssssooss | 1363 | 1379 | 935 |
| 673373 | TTATCAGGTCTTTTCTT | ekek-d8-kekee | soosssssssssooss | 1364 | 1380 | 936 |
| 673374 | ATCTTTATCAGGTCTTT | ekek-d8-kekee | soosssssssssooss | 1368 | 1384 | 937 |
| 673375 | AATCTTTATCAGGTCTT | ekek-d8-kekee | soosssssssssooss | 1369 | 1385 | 938 |
| 673376 | TAATCTTTATCAGGTCT | ekek-d8-kekee | soosssssssssooss | 1370 | 1386 | 939 |
| 673377 | TTAATCTTTATCAGGTC | ekek-d8-kekee | soosssssssssooss | 1371 | 1387 | 940 |
| 673378 | GTTAATCTTTATCAGGT | ekek-d8-kekee | soosssssssssooss | 1372 | 1388 | 941 |
| 673379 | GGTTAATCTTTATCAGG | ekek-d8-kekee | soosssssssssooss | 1373 | 1389 | 942 |
| 673380 | TGGTTAATCTTTATCAG | ekek-d8-kekee | soosssssssssooss | 1374 | 1390 | 943 |
| 673381 | CTGGTTAATCTTTATCA | ekek-d8-kekee | soosssssssssooss | 1375 | 1391 | 944 |
| 673382 | TCTGGTTAATCTTTATC | ekek-d8-kekee | soosssssssssooss | 1376 | 1392 | 945 |
| 673383 | CCCTCCTTGTTTTCTTC | ekek-d8-kekee | soosssssssssooss | 1391 | 1407 | 946 |

TABLE 28-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673384 | TCCCTCCTTGTTTTCTT | ekek-d8-kekee | soosssssssssooss | 1392 | 1408 | 947 |
| 673385 | TTCCCTCCTTGTTTTCT | ekek-d8-kekee | soosssssssssooss | 1393 | 1409 | 948 |
| 673386 | TTTCCCTCCTTGTTTTC | ekek-d8-kekee | soosssssssssooss | 1394 | 1410 | 949 |
| 673387 | GTTTCCCTCCTTGTTTT | ekek-d8-kekee | soosssssssssooss | 1395 | 1411 | 950 |
| 673388 | TGTTTCCCTCCTTGTTT | ekek-d8-kekee | soosssssssssooss | 1396 | 1412 | 951 |
| 673389 | TTGTTTCCCTCCTTGTT | ekek-d8-kekee | soosssssssssooss | 1397 | 1413 | 952 |
| 673390 | GGTTGTTTCCCTCCTTG | ekek-d8-kekee | soosssssssssooss | 1399 | 1415 | 953 |
| 673391 | CGGTTGTTTCCCTCCTT | ekek-d8-kekee | soosssssssssooss | 1400 | 1416 | 954 |
| 673392 | GCGGTTGTTTCCCTCCT | ekek-d8-kekee | soosssssssssooss | 1401 | 1417 | 955 |
| 673393 | TGCGGTTGTTTCCCTCC | ekek-d8-kekee | soosssssssssooss | 1402 | 1418 | 956 |
| 673394 | CTGCGGTTGTTTCCCTC | ekek-d8-kekee | soosssssssssooss | 1403 | 1419 | 957 |
| 673395 | GCTGCGGTTGTTTCCCT | ekek-d8-kekee | soosssssssssooss | 1404 | 1420 | 958 |
| 673396 | GGCTGCGGTTGTTTCCC | ekek-d8-kekee | soosssssssssooss | 1405 | 1421 | 959 |
| 673397 | AGGCTGCGGTTGTTTCC | ekek-d8-kekee | soosssssssssooss | 1406 | 1422 | 960 |
| 673398 | CAGGCTGCGGTTGTTTC | ekek-d8-kekee | soosssssssssooss | 1407 | 1423 | 961 |
| 673399 | ACAGGCTGCGGTTGTTT | ekek-d8-kekee | soosssssssssooss | 1408 | 1424 | 962 |
| 673400 | TACAGGCTGCGGTTGTT | ekek-d8-kekee | soosssssssssooss | 1409 | 1425 | 963 |
| 673401 | CTACAGGCTGCGGTTGT | ekek-d8-kekee | soosssssssssooss | 1410 | 1426 | 964 |
| 673402 | GCTACAGGCTGCGGTTG | ekek-d8-kekee | soosssssssssooss | 1411 | 1427 | 965 |
| 673403 | TGCTACAGGCTGCGGTT | ekek-d8-kekee | soosssssssssooss | 1412 | 1428 | 966 |
| 673404 | TTGCTACAGGCTGCGGT | ekek-d8-kekee | soosssssssssooss | 1413 | 1429 | 967 |
| 673405 | CTTGCTACAGGCTGCGG | ekek-d8-kekee | soosssssssssooss | 1414 | 1430 | 968 |
| 673406 | GCTTGCTACAGGCTGCG | ekek-d8-kekee | soosssssssssooss | 1415 | 1431 | 969 |
| 673407 | AGCTTGCTACAGGCTGC | ekek-d8-kekee | soosssssssssooss | 1416 | 1432 | 970 |
| 673408 | GAGCTTGCTACAGGCTG | ekek-d8-kekee | soosssssssssooss | 1417 | 1433 | 971 |
| 673409 | AGAGCTTGCTACAGGCT | ekek-d8-kekee | soosssssssssooss | 1418 | 1434 | 972 |
| 673410 | CAGAGCTTGCTACAGGC | ekek-d8-kekee | soosssssssssooss | 1419 | 1435 | 973 |
| 673411 | CCAGAGCTTGCTACAGG | ekek-d8-kekee | soosssssssssooss | 1420 | 1436 | 974 |
| 673412 | TCCAGAGCTTGCTACAG | ekek-d8-kekee | soosssssssssooss | 1421 | 1437 | 975 |
| 673413 | TTCCAGAGCTTGCTACA | ekek-d8-kekee | soosssssssssooss | 1422 | 1438 | 976 |
| 673414 | GTTCCAGAGCTTGCTAC | ekek-d8-kekee | soosssssssssooss | 1423 | 1439 | 977 |
| 673415 | AGTTCCAGAGCTTGCTA | ekek-d8-kekee | soosssssssssooss | 1424 | 1440 | 978 |
| 673416 | GAGTTCCAGAGCTTGCT | ekek-d8-kekee | soosssssssssooss | 1425 | 1441 | 979 |
| 673417 | TGAGTTCCAGAGCTTGC | ekek-d8-kekee | soosssssssssooss | 1426 | 1442 | 980 |
| 673418 | CTGAGTTCCAGAGCTTG | ekek-d8-kekee | soosssssssssooss | 1427 | 1443 | 981 |
| 673419 | CCTGAGTTCCAGAGCTT | ekek-d8-kekee | soosssssssssooss | 1428 | 1444 | 982 |

TABLE 28-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673420 | TCCTGAGTTCCAGAGCT | ekek-d8-kekee | sooss ssssssss sooss | 1429 | 1445 | 983 |
| 673421 | CTCCTGAGTTCCAGAGC | ekek-d8-kekee | sooss ssssssss sooss | 1430 | 1446 | 984 |
| 673422 | ACTCCTGAGTTCCAGAG | ekek-d8-kekee | sooss ssssssss sooss | 1431 | 1447 | 985 |
| 673423 | GACTCCTGAGTTCCAGA | ekek-d8-kekee | sooss ssssssss sooss | 1432 | 1448 | 986 |
| 673424 | CGACTCCTGAGTTCCAG | ekek-d8-kekee | sooss ssssssss sooss | 1433 | 1449 | 987 |
| 673425 | GCGACTCCTGAGTTCCA | ekek-d8-kekee | sooss ssssssss sooss | 1434 | 1450 | 988 |
| 673426 | CGCGACTCCTGAGTTCC | ekek-d8-kekee | sooss ssssssss sooss | 1435 | 1451 | 989 |
| 673427 | GCGCGACTCCTGAGTTC | ekek-d8-kekee | sooss ssssssss sooss | 1436 | 1452 | 990 |
| 673428 | CGCGCGACTCCTGAGTT | ekek-d8-kekee | sooss ssssssss sooss | 1437 | 1453 | 991 |
| 673429 | GCGCGCGACTCCTGAGT | ekek-d8-kekee | sooss ssssssss sooss | 1438 | 1454 | 992 |
| 673430 | AGCGCGCGACTCCTGAG | ekek-d8-kekee | sooss ssssssss sooss | 1439 | 1455 | 993 |
| 673431 | TAGCGCGCGACTCCTGA | ekek-d8-kekee | sooss ssssssss sooss | 1440 | 1456 | 994 |
| 673432 | CTAGCGCGCGACTCCTG | ekek-d8-kekee | sooss ssssssss sooss | 1441 | 1457 | 995 |
| 673433 | CCTAGCGCGCGACTCCT | ekek-d8-kekee | sooss ssssssss sooss | 1442 | 1458 | 996 |
| 673434 | CCCTAGCGCGCGACTCC | ekek-d8-kekee | sooss ssssssss sooss | 1443 | 1459 | 997 |
| 673435 | CCCCTAGCGCGCGACTC | ekek-d8-kekee | sooss ssssssss sooss | 1444 | 1460 | 998 |
| 673436 | GCCCCTAGCGCGCGACT | ekek-d8-kekee | sooss ssssssss sooss | 1445 | 1461 | 999 |
| 673437 | GGCCCCTAGCGCGCGAC | ekek-d8-kekee | sooss ssssssss sooss | 1446 | 1462 | 1000 |
| 673438 | CGGCCCCTAGCGCGCGA | ekek-d8-kekee | sooss ssssssss sooss | 1447 | 1463 | 1001 |
| 673439 | CCGGCCCCTAGCGCGCG | ekek-d8-kekee | sooss ssssssss sooss | 1448 | 1464 | 1002 |
| 673440 | CCCGGCCCCTAGCGCGC | ekek-d8-kekee | sooss ssssssss sooss | 1449 | 1465 | 1003 |
| 673441 | CCCCGGCCCCTAGCGCG | ekek-d8-kekee | sooss ssssssss sooss | 1450 | 1466 | 1004 |
| 673442 | GCCCCGGCCCCTAGCGC | ekek-d8-kekee | sooss ssssssss sooss | 1451 | 1467 | 1005 |
| 673443 | GGCCCCGGCCCCTAGCG | ekek-d8-kekee | sooss ssssssss sooss | 1452 | 1468 | 1006 |
| 673444 | CGGCCCCGGCCCCTAGC | ekek-d8-kekee | sooss ssssssss sooss | 1453 | 1469 | 1007 |
| 673445 | CCGGCCCCGGCCCCTAG | ekek-d8-kekee | sooss ssssssss sooss | 1454 | 1470 | 1008 |
| 673446 | CCCGGCCCCGGCCCCTA | ekek-d8-kekee | sooss ssssssss sooss | 1455 | 1471 | 1009 |
| 673447 | ACGCCCCGGCCCCGGCC | ekek-d8-kekee | sooss ssssssss sooss | 1465 | 1481 | 1010 |
| 673448 | CACGCCCCGGCCCCGGC | ekek-d8-kekee | sooss ssssssss sooss | 1466 | 1482 | 1011 |
| 673449 | CCACGCCCCGGCCCCGG | ekek-d8-kekee | sooss ssssssss sooss | 1467 | 1483 | 1012 |
| 673450 | ACCACGCCCCGGCCCCG | ekek-d8-kekee | sooss ssssssss sooss | 1468 | 1484 | 1013 |
| 673451 | GACCACGCCCCGGCCCC | ekek-d8-kekee | sooss ssssssss sooss | 1469 | 1485 | 1014 |
| 673452 | CGACCACGCCCCGGCCC | ekek-d8-kekee | sooss ssssssss sooss | 1470 | 1486 | 1015 |
| 673453 | CCGACCACGCCCCGGCC | ekek-d8-kekee | sooss ssssssss sooss | 1471 | 1487 | 1016 |
| 673454 | CCCGACCACGCCCCGGC | ekek-d8-kekee | sooss ssssssss sooss | 1472 | 1488 | 1017 |
| 673455 | CCCCGACCACGCCCCGG | ekek-d8-kekee | sooss ssssssss sooss | 1473 | 1489 | 1018 |

TABLE 28-continued

Deoxy, MOE and cEt oligonucleotides targeting SEQ ID NO: 2

| ISIS NO | Sequence | Chemistry | Linkage | SEQ ID NO: 2 Start Site | SEQ ID NO: 2 Stop Site | SEQ ID NO |
|---|---|---|---|---|---|---|
| 673456 | GCCCCGACCACGCCCCG | ekek-d8-kekee | sooossssssssssooss | 1474 | 1490 | 1019 |
| 673457 | CGCCCCGACCACGCCCC | ekek-d8-kekee | sooossssssssssooss | 1475 | 1491 | 1020 |
| 673458 | CCGCCCCGACCACGCCC | ekek-d8-kekee | sooossssssssssooss | 1476 | 1492 | 1021 |
| 673459 | CCCGCCCCGACCACGCC | ekek-d8-kekee | sooossssssssssooss | 1477 | 1493 | 1022 |
| 673460 | GCCCGCCCCGACCACGC | ekek-d8-kekee | sooossssssssssooss | 1478 | 1494 | 1023 |
| 673461 | GGCCCGCCCCGACCACG | ekek-d8-kekee | sooossssssssssooss | 1479 | 1495 | 1024 |
| 673462 | GGGCCCGCCCCGACCAC | ekek-d8-kekee | sooossssssssssooss | 1480 | 1496 | 1025 |
| 673463 | CGGGCCCGCCCCGACCA | ekek-d8-kekee | sooossssssssssooss | 1481 | 1497 | 1026 |
| 673464 | CCGGGCCCGCCCCGACC | ekek-d8-kekee | sooossssssssssooss | 1482 | 1498 | 1027 |
| 673465 | CCCGGGCCCGCCCCGAC | ekek-d8-kekee | sooossssssssssooss | 1483 | 1499 | 1028 |
| 673466 | GCAGCCCCGCCCCGGGC | ekek-d8-kekee | sooossssssssssooss | 1505 | 1521 | 1029 |
| 673467 | CGCAGCCCCGCCCCGGG | ekek-d8-kekee | sooossssssssssooss | 1506 | 1522 | 1030 |
| 673468 | CCGCAGCCCCGCCCCGG | ekek-d8-kekee | sooossssssssssooss | 1507 | 1523 | 1031 |
| 673469 | ACCGCAGCCCCGCCCCG | ekek-d8-kekee | sooossssssssssooss | 1508 | 1524 | 1032 |
| 673470 | AACCGCAGCCCCGCCCC | ekek-d8-kekee | sooossssssssssooss | 1509 | 1525 | 1033 |
| 673471 | CAACCGCAGCCCCGCCC | ekek-d8-kekee | sooossssssssssooss | 1510 | 1526 | 1034 |
| 673472 | GCAACCGCAGCCCCGCC | ekek-d8-kekee | sooossssssssssooss | 1511 | 1527 | 1035 |
| 673473 | CGCAACCGCAGCCCCGC | ekek-d8-kekee | sooossssssssssooss | 1512 | 1528 | 1036 |
| 673474 | CCGCAACCGCAGCCCCG | ekek-d8-kekee | sooossssssssssooss | 1513 | 1529 | 1037 |
| 673475 | ACCGCAACCGCAGCCCC | ekek-d8-kekee | sooossssssssssooss | 1514 | 1530 | 1038 |
| 673476 | CACCGCAACCGCAGCCC | ekek-d8-kekee | sooossssssssssooss | 1515 | 1531 | 1039 |
| 673477 | GCACCGCAACCGCAGCC | ekek-d8-kekee | sooossssssssssooss | 1516 | 1532 | 1040 |
| 673478 | GGCACCGCAACCGCAGC | ekek-d8-kekee | sooossssssssssooss | 1517 | 1533 | 1041 |
| 673479 | AGGCACCGCAACCGCAG | ekek-d8-kekee | sooossssssssssooss | 1518 | 1534 | 1042 |
| 673480 | CAGGCACCGCAACCGCA | ekek-d8-kekee | sooossssssssssooss | 1519 | 1535 | 1043 |
| 673481 | GCAGGCACCGCAACCGC | ekek-d8-kekee | sooossssssssssooss | 1520 | 1536 | 1044 |
| 673482 | CGCAGGCACCGCAACCG | ekek-d8-kekee | sooossssssssssooss | 1521 | 1537 | 1045 |
| 673483 | GCGCAGGCACCGCAACC | ekek-d8-kekee | sooossssssssssooss | 1522 | 1538 | 1046 |
| 673484 | GGCGCAGGCACCGCAAC | ekek-d8-kekee | sooossssssssssooss | 1523 | 1539 | 1047 |

TABLE 29

5-10-5 MOE gapmers targeting SEQ ID NO: 2

| ISIS NO | Sequence | Linkage | SEQ ID NO: 2 Start Site | SEQ ID NO: 2 Stop Site | SEQ ID NO |
|---|---|---|---|---|---|
| 653222 | CCACTCGCCACCGCCTGCGC | soooosssssssssssooss | 1553 | 1572 | 1048 |
| 653223 | TGCATTCCTAAGCAATGTGT | soooosssssssssssooss | 5325 | 5344 | 1049 |
| 655016 | CCCGGCCCCGGCCCCGGCCC | soooosssssssssssooss | 1458 | 1477 | 1050 |
| 655017 | CCCCGGCCCCGGCCCCGGCC | soooosssssssssssooss | 1459 | 1478 | 1051 |
| 671081 | TTACATCTATAGCACCACTC | soooosssssssssssooss | 8110 | 8129 | 1052 |
| 671082 | TCACTCCCTTTTCAGACAAG | soooosssssssssssooss | 8140 | 8159 | 1053 |
| 671083 | AACTAAGTTCTGTCTGTGGA | soooosssssssssssooss | 8230 | 8249 | 1054 |
| 671084 | ATACAGGACTAAAGTGCTTC | soooosssssssssssooss | 14316 | 14335 | 1055 |

TABLE 30

5-10-5 MOE gapmers targeting SEQ ID NO: 1

| ISIS NO | Sequence | Linkage | SEQ ID NO: 1 Start Site | SEQ ID NO: 1 Stop Site | SEQ ID NO |
|---|---|---|---|---|---|
| 672561 | CTCTGACCCTGATCTTCCAT | soooosssssssssssooss | 695 | 714 | 1056 |

Example 7: In Vivo Rodent Inhibition and Tolerability with Treatment of C9ORF72 Antisense Oligonucleotides In order to assess the tolerability of inhibition of C9ORF72 expression in vivo, antisense oligonucleotides targeting a murine C9ORF72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 11 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A; wherein 's' denotes a phosphorothioate internucleoside linkage; 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 12 (GENBANK Accession No. NM_001007702.1).

Mouse Experiment 1

Groups of 4 C57BL/6 mice each were injected with 50 µg, 100 µg, 300 µg, 500 µg, or 700 µg of ISIS 571883 administered via an intracerebroventricular bolus injection. A control group of four C57/BL6 mice were similarly treated with PBS. Animals were anesthetized with 3% isofluorane and placed in a stereotactic frame. After sterilizing the surgical site, each mouse was injected −0.2 mm anterior-posterior from the bregma na d 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9ORF72 mRNA expression. C9ORF72 mRNA expression was measured by RT-PCR. The data is presented in Table 31. The results indicate that treatment with increasing doses of ISIS 571883 resulted in dose-dependent inhibition of C9ORF72 mRNA expression.

The induction of the microglial marker AIF-1 as a measure of CNS toxicity was also assessed. The data is presented in Table 32. The results indicate that treatment with increasing doses of ISIS 571883 did not result in significant increases in AIF-1 mRNA expression. Hence, the injection of ISIS 571883 was deemed tolerable in this model.

TABLE 31

Percentage inhibition of C9ORF72 mRNA expression compared to the PBS control

| Dose (μg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 32

Percentage expression of AIF-1 mRNA expression compared to the PBS control

| Dose (μg) | Posterior brain | Spinal cord |
|---|---|---|
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 μg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 33 and 34. The results indicate that there were no significant changes in the motor behavior of the mice as a result of antisense inhibition of ISIS 571883 or due to the ICV injection. Hence, antisense inhibition of C9ORF72 was deemed tolerable in this model.

TABLE 33

Latency to fall (sec) in the rotarod assay

| Weeks after injection | PBS | ISIS 571883 |
|---|---|---|
| 0 | 66 | 66 |
| 4 | 91 | 70 |
| 8 | 94 | 84 |

TABLE 34

Mean hindlimb grip strength (g) in the grip strength assay

| Weeks after injection | PBS | ISIS 571883 |
|---|---|---|
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 μg, 1,000 μg, or 3,000 μg of ISIS 603538 administered via an intrathecal bolus injection. A control group of four Sprague-Dawley rats were similarly treated with PBS. Animals were anesthetized with 3% isofluorane and placed in a stereotactic frame. After sterilizing the surgical site, each rat was injected with 30 μL of ASO solution administered via 8 cm intrathecal catheter 2 cm into the spinal canal with a 50 μL flush. The rats were allowed to recover for 4 weeks, after which animals were euthanized according to a humane protocol approved by the Institutional Animal Care and Use Committee.

RNA Analysis

RNA was extracted from a 2-3 mm brain section posterior to the injection site, from brain frontal cortex, and from the cervical and lumbar sections of the spinal cord tissue for analysis of C9ORF72 mRNA expression. C9ORF72 mRNA expression was measured by RT-PCR. The data is presented in Table 35. The results indicate that treatment with increasing doses of ISIS 603538 resulted in dose-dependent inhibition of C9ORF72 mRNA expression.

The induction of the microglial marker AIF-1 as a measure of CNS toxicity was also assessed. The data is presented in Table 36. The results indicate that treatment with increasing doses of ISIS 603538 did not result in significant increases in AIF-1 mRNA expression. Hence, the injection of ISIS 603538 was deemed tolerable in this model.

TABLE 35

Percentage inhibition of C9ORF72 mRNA expression compared to the PBS control

| Dose (μg) | Brain (1 mm section) | Cortex | Spinal cord (lumbar) | Spinal cord (cervical) |
|---|---|---|---|---|
| 700 | 21 | 4 | 86 | 74 |
| 1000 | 53 | 49 | 88 | 82 |
| 3000 | 64 | 62 | 88 | 80 |

TABLE 36

Percentage expression of AIF-1 mRNA expression compared to the PBS control

| Dose (μg) | Brain (1 mm section) | Cortex | Spinal cord (lumbar) | Spinal cord (cervical) |
|---|---|---|---|---|
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 37. The results indicate that treatment with increasing doses of ISIS 603538 did not have any significant changes in the body weights of the rats.

TABLE 37

Body weights of the rats (% initial body weight)

|  | Dose (μg) | Week 1 | Week 2 | Week 3 | Week 4 | Week 5 |
|---|---|---|---|---|---|---|
| PBS |  | 100 | 94 | 103 | 105 | 109 |
| ISIS 603538 | 700 | 100 | 94 | 98 | 103 | 107 |
|  | 1000 | 100 | 95 | 97 | 101 | 103 |
|  | 3000 | 100 | 92 | 98 | 102 | 105 |

Example 8: Antisense Inhibition of C9ORF72 by 5-8-5 MOE Gapmers with Mixed Backbones and Deoxy, MOE and cEt Antisense Oligonucleotides with Mixed Backbones Antisense oligonucleotides described in Example 6 hereinabove (see Table 23 and Table 24 hereinabove) were tested in HepG2 cells in a series of experiments that had similar culture conditions. ISIS 576816, previously tested in PCT/US2013/065073 (claiming priority to U.S. Application No. 61/714,132, filed Oct. 15, 2012, was used as a benchmark oligonucleotide for study with deoxy, MOE, and cEt antisense oligonucleotides. The results for each experiment are presented in tables shown below. Cultured HepG2 cells at a density of 20,000 cells per well were transfected using electroporation with 500 nM antisense oligonucleotide. After a treatment period of approximately 24 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. The levels of the C9ORF72 pathogenic associated mRNA variant were normalized to the total RNA content of the cell, as measured by RIBOGREEN®. Results are presented as percent inhibition of C9ORF72, relative to untreated control cells.

TABLE 38

Percent inhibition of the C9ORF72 pathogenic associated mRNA variant compared to PBS control by 5-8-5 MOE gapmers with mixed backbones targeting SEQ ID NO: 2

| ISIS NO | Sequence | Linkage | SEQ ID NO: 2 Start Site | SEQ ID NO: 2 Stop Site | % inhibition | SEQ ID NO |
|---|---|---|---|---|---|---|
| 672581 | GTGAGAGCAAGTAGTGGG | sooosssssssssssooss | 1326 | 1343 | 11 | 744 |
| 672582 | TGTGAGAGCAAGTAGTGG | sooosssssssssssooss | 1327 | 1344 | 32 | 745 |
| 672583 | CTGTGAGAGCAAGTAGTG | sooosssssssssssooss | 1328 | 1345 | 14 | 746 |
| 672584 | ACTGTGAGAGCAAGTAGT | sooosssssssssssooss | 1329 | 1346 | 1 | 747 |
| 672585 | TACTGTGAGAGCAAGTAG | sooosssssssssssooss | 1330 | 1347 | 14 | 748 |
| 672586 | GTACTGTGAGAGCAAGTA | sooosssssssssssooss | 1331 | 1348 | 22 | 749 |
| 672587 | AGTACTGTGAGAGCAAGT | sooosssssssssssooss | 1332 | 1349 | 0 | 750 |
| 672588 | GAGTACTGTGAGAGCAAG | sooosssssssssssooss | 1333 | 1350 | 8 | 751 |
| 672589 | CGAGTACTGTGAGAGCAA | sooosssssssssssooss | 1334 | 1351 | 15 | 752 |
| 672590 | GCGAGTACTGTGAGAGCA | sooosssssssssssooss | 1335 | 1352 | 13 | 753 |
| 672591 | AGCGAGTACTGTGAGAGC | sooosssssssssssooss | 1336 | 1353 | 32 | 754 |
| 672592 | CAGCGAGTACTGTGAGAG | sooosssssssssssooss | 1337 | 1354 | 39 | 755 |
| 672593 | TCAGCGAGTACTGTGAGA | sooosssssssssssooss | 1338 | 1355 | 15 | 756 |
| 672594 | CTCAGCGAGTACTGTGAG | sooosssssssssssooss | 1339 | 1356 | 14 | 757 |
| 672595 | CCTCAGCGAGTACTGTGA | sooosssssssssssooss | 1340 | 1357 | 40 | 758 |
| 672596 | CCCTCAGCGAGTACTGTG | sooosssssssssssooss | 1341 | 1358 | 28 | 759 |
| 672597 | ACCCTCAGCGAGTACTGT | sooosssssssssssooss | 1342 | 1359 | 30 | 760 |
| 672598 | CACCCTCAGCGAGTACTG | sooosssssssssssooss | 1343 | 1360 | 46 | 761 |
| 672599 | TCACCCTCAGCGAGTACT | sooosssssssssssooss | 1344 | 1361 | 40 | 762 |
| 672600 | TTCACCCTCAGCGAGTAC | sooosssssssssssooss | 1345 | 1362 | 25 | 763 |
| 672601 | GTTCACCCTCAGCGAGTA | sooosssssssssssooss | 1346 | 1363 | 15 | 764 |
| 672602 | TGTTCACCCTCAGCGAGT | sooosssssssssssooss | 1347 | 1364 | 35 | 765 |
| 672603 | TTGTTCACCCTCAGCGAG | sooosssssssssssooss | 1348 | 1365 | 22 | 766 |

TABLE 38-continued

Percent inhibition of the C9ORF72 pathogenic associated mRNA variant compared to PBS control by 5-8-5 MOE gapmers with mixed backbones targeting SEQ ID NO: 2

| ISIS NO | Sequence | Linkage | SEQ ID NO: 2 Start Site | SEQ ID NO: 2 Stop Site | % inhibition | SEQ ID NO |
|---|---|---|---|---|---|---|
| 672604 | CTTGTTCACCCTCAGCGA | sooossssssssssooss | 1349 | 1366 | 6 | 767 |
| 672605 | TCTTGTTCACCCTCAGCG | sooossssssssssooss | 1350 | 1367 | 26 | 768 |
| 672606 | TTCTTGTTCACCCTCAGC | sooossssssssssooss | 1351 | 1368 | 11 | 769 |
| 672607 | TTTCTTGTTCACCCTCAG | sooossssssssssooss | 1352 | 1369 | 9 | 770 |
| 672608 | TTTTCTTGTTCACCCTCA | sooossssssssssooss | 1353 | 1370 | 36 | 771 |
| 672609 | CTTTTCTTGTTCACCCTC | sooossssssssssooss | 1354 | 1371 | 25 | 772 |
| 672610 | TCTTTTCTTGTTCACCCT | sooossssssssssooss | 1355 | 1372 | 16 | 773 |
| 672611 | GTCTTTTCTTGTTCACCC | sooossssssssssooss | 1356 | 1373 | 45 | 774 |
| 672612 | GGTCTTTTCTTGTTCACC | sooossssssssssooss | 1357 | 1374 | 15 | 775 |
| 672613 | AGGTCTTTTCTTGTTCAC | sooossssssssssooss | 1358 | 1375 | 10 | 776 |
| 672614 | CAGGTCTTTTCTTGTTCA | sooossssssssssooss | 1359 | 1376 | 25 | 777 |
| 672615 | TCAGGTCTTTTCTTGTTC | sooossssssssssooss | 1360 | 1377 | 21 | 778 |
| 672616 | ATCAGGTCTTTTCTTGTT | sooossssssssssooss | 1361 | 1378 | 15 | 779 |
| 672617 | TATCAGGTCTTTTCTTGT | sooossssssssssooss | 1362 | 1379 | 27 | 780 |
| 672618 | TTATCAGGTCTTTTCTTG | sooossssssssssooss | 1363 | 1380 | 14 | 781 |
| 672619 | TTTATCAGGTCTTTTCTT | sooossssssssssooss | 1364 | 1381 | 46 | 782 |
| 672620 | AATCTTTATCAGGTCTTT | sooossssssssssooss | 1368 | 1385 | 31 | 783 |
| 672621 | TAATCTTTATCAGGTCTT | sooossssssssssooss | 1369 | 1386 | 12 | 784 |
| 672622 | TTAATCTTTATCAGGTCT | sooossssssssssooss | 1370 | 1387 | 27 | 785 |
| 672623 | GTTAATCTTTATCAGGTC | sooossssssssssooss | 1371 | 1388 | 9 | 786 |
| 672624 | GGTTAATCTTTATCAGGT | sooossssssssssooss | 1372 | 1389 | 53 | 787 |
| 672625 | TGGTTAATCTTTATCAGG | sooossssssssssooss | 1373 | 1390 | 17 | 788 |
| 672626 | CTGGTTAATCTTTATCAG | sooossssssssssooss | 1374 | 1391 | 11 | 789 |
| 672627 | TCTGGTTAATCTTTATCA | sooossssssssssooss | 1375 | 1392 | 16 | 790 |
| 672628 | TTCTGGTTAATCTTTATC | sooossssssssssooss | 1376 | 1393 | 22 | 791 |
| 672629 | TCCCTCCTTGTTTTCTTC | sooossssssssssooss | 1391 | 1408 | 0 | 792 |
| 672630 | TTTCCCTCCTTGTTTTCT | sooossssssssssooss | 1393 | 1410 | 8 | 793 |
| 672631 | GTTTCCCTCCTTGTTTTC | sooossssssssssooss | 1394 | 1411 | 0 | 794 |
| 672632 | TGTTTCCCTCCTTGTTTT | sooossssssssssooss | 1395 | 1412 | 25 | 795 |
| 672633 | TTGTTTCCCTCCTTGTTT | sooossssssssssooss | 1396 | 1413 | 0 | 796 |
| 672634 | GTTGTTTCCCTCCTTGTT | sooossssssssssooss | 1397 | 1414 | 10 | 797 |
| 672635 | GGTTGTTTCCCTCCTTGT | sooossssssssssooss | 1398 | 1415 | 15 | 798 |
| 672636 | CGGTTGTTTCCCTCCTTG | sooossssssssssooss | 1399 | 1416 | 49 | 799 |
| 672637 | GCGGTTGTTTCCCTCCTT | sooossssssssssooss | 1400 | 1417 | 49 | 800 |
| 672638 | TGCGGTTGTTTCCCTCCT | sooossssssssssooss | 1401 | 1418 | 23 | 801 |
| 672639 | CTGCGGTTGTTTCCCTCC | sooossssssssssooss | 1402 | 1419 | 21 | 802 |

TABLE 38-continued

Percent inhibition of the C9ORF72 pathogenic associated mRNA variant compared to PBS control by 5-8-5 MOE gapmers with mixed backbones targeting SEQ ID NO: 2

| ISIS NO | Sequence | Linkage | SEQ ID NO: 2 Start Site | SEQ ID NO: 2 Stop Site | % inhibition | SEQ ID NO |
|---|---|---|---|---|---|---|
| 672640 | GCTGCGGTTGTTTCCCTC | sooossssssssssooss | 1403 | 1420 | 52 | 803 |
| 672641 | GGCTGCGGTTGTTTCCCT | sooossssssssssooss | 1404 | 1421 | 23 | 804 |
| 672642 | AGGCTGCGGTTGTTTCCC | sooossssssssssooss | 1405 | 1422 | 35 | 805 |
| 672643 | CAGGCTGCGGTTGTTTCC | sooossssssssssooss | 1406 | 1423 | 22 | 806 |
| 672644 | ACAGGCTGCGGTTGTTTC | sooossssssssssooss | 1407 | 1424 | 27 | 807 |
| 672645 | TACAGGCTGCGGTTGTTT | sooossssssssssooss | 1408 | 1425 | 21 | 808 |
| 672646 | CTACAGGCTGCGGTTGTT | sooossssssssssooss | 1409 | 1426 | 18 | 809 |
| 672647 | GCTACAGGCTGCGGTTGT | sooossssssssssooss | 1410 | 1427 | 16 | 810 |
| 672648 | TGCTACAGGCTGCGGTTG | sooossssssssssooss | 1411 | 1428 | 10 | 811 |
| 672649 | TTGCTACAGGCTGCGGTT | sooossssssssssooss | 1412 | 1429 | 0 | 812 |
| 672650 | CTTGCTACAGGCTGCGGT | sooossssssssssooss | 1413 | 1430 | 27 | 813 |
| 672651 | GCTTGCTACAGGCTGCGG | sooossssssssssooss | 1414 | 1431 | 53 | 814 |
| 672652 | AGCTTGCTACAGGCTGCG | sooossssssssssooss | 1415 | 1432 | 38 | 815 |
| 672653 | GAGCTTGCTACAGGCTGC | sooossssssssssooss | 1416 | 1433 | 7 | 816 |
| 672654 | AGAGCTTGCTACAGGCTG | sooossssssssssooss | 1417 | 1434 | 7 | 817 |
| 672655 | CAGAGCTTGCTACAGGCT | sooossssssssssooss | 1418 | 1435 | 15 | 818 |
| 672656 | CCAGAGCTTGCTACAGGC | sooossssssssssooss | 1419 | 1436 | 22 | 819 |
| 672657 | TCCAGAGCTTGCTACAGG | sooossssssssssooss | 1420 | 1437 | 43 | 820 |
| 672658 | TTCCAGAGCTTGCTACAG | sooossssssssssooss | 1421 | 1438 | 20 | 821 |
| 672659 | GTTCCAGAGCTTGCTACA | sooossssssssssooss | 1422 | 1439 | 12 | 822 |
| 672660 | AGTTCCAGAGCTTGCTAC | sooossssssssssooss | 1423 | 1440 | 11 | 823 |
| 672661 | GAGTTCCAGAGCTTGCTA | sooossssssssssooss | 1424 | 1441 | 39 | 824 |
| 672662 | TGAGTTCCAGAGCTTGCT | sooossssssssssooss | 1425 | 1442 | 18 | 825 |
| 672663 | CTGAGTTCCAGAGCTTGC | sooossssssssssooss | 1426 | 1443 | 26 | 826 |
| 672664 | CCTGAGTTCCAGAGCTTG | sooossssssssssooss | 1427 | 1444 | 69 | 827 |
| 672665 | TCCTGAGTTCCAGAGCTT | sooossssssssssooss | 1428 | 1445 | 56 | 828 |
| 672666 | CTCCTGAGTTCCAGAGCT | sooossssssssssooss | 1429 | 1446 | 28 | 829 |
| 672667 | ACTCCTGAGTTCCAGAGC | sooossssssssssooss | 1430 | 1447 | 51 | 830 |
| 672668 | GACTCCTGAGTTCCAGAG | sooossssssssssooss | 1431 | 1448 | 39 | 831 |
| 672669 | CGACTCCTGAGTTCCAGA | sooossssssssssooss | 1432 | 1449 | 32 | 832 |
| 672670 | GCGACTCCTGAGTTCCAG | sooossssssssssooss | 1433 | 1450 | 66 | 833 |
| 672671 | CGCGACTCCTGAGTTCCA | sooossssssssssooss | 1434 | 1451 | 67 | 834 |
| 672672 | GCGCGACTCCTGAGTTCC | sooossssssssssooss | 1435 | 1452 | 48 | 835 |
| 672673 | CGCGCGACTCCTGAGTTC | sooossssssssssooss | 1436 | 1453 | 38 | 836 |
| 672674 | GCGCGCGACTCCTGAGTT | sooossssssssssooss | 1437 | 1454 | 53 | 837 |

TABLE 38-continued

Percent inhibition of the C9ORF72 pathogenic associated mRNA variant compared to PBS control by 5-8-5 MOE gapmers with mixed backbones targeting SEQ ID NO: 2

| ISIS NO | Sequence | Linkage | SEQ ID NO: 2 Start Site | SEQ ID NO: 2 Stop Site | % inhibition | SEQ ID NO |
|---|---|---|---|---|---|---|
| 672675 | AGCGCGCGACTCCTGAGT | sooossssssssssooss | 1438 | 1455 | 58 | 838 |
| 672676 | TAGCGCGCGACTCCTGAG | sooossssssssssooss | 1439 | 1456 | 55 | 839 |
| 672677 | CTAGCGCGCGACTCCTGA | sooossssssssssooss | 1440 | 1457 | 47 | 840 |
| 672678 | CCTAGCGCGCGACTCCTG | sooossssssssssooss | 1441 | 1458 | 56 | 841 |
| 672679 | CCCTAGCGCGCGACTCCT | sooossssssssssooss | 1442 | 1459 | 74 | 842 |
| 672680 | CCCCTAGCGCGCGACTCC | sooossssssssssooss | 1443 | 1460 | 43 | 843 |
| 672681 | GCCCCTAGCGCGCGACTC | sooossssssssssooss | 1444 | 1461 | 53 | 844 |
| 672682 | GGCCCCTAGCGCGCGACT | sooossssssssssooss | 1445 | 1462 | 42 | 845 |
| 672683 | CGGCCCCTAGCGCGCGAC | sooossssssssssooss | 1446 | 1463 | 69 | 846 |
| 672684 | CCGGCCCCTAGCGCGCGA | sooossssssssssooss | 1447 | 1464 | 29 | 847 |
| 672685 | CCCGGCCCCTAGCGCGCG | sooossssssssssooss | 1448 | 1465 | 21 | 848 |
| 672686 | CCCCGGCCCCTAGCGCGC | sooossssssssssooss | 1449 | 1466 | 35 | 849 |
| 672687 | GCCCCGGCCCCTAGCGCG | sooossssssssssooss | 1450 | 1467 | 41 | 850 |
| 672688 | GGCCCCGGCCCCTAGCGC | sooossssssssssooss | 1451 | 1468 | 46 | 851 |
| 672689 | CGGCCCCGGCCCCTAGCG | sooossssssssssooss | 1452 | 1469 | 28 | 852 |
| 672690 | CCGGCCCCGGCCCCTAGC | sooossssssssssooss | 1453 | 1470 | 33 | 853 |
| 672691 | CCCGGCCCCGGCCCCTAG | sooossssssssssooss | 1454 | 1471 | 10 | 854 |
| 672692 | CCCCGGCCCCGGCCCCTA | sooossssssssssooss | 1455 | 1472 | 35 | 855 |
| 672693 | ACGCCCCGGCCCCGGCCC | sooossssssssssooss | 1464 | 1481 | 57 | 856 |
| 672694 | CACGCCCCGGCCCCGGCC | sooossssssssssooss | 1465 | 1482 | 39 | 857 |
| 672695 | CCACGCCCCGGCCCCGGC | sooossssssssssooss | 1466 | 1483 | 48 | 858 |
| 672696 | ACCACGCCCCGGCCCCGG | sooossssssssssooss | 1467 | 1484 | 39 | 859 |
| 672697 | GACCACGCCCCGGCCCCG | sooossssssssssooss | 1468 | 1485 | 54 | 860 |
| 672698 | CGACCACGCCCCGGCCCC | sooossssssssssooss | 1469 | 1486 | 48 | 861 |
| 672699 | CCGACCACGCCCCGGCCC | sooossssssssssooss | 1470 | 1487 | 52 | 862 |
| 672700 | CCCGACCACGCCCCGGCC | sooossssssssssooss | 1471 | 1488 | 67 | 863 |
| 672701 | CCCCGACCACGCCCCGGC | sooossssssssssooss | 1472 | 1489 | 42 | 864 |
| 672702 | GCCCCGACCACGCCCCGG | sooossssssssssooss | 1473 | 1490 | 11 | 865 |
| 672703 | CGCCCCGACCACGCCCCG | sooossssssssssooss | 1474 | 1491 | 23 | 866 |
| 672704 | CCGCCCCGACCACGCCCC | sooossssssssssooss | 1475 | 1492 | 50 | 867 |
| 672705 | CCCGCCCCGACCACGCCC | sooossssssssssooss | 1476 | 1493 | 23 | 868 |
| 672706 | GCCCGCCCCGACCACGCC | sooossssssssssooss | 1477 | 1494 | 24 | 869 |
| 672707 | GGCCCGCCCCGACCACGC | sooossssssssssooss | 1478 | 1495 | 44 | 870 |
| 672708 | GGGCCCGCCCCGACCACG | sooossssssssssooss | 1479 | 1496 | 29 | 871 |
| 672709 | CGGGCCCGCCCCGACCAC | sooossssssssssooss | 1480 | 1497 | 7 | 872 |
| 672710 | CCGGGCCCGCCCCGACCA | sooossssssssssooss | 1481 | 1498 | 30 | 873 |

TABLE 38-continued

Percent inhibition of the C9ORF72 pathogenic associated mRNA variant compared to PBS control by 5-8-5 MOE gapmers with mixed backbones targeting SEQ ID NO: 2

| ISIS NO | Sequence | Linkage | SEQ ID NO: 2 Start Site | SEQ ID NO: 2 Stop Site | % inhibition | SEQ ID NO |
|---|---|---|---|---|---|---|
| 672711 | CCCGGGCCCGCCCCGACC | sooosssssssssooss | 1482 | 1499 | 16 | 874 |
| 672712 | CCCCGGGCCCGCCCCGAC | sooosssssssssooss | 1483 | 1500 | 14 | 875 |
| 672713 | AGCCCCGCCCCGGGCCCG | sooosssssssssooss | 1502 | 1519 | 32 | 876 |
| 672714 | CAGCCCCGCCCCGGGCCC | sooosssssssssooss | 1503 | 1520 | 22 | 877 |
| 672715 | GCAGCCCCGCCCCGGGCC | sooosssssssssooss | 1504 | 1521 | 1 | 878 |
| 672716 | CGCAGCCCCGCCCCGGGC | sooosssssssssooss | 1505 | 1522 | 29 | 879 |
| 672717 | CCGCAGCCCCGCCCCGGG | sooosssssssssooss | 1506 | 1523 | 51 | 880 |
| 672718 | ACCGCAGCCCCGCCCCGG | sooosssssssssooss | 1507 | 1524 | 45 | 881 |
| 672719 | AACCGCAGCCCCGCCCCG | sooosssssssssooss | 1508 | 1525 | 12 | 882 |
| 672720 | CAACCGCAGCCCCGCCCC | sooosssssssssooss | 1509 | 1526 | 7 | 883 |
| 672721 | GCAACCGCAGCCCCGCCC | sooosssssssssooss | 1510 | 1527 | 38 | 884 |
| 672722 | CGCAACCGCAGCCCCGCC | sooosssssssssooss | 1511 | 1528 | 34 | 885 |
| 672723 | CCGCAACCGCAGCCCCGC | sooosssssssssooss | 1512 | 1529 | 58 | 886 |
| 672724 | ACCGCAACCGCAGCCCCG | sooosssssssssooss | 1513 | 1530 | 39 | 887 |
| 672725 | CACCGCAACCGCAGCCCC | sooosssssssssooss | 1514 | 1531 | 43 | 888 |
| 672726 | GCACCGCAACCGCAGCCC | sooosssssssssooss | 1515 | 1532 | 41 | 889 |
| 672727 | GGCACCGCAACCGCAGCC | sooosssssssssooss | 1516 | 1533 | 18 | 890 |
| 672728 | AGGCACCGCAACCGCAGC | sooosssssssssooss | 1517 | 1534 | 53 | 891 |
| 672729 | CAGGCACCGCAACCGCAG | sooosssssssssooss | 1518 | 1535 | 26 | 892 |
| 672730 | GCAGGCACCGCAACCGCA | sooosssssssssooss | 1519 | 1536 | 54 | 893 |
| 672731 | CGCAGGCACCGCAACCGC | sooosssssssssooss | 1520 | 1537 | 41 | 894 |
| 672732 | GCGCAGGCACCGCAACCG | sooosssssssssooss | 1521 | 1538 | 46 | 895 |
| 672733 | GGCGCAGGCACCGCAACC | sooosssssssssooss | 1522 | 1539 | 7 | 896 |
| 672734 | GGGCGCAGGCACCGCAAC | sooosssssssssooss | 1523 | 1540 | 26 | 897 |

TABLE 39

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 576816 | GCCTTACTCTAGGACCAAGA | eeeee-d10-eeeee | ssssssssssssssssssss | 7990 | 8009 | 71 | 20 |
| 672735 | TGAGAGCAAGTAGTGGG | eeekk-d7-kkeee | soosssssssssooss | 1326 | 1342 | 5 | 898 |
| 672736 | GTGAGAGCAAGTAGTGG | eeekk-d7-kkeee | soosssssssssooss | 1327 | 1343 | 35 | 899 |
| 672737 | TGTGAGAGCAAGTAGTG | eeekk-d7-kkeee | soosssssssssooss | 1328 | 1344 | 0 | 900 |

TABLE 39-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672738 | CTGTGAGAGCAAGTAGT | eeekk-d7-kkeee | soosssssssssooss | 1329 | 1345 | 63 | 901 |
| 672739 | ACTGTGAGAGCAAGTAG | eeekk-d7-kkeee | soosssssssssooss | 1330 | 1346 | 0 | 902 |
| 672740 | TACTGTGAGAGCAAGTA | eeekk-d7-kkeee | soosssssssssooss | 1331 | 1347 | 65 | 903 |
| 672741 | GTACTGTGAGAGCAAGT | eeekk-d7-kkeee | soosssssssssooss | 1332 | 1348 | 13 | 904 |
| 672742 | AGTACTGTGAGAGCAAG | eeekk-d7-kkeee | soosssssssssooss | 1333 | 1349 | 46 | 905 |
| 672743 | GAGTACTGTGAGAGCAA | eeekk-d7-kkeee | soosssssssssooss | 1334 | 1350 | 55 | 906 |
| 672744 | CGAGTACTGTGAGAGCA | eeekk-d7-kkeee | soosssssssssooss | 1335 | 1351 | 76 | 907 |
| 672745 | GCGAGTACTGTGAGAGC | eeekk-d7-kkeee | soosssssssssooss | 1336 | 1352 | 11 | 908 |
| 672746 | AGCGAGTACTGTGAGAG | eeekk-d7-kkeee | soosssssssssooss | 1337 | 1353 | 11 | 909 |
| 672747 | CAGCGAGTACTGTGAGA | eeekk-d7-kkeee | soosssssssssooss | 1338 | 1354 | 51 | 910 |
| 672748 | TCAGCGAGTACTGTGAG | eeekk-d7-kkeee | soosssssssssooss | 1339 | 1355 | 20 | 911 |
| 672749 | CTCAGCGAGTACTGTGA | eeekk-d7-kkeee | soosssssssssooss | 1340 | 1356 | 12 | 912 |
| 672750 | CCTCAGCGAGTACTGTG | eeekk-d7-kkeee | soosssssssssooss | 1341 | 1357 | 2 | 913 |
| 672751 | CCCTCAGCGAGTACTGT | eeekk-d7-kkeee | soosssssssssooss | 1342 | 1358 | 39 | 914 |
| 672752 | ACCCTCAGCGAGTACTG | eeekk-d7-kkeee | soosssssssssooss | 1343 | 1359 | 27 | 915 |
| 672753 | CACCCTCAGCGAGTACT | eeekk-d7-kkeee | soosssssssssooss | 1344 | 1360 | 33 | 916 |
| 672754 | TCACCCTCAGCGAGTAC | eeekk-d7-kkeee | soosssssssssooss | 1345 | 1361 | 0 | 917 |
| 672755 | TTCACCCTCAGCGAGTA | eeekk-d7-kkeee | soosssssssssooss | 1346 | 1362 | 13 | 918 |
| 672756 | GTTCACCCTCAGCGAGT | eeekk-d7-kkeee | soosssssssssooss | 1347 | 1363 | 45 | 919 |
| 672757 | TGTTCACCCTCAGCGAG | eeekk-d7-kkeee | soosssssssssooss | 1348 | 1364 | 11 | 920 |
| 672758 | TTGTTCACCCTCAGCGA | eeekk-d7-kkeee | soosssssssssooss | 1349 | 1365 | 0 | 921 |
| 672759 | CTTGTTCACCCTCAGCG | eeekk-d7-kkeee | soosssssssssooss | 1350 | 1366 | 12 | 922 |
| 672760 | TCTTGTTCACCCTCAGC | eeekk-d7-kkeee | soosssssssssooss | 1351 | 1367 | 21 | 923 |
| 672761 | TTCTTGTTCACCCTCAG | eeekk-d7-kkeee | soosssssssssooss | 1352 | 1368 | 0 | 924 |
| 672762 | TTTCTTGTTCACCCTCA | eeekk-d7-kkeee | soosssssssssooss | 1353 | 1369 | 34 | 925 |
| 672763 | TTTTCTTGTTCACCCTC | eeekk-d7-kkeee | soosssssssssooss | 1354 | 1370 | 16 | 926 |
| 672764 | CTTTTCTTGTTCACCCT | eeekk-d7-kkeee | soosssssssssooss | 1355 | 1371 | 2 | 927 |
| 672765 | TCTTTTCTTGTTCACCC | eeekk-d7-kkeee | soosssssssssooss | 1356 | 1372 | 24 | 928 |
| 672766 | GTCTTTTCTTGTTCACC | eeekk-d7-kkeee | soosssssssssooss | 1357 | 1373 | 28 | 929 |
| 672767 | GGTCTTTTCTTGTTCAC | eeekk-d7-kkeee | soosssssssssooss | 1358 | 1374 | 30 | 930 |
| 672768 | AGGTCTTTTCTTGTTCA | eeekk-d7-kkeee | soosssssssssooss | 1359 | 1375 | 14 | 931 |
| 672769 | CAGGTCTTTTCTTGTTC | eeekk-d7-kkeee | soosssssssssooss | 1360 | 1376 | 20 | 932 |
| 672770 | TCAGGTCTTTTCTTGTT | eeekk-d7-kkeee | soosssssssssooss | 1361 | 1377 | 2 | 933 |
| 672771 | ATCAGGTCTTTTCTTGT | eeekk-d7-kkeee | soosssssssssooss | 1362 | 1378 | 0 | 934 |
| 672772 | TATCAGGTCTTTTCTTG | eeekk-d7-kkeee | soosssssssssooss | 1363 | 1379 | 23 | 935 |
| 672773 | TTATCAGGTCTTTTCTT | eeekk-d7-kkeee | soosssssssssooss | 1364 | 1380 | 39 | 936 |

TABLE 39-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672774 | ATCTTTATCAGGTCTTT | eeekk-d7-kkeee | soosssssssssooss | 1368 | 1384 | 92 | 937 |
| 672775 | AATCTTTATCAGGTCTT | eeekk-d7-kkeee | soosssssssssooss | 1369 | 1385 | 61 | 938 |
| 672776 | TAATCTTTATCAGGTCT | eeekk-d7-kkeee | soosssssssssooss | 1370 | 1386 | 2 | 939 |
| 672777 | TTAATCTTTATCAGGTC | eeekk-d7-kkeee | soosssssssssooss | 1371 | 1387 | 33 | 940 |
| 672778 | GTTAATCTTTATCAGGT | eeekk-d7-kkeee | soosssssssssooss | 1372 | 1388 | 53 | 941 |
| 672779 | GGTTAATCTTTATCAGG | eeekk-d7-kkeee | soosssssssssooss | 1373 | 1389 | 40 | 942 |
| 672780 | TGGTTAATCTTTATCAG | eeekk-d7-kkeee | soosssssssssooss | 1374 | 1390 | 26 | 943 |
| 672781 | CTGGTTAATCTTTATCA | eeekk-d7-kkeee | soosssssssssooss | 1375 | 1391 | 25 | 944 |
| 672782 | TCTGGTTAATCTTTATC | eeekk-d7-kkeee | soosssssssssooss | 1376 | 1392 | 44 | 945 |
| 672783 | CCCTCCTTGTTTTCTTC | eeekk-d7-kkeee | soosssssssssooss | 1391 | 1407 | 37 | 946 |
| 672784 | TCCCTCCTTGTTTTCTT | eeekk-d7-kkeee | soosssssssssooss | 1392 | 1408 | 10 | 947 |
| 672785 | TTCCCTCCTTGTTTTCT | eeekk-d7-kkeee | soosssssssssooss | 1393 | 1409 | 0 | 948 |
| 672786 | TTTCCCTCCTTGTTTTC | eeekk-d7-kkeee | soosssssssssooss | 1394 | 1410 | 0 | 949 |
| 672787 | GTTTCCCTCCTTGTTTT | eeekk-d7-kkeee | soosssssssssooss | 1395 | 1411 | 0 | 950 |
| 672788 | TGTTTCCCTCCTTGTTT | eeekk-d7-kkeee | soosssssssssooss | 1396 | 1412 | 0 | 951 |
| 672789 | TTGTTTCCCTCCTTGTT | eeekk-d7-kkeee | soosssssssssooss | 1397 | 1413 | 0 | 952 |
| 672790 | GGTTGTTTCCCTCCTTG | eeekk-d7-kkeee | soosssssssssooss | 1399 | 1415 | 33 | 953 |
| 672791 | CGGTTGTTTCCCTCCTT | eeekk-d7-kkeee | soosssssssssooss | 1400 | 1416 | 0 | 954 |
| 672792 | GCGGTTGTTTCCCTCCT | eeekk-d7-kkeee | soosssssssssooss | 1401 | 1417 | 23 | 955 |
| 672793 | TGCGGTTGTTTCCCTCC | eeekk-d7-kkeee | soosssssssssooss | 1402 | 1418 | 0 | 956 |
| 672794 | CTGCGGTTGTTTCCCTC | eeekk-d7-kkeee | soosssssssssooss | 1403 | 1419 | 25 | 957 |
| 672795 | GCTGCGGTTGTTTCCCT | eeekk-d7-kkeee | soosssssssssooss | 1404 | 1420 | 5 | 958 |
| 672796 | GGCTGCGGTTGTTTCCC | eeekk-d7-kkeee | soosssssssssooss | 1405 | 1421 | 16 | 959 |
| 672797 | AGGCTGCGGTTGTTTCC | eeekk-d7-kkeee | soosssssssssooss | 1406 | 1422 | 7 | 960 |
| 672798 | CAGGCTGCGGTTGTTTC | eeekk-d7-kkeee | soosssssssssooss | 1407 | 1423 | 0 | 961 |
| 672799 | ACAGGCTGCGGTTGTTT | eeekk-d7-kkeee | soosssssssssooss | 1408 | 1424 | 28 | 962 |
| 672800 | TACAGGCTGCGGTTGTT | eeekk-d7-kkeee | soosssssssssooss | 1409 | 1425 | 33 | 963 |
| 672801 | CTACAGGCTGCGGTTGT | eeekk-d7-kkeee | soosssssssssooss | 1410 | 1426 | 53 | 964 |
| 672802 | GCTACAGGCTGCGGTTG | eeekk-d7-kkeee | soosssssssssooss | 1411 | 1427 | 0 | 965 |
| 672803 | TGCTACAGGCTGCGGTT | eeekk-d7-kkeee | soosssssssssooss | 1412 | 1428 | 0 | 966 |
| 672804 | TTGCTACAGGCTGCGGT | eeekk-d7-kkeee | soosssssssssooss | 1413 | 1429 | 0 | 967 |
| 672805 | CTTGCTACAGGCTGCGG | eeekk-d7-kkeee | soosssssssssooss | 1414 | 1430 | 1 | 968 |
| 672806 | GCTTGCTACAGGCTGCG | eeekk-d7-kkeee | soosssssssssooss | 1415 | 1431 | 58 | 969 |
| 672807 | AGCTTGCTACAGGCTGC | eeekk-d7-kkeee | soosssssssssooss | 1416 | 1432 | 0 | 970 |
| 672808 | GAGCTTGCTACAGGCTG | eeekk-d7-kkeee | soosssssssssooss | 1417 | 1433 | 0 | 971 |

TABLE 39-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672809 | AGAGCTTGCTACAGGCT | eeekk-d7-kkeee | soosssssssssooss | 1418 | 1434 | 71 | 972 |
| 672810 | CAGAGCTTGCTACAGGC | eeekk-d7-kkeee | soosssssssssooss | 1419 | 1435 | 18 | 973 |
| 672811 | CCAGAGCTTGCTACAGG | eeekk-d7-kkeee | soosssssssssooss | 1420 | 1436 | 0 | 974 |
| 672812 | TCCAGAGCTTGCTACAG | eeekk-d7-kkeee | soosssssssssooss | 1421 | 1437 | 19 | 975 |
| 672813 | TTCCAGAGCTTGCTACA | eeekk-d7-kkeee | soosssssssssooss | 1422 | 1438 | 19 | 976 |
| 672814 | GTTCCAGAGCTTGCTAC | eeekk-d7-kkeee | soosssssssssooss | 1423 | 1439 | 0 | 977 |
| 672815 | AGTTCCAGAGCTTGCTA | eeekk-d7-kkeee | soosssssssssooss | 1424 | 1440 | 0 | 978 |
| 672816 | GAGTTCCAGAGCTTGCT | eeekk-d7-kkeee | soosssssssssooss | 1425 | 1441 | 14 | 979 |
| 672817 | TGAGTTCCAGAGCTTGC | eeekk-d7-kkeee | soosssssssssooss | 1426 | 1442 | 31 | 980 |
| 672818 | CTGAGTTCCAGAGCTTG | eeekk-d7-kkeee | soosssssssssooss | 1427 | 1443 | 21 | 981 |
| 672819 | CCTGAGTTCCAGAGCTT | eeekk-d7-kkeee | soosssssssssooss | 1428 | 1444 | 19 | 982 |
| 672820 | TCCTGAGTTCCAGAGCT | eeekk-d7-kkeee | soosssssssssooss | 1429 | 1445 | 46 | 983 |
| 672821 | CTCCTGAGTTCCAGAGC | eeekk-d7-kkeee | soosssssssssooss | 1430 | 1446 | 7 | 984 |
| 672822 | ACTCCTGAGTTCCAGAG | eeekk-d7-kkeee | soosssssssssooss | 1431 | 1447 | 13 | 985 |
| 672823 | GACTCCTGAGTTCCAGA | eeekk-d7-kkeee | soosssssssssooss | 1432 | 1448 | 19 | 986 |
| 672824 | CGACTCCTGAGTTCCAG | eeekk-d7-kkeee | soosssssssssooss | 1433 | 1449 | 23 | 987 |
| 672825 | GCGACTCCTGAGTTCCA | eeekk-d7-kkeee | soosssssssssooss | 1434 | 1450 | 0 | 988 |
| 672826 | CGCGACTCCTGAGTTCC | eeekk-d7-kkeee | soosssssssssooss | 1435 | 1451 | 19 | 989 |
| 672827 | GCGCGACTCCTGAGTTC | eeekk-d7-kkeee | soosssssssssooss | 1436 | 1452 | 31 | 990 |
| 672828 | CGCGCGACTCCTGAGTT | eeekk-d7-kkeee | soosssssssssooss | 1437 | 1453 | 63 | 991 |
| 672829 | GCGCGCGACTCCTGAGT | eeekk-d7-kkeee | soosssssssssooss | 1438 | 1454 | 28 | 992 |
| 672830 | AGCGCGCGACTCCTGAG | eeekk-d7-kkeee | soosssssssssooss | 1439 | 1455 | 58 | 993 |
| 672831 | TAGCGCGCGACTCCTGA | eeekk-d7-kkeee | soosssssssssooss | 1440 | 1456 | 42 | 994 |
| 672832 | CTAGCGCGCGACTCCTG | eeekk-d7-kkeee | soosssssssssooss | 1441 | 1457 | 42 | 995 |
| 672833 | CCTAGCGCGCGACTCCT | eeekk-d7-kkeee | soosssssssssooss | 1442 | 1458 | 24 | 996 |
| 672834 | CCCTAGCGCGCGACTCC | eeekk-d7-kkeee | soosssssssssooss | 1443 | 1459 | 58 | 997 |
| 672835 | CCCCTAGCGCGCGACTC | eeekk-d7-kkeee | soosssssssssooss | 1444 | 1460 | 40 | 998 |
| 672836 | GCCCCTAGCGCGCGACT | eeekk-d7-kkeee | soosssssssssooss | 1445 | 1461 | 0 | 999 |
| 672837 | GGCCCCTAGCGCGCGAC | eeekk-d7-kkeee | soosssssssssooss | 1446 | 1462 | 2 | 1000 |
| 672838 | CGGCCCCTAGCGCGCGA | eeekk-d7-kkeee | soosssssssssooss | 1447 | 1463 | 72 | 1001 |
| 672839 | CCGGCCCCTAGCGCGCG | eeekk-d7-kkeee | soosssssssssooss | 1448 | 1464 | 0 | 1002 |
| 672840 | CCCGGCCCCTAGCGCGC | eeekk-d7-kkeee | soosssssssssooss | 1449 | 1465 | 28 | 1003 |
| 672841 | CCCCGGCCCCTAGCGCG | eeekk-d7-kkeee | soosssssssssooss | 1450 | 1466 | 28 | 1004 |
| 672842 | GCCCCGGCCCCTAGCGC | eeekk-d7-kkeee | soosssssssssooss | 1451 | 1467 | 0 | 1005 |
| 672843 | GGCCCCGGCCCCTAGCG | eeekk-d7-kkeee | soosssssssssooss | 1452 | 1468 | 23 | 1006 |
| 672844 | CGGCCCCGGCCCCTAGC | eeekk-d7-kkeee | soosssssssssooss | 1453 | 1469 | 26 | 1007 |

TABLE 39-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672845 | CCGGCCCCGGCCCCTAG | eeekk-d7-kkeee | soosssssssssooss | 1454 | 1470 | 24 | 1008 |
| 672846 | CCCGGCCCCGGCCCCTA | eeekk-d7-kkeee | soosssssssssooss | 1455 | 1471 | 9 | 1009 |
| 672847 | ACGCCCCGGCCCCGGCC | eeekk-d7-kkeee | soosssssssssooss | 1465 | 1481 | 3 | 1010 |
| 672848 | CACGCCCCGGCCCCGGC | eeekk-d7-kkeee | soosssssssssooss | 1466 | 1482 | 19 | 1011 |
| 672849 | CCACGCCCCGGCCCCGG | eeekk-d7-kkeee | soosssssssssooss | 1467 | 1483 | 50 | 1012 |
| 672850 | ACCACGCCCCGGCCCCG | eeekk-d7-kkeee | soosssssssssooss | 1468 | 1484 | 0 | 1013 |
| 672851 | GACCACGCCCCGGCCCC | eeekk-d7-kkeee | soosssssssssooss | 1469 | 1485 | 3 | 1014 |
| 672852 | CGACCACGCCCCGGCCC | eeekk-d7-kkeee | soosssssssssooss | 1470 | 1486 | 9 | 1015 |
| 672853 | CCGACCACGCCCCGGCC | eeekk-d7-kkeee | soosssssssssooss | 1471 | 1487 | 24 | 1016 |
| 672854 | CCCGACCACGCCCCGGC | eeekk-d7-kkeee | soosssssssssooss | 1472 | 1488 | 9 | 1017 |
| 672855 | CCCCGACCACGCCCCGG | eeekk-d7-kkeee | soosssssssssooss | 1473 | 1489 | 18 | 1018 |
| 672856 | GCCCCGACCACGCCCCG | eeekk-d7-kkeee | soosssssssssooss | 1474 | 1490 | 8 | 1019 |
| 672857 | CGCCCCGACCACGCCCC | eeekk-d7-kkeee | soosssssssssooss | 1475 | 1491 | 0 | 1020 |
| 672858 | CCGCCCCGACCACGCCC | eeekk-d7-kkeee | soosssssssssooss | 1476 | 1492 | 48 | 1021 |
| 672859 | CCCGCCCCGACCACGCC | eeekk-d7-kkeee | soosssssssssooss | 1477 | 1493 | 28 | 1022 |
| 672860 | GCCCGCCCCGACCACGC | eeekk-d7-kkeee | soosssssssssooss | 1478 | 1494 | 0 | 1023 |
| 672861 | GGCCCGCCCCGACCACG | eeekk-d7-kkeee | soosssssssssooss | 1479 | 1495 | 33 | 1024 |
| 672862 | GGGCCCGCCCCGACCAC | eeekk-d7-kkeee | soosssssssssooss | 1480 | 1496 | 32 | 1025 |
| 672863 | CGGGCCCGCCCCGACCA | eeekk-d7-kkeee | soosssssssssooss | 1481 | 1497 | 0 | 1026 |
| 672864 | CCGGGCCCGCCCCGACC | eeekk-d7-kkeee | soosssssssssooss | 1482 | 1498 | 0 | 1027 |
| 672865 | CCCGGGCCCGCCCCGAC | eeekk-d7-kkeee | soosssssssssooss | 1483 | 1499 | 11 | 1028 |
| 672866 | GCAGCCCCGCCCCGGGC | eeekk-d7-kkeee | soosssssssssooss | 1505 | 1521 | 23 | 1029 |
| 672867 | CGCAGCCCCGCCCCGGG | eeekk-d7-kkeee | soosssssssssooss | 1506 | 1522 | 26 | 1030 |
| 672868 | CCGCAGCCCCGCCCCGG | eeekk-d7-kkeee | soosssssssssooss | 1507 | 1523 | 2 | 1031 |
| 672869 | ACCGCAGCCCCGCCCCG | eeekk-d7-kkeee | soosssssssssooss | 1508 | 1524 | 8 | 1032 |
| 672870 | AACCGCAGCCCCGCCCC | eeekk-d7-kkeee | soosssssssssooss | 1509 | 1525 | 7 | 1033 |
| 672871 | CAACCGCAGCCCCGCCC | eeekk-d7-kkeee | soosssssssssooss | 1510 | 1526 | 1 | 1034 |
| 672872 | GCAACCGCAGCCCCGCC | eeekk-d7-kkeee | soosssssssssooss | 1511 | 1527 | 37 | 1035 |
| 672873 | CGCAACCGCAGCCCCGC | eeekk-d7-kkeee | soosssssssssooss | 1512 | 1528 | 20 | 1036 |
| 672874 | CCGCAACCGCAGCCCCG | eeekk-d7-kkeee | soosssssssssooss | 1513 | 1529 | 23 | 1037 |
| 672875 | ACCGCAACCGCAGCCCC | eeekk-d7-kkeee | soosssssssssooss | 1514 | 1530 | 8 | 1038 |
| 672876 | CACCGCAACCGCAGCCC | eeekk-d7-kkeee | soosssssssssooss | 1515 | 1531 | 22 | 1039 |
| 672877 | GCACCGCAACCGCAGCC | eeekk-d7-kkeee | soosssssssssooss | 1516 | 1532 | 19 | 1040 |
| 672878 | GGCACCGCAACCGCAGC | eeekk-d7-kkeee | soosssssssssooss | 1517 | 1533 | 25 | 1041 |
| 672879 | AGGCACCGCAACCGCAG | eeekk-d7-kkeee | soosssssssssooss | 1518 | 1534 | 21 | 1042 |

TABLE 39-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672880 | CAGGCACCGCAACCGCA | eeekk-d7-kkeee | soossssssssssooss | 1519 | 1535 | 12 | 1043 |
| 672881 | GCAGGCACCGCAACCGC | eeekk-d7-kkeee | soossssssssssooss | 1520 | 1536 | 18 | 1044 |
| 672882 | CGCAGGCACCGCAACCG | eeekk-d7-kkeee | soossssssssssooss | 1521 | 1537 | 15 | 1045 |
| 672883 | GCGCAGGCACCGCAACC | eeekk-d7-kkeee | soossssssssssooss | 1522 | 1538 | 0 | 1046 |
| 672884 | GGCGCAGGCACCGCAAC | eeekk-d7-kkeee | soossssssssssooss | 1523 | 1539 | 0 | 1047 |

Example 9: Dose-Dependent Antisense Inhibition of Human C9ORF72 mRNA in HepG2 Cells Antisense oligonucleotides from the study described in Example 8 hereinabove exhibiting significant in vitro inhibition of C9ORF72 mRNA were selected and tested at various doses in HepG2 cells. ISIS 576816, previously tested in PCT/US2013/065073 (claiming priority to U.S. Application No. 61/714,132, filed Oct. 15, 2012, was used as a benchmark oligonucleotide. Cells were plated at a density of 20,000 cells per well and transfected using electroporation with 0.11 µM, 0.33 µM, 1.00 M, or 3.00 µM concentrations of antisense oligonucleotide. After a treatment period of approximately 16 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. C9ORF72 mRNA levels were adjusted according to total RNA content, as measured by RIBOGREEN®. Results are presented as percent inhibition of C9ORF72 levels, relative to untreated control cells.

As shown in Tables 39 and 40, total C9ORF72 mRNA levels were reduced in a dose-dependent manner in some of the antisense oligonucleotide treated cells.

TABLE 39

Dose-dependent inhibition of the C9ORF72 pathogenic associated mRNA variant transcript levels in HepG2 cells

| ISIS No | 0.11 µM | 0.33 µM | 1.00 µM | 3.00 µM |
|---|---|---|---|---|
| 672651 | 12 | 39 | 63 | 88 |
| 672611 | 13 | 50 | 59 | 79 |
| 672602 | 16 | 36 | 62 | 79 |
| 672624 | 25 | 54 | 80 | 95 |
| 672657 | 19 | 30 | 53 | 75 |
| 672582 | 0 | 0 | 20 | 57 |
| 672683 | 33 | 57 | 73 | 84 |
| 672595 | 39 | 39 | 66 | 88 |
| 576816 | 23 | 53 | 78 | 87 |
| 672640 | 17 | 26 | 56 | 84 |
| 672599 | 28 | 59 | 69 | 87 |
| 672637 | 36 | 50 | 66 | 88 |
| 672592 | 16 | 38 | 37 | 65 |
| 672636 | 24 | 39 | 69 | 88 |
| 672652 | 26 | 48 | 63 | 94 |
| 672619 | 8 | 12 | 6 | 0 |
| 672608 | 12 | 45 | 37 | 59 |

TABLE 39-continued

Dose-dependent inhibition of the C9ORF72 pathogenic associated mRNA variant transcript levels in HepG2 cells

| ISIS No | 0.11 µM | 0.33 µM | 1.00 µM | 3.00 µM |
|---|---|---|---|---|
| 672598 | 21 | 9 | 55 | 69 |
| 672642 | 28 | 35 | 59 | 72 |

TABLE 40

Dose-dependent inhibition of the C9ORF72 pathogenic associated mRNA variant transcript levels in HepG2 cells

| ISIS No | 0.11 µM | 0.33 µM | 1.00 µM | 3.00 µM |
|---|---|---|---|---|
| 672679 | 2 | 52 | 81 | 95 |
| 672693 | 14 | 41 | 53 | 83 |
| 672681 | 27 | 42 | 63 | 87 |
| 672683 | 10 | 35 | 64 | 82 |
| 672678 | 24 | 56 | 77 | 91 |
| 672699 | 17 | 31 | 46 | 83 |
| 672664 | 7 | 28 | 58 | 87 |
| 672665 | 35 | 46 | 62 | 75 |
| 576816 | 15 | 55 | 71 | 84 |
| 672671 | 36 | 66 | 79 | 87 |
| 672676 | 33 | 53 | 71 | 77 |
| 672700 | 25 | 45 | 68 | 81 |
| 672730 | 24 | 41 | 59 | 80 |
| 672670 | 25 | 40 | 60 | 75 |
| 672697 | 11 | 41 | 64 | 80 |
| 672723 | 30 | 48 | 68 | 88 |
| 672728 | 11 | 44 | 49 | 68 |
| 672675 | 41 | 48 | 74 | 88 |
| 672674 | 19 | 34 | 55 | 61 |

Example 10: Antisense Inhibition of C9ORF72 by Deoxy, MOE and cEt Antisense Oligonucleotides with Mixed Backbones Antisense oligonucleotides described in Example 6 hereinabove (see Tables 25-28 hereinabove) were tested in HepG2 cells in a series of experiments that had similar culture conditions. ISIS 576816, which was previously tested in PCT/US2013/065073 (claiming priority to U.S. Application No. 61/714,132, filed Oct. 15, 2012) was used as a benchmark oligonucleotide for study with deoxy, MOE, and cEt antisense oligonucleotides. The results for each experiment are presented in tables shown below. Cultured HepG2 cells at a density of 20,000 cells per well were transfected using electroporation with 700 nM antisense oligonucleotide. After a treatment period of approximately 24 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. The levels of the C9ORF72 pathogenic associated mRNA variant were normalized to the total RNA content of the cell, as measured by RIBOGREEN®. Results are presented as percent inhibition of C9ORF72, relative to untreated control cells.

TABLE 41

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 576816 | GCCTTACTCTAGGACCAAGA | eeeee-d10-eeeee | sssssssssssssssssss | 7990 | 8009 | 52 | 20 |
| 672885 | TGAGAGCAAGTAGTGGG | eekk-d8-kkeee | sooosssssssssooss | 1326 | 1342 | 10 | 898 |
| 672886 | GTGAGAGCAAGTAGTGG | eekk-d8-kkeee | sooosssssssssooss | 1327 | 1343 | 24 | 899 |
| 672887 | TGTGAGAGCAAGTAGTG | eekk-d8-kkeee | sooosssssssssooss | 1328 | 1344 | 38 | 900 |
| 672888 | CTGTGAGAGCAAGTAGT | eekk-d8-kkeee | sooosssssssssooss | 1329 | 1345 | 37 | 901 |
| 672889 | ACTGTGAGAGCAAGTAG | eekk-d8-kkeee | sooosssssssssooss | 1330 | 1346 | 16 | 902 |
| 672890 | TACTGTGAGAGCAAGTA | eekk-d8-kkeee | sooosssssssssooss | 1331 | 1347 | 26 | 903 |
| 672891 | GTACTGTGAGAGCAAGT | eekk-d8-kkeee | sooosssssssssooss | 1332 | 1348 | 38 | 904 |
| 672892 | AGTACTGTGAGAGCAAG | eekk-d8-kkeee | sooosssssssssooss | 1333 | 1349 | 44 | 905 |
| 672893 | GAGTACTGTGAGAGCAA | eekk-d8-kkeee | sooosssssssssooss | 1334 | 1350 | 57 | 906 |
| 672894 | CGAGTACTGTGAGAGCA | eekk-d8-kkeee | sooosssssssssooss | 1335 | 1351 | 62 | 907 |
| 672895 | GCGAGTACTGTGAGAGC | eekk-d8-kkeee | sooosssssssssooss | 1336 | 1352 | 39 | 908 |
| 672896 | AGCGAGTACTGTGAGAG | eekk-d8-kkeee | sooosssssssssooss | 1337 | 1353 | 54 | 909 |
| 672897 | CAGCGAGTACTGTGAGA | eekk-d8-kkeee | sooosssssssssooss | 1338 | 1354 | 57 | 910 |
| 672898 | TCAGCGAGTACTGTGAG | eekk-d8-kkeee | sooosssssssssooss | 1339 | 1355 | 23 | 911 |
| 672899 | CTCAGCGAGTACTGTGA | eekk-d8-kkeee | sooosssssssssooss | 1340 | 1356 | 34 | 912 |
| 672900 | CCTCAGCGAGTACTGTG | eekk-d8-kkeee | sooosssssssssooss | 1341 | 1357 | 33 | 913 |
| 672901 | CCCTCAGCGAGTACTGT | eekk-d8-kkeee | sooosssssssssooss | 1342 | 1358 | 32 | 914 |
| 672902 | ACCCTCAGCGAGTACTG | eekk-d8-kkeee | sooosssssssssooss | 1343 | 1359 | 62 | 915 |
| 672903 | CACCCTCAGCGAGTACT | eekk-d8-kkeee | sooosssssssssooss | 1344 | 1360 | 59 | 916 |
| 672904 | TCACCCTCAGCGAGTAC | eekk-d8-kkeee | sooosssssssssooss | 1345 | 1361 | 52 | 917 |
| 672905 | TTCACCCTCAGCGAGTA | eekk-d8-kkeee | sooosssssssssooss | 1346 | 1362 | 50 | 918 |
| 672906 | GTTCACCCTCAGCGAGT | eekk-d8-kkeee | sooosssssssssooss | 1347 | 1363 | 38 | 919 |
| 672907 | TGTTCACCCTCAGCGAG | eekk-d8-kkeee | sooosssssssssooss | 1348 | 1364 | 20 | 920 |
| 672908 | TTGTTCACCCTCAGCGA | eekk-d8-kkeee | sooosssssssssooss | 1349 | 1365 | 57 | 921 |
| 672909 | CTTGTTCACCCTCAGCG | eekk-d8-kkeee | sooosssssssssooss | 1350 | 1366 | 66 | 922 |
| 672910 | TCTTGTTCACCCTCAGC | eekk-d8-kkeee | sooosssssssssooss | 1351 | 1367 | 47 | 923 |
| 672911 | TTCTTGTTCACCCTCAG | eekk-d8-kkeee | sooosssssssssooss | 1352 | 1368 | 37 | 924 |
| 672912 | TTTCTTGTTCACCCTCA | eekk-d8-kkeee | sooosssssssssooss | 1353 | 1369 | 36 | 925 |
| 672913 | TTTTCTTGTTCACCCTC | eekk-d8-kkeee | sooosssssssssooss | 1354 | 1370 | 34 | 926 |
| 672914 | CTTTTCTTGTTCACCCT | eekk-d8-kkeee | sooosssssssssooss | 1355 | 1371 | 35 | 927 |

TABLE 41-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672915 | TCTTTTCTTGTTCACCC | eekk-d8-kkeee | sooss sssss sooss | 1356 | 1372 | 41 | 928 |
| 672916 | GTCTTTTCTTGTTCACC | eekk-d8-kkeee | sooss sssss sooss | 1357 | 1373 | 34 | 929 |
| 672917 | GGTCTTTTCTTGTTCAC | eekk-d8-kkeee | sooss sssss sooss | 1358 | 1374 | 23 | 930 |
| 672918 | AGGTCTTTTCTTGTTCA | eekk-d8-kkeee | sooss sssss sooss | 1359 | 1375 | 31 | 931 |
| 672919 | CAGGTCTTTTCTTGTTC | eekk-d8-kkeee | sooss sssss sooss | 1360 | 1376 | 51 | 932 |
| 672920 | TCAGGTCTTTTCTTGTT | eekk-d8-kkeee | sooss sssss sooss | 1361 | 1377 | 15 | 933 |
| 672921 | ATCAGGTCTTTTCTTGT | eekk-d8-kkeee | sooss sssss sooss | 1362 | 1378 | 0 | 934 |
| 672922 | TATCAGGTCTTTTCTTG | eekk-d8-kkeee | sooss sssss sooss | 1363 | 1379 | 31 | 935 |
| 672923 | TTATCAGGTCTTTTCTT | eekk-d8-kkeee | sooss sssss sooss | 1364 | 1380 | 14 | 936 |
| 672924 | ATCTTTATCAGGTCTTT | eekk-d8-kkeee | sooss sssss sooss | 1368 | 1384 | 71 | 937 |
| 672925 | AATCTTTATCAGGTCTT | eekk-d8-kkeee | sooss sssss sooss | 1369 | 1385 | 72 | 938 |
| 672926 | TAATCTTTATCAGGTCT | eekk-d8-kkeee | sooss sssss sooss | 1370 | 1386 | 40 | 939 |
| 672927 | TTAATCTTTATCAGGTC | eekk-d8-kkeee | sooss sssss sooss | 1371 | 1387 | 66 | 940 |
| 672928 | GTTAATCTTTATCAGGT | eekk-d8-kkeee | sooss sssss sooss | 1372 | 1388 | 56 | 941 |
| 672929 | GGTTAATCTTTATCAGG | eekk-d8-kkeee | sooss sssss sooss | 1373 | 1389 | 80 | 942 |
| 672930 | TGGTTAATCTTTATCAG | eekk-d8-kkeee | sooss sssss sooss | 1374 | 1390 | 48 | 943 |
| 672931 | CTGGTTAATCTTTATCA | eekk-d8-kkeee | sooss sssss sooss | 1375 | 1391 | 48 | 944 |
| 672932 | TCTGGTTAATCTTTATC | eekk-d8-kkeee | sooss sssss sooss | 1376 | 1392 | 54 | 945 |
| 672933 | CCCTCCTTGTTTTCTTC | eekk-d8-kkeee | sooss sssss sooss | 1391 | 1407 | 18 | 946 |
| 672934 | TCCCTCCTTGTTTTCTT | eekk-d8-kkeee | sooss sssss sooss | 1392 | 1408 | 7 | 947 |
| 672935 | TTCCCTCCTTGTTTTCT | eekk-d8-kkeee | sooss sssss sooss | 1393 | 1409 | 10 | 948 |
| 672936 | TTTCCCTCCTTGTTTTC | eekk-d8-kkeee | sooss sssss sooss | 1394 | 1410 | 0 | 949 |
| 672937 | GTTTCCCTCCTTGTTTT | eekk-d8-kkeee | sooss sssss sooss | 1395 | 1411 | 0 | 950 |
| 672938 | TGTTTCCCTCCTTGTTT | eekk-d8-kkeee | sooss sssss sooss | 1396 | 1412 | 9 | 951 |
| 672939 | TTGTTTCCCTCCTTGTT | eekk-d8-kkeee | sooss sssss sooss | 1397 | 1413 | 27 | 952 |
| 672940 | GGTTGTTTCCCTCCTTG | eekk-d8-kkeee | sooss sssss sooss | 1399 | 1415 | 49 | 953 |
| 672941 | CGGTTGTTTCCCTCCTT | eekk-d8-kkeee | sooss sssss sooss | 1400 | 1416 | 17 | 954 |
| 672942 | GCGGTTGTTTCCCTCCT | eekk-d8-kkeee | sooss sssss sooss | 1401 | 1417 | 10 | 955 |
| 672943 | TGCGGTTGTTTCCCTCC | eekk-d8-kkeee | sooss sssss sooss | 1402 | 1418 | 33 | 956 |
| 672944 | CTGCGGTTGTTTCCCTC | eekk-d8-kkeee | sooss sssss sooss | 1403 | 1419 | 29 | 957 |
| 672945 | GCTGCGGTTGTTTCCCT | eekk-d8-kkeee | sooss sssss sooss | 1404 | 1420 | 23 | 958 |
| 672946 | GGCTGCGGTTGTTTCCC | eekk-d8-kkeee | sooss sssss sooss | 1405 | 1421 | 15 | 959 |
| 672947 | AGGCTGCGGTTGTTTCC | eekk-d8-kkeee | sooss sssss sooss | 1406 | 1422 | 24 | 960 |
| 672948 | CAGGCTGCGGTTGTTTC | eekk-d8-kkeee | sooss sssss sooss | 1407 | 1423 | 49 | 961 |
| 672949 | ACAGGCTGCGGTTGTTT | eekk-d8-kkeee | sooss sssss sooss | 1408 | 1424 | 35 | 962 |

TABLE 41-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672950 | TACAGGCTGCGGTTGTT | eekk-d8-kkeee | sooossssssssooss | 1409 | 1425 | 37 | 963 |
| 672951 | CTACAGGCTGCGGTTGT | eekk-d8-kkeee | sooossssssssooss | 1410 | 1426 | 4 | 964 |
| 672952 | GCTACAGGCTGCGGTTG | eekk-d8-kkeee | sooossssssssooss | 1411 | 1427 | 4 | 965 |
| 672953 | TGCTACAGGCTGCGGTT | eekk-d8-kkeee | sooossssssssooss | 1412 | 1428 | 24 | 966 |
| 672954 | TTGCTACAGGCTGCGGT | eekk-d8-kkeee | sooossssssssooss | 1413 | 1429 | 8 | 967 |
| 672955 | CTTGCTACAGGCTGCGG | eekk-d8-kkeee | sooossssssssooss | 1414 | 1430 | 28 | 968 |
| 672956 | GCTTGCTACAGGCTGCG | eekk-d8-kkeee | sooossssssssooss | 1415 | 1431 | 8 | 969 |
| 672957 | AGCTTGCTACAGGCTGC | eekk-d8-kkeee | sooossssssssooss | 1416 | 1432 | 5 | 970 |
| 672958 | GAGCTTGCTACAGGCTG | eekk-d8-kkeee | sooossssssssooss | 1417 | 1433 | 4 | 971 |
| 672959 | AGAGCTTGCTACAGGCT | eekk-d8-kkeee | sooossssssssooss | 1418 | 1434 | 0 | 972 |
| 672960 | CAGAGCTTGCTACAGGC | eekk-d8-kkeee | sooossssssssooss | 1419 | 1435 | 12 | 973 |
| 672961 | CCAGAGCTTGCTACAGG | eekk-d8-kkeee | sooossssssssooss | 1420 | 1436 | 36 | 974 |
| 672962 | TCCAGAGCTTGCTACAG | eekk-d8-kkeee | sooossssssssooss | 1421 | 1437 | 0 | 975 |
| 672963 | TTCCAGAGCTTGCTACA | eekk-d8-kkeee | sooossssssssooss | 1422 | 1438 | 11 | 976 |
| 672964 | GTTCCAGAGCTTGCTAC | eekk-d8-kkeee | sooossssssssooss | 1423 | 1439 | 8 | 977 |
| 672965 | AGTTCCAGAGCTTGCTA | eekk-d8-kkeee | sooossssssssooss | 1424 | 1440 | 19 | 978 |
| 672966 | GAGTTCCAGAGCTTGCT | eekk-d8-kkeee | sooossssssssooss | 1425 | 1441 | 48 | 979 |
| 672967 | TGAGTTCCAGAGCTTGC | eekk-d8-kkeee | sooossssssssooss | 1426 | 1442 | 41 | 980 |
| 672968 | CTGAGTTCCAGAGCTTG | eekk-d8-kkeee | sooossssssssooss | 1427 | 1443 | 54 | 981 |
| 672969 | CCTGAGTTCCAGAGCTT | eekk-d8-kkeee | sooossssssssooss | 1428 | 1444 | 58 | 982 |
| 672970 | TCCTGAGTTCCAGAGCT | eekk-d8-kkeee | sooossssssssooss | 1429 | 1445 | 12 | 983 |
| 672971 | CTCCTGAGTTCCAGAGC | eekk-d8-kkeee | sooossssssssooss | 1430 | 1446 | 23 | 984 |
| 672972 | ACTCCTGAGTTCCAGAG | eekk-d8-kkeee | sooossssssssooss | 1431 | 1447 | 30 | 985 |
| 672973 | GACTCCTGAGTTCCAGA | eekk-d8-kkeee | sooossssssssooss | 1432 | 1448 | 39 | 986 |
| 672974 | CGACTCCTGAGTTCCAG | eekk-d8-kkeee | sooossssssssooss | 1433 | 1449 | 41 | 987 |
| 672975 | GCGACTCCTGAGTTCCA | eekk-d8-kkeee | sooossssssssooss | 1434 | 1450 | 31 | 988 |
| 672976 | CGCGACTCCTGAGTTCC | eekk-d8-kkeee | sooossssssssooss | 1435 | 1451 | 56 | 989 |
| 672977 | GCGCGACTCCTGAGTTC | eekk-d8-kkeee | sooossssssssooss | 1436 | 1452 | 31 | 990 |
| 672978 | CGCGCGACTCCTGAGTT | eekk-d8-kkeee | sooossssssssooss | 1437 | 1453 | 45 | 991 |
| 672979 | GCGCGCGACTCCTGAGT | eekk-d8-kkeee | sooossssssssooss | 1438 | 1454 | 29 | 992 |
| 672980 | AGCGCGCGACTCCTGAG | eekk-d8-kkeee | sooossssssssooss | 1439 | 1455 | 48 | 993 |
| 672981 | TAGCGCGCGACTCCTGA | eekk-d8-kkeee | sooossssssssooss | 1440 | 1456 | 68 | 994 |
| 672982 | CTAGCGCGCGACTCCTG | eekk-d8-kkeee | sooossssssssooss | 1441 | 1457 | 59 | 995 |
| 672983 | CCTAGCGCGCGACTCCT | eekk-d8-kkeee | sooossssssssooss | 1442 | 1458 | 62 | 996 |
| 672984 | CCCTAGCGCGCGACTCC | eekk-d8-kkeee | sooossssssssooss | 1443 | 1459 | 69 | 997 |

TABLE 41-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 672985 | CCCCTAGCGCGCGACTC | eekk-d8-kkeee | sooossssssssooss | 1444 | 1460 | 65 | 998 |
| 672986 | GCCCCTAGCGCGCGACT | eekk-d8-kkeee | sooossssssssooss | 1445 | 1461 | 34 | 999 |
| 672987 | GGCCCCTAGCGCGCGAC | eekk-d8-kkeee | sooossssssssooss | 1446 | 1462 | 22 | 1000 |
| 672988 | CGGCCCCTAGCGCGCGA | eekk-d8-kkeee | sooossssssssooss | 1447 | 1463 | 16 | 1001 |
| 672989 | CCGGCCCCTAGCGCGCG | eekk-d8-kkeee | sooossssssssooss | 1448 | 1464 | 24 | 1002 |
| 672990 | CCCGGCCCCTAGCGCGC | eekk-d8-kkeee | sooossssssssooss | 1449 | 1465 | 10 | 1003 |
| 672991 | CCCCGGCCCCTAGCGCG | eekk-d8-kkeee | sooossssssssooss | 1450 | 1466 | 24 | 1004 |
| 672992 | GCCCCGGCCCCTAGCGC | eekk-d8-kkeee | sooossssssssooss | 1451 | 1467 | 29 | 1005 |
| 672993 | GGCCCCGGCCCCTAGCG | eekk-d8-kkeee | sooossssssssooss | 1452 | 1468 | 24 | 1006 |
| 672994 | CGGCCCCGGCCCCTAGC | eekk-d8-kkeee | sooossssssssooss | 1453 | 1469 | 25 | 1007 |
| 672995 | CCGGCCCCGGCCCCTAG | eekk-d8-kkeee | sooossssssssooss | 1454 | 1470 | 28 | 1008 |
| 672996 | CCCGGCCCCGGCCCCTA | eekk-d8-kkeee | sooossssssssooss | 1455 | 1471 | 25 | 1009 |
| 672997 | ACGCCCCGGCCCCGGCC | eekk-d8-kkeee | sooossssssssooss | 1465 | 1481 | 21 | 1010 |
| 672998 | CACGCCCCGGCCCCGGC | eekk-d8-kkeee | sooossssssssooss | 1466 | 1482 | 17 | 1011 |
| 672999 | CCACGCCCCGGCCCCGG | eekk-d8-kkeee | sooossssssssooss | 1467 | 1483 | 30 | 1012 |
| 673000 | ACCACGCCCCGGCCCCG | eekk-d8-kkeee | sooossssssssooss | 1468 | 1484 | 29 | 1013 |
| 673001 | GACCACGCCCCGGCCCC | eekk-d8-kkeee | sooossssssssooss | 1469 | 1485 | 25 | 1014 |
| 673002 | CGACCACGCCCCGGCCC | eekk-d8-kkeee | sooossssssssooss | 1470 | 1486 | 37 | 1015 |
| 673003 | CCGACCACGCCCCGGCC | eekk-d8-kkeee | sooossssssssooss | 1471 | 1487 | 23 | 1016 |
| 673004 | CCCGACCACGCCCCGGC | eekk-d8-kkeee | sooossssssssooss | 1472 | 1488 | 21 | 1017 |
| 673005 | CCCCGACCACGCCCCGG | eekk-d8-kkeee | sooossssssssooss | 1473 | 1489 | 9 | 1018 |
| 673006 | GCCCCGACCACGCCCCG | eekk-d8-kkeee | sooossssssssooss | 1474 | 1490 | 13 | 1019 |
| 673007 | CGCCCCGACCACGCCCC | eekk-d8-kkeee | sooossssssssooss | 1475 | 1491 | 17 | 1020 |
| 673008 | CCGCCCCGACCACGCCC | eekk-d8-kkeee | sooossssssssooss | 1476 | 1492 | 20 | 1021 |
| 673009 | CCCGCCCCGACCACGCC | eekk-d8-kkeee | sooossssssssooss | 1477 | 1493 | 36 | 1022 |
| 673010 | GCCCGCCCCGACCACGC | eekk-d8-kkeee | sooossssssssooss | 1478 | 1494 | 16 | 1023 |
| 673011 | GGCCCGCCCCGACCACG | eekk-d8-kkeee | sooossssssssooss | 1479 | 1495 | 3 | 1024 |
| 673012 | GGGCCCGCCCCGACCAC | eekk-d8-kkeee | sooossssssssooss | 1480 | 1496 | 21 | 1025 |
| 673013 | CGGGCCCGCCCCGACCA | eekk-d8-kkeee | sooossssssssooss | 1481 | 1497 | 4 | 1026 |
| 673014 | CCGGGCCCGCCCCGACC | eekk-d8-kkeee | sooossssssssooss | 1482 | 1498 | 21 | 1027 |
| 673015 | CCCGGGCCCGCCCCGAC | eekk-d8-kkeee | sooossssssssooss | 1483 | 1499 | 15 | 1028 |
| 673016 | GCAGCCCCGCCCCGGGC | eekk-d8-kkeee | sooossssssssooss | 1505 | 1521 | 3 | 1029 |
| 673017 | CGCAGCCCCGCCCCGGG | eekk-d8-kkeee | sooossssssssooss | 1506 | 1522 | 7 | 1030 |
| 673018 | CCGCAGCCCCGCCCCGG | eekk-d8-kkeee | sooossssssssooss | 1507 | 1523 | 7 | 1031 |
| 673019 | ACCGCAGCCCCGCCCCG | eekk-d8-kkeee | sooossssssssooss | 1508 | 1524 | 8 | 1032 |

TABLE 41-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673020 | AACCGCAGCCCCGCCCC | eekk-d8-kkeee | soossssssssssooss | 1509 | 1525 | 42 | 1033 |
| 673021 | CAACCGCAGCCCCGCCC | eekk-d8-kkeee | soossssssssssooss | 1510 | 1526 | 58 | 1034 |
| 673022 | GCAACCGCAGCCCCGCC | eekk-d8-kkeee | soossssssssssooss | 1511 | 1527 | 44 | 1035 |
| 673023 | CGCAACCGCAGCCCCGC | eekk-d8-kkeee | soossssssssssooss | 1512 | 1528 | 46 | 1036 |
| 673024 | CCGCAACCGCAGCCCCG | eekk-d8-kkeee | soossssssssssooss | 1513 | 1529 | 26 | 1037 |
| 673025 | ACCGCAACCGCAGCCCC | eekk-d8-kkeee | soossssssssssooss | 1514 | 1530 | 20 | 1038 |
| 673026 | CACCGCAACCGCAGCCC | eekk-d8-kkeee | soossssssssssooss | 1515 | 1531 | 52 | 1039 |
| 673027 | GCACCGCAACCGCAGCC | eekk-d8-kkeee | soossssssssssooss | 1516 | 1532 | 22 | 1040 |
| 673028 | GGCACCGCAACCGCAGC | eekk-d8-kkeee | soossssssssssooss | 1517 | 1533 | 32 | 1041 |
| 673029 | AGGCACCGCAACCGCAG | eekk-d8-kkeee | soossssssssssooss | 1518 | 1534 | 27 | 1042 |
| 673030 | CAGGCACCGCAACCGCA | eekk-d8-kkeee | soossssssssssooss | 1519 | 1535 | 32 | 1043 |
| 673031 | GCAGGCACCGCAACCGC | eekk-d8-kkeee | soossssssssssooss | 1520 | 1536 | 38 | 1044 |
| 673032 | CGCAGGCACCGCAACCG | eekk-d8-kkeee | soossssssssssooss | 1521 | 1537 | 54 | 1045 |
| 673033 | GCGCAGGCACCGCAACC | eekk-d8-kkeee | soossssssssssooss | 1522 | 1538 | 24 | 1046 |
| 673034 | GGCGCAGGCACCGCAAC | eekk-d8-kkeee | soossssssssssooss | 1523 | 1539 | 17 | 1047 |

TABLE 42

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 576816 | GCCTTACTCTAGGACCAAGA | eeeee-d10-eeeee | sssssssssssssssssss | 7990 | 8009 | 75 | 20 |
| 673035 | TGAGAGCAAGTAGTGGG | ek-d8-ekekeee | sosssssssssooss | 1326 | 1342 | 47 | 898 |
| 673036 | GTGAGAGCAAGTAGTGG | ek-d8-ekekeee | sosssssssssooss | 1327 | 1343 | 57 | 899 |
| 673037 | TGTGAGAGCAAGTAGTG | ek-d8-ekekeee | sosssssssssooss | 1328 | 1344 | 39 | 900 |
| 673038 | CTGTGAGAGCAAGTAGT | ek-d8-ekekeee | sosssssssssooss | 1329 | 1345 | 48 | 901 |
| 673039 | ACTGTGAGAGCAAGTAG | ek-d8-ekekeee | sosssssssssooss | 1330 | 1346 | 35 | 902 |
| 673040 | TACTGTGAGAGCAAGTA | ek-d8-ekekeee | sosssssssssooss | 1331 | 1347 | 40 | 903 |
| 673041 | GTACTGTGAGAGCAAGT | ek-d8-ekekeee | sosssssssssooss | 1332 | 1348 | 35 | 904 |
| 673042 | AGTACTGTGAGAGCAAG | ek-d8-ekekeee | sosssssssssooss | 1333 | 1349 | 26 | 905 |
| 673043 | GAGTACTGTGAGAGCAA | ek-d8-ekekeee | sosssssssssooss | 1334 | 1350 | 44 | 906 |
| 673044 | CGAGTACTGTGAGAGCA | ek-d8-ekekeee | sosssssssssooss | 1335 | 1351 | 44 | 907 |
| 673045 | GCGAGTACTGTGAGAGC | ek-d8-ekekeee | sosssssssssooss | 1336 | 1352 | 36 | 908 |

TABLE 42-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673046 | AGCGAGTACTGTGAGAG | ek-d8-ekekeee | sossssssssooss | 1337 | 1353 | 37 | 909 |
| 673047 | CAGCGAGTACTGTGAGA | ek-d8-ekekeee | sossssssssooss | 1338 | 1354 | 66 | 910 |
| 673048 | TCAGCGAGTACTGTGAG | ek-d8-ekekeee | sossssssssooss | 1339 | 1355 | 22 | 911 |
| 673049 | CTCAGCGAGTACTGTGA | ek-d8-ekekeee | sossssssssooss | 1340 | 1356 | 49 | 912 |
| 673050 | CCTCAGCGAGTACTGTG | ek-d8-ekekeee | sossssssssooss | 1341 | 1357 | 53 | 913 |
| 673051 | CCCTCAGCGAGTACTGT | ek-d8-ekekeee | sossssssssooss | 1342 | 1358 | 52 | 914 |
| 673052 | ACCCTCAGCGAGTACTG | ek-d8-ekekeee | sossssssssooss | 1343 | 1359 | 20 | 915 |
| 673053 | CACCCTCAGCGAGTACT | ek-d8-ekekeee | sossssssssooss | 1344 | 1360 | 66 | 916 |
| 673054 | TCACCCTCAGCGAGTAC | ek-d8-ekekeee | sossssssssooss | 1345 | 1361 | 50 | 917 |
| 673055 | TTCACCCTCAGCGAGTA | ek-d8-ekekeee | sossssssssooss | 1346 | 1362 | 35 | 918 |
| 673056 | GTTCACCCTCAGCGAGT | ek-d8-ekekeee | sossssssssooss | 1347 | 1363 | 46 | 919 |
| 673057 | TGTTCACCCTCAGCGAG | ek-d8-ekekeee | sossssssssooss | 1348 | 1364 | 51 | 920 |
| 673058 | TTGTTCACCCTCAGCGA | ek-d8-ekekeee | sossssssssooss | 1349 | 1365 | 57 | 921 |
| 673059 | CTTGTTCACCCTCAGCG | ek-d8-ekekeee | sossssssssooss | 1350 | 1366 | 50 | 922 |
| 673060 | TCTTGTTCACCCTCAGC | ek-d8-ekekeee | sossssssssooss | 1351 | 1367 | 41 | 923 |
| 673061 | TTCTTGTTCACCCTCAG | ek-d8-ekekeee | sossssssssooss | 1352 | 1368 | 14 | 924 |
| 673062 | TTTCTTGTTCACCCTCA | ek-d8-ekekeee | sossssssssooss | 1353 | 1369 | 28 | 925 |
| 673063 | TTTTCTTGTTCACCCTC | ek-d8-ekekeee | sossssssssooss | 1354 | 1370 | 38 | 926 |
| 673064 | CTTTTCTTGTTCACCCT | ek-d8-ekekeee | sossssssssooss | 1355 | 1371 | 38 | 927 |
| 673065 | TCTTTTCTTGTTCACCC | ek-d8-ekekeee | sossssssssooss | 1356 | 1372 | 30 | 928 |
| 673066 | GTCTTTTCTTGTTCACC | ek-d8-ekekeee | sossssssssooss | 1357 | 1373 | 47 | 929 |
| 673067 | GGTCTTTTCTTGTTCAC | ek-d8-ekekeee | sossssssssooss | 1358 | 1374 | 63 | 930 |
| 673068 | AGGTCTTTTCTTGTTCA | ek-d8-ekekeee | sossssssssooss | 1359 | 1375 | 71 | 931 |
| 673069 | CAGGTCTTTTCTTGTTC | ek-d8-ekekeee | sossssssssooss | 1360 | 1376 | 41 | 932 |
| 673070 | TCAGGTCTTTTCTTGTT | ek-d8-ekekeee | sossssssssooss | 1361 | 1377 | 24 | 933 |
| 673071 | ATCAGGTCTTTTCTTGT | ek-d8-ekekeee | sossssssssooss | 1362 | 1378 | 53 | 934 |
| 673072 | TATCAGGTCTTTTCTTG | ek-d8-ekekeee | sossssssssooss | 1363 | 1379 | 44 | 935 |
| 673073 | TTATCAGGTCTTTTCTT | ek-d8-ekekeee | sossssssssooss | 1364 | 1380 | 28 | 936 |
| 673074 | ATCTTTATCAGGTCTTT | ek-d8-ekekeee | sossssssssooss | 1368 | 1384 | 57 | 937 |
| 673075 | AATCTTTATCAGGTCTT | ek-d8-ekekeee | sossssssssooss | 1369 | 1385 | 49 | 938 |
| 673076 | TAATCTTTATCAGGTCT | ek-d8-ekekeee | sossssssssooss | 1370 | 1386 | 40 | 939 |
| 673077 | TTAATCTTTATCAGGTC | ek-d8-ekekeee | sossssssssooss | 1371 | 1387 | 33 | 940 |
| 673078 | GTTAATCTTTATCAGGT | ek-d8-ekekeee | sossssssssooss | 1372 | 1388 | 46 | 941 |
| 673079 | GGTTAATCTTTATCAGG | ek-d8-ekekeee | sossssssssooss | 1373 | 1389 | 87 | 942 |
| 673080 | TGGTTAATCTTTATCAG | ek-d8-ekekeee | sossssssssooss | 1374 | 1390 | 35 | 943 |

TABLE 42-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673081 | CTGGTTAATCTTTATCA | ek-d8-ekekeee | sosssssssssooss | 1375 | 1391 | 56 | 944 |
| 673082 | TCTGGTTAATCTTTATC | ek-d8-ekekeee | sosssssssssooss | 1376 | 1392 | 59 | 945 |
| 673083 | CCCTCCTTGTTTTCTTC | ek-d8-ekekeee | sosssssssssooss | 1391 | 1407 | 11 | 946 |
| 673084 | TCCCTCCTTGTTTTCTT | ek-d8-ekekeee | sosssssssssooss | 1392 | 1408 | 10 | 947 |
| 673085 | TTCCCTCCTTGTTTTCT | ek-d8-ekekeee | sosssssssssooss | 1393 | 1409 | 8 | 948 |
| 673086 | TTTCCCTCCTTGTTTTC | ek-d8-ekekeee | sosssssssssooss | 1394 | 1410 | 26 | 949 |
| 673087 | GTTTCCCTCCTTGTTTT | ek-d8-ekekeee | sosssssssssooss | 1395 | 1411 | 25 | 950 |
| 673088 | TGTTTCCCTCCTTGTTT | ek-d8-ekekeee | sosssssssssooss | 1396 | 1412 | 62 | 951 |
| 673089 | TTGTTTCCCTCCTTGTT | ek-d8-ekekeee | sosssssssssooss | 1397 | 1413 | 51 | 952 |
| 673090 | GGTTGTTTCCCTCCTTG | ek-d8-ekekeee | sosssssssssooss | 1399 | 1415 | 34 | 953 |
| 673091 | CGGTTGTTTCCCTCCTT | ek-d8-ekekeee | sosssssssssooss | 1400 | 1416 | 13 | 954 |
| 673092 | GCGGTTGTTTCCCTCCT | ek-d8-ekekeee | sosssssssssooss | 1401 | 1417 | 37 | 955 |
| 673093 | TGCGGTTGTTTCCCTCC | ek-d8-ekekeee | sosssssssssooss | 1402 | 1418 | 49 | 956 |
| 673094 | CTGCGGTTGTTTCCCTC | ek-d8-ekekeee | sosssssssssooss | 1403 | 1419 | 15 | 957 |
| 673095 | GCTGCGGTTGTTTCCCT | ek-d8-ekekeee | sosssssssssooss | 1404 | 1420 | 17 | 958 |
| 673096 | GGCTGCGGTTGTTTCCC | ek-d8-ekekeee | sosssssssssooss | 1405 | 1421 | 33 | 959 |
| 673097 | AGGCTGCGGTTGTTTCC | ek-d8-ekekeee | sosssssssssooss | 1406 | 1422 | 43 | 960 |
| 673098 | CAGGCTGCGGTTGTTTC | ek-d8-ekekeee | sosssssssssooss | 1407 | 1423 | 53 | 961 |
| 673099 | ACAGGCTGCGGTTGTTT | ek-d8-ekekeee | sosssssssssooss | 1408 | 1424 | 21 | 962 |
| 673100 | TACAGGCTGCGGTTGTT | ek-d8-ekekeee | sosssssssssooss | 1409 | 1425 | 23 | 963 |
| 673101 | CTACAGGCTGCGGTTGT | ek-d8-ekekeee | sosssssssssooss | 1410 | 1426 | 16 | 964 |
| 673102 | GCTACAGGCTGCGGTTG | ek-d8-ekekeee | sosssssssssooss | 1411 | 1427 | 24 | 965 |
| 673103 | TGCTACAGGCTGCGGTT | ek-d8-ekekeee | sosssssssssooss | 1412 | 1428 | 41 | 966 |
| 673104 | TTGCTACAGGCTGCGGT | ek-d8-ekekeee | sosssssssssooss | 1413 | 1429 | 30 | 967 |
| 673105 | CTTGCTACAGGCTGCGG | ek-d8-ekekeee | sosssssssssooss | 1414 | 1430 | 13 | 968 |
| 673106 | GCTTGCTACAGGCTGCG | ek-d8-ekekeee | sosssssssssooss | 1415 | 1431 | 7 | 969 |
| 673107 | AGCTTGCTACAGGCTGC | ek-d8-ekekeee | sosssssssssooss | 1416 | 1432 | 7 | 970 |
| 673108 | GAGCTTGCTACAGGCTG | ek-d8-ekekeee | sosssssssssooss | 1417 | 1433 | 23 | 971 |
| 673109 | AGAGCTTGCTACAGGCT | ek-d8-ekekeee | sosssssssssooss | 1418 | 1434 | 38 | 972 |
| 673110 | CAGAGCTTGCTACAGGC | ek-d8-ekekeee | sosssssssssooss | 1419 | 1435 | 22 | 973 |
| 673111 | CCAGAGCTTGCTACAGG | ek-d8-ekekeee | sosssssssssooss | 1420 | 1436 | 14 | 974 |
| 673112 | TCCAGAGCTTGCTACAG | ek-d8-ekekeee | sosssssssssooss | 1421 | 1437 | 11 | 975 |
| 673113 | TTCCAGAGCTTGCTACA | ek-d8-ekekeee | sosssssssssooss | 1422 | 1438 | 24 | 976 |
| 673114 | GTTCCAGAGCTTGCTAC | ek-d8-ekekeee | sosssssssssooss | 1423 | 1439 | 37 | 977 |
| 673115 | AGTTCCAGAGCTTGCTA | ek-d8-ekekeee | sosssssssssooss | 1424 | 1440 | 34 | 978 |

TABLE 42-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673116 | GAGTTCCAGAGCTTGCT | ek-d8-ekekeee | sossssssssssooss | 1425 | 1441 | 21 | 979 |
| 673117 | TGAGTTCCAGAGCTTGC | ek-d8-ekekeee | sossssssssssooss | 1426 | 1442 | 47 | 980 |
| 673118 | CTGAGTTCCAGAGCTTG | ek-d8-ekekeee | sossssssssssooss | 1427 | 1443 | 27 | 981 |
| 673119 | CCTGAGTTCCAGAGCTT | ek-d8-ekekeee | sossssssssssooss | 1428 | 1444 | 44 | 982 |
| 673120 | TCCTGAGTTCCAGAGCT | ek-d8-ekekeee | sossssssssssooss | 1429 | 1445 | 39 | 983 |
| 673121 | CTCCTGAGTTCCAGAGC | ek-d8-ekekeee | sossssssssssooss | 1430 | 1446 | 37 | 984 |
| 673122 | ACTCCTGAGTTCCAGAG | ek-d8-ekekeee | sossssssssssooss | 1431 | 1447 | 40 | 985 |
| 673123 | GACTCCTGAGTTCCAGA | ek-d8-ekekeee | sossssssssssooss | 1432 | 1448 | 26 | 986 |
| 673124 | CGACTCCTGAGTTCCAG | ek-d8-ekekeee | sossssssssssooss | 1433 | 1449 | 36 | 987 |
| 673125 | GCGACTCCTGAGTTCCA | ek-d8-ekekeee | sossssssssssooss | 1434 | 1450 | 55 | 988 |
| 673126 | CGCGACTCCTGAGTTCC | ek-d8-ekekeee | sossssssssssooss | 1435 | 1451 | 55 | 989 |
| 673127 | GCGCGACTCCTGAGTTC | ek-d8-ekekeee | sossssssssssooss | 1436 | 1452 | 64 | 990 |
| 673128 | CGCGCGACTCCTGAGTT | ek-d8-ekekeee | sossssssssssooss | 1437 | 1453 | 59 | 991 |
| 673129 | GCGCGCGACTCCTGAGT | ek-d8-ekekeee | sossssssssssooss | 1438 | 1454 | 42 | 992 |
| 673130 | AGCGCGCGACTCCTGAG | ek-d8-ekekeee | sossssssssssooss | 1439 | 1455 | 60 | 993 |
| 673131 | TAGCGCGCGACTCCTGA | ek-d8-ekekeee | sossssssssssooss | 1440 | 1456 | 59 | 994 |
| 673132 | CTAGCGCGCGACTCCTG | ek-d8-ekekeee | sossssssssssooss | 1441 | 1457 | 49 | 995 |
| 673133 | CCTAGCGCGCGACTCCT | ek-d8-ekekeee | sossssssssssooss | 1442 | 1458 | 62 | 996 |
| 673134 | CCCTAGCGCGCGACTCC | ek-d8-ekekeee | sossssssssssooss | 1443 | 1459 | 62 | 997 |
| 673135 | CCCCTAGCGCGCGACTC | ek-d8-ekekeee | sossssssssssooss | 1444 | 1460 | 65 | 998 |
| 673136 | GCCCCTAGCGCGCGACT | ek-d8-ekekeee | sossssssssssooss | 1445 | 1461 | 27 | 999 |
| 673137 | GGCCCCTAGCGCGCGAC | ek-d8-ekekeee | sossssssssssooss | 1446 | 1462 | 6 | 1000 |
| 673138 | CGGCCCCTAGCGCGCGA | ek-d8-ekekeee | sossssssssssooss | 1447 | 1463 | 26 | 1001 |
| 673139 | CCGGCCCCTAGCGCGCG | ek-d8-ekekeee | sossssssssssooss | 1448 | 1464 | 15 | 1002 |
| 673140 | CCCGGCCCCTAGCGCGC | ek-d8-ekekeee | sossssssssssooss | 1449 | 1465 | 24 | 1003 |
| 673141 | CCCCGGCCCCTAGCGCG | ek-d8-ekekeee | sossssssssssooss | 1450 | 1466 | 27 | 1004 |
| 673142 | GCCCCGGCCCCTAGCGC | ek-d8-ekekeee | sossssssssssooss | 1451 | 1467 | 28 | 1005 |
| 673143 | GGCCCCGGCCCCTAGCG | ek-d8-ekekeee | sossssssssssooss | 1452 | 1468 | 28 | 1006 |
| 673144 | CGGCCCCGGCCCCTAGC | ek-d8-ekekeee | sossssssssssooss | 1453 | 1469 | 49 | 1007 |
| 673145 | CCGGCCCCGGCCCCTAG | ek-d8-ekekeee | sossssssssssooss | 1454 | 1470 | 24 | 1008 |
| 673146 | CCCGGCCCCGGCCCCTA | ek-d8-ekekeee | sossssssssssooss | 1455 | 1471 | 32 | 1009 |
| 673147 | ACGCCCCGGCCCCGGCC | ek-d8-ekekeee | sossssssssssooss | 1465 | 1481 | 12 | 1010 |
| 673148 | CACGCCCCGGCCCCGGC | ek-d8-ekekeee | sossssssssssooss | 1466 | 1482 | 4 | 1011 |
| 673149 | CCACGCCCCGGCCCCGG | ek-d8-ekekeee | sossssssssssooss | 1467 | 1483 | 18 | 1012 |
| 673150 | ACCACGCCCCGGCCCCG | ek-d8-ekekeee | sossssssssssooss | 1468 | 1484 | 5 | 1013 |

TABLE 42-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673151 | GACCACGCCCCGGCCCC | ek-d8-ekekeee | sosssssssssooosss | 1469 | 1485 | 20 | 1014 |
| 673152 | CGACCACGCCCCGGCCC | ek-d8-ekekeee | sosssssssssooosss | 1470 | 1486 | 52 | 1015 |
| 673153 | CCGACCACGCCCCGGCC | ek-d8-ekekeee | sosssssssssooosss | 1471 | 1487 | 4 | 1016 |
| 673154 | CCCGACCACGCCCCGGC | ek-d8-ekekeee | sosssssssssooosss | 1472 | 1488 | 9 | 1017 |
| 673155 | CCCCGACCACGCCCCGG | ek-d8-ekekeee | sosssssssssooosss | 1473 | 1489 | 23 | 1018 |
| 673156 | GCCCCGACCACGCCCCG | ek-d8-ekekeee | sosssssssssooosss | 1474 | 1490 | 9 | 1019 |
| 673157 | CGCCCCGACCACGCCCC | ek-d8-ekekeee | sosssssssssooosss | 1475 | 1491 | 22 | 1020 |
| 673158 | CCGCCCCGACCACGCCC | ek-d8-ekekeee | sosssssssssooosss | 1476 | 1492 | 27 | 1021 |
| 673159 | CCCGCCCCGACCACGCC | ek-d8-ekekeee | sosssssssssooosss | 1477 | 1493 | 49 | 1022 |
| 673160 | GCCCGCCCCGACCACGC | ek-d8-ekekeee | sosssssssssooosss | 1478 | 1494 | 33 | 1023 |
| 673161 | GGCCCGCCCCGACCACG | ek-d8-ekekeee | sosssssssssooosss | 1479 | 1495 | 7 | 1024 |
| 673162 | GGGCCCGCCCCGACCAC | ek-d8-ekekeee | sosssssssssooosss | 1480 | 1496 | 8 | 1025 |
| 673163 | CGGGCCCGCCCCGACCA | ek-d8-ekekeee | sosssssssssooosss | 1481 | 1497 | 12 | 1026 |
| 673164 | CCGGGCCCGCCCCGACC | ek-d8-ekekeee | sosssssssssooosss | 1482 | 1498 | 2 | 1027 |
| 673165 | CCCGGGCCCGCCCCGAC | ek-d8-ekekeee | sosssssssssooosss | 1483 | 1499 | 13 | 1028 |
| 673166 | GCAGCCCCGCCCCGGGC | ek-d8-ekekeee | sosssssssssooosss | 1505 | 1521 | 7 | 1029 |
| 673167 | CGCAGCCCCGCCCCGGG | ek-d8-ekekeee | sosssssssssooosss | 1506 | 1522 | 14 | 1030 |
| 673168 | CCGCAGCCCCGCCCCGG | ek-d8-ekekeee | sosssssssssooosss | 1507 | 1523 | 17 | 1031 |
| 673169 | ACCGCAGCCCCGCCCCG | ek-d8-ekekeee | sosssssssssooosss | 1508 | 1524 | 44 | 1032 |
| 673170 | AACCGCAGCCCCGCCCC | ek-d8-ekekeee | sosssssssssooosss | 1509 | 1525 | 40 | 1033 |
| 673171 | CAACCGCAGCCCCGCCC | ek-d8-ekekeee | sosssssssssooosss | 1510 | 1526 | 45 | 1034 |
| 673172 | GCAACCGCAGCCCCGCC | ek-d8-ekekeee | sosssssssssooosss | 1511 | 1527 | 28 | 1035 |
| 673173 | CGCAACCGCAGCCCCGC | ek-d8-ekekeee | sosssssssssooosss | 1512 | 1528 | 31 | 1036 |
| 673174 | CCGCAACCGCAGCCCCG | ek-d8-ekekeee | sosssssssssooosss | 1513 | 1529 | 38 | 1037 |
| 673175 | ACCGCAACCGCAGCCCC | ek-d8-ekekeee | sosssssssssooosss | 1514 | 1530 | 47 | 1038 |
| 673176 | CACCGCAACCGCAGCCC | ek-d8-ekekeee | sosssssssssooosss | 1515 | 1531 | 37 | 1039 |
| 673177 | GCACCGCAACCGCAGCC | ek-d8-ekekeee | sosssssssssooosss | 1516 | 1532 | 41 | 1040 |
| 673178 | GGCACCGCAACCGCAGC | ek-d8-ekekeee | sosssssssssooosss | 1517 | 1533 | 34 | 1041 |
| 673179 | AGGCACCGCAACCGCAG | ek-d8-ekekeee | sosssssssssooosss | 1518 | 1534 | 19 | 1042 |
| 673180 | CAGGCACCGCAACCGCA | ek-d8-ekekeee | sosssssssssooosss | 1519 | 1535 | 36 | 1043 |
| 673181 | GCAGGCACCGCAACCGC | ek-d8-ekekeee | sosssssssssooosss | 1520 | 1536 | 33 | 1044 |
| 673182 | CGCAGGCACCGCAACCG | ek-d8-ekekeee | sosssssssssooosss | 1521 | 1537 | 37 | 1045 |
| 673183 | GCGCAGGCACCGCAACC | ek-d8-ekekeee | sosssssssssooosss | 1522 | 1538 | 6 | 1046 |
| 673184 | GGCGCAGGCACCGCAAC | ek-d8-ekekeee | sosssssssssooosss | 1523 | 1539 | 11 | 1047 |

TABLE 43

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 576816 | GCCTTACTCTAGGACCAAGA | eeeee-d10-eeeee | sssssssssssssssssss | 7990 | 8009 | 79 | 20 |
| 673185 | TGAGAGCAAGTAGTGGG | keke-d8-ekeke | soosssssssssooss | 1326 | 1342 | 37 | 898 |
| 673186 | GTGAGAGCAAGTAGTGG | keke-d8-ekeke | soosssssssssooss | 1327 | 1343 | 39 | 899 |
| 673187 | TGTGAGAGCAAGTAGTG | keke-d8-ekeke | soosssssssssooss | 1328 | 1344 | 33 | 900 |
| 673188 | CTGTGAGAGCAAGTAGT | keke-d8-ekeke | soosssssssssooss | 1329 | 1345 | 40 | 901 |
| 673189 | ACTGTGAGAGCAAGTAG | keke-d8-ekeke | soosssssssssooss | 1330 | 1346 | 26 | 902 |
| 673190 | TACTGTGAGAGCAAGTA | keke-d8-ekeke | soosssssssssooss | 1331 | 1347 | 23 | 903 |
| 673191 | GTACTGTGAGAGCAAGT | keke-d8-ekeke | soosssssssssooss | 1332 | 1348 | 50 | 904 |
| 673192 | AGTACTGTGAGAGCAAG | keke-d8-ekeke | soosssssssssooss | 1333 | 1349 | 39 | 905 |
| 673193 | GAGTACTGTGAGAGCAA | keke-d8-ekeke | soosssssssssooss | 1334 | 1350 | 69 | 906 |
| 673194 | CGAGTACTGTGAGAGCA | keke-d8-ekeke | soosssssssssooss | 1335 | 1351 | 72 | 907 |
| 673195 | GCGAGTACTGTGAGAGC | keke-d8-ekeke | soosssssssssooss | 1336 | 1352 | 51 | 908 |
| 673196 | AGCGAGTACTGTGAGAG | keke-d8-ekeke | soosssssssssooss | 1337 | 1353 | 51 | 909 |
| 673197 | CAGCGAGTACTGTGAGA | keke-d8-ekeke | soosssssssssooss | 1338 | 1354 | 59 | 910 |
| 673198 | TCAGCGAGTACTGTGAG | keke-d8-ekeke | soosssssssssooss | 1339 | 1355 | 33 | 911 |
| 673199 | CTCAGCGAGTACTGTGA | keke-d8-ekeke | soosssssssssooss | 1340 | 1356 | 32 | 912 |
| 673200 | CCTCAGCGAGTACTGTG | keke-d8-ekeke | soosssssssssooss | 1341 | 1357 | 46 | 913 |
| 673201 | CCCTCAGCGAGTACTGT | keke-d8-ekeke | soosssssssssooss | 1342 | 1358 | 53 | 914 |
| 673202 | ACCCTCAGCGAGTACTG | keke-d8-ekeke | soosssssssssooss | 1343 | 1359 | 58 | 915 |
| 673203 | CACCCTCAGCGAGTACT | keke-d8-ekeke | soosssssssssooss | 1344 | 1360 | 68 | 916 |
| 673204 | TCACCCTCAGCGAGTAC | keke-d8-ekeke | soosssssssssooss | 1345 | 1361 | 70 | 917 |
| 673205 | TTCACCCTCAGCGAGTA | keke-d8-ekeke | soosssssssssooss | 1346 | 1362 | 47 | 918 |
| 673206 | GTTCACCCTCAGCGAGT | keke-d8-ekeke | soosssssssssooss | 1347 | 1363 | 65 | 919 |
| 673207 | TGTTCACCCTCAGCGAG | keke-d8-ekeke | soosssssssssooss | 1348 | 1364 | 31 | 920 |
| 673208 | TTGTTCACCCTCAGCGA | keke-d8-ekeke | soosssssssssooss | 1349 | 1365 | 51 | 921 |
| 673209 | CTTGTTCACCCTCAGCG | keke-d8-ekeke | soosssssssssooss | 1350 | 1366 | 49 | 922 |
| 673210 | TCTTGTTCACCCTCAGC | keke-d8-ekeke | soosssssssssooss | 1351 | 1367 | 61 | 923 |
| 673211 | TTCTTGTTCACCCTCAG | keke-d8-ekeke | soosssssssssooss | 1352 | 1368 | 49 | 924 |
| 673212 | TTTCTTGTTCACCCTCA | keke-d8-ekeke | soosssssssssooss | 1353 | 1369 | 42 | 925 |
| 673213 | TTTTCTTGTTCACCCTC | keke-d8-ekeke | soosssssssssooss | 1354 | 1370 | 36 | 926 |
| 673214 | CTTTTCTTGTTCACCCT | keke-d8-ekeke | soosssssssssooss | 1355 | 1371 | 41 | 927 |
| 673215 | TCTTTTCTTGTTCACCC | keke-d8-ekeke | soosssssssssooss | 1356 | 1372 | 41 | 928 |
| 673216 | GTCTTTTCTTGTTCACC | keke-d8-ekeke | soosssssssssooss | 1357 | 1373 | 36 | 929 |
| 673217 | GGTCTTTTCTTGTTCAC | keke-d8-ekeke | soosssssssssooss | 1358 | 1374 | 29 | 930 |
| 673218 | AGGTCTTTTCTTGTTCA | keke-d8-ekeke | soosssssssssooss | 1359 | 1375 | 50 | 931 |

TABLE 43-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673219 | CAGGTCTTTTCTTGTTC | keke-d8-ekeke | soosssssssssooss | 1360 | 1376 | 60 | 932 |
| 673220 | TCAGGTCTTTTCTTGTT | keke-d8-ekeke | soosssssssssooss | 1361 | 1377 | 34 | 933 |
| 673221 | ATCAGGTCTTTTCTTGT | keke-d8-ekeke | soosssssssssooss | 1362 | 1378 | 33 | 934 |
| 673222 | TATCAGGTCTTTTCTTG | keke-d8-ekeke | soosssssssssooss | 1363 | 1379 | 31 | 935 |
| 673223 | TTATCAGGTCTTTTCTT | keke-d8-ekeke | soosssssssssooss | 1364 | 1380 | 10 | 936 |
| 673224 | ATCTTTATCAGGTCTTT | keke-d8-ekeke | soosssssssssooss | 1368 | 1384 | 61 | 937 |
| 673225 | AATCTTTATCAGGTCTT | keke-d8-ekeke | soosssssssssooss | 1369 | 1385 | 74 | 938 |
| 673226 | TAATCTTTATCAGGTCT | keke-d8-ekeke | soosssssssssooss | 1370 | 1386 | 62 | 939 |
| 673227 | TTAATCTTTATCAGGTC | keke-d8-ekeke | soosssssssssooss | 1371 | 1387 | 51 | 940 |
| 673228 | GTTAATCTTTATCAGGT | keke-d8-ekeke | soosssssssssooss | 1372 | 1388 | 73 | 941 |
| 673229 | GGTTAATCTTTATCAGG | keke-d8-ekeke | soosssssssssooss | 1373 | 1389 | 66 | 942 |
| 673230 | TGGTTAATCTTTATCAG | keke-d8-ekeke | soosssssssssooss | 1374 | 1390 | 38 | 943 |
| 673231 | CTGGTTAATCTTTATCA | keke-d8-ekeke | soosssssssssooss | 1375 | 1391 | 41 | 944 |
| 673232 | TCTGGTTAATCTTTATC | keke-d8-ekeke | soosssssssssooss | 1376 | 1392 | 37 | 945 |
| 673233 | CCCTCCTTGTTTTCTTC | keke-d8-ekeke | soosssssssssooss | 1391 | 1407 | 26 | 946 |
| 673234 | TCCCTCCTTGTTTTCTT | keke-d8-ekeke | soosssssssssooss | 1392 | 1408 | 10 | 947 |
| 673235 | TTCCCTCCTTGTTTTCT | keke-d8-ekeke | soosssssssssooss | 1393 | 1409 | 20 | 948 |
| 673236 | TTTCCCTCCTTGTTTTC | keke-d8-ekeke | soosssssssssooss | 1394 | 1410 | 1 | 949 |
| 673237 | GTTTCCCTCCTTGTTTT | keke-d8-ekeke | soosssssssssooss | 1395 | 1411 | 7 | 950 |
| 673238 | TGTTTCCCTCCTTGTTT | keke-d8-ekeke | soosssssssssooss | 1396 | 1412 | 26 | 951 |
| 673239 | TTGTTTCCCTCCTTGTT | keke-d8-ekeke | soosssssssssooss | 1397 | 1413 | 28 | 952 |
| 673240 | GGTTGTTTCCCTCCTTG | keke-d8-ekeke | soosssssssssooss | 1399 | 1415 | 70 | 953 |
| 673241 | CGGTTGTTTCCCTCCTT | keke-d8-ekeke | soosssssssssooss | 1400 | 1416 | 36 | 954 |
| 673242 | GCGGTTGTTTCCCTCCT | keke-d8-ekeke | soosssssssssooss | 1401 | 1417 | 21 | 955 |
| 673243 | TGCGGTTGTTTCCCTCC | keke-d8-ekeke | soosssssssssooss | 1402 | 1418 | 24 | 956 |
| 673244 | CTGCGGTTGTTTCCCTC | keke-d8-ekeke | soosssssssssooss | 1403 | 1419 | 41 | 957 |
| 673245 | GCTGCGGTTGTTTCCCT | keke-d8-ekeke | soosssssssssooss | 1404 | 1420 | 23 | 958 |
| 673246 | GGCTGCGGTTGTTTCCC | keke-d8-ekeke | soosssssssssooss | 1405 | 1421 | 39 | 959 |
| 673247 | AGGCTGCGGTTGTTTCC | keke-d8-ekeke | soosssssssssooss | 1406 | 1422 | 50 | 960 |
| 673248 | CAGGCTGCGGTTGTTTC | keke-d8-ekeke | soosssssssssooss | 1407 | 1423 | 32 | 961 |
| 673249 | ACAGGCTGCGGTTGTTT | keke-d8-ekeke | soosssssssssooss | 1408 | 1424 | 28 | 962 |
| 673250 | TACAGGCTGCGGTTGTT | keke-d8-ekeke | soosssssssssooss | 1409 | 1425 | 41 | 963 |
| 673251 | CTACAGGCTGCGGTTGT | keke-d8-ekeke | soosssssssssooss | 1410 | 1426 | 18 | 964 |
| 673252 | GCTACAGGCTGCGGTTG | keke-d8-ekeke | soosssssssssooss | 1411 | 1427 | 28 | 965 |
| 673253 | TGCTACAGGCTGCGGTT | keke-d8-ekeke | soosssssssssooss | 1412 | 1428 | 28 | 966 |

TABLE 43-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673254 | TTGCTACAGGCTGCGGT | keke-d8-ekeke | sooossssssssssooss | 1413 | 1429 | 9 | 967 |
| 673255 | CTTGCTACAGGCTGCGG | keke-d8-ekeke | sooossssssssssooss | 1414 | 1430 | 34 | 968 |
| 673256 | GCTTGCTACAGGCTGCG | keke-d8-ekeke | sooossssssssssooss | 1415 | 1431 | 28 | 969 |
| 673257 | AGCTTGCTACAGGCTGC | keke-d8-ekeke | sooossssssssssooss | 1416 | 1432 | 25 | 970 |
| 673258 | GAGCTTGCTACAGGCTG | keke-d8-ekeke | sooossssssssssooss | 1417 | 1433 | 23 | 971 |
| 673259 | AGAGCTTGCTACAGGCT | keke-d8-ekeke | sooossssssssssooss | 1418 | 1434 | 0 | 972 |
| 673260 | CAGAGCTTGCTACAGGC | keke-d8-ekeke | sooossssssssssooss | 1419 | 1435 | 4 | 973 |
| 673261 | CCAGAGCTTGCTACAGG | keke-d8-ekeke | sooossssssssssooss | 1420 | 1436 | 40 | 974 |
| 673262 | TCCAGAGCTTGCTACAG | keke-d8-ekeke | sooossssssssssooss | 1421 | 1437 | 35 | 975 |
| 673263 | TTCCAGAGCTTGCTACA | keke-d8-ekeke | sooossssssssssooss | 1422 | 1438 | 23 | 976 |
| 673264 | GTTCCAGAGCTTGCTAC | keke-d8-ekeke | sooossssssssssooss | 1423 | 1439 | 36 | 977 |
| 673265 | AGTTCCAGAGCTTGCTA | keke-d8-ekeke | sooossssssssssooss | 1424 | 1440 | 54 | 978 |
| 673266 | GAGTTCCAGAGCTTGCT | keke-d8-ekeke | sooossssssssssooss | 1425 | 1441 | 32 | 979 |
| 673267 | TGAGTTCCAGAGCTTGC | keke-d8-ekeke | sooossssssssssooss | 1426 | 1442 | 32 | 980 |
| 673268 | CTGAGTTCCAGAGCTTG | keke-d8-ekeke | sooossssssssssooss | 1427 | 1443 | 44 | 981 |
| 673269 | CCTGAGTTCCAGAGCTT | keke-d8-ekeke | sooossssssssssooss | 1428 | 1444 | 70 | 982 |
| 673270 | TCCTGAGTTCCAGAGCT | keke-d8-ekeke | sooossssssssssooss | 1429 | 1445 | 43 | 983 |
| 673271 | CTCCTGAGTTCCAGAGC | keke-d8-ekeke | sooossssssssssooss | 1430 | 1446 | 41 | 984 |
| 673272 | ACTCCTGAGTTCCAGAG | keke-d8-ekeke | sooossssssssssooss | 1431 | 1447 | 23 | 985 |
| 673273 | GACTCCTGAGTTCCAGA | keke-d8-ekeke | sooossssssssssooss | 1432 | 1448 | 48 | 986 |
| 673274 | CGACTCCTGAGTTCCAG | keke-d8-ekeke | sooossssssssssooss | 1433 | 1449 | 34 | 987 |
| 673275 | GCGACTCCTGAGTTCCA | keke-d8-ekeke | sooossssssssssooss | 1434 | 1450 | 64 | 988 |
| 673276 | CGCGACTCCTGAGTTCC | keke-d8-ekeke | sooossssssssssooss | 1435 | 1451 | 65 | 989 |
| 673277 | GCGCGACTCCTGAGTTC | keke-d8-ekeke | sooossssssssssooss | 1436 | 1452 | 62 | 990 |
| 673278 | CGCGCGACTCCTGAGTT | keke-d8-ekeke | sooossssssssssooss | 1437 | 1453 | 45 | 991 |
| 673279 | GCGCGCGACTCCTGAGT | keke-d8-ekeke | sooossssssssssooss | 1438 | 1454 | 52 | 992 |
| 673280 | AGCGCGCGACTCCTGAG | keke-d8-ekeke | sooossssssssssooss | 1439 | 1455 | 65 | 993 |
| 673281 | TAGCGCGCGACTCCTGA | keke-d8-ekeke | sooossssssssssooss | 1440 | 1456 | 89 | 994 |
| 673282 | CTAGCGCGCGACTCCTG | keke-d8-ekeke | sooossssssssssooss | 1441 | 1457 | 69 | 995 |
| 673283 | CCTAGCGCGCGACTCCT | keke-d8-ekeke | sooossssssssssooss | 1442 | 1458 | 68 | 996 |
| 673284 | CCCTAGCGCGCGACTCC | keke-d8-ekeke | sooossssssssssooss | 1443 | 1459 | 73 | 997 |
| 673285 | CCCCTAGCGCGCGACTC | keke-d8-ekeke | sooossssssssssooss | 1444 | 1460 | 70 | 998 |
| 673286 | GCCCCTAGCGCGCGACT | keke-d8-ekeke | sooossssssssssooss | 1445 | 1461 | 45 | 999 |
| 673287 | GGCCCCTAGCGCGCGAC | keke-d8-ekeke | sooossssssssssooss | 1446 | 1462 | 33 | 1000 |
| 673288 | CGGCCCCTAGCGCGCGA | keke-d8-ekeke | sooossssssssssooss | 1447 | 1463 | 29 | 1001 |

TABLE 43-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673289 | CCGGCCCCTAGCGCGCG | keke-d8-ekeke | soossssssssssooss | 1448 | 1464 | 0 | 1002 |
| 673290 | CCCGGCCCCTAGCGCGC | keke-d8-ekeke | soossssssssssooss | 1449 | 1465 | 31 | 1003 |
| 673291 | CCCCGGCCCCTAGCGCG | keke-d8-ekeke | soossssssssssooss | 1450 | 1466 | 28 | 1004 |
| 673292 | GCCCCGGCCCCTAGCGC | keke-d8-ekeke | soossssssssssooss | 1451 | 1467 | 12 | 1005 |
| 673293 | GGCCCCGGCCCCTAGCG | keke-d8-ekeke | soossssssssssooss | 1452 | 1468 | 29 | 1006 |
| 673294 | CGGCCCCGGCCCCTAGC | keke-d8-ekeke | soossssssssssooss | 1453 | 1469 | 39 | 1007 |
| 673295 | CCGGCCCCGGCCCCTAG | keke-d8-ekeke | soossssssssssooss | 1454 | 1470 | 28 | 1008 |
| 673296 | CCCGGCCCCGGCCCCTA | keke-d8-ekeke | soossssssssssooss | 1455 | 1471 | 4 | 1009 |
| 673297 | ACGCCCCGGCCCCGGCC | keke-d8-ekeke | soossssssssssooss | 1465 | 1481 | 17 | 1010 |
| 673298 | CACGCCCCGGCCCCGGC | keke-d8-ekeke | soossssssssssooss | 1466 | 1482 | 35 | 1011 |
| 673299 | CCACGCCCCGGCCCCGG | keke-d8-ekeke | soossssssssssooss | 1467 | 1483 | 28 | 1012 |
| 673300 | ACCACGCCCCGGCCCCG | keke-d8-ekeke | soossssssssssooss | 1468 | 1484 | 21 | 1013 |
| 673301 | GACCACGCCCCGGCCCC | keke-d8-ekeke | soossssssssssooss | 1469 | 1485 | 28 | 1014 |
| 673302 | CGACCACGCCCCGGCCC | keke-d8-ekeke | soossssssssssooss | 1470 | 1486 | 46 | 1015 |
| 673303 | CCGACCACGCCCCGGCC | keke-d8-ekeke | soossssssssssooss | 1471 | 1487 | 40 | 1016 |
| 673304 | CCCGACCACGCCCCGGC | keke-d8-ekeke | soossssssssssooss | 1472 | 1488 | 16 | 1017 |
| 673305 | CCCCGACCACGCCCCGG | keke-d8-ekeke | soossssssssssooss | 1473 | 1489 | 11 | 1018 |
| 673306 | GCCCCGACCACGCCCCG | keke-d8-ekeke | soossssssssssooss | 1474 | 1490 | 13 | 1019 |
| 673307 | CGCCCCGACCACGCCCC | keke-d8-ekeke | soossssssssssooss | 1475 | 1491 | 43 | 1020 |
| 673308 | CCGCCCCGACCACGCCC | keke-d8-ekeke | soossssssssssooss | 1476 | 1492 | 20 | 1021 |
| 673309 | CCCGCCCCGACCACGCC | keke-d8-ekeke | soossssssssssooss | 1477 | 1493 | 16 | 1022 |
| 673310 | GCCCGCCCCGACCACGC | keke-d8-ekeke | soossssssssssooss | 1478 | 1494 | 44 | 1023 |
| 673311 | GGCCCGCCCCGACCACG | keke-d8-ekeke | soossssssssssooss | 1479 | 1495 | 33 | 1024 |
| 673312 | GGGCCCGCCCCGACCAC | keke-d8-ekeke | soossssssssssooss | 1480 | 1496 | 1 | 1025 |
| 673313 | CGGGCCCGCCCCGACCA | keke-d8-ekeke | soossssssssssooss | 1481 | 1497 | 0 | 1026 |
| 673314 | CCGGGCCCGCCCCGACC | keke-d8-ekeke | soossssssssssooss | 1482 | 1498 | 0 | 1027 |
| 673315 | CCCGGGCCCGCCCCGAC | keke-d8-ekeke | soossssssssssooss | 1483 | 1499 | 8 | 1028 |
| 673316 | GCAGCCCCGCCCCGGGC | keke-d8-ekeke | soossssssssssooss | 1505 | 1521 | 31 | 1029 |
| 673317 | CGCAGCCCCGCCCCGGG | keke-d8-ekeke | soossssssssssooss | 1506 | 1522 | 4 | 1030 |
| 673318 | CCGCAGCCCCGCCCCGG | keke-d8-ekeke | soossssssssssooss | 1507 | 1523 | 18 | 1031 |
| 673319 | ACCGCAGCCCCGCCCCG | keke-d8-ekeke | soossssssssssooss | 1508 | 1524 | 16 | 1032 |
| 673320 | AACCGCAGCCCCGCCCC | keke-d8-ekeke | soossssssssssooss | 1509 | 1525 | 39 | 1033 |
| 673321 | CAACCGCAGCCCCGCCC | keke-d8-ekeke | soossssssssssooss | 1510 | 1526 | 50 | 1034 |
| 673322 | GCAACCGCAGCCCCGCC | keke-d8-ekeke | soossssssssssooss | 1511 | 1527 | 45 | 1035 |
| 673323 | CGCAACCGCAGCCCCGC | keke-d8-ekeke | soossssssssssooss | 1512 | 1528 | 56 | 1036 |

TABLE 43-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673324 | CCGCAACCGCAGCCCCG | keke-d8-ekeke | soossssssssssooss | 1513 | 1529 | 10 | 1037 |
| 673325 | ACCGCAACCGCAGCCCC | keke-d8-ekeke | soossssssssssooss | 1514 | 1530 | 43 | 1038 |
| 673326 | CACCGCAACCGCAGCCC | keke-d8-ekeke | soossssssssssooss | 1515 | 1531 | 49 | 1039 |
| 673327 | GCACCGCAACCGCAGCC | keke-d8-ekeke | soossssssssssooss | 1516 | 1532 | 35 | 1040 |
| 673328 | GGCACCGCAACCGCAGC | keke-d8-ekeke | soossssssssssooss | 1517 | 1533 | 24 | 1041 |
| 673329 | AGGCACCGCAACCGCAG | keke-d8-ekeke | soossssssssssooss | 1518 | 1534 | 52 | 1042 |
| 673330 | CAGGCACCGCAACCGCA | keke-d8-ekeke | soossssssssssooss | 1519 | 1535 | 38 | 1043 |
| 673331 | GCAGGCACCGCAACCGC | keke-d8-ekeke | soossssssssssooss | 1520 | 1536 | 51 | 1044 |
| 673332 | CGCAGGCACCGCAACCG | keke-d8-ekeke | soossssssssssooss | 1521 | 1537 | 59 | 1045 |
| 673333 | GCGCAGGCACCGCAACC | keke-d8-ekeke | soossssssssssooss | 1522 | 1538 | 24 | 1046 |
| 673334 | GGCGCAGGCACCGCAAC | keke-d8-ekeke | soossssssssssooss | 1523 | 1539 | 18 | 1047 |

TABLE 44

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 576816 | GCCTTACTCTAGGACCAAGA | eeeee-d10-eeeee | sssssssssssssssssss | 7990 | 8009 | 60 | 20 |
| 673335 | TGAGAGCAAGTAGTGGG | ekek-d8-kekee | soossssssssssooss | 1326 | 1342 | 28 | 898 |
| 673336 | GTGAGAGCAAGTAGTGG | ekek-d8-kekee | soossssssssssooss | 1327 | 1343 | 27 | 899 |
| 673337 | TGTGAGAGCAAGTAGTG | ekek-d8-kekee | soossssssssssooss | 1328 | 1344 | 32 | 900 |
| 673338 | CTGTGAGAGCAAGTAGT | ekek-d8-kekee | soossssssssssooss | 1329 | 1345 | 43 | 901 |
| 673339 | ACTGTGAGAGCAAGTAG | ekek-d8-kekee | soossssssssssooss | 1330 | 1346 | 22 | 902 |
| 673340 | TACTGTGAGAGCAAGTA | ekek-d8-kekee | soossssssssssooss | 1331 | 1347 | 20 | 903 |
| 673341 | GTACTGTGAGAGCAAGT | ekek-d8-kekee | soossssssssssooss | 1332 | 1348 | 53 | 904 |
| 673342 | AGTACTGTGAGAGCAAG | ekek-d8-kekee | soossssssssssooss | 1333 | 1349 | 20 | 905 |
| 673343 | GAGTACTGTGAGAGCAA | ekek-d8-kekee | soossssssssssooss | 1334 | 1350 | 50 | 906 |
| 673344 | CGAGTACTGTGAGAGCA | ekek-d8-kekee | soossssssssssooss | 1335 | 1351 | 45 | 907 |
| 673345 | GCGAGTACTGTGAGAGC | ekek-d8-kekee | soossssssssssooss | 1336 | 1352 | 45 | 908 |
| 673346 | AGCGAGTACTGTGAGAG | ekek-d8-kekee | soossssssssssooss | 1337 | 1353 | 53 | 909 |
| 673347 | CAGCGAGTACTGTGAGA | ekek-d8-kekee | soossssssssssooss | 1338 | 1354 | 35 | 910 |
| 673348 | TCAGCGAGTACTGTGAG | ekek-d8-kekee | soossssssssssooss | 1339 | 1355 | 36 | 911 |
| 673349 | CTCAGCGAGTACTGTGA | ekek-d8-kekee | soossssssssssooss | 1340 | 1356 | 19 | 912 |
| 673350 | CCTCAGCGAGTACTGTG | ekek-d8-kekee | soossssssssssooss | 1341 | 1357 | 21 | 913 |

TABLE 44-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673351 | CCCTCAGCGAGTACTGT | ekek-d8-kekee | sooossssssssooss | 1342 | 1358 | 46 | 914 |
| 673352 | ACCCTCAGCGAGTACTG | ekek-d8-kekee | sooossssssssooss | 1343 | 1359 | 43 | 915 |
| 673353 | CACCCTCAGCGAGTACT | ekek-d8-kekee | sooossssssssooss | 1344 | 1360 | 46 | 916 |
| 673354 | TCACCCTCAGCGAGTAC | ekek-d8-kekee | sooossssssssooss | 1345 | 1361 | 40 | 917 |
| 673355 | TTCACCCTCAGCGAGTA | ekek-d8-kekee | sooossssssssooss | 1346 | 1362 | 33 | 918 |
| 673356 | GTTCACCCTCAGCGAGT | ekek-d8-kekee | sooossssssssooss | 1347 | 1363 | 11 | 919 |
| 673357 | TGTTCACCCTCAGCGAG | ekek-d8-kekee | sooossssssssooss | 1348 | 1364 | 34 | 920 |
| 673358 | TTGTTCACCCTCAGCGA | ekek-d8-kekee | sooossssssssooss | 1349 | 1365 | 47 | 921 |
| 673359 | CTTGTTCACCCTCAGCG | ekek-d8-kekee | sooossssssssooss | 1350 | 1366 | 54 | 922 |
| 673360 | TCTTGTTCACCCTCAGC | ekek-d8-kekee | sooossssssssooss | 1351 | 1367 | 26 | 923 |
| 673361 | TTCTTGTTCACCCTCAG | ekek-d8-kekee | sooossssssssooss | 1352 | 1368 | 36 | 924 |
| 673362 | TTTCTTGTTCACCCTCA | ekek-d8-kekee | sooossssssssooss | 1353 | 1369 | 29 | 925 |
| 673363 | TTTTCTTGTTCACCCTC | ekek-d8-kekee | sooossssssssooss | 1354 | 1370 | 29 | 926 |
| 673364 | CTTTTCTTGTTCACCCT | ekek-d8-kekee | sooossssssssooss | 1355 | 1371 | 23 | 927 |
| 673365 | TCTTTTCTTGTTCACCC | ekek-d8-kekee | sooossssssssooss | 1356 | 1372 | 36 | 928 |
| 673366 | GTCTTTTCTTGTTCACC | ekek-d8-kekee | sooossssssssooss | 1357 | 1373 | 27 | 929 |
| 673367 | GGTCTTTTCTTGTTCAC | ekek-d8-kekee | sooossssssssooss | 1358 | 1374 | 21 | 930 |
| 673368 | AGGTCTTTTCTTGTTCA | ekek-d8-kekee | sooossssssssooss | 1359 | 1375 | 29 | 931 |
| 673369 | CAGGTCTTTTCTTGTTC | ekek-d8-kekee | sooossssssssooss | 1360 | 1376 | 65 | 932 |
| 673370 | TCAGGTCTTTTCTTGTT | ekek-d8-kekee | sooossssssssooss | 1361 | 1377 | 2 | 933 |
| 673371 | ATCAGGTCTTTTCTTGT | ekek-d8-kekee | sooossssssssooss | 1362 | 1378 | 23 | 934 |
| 673372 | TATCAGGTCTTTTCTTG | ekek-d8-kekee | sooossssssssooss | 1363 | 1379 | 40 | 935 |
| 673373 | TTATCAGGTCTTTTCTT | ekek-d8-kekee | sooossssssssooss | 1364 | 1380 | 13 | 936 |
| 673374 | ATCTTTATCAGGTCTTT | ekek-d8-kekee | sooossssssssooss | 1368 | 1384 | 76 | 937 |
| 673375 | AATCTTTATCAGGTCTT | ekek-d8-kekee | sooossssssssooss | 1369 | 1385 | 62 | 938 |
| 673376 | TAATCTTTATCAGGTCT | ekek-d8-kekee | sooossssssssooss | 1370 | 1386 | 39 | 939 |
| 673377 | TTAATCTTTATCAGGTC | ekek-d8-kekee | sooossssssssooss | 1371 | 1387 | 71 | 940 |
| 673378 | GTTAATCTTTATCAGGT | ekek-d8-kekee | sooossssssssooss | 1372 | 1388 | 61 | 941 |
| 673379 | GGTTAATCTTTATCAGG | ekek-d8-kekee | sooossssssssooss | 1373 | 1389 | 74 | 942 |
| 673380 | TGGTTAATCTTTATCAG | ekek-d8-kekee | sooossssssssooss | 1374 | 1390 | 24 | 943 |
| 673381 | CTGGTTAATCTTTATCA | ekek-d8-kekee | sooossssssssooss | 1375 | 1391 | 32 | 944 |
| 673382 | TCTGGTTAATCTTTATC | ekek-d8-kekee | sooossssssssooss | 1376 | 1392 | 38 | 945 |
| 673383 | CCCTCCTTGTTTTCTTC | ekek-d8-kekee | sooossssssssooss | 1391 | 1407 | 21 | 946 |
| 673384 | TCCCTCCTTGTTTTCTT | ekek-d8-kekee | sooossssssssooss | 1392 | 1408 | 0 | 947 |
| 673385 | TTCCCTCCTTGTTTTCT | ekek-d8-kekee | sooossssssssooss | 1393 | 1409 | 0 | 948 |

TABLE 44-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673386 | TTTCCCTCCTTGTTTTC | ekek-d8-kekee | soossssssssssooss | 1394 | 1410 | 5 | 949 |
| 673387 | GTTTCCCTCCTTGTTTT | ekek-d8-kekee | soossssssssssooss | 1395 | 1411 | 0 | 950 |
| 673388 | TGTTTCCCTCCTTGTTT | ekek-d8-kekee | soossssssssssooss | 1396 | 1412 | 0 | 951 |
| 673389 | TTGTTTCCCTCCTTGTT | ekek-d8-kekee | soossssssssssooss | 1397 | 1413 | 22 | 952 |
| 673390 | GGTTGTTTCCCTCCTTG | ekek-d8-kekee | soossssssssssooss | 1399 | 1415 | 55 | 953 |
| 673391 | CGGTTGTTTCCCTCCTT | ekek-d8-kekee | soossssssssssooss | 1400 | 1416 | 25 | 954 |
| 673392 | GCGGTTGTTTCCCTCCT | ekek-d8-kekee | soossssssssssooss | 1401 | 1417 | 19 | 955 |
| 673393 | TGCGGTTGTTTCCCTCC | ekek-d8-kekee | soossssssssssooss | 1402 | 1418 | 0 | 956 |
| 673394 | CTGCGGTTGTTTCCCTC | ekek-d8-kekee | soossssssssssooss | 1403 | 1419 | 13 | 957 |
| 673395 | GCTGCGGTTGTTTCCCT | ekek-d8-kekee | soossssssssssooss | 1404 | 1420 | 19 | 958 |
| 673396 | GGCTGCGGTTGTTTCCC | ekek-d8-kekee | soossssssssssooss | 1405 | 1421 | 27 | 959 |
| 673397 | AGGCTGCGGTTGTTTCC | ekek-d8-kekee | soossssssssssooss | 1406 | 1422 | 13 | 960 |
| 673398 | CAGGCTGCGGTTGTTTC | ekek-d8-kekee | soossssssssssooss | 1407 | 1423 | 22 | 961 |
| 673399 | ACAGGCTGCGGTTGTTT | ekek-d8-kekee | soossssssssssooss | 1408 | 1424 | 5 | 962 |
| 673400 | TACAGGCTGCGGTTGTT | ekek-d8-kekee | soossssssssssooss | 1409 | 1425 | 0 | 963 |
| 673401 | CTACAGGCTGCGGTTGT | ekek-d8-kekee | soossssssssssooss | 1410 | 1426 | 0 | 964 |
| 673402 | GCTACAGGCTGCGGTTG | ekek-d8-kekee | soossssssssssooss | 1411 | 1427 | 39 | 965 |
| 673403 | TGCTACAGGCTGCGGTT | ekek-d8-kekee | soossssssssssooss | 1412 | 1428 | 20 | 966 |
| 673404 | TTGCTACAGGCTGCGGT | ekek-d8-kekee | soossssssssssooss | 1413 | 1429 | 24 | 967 |
| 673405 | CTTGCTACAGGCTGCGG | ekek-d8-kekee | soossssssssssooss | 1414 | 1430 | 0 | 968 |
| 673406 | GCTTGCTACAGGCTGCG | ekek-d8-kekee | soossssssssssooss | 1415 | 1431 | 18 | 969 |
| 673407 | AGCTTGCTACAGGCTGC | ekek-d8-kekee | soossssssssssooss | 1416 | 1432 | 3 | 970 |
| 673408 | GAGCTTGCTACAGGCTG | ekek-d8-kekee | soossssssssssooss | 1417 | 1433 | 13 | 971 |
| 673409 | AGAGCTTGCTACAGGCT | ekek-d8-kekee | soossssssssssooss | 1418 | 1434 | 29 | 972 |
| 673410 | CAGAGCTTGCTACAGGC | ekek-d8-kekee | soossssssssssooss | 1419 | 1435 | 22 | 973 |
| 673411 | CCAGAGCTTGCTACAGG | ekek-d8-kekee | soossssssssssooss | 1420 | 1436 | 24 | 974 |
| 673412 | TCCAGAGCTTGCTACAG | ekek-d8-kekee | soossssssssssooss | 1421 | 1437 | 4 | 975 |
| 673413 | TTCCAGAGCTTGCTACA | ekek-d8-kekee | soossssssssssooss | 1422 | 1438 | 0 | 976 |
| 673414 | GTTCCAGAGCTTGCTAC | ekek-d8-kekee | soossssssssssooss | 1423 | 1439 | 19 | 977 |
| 673415 | AGTTCCAGAGCTTGCTA | ekek-d8-kekee | soossssssssssooss | 1424 | 1440 | 0 | 978 |
| 673416 | GAGTTCCAGAGCTTGCT | ekek-d8-kekee | soossssssssssooss | 1425 | 1441 | 48 | 979 |
| 673417 | TGAGTTCCAGAGCTTGC | ekek-d8-kekee | soossssssssssooss | 1426 | 1442 | 14 | 980 |
| 673418 | CTGAGTTCCAGAGCTTG | ekek-d8-kekee | soossssssssssooss | 1427 | 1443 | 37 | 981 |
| 673419 | CCTGAGTTCCAGAGCTT | ekek-d8-kekee | soossssssssssooss | 1428 | 1444 | 80 | 982 |
| 673420 | TCCTGAGTTCCAGAGCT | ekek-d8-kekee | soossssssssssooss | 1429 | 1445 | 26 | 983 |

TABLE 44-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673421 | CTCCTGAGTTCCAGAGC | ekek-d8-kekee | soosssssssssooss | 1430 | 1446 | 5 | 984 |
| 673422 | ACTCCTGAGTTCCAGAG | ekek-d8-kekee | soosssssssssooss | 1431 | 1447 | 23 | 985 |
| 673423 | GACTCCTGAGTTCCAGA | ekek-d8-kekee | soosssssssssooss | 1432 | 1448 | 37 | 986 |
| 673424 | CGACTCCTGAGTTCCAG | ekek-d8-kekee | soosssssssssooss | 1433 | 1449 | 5 | 987 |
| 673425 | GCGACTCCTGAGTTCCA | ekek-d8-kekee | soosssssssssooss | 1434 | 1450 | 39 | 988 |
| 673426 | CGCGACTCCTGAGTTCC | ekek-d8-kekee | soosssssssssooss | 1435 | 1451 | 46 | 989 |
| 673427 | GCGCGACTCCTGAGTTC | ekek-d8-kekee | soosssssssssooss | 1436 | 1452 | 50 | 990 |
| 673428 | CGCGCGACTCCTGAGTT | ekek-d8-kekee | soosssssssssooss | 1437 | 1453 | 19 | 991 |
| 673429 | GCGCGCGACTCCTGAGT | ekek-d8-kekee | soosssssssssooss | 1438 | 1454 | 13 | 992 |
| 673430 | AGCGCGCGACTCCTGAG | ekek-d8-kekee | soosssssssssooss | 1439 | 1455 | 51 | 993 |
| 673431 | TAGCGCGCGACTCCTGA | ekek-d8-kekee | soosssssssssooss | 1440 | 1456 | 83 | 994 |
| 673432 | CTAGCGCGCGACTCCTG | ekek-d8-kekee | soosssssssssooss | 1441 | 1457 | 60 | 995 |
| 673433 | CCTAGCGCGCGACTCCT | ekek-d8-kekee | soosssssssssooss | 1442 | 1458 | 37 | 996 |
| 673434 | CCCTAGCGCGCGACTCC | ekek-d8-kekee | soosssssssssooss | 1443 | 1459 | 60 | 997 |
| 673435 | CCCCTAGCGCGCGACTC | ekek-d8-kekee | soosssssssssooss | 1444 | 1460 | 62 | 998 |
| 673436 | GCCCCTAGCGCGCGACT | ekek-d8-kekee | soosssssssssooss | 1445 | 1461 | 41 | 999 |
| 673437 | GGCCCCTAGCGCGCGAC | ekek-d8-kekee | soosssssssssooss | 1446 | 1462 | 8 | 1000 |
| 673438 | CGGCCCCTAGCGCGCGA | ekek-d8-kekee | soosssssssssooss | 1447 | 1463 | 31 | 1001 |
| 673439 | CCGGCCCCTAGCGCGCG | ekek-d8-kekee | soosssssssssooss | 1448 | 1464 | 18 | 1002 |
| 673440 | CCCGGCCCCTAGCGCGC | ekek-d8-kekee | soosssssssssooss | 1449 | 1465 | 6 | 1003 |
| 673441 | CCCCGGCCCCTAGCGCG | ekek-d8-kekee | soosssssssssooss | 1450 | 1466 | 23 | 1004 |
| 673442 | GCCCCGGCCCCTAGCGC | ekek-d8-kekee | soosssssssssooss | 1451 | 1467 | 8 | 1005 |
| 673443 | GGCCCCGGCCCCTAGCG | ekek-d8-kekee | soosssssssssooss | 1452 | 1468 | 18 | 1006 |
| 673444 | CGGCCCCGGCCCCTAGC | ekek-d8-kekee | soosssssssssooss | 1453 | 1469 | 28 | 1007 |
| 673445 | CCGGCCCCGGCCCCTAG | ekek-d8-kekee | soosssssssssooss | 1454 | 1470 | 9 | 1008 |
| 673446 | CCCGGCCCCGGCCCCTA | ekek-d8-kekee | soosssssssssooss | 1455 | 1471 | 5 | 1009 |
| 673447 | ACGCCCCGGCCCCGGCC | ekek-d8-kekee | soosssssssssooss | 1465 | 1481 | 23 | 1010 |
| 673448 | CACGCCCCGGCCCCGGC | ekek-d8-kekee | soosssssssssooss | 1466 | 1482 | 14 | 1011 |
| 673449 | CCACGCCCCGGCCCCGG | ekek-d8-kekee | soosssssssssooss | 1467 | 1483 | 35 | 1012 |
| 673450 | ACCACGCCCCGGCCCCG | ekek-d8-kekee | soosssssssssooss | 1468 | 1484 | 30 | 1013 |
| 673451 | GACCACGCCCCGGCCCC | ekek-d8-kekee | soosssssssssooss | 1469 | 1485 | 0 | 1014 |
| 673452 | CGACCACGCCCCGGCCC | ekek-d8-kekee | soosssssssssooss | 1470 | 1486 | 15 | 1015 |
| 673453 | CCGACCACGCCCCGGCC | ekek-d8-kekee | soosssssssssooss | 1471 | 1487 | 42 | 1016 |
| 673454 | CCCGACCACGCCCCGGC | ekek-d8-kekee | soosssssssssooss | 1472 | 1488 | 19 | 1017 |
| 673455 | CCCCGACCACGCCCCGG | ekek-d8-kekee | soosssssssssooss | 1473 | 1489 | 21 | 1018 |

TABLE 44-continued

Percent inhibition of the C9ORF72 pathogenic associated mRNA variant compared to PBS control by Deoxy, MOE and cEt antisense oligonucleotides with mixed backbones targeting SEQ ID NO: 2

| ISIS NO | Sequence | Chemistry | Linkage | SEQ ID NO: 2 Start Site | SEQ ID NO: 2 Stop Site | % inhibition | SEQ ID NO |
|---|---|---|---|---|---|---|---|
| 673456 | GCCCCGACCACGCCCG | ekek-d8-kekee | soosssssssssooss | 1474 | 1490 | 9 | 1019 |
| 673457 | CGCCCCGACCACGCCCC | ekek-d8-kekee | soosssssssssooss | 1475 | 1491 | 45 | 1020 |
| 673458 | CCGCCCCGACCACGCCC | ekek-d8-kekee | soosssssssssooss | 1476 | 1492 | 14 | 1021 |
| 673459 | CCCGCCCCGACCACGCC | ekek-d8-kekee | soosssssssssooss | 1477 | 1493 | 2 | 1022 |
| 673460 | GCCCGCCCCGACCACGC | ekek-d8-kekee | soosssssssssooss | 1478 | 1494 | 28 | 1023 |
| 673461 | GGCCCGCCCCGACCACG | ekek-d8-kekee | soosssssssssooss | 1479 | 1495 | 19 | 1024 |
| 673462 | GGGCCCGCCCCGACCAC | ekek-d8-kekee | soosssssssssooss | 1480 | 1496 | 26 | 1025 |
| 673463 | CGGGCCCGCCCCGACCA | ekek-d8-kekee | soosssssssssooss | 1481 | 1497 | 12 | 1026 |
| 673464 | CCGGGCCCGCCCCGACC | ekek-d8-kekee | soosssssssssooss | 1482 | 1498 | 18 | 1027 |
| 673465 | CCCGGGCCCGCCCCGAC | ekek-d8-kekee | soosssssssssooss | 1483 | 1499 | 19 | 1028 |
| 673466 | GCAGCCCCGCCCCGGGC | ekek-d8-kekee | soosssssssssooss | 1505 | 1521 | 11 | 1029 |
| 673467 | CGCAGCCCCGCCCCGGG | ekek-d8-kekee | soosssssssssooss | 1506 | 1522 | 40 | 1030 |
| 673468 | CCGCAGCCCCGCCCCGG | ekek-d8-kekee | soosssssssssooss | 1507 | 1523 | 12 | 1031 |
| 673469 | ACCGCAGCCCCGCCCCG | ekek-d8-kekee | soosssssssssooss | 1508 | 1524 | 26 | 1032 |
| 673470 | AACCGCAGCCCCGCCCC | ekek-d8-kekee | soosssssssssooss | 1509 | 1525 | 36 | 1033 |
| 673471 | CAACCGCAGCCCCGCCC | ekek-d8-kekee | soosssssssssooss | 1510 | 1526 | 63 | 1034 |
| 673472 | GCAACCGCAGCCCCGCC | ekek-d8-kekee | soosssssssssooss | 1511 | 1527 | 35 | 1035 |
| 673473 | CGCAACCGCAGCCCCGC | ekek-d8-kekee | soosssssssssooss | 1512 | 1528 | 51 | 1036 |
| 673474 | CCGCAACCGCAGCCCCG | ekek-d8-kekee | soosssssssssooss | 1513 | 1529 | 27 | 1037 |
| 673475 | ACCGCAACCGCAGCCCC | ekek-d8-kekee | soosssssssssooss | 1514 | 1530 | 49 | 1038 |
| 673476 | CACCGCAACCGCAGCCC | ekek-d8-kekee | soosssssssssooss | 1515 | 1531 | 34 | 1039 |
| 673477 | GCACCGCAACCGCAGCC | ekek-d8-kekee | soosssssssssooss | 1516 | 1532 | 36 | 1040 |
| 673478 | GGCACCGCAACCGCAGC | ekek-d8-kekee | soosssssssssooss | 1517 | 1533 | 22 | 1041 |
| 673479 | AGGCACCGCAACCGCAG | ekek-d8-kekee | soosssssssssooss | 1518 | 1534 | 23 | 1042 |
| 673480 | CAGGCACCGCAACCGCA | ekek-d8-kekee | soosssssssssooss | 1519 | 1535 | 27 | 1043 |
| 673481 | GCAGGCACCGCAACCGC | ekek-d8-kekee | soosssssssssooss | 1520 | 1536 | 41 | 1044 |
| 673482 | CGCAGGCACCGCAACCG | ekek-d8-kekee | soosssssssssooss | 1521 | 1537 | 60 | 1045 |
| 673483 | GCGCAGGCACCGCAACC | ekek-d8-kekee | soosssssssssooss | 1522 | 1538 | 22 | 1046 |
| 673484 | GGCGCAGGCACCGCAAC | ekek-d8-kekee | soosssssssssooss | 1523 | 1539 | 11 | 1047 |

Example 11: Dose-Dependent Antisense Inhibition of Human C9ORF72 mRNA in HepG2 Cells Antisense oligonucleotides from the study described in Example 10 hereinabove exhibiting significant in vitro inhibition of C9ORF72 mRNA were selected and tested at various doses in HepG2 cells. ISIS 576816, which was previously tested in PCT/US2013/065073 (claiming priority to U.S. Application No. 61/714,132, filed Oct. 15, 2012) was used as a benchmark oligonucleotide. Cells were plated at a density of 20,000 cells per well and transfected using electroporation with 0.185 M, 0.56 M, 1.67 M, or 5.00 μM concentrations of antisense oligonucleotide. After a treatment period of approximately 16 hours, RNA was isolated from the cells and C9ORF72 mRNA levels were measured by quantitative real-time PCR. Human primer probe set RTS3905 was used to measure the C9ORF72 pathogenic associated mRNA variant, which is the product of a pre-mRNA containing a hexanucleotide repeat. C9ORF72 mRNA levels were adjusted according to total RNA content, as measured by RIBOGREEN®. Results are presented as percent inhibition of C9ORF72 levels, relative to untreated control cells.

As shown in Tables 45-52, total C9ORF72 mRNA levels were reduced in a dose-dependent manner in some of the antisense oligonucleotide treated cells.

TABLE 45

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 21 | 66 | 82 | 91 | 0.5 |
| 672893 | 4 | 50 | 83 | 82 | 0.8 |
| 672894 | 13 | 55 | 70 | 88 | 0.7 |
| 672896 | 13 | 57 | 81 | 89 | 0.6 |
| 672897 | 2 | 38 | 72 | 79 | 1.1 |
| 672902 | 20 | 40 | 83 | 88 | 0.7 |
| 672903 | 19 | 44 | 73 | 80 | 0.8 |
| 672904 | 16 | 35 | 49 | 85 | 1.2 |
| 672905 | 15 | 30 | 67 | 82 | 1.0 |
| 672908 | 41 | 49 | 79 | 83 | 0.4 |
| 672909 | 20 | 54 | 72 | 90 | 0.6 |
| 672919 | 31 | 58 | 69 | 92 | 0.5 |
| 672924 | 34 | 60 | 89 | 97 | 0.4 |
| 672925 | 41 | 58 | 88 | 94 | 0.3 |
| 672927 | 31 | 78 | 81 | 92 | 0.3 |
| 672928 | 30 | 62 | 79 | 92 | 0.4 |
| 672929 | 51 | 71 | 89 | 94 | 0.1 |
| 672932 | 10 | 54 | 83 | 88 | 0.7 |
| 672940 | 14 | 36 | 58 | 87 | 1.0 |

TABLE 46

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 24 | 51 | 78 | 88 | 0.6 |
| 672948 | 17 | 27 | 52 | 65 | 1.8 |
| 672966 | 1 | 36 | 77 | 73 | 1.1 |
| 672967 | 24 | 36 | 44 | 75 | 1.4 |
| 672968 | 15 | 46 | 69 | 83 | 0.8 |
| 672969 | 1 | 39 | 66 | 93 | 1.0 |
| 672976 | 47 | 65 | 74 | 80 | 0.2 |
| 672978 | 36 | 32 | 52 | 76 | 1.0 |
| 672980 | 24 | 45 | 77 | 86 | 0.6 |
| 672981 | 48 | 74 | 86 | 93 | 0.1 |
| 672982 | 42 | 63 | 91 | 90 | 0.2 |
| 672983 | 38 | 56 | 83 | 92 | 0.4 |
| 672984 | 33 | 53 | 72 | 88 | 0.5 |
| 672985 | 38 | 46 | 66 | 78 | 0.6 |
| 673021 | 43 | 48 | 76 | 79 | 0.4 |
| 673022 | 2 | 52 | 58 | 89 | 1.0 |
| 673023 | 44 | 36 | 76 | 78 | 0.5 |
| 673026 | 22 | 77 | 70 | 76 | 0.4 |
| 673032 | 19 | 37 | 55 | 80 | 1.1 |

TABLE 47

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 48 | 49 | 80 | 95 | 0.3 |
| 673036 | 38 | 54 | 73 | 88 | 0.4 |
| 673047 | 27 | 75 | 93 | 87 | 0.3 |
| 673050 | 6 | 66 | 83 | 82 | 0.6 |
| 673051 | 31 | 57 | 69 | 85 | 0.5 |
| 673053 | 17 | 59 | 76 | 92 | 0.6 |
| 673054 | 15 | 45 | 76 | 90 | 0.7 |
| 673057 | 37 | 67 | 64 | 81 | 0.3 |
| 673058 | 35 | 62 | 79 | 87 | 0.4 |
| 673067 | 59 | 74 | 98 | 97 | <0.2 |
| 673068 | 37 | 71 | 85 | 95 | 0.3 |
| 673071 | 43 | 5 | 59 | 64 | 1.9 |
| 673074 | 37 | 44 | 89 | 89 | 0.4 |
| 673079 | 41 | 71 | 89 | 95 | 0.2 |
| 673081 | 21 | 37 | 80 | 76 | 0.8 |
| 673082 | 27 | 58 | 87 | 92 | 0.4 |
| 673088 | 63 | 79 | 96 | 97 | <0.2 |
| 673089 | 11 | 41 | 71 | 83 | 0.9 |
| 673098 | 15 | 61 | 68 | 93 | 0.6 |

TABLE 48

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 43 | 71 | 80 | 93 | 0.2 |
| 673098 | 18 | 53 | 81 | 88 | 0.6 |
| 673117 | 22 | 45 | 76 | 80 | 0.7 |
| 673119 | 17 | 47 | 65 | 90 | 0.8 |
| 673125 | 33 | 64 | 79 | 79 | 0.4 |
| 673126 | 41 | 56 | 70 | 82 | 0.4 |
| 673127 | 46 | 85 | 92 | 96 | <0.2 |
| 673128 | 32 | 71 | 88 | 99 | 0.3 |
| 673130 | 42 | 69 | 91 | 91 | 0.2 |
| 673131 | 34 | 62 | 74 | 99 | 0.4 |
| 673132 | 47 | 44 | 75 | 89 | 0.4 |
| 673133 | 54 | 61 | 78 | 84 | <0.2 |
| 673134 | 41 | 62 | 77 | 77 | 0.3 |
| 673135 | 28 | 60 | 77 | 82 | 0.5 |
| 673144 | 24 | 58 | 64 | 92 | 0.6 |
| 673152 | 18 | 59 | 70 | 72 | 0.7 |
| 673159 | 4 | 50 | 75 | 80 | 0.9 |
| 673171 | 17 | 43 | 58 | 86 | 0.9 |
| 673175 | 30 | 45 | 76 | 78 | 0.6 |

TABLE 49

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 22 | 69 | 78 | 93 | 0.4 |
| 673193 | 60 | 74 | 90 | 89 | <0.2 |
| 673194 | 15 | 54 | 75 | 77 | 0.7 |
| 673196 | 36 | 38 | 71 | 73 | 0.7 |
| 673197 | 28 | 39 | 68 | 78 | 0.8 |
| 673201 | 0 | 40 | 69 | 91 | 1.0 |
| 673202 | 9 | 50 | 77 | 89 | 0.7 |
| 673203 | 40 | 52 | 84 | 98 | 0.4 |
| 673204 | 44 | 67 | 91 | 92 | 0.2 |
| 673206 | 27 | 40 | 70 | 90 | 0.7 |
| 673210 | 22 | 43 | 79 | 94 | 0.6 |
| 673211 | 0 | 45 | 53 | 85 | 1.2 |
| 673219 | 27 | 36 | 67 | 88 | 0.8 |

TABLE 49-continued

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 673224 | 41 | 65 | 86 | 95 | 0.3 |
| 673225 | 34 | 73 | 78 | 97 | 0.3 |
| 673226 | 19 | 59 | 83 | 94 | 0.5 |
| 673228 | 8 | 67 | 79 | 94 | 0.6 |
| 673229 | 46 | 76 | 89 | 86 | <0.2 |
| 673240 | 18 | 58 | 75 | 93 | 0.6 |

TABLE 50

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 31 | 65 | 81 | 89 | 0.4 |
| 673265 | 24 | 43 | 73 | 83 | 0.7 |
| 673269 | 12 | 58 | 81 | 89 | 0.6 |
| 673275 | 31 | 57 | 63 | 94 | 0.5 |
| 673276 | 33 | 56 | 69 | 91 | 0.5 |
| 673277 | 37 | 51 | 65 | 66 | 0.6 |
| 673279 | 11 | 57 | 68 | 86 | 0.8 |
| 673280 | 38 | 60 | 80 | 95 | 0.3 |
| 673281 | 51 | 83 | 92 | 86 | <0.2 |
| 673282 | 60 | 73 | 93 | 95 | <0.2 |
| 673283 | 59 | 66 | 94 | 96 | <0.2 |
| 673284 | 45 | 59 | 78 | 91 | 0.3 |
| 673285 | 30 | 59 | 78 | 86 | 0.4 |
| 673321 | 10 | 44 | 72 | 79 | 0.9 |
| 673323 | 43 | 54 | 76 | 86 | 0.3 |
| 673326 | 0 | 46 | 72 | 81 | 0.8 |
| 673329 | 15 | 30 | 64 | 76 | 1.2 |
| 673331 | 47 | 40 | 66 | 79 | 0.5 |
| 673332 | 58 | 49 | 71 | 78 | <0.2 |

TABLE 51

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 38 | 61 | 75 | 92 | 0.3 |
| 673338 | 0 | 13 | 48 | 61 | 2.6 |
| 673341 | 29 | 39 | 66 | 82 | 0.8 |
| 673343 | 38 | 33 | 58 | 81 | 0.8 |
| 673344 | 29 | 40 | 69 | 72 | 0.8 |
| 673345 | 24 | 11 | 51 | 66 | 2.2 |
| 673346 | 19 | 27 | 52 | 74 | 1.4 |
| 673351 | 17 | 40 | 61 | 82 | 1.0 |
| 673352 | 18 | 36 | 62 | 71 | 1.2 |
| 673353 | 29 | 38 | 47 | 74 | 1.2 |
| 673358 | 11 | 39 | 63 | 71 | 1.2 |
| 673359 | 15 | 46 | 51 | 65 | 1.4 |
| 673369 | 17 | 33 | 55 | 70 | 1.4 |
| 673374 | 42 | 62 | 77 | 87 | 0.3 |
| 673375 | 28 | 66 | 79 | 94 | 0.4 |
| 673377 | 32 | 51 | 77 | 87 | 0.5 |
| 673378 | 32 | 47 | 76 | 89 | 0.5 |
| 673379 | 33 | 58 | 76 | 83 | 0.4 |
| 673390 | 21 | 40 | 57 | 74 | 1.1 |

TABLE 52

Dose-dependent inhibition of the C9ORF72 pathogenic associated mRNA variant transcript levels in HepG2 cells

| ISIS No | 0.185 µM | 0.56 µM | 1.67 µM | 5.00 µM | IC$_{50}$ (µM) |
|---|---|---|---|---|---|
| 576816 | 6 | 54 | 75 | 88 | 0.7 |
| 673416 | 31 | 51 | 61 | 67 | 0.7 |
| 673419 | 16 | 34 | 41 | 67 | 2.0 |
| 673426 | 31 | 62 | 53 | 68 | 0.7 |
| 673427 | 41 | 52 | 52 | 59 | 0.8 |
| 673430 | 27 | 46 | 76 | 83 | 0.6 |
| 673431 | 49 | 68 | 83 | 96 | 0.2 |
| 673432 | 43 | 72 | 72 | 86 | 0.2 |
| 673434 | 41 | 70 | 80 | 90 | 0.2 |
| 673435 | 8 | 48 | 71 | 69 | 1.0 |
| 673436 | 15 | 20 | 65 | 66 | 1.6 |
| 673453 | 18 | 49 | 57 | 72 | 1.0 |
| 673457 | 0 | 19 | 43 | 63 | 2.5 |
| 673467 | 12 | 25 | 35 | 42 | >5.0 |
| 673471 | 13 | 45 | 57 | 79 | 1.0 |
| 673473 | 13 | 48 | 62 | 92 | 0.8 |
| 673475 | 23 | 30 | 65 | 61 | 1.4 |
| 673481 | 26 | 33 | 52 | 41 | >5.0 |
| 673482 | 14 | 45 | 56 | 75 | 1.1 |

Example 12: Antisense Inhibition of C9ORF72 by Human-Rhesus Cross-Reactive Antisense Oligonucleotides in LLC-MK2 Cells by Mixed Backbone 5-8-5 MOE and 5-10-5 MOE Gapmers Antisense oligonucleotides targeting a human C9ORF72 nucleic acid and cross-reactive with a rhesus C9ORF72 nucleic acid were designed and tested for their effects on rhesus C9ORF72 mRNA expression in vitro. ISIS 576816, previously tested in U.S. Application No. 61/714,132, filed Oct. 15, 2012, was used as a benchmark oligonucleotide. ISIS 619420, which is the mixed backbone version of ISIS 576816, described in Example 2 hereinabove was also tested. The antisense oligonucleotides were tested in a series of experiments that had similar culture conditions. The results for each experiment are presented in separate tables shown below. Cultured LLC-MK2 cells at a density of 20,000 cells per well were transfected using electroporation with 3,500 nM antisense oligonucleotide. After a treatment period of approximately 24 hours, RNA was isolated from the cells and C9ORF72 mRNA levels were measured by quantitative real-time PCR. Human primer probe set RTS3750 (a TAQ-man primer probe set) was used to measure total C9ORF72 mRNA levels. RTS3750 targets exon 2 of the mRNA transcripts and, therefore, measures total mRNA transcripts. In cases where the oligonucleotide overlapped the amplicon of the primer probe set RTS3750 (see, e.g., Table 53), an alternative primer probe set, RTS3760_MGB (forward sequence TCCAATGCITACTG-GAGAAGTGA, designated herein as SEQ ID NO: 1546; reverse sequence GGAACACTGTGTGATITCATA-GATGA, designated herein as SEQ ID NO: 1547; probe sequence TCCTGTAATGGAACTGC, designated herein as SEQ ID NO: 1548—a TAQ-man primer probe set) was used to measure total mRNA transcripts. The levels of the C9ORF72 mRNA were normalized to the total RNA content of the cell, as measured by RIBOGREEN®. Results are presented as percent inhibition of rhesus C9ORF72 mRNA expression, relative to untreated control cells. The oligonucleotides marked with as asterisk (*) target the amplicon region of the primer probe set. Additional assays may be used to measure the potency and efficacy of these oligonucleotides. 'n.d.' indicates that there was no signal reading in the assay for that particular oligonucleotide.

The newly designed chimeric antisense oligonucleotides in the Tables below were designed as 5-8-5 MOE gapmers and 5-10-5 MOE gapmers.

The 5-8-5 MOE gapmers are 18 nucleosides in length, wherein the central gap segment comprises eight 2'-deoxynucleosides and is flanked by wing segments on both the 5' end and the 3' end comprising five nucleosides each. Each nucleoside in the 5' wing segment and each nucleoside in the 3' wing segment has a 2'-MOE group. All cytosine residues throughout each gapmer are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

The 5-10-5 MOE gapmers are 20 nucleosides in length, wherein the central gap segment comprises ten 2'-deoxynucleosides and is flanked by wing segments on both the 5' end and the 3' end comprising five nucleosides each. Each nucleoside in the 5' wing segment and each nucleoside in the 3' wing segment has a 2'-MOE group. All cytosine residues throughout each gapmer are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

"Start site" indicates the 5'-most nucleoside to which the gapmer is targeted in the gene sequence. "Stop site" indicates the 3'-most nucleoside to which the gapmer is targeted in the gene sequence. Each gapmer listed in the Tables below is targeted to one or more of human C9ORF72 mRNA sequence, designated herein as SEQ ID NO: 1 (GENBANK Accession No. NM_001256054.1), human C9ORF72 genomic sequence, designated herein as SEQ ID NO: 2 (the complement of GENBANK Accession No. NT_008413.18 truncated from nucleosides 27535000 to 27565000), and rhesus C9ORF72 genomic sequence designated herein as SEQ ID NO: 19 (GENBANK Accession No. NW_001101662.1 truncated from nucleosides 8522000 to 8552000). The 'Mismatches' column indicates the number of mismatches the human antisense oligonucleotide has with the rhesus genomic sequence. 'n/a' in the rhesus sequence columns indicates that the human oligonucleotide has more than 3 mismatches with the rhesus genomic sequence. Where the 'Mismtaches' column is not provided in a Table, it is understood that the human oligonucleotides of the Table are fully cross-reactive with the rhesus genomic sequence.

TABLE 53

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | % inhibition (RTS3760_MGB) | SEQ ID NO |
|---|---|---|---|---|---|---|---|---|---|
| 576816 | 310 | 7990 | 8043 | GCCTTACTCTAGGACCAAGA | sssssssssssssssssss | 5-10-5 | 60 | 54 | 20 |
| 619420 | 310 | 7990 | 8043 | GCCTTACTCTAGGACCAAGA | sooooosssssssssssooss | 5-10-5 | 69 | 68 | 20 |
| 688005* | 221 | 7901 | 7954 | AACAGCTGGAGATGGCGG | sooossssssssssooss | 5-8-5 | 12 | 36 | 1057 |
| 688006* | 222 | 7902 | 7955 | CAACAGCTGGAGATGGCG | sooossssssssssooss | 5-8-5 | 29 | 20 | 1058 |
| 688007* | 223 | 7903 | 7956 | GCAACAGCTGGAGATGGC | sooossssssssssooss | 5-8-5 | 46 | 33 | 1059 |
| 688008* | 224 | 7904 | 7957 | GGCAACAGCTGGAGATGG | sooossssssssssooss | 5-8-5 | 59 | 41 | 1060 |
| 688009* | 225 | 7905 | 7958 | TGGCAACAGCTGGAGATG | sooossssssssssooss | 5-8-5 | 43 | 24 | 1061 |
| 688010* | 226 | 7906 | 7959 | TTGGCAACAGCTGGAGAT | sooossssssssssooss | 5-8-5 | 31 | 0 | 1062 |
| 688011* | 227 | 7907 | 7960 | CTTGGCAACAGCTGGAGA | sooossssssssssooss | 5-8-5 | 45 | 18 | 1063 |
| 688012* | 228 | 7908 | 7961 | TCTTGGCAACAGCTGGAG | sooossssssssssooss | 5-8-5 | 67 | 0 | 1064 |
| 688013* | 229 | 7909 | 7962 | GTCTTGGCAACAGCTGGA | sooossssssssssooss | 5-8-5 | 48 | 13 | 1065 |
| 688014* | 230 | 7910 | 7963 | TGTCTTGGCAACAGCTGG | sooossssssssssooss | 5-8-5 | 16 | 16 | 1066 |
| 688015* | 231 | 7911 | 7964 | CTGTCTTGGCAACAGCTG | sooossssssssssooss | 5-8-5 | 75 | 33 | 1067 |
| 688016* | 232 | 7912 | 7965 | TCTGTCTTGGCAACAGCT | sooossssssssssooss | 5-8-5 | 37 | 36 | 1068 |
| 688017* | 233 | 7913 | 7966 | CTCTGTCTTGGCAACAGC | sooossssssssssooss | 5-8-5 | 59 | 28 | 1069 |
| 688018* | 234 | 7914 | 7967 | TCTCTGTCTTGGCAACAG | sooossssssssssooss | 5-8-5 | 40 | 36 | 1070 |
| 688019* | 235 | 7915 | 7968 | ATCTCTGTCTTGGCAACA | sooossssssssssooss | 5-8-5 | 34 | 31 | 1071 |
| 688020* | 236 | 7916 | 7969 | AATCTCTGTCTTGGCAAC | sooossssssssssooss | 5-8-5 | 30 | 26 | 1072 |
| 688021* | 237 | 7917 | 7970 | CAATCTCTGTCTTGGCAA | sooossssssssssooss | 5-8-5 | 58 | 0 | 1073 |

TABLE 53-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | % inhibition (RTS3760_MGB) | SEQ ID NO |
|---|---|---|---|---|---|---|---|---|---|
| 688022* | 238 | 7918 | 7971 | GCAATCTCTGTCTTGGCA | sooosssssssssooss | 5-8-5 | 90 | 52 | 1074 |
| 688023* | 239 | 7919 | 7972 | AGCAATCTCTGTCTTGGC | sooosssssssssooss | 5-8-5 | 92 | 73 | 1075 |
| 688024* | 240 | 7920 | 7973 | AAGCAATCTCTGTCTTGG | sooosssssssssooss | 5-8-5 | 74 | 24 | 1076 |
| 688025* | 241 | 7921 | 7974 | AAAGCAATCTCTGTCTTG | sooosssssssssooss | 5-8-5 | 76 | 0 | 1077 |
| 688026* | 242 | 7922 | 7975 | TAAAGCAATCTCTGTCTT | sooosssssssssooss | 5-8-5 | 28 | 6 | 1078 |
| 688027* | 243 | 7923 | 7976 | TTAAAGCAATCTCTGTCT | sooosssssssssooss | 5-8-5 | 32 | 18 | 1079 |
| 688028* | 244 | 7924 | 7977 | CTTAAAGCAATCTCTGTC | sooosssssssssooss | 5-8-5 | 41 | 4 | 1080 |
| 688029* | 245 | 7925 | 7978 | ACTTAAAGCAATCTCTGT | sooosssssssssooss | 5-8-5 | 63 | 0 | 1081 |
| 688030* | 246 | 7926 | 7979 | CACTTAAAGCAATCTCTG | sooosssssssssooss | 5-8-5 | 26 | 31 | 1082 |
| 688031* | 247 | 7927 | 7980 | CCACTTAAAGCAATCTCT | sooosssssssssooss | 5-8-5 | 73 | 33 | 1083 |
| 688032 | 267 | 7947 | 8000 | CTGCTAATAAAGGTGATT | sooosssssssssooss | 5-8-5 | 24 | 34 | 1084 |
| 688033 | 268 | 7948 | 8001 | GCTGCTAATAAAGGTGAT | sooosssssssssooss | 5-8-5 | 11 | 18 | 1085 |
| 688034 | 269 | 7949 | 8002 | AGCTGCTAATAAAGGTGA | sooosssssssssooss | 5-8-5 | 40 | 34 | 1086 |
| 688035 | 270 | 7950 | 8003 | TAGCTGCTAATAAAGGTG | sooosssssssssooss | 5-8-5 | 46 | 1 | 1087 |
| 688036 | 271 | 7951 | 8004 | GTAGCTGCTAATAAAGGT | sooosssssssssooss | 5-8-5 | 13 | 17 | 1088 |
| 688037 | 272 | 7952 | 8005 | AGTAGCTGCTAATAAAGG | sooosssssssssooss | 5-8-5 | 0 | 0 | 1089 |
| 688038 | 273 | 7953 | 8006 | AAGTAGCTGCTAATAAAG | sooosssssssssooss | 5-8-5 | 0 | 0 | 1090 |
| 688039 | 274 | 7954 | 8007 | AAAGTAGCTGCTAATAAA | sooosssssssssooss | 5-8-5 | 0 | 3 | 1091 |
| 688040 | 275 | 7955 | 8008 | AAAAGTAGCTGCTAATAA | sooosssssssssooss | 5-8-5 | 0 | 0 | 1092 |
| 688041 | 276 | 7956 | 8009 | CAAAAGTAGCTGCTAATA | sooosssssssssooss | 5-8-5 | 0 | 0 | 1093 |
| 688042 | 277 | 7957 | 8010 | GCAAAAGTAGCTGCTAAT | sooosssssssssooss | 5-8-5 | 32 | 31 | 1094 |
| 688043 | 278 | 7958 | 8011 | AGCAAAAGTAGCTGCTAA | sooosssssssssooss | 5-8-5 | 18 | 14 | 1095 |
| 688044 | 279 | 7959 | 8012 | AAGCAAAAGTAGCTGCTA | sooosssssssssooss | 5-8-5 | 17 | 24 | 1096 |
| 688045 | 280 | 7960 | 8013 | TAAGCAAAAGTAGCTGCT | sooosssssssssooss | 5-8-5 | 38 | 7 | 1097 |
| 688046 | 281 | 7961 | 8014 | GTAAGCAAAAGTAGCTGC | sooosssssssssooss | 5-8-5 | 37 | 38 | 1098 |
| 688047 | 282 | 7962 | 8015 | AGTAAGCAAAAGTAGCTG | sooosssssssssooss | 5-8-5 | 12 | 33 | 1099 |
| 688048 | 283 | 7963 | 8016 | CAGTAAGCAAAAGTAGCT | sooosssssssssooss | 5-8-5 | 17 | 29 | 1100 |
| 688049 | 284 | 7964 | 8017 | CCAGTAAGCAAAAGTAGC | sooosssssssssooss | 5-8-5 | 17 | 0 | 1101 |
| 688050 | 285 | 7965 | 8018 | CCCAGTAAGCAAAAGTAG | sooosssssssssooss | 5-8-5 | 7 | 27 | 1102 |
| 688051 | 286 | 7966 | 8019 | TCCCAGTAAGCAAAAGTA | sooosssssssssooss | 5-8-5 | 0 | 0 | 1103 |
| 688052 | 287 | 7967 | 8020 | GTCCCAGTAAGCAAAAGT | sooosssssssssooss | 5-8-5 | 16 | 24 | 1104 |
| 688053 | 288 | 7968 | 8021 | TGTCCCAGTAAGCAAAAG | sooosssssssssooss | 5-8-5 | 0 | 0 | 1105 |
| 688054 | 289 | 7969 | 8022 | TTGTCCCAGTAAGCAAAA | sooosssssssssooss | 5-8-5 | 9 | 10 | 1106 |
| 688055 | 290 | 7970 | 8023 | ATTGTCCCAGTAAGCAAA | sooosssssssssooss | 5-8-5 | 6 | 15 | 1107 |
| 688056 | 291 | 7971 | 8024 | TATTGTCCCAGTAAGCAA | sooosssssssssooss | 5-8-5 | 21 | 0 | 1108 |

TABLE 53-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | % inhibition (RTS3760_MGB) | SEQ ID NO |
|---|---|---|---|---|---|---|---|---|---|
| 688057 | 292 | 7972 | 8025 | ATATTGTCCCAGTAAGCA | sooossssssssssooss | 5-8-5 | 11 | 4 | 1109 |
| 688058 | 293 | 7973 | 8026 | AATATTGTCCCAGTAAGC | sooossssssssssooss | 5-8-5 | 23 | 29 | 1110 |
| 688059 | 294 | 7974 | 8027 | GAATATTGTCCCAGTAAG | sooossssssssssooss | 5-8-5 | 5 | 13 | 1111 |
| 688060 | 295 | 7975 | 8028 | AGAATATTGTCCCAGTAA | sooossssssssssooss | 5-8-5 | 0 | 31 | 1112 |
| 688061 | 296 | 7976 | 8029 | AAGAATATTGTCCCAGTA | sooossssssssssooss | 5-8-5 | 0 | 16 | 1113 |
| 688062 | 297 | 7977 | 8030 | CAAGAATATTGTCCCAGT | sooossssssssssooss | 5-8-5 | 29 | 0 | 1114 |
| 688063 | 298 | 7978 | 8031 | CCAAGAATATTGTCCCAG | sooossssssssssooss | 5-8-5 | 26 | 42 | 1115 |
| 688064 | 299 | 7979 | 8032 | ACCAAGAATATTGTCCCA | sooossssssssssooss | 5-8-5 | 19 | 11 | 1116 |
| 688065 | 300 | 7980 | 8033 | GACCAAGAATATTGTCCC | sooossssssssssooss | 5-8-5 | 31 | 26 | 1117 |
| 688066 | 301 | 7981 | 8034 | GGACCAAGAATATTGTCC | sooossssssssssooss | 5-8-5 | 0 | 0 | 1118 |
| 688067 | 302 | 7982 | 8035 | AGGACCAAGAATATTGTC | sooossssssssssooss | 5-8-5 | 5 | 10 | 1119 |
| 688068 | 303 | 7983 | 8036 | TAGGACCAAGAATATTGT | sooossssssssssooss | 5-8-5 | 20 | 13 | 1120 |
| 688069 | 304 | 7984 | 8037 | CTAGGACCAAGAATATTG | sooossssssssssooss | 5-8-5 | 0 | 22 | 1121 |
| 688070 | 305 | 7985 | 8038 | TCTAGGACCAAGAATATT | sooossssssssssooss | 5-8-5 | 0 | 0 | 1122 |
| 688071 | 306 | 7986 | 8039 | CTCTAGGACCAAGAATAT | sooossssssssssooss | 5-8-5 | 5 | 18 | 1123 |
| 688072 | 307 | 7987 | 8040 | ACTCTAGGACCAAGAATA | sooossssssssssooss | 5-8-5 | 17 | 27 | 1124 |
| 688073 | 308 | 7988 | 8041 | TACTCTAGGACCAAGAAT | sooossssssssssooss | 5-8-5 | 13 | 8 | 1125 |
| 688074 | 309 | 7989 | 8042 | TTACTCTAGGACCAAGAA | sooossssssssssooss | 5-8-5 | 0 | 0 | 1126 |
| 688075 | 310 | 7990 | 8043 | CTTACTCTAGGACCAAGA | sooossssssssssooss | 5-8-5 | 0 | 0 | 1127 |
| 688076 | 311 | 7991 | 8044 | CCTTACTCTAGGACCAAG | sooossssssssssooss | 5-8-5 | 45 | 71 | 1128 |
| 688077 | 312 | 7992 | 8045 | GCCTTACTCTAGGACCAA | sooossssssssssooss | 5-8-5 | 62 | 67 | 1129 |
| 688078 | 313 | 7993 | 8046 | TGCCTTACTCTAGGACCA | sooossssssssssooss | 5-8-5 | 33 | 30 | 1130 |
| 688079 | 314 | 7994 | 8047 | GTGCCTTACTCTAGGACC | sooossssssssssooss | 5-8-5 | 59 | 49 | 1131 |
| 688080 | 315 | 7995 | 8048 | TGTGCCTTACTCTAGGAC | sooossssssssssooss | 5-8-5 | 47 | 41 | 1132 |
| 688081 | 316 | 7996 | 8049 | ATGTGCCTTACTCTAGGA | sooossssssssssooss | 5-8-5 | 44 | 13 | 1133 |
| 688082 | 317 | 7997 | 8050 | AATGTGCCTTACTCTAGG | sooossssssssssooss | 5-8-5 | 6 | 0 | 1134 |

TABLE 54

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 576816 | 310 | 7990 | 8043 | GCCTTACTCTAGGACCAAGA | ssssssssssssssssssss | 5-10-5 | 58 | 20 |
| 619420 | 310 | 7990 | 8043 | GCCTTACTCTAGGACCAAGA | sooossssssssssssooss | 5-10-5 | 70 | 20 |

TABLE 54-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688078 | 313 | 7993 | 8046 | TGCCTTACTCTAGGACCA | sooosssssssssooss | 5-8-5 | 50 | 1130 |
| 688083 | 318 | 7998 | 8051 | AAATGTGCCTTACTCTAG | sooosssssssssooss | 5-8-5 | 7 | 1135 |
| 688084 | 319 | 7999 | 8052 | CAAATGTGCCTTACTCTA | sooosssssssssooss | 5-8-5 | 11 | 1136 |
| 688085 | 320 | 8000 | 8053 | CCAAATGTGCCTTACTCT | sooosssssssssooss | 5-8-5 | 29 | 1137 |
| 688086 | 321 | 8001 | 8054 | CCCAAATGTGCCTTACTC | sooosssssssssooss | 5-8-5 | 43 | 1138 |
| 688087 | 322 | 8002 | 8055 | GCCCAAATGTGCCTTACT | sooosssssssssooss | 5-8-5 | 58 | 1139 |
| 688088 | 323 | 8003 | 8056 | AGCCCAAATGTGCCTTAC | sooosssssssssooss | 5-8-5 | 66 | 1140 |
| 688089 | 324 | 8004 | 8057 | GAGCCCAAATGTGCCTTA | sooosssssssssooss | 5-8-5 | 61 | 1141 |
| 688090 | 325 | 8005 | 8058 | GGAGCCCAAATGTGCCTT | sooosssssssssooss | 5-8-5 | 52 | 1142 |
| 688091 | 326 | 8006 | 8059 | TGGAGCCCAAATGTGCCT | sooosssssssssooss | 5-8-5 | 34 | 1143 |
| 688092 | 327 | 8007 | 8060 | TTGGAGCCCAAATGTGCC | sooosssssssssooss | 5-8-5 | 15 | 1144 |
| 688093 | 328 | 8008 | 8061 | TTTGGAGCCCAAATGTGC | sooosssssssssooss | 5-8-5 | 31 | 1145 |
| 688094 | 329 | 8009 | 8062 | CTTTGGAGCCCAAATGTG | sooosssssssssooss | 5-8-5 | 23 | 1146 |
| 688095 | 330 | 8010 | 8063 | TCTTTGGAGCCCAAATGT | sooosssssssssooss | 5-8-5 | 13 | 1147 |
| 688096 | 331 | 8011 | 8064 | GTCTTTGGAGCCCAAATG | sooosssssssssooss | 5-8-5 | 30 | 1148 |
| 688097 | 332 | 8012 | 8065 | TGTCTTTGGAGCCCAAAT | sooosssssssssooss | 5-8-5 | 32 | 1149 |
| 688098 | 333 | 8013 | 8066 | CTGTCTTTGGAGCCCAAA | sooosssssssssooss | 5-8-5 | 48 | 1150 |
| 688099 | 334 | 8014 | 8067 | TCTGTCTTTGGAGCCCAA | sooosssssssssooss | 5-8-5 | 62 | 1151 |
| 688100 | 335 | 8015 | 8068 | TTCTGTCTTTGGAGCCCA | sooosssssssssooss | 5-8-5 | 61 | 1152 |
| 688101 | 336 | 8016 | 8069 | GTTCTGTCTTTGGAGCCC | sooosssssssssooss | 5-8-5 | 77 | 1153 |
| 688102 | 337 | 8017 | 8070 | TGTTCTGTCTTTGGAGCC | sooosssssssssooss | 5-8-5 | 58 | 1154 |
| 688103 | 338 | 8018 | 8071 | CTGTTCTGTCTTTGGAGC | sooosssssssssooss | 5-8-5 | 57 | 1155 |
| 688104 | 339 | 8019 | 8072 | CCTGTTCTGTCTTTGGAG | sooosssssssssooss | 5-8-5 | 55 | 1156 |
| 688105 | 340 | 8020 | 8073 | ACCTGTTCTGTCTTTGGA | sooosssssssssooss | 5-8-5 | 51 | 1157 |
| 688106 | 341 | 8021 | 8074 | TACCTGTTCTGTCTTTGG | sooosssssssssooss | 5-8-5 | 42 | 1158 |
| 688107 | 342 | 8022 | 8075 | GTACCTGTTCTGTCTTTG | sooosssssssssooss | 5-8-5 | 49 | 1159 |
| 688108 | 343 | 8023 | 8076 | AGTACCTGTTCTGTCTTT | sooosssssssssooss | 5-8-5 | 25 | 1160 |
| 688109 | 344 | 8024 | 8077 | AAGTACCTGTTCTGTCTT | sooosssssssssooss | 5-8-5 | 22 | 1161 |
| 688110 | 345 | 8025 | 8078 | GAAGTACCTGTTCTGTCT | sooosssssssssooss | 5-8-5 | 42 | 1162 |
| 688111 | 346 | 8026 | 8079 | AGAAGTACCTGTTCTGTC | sooosssssssssooss | 5-8-5 | 21 | 1163 |
| 688112 | 347 | 8027 | 8080 | GAGAAGTACCTGTTCTGT | sooosssssssssooss | 5-8-5 | 22 | 1164 |
| 688113 | 348 | 8028 | 8081 | TGAGAAGTACCTGTTCTG | sooosssssssssooss | 5-8-5 | 13 | 1165 |
| 688114 | 349 | 8029 | 8082 | CTGAGAAGTACCTGTTCT | sooosssssssssooss | 5-8-5 | 25 | 1166 |
| 688115 | 350 | 8030 | 8083 | ACTGAGAAGTACCTGTTC | sooosssssssssooss | 5-8-5 | 14 | 1167 |
| 688116 | 351 | 8031 | 8084 | CACTGAGAAGTACCTGTT | sooosssssssssooss | 5-8-5 | 36 | 1168 |

TABLE 54-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688117 | 352 | 8032 | 8085 | TCACTGAGAAGTACCTGT | sooosssssssssooss | 5-8-5 | 28 | 1169 |
| 688118 | 353 | 8033 | 8086 | ATCACTGAGAAGTACCTG | sooosssssssssooss | 5-8-5 | 36 | 1170 |
| 688119 | 354 | 8034 | 8087 | CATCACTGAGAAGTACCT | sooosssssssssooss | 5-8-5 | 32 | 1171 |
| 688120 | 355 | 8035 | 8088 | CCATCACTGAGAAGTACC | sooosssssssssooss | 5-8-5 | 44 | 1172 |
| 688121 | 356 | 8036 | 8089 | TCCATCACTGAGAAGTAC | sooosssssssssooss | 5-8-5 | 31 | 1173 |
| 688122 | 357 | 8037 | 8090 | CTCCATCACTGAGAAGTA | sooosssssssssooss | 5-8-5 | 56 | 1174 |
| 688123 | 358 | 8038 | 8091 | TCTCCATCACTGAGAAGT | sooosssssssssooss | 5-8-5 | 53 | 1175 |
| 688124 | 359 | 8039 | 8092 | TTCTCCATCACTGAGAAG | sooosssssssssooss | 5-8-5 | 14 | 1176 |
| 688125 | 360 | 8040 | 8093 | TTTCTCCATCACTGAGAA | sooosssssssssooss | 5-8-5 | 12 | 1177 |
| 688126 | 361 | 8041 | 8094 | ATTTCTCCATCACTGAGA | sooosssssssssooss | 5-8-5 | 18 | 1178 |
| 688127 | 362 | 8042 | 8095 | TATTTCTCCATCACTGAG | sooosssssssssooss | 5-8-5 | 11 | 1179 |
| 688128 | 364 | 8044 | 8097 | GTTATTTCTCCATCACTG | sooosssssssssooss | 5-8-5 | 40 | 1180 |
| 688129 | 365 | 8045 | 8098 | AGTTATTTCTCCATCACT | sooosssssssssooss | 5-8-5 | 37 | 1181 |
| 688130 | 366 | 8046 | 8099 | AAGTTATTTCTCCATCAC | sooosssssssssooss | 5-8-5 | 20 | 1182 |
| 688131 | 367 | 8047 | 8100 | AAAGTTATTTCTCCATCA | sooosssssssssooss | 5-8-5 | 22 | 1183 |
| 688132 | 368 | 8048 | 8101 | AAAAGTTATTTCTCCATC | sooosssssssssooss | 5-8-5 | 31 | 1184 |
| 688133 | 369 | 8049 | 8102 | GAAAAGTTATTTCTCCAT | sooosssssssssooss | 5-8-5 | 19 | 1185 |
| 688134 | 371 | 8051 | 8104 | AAGAAAAGTTATTTCTCC | sooosssssssssooss | 5-8-5 | 34 | 1186 |
| 688135 | 372 | 8052 | 8105 | CAAGAAAAGTTATTTCTC | sooosssssssssooss | 5-8-5 | 0 | 1187 |
| 688136 | 373 | 8053 | 8106 | GCAAGAAAAGTTATTTCT | sooosssssssssooss | 5-8-5 | 21 | 1188 |
| 688137 | 374 | 8054 | 8107 | GGCAAGAAAAGTTATTTC | sooosssssssssooss | 5-8-5 | 51 | 1189 |
| 688138 | 375 | 8055 | 8108 | TGGCAAGAAAAGTTATTT | sooosssssssssooss | 5-8-5 | 42 | 1190 |
| 688139 | 376 | 8056 | 8109 | TTGGCAAGAAAAGTTATT | sooosssssssssooss | 5-8-5 | 13 | 1191 |
| 688140 | 377 | 8057 | 8110 | GTTGGCAAGAAAAGTTAT | sooosssssssssooss | 5-8-5 | 16 | 1192 |
| 688141 | 378 | 8058 | 8111 | GGTTGGCAAGAAAAGTTA | sooosssssssssooss | 5-8-5 | 23 | 1193 |
| 688142 | 379 | 8059 | 8112 | TGGTTGGCAAGAAAAGTT | sooosssssssssooss | 5-8-5 | 7 | 1194 |
| 688143 | 380 | 8060 | 8113 | GTGGTTGGCAAGAAAAGT | sooosssssssssooss | 5-8-5 | 30 | 1195 |
| 688144 | 381 | 8061 | 8114 | TGTGGTTGGCAAGAAAAG | sooosssssssssooss | 5-8-5 | 12 | 1196 |
| 688145 | 382 | 8062 | 8115 | GTGTGGTTGGCAAGAAAA | sooosssssssssooss | 5-8-5 | 7 | 1197 |
| 688146 | 383 | 8063 | 8116 | AGTGTGGTTGGCAAGAAA | sooosssssssssooss | 5-8-5 | 0 | 1198 |
| 688147 | 384 | 8064 | 8117 | GAGTGTGGTTGGCAAGAA | sooosssssssssooss | 5-8-5 | 27 | 1199 |
| 688148 | 385 | 8065 | 8118 | AGAGTGTGGTTGGCAAGA | sooosssssssssooss | 5-8-5 | 17 | 1200 |
| 688149 | 386 | 8066 | 8119 | TAGAGTGTGGTTGGCAAG | sooosssssssssooss | 5-8-5 | 17 | 1201 |
| 688150 | 387 | 8067 | 8120 | TTAGAGTGTGGTTGGCAA | sooosssssssssooss | 5-8-5 | 20 | 1202 |
| 688151 | 388 | 8068 | 8121 | TTTAGAGTGTGGTTGGCA | sooosssssssssooss | 5-8-5 | 22 | 1203 |

TABLE 54-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688152 | 389 | 8069 | 8122 | ATTTAGAGTGTGGTTGGC | sooosssssssssssooss | 5-8-5 | 47 | 1204 |
| 688153 | 390 | 8070 | 8123 | CATTTAGAGTGTGGTTGG | sooosssssssssssooss | 5-8-5 | 21 | 1205 |
| 688154 | 391 | 8071 | 8124 | CCATTTAGAGTGTGGTTG | sooosssssssssssooss | 5-8-5 | 23 | 1206 |
| 688155 | 392 | 8072 | 8125 | TCCATTTAGAGTGTGGTT | sooosssssssssssooss | 5-8-5 | 9 | 1207 |
| 688156 | 393 | 8073 | 8126 | CTCCATTTAGAGTGTGGT | sooosssssssssssooss | 5-8-5 | 25 | 1208 |
| 688157 | 394 | 8074 | 8127 | TCTCCATTTAGAGTGTGG | sooosssssssssssooss | 5-8-5 | 41 | 1209 |
| 688158 | 395 | 8075 | 8128 | TTCTCCATTTAGAGTGTG | sooosssssssssssooss | 5-8-5 | 19 | 1210 |
| 688159 | 396 | 8076 | 8129 | TTTCTCCATTTAGAGTGT | sooosssssssssssooss | 5-8-5 | 0 | 1211 |

TABLE 55

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 576816 | 310 | 7990 | 8043 | GCCTTACTCTAGGACCAAGA | sssssssssssssssssss | 5-10-5 | 57 | 20 |
| 619420 | 310 | 7990 | 8043 | GCCTTACTCTAGGACCAAGA | sooosssssssssssooss | 5-10-5 | 64 | 20 |
| 688078 | 313 | 7993 | 8046 | TGCCTTACTCTAGGACCA | sooosssssssssssooss | 5-8-5 | 37 | 1130 |
| 688160 | 397 | 8077 | 8130 | ATTTCTCCATTTAGAGTG | sooosssssssssssooss | 5-8-5 | 0 | 1212 |
| 688161 | 398 | 8078 | 8131 | GATTTCTCCATTTAGAGT | sooosssssssssssooss | 5-8-5 | 9 | 1213 |
| 688162 | 399 | 8079 | 8132 | GGATTTCTCCATTTAGAG | sooosssssssssssooss | 5-8-5 | 2 | 1214 |
| 688163 | 400 | 8080 | 8133 | AGGATTTCTCCATTTAGA | sooosssssssssssooss | 5-8-5 | 0 | 1215 |
| 688164 | 401 | 8081 | 8134 | AAGGATTTCTCCATTTAG | sooosssssssssssooss | 5-8-5 | 12 | 1216 |
| 688165 | 402 | 8082 | 8135 | GAAGGATTTCTCCATTTA | sooosssssssssssooss | 5-8-5 | 0 | 1217 |
| 688166 | 403 | 8083 | 8136 | CGAAGGATTTCTCCATTT | sooosssssssssssooss | 5-8-5 | 18 | 1218 |
| 688167 | 404 | 8084 | 8137 | TCGAAGGATTTCTCCATT | sooosssssssssssooss | 5-8-5 | 12 | 1219 |
| 688168 | 405 | 8085 | 8138 | TTCGAAGGATTTCTCCAT | sooosssssssssssooss | 5-8-5 | 6 | 1220 |
| 688169 | 406 | 8086 | 8139 | TTTCGAAGGATTTCTCCA | sooosssssssssssooss | 5-8-5 | 0 | 1221 |
| 688170 | 407 | 8087 | 8140 | ATTTCGAAGGATTTCTCC | sooosssssssssssooss | 5-8-5 | 8 | 1222 |
| 688171 | 408 | 8088 | 8141 | CATTTCGAAGGATTTCTC | sooosssssssssssooss | 5-8-5 | 16 | 1223 |
| 688172 | 409 | 8089 | 8142 | GCATTTCGAAGGATTTCT | sooosssssssssssooss | 5-8-5 | 55 | 1224 |
| 688173 | 410 | 8090 | 8143 | TGCATTTCGAAGGATTTC | sooosssssssssssooss | 5-8-5 | 0 | 1225 |
| 688174 | 411 | 8091 | 8144 | CTGCATTTCGAAGGATTT | sooosssssssssssooss | 5-8-5 | 25 | 1226 |
| 688175 | 412 | 8092 | 8145 | TCTGCATTTCGAAGGATT | sooosssssssssssooss | 5-8-5 | 33 | 1227 |

TABLE 55-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688176 | 413 | 8093 | 8146 | CTCTGCATTTCGAAGGAT | sooossssssssssooss | 5-8-5 | 12 | 1228 |
| 688177 | 414 | 8094 | 8147 | TCTCTGCATTTCGAAGGA | sooossssssssssooss | 5-8-5 | 14 | 1229 |
| 688178 | 415 | 8095 | 8148 | CTCTCTGCATTTCGAAGG | sooossssssssssooss | 5-8-5 | 5 | 1230 |
| 688179 | 416 | 8096 | 8149 | ACTCTCTGCATTTCGAAG | sooossssssssssooss | 5-8-5 | 0 | 1231 |
| 688180 | 417 | 8097 | 8150 | CACTCTCTGCATTTCGAA | sooossssssssssooss | 5-8-5 | 12 | 1232 |
| 688181 | 418 | 8098 | 8151 | CCACTCTCTGCATTTCGA | sooossssssssssooss | 5-8-5 | 40 | 1233 |
| 688182 | 419 | 8099 | 8152 | ACCACTCTCTGCATTTCG | sooossssssssssooss | 5-8-5 | 40 | 1234 |
| 688183 | 420 | 8100 | 8153 | CACCACTCTCTGCATTTC | sooossssssssssooss | 5-8-5 | 45 | 1235 |
| 688184 | 421 | 8101 | 8154 | GCACCACTCTCTGCATTT | sooossssssssssooss | 5-8-5 | 24 | 1236 |
| 688185 | 422 | 8102 | 8155 | AGCACCACTCTCTGCATT | sooossssssssssooss | 5-8-5 | 12 | 1237 |
| 688186 | 423 | 8103 | 8156 | TAGCACCACTCTCTGCAT | sooossssssssssooss | 5-8-5 | 21 | 1238 |
| 688187 | 424 | 8104 | 8157 | ATAGCACCACTCTCTGCA | sooossssssssssooss | 5-8-5 | 25 | 1239 |
| 688188 | 425 | 8105 | 8158 | TATAGCACCACTCTCTGC | sooossssssssssooss | 5-8-5 | 12 | 1240 |
| 688189 | 426 | 8106 | 8159 | CTATAGCACCACTCTCTG | sooossssssssssooss | 5-8-5 | 0 | 1241 |
| 688190 | 427 | 8107 | 8160 | TCTATAGCACCACTCTCT | sooossssssssssooss | 5-8-5 | 0 | 1242 |
| 688191 | 428 | 8108 | 8161 | ATCTATAGCACCACTCTC | sooossssssssssooss | 5-8-5 | 20 | 1243 |
| 688192 | 429 | 8109 | 8162 | CATCTATAGCACCACTCT | sooossssssssssooss | 5-8-5 | 0 | 1244 |
| 688193 | 430 | 8110 | 8163 | ACATCTATAGCACCACTC | sooossssssssssooss | 5-8-5 | 31 | 1245 |
| 688194 | 431 | 8111 | 8164 | TACATCTATAGCACCACT | sooossssssssssooss | 5-8-5 | 4 | 1246 |
| 688195 | 432 | 8112 | 8165 | TTACATCTATAGCACCAC | sooossssssssssooss | 5-8-5 | 32 | 1247 |
| 688196 | 433 | 8113 | 8166 | TTTACATCTATAGCACCA | sooossssssssssooss | 5-8-5 | 37 | 1248 |
| 688197 | 434 | 8114 | 8167 | CTTTACATCTATAGCACC | sooossssssssssooss | 5-8-5 | 25 | 1249 |
| 688198 | 435 | 8115 | 8168 | ACTTTACATCTATAGCAC | sooossssssssssooss | 5-8-5 | 0 | 1250 |
| 688199 | 436 | 8116 | 8169 | AACTTTACATCTATAGCA | sooossssssssssooss | 5-8-5 | 9 | 1251 |
| 688200 | 437 | 8117 | 8170 | AAACTTTACATCTATAGC | sooossssssssssooss | 5-8-5 | 8 | 1252 |
| 688201 | 438 | 8118 | 8171 | AAAACTTTACATCTATAG | sooossssssssssooss | 5-8-5 | 4 | 1253 |
| 688202 | 440 | 8120 | 8173 | AAAAAACTTTACATCTAT | sooossssssssssooss | 5-8-5 | 8 | 1254 |
| 688203 | 441 | 8121 | 8174 | CAAAAAACTTTACATCTA | sooossssssssssooss | 5-8-5 | 4 | 1255 |
| 688204 | 442 | 8122 | 8175 | ACAAAAAACTTTACATCT | sooossssssssssooss | 5-8-5 | 0 | 1256 |
| 688205 | 443 | 8123 | 8176 | GACAAAAAACTTTACATC | sooossssssssssooss | 5-8-5 | 0 | 1257 |
| 688206 | 446 | 8126 | 8179 | CAAGACAAAAAACTTTAC | sooossssssssssooss | 5-8-5 | 5 | 1258 |
| 688207 | 448 | 8128 | 8181 | GACAAGACAAAAAACTTT | sooossssssssssooss | 5-8-5 | 27 | 1259 |
| 688208 | 449 | 8129 | 8182 | AGACAAGACAAAAAACTT | sooossssssssssooss | 5-8-5 | 9 | 1260 |
| 688209 | 450 | 8130 | 8183 | CAGACAAGACAAAAAACT | sooossssssssssooss | 5-8-5 | 0 | 1261 |
| 688210 | 451 | 8131 | 8184 | TCAGACAAGACAAAAAAC | sooossssssssssooss | 5-8-5 | 11 | 1262 |

TABLE 55-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688211 | 452 | 8132 | 8185 | TTCAGACAAGACAAAAA | sooossssssssssooss | 5-8-5 | 0 | 1263 |
| 688212 | 454 | 8134 | 8187 | TTTTCAGACAAGACAAA | sooossssssssssooss | 5-8-5 | 0 | 1264 |
| 688213 | 455 | 8135 | 8188 | CTTTTCAGACAAGACAA | sooossssssssssooss | 5-8-5 | 0 | 1265 |
| 688214 | 456 | 8136 | 8189 | CCTTTTCAGACAAGACAA | sooossssssssssooss | 5-8-5 | 30 | 1266 |
| 688215 | 457 | 8137 | 8190 | CCCTTTTCAGACAAGACA | sooossssssssssooss | 5-8-5 | 31 | 1267 |
| 688216 | 458 | 8138 | 8191 | TCCCTTTTCAGACAAGAC | sooossssssssssooss | 5-8-5 | 24 | 1268 |
| 688217 | 459 | 8139 | 8192 | CTCCCTTTTCAGACAAGA | sooossssssssssooss | 5-8-5 | 47 | 1269 |
| 688218 | 460 | 8140 | 8193 | ACTCCCTTTTCAGACAAG | sooossssssssssooss | 5-8-5 | 34 | 1270 |
| 688219 | 461 | 8141 | 8194 | CACTCCCTTTTCAGACAA | sooossssssssssooss | 5-8-5 | 5 | 1271 |
| 688220 | 462 | 8142 | 8195 | TCACTCCCTTTTCAGACA | sooossssssssssooss | 5-8-5 | 15 | 1272 |
| 688221 | 463 | 8143 | 8196 | ATCACTCCCTTTTCAGAC | sooossssssssssooss | 5-8-5 | 14 | 1273 |
| 688222 | 464 | 8144 | 8197 | AATCACTCCCTTTTCAGA | sooossssssssssooss | 5-8-5 | 18 | 1274 |
| 688223 | 465 | 8145 | 8198 | TAATCACTCCCTTTTCAG | sooossssssssssooss | 5-8-5 | 14 | 1275 |
| 688224 | 466 | 8146 | 8199 | ATAATCACTCCCTTTTCA | sooossssssssssooss | 5-8-5 | 15 | 1276 |
| 688225 | 467 | 8147 | 8200 | AATAATCACTCCCTTTTC | sooossssssssssooss | 5-8-5 | 8 | 1277 |
| 688226 | 468 | 8148 | 8201 | CAATAATCACTCCCTTTT | sooossssssssssooss | 5-8-5 | 9 | 1278 |
| 688227 | 469 | 8149 | 8202 | ACAATAATCACTCCCTTT | sooossssssssssooss | 5-8-5 | 24 | 1279 |
| 688228 | 470 | 8150 | 8203 | AACAATAATCACTCCCTT | sooossssssssssooss | 5-8-5 | 21 | 1280 |
| 688229 | 471 | 8151 | 8204 | AAACAATAATCACTCCCT | sooossssssssssooss | 5-8-5 | 21 | 1281 |
| 688230 | 472 | 8152 | 8205 | GAAACAATAATCACTCCC | sooossssssssssooss | 5-8-5 | 36 | 1282 |
| 688231 | 473 | 8153 | 8206 | TGAAACAATAATCACTCC | sooossssssssssooss | 5-8-5 | 7 | 1283 |
| 688232 | 474 | 8154 | 8207 | ATGAAACAATAATCACTC | sooossssssssssooss | 5-8-5 | 20 | 1284 |
| 688233 | 475 | 8155 | 8208 | AATGAAACAATAATCACT | sooossssssssssooss | 5-8-5 | 0 | 1285 |
| 688234 | 476 | 8156 | 8209 | TAATGAAACAATAATCAC | sooossssssssssooss | 5-8-5 | 16 | 1286 |
| 688235 | 477 | 8157 | 8210 | TTAATGAAACAATAATCA | sooossssssssssooss | 5-8-5 | 0 | 1287 |
| 688236 | 478 | 8158 | 8211 | ATTAATGAAACAATAATC | sooossssssssssooss | 5-8-5 | 0 | 1288 |

TABLE 56

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 576816 | 310 | 7990 | 8043 | GCCTTACTCTAGGACCAAGA | ssssssssssssssssssss | 5-10-5 | 61 | 20 |
| 619420 | 310 | 7990 | 8043 | GCCTTACTCTAGGACCAAGA | sooossssssssssooss | 5-10-5 | 75 | 20 |

TABLE 56-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688078 | 313 | 7993 | 8046 | TGCCTTACTCTAGGACCA | sooosssssssssooss | 5-8-5 | 67 | 1130 |
| 688237 | 485 | 8165 | 8218 | ATCAAAGATTAATGAAAC | sooosssssssssooss | 5-8-5 | 43 | 1289 |
| 688238 | 486 | 8166 | 8219 | CATCAAAGATTAATGAAA | sooosssssssssooss | 5-8-5 | 0 | 1290 |
| 688239 | 487 | 8167 | 8220 | CCATCAAAGATTAATGAA | sooosssssssssooss | 5-8-5 | 42 | 1291 |
| 688240 | 488 | 8168 | 8221 | TCCATCAAAGATTAATGA | sooosssssssssooss | 5-8-5 | 46 | 1292 |
| 688241 | 489 | 8169 | 8222 | TTCCATCAAAGATTAATG | sooosssssssssooss | 5-8-5 | 0 | 1293 |
| 688242 | 490 | 8170 | 8223 | TTTCCATCAAAGATTAAT | sooosssssssssooss | 5-8-5 | 55 | 1294 |
| 688243 | 491 | 8171 | 8224 | GTTTCCATCAAAGATTAA | sooosssssssssooss | 5-8-5 | 49 | 1295 |
| 688244 | 492 | 8172 | 8225 | AGTTTCCATCAAAGATTA | sooosssssssssooss | 5-8-5 | 44 | 1296 |
| 688245 | 493 | 8173 | 8226 | CAGTTTCCATCAAAGATT | sooosssssssssooss | 5-8-5 | 0 | 1297 |
| 688246 | 494 | 8174 | 8227 | CCAGTTTCCATCAAAGAT | sooosssssssssooss | 5-8-5 | 46 | 1298 |
| 688247 | 495 | 8175 | 8228 | TCCAGTTTCCATCAAAGA | sooosssssssssooss | 5-8-5 | 46 | 1299 |
| 688248 | 496 | 8176 | 8229 | TTCCAGTTTCCATCAAAG | sooosssssssssooss | 5-8-5 | 59 | 1300 |
| 688249 | 497 | 8177 | 8230 | ATTCCAGTTTCCATCAAA | sooosssssssssooss | 5-8-5 | 48 | 1301 |
| 688250 | 498 | 8178 | 8231 | CATTCCAGTTTCCATCAA | sooosssssssssooss | 5-8-5 | 54 | 1302 |
| 688251 | 499 | 8179 | 8232 | CCATTCCAGTTTCCATCA | sooosssssssssooss | 5-8-5 | 59 | 1303 |
| 688252 | 500 | 8180 | 8233 | CCCATTCCAGTTTCCATC | sooosssssssssooss | 5-8-5 | 67 | 1304 |
| 688253 | 501 | 8181 | 8234 | CCCCATTCCAGTTTCCAT | sooosssssssssooss | 5-8-5 | 58 | 1305 |
| 688254 | 502 | 8182 | 8235 | TCCCCATTCCAGTTTCCA | sooosssssssssooss | 5-8-5 | 55 | 1306 |
| 688255 | 503 | 8183 | 8236 | ATCCCCATTCCAGTTTCC | sooosssssssssooss | 5-8-5 | 61 | 1307 |
| 688256 | 504 | 8184 | 8237 | GATCCCCATTCCAGTTTC | sooosssssssssooss | 5-8-5 | 51 | 1308 |
| 688257 | 505 | 8185 | 8238 | CGATCCCCATTCCAGTTT | sooosssssssssooss | 5-8-5 | 49 | 1309 |
| 688258 | 506 | 8186 | 8239 | GCGATCCCCATTCCAGTT | sooosssssssssooss | 5-8-5 | 43 | 1310 |
| 688259 | 507 | 8187 | 8240 | TGCGATCCCCATTCCAGT | sooosssssssssooss | 5-8-5 | 51 | 1311 |
| 688260 | 508 | 8188 | 8241 | CTGCGATCCCCATTCCAG | sooosssssssssooss | 5-8-5 | 70 | 1312 |
| 688261 | 509 | 8189 | 8242 | GCTGCGATCCCCATTCCA | sooosssssssssooss | 5-8-5 | 72 | 1313 |
| 688262 | 510 | 8190 | 8243 | TGCTGCGATCCCCATTCC | sooosssssssssooss | 5-8-5 | 49 | 1314 |
| 688263 | 511 | 8191 | 8244 | GTGCTGCGATCCCCATTC | sooosssssssssooss | 5-8-5 | 0 | 1315 |
| 688264 | 512 | 8192 | 8245 | TGTGCTGCGATCCCCATT | sooosssssssssooss | 5-8-5 | 58 | 1316 |
| 688265 | 513 | 8193 | 8246 | ATGTGCTGCGATCCCCAT | sooosssssssssooss | 5-8-5 | 66 | 1317 |
| 688266 | 514 | 8194 | 8247 | TATGTGCTGCGATCCCCA | sooosssssssssooss | 5-8-5 | 63 | 1318 |
| 688267 | 533 | 8213 | 8266 | AAGTATAATTGATAGTCC | sooosssssssssooss | 5-8-5 | 49 | 1319 |
| 688268 | 534 | 8214 | 8267 | GAAGTATAATTGATAGTC | sooosssssssssooss | 5-8-5 | 50 | 1320 |
| 688269 | 535 | 8215 | 8268 | GGAAGTATAATTGATAGT | sooosssssssssooss | 5-8-5 | 39 | 1321 |
| 688270 | 536 | 8216 | 8269 | TGGAAGTATAATTGATAG | sooosssssssssooss | 5-8-5 | 43 | 1322 |

TABLE 56-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688271 | 537 | 8217 | 8270 | GTGGAAGTATAATTGATA | sooossssssssssooss | 5-8-5 | 49 | 1323 |
| 688272 | 538 | 8218 | 8271 | TGTGGAAGTATAATTGAT | sooossssssssssooss | 5-8-5 | 40 | 1324 |
| 688273 | 539 | 8219 | 8272 | CTGTGGAAGTATAATTGA | sooossssssssssooss | 5-8-5 | 34 | 1325 |
| 688274 | 540 | 8220 | 8273 | TCTGTGGAAGTATAATTG | sooossssssssssooss | 5-8-5 | 0 | 1326 |
| 688275 | 541 | 8221 | 8274 | GTCTGTGGAAGTATAATT | sooossssssssssooss | 5-8-5 | 0 | 1327 |
| 688276 | 542 | 8222 | 8275 | TGTCTGTGGAAGTATAAT | sooossssssssssooss | 5-8-5 | 66 | 1328 |
| 688277 | 543 | 8223 | 8276 | CTGTCTGTGGAAGTATAA | sooossssssssssooss | 5-8-5 | 0 | 1329 |
| 688278 | 544 | 8224 | 8277 | TCTGTCTGTGGAAGTATA | sooossssssssssooss | 5-8-5 | 63 | 1330 |
| 688279 | 545 | 8225 | 8278 | TTCTGTCTGTGGAAGTAT | sooossssssssssooss | 5-8-5 | 55 | 1331 |
| 688280 | 546 | 8226 | 8279 | GTTCTGTCTGTGGAAGTA | sooossssssssssooss | 5-8-5 | 78 | 1332 |
| 688281 | 547 | 8227 | 8280 | AGTTCTGTCTGTGGAAGT | sooossssssssssooss | 5-8-5 | 63 | 1333 |
| 688282 | 548 | 8228 | 8281 | AAGTTCTGTCTGTGGAAG | sooossssssssssooss | 5-8-5 | 50 | 1334 |
| 688283 | 549 | 8229 | 8282 | TAAGTTCTGTCTGTGGAA | sooossssssssssooss | 5-8-5 | 0 | 1335 |
| 688284 | 550 | 8230 | 8283 | CTAAGTTCTGTCTGTGGA | sooossssssssssooss | 5-8-5 | 55 | 1336 |
| 688285 | 551 | 8231 | 8284 | ACTAAGTTCTGTCTGTGG | sooossssssssssooss | 5-8-5 | 69 | 1337 |
| 688286 | 552 | 8232 | 8285 | AACTAAGTTCTGTCTGTG | sooossssssssssooss | 5-8-5 | 66 | 1338 |
| 688287 | 553 | 8233 | 8286 | AAACTAAGTTCTGTCTGT | sooossssssssssooss | 5-8-5 | 43 | 1339 |
| 688288 | 554 | 8234 | 8287 | GAAACTAAGTTCTGTCTG | sooossssssssssooss | 5-8-5 | 37 | 1340 |
| 688289 | 555 | 8235 | 8288 | AGAAACTAAGTTCTGTCT | sooossssssssssooss | 5-8-5 | 47 | 1341 |
| 688290 | 556 | 8236 | 8289 | TAGAAACTAAGTTCTGTC | sooossssssssssooss | 5-8-5 | 50 | 1342 |
| 688291 | 557 | 8237 | 8290 | GTAGAAACTAAGTTCTGT | sooossssssssssooss | 5-8-5 | 47 | 1343 |
| 688292 | 558 | 8238 | 8291 | GGTAGAAACTAAGTTCTG | sooossssssssssooss | 5-8-5 | 46 | 1344 |
| 688293 | 559 | 8239 | 8292 | AGGTAGAAACTAAGTTCT | sooossssssssssooss | 5-8-5 | 59 | 1345 |
| 688294 | 560 | 8240 | 8293 | GAGGTAGAAACTAAGTTC | sooossssssssssooss | 5-8-5 | 48 | 1346 |
| 688295 | 561 | 8241 | 8294 | GGAGGTAGAAACTAAGTT | sooossssssssssooss | 5-8-5 | 47 | 1347 |
| 688296 | 562 | 8242 | 8295 | GGGAGGTAGAAACTAAGT | sooossssssssssooss | 5-8-5 | 43 | 1348 |
| 688297 | 563 | 8243 | 8296 | TGGGAGGTAGAAACTAAG | sooossssssssssooss | 5-8-5 | 49 | 1349 |
| 688298 | 564 | 8244 | 8297 | GTGGGAGGTAGAAACTAA | sooossssssssssooss | 5-8-5 | 51 | 1350 |
| 688299 | 565 | 8245 | 8298 | AGTGGGAGGTAGAAACTA | sooossssssssssooss | 5-8-5 | 45 | 1351 |
| 688300 | 566 | 8246 | 8299 | AAGTGGGAGGTAGAAACT | sooossssssssssooss | 5-8-5 | 40 | 1352 |
| 688301 | 567 | 8247 | 8300 | GAAGTGGGAGGTAGAAAC | sooossssssssssooss | 5-8-5 | 39 | 1353 |
| 688302 | 568 | 8248 | 8301 | TGAAGTGGGAGGTAGAAA | sooossssssssssooss | 5-8-5 | 0 | 1354 |
| 688303 | 569 | 8249 | 8302 | ATGAAGTGGGAGGTAGAA | sooossssssssssooss | 5-8-5 | 42 | 1355 |
| 688304 | 570 | 8250 | 8303 | TATGAAGTGGGAGGTAGA | sooossssssssssooss | 5-8-5 | 32 | 1356 |
| 688305 | 571 | 8251 | 8304 | CTATGAAGTGGGAGGTAG | sooossssssssssooss | 5-8-5 | 47 | 1357 |

TABLE 56-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688306 | 572 | 8252 | 8305 | TCTATGAAGTGGGAGGTA | sooossssssssssooss | 5-8-5 | 33 | 1358 |
| 688307 | 573 | 8253 | 8306 | CTCTATGAAGTGGGAGGT | sooossssssssssooss | 5-8-5 | 55 | 1359 |
| 688308 | 574 | 8254 | 8307 | ACTCTATGAAGTGGGAGG | sooossssssssssooss | 5-8-5 | 51 | 1360 |
| 688309 | 575 | 8255 | 8308 | CACTCTATGAAGTGGGAG | sooossssssssssooss | 5-8-5 | 59 | 1361 |
| 688310 | 576 | 8256 | 8309 | ACACTCTATGAAGTGGGA | sooossssssssssooss | 5-8-5 | 58 | 1362 |
| 688311 | 577 | 8257 | 8310 | CACACTCTATGAAGTGGG | sooossssssssssooss | 5-8-5 | 59 | 1363 |
| 688312 | 578 | 8258 | 8311 | ACACACTCTATGAAGTGG | sooossssssssssooss | 5-8-5 | 42 | 1364 |
| 688313 | 579 | 8259 | 8312 | CACACACTCTATGAAGTG | sooossssssssssooss | 5-8-5 | 40 | 1365 |

TABLE 57

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mismatches with SEQ ID NO: 19 | Sequence | Linkage | Motif | % inhibition (RTS3750) | SEQ ID NO |
|---|---|---|---|---|---|---|---|---|---|
| 576816 | 310 | 7990 | 8043 | 0 | GCCTTACTCTAGGACCAAGA | sssssssssssssssssss | 5-10-5 | 47 | 20 |
| 619420 | 310 | 7990 | 8043 | 0 | GCCTTACTCTAGGACCAAGA | sooosssssssssssooss | 5-10-5 | 51 | 20 |
| 688078 | 313 | 7993 | 8046 | 0 | TGCCTTACTCTAGGACCA | sooossssssssssooss | 5-8-5 | 32 | 1130 |
| 688314 | 580 | 8260 | 8313 | 0 | ACACACACTCTATGAAGT | sooossssssssssooss | 5-8-5 | 9 | 1366 |
| 688315 | 691 | n/a | 9505 | 1 | CCCTGATCTTCCATTCTC | sooossssssssssooss | 5-8-5 | 21 | 1367 |
| 688316 | 692 | n/a | 9506 | 2 | ACCCTGATCTTCCATTCT | sooossssssssssooss | 5-8-5 | 2 | 1368 |
| 688317 | 693 | n/a | 9507 | 3 | GACCCTGATCTTCCATTC | sooossssssssssooss | 5-8-5 | 16 | 1369 |
| 688318 | 694 | n/a | 9508 | 3 | TGACCCTGATCTTCCATT | sooossssssssssooss | 5-8-5 | 18 | 1370 |
| 688319 | 695 | n/a | n/a | n/a | CTGACCCTGATCTTCCAT | sooossssssssssooss | 5-8-5 | 5 | 1371 |
| 688320 | 696 | n/a | n/a | n/a | TCTGACCCTGATCTTCCA | sooossssssssssooss | 5-8-5 | 11 | 1372 |
| 688321 | 697 | n/a | n/a | n/a | CTCTGACCCTGATCTTCC | sooossssssssssooss | 5-8-5 | 21 | 1373 |
| 688322 | 698 | n/a | n/a | n/a | ACTCTGACCCTGATCTTC | sooossssssssssooss | 5-8-5 | 26 | 1374 |
| 688323 | 699 | n/a | n/a | n/a | TACTCTGACCCTGATCTT | sooossssssssssooss | 5-8-5 | 6 | 1375 |
| 688324 | 700 | n/a | 12554 | 3 | ATACTCTGACCCTGATCT | sooossssssssssooss | 5-8-5 | 7 | 1376 |
| 688325 | 701 | n/a | 12555 | 2 | AATACTCTGACCCTGATC | sooossssssssssooss | 5-8-5 | 0 | 1377 |
| 687955 | n/a | 13641 | 13680 | 0 | ATGATTTCTTGTCTGGGA | sooossssssssssooss | 5-8-5 | 31 | 1378 |
| 687956 | n/a | 13642 | 13681 | 0 | CATGATTTCTTGTCTGGG | sooossssssssssooss | 5-8-5 | 38 | 1379 |
| 687957 | n/a | 13643 | 13682 | 0 | CCATGATTTCTTGTCTGG | sooossssssssssooss | 5-8-5 | 12 | 1380 |
| 687958 | n/a | 13644 | 13683 | 0 | GCCATGATTTCTTGTCTG | sooossssssssssooss | 5-8-5 | 27 | 1381 |

TABLE 57-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mis-matches with SEQ ID NO: 19 | Sequence | Linkage | Motif | % inhibition (RTS3750) | SEQ ID NO |
|---|---|---|---|---|---|---|---|---|---|
| 687959 | n/a | 13645 | 13684 | 0 | GGCCATGATTTCTTGTCT | sooossssssssooss | 5-8-5 | 26 | 1382 |
| 687960 | n/a | 13646 | 13685 | 0 | GGGCCATGATTTCTTGTC | sooossssssssooss | 5-8-5 | 18 | 1383 |
| 687961 | n/a | 14089 | 14136 | 0 | AACTAACATGTAGGCACT | sooossssssssooss | 5-8-5 | 38 | 1384 |
| 687962 | n/a | 14090 | 14137 | 0 | GAACTAACATGTAGGCAC | sooossssssssooss | 5-8-5 | 57 | 1385 |
| 687963 | n/a | 14091 | 14138 | 0 | GGAACTAACATGTAGGCA | sooossssssssooss | 5-8-5 | 63 | 1386 |
| 687964 | n/a | 14092 | 14139 | 0 | AGGAACTAACATGTAGGC | sooossssssssooss | 5-8-5 | 29 | 1387 |
| 687965 | n/a | 14302 | 14349 | 0 | CTTCTGATTCAAGCCATT | sooossssssssooss | 5-8-5 | 25 | 1388 |
| 687966 | n/a | 14303 | 14350 | 0 | GCTTCTGATTCAAGCCAT | sooossssssssooss | 5-8-5 | 51 | 1389 |
| 687967 | n/a | 14304 | 14351 | 0 | TGCTTCTGATTCAAGCCA | sooossssssssooss | 5-8-5 | 46 | 1390 |
| 687968 | n/a | 14305 | 14352 | 0 | GTGCTTCTGATTCAAGCC | sooossssssssooss | 5-8-5 | 21 | 1391 |
| 687969 | n/a | 14306 | 14353 | 0 | AGTGCTTCTGATTCAAGC | sooossssssssooss | 5-8-5 | 36 | 1392 |
| 687970 | n/a | 14307 | 14354 | 0 | AAGTGCTTCTGATTCAAG | sooossssssssooss | 5-8-5 | 25 | 1393 |
| 687971 | n/a | 14308 | 14355 | 0 | AAAGTGCTTCTGATTCAA | sooossssssssooss | 5-8-5 | 28 | 1394 |
| 687972 | n/a | 14309 | 14356 | 0 | TAAAGTGCTTCTGATTCA | sooossssssssooss | 5-8-5 | 0 | 1395 |
| 687973 | n/a | 14310 | 14357 | 0 | CTAAAGTGCTTCTGATTC | sooossssssssooss | 5-8-5 | 25 | 1396 |
| 687974 | n/a | 14311 | 14358 | 0 | ACTAAAGTGCTTCTGATT | sooossssssssooss | 5-8-5 | 17 | 1397 |
| 687975 | n/a | 14312 | 14359 | 0 | GACTAAAGTGCTTCTGAT | sooossssssssooss | 5-8-5 | 33 | 1398 |
| 687976 | n/a | 14313 | 14360 | 0 | GGACTAAAGTGCTTCTGA | sooossssssssooss | 5-8-5 | 47 | 1399 |
| 687977 | n/a | 14314 | 14361 | 0 | AGGACTAAAGTGCTTCTG | sooossssssssooss | 5-8-5 | 44 | 1400 |
| 687978 | n/a | 14315 | 14362 | 0 | CAGGACTAAAGTGCTTCT | sooossssssssooss | 5-8-5 | 57 | 1401 |
| 687979 | n/a | 14316 | 14363 | 0 | ACAGGACTAAAGTGCTTC | sooossssssssooss | 5-8-5 | 31 | 1402 |
| 687980 | n/a | 14317 | 14364 | 0 | TACAGGACTAAAGTGCTT | sooossssssssooss | 5-8-5 | 24 | 1403 |
| 687981 | n/a | 14318 | 14365 | 0 | ATACAGGACTAAAGTGCT | sooossssssssooss | 5-8-5 | 21 | 1404 |
| 687982 | n/a | 14319 | 14366 | 0 | GATACAGGACTAAAGTGC | sooossssssssooss | 5-8-5 | 15 | 1405 |
| 687983 | n/a | 14320 | 14367 | 0 | AGATACAGGACTAAAGTG | sooossssssssooss | 5-8-5 | 8 | 1406 |
| 687984 | n/a | 14321 | 14368 | 0 | CAGATACAGGACTAAAGT | sooossssssssooss | 5-8-5 | 1 | 1407 |
| 687985 | n/a | 14322 | 14369 | 0 | ACAGATACAGGACTAAAG | sooossssssssooss | 5-8-5 | 10 | 1408 |
| 687986 | n/a | 14323 | 14370 | 0 | AACAGATACAGGACTAAA | sooossssssssooss | 5-8-5 | 11 | 1409 |
| 687987 | n/a | 14324 | 14371 | 0 | GAACAGATACAGGACTAA | sooossssssssooss | 5-8-5 | 20 | 1410 |
| 687988 | n/a | 14325 | 14372 | 0 | TGAACAGATACAGGACTA | sooossssssssooss | 5-8-5 | 25 | 1411 |
| 687989 | n/a | 14326 | 14373 | 0 | CTGAACAGATACAGGACT | sooossssssssooss | 5-8-5 | 12 | 1412 |
| 687990 | n/a | 14327 | 14374 | 0 | ACTGAACAGATACAGGAC | sooossssssssooss | 5-8-5 | 25 | 1413 |
| 687991 | n/a | 14328 | 14375 | 0 | CACTGAACAGATACAGGA | sooossssssssooss | 5-8-5 | 8 | 1414 |
| 687992 | n/a | 14329 | 14376 | 0 | ACACTGAACAGATACAGG | sooossssssssooss | 5-8-5 | 10 | 1415 |
| 687993 | n/a | 14330 | 14377 | 0 | GACACTGAACAGATACAG | sooossssssssooss | 5-8-5 | 13 | 1416 |

TABLE 57-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mismatches with SEQ ID NO: 19 | Sequence | Linkage | Motif | % inhibition (RTS3750) | SEQ ID NO |
|---|---|---|---|---|---|---|---|---|---|
| 687994 | n/a | 14331 | 14378 | 0 | TGACACTGAACAGATACA | sooosssssssssooss | 5-8-5 | 25 | 1417 |
| 687995 | n/a | 14332 | 14379 | 0 | CTGACACTGAACAGATAC | sooosssssssssooss | 5-8-5 | 35 | 1418 |
| 687996 | n/a | 14333 | 14380 | 0 | GCTGACACTGAACAGATA | sooosssssssssooss | 5-8-5 | 24 | 1419 |
| 687997 | n/a | 14334 | 14381 | 0 | GGCTGACACTGAACAGAT | sooosssssssssooss | 5-8-5 | 40 | 1420 |
| 687998 | n/a | 14335 | 14382 | 0 | AGGCTGACACTGAACAGA | sooosssssssssooss | 5-8-5 | 10 | 1421 |
| 687999 | n/a | 14336 | 14383 | 0 | AAGGCTGACACTGAACAG | sooosssssssssooss | 5-8-5 | 3 | 1422 |
| 688000 | n/a | 14337 | 14384 | 0 | AAAGGCTGACACTGAACA | sooosssssssssooss | 5-8-5 | 18 | 1423 |
| 688001 | n/a | 14338 | 14385 | 0 | GAAAGGCTGACACTGAAC | sooosssssssssooss | 5-8-5 | 17 | 1424 |
| 688002 | n/a | 14339 | 14386 | 0 | TGAAAGGCTGACACTGAA | sooosssssssssooss | 5-8-5 | 12 | 1425 |
| 688003 | n/a | 14358 | 14405 | 0 | TGGGATTTAAAATGATGT | sooosssssssssooss | 5-8-5 | 17 | 1426 |
| 688004 | n/a | 14359 | 14406 | 0 | ATGGGATTTAAAATGATG | sooosssssssssooss | 5-8-5 | 11 | 1427 |
| 688326 | n/a | 13402 | 13443 | 0 | CTTGAGAAGAAAGCCTTC | sooosssssssssooss | 5-8-5 | 6 | 1428 |
| 688327 | n/a | 14287 | 14334 | 0 | ATTAAGGCTCTTAGGTTA | sooosssssssssooss | 5-8-5 | 0 | 1429 |
| 688328 | n/a | 13499 | 13530 | 0 | GTAGACAGTCTGTTATTT | sooosssssssssooss | 5-8-5 | 27 | 1430 |
| 688329 | n/a | 14397 | 14444 | 0 | TGACATGTAGAGAGATTA | sooosssssssssooss | 5-8-5 | 43 | 1431 |
| 688330 | n/a | 13827 | 13866 | 0 | TGGTTTAAGGGCACAAAC | sooosssssssssooss | 5-8-5 | 0 | 1432 |
| 688331 | n/a | 13403 | 13444 | 0 | ACTTGAGAAGAAAGCCTT | sooosssssssssooss | 5-8-5 | 27 | 1433 |
| 688332 | n/a | 14257 | 14304 | 0 | CCTCTGATACTCCATCAT | sooosssssssssooss | 5-8-5 | 28 | 1434 |
| 688333 | n/a | 13471 | 13502 | 0 | AAATCTTGTCATAGGTGA | sooosssssssssooss | 5-8-5 | 21 | 1435 |
| 688334 | n/a | 13410 | 13451 | 0 | AATTCTTACTTGAGAAGA | sooosssssssssooss | 5-8-5 | 7 | 1436 |
| 688335 | n/a | 13885 | 13924 | 0 | GGTGTATAGAGAATTCAG | sooosssssssssooss | 5-8-5 | 41 | 1437 |
| 688336 | n/a | 14250 | 14297 | 0 | TACTCCATCATGAGCCTA | sooosssssssssooss | 5-8-5 | 35 | 1438 |
| 688337 | n/a | 13788 | 13827 | 0 | GCTGGATGGAAAAGATC | sooosssssssssooss | 5-8-5 | 12 | 1439 |
| 688338 | n/a | 13517 | 13548 | 0 | GTCCCTAGAACAATCTAA | sooosssssssssooss | 5-8-5 | 28 | 1440 |
| 688339 | n/a | 14405 | 14452 | 0 | GAAGAAATTGACATGTAG | sooosssssssssooss | 5-8-5 | 12 | 1441 |
| 688340 | n/a | 13724 | 13763 | 0 | CATCTACAGTACAACTTA | sooosssssssssooss | 5-8-5 | 4 | 1442 |

TABLE 58

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688341 | 233 | 7913 | 7966 | ATCTCTGTCTTGGCAACAGC | soooossssssssssssooss | 5-10-5 | 57 | 1443 |
| 688342 | 234 | 7914 | 7967 | AATCTCTGTCTTGGCAACAG | soooossssssssssssooss | 5-10-5 | 35 | 1444 |

TABLE 58-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688343 | 235 | 7915 | 7968 | CAATCTCTGTCTTGGCAACA | sooooossssssssssooss | 5-10-5 | 36 | 1445 |
| 655153 | 236 | 7916 | 7969 | GCAATCTCTGTCTTGGCAAC | sooooossssssssssooss | 5-10-5 | 89 | 463 |
| 655154 | 237 | 7917 | 7970 | AGCAATCTCTGTCTTGGCAA | sooooossssssssssooss | 5-10-5 | 81 | 464 |
| 688344 | 238 | 7918 | 7971 | AAGCAATCTCTGTCTTGGCA | sooooossssssssssooss | 5-10-5 | 83 | 1446 |
| 655172 | 306 | 7986 | 8039 | TACTCTAGGACCAAGAATAT | sooooossssssssssooss | 5-10-5 | 10 | 483 |
| 688345 | 307 | 7987 | 8040 | TTACTCTAGGACCAAGAATA | sooooossssssssssooss | 5-10-5 | 1 | 1447 |
| 688346 | 308 | 7988 | 8041 | CTTACTCTAGGACCAAGAAT | sooooossssssssssooss | 5-10-5 | 10 | 1448 |
| 625183 | 309 | 7989 | 8042 | CCTTACTCTAGGACCAAGAA | sooooossssssssssooss | 5-10-5 | 44 | 484 |
| 576816 | 310 | 7990 | 8043 | GCCTTACTCTAGGACCAAGA | ssssssssssssssssssss | 5-10-5 | 56 | 20 |
| 619420 | 310 | 7990 | 8043 | GCCTTACTCTAGGACCAAGA | sooooossssssssssooss | 5-10-5 | 73 | 20 |
| 688347 | 311 | 7991 | 8044 | TGCCTTACTCTAGGACCAAG | sooooossssssssssooss | 5-10-5 | 62 | 1449 |
| 655173 | 312 | 7992 | 8045 | GTGCCTTACTCTAGGACCAA | sooooossssssssssooss | 5-10-5 | 59 | 485 |
| 688348 | 313 | 7993 | 8046 | TGTGCCTTACTCTAGGACCA | sooooossssssssssooss | 5-10-5 | 62 | 1450 |
| 688349 | 314 | 7994 | 8047 | ATGTGCCTTACTCTAGGACC | sooooossssssssssooss | 5-10-5 | 62 | 1451 |
| 655174 | 315 | 7995 | 8048 | AATGTGCCTTACTCTAGGAC | sooooossssssssssooss | 5-10-5 | 60 | 486 |
| 688350 | 319 | 7999 | 8052 | CCCAAATGTGCCTTACTCTA | sooooossssssssssooss | 5-10-5 | 41 | 1452 |
| 688351 | 320 | 8000 | 8053 | GCCCAAATGTGCCTTACTCT | sooooossssssssssooss | 5-10-5 | 62 | 1453 |
| 627833 | 321 | 8001 | 8054 | AGCCCAAATGTGCCTTACTC | sooooossssssssssooss | 5-10-5 | 51 | 487 |
| 688352 | 322 | 8002 | 8055 | GAGCCCAAATGTGCCTTACT | sooooossssssssssooss | 5-10-5 | 66 | 1454 |
| 688353 | 323 | 8003 | 8056 | GGAGCCCAAATGTGCCTTAC | sooooossssssssssooss | 5-10-5 | 48 | 1455 |
| 619411 | 324 | 8004 | 8057 | TGGAGCCCAAATGTGCCTTA | sooooossssssssssooss | 5-10-5 | 67 | 51 |
| 688354 | 325 | 8005 | 8058 | TTGGAGCCCAAATGTGCCTT | sooooossssssssssooss | 5-10-5 | 53 | 1456 |
| 627608 | 326 | 8006 | 8059 | TTTGGAGCCCAAATGTGCCT | sooooossssssssssooss | 5-10-5 | 42 | 1457 |
| 655175 | 327 | 8007 | 8060 | CTTTGGAGCCCAAATGTGCC | sooooossssssssssooss | 5-10-5 | 26 | 488 |
| 655176 | 330 | 8010 | 8063 | TGTCTTTGGAGCCCAAATGT | sooooossssssssssooss | 5-10-5 | 33 | 489 |
| 688355 | 331 | 8011 | 8064 | CTGTCTTTGGAGCCCAAATG | sooooossssssssssooss | 5-10-5 | 56 | 1458 |
| 619412 | 332 | 8012 | 8065 | TCTGTCTTTGGAGCCCAAAT | sooooossssssssssooss | 5-10-5 | 60 | 53 |
| 655177 | 333 | 8013 | 8066 | TTCTGTCTTTGGAGCCCAAA | sooooossssssssssooss | 5-10-5 | 47 | 490 |
| 655178 | 334 | 8014 | 8067 | GTTCTGTCTTTGGAGCCCAA | sooooossssssssssooss | 5-10-5 | 67 | 491 |
| 688356 | 335 | 8015 | 8068 | TGTTCTGTCTTTGGAGCCCA | sooooossssssssssooss | 5-10-5 | 60 | 1459 |
| 655179 | 336 | 8016 | 8069 | CTGTTCTGTCTTTGGAGCCC | sooooossssssssssooss | 5-10-5 | 59 | 492 |
| 688357 | 337 | 8017 | 8070 | CCTGTTCTGTCTTTGGAGCC | sooooossssssssssooss | 5-10-5 | 50 | 1460 |
| 688358 | 338 | 8018 | 8071 | ACCTGTTCTGTCTTTGGAGC | sooooossssssssssooss | 5-10-5 | 44 | 1461 |
| 655180 | 339 | 8019 | 8072 | TACCTGTTCTGTCTTTGGAG | sooooossssssssssooss | 5-10-5 | 42 | 493 |
| 619413 | 340 | 8020 | 8073 | GTACCTGTTCTGTCTTTGGA | sooooossssssssssooss | 5-10-5 | 56 | 135 |

TABLE 58-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688359 | 341 | 8021 | 8074 | AGTACCTGTTCTGTCTTTGG | soooosssssssssssooss | 5-10-5 | 38 | 1462 |
| 655181 | 342 | 8022 | 8075 | AAGTACCTGTTCTGTCTTTG | soooosssssssssssooss | 5-10-5 | 31 | 494 |
| 655185 | 351 | 8031 | 8084 | ATCACTGAGAAGTACCTGTT | soooosssssssssssooss | 5-10-5 | 32 | 498 |
| 688360 | 352 | 8032 | 8085 | CATCACTGAGAAGTACCTGT | soooosssssssssssooss | 5-10-5 | 53 | 1463 |
| 619414 | 353 | 8033 | 8086 | CCATCACTGAGAAGTACCTG | soooosssssssssssooss | 5-10-5 | 48 | 136 |
| 655186 | 354 | 8034 | 8087 | TCCATCACTGAGAAGTACCT | soooosssssssssssooss | 5-10-5 | 56 | 499 |
| 688361 | 355 | 8035 | 8088 | CTCCATCACTGAGAAGTACC | soooosssssssssssooss | 5-10-5 | 54 | 1464 |
| 655201 | 415 | 8095 | 8148 | CACTCTCTGCATTTCGAAGG | soooosssssssssssooss | 5-10-5 | 32 | 521 |
| 688362 | 416 | 8096 | 8149 | CCACTCTCTGCATTTCGAAG | soooosssssssssssooss | 5-10-5 | 39 | 1465 |
| 688363 | 417 | 8097 | 8150 | ACCACTCTCTGCATTTCGAA | soooosssssssssssooss | 5-10-5 | 37 | 1466 |
| 655202 | 418 | 8098 | 8151 | CACCACTCTCTGCATTTCGA | soooosssssssssssooss | 5-10-5 | 50 | 522 |
| 688364 | 419 | 8099 | 8152 | GCACCACTCTCTGCATTTCG | soooosssssssssssooss | 5-10-5 | 56 | 1467 |
| 655203 | 420 | 8100 | 8153 | AGCACCACTCTCTGCATTTC | soooosssssssssssooss | 5-10-5 | 56 | 523 |
| 655204 | 421 | 8101 | 8154 | TAGCACCACTCTCTGCATTT | soooosssssssssssooss | 5-10-5 | 25 | 524 |
| 688365 | 422 | 8102 | 8155 | ATAGCACCACTCTCTGCATT | soooosssssssssssooss | 5-10-5 | 29 | 1468 |
| 688366 | 423 | 8103 | 8156 | TATAGCACCACTCTCTGCAT | soooosssssssssssooss | 5-10-5 | 31 | 1469 |
| 655206 | 427 | 8107 | 8160 | CATCTATAGCACCACTCTCT | soooosssssssssssooss | 5-10-5 | 20 | 526 |
| 688367 | 428 | 8108 | 8161 | ACATCTATAGCACCACTCTC | soooosssssssssssooss | 5-10-5 | 28 | 1470 |
| 688368 | 429 | 8109 | 8162 | TACATCTATAGCACCACTCT | soooosssssssssssooss | 5-10-5 | 24 | 1471 |
| 671081 | 430 | 8110 | 8163 | TTACATCTATAGCACCACTC | soooosssssssssssooss | 5-10-5 | 26 | 1052 |
| 688369 | 431 | 8111 | 8164 | TTTACATCTATAGCACCACT | soooosssssssssssooss | 5-10-5 | 40 | 1472 |
| 688370 | 432 | 8112 | 8165 | CTTTACATCTATAGCACCAC | soooosssssssssssooss | 5-10-5 | 43 | 1473 |
| 655207 | 433 | 8113 | 8166 | ACTTTACATCTATAGCACCA | soooosssssssssssooss | 5-10-5 | 33 | 527 |
| 688371 | 434 | 8114 | 8167 | AACTTTACATCTATAGCACC | soooosssssssssssooss | 5-10-5 | 15 | 1474 |
| 688372 | 435 | 8115 | 8168 | AAACTTTACATCTATAGCAC | soooosssssssssssooss | 5-10-5 | 24 | 1475 |
| 655208 | 436 | 8116 | 8169 | AAAACTTTACATCTATAGCA | soooosssssssssssooss | 5-10-5 | 28 | 528 |
| 655215 | 456 | 8136 | 8189 | TCCCTTTTCAGACAAGACAA | soooosssssssssssooss | 5-10-5 | 35 | 535 |
| 688373 | 457 | 8137 | 8190 | CTCCCTTTTCAGACAAGACA | soooosssssssssssooss | 5-10-5 | 42 | 1476 |
| 688374 | 458 | 8138 | 8191 | ACTCCCTTTTCAGACAAGAC | soooosssssssssssooss | 5-10-5 | 57 | 1477 |
| 655216 | 459 | 8139 | 8192 | CACTCCCTTTTCAGACAAGA | soooosssssssssssooss | 5-10-5 | 51 | 536 |
| 671082 | 460 | 8140 | 8193 | TCACTCCCTTTTCAGACAAG | soooosssssssssssooss | 5-10-5 | 45 | 1053 |
| 688375 | 461 | 8141 | 8194 | ATCACTCCCTTTTCAGACAA | soooosssssssssssooss | 5-10-5 | 39 | 1478 |
| 655217 | 462 | 8142 | 8195 | AATCACTCCCTTTTCAGACA | soooosssssssssssooss | 5-10-5 | 45 | 537 |
| 688376 | 463 | 8143 | 8196 | TAATCACTCCCTTTTCAGAC | soooosssssssssssooss | 5-10-5 | 7 | 1479 |
| 688377 | 464 | 8144 | 8197 | ATAATCACTCCCTTTTCAGA | soooosssssssssssooss | 5-10-5 | 1 | 1480 |

TABLE 58-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 655218 | 465 | 8145 | 8198 | AATAATCACTCCCTTTTCAG | soooosssssssssssooss | 5-10-5 | 23 | 538 |
| 655230 | 500 | 8180 | 8233 | TCCCCATTCCAGTTTCCATC | soooosssssssssssooss | 5-10-5 | 57 | 550 |
| 688378 | 501 | 8181 | 8234 | ATCCCCATTCCAGTTTCCAT | soooosssssssssssooss | 5-10-5 | 60 | 1481 |
| 688379 | 502 | 8182 | 8235 | GATCCCCATTCCAGTTTCCA | soooosssssssssssooss | 5-10-5 | 55 | 1482 |
| 655231 | 503 | 8183 | 8236 | CGATCCCCATTCCAGTTTCC | soooosssssssssssooss | 5-10-5 | 58 | 551 |
| 688380 | 504 | 8184 | 8237 | GCGATCCCCATTCCAGTTTC | soooosssssssssssooss | 5-10-5 | 56 | 1483 |
| 688381 | 505 | 8185 | 8238 | TGCGATCCCCATTCCAGTTT | soooosssssssssssooss | 5-10-5 | 46 | 1484 |

TABLE 59

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mismatches with SEQ ID NO: 19 | Sequence | Linkage | Motif | % inhibition (RTS3750) | SEQ ID NO |
|---|---|---|---|---|---|---|---|---|---|
| 576816 | 310 | 7990 | 8043 | 0 | GCCTTACTCTAGGACCAAGA | ssssssssssssssssssss | 5-10-5 | 53 | 20 |
| 619420 | 310 | 7990 | 8043 | 0 | GCCTTACTCTAGGACCAAGA | soooosssssssssssooss | 5-10-5 | 54 | 20 |
| 655173 | 312 | 7992 | 8045 | 0 | GTGCCTTACTCTAGGACCAA | soooosssssssssssooss | 5-10-5 | 77 | 485 |
| 655232 | 506 | 8186 | 8239 | 0 | CTGCGATCCCCATTCCAGTT | soooosssssssssssooss | 5-10-5 | 46 | 552 |
| 688382 | 507 | 8187 | 8240 | 0 | GCTGCGATCCCCATTCCAGT | soooosssssssssssooss | 5-10-5 | 65 | 1485 |
| 688383 | 508 | 8188 | 8241 | 0 | TGCTGCGATCCCCATTCCAG | soooosssssssssssooss | 5-10-5 | 60 | 1486 |
| 655233 | 509 | 8189 | 8242 | 0 | GTGCTGCGATCCCCATTCCA | soooosssssssssssooss | 5-10-5 | 57 | 553 |
| 688384 | 510 | 8190 | 8243 | 0 | TGTGCTGCGATCCCCATTCC | soooosssssssssssooss | 5-10-5 | 45 | 1487 |
| 688385 | 511 | 8191 | 8244 | 0 | ATGTGCTGCGATCCCCATTC | soooosssssssssssooss | 5-10-5 | 68 | 1488 |
| 655234 | 512 | 8192 | 8245 | 0 | TATGTGCTGCGATCCCCATT | soooosssssssssssooss | 5-10-5 | 32 | 554 |
| 655240 | 548 | 8228 | 8281 | 0 | CTAAGTTCTGTCTGTGGAAG | soooosssssssssssooss | 5-10-5 | 23 | 560 |
| 688386 | 549 | 8229 | 8282 | 0 | ACTAAGTTCTGTCTGTGGAA | soooosssssssssssooss | 5-10-5 | 45 | 1489 |
| 671083 | 550 | 8230 | 8283 | 0 | AACTAAGTTCTGTCTGTGGA | soooosssssssssssooss | 5-10-5 | 41 | 1054 |
| 655241 | 551 | 8231 | 8284 | 0 | AAACTAAGTTCTGTCTGTGG | soooosssssssssssooss | 5-10-5 | 28 | 561 |
| 688387 | 552 | 8232 | 8285 | 0 | GAAACTAAGTTCTGTCTGTG | soooosssssssssssooss | 5-10-5 | 49 | 1490 |
| 688388 | 553 | 8233 | 8286 | 0 | AGAAACTAAGTTCTGTCTGT | soooosssssssssssooss | 5-10-5 | 46 | 1491 |
| 655242 | 554 | 8234 | 8287 | 0 | TAGAAACTAAGTTCTGTCTG | soooosssssssssssooss | 5-10-5 | 25 | 562 |
| 655289 | 691 | n/a | 9505 | 3 | GACCCTGATCTTCCATTCTC | soooosssssssssssooss | 5-10-5 | 34 | 627 |
| 688389 | 692 | n/a | 9506 | 3 | TGACCCTGATCTTCCATTCT | soooosssssssssssooss | 5-10-5 | 19 | 1492 |
| 688390 | 693 | n/a | n/a | n/a | CTGACCCTGATCTTCCATTC | soooosssssssssssooss | 5-10-5 | 21 | 1493 |
| 655290 | 694 | n/a | n/a | n/a | TCTGACCCTGATCTTCCATT | soooosssssssssssooss | 5-10-5 | 67 | 628 |

TABLE 59-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mismatches with SEQ ID NO: 19 | Sequence | Linkage | Motif | % inhibition (RTS3750) | SEQ ID NO |
|---|---|---|---|---|---|---|---|---|---|
| 672561 | 695 | n/a | n/a | n/a | CTCTGACCCTGATCTTCCAT | soooosssssssssssooss | 5-10-5 | 25 | 1056 |
| 625345 | 696 | n/a | n/a | n/a | ACTCTGACCCTGATCTTCCA | soooosssssssssssooss | 5-10-5 | 15 | 1494 |
| 655291 | 697 | n/a | n/a | n/a | TACTCTGACCCTGATCTTCC | soooosssssssssssooss | 5-10-5 | 18 | 629 |
| 688391 | 698 | n/a | n/a | n/a | ATACTCTGACCCTGATCTTC | soooosssssssssssooss | 5-10-5 | 40 | 1495 |
| 688392 | 699 | n/a | n/a | n/a | AATACTCTGACCCTGATCTT | soooosssssssssssooss | 5-10-5 | 8 | 1496 |
| 619423 | n/a | 13642 | 13681 | 0 | GCCATGATTTCTTGTCTGGG | soooosssssssssssooss | 5-10-5 | 77 | 383 |
| 655417 | n/a | 14089 | 14136 | 0 | GGAACTAACATGTAGGCACT | soooosssssssssssooss | 5-10-5 | 83 | 738 |
| 655420 | n/a | 14331 | 14378 | 0 | GCTGACACTGAACAGATACA | soooosssssssssssooss | 5-10-5 | 51 | 741 |
| 655422 | n/a | 14452 | 14499 | 0 | ATCATTTAATTAATGTATTT | soooosssssssssssooss | 5-10-5 | 33 | 743 |
| 671084 | n/a | 14316 | 14363 | 0 | ATACAGGACTAAAGTGCTTC | soooosssssssssssooss | 5-10-5 | 74 | 1055 |
| 688393 | n/a | 13641 | 13680 | 0 | CCATGATTTCTTGTCTGGGA | soooosssssssssssooss | 5-10-5 | 54 | 1497 |
| 688394 | n/a | 13643 | 13682 | 0 | GGCCATGATTTCTTGTCTGG | soooosssssssssssooss | 5-10-5 | 52 | 1498 |
| 688395 | n/a | 13644 | 13683 | 0 | GGGCCATGATTTCTTGTCTG | soooosssssssssssooss | 5-10-5 | 46 | 1499 |
| 688396 | n/a | 13731 | 13770 | 0 | ACTTAAGTTCATCTACAGTA | soooosssssssssssooss | 5-10-5 | 18 | 1500 |
| 688397 | n/a | 13792 | 13831 | 0 | TCCACTGCTGGATGGAAAAA | soooosssssssssssooss | 5-10-5 | 20 | 1501 |
| 688398 | n/a | 13968 | 14007 | 0 | ATATTATTTATCTTACTCAA | soooosssssssssssooss | 5-10-5 | 32 | 1502 |
| 688399 | n/a | 13982 | 14021 | 0 | GTTCTAAGTGCTTTATATTA | soooosssssssssssooss | 5-10-5 | 30 | 1503 |
| 688400 | n/a | 14090 | 14137 | 0 | AGGAACTAACATGTAGGCAC | soooosssssssssssooss | 5-10-5 | 87 | 1504 |
| 688401 | n/a | 14122 | 14169 | 0 | ATATAAGATAATACATGTAA | soooosssssssssssooss | 5-10-5 | 6 | 1505 |
| 688402 | n/a | 14243 | 14290 | 0 | CATCATGAGCCTAAAGGAAA | soooosssssssssssooss | 5-10-5 | 22 | 1506 |
| 688403 | n/a | 14244 | 14291 | 0 | CCATCATGAGCCTAAAGGAA | soooosssssssssssooss | 5-10-5 | 37 | 1507 |
| 688404 | n/a | 14300 | 14347 | 0 | CTTCTGATTCAAGCCATTAA | soooosssssssssssooss | 5-10-5 | 76 | 1508 |
| 688405 | n/a | 14302 | 14349 | 0 | TGCTTCTGATTCAAGCCATT | soooosssssssssssooss | 5-10-5 | 55 | 1509 |
| 688406 | n/a | 14303 | 14350 | 0 | GTGCTTCTGATTCAAGCCAT | soooosssssssssssooss | 5-10-5 | 50 | 1510 |
| 688407 | n/a | 14304 | 14351 | 0 | AGTGCTTCTGATTCAAGCCA | soooosssssssssssooss | 5-10-5 | 68 | 1511 |
| 688408 | n/a | 14305 | 14352 | 0 | AAGTGCTTCTGATTCAAGCC | soooosssssssssssooss | 5-10-5 | 41 | 1512 |
| 688409 | n/a | 14306 | 14353 | 0 | AAAGTGCTTCTGATTCAAGC | soooosssssssssssooss | 5-10-5 | 18 | 1513 |
| 688410 | n/a | 14307 | 14354 | 0 | TAAAGTGCTTCTGATTCAAG | soooosssssssssssooss | 5-10-5 | 29 | 1514 |
| 688411 | n/a | 14308 | 14355 | 0 | CTAAAGTGCTTCTGATTCAA | soooosssssssssssooss | 5-10-5 | 43 | 1515 |
| 688412 | n/a | 14309 | 14356 | 0 | ACTAAAGTGCTTCTGATTCA | soooosssssssssssooss | 5-10-5 | 33 | 1516 |
| 688413 | n/a | 14310 | 14357 | 0 | GACTAAAGTGCTTCTGATTC | soooosssssssssssooss | 5-10-5 | 49 | 1517 |
| 688414 | n/a | 14311 | 14358 | 0 | GGACTAAAGTGCTTCTGATT | soooosssssssssssooss | 5-10-5 | 49 | 1518 |
| 688415 | n/a | 14312 | 14359 | 0 | AGGACTAAAGTGCTTCTGAT | soooosssssssssssooss | 5-10-5 | 55 | 1519 |
| 688416 | n/a | 14313 | 14360 | 0 | CAGGACTAAAGTGCTTCTGA | soooosssssssssssooss | 5-10-5 | 71 | 1520 |
| 688417 | n/a | 14314 | 14361 | 0 | ACAGGACTAAAGTGCTTCTG | soooosssssssssssooss | 5-10-5 | 66 | 1521 |

TABLE 59-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Mismatches with SEQ ID NO: 19 | Sequence | Linkage | Motif | % inhibition (RTS3750) | SEQ ID NO |
|---|---|---|---|---|---|---|---|---|---|
| 688418 | n/a | 14315 | 14362 | 0 | TACAGGACTAAAGTGCTTCT | soooossssssssssssooss | 5-10-5 | 61 | 1522 |
| 688419 | n/a | 14317 | 14364 | 0 | GATACAGGACTAAAGTGCTT | soooossssssssssssooss | 5-10-5 | 76 | 1523 |
| 688420 | n/a | 14318 | 14365 | 0 | AGATACAGGACTAAAGTGCT | soooossssssssssssooss | 5-10-5 | 46 | 1524 |
| 688421 | n/a | 14319 | 14366 | 0 | CAGATACAGGACTAAAGTGC | soooossssssssssssooss | 5-10-5 | 53 | 1525 |
| 688422 | n/a | 14320 | 14367 | 0 | ACAGATACAGGACTAAAGTG | soooossssssssssssooss | 5-10-5 | 23 | 1526 |
| 688423 | n/a | 14321 | 14368 | 0 | AACAGATACAGGACTAAAGT | soooossssssssssssooss | 5-10-5 | 28 | 1527 |
| 688424 | n/a | 14322 | 14369 | 0 | GAACAGATACAGGACTAAAG | soooossssssssssssooss | 5-10-5 | 26 | 1528 |
| 688425 | n/a | 14323 | 14370 | 0 | TGAACAGATACAGGACTAAA | soooossssssssssssooss | 5-10-5 | 13 | 1529 |
| 688426 | n/a | 14324 | 14371 | 0 | CTGAACAGATACAGGACTAA | soooossssssssssssooss | 5-10-5 | 27 | 1530 |
| 688427 | n/a | 14325 | 14372 | 0 | ACTGAACAGATACAGGACTA | soooossssssssssssooss | 5-10-5 | 37 | 1531 |
| 688428 | n/a | 14326 | 14373 | 0 | CACTGAACAGATACAGGACT | soooossssssssssssooss | 5-10-5 | 35 | 1532 |
| 688429 | n/a | 14327 | 14374 | 0 | ACACTGAACAGATACAGGAC | soooossssssssssssooss | 5-10-5 | 28 | 1533 |
| 688430 | n/a | 14328 | 14375 | 0 | GACACTGAACAGATACAGGA | soooossssssssssssooss | 5-10-5 | 39 | 1534 |
| 688431 | n/a | 14329 | 14376 | 0 | TGACACTGAACAGATACAGG | soooossssssssssssooss | 5-10-5 | 38 | 1535 |
| 688432 | n/a | 14330 | 14377 | 0 | CTGACACTGAACAGATACAG | soooossssssssssssooss | 5-10-5 | 64 | 1536 |
| 688433 | n/a | 14332 | 14379 | 0 | GGCTGACACTGAACAGATAC | soooossssssssssssooss | 5-10-5 | 50 | 1537 |
| 688434 | n/a | 14333 | 14380 | 0 | AGGCTGACACTGAACAGATA | soooossssssssssssooss | 5-10-5 | 18 | 1538 |
| 688435 | n/a | 14334 | 14381 | 0 | AAGGCTGACACTGAACAGAT | soooossssssssssssooss | 5-10-5 | 45 | 1539 |
| 688436 | n/a | 14335 | 14382 | 0 | AAAGGCTGACACTGAACAGA | soooossssssssssssooss | 5-10-5 | 28 | 1540 |
| 688437 | n/a | 14336 | 14383 | 0 | GAAAGGCTGACACTGAACAG | soooossssssssssssooss | 5-10-5 | 18 | 1541 |
| 688438 | n/a | 14337 | 14384 | 0 | TGAAAGGCTGACACTGAACA | soooossssssssssssooss | 5-10-5 | 23 | 1542 |
| 688439 | n/a | 14358 | 14405 | 0 | AATGGGATTTAAAATGATGT | soooossssssssssssooss | 5-10-5 | 26 | 1543 |
| 688440 | n/a | 14359 | 14406 | 0 | AAATGGGATTTAAAATGATG | soooossssssssssssooss | 5-10-5 | 30 | 1544 |
| 688441 | n/a | 14360 | 14407 | 0 | CAAATGGGATTTAAAATGAT | soooossssssssssssooss | 5-10-5 | 16 | 1545 |

TABLE 60

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 576816 | 310 | 7990 | 8043 | GCCTTACTCTAGGACCAAGA | sssssssssssssssssss | 5-10-5 | 62 | 20 |
| 619420 | 310 | 7990 | 8043 | GCCTTACTCTAGGACCAAGA | soooossssssssssssooss | 5-10-5 | 75 | 20 |
| 688078 | 313 | 7993 | 8046 | TGCCTTACTCTAGGACCA | sooossssssssssooss | 5-8-5 | 67 | 1130 |
| 688237 | 485 | 8165 | 8218 | ATCAAAGATTAATGAAAC | sooosssssssssssooss | 5-8-5 | 42 | 1289 |

TABLE 60-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688238 | 486 | 8166 | 8219 | CATCAAAGATTAATGAAA | sooossssssssssooss | 5-8-5 | 0 | 1290 |
| 688239 | 487 | 8167 | 8220 | CCATCAAAGATTAATGAA | sooossssssssssooss | 5-8-5 | 39 | 1291 |
| 688240 | 488 | 8168 | 8221 | TCCATCAAAGATTAATGA | sooossssssssssooss | 5-8-5 | 45 | 1292 |
| 688241 | 489 | 8169 | 8222 | TTCCATCAAAGATTAATG | sooossssssssssooss | 5-8-5 | 0 | 1293 |
| 688242 | 490 | 8170 | 8223 | TTTCCATCAAAGATTAAT | sooossssssssssooss | 5-8-5 | 53 | 1294 |
| 688243 | 491 | 8171 | 8224 | GTTTCCATCAAAGATTAA | sooossssssssssooss | 5-8-5 | 46 | 1295 |
| 688244 | 492 | 8172 | 8225 | AGTTTCCATCAAAGATTA | sooossssssssssooss | 5-8-5 | 43 | 1296 |
| 688245 | 493 | 8173 | 8226 | CAGTTTCCATCAAAGATT | sooossssssssssooss | 5-8-5 | 0 | 1297 |
| 688246 | 494 | 8174 | 8227 | CCAGTTTCCATCAAAGAT | sooossssssssssooss | 5-8-5 | 44 | 1298 |
| 688247 | 495 | 8175 | 8228 | TCCAGTTTCCATCAAAGA | sooossssssssssooss | 5-8-5 | 46 | 1299 |
| 688248 | 496 | 8176 | 8229 | TTCCAGTTTCCATCAAAG | sooossssssssssooss | 5-8-5 | 58 | 1300 |
| 688249 | 497 | 8177 | 8230 | ATTCCAGTTTCCATCAAA | sooossssssssssooss | 5-8-5 | 46 | 1301 |
| 688250 | 498 | 8178 | 8231 | CATTCCAGTTTCCATCAA | sooossssssssssooss | 5-8-5 | 50 | 1302 |
| 688251 | 499 | 8179 | 8232 | CCATTCCAGTTTCCATCA | sooossssssssssooss | 5-8-5 | 58 | 1303 |
| 688252 | 500 | 8180 | 8233 | CCCATTCCAGTTTCCATC | sooossssssssssooss | 5-8-5 | 66 | 1304 |
| 688253 | 501 | 8181 | 8234 | CCCCATTCCAGTTTCCAT | sooossssssssssooss | 5-8-5 | 59 | 1305 |
| 688254 | 502 | 8182 | 8235 | TCCCCATTCCAGTTTCCA | sooossssssssssooss | 5-8-5 | 52 | 1306 |
| 688255 | 503 | 8183 | 8236 | ATCCCCATTCCAGTTTCC | sooossssssssssooss | 5-8-5 | 61 | 1307 |
| 688256 | 504 | 8184 | 8237 | GATCCCCATTCCAGTTTC | sooossssssssssooss | 5-8-5 | 50 | 1308 |
| 688257 | 505 | 8185 | 8238 | CGATCCCCATTCCAGTTT | sooossssssssssooss | 5-8-5 | 48 | 1309 |
| 688258 | 506 | 8186 | 8239 | GCGATCCCCATTCCAGTT | sooossssssssssooss | 5-8-5 | 44 | 1310 |
| 688259 | 507 | 8187 | 8240 | TGCGATCCCCATTCCAGT | sooossssssssssooss | 5-8-5 | 49 | 1311 |
| 688260 | 508 | 8188 | 8241 | CTGCGATCCCCATTCCAG | sooossssssssssooss | 5-8-5 | 70 | 1312 |
| 688261 | 509 | 8189 | 8242 | GCTGCGATCCCCATTCCA | sooossssssssssooss | 5-8-5 | 72 | 1313 |
| 688262 | 510 | 8190 | 8243 | TGCTGCGATCCCCATTCC | sooossssssssssooss | 5-8-5 | 47 | 1314 |
| 688263 | 511 | 8191 | 8244 | GTGCTGCGATCCCCATTC | sooossssssssssooss | 5-8-5 | 0 | 1315 |
| 688264 | 512 | 8192 | 8245 | TGTGCTGCGATCCCCATT | sooossssssssssooss | 5-8-5 | 56 | 1316 |
| 688265 | 513 | 8193 | 8246 | ATGTGCTGCGATCCCCAT | sooossssssssssooss | 5-8-5 | 65 | 1317 |
| 688266 | 514 | 8194 | 8247 | TATGTGCTGCGATCCCCA | sooossssssssssooss | 5-8-5 | 61 | 1318 |
| 688267 | 533 | 8213 | 8266 | AAGTATAATTGATAGTCC | sooossssssssssooss | 5-8-5 | 47 | 1319 |
| 688268 | 534 | 8214 | 8267 | GAAGTATAATTGATAGTC | sooossssssssssooss | 5-8-5 | 48 | 1320 |
| 688269 | 535 | 8215 | 8268 | GGAAGTATAATTGATAGT | sooossssssssssooss | 5-8-5 | 35 | 1321 |
| 688270 | 536 | 8216 | 8269 | TGGAAGTATAATTGATAG | sooossssssssssooss | 5-8-5 | 41 | 1322 |
| 688271 | 537 | 8217 | 8270 | GTGGAAGTATAATTGATA | sooossssssssssooss | 5-8-5 | 48 | 1323 |
| 688272 | 538 | 8218 | 8271 | TGTGGAAGTATAATTGAT | sooossssssssssooss | 5-8-5 | 42 | 1324 |

TABLE 60-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688273 | 539 | 8219 | 8272 | CTGTGGAAGTATAATTGA | sooossssssssssooss | 5-8-5 | 32 | 1325 |
| 688274 | 540 | 8220 | 8273 | TCTGTGGAAGTATAATTG | sooossssssssssooss | 5-8-5 | 0 | 1326 |
| 688275 | 541 | 8221 | 8274 | GTCTGTGGAAGTATAATT | sooossssssssssooss | 5-8-5 | 0 | 1327 |
| 688276 | 542 | 8222 | 8275 | TGTCTGTGGAAGTATAAT | sooossssssssssooss | 5-8-5 | 65 | 1328 |
| 688277 | 543 | 8223 | 8276 | CTGTCTGTGGAAGTATAA | sooossssssssssooss | 5-8-5 | 0 | 1329 |
| 688278 | 544 | 8224 | 8277 | TCTGTCTGTGGAAGTATA | sooossssssssssooss | 5-8-5 | 62 | 1330 |
| 688279 | 545 | 8225 | 8278 | TTCTGTCTGTGGAAGTAT | sooossssssssssooss | 5-8-5 | 55 | 1331 |
| 688280 | 546 | 8226 | 8279 | GTTCTGTCTGTGGAAGTA | sooossssssssssooss | 5-8-5 | 77 | 1332 |
| 688281 | 547 | 8227 | 8280 | AGTTCTGTCTGTGGAAGT | sooossssssssssooss | 5-8-5 | 63 | 1333 |
| 688282 | 548 | 8228 | 8281 | AAGTTCTGTCTGTGGAAG | sooossssssssssooss | 5-8-5 | 49 | 1334 |
| 688283 | 549 | 8229 | 8282 | TAAGTTCTGTCTGTGGAA | sooossssssssssooss | 5-8-5 | 0 | 1335 |
| 688284 | 550 | 8230 | 8283 | CTAAGTTCTGTCTGTGGA | sooossssssssssooss | 5-8-5 | 54 | 1336 |
| 688285 | 551 | 8231 | 8284 | ACTAAGTTCTGTCTGTGG | sooossssssssssooss | 5-8-5 | 69 | 1337 |
| 688286 | 552 | 8232 | 8285 | AACTAAGTTCTGTCTGTG | sooossssssssssooss | 5-8-5 | 65 | 1338 |
| 688287 | 553 | 8233 | 8286 | AAACTAAGTTCTGTCTGT | sooossssssssssooss | 5-8-5 | 40 | 1339 |
| 688288 | 554 | 8234 | 8287 | GAAACTAAGTTCTGTCTG | sooossssssssssooss | 5-8-5 | 36 | 1340 |
| 688289 | 555 | 8235 | 8288 | AGAAACTAAGTTCTGTCT | sooossssssssssooss | 5-8-5 | 47 | 1341 |
| 688290 | 556 | 8236 | 8289 | TAGAAACTAAGTTCTGTC | sooossssssssssooss | 5-8-5 | 48 | 1342 |
| 688291 | 557 | 8237 | 8290 | GTAGAAACTAAGTTCTGT | sooossssssssssooss | 5-8-5 | 45 | 1343 |
| 688292 | 558 | 8238 | 8291 | GGTAGAAACTAAGTTCTG | sooossssssssssooss | 5-8-5 | 44 | 1344 |
| 688293 | 559 | 8239 | 8292 | AGGTAGAAACTAAGTTCT | sooossssssssssooss | 5-8-5 | 58 | 1345 |
| 688294 | 560 | 8240 | 8293 | GAGGTAGAAACTAAGTTC | sooossssssssssooss | 5-8-5 | 45 | 1346 |
| 688295 | 561 | 8241 | 8294 | GGAGGTAGAAACTAAGTT | sooossssssssssooss | 5-8-5 | 47 | 1347 |
| 688296 | 562 | 8242 | 8295 | GGGAGGTAGAAACTAAGT | sooossssssssssooss | 5-8-5 | 44 | 1348 |
| 688297 | 563 | 8243 | 8296 | TGGGAGGTAGAAACTAAG | sooossssssssssooss | 5-8-5 | 47 | 1349 |
| 688298 | 564 | 8244 | 8297 | GTGGGAGGTAGAAACTAA | sooossssssssssooss | 5-8-5 | 53 | 1350 |
| 688299 | 565 | 8245 | 8298 | AGTGGGAGGTAGAAACTA | sooossssssssssooss | 5-8-5 | 43 | 1351 |
| 688300 | 566 | 8246 | 8299 | AAGTGGGAGGTAGAAACT | sooossssssssssooss | 5-8-5 | 36 | 1352 |
| 688301 | 567 | 8247 | 8300 | GAAGTGGGAGGTAGAAAC | sooossssssssssooss | 5-8-5 | 41 | 1353 |
| 688302 | 568 | 8248 | 8301 | TGAAGTGGGAGGTAGAAA | sooossssssssssooss | 5-8-5 | 0 | 1354 |
| 688303 | 569 | 8249 | 8302 | ATGAAGTGGGAGGTAGAA | sooossssssssssooss | 5-8-5 | 41 | 1355 |
| 688304 | 570 | 8250 | 8303 | TATGAAGTGGGAGGTAGA | sooossssssssssooss | 5-8-5 | 31 | 1356 |
| 688305 | 571 | 8251 | 8304 | CTATGAAGTGGGAGGTAG | sooossssssssssooss | 5-8-5 | 46 | 1357 |
| 688306 | 572 | 8252 | 8305 | TCTATGAAGTGGGAGGTA | sooossssssssssooss | 5-8-5 | 30 | 1358 |
| 688307 | 573 | 8253 | 8306 | CTCTATGAAGTGGGAGGT | sooossssssssssooss | 5-8-5 | 54 | 1359 |

TABLE 60-continued

Percent inhibition of the C9ORF72 mRNA levels compared to PBS control by antisense oligonucleotides targeting SEQ ID NOs: 1, 2 and 19

| ISIS NO | SEQ ID NO: 1 Start Site | SEQ ID NO: 2 Start Site | SEQ ID NO: 19 Start Site | Sequence | Linkage | Motif | % inhibition (RTS3750) | SEQ ID NO |
|---|---|---|---|---|---|---|---|---|
| 688308 | 574 | 8254 | 8307 | ACTCTATGAAGTGGGAGG | sooosssssssssooss | 5-8-5 | 50 | 1360 |
| 688309 | 575 | 8255 | 8308 | CACTCTATGAAGTGGGAG | sooosssssssssooss | 5-8-5 | 60 | 1361 |
| 688310 | 576 | 8256 | 8309 | ACACTCTATGAAGTGGGA | sooosssssssssooss | 5-8-5 | 56 | 1362 |
| 688311 | 577 | 8257 | 8310 | CACACTCTATGAAGTGGG | sooosssssssssooss | 5-8-5 | 57 | 1363 |
| 688312 | 578 | 8258 | 8311 | ACACACTCTATGAAGTGG | sooosssssssssooss | 5-8-5 | 41 | 1364 |
| 688313 | 579 | 8259 | 8312 | CACACACTCTATGAAGTG | sooosssssssssooss | 5-8-5 | 38 | 1365 |

Example 13: Dose-Dependent Antisense Inhibition of Human C9ORF72 mRNA in HepG2 Cells Antisense oligonucleotides from the study described above exhibiting significant in vitro inhibition of C9ORF72 mRNA were selected and tested at various doses in HepG2 cells. ISIS 619420 described in Example 2 hereinabove was also tested. The antisense oligonucleotides were tested in a series of experiments that had similar culture conditions. The results for each experiment are presented in separate tables shown below. Cells were plated at a density of 20,000 cells per well and transfected using electroporation with 0.33 µM, 1.00 µM, 3.00 µM, or 9.00 µM concentrations of antisense oligonucleotide. After a treatment period of approximately 16 hours, RNA was isolated from the cells and C9ORF72 mRNA levels were measured by quantitative real-time PCR. Human primer probe set RTS3750 was used to measure the total C9ORF72 mRNA levels. C9ORF72 mRNA levels were adjusted according to total RNA content, as measured by RIBOGREEN®. Results are presented as percent inhibition of C9ORF72 levels, relative to untreated control cells.

The half maximal inhibitory concentration ($IC_{50}$) of each oligonucleotide is also presented in the Tables below. As shown in the Tables below, total C9ORF72 mRNA levels were reduced in a dose-dependent manner in some of the antisense oligonucleotide treated cells.

TABLE 61

Dose-dependent inhibition of total C9ORF72 mRNA levels in HepG2 cells

| ISIS No | 0.33 µM | 1.00 µM | 3.00 µM | 9.00 µM | $IC_{50}$ (µM) |
|---|---|---|---|---|---|
| 619411 | 55 | 68 | 89 | 90 | <0.3 |
| 619420 | 41 | 74 | 87 | 95 | 0.4 |
| 655178 | 45 | 63 | 84 | 92 | 0.4 |
| 687962 | 48 | 61 | 83 | 86 | 0.4 |
| 687963 | 34 | 53 | 77 | 76 | 0.8 |
| 687978 | 50 | 60 | 70 | 65 | <0.3 |
| 688077 | 49 | 63 | 70 | 86 | 0.3 |
| 688088 | 51 | 72 | 86 | 92 | <0.3 |
| 688089 | 51 | 66 | 76 | 85 | <0.3 |
| 688099 | 41 | 66 | 73 | 85 | 0.5 |
| 688100 | 44 | 64 | 79 | 86 | 0.4 |
| 688101 | 53 | 64 | 77 | 74 | <0.3 |
| 688102 | 29 | 43 | 52 | 62 | 2.4 |
| 688172 | 31 | 47 | 77 | 88 | 1.0 |

TABLE 61-continued

Dose-dependent inhibition of total C9ORF72 mRNA levels in HepG2 cells

| ISIS No | 0.33 µM | 1.00 µM | 3.00 µM | 9.00 µM | $IC_{50}$ (µM) |
|---|---|---|---|---|---|
| 688261 | 35 | 41 | 50 | 49 | 6.7 |
| 688347 | 41 | 60 | 79 | 89 | 0.5 |
| 688348 | 57 | 61 | 85 | 92 | <0.3 |
| 688352 | 51 | 64 | 71 | 75 | <0.3 |

TABLE 62

Dose-dependent inhibition of total C9ORF72 mRNA levels in HepG2 cells

| ISIS No | 0.33 µM | 1.00 µM | 3.00 µM | 9.00 µM | $IC_{50}$ (µM) |
|---|---|---|---|---|---|
| 619412 | 48 | 69 | 83 | 87 | 0.3 |
| 619413 | 34 | 33 | 47 | 85 | 1.8 |
| 619420 | 53 | 72 | 80 | 84 | <0.3 |
| 655173 | 48 | 62 | 76 | 89 | 0.4 |
| 655174 | 38 | 59 | 82 | 79 | 0.6 |
| 655179 | 47 | 68 | 83 | 80 | 0.3 |
| 655186 | 40 | 53 | 82 | 85 | 0.6 |
| 655203 | 28 | 61 | 87 | 79 | 0.7 |
| 655230 | 36 | 59 | 77 | 89 | 0.7 |
| 655231 | 49 | 69 | 78 | 81 | <0.3 |
| 688349 | 40 | 63 | 84 | 79 | 0.5 |
| 688351 | 47 | 74 | 81 | 88 | 0.3 |
| 688355 | 50 | 56 | 79 | 83 | 0.4 |
| 688356 | 47 | 64 | 78 | 85 | 0.3 |
| 688364 | 29 | 44 | 57 | 78 | 1.5 |
| 688374 | 38 | 50 | 79 | 70 | 0.8 |
| 688378 | 41 | 67 | 85 | 87 | 0.4 |
| 688379 | 39 | 42 | 83 | 83 | 0.8 |
| 688380 | 50 | 62 | 68 | 82 | 0.3 |

TABLE 63

Dose-dependent inhibition of total C9ORF72 mRNA levels in HepG2 cells

| ISIS No | 0.33 µM | 1.00 µM | 3.00 µM | 9.00 µM | $IC_{50}$ (µM) |
|---|---|---|---|---|---|
| 619420 | 37 | 39 | 87 | 92 | 0.3 |
| 619423 | 55 | 73 | 84 | 82 | <0.3 |

TABLE 63-continued

Dose-dependent inhibition of total C9ORF72 mRNA levels in HepG2 cells

| ISIS No | 0.33 µM | 1.00 µM | 3.00 µM | 9.00 µM | IC$_{50}$ (µM) |
|---|---|---|---|---|---|
| 655173 | 53 | 83 | 82 | 94 | <0.3 |
| 655233 | 34 | 28 | 41 | 79 | 2.4 |
| 655290 | 16 | 27 | 68 | 78 | 2.0 |
| 655417 | 73 | 42 | 87 | 84 | <0.3 |
| 688022 | 51 | 71 | 80 | 76 | <0.3 |
| 688360 | 32 | 63 | 85 | 72 | 0.6 |
| 688361 | 46 | 70 | 34 | 85 | 0.5 |
| 688382 | 42 | 58 | 79 | 81 | 0.5 |
| 688383 | 43 | 63 | 80 | 87 | 0.5 |
| 688385 | 41 | 60 | 82 | 84 | 0.5 |
| 688400 | 61 | 81 | 85 | 85 | <0.3 |
| 688404 | 38 | 62 | 78 | 81 | 0.6 |
| 688407 | 37 | 53 | 71 | 85 | 0.8 |
| 688415 | 43 | 18 | 79 | 73 | 1.3 |
| 688416 | 48 | 74 | 73 | 81 | <0.3 |
| 688417 | 33 | 61 | 67 | 74 | 0.8 |
| 688418 | 34 | 55 | 77 | 82 | 0.8 |

Example 14: Tolerability of Antisense Oligonucleotides Targeting Human C9ORF72 in Mice Antisense oligonucleotides from the Examples above were tested in a standard mouse model to assess tolerability of the oligonucleotides. The rodents were assessed by standard FOB assays and measurement of GFAP and/or AIF expression levels.

Groups of mice were administered a single ICV dose of 700 µg of ISIS oligonucleotides.

Mouse FOB Assay

At 3 hours, one week, 2 weeks, 4 weeks, 6 weeks, and 8 weeks post injection, each mouse was evaluated according to 7 different criteria. The 7 criteria are (1) the mouse was bright, alert, and responsive; (2) the mouse was standing or hunched without stimuli; (3) the mouse showed any movement without stimuli (4) the mouse demonstrated forward movement after it was lifted; (5) the mouse demonstrated any movement after it was lifted; (6) the mouse responded to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 700 µg ICV dose, and met all other criteria, it would get a summed score of 0. If another mouse was not bright, alert, and responsive 3 hours after the 700 µg ICV dose but met all other criteria, it would receive a score of 1.

The results are presented as individual scores for each mouse in each group. The expression levels of GFAP and AIF1 in the thoracic spinal cord of the mice were assessed by qRT-PCR after 8 weeks.

Study 1 with cEt Oligonucleotides

The oligonucleotides tested in this study are presented in the Table below. The FOB scores are given below.

TABLE 64

Antisense oligonucleotides targeted to SEQ ID NO: 2

| ISIS No | Start Site |
|---|---|
| 672744 | 1335 |
| 672747 | 1338 |
| 672774 | 1368 |
| 672775 | 1369 |
| 672778 | 1372 |
| 672779 | 1373 |
| 672831 | 1440 |
| 672908 | 1349 |
| 672909 | 1350 |
| 672919 | 1360 |
| 672924 | 1368 |
| 672925 | 1369 |
| 672927 | 1371 |
| 672928 | 1372 |
| 672929 | 1373 |
| 672976 | 1435 |
| 672980 | 1439 |
| 672981 | 1440 |

TABLE 65

FOB scores in C57/B16 mice

|  | 3 hr |
|---|---|
| PBS | 0, 0, 0, 0 |
| 672744 | 7, 7, 7, 7 |
| 672747 | 7, 7, 7, 7 |
| 672774 | 5, 5, 5, 5 |
| 672775 | 5, 7, 5, 7 |
| 672778 | 1, 7, 1, 1 |
| 672779 | 7, 2, 5, 7 |
| 672831 | 7, 7, 7, 7 |
| 672908 | 6, 1, 1, 1 |
| 672909 | 6, 6, 6, 4 |
| 672919 | 5, 5, 5, 5 |
| 672924 | 4, 6, 7, 6 |
| 672925 | 4, 4, 4, 4 |
| 672927 | 0, 0, 0, 0 |
| 672928 | 0, 0, 0, 0 |
| 672929 | 7, 7, 7, 7 |
| 672976 | 5, 7, 7, 7 |
| 672980 | 2, 2, 2, 2 |
| 672981 | 6, 6, 6, 6 |

Study 2 with cEt Oligonucleotides

The oligonucleotides tested in this study are presented in the Table below. The FOB scores are given below.

TABLE 66

Antisense oligonucleotides targeted to SEQ ID NO: 2

| ISIS No | Start Site of SEQ ID NO: 2 |
|---|---|
| 672982 | 1441 |
| 672983 | 1442 |
| 672984 | 1443 |
| 672985 | 1444 |
| 673021 | 1510 |
| 673023 | 1512 |
| 673026 | 1515 |
| 673036 | 1327 |
| 673047 | 1338 |
| 673057 | 1348 |
| 673058 | 1349 |
| 673067 | 1358 |

TABLE 66-continued

Antisense oligonucleotides targeted to SEQ ID NO: 2

| ISIS No | Start Site of SEQ ID NO: 2 |
|---|---|
| 673068 | 1359 |
| 673074 | 1368 |
| 673079 | 1373 |
| 673082 | 1376 |
| 673088 | 1396 |
| 673125 | 1434 |
| 673126 | 1435 |
| 673127 | 1436 |
| 672832 | 1441 |

TABLE 67

FOB scores in C57/B16 mice

| | 3 hr |
|---|---|
| PBS | 0, 0, 0, 0 |
| 672982 | 7, 7, 7, 7 |
| 672983 | 5, 7, 5, 7 |
| 672984 | 4, 6, 6, 6 |
| 672985 | 5, 4, 4, 4 |
| 673021 | 5, 5, 5, 5 |
| 673023 | 7, 7, 7, 7 |
| 673026 | 0, 0, 0, 0 |
| 673036 | 7, 7, 7, 7 |
| 673047 | 5, 5, 5, 6 |
| 673057 | 5, 0, 5, 7 |
| 673058 | 3, 3, 3, 3 |
| 673067 | 7, 0, 0, 6 |
| 673068 | 6, 6, 6, 6 |
| 673074 | 1, 1, 1, 1 |
| 673079 | 6, 6, 7, 6 |
| 673082 | 1, 3, 0, 3 |
| 673088 | 6, 6, 6, 6 |
| 673125 | 0, 0, 0, 0 |
| 673126 | 0, 0, 0, 0 |
| 673127 | 7, 7, 7, 7 |
| 672832 | 6, 6, 6, 7 |

Study 3 with cEt Oligonucleotides

The oligonucleotides tested in this study are presented in the Table below. The FOB scores are given below.

TABLE 68

Antisense oligonucleotides targeted to SEQ ID NO: 2

| ISIS No | Start Site of SEQ ID NO: 2 |
|---|---|
| 673131 | 1440 |
| 673132 | 1441 |
| 673133 | 1442 |
| 673134 | 1443 |
| 673135 | 1444 |
| 673193 | 1334 |
| 673203 | 1344 |
| 673204 | 1345 |
| 673224 | 1368 |
| 673225 | 1369 |
| 673226 | 1370 |
| 673228 | 1372 |
| 673229 | 1373 |

TABLE 68-continued

Antisense oligonucleotides targeted to SEQ ID NO: 2

| ISIS No | Start Site of SEQ ID NO: 2 |
|---|---|
| 673275 | 1434 |
| 673276 | 1435 |
| 673280 | 1439 |

TABLE 69

FOB scores in C57/B16 mice

| | 3 hr |
|---|---|
| PBS | 0, 0, 0, 0 |
| 673131 | 4, 4, 4, 5 |
| 673132 | 4, 4, 4, 4 |
| 673133 | 4, 3, 4, 3 |
| 673134 | 5, 6, 3, 6 |
| 673135 | 5, 3, 4, 5 |
| 673193 | 6, 6, 6, 6 |
| 673203 | 4, 3, 4, 4 |
| 673204 | 2, 3, 2, 2 |
| 673224 | 5, 5, 5, 5 |
| 673225 | 1, 2, 2, 2 |
| 673226 | 1, 1, 1, 1 |
| 673228 | 2, 2, 2, 2 |
| 673229 | 6, 6, 6, 6 |
| 673275 | 1, 1, 1, 1 |
| 673276 | 3, 3, 3, 3 |
| 673280 | 1, 1, 1, 1 |

Study 4 with cEt Oligonucleotides

The oligonucleotides tested in this study are presented in the Table below. The FOB scores are given below.

TABLE 70

Antisense oligonucleotides targeted to SEQ ID NO: 2

| ISIS No | Start Site of SEQ ID NO: 2 |
|---|---|
| 673128 | 1437 |
| 673130 | 1439 |
| 673281 | 1440 |
| 673282 | 1441 |
| 673283 | 1442 |
| 673284 | 1443 |
| 673285 | 1444 |
| 673323 | 1512 |
| 673331 | 1520 |
| 673332 | 1521 |
| 673374 | 1368 |
| 673375 | 1369 |
| 673377 | 1371 |
| 673378 | 1372 |
| 673379 | 1373 |
| 673430 | 1439 |
| 673431 | 1440 |
| 673432 | 1441 |
| 673434 | 1443 |

TABLE 71

FOB scores in C57/B16 mice

| | 3 hr |
|---|---|
| PBS | 0, 0, 0, 0 |
| 673128 | 0, 0, 0, 0 |
| 673130 | 0, 0, 0, 0 |
| 673281 | 7, 7, 7, 7 |
| 673282 | 7, 7, 7, 7 |
| 673283 | 5, 6, 6, 7 |
| 673284 | 5, 0, 0, 0 |
| 673285 | 3, 3, 3, 3 |
| 673323 | 7, 7, 7, 7 |
| 673331 | 7, 7, 7, 7 |
| 673332 | 7, 7, 7, 7 |
| 673374 | 7, 7, 7, 7 |
| 673375 | 2, 3, 2, 3 |
| 673377 | 0, 0, 0, 0 |
| 673378 | 1, 1, 1, 1 |
| 673379 | 4, 6, 6, 7 |
| 673430 | 7, 7, 7, 7 |
| 673431 | 7, 7, 7, 7 |
| 673432 | 7, 6, 6, 7 |
| 673434 | 7, 7, 7, 7 |

Study 1 with MOE Oligonucleotides

The oligonucleotides tested in this study are presented in the Table below. The FOB scores are given below.

TABLE 72

Antisense oligonucleotides targeted to SEQ ID NO: 2

| ISIS No | Start Site of SEQ ID NO: 2 |
|---|---|
| 619253 | 1406 |
| 619293 | 1446 |
| 619322 | 1481 |
| 619352 | 1519 |
| 619353 | 1520 |
| 619410 | 7840 |
| 619414 | 8033 |
| 619420 | 7990 |
| 619421 | 28251 |
| 619422 | 3452 |
| 619423 | 13642 |
| 653222 | 1553 |
| 653223 | 5325 |
| 655016 | 1458 |
| 655017 | 1459 |

TABLE 73

FOB scores in C57/B16 mice

| | 3 hrs |
|---|---|
| PBS | 0,0,0,0 |
| 619253 | 3,3,7,7 |
| 619293 | 6,4,2,4 |
| 619322 | 2,2,2,4 |
| 619352 | 0,0,7,0 |
| 619353 | 6,4,7,6 |
| 619410 | 7,3,3,3 |
| 619414 | 6,6,6,6 |
| 619420 | 7,7,7,7 |
| 619421 | 1,1,1,1 |
| 619422 | 5,5,5,5 |
| 619423 | 6,6,6,6 |
| 653222 | 3,3,3,3 |
| 653223 | 1,1,7,1 |
| 655016 | 5,5,3,3 |
| 655017 | 0,0,0,0 |

Study 2 with MOE Oligonucleotides

The oligonucleotides tested in this study are presented in the Table below. The FOB scores are given below.

TABLE 74

Antisense oligonucleotides targeted to SEQ ID NO: 2

| ISIS No | Start Site of SEQ ID NO: 2 |
|---|---|
| 619173 | 1326 |
| 619174 | 1327 |
| 619178 | 1331 |
| 619179 | 1332 |
| 619180 | 1333 |
| 619181 | 1334 |
| 619182 | 1335 |
| 619185 | 1338 |
| 619186 | 1339 |
| 619187 | 1340 |
| 619191 | 1344 |
| 619201 | 1354 |
| 619202 | 1355 |
| 619203 | 1356 |
| 619216 | 1369 |
| 619217 | 1370 |

TABLE 75

FOB scores in C57/B16 mice

| | 3 hrs |
|---|---|
| PBS | 0,0,0,0 |
| 619173 | 7,7,7,7 |
| 619174 | 7,7,7,7 |
| 619178 | 7,7,7,7 |
| 619179 | 7,7,7,7 |
| 619180 | 7,7,7,7 |
| 619181 | 7,7,7,7 |
| 619182 | 7,7,7,7 |
| 619185 | 7,6,6,7 |
| 619186 | 6,6,6,7 |
| 619187 | 5,7,5,7 |
| 619191 | 5,5,3,5 |
| 619201 | 3,3,3,1 |
| 619202 | 6,6,6,6 |
| 619203 | 5,1,5,5 |
| 619216 | 4,4,4,4 |
| 619217 | 2,2,2,2 |

Study 3 with MOE Oligonucleotides

The oligonucleotides tested in this study are presented in the Table below. The FOB scores are given below.

TABLE 76

Antisense oligonucleotides targeted to SEQ ID NO: 2

| ISIS No | Start Site of SEQ ID NO: 2 |
|---|---|
| 619218 | 1371 |
| 619245 | 1398 |
| 619246 | 1399 |
| 619247 | 1400 |
| 619251 | 1404 |
| 619252 | 1405 |
| 619259 | 1412 |
| 619260 | 1413 |
| 619276 | 1429 |
| 619278 | 1431 |

TABLE 76-continued

Antisense oligonucleotides targeted to SEQ ID NO: 2

| ISIS No | Start Site of SEQ ID NO: 2 |
|---|---|
| 619280 | 1433 |
| 619284 | 1437 |
| 619292 | 1445 |
| 619297 | 1450 |
| 619298 | 1451 |
| 619307 | 1466 |

TABLE 77

FOB scores in C57/B16 mice

| | 3 hrs |
|---|---|
| PBS | 0,0,0,0 |
| 619218 | 4,2,7,7 |
| 619245 | 4,4,4,4 |
| 619246 | 4,5,5,4 |
| 619247 | 1,1,1,1 |
| 619251 | 4,7,4,4 |
| 619252 | 6,6,6,0 |
| 619259 | 6,6,4,5 |
| 619260 | 4,4,4,4 |
| 619276 | 3,3,4,4 |
| 619278 | 4,7,2,7 |
| 619280 | 7,7,7,7 |
| 619284 | 0,0,0,0 |
| 619292 | 6,5,5,5 |
| 619297 | 7,4,4,4 |
| 619298 | 0,0,0,0 |
| 619307 | 0,0,0,0 |

Study 4 with MOE Oligonucleotides

The oligonucleotides tested in this study are presented in the Table below. The FOB scores are given below.

TABLE 78

Antisense oligonucleotides targeted to SEQ ID NO: 2

| ISIS No | Start Site of SEQ ID NO: 2 |
|---|---|
| 619266 | 1419 |
| 619268 | 1421 |
| 619316 | 1475 |
| 619317 | 1476 |
| 619336 | 1503 |
| 619337 | 1504 |
| 619338 | 1505 |
| 619339 | 1506 |
| 619341 | 1508 |
| 619342 | 1509 |
| 619343 | 1510 |
| 619344 | 1511 |
| 619346 | 1513 |
| 619350 | 1517 |
| 619351 | 1518 |
| 619413 | 8020 |

TABLE 79

FOB scores in C57/B16 mice

| | 3 hrs |
|---|---|
| PBS | 0,0,0,0 |
| 619266 | 2,2,2,2 |
| 619268 | 6,6,7,7 |
| 619316 | 5,5,5,7 |
| 619317 | 2,3,3,4 |
| 619336 | 1,1,1,7 |
| 619338 | 0,0,7,7 |
| 619339 | 0,5,7,7 |
| 619341 | 7,7,7,7 |
| 619342 | 6,6,6,6 |
| 619343 | 6,6,6,6 |
| 619344 | 7,7,7,7 |
| 619346 | 5,5,7,7 |
| 619350 | 6,6,7,7 |
| 619351 | 6,6,7,7 |
| 619413 | 7,6,7,6 |

Example 15: Tolerability of Antisense Oligonucleotides Targeting Human C9ORF72 in Rats Antisense oligonucleotides from the Examples above were tested in a standard rat model to assess tolerability of the oligonucleotides. The rodents were assessed by standard FOB assays and measurement of GFAP and/or AIF expression levels. Groups of Sprague-Dawley rats were administered intrathecally with 2,000 μg or 3,000 μg of ISIS oligonucleotide as specified in the Tables below.

Rat FOB Assay

At 3 hours, one week, 2 weeks, 4 weeks, 6 weeks, and 8 weeks post injection the movement of 7 different parts of the body was evaluated for each rat. The 7 body parts were (1) the rat's tail; (2) the rat's posterior posture; (3) the rat's hind limbs; (4) the rat's hind paws; (5) the rat's forepaws; (6) the rat's anterior posture; and (7) the rat's head. For each of the 7 different body parts, each rat was given a sub-score of 0 if the body part was moving or 1 if the body part was paralyzed. After each of the 7 body parts was evaluated, the sub-scores were summed for each rat and then averaged for each group. Saline treated rats generally receive a score of 0.

Study 1 with 5-10-5 MOE Oligonucleotides at 3.000 g

The oligonucleotides tested in this study are presented in the Table below. The FOB scores are given below.

TABLE 80

Antisense oligonucleotides targeted to SEQ ID NO: 2

| ISIS No | Start Site of SEQ ID NO: 2 |
|---|---|
| 619185 | 1338 |
| 619186 | 1339 |
| 619187 | 1340 |
| 619191 | 1344 |
| 619201 | 1354 |
| 619203 | 1356 |
| 619217 | 1370 |
| 619218 | 1371 |
| 619251 | 1404 |
| 619252 | 1405 |
| 619259 | 1412 |
| 619266 | 1419 |
| 619268 | 1421 |
| 619278 | 1431 |

TABLE 80-continued

Antisense oligonucleotides targeted to SEQ ID NO: 2

| ISIS No | Start Site of SEQ ID NO: 2 |
|---|---|
| 619284 | 1437 |
| 619346 | 1513 |
| 619350 | 1517 |
| 619351 | 1518 |

TABLE 81

FOB scores in Sprague-Dawley rats

| | 3 hrs |
|---|---|
| PBS | 0,0,0 |
| 619185 | 7,7,6 |
| 619186 | 0,6,6 |
| 619187 | 7,0,6 |
| 619191 | 6,0,0 |
| 619201 | 1,4,4 |
| 619203 | 5,1,5 |
| 619217 | 4,4,4 |
| 619218 | 4,2,4 |
| 619251 | 6,6,6 |
| 619252 | 6,6,6 |
| 619259 | 0,6,6 |
| 619266 | 4,4,3 |
| 619268 | 6,6,6 |
| 619278 | 6,6,6 |
| 619284 | 1 |
| 619346 | 0,0,6 |
| 619350 | 4,0,3 |
| 619351 | 3,3,3 |

Study 2 with 5-10-5 MOE Oligonucleotides at 3,000 μg

The oligonucleotides tested in this study are presented in the Table below. The FOB scores are given below.

TABLE 82

Antisense oligonucleotides targeted to SEQ ID NO: 2

| ISIS No | Start Site of SEQ ID NO: 2 |
|---|---|
| 619176 | 1329 |
| 619183 | 1336 |
| 619253 | 1406 |
| 619260 | 1413 |
| 619276 | 1429 |
| 619292 | 1445 |
| 619293 | 1446 |
| 619307 | 1466 |
| 619317 | 1476 |
| 619338 | 1505 |
| 619339 | 1506 |
| 619342 | 1509 |

TABLE 83

FOB scores in Sprague-Dawley rats

| | 3 hrs |
|---|---|
| PBS | 0,1,1 |
| 619176 | 7,7,6 |
| 619183 | 6,6,6 |

TABLE 83-continued

FOB scores in Sprague-Dawley rats

| | 3 hrs |
|---|---|
| 619253 | 7,6,6 |
| 619260 | 6,5,5 |
| 619276 | 4,5,5 |
| 619292 | 6,6,0 |
| 619293 | ND |
| 619307 | ND |
| 619317 | 6,6,7 |
| 619338 | 7,7,7 |
| 619339 | 7,6,3 |
| 619342 | 6,6,6 |

Study 3 with 5-8-5 MOE Oligonucleotides at 3,000 μg

The oligonucleotides tested in this study are presented in the Table below. The FOB scores are given below.

TABLE 84

Antisense agonucleotides targeted to SEQ ID NO: 2

| ISIS No | Start Site of SEQ ID NO: 2 |
|---|---|
| 672595 | 1340 |
| 672599 | 1344 |
| 672602 | 1347 |
| 672624 | 1372 |
| 672636 | 1399 |
| 672637 | 1400 |
| 672640 | 1403 |
| 672642 | 1405 |
| 672651 | 1414 |
| 672652 | 1415 |

TABLE 85

FOB scores in Sprague-Dawley rats

| | 3 hr |
|---|---|
| PBS | 0, 0, 0, 0 |
| 672595 | 4, 0, 3, 0, 4, 4, 4 |
| 672599 | 3, 0, 3, 0, 1, 3 |
| 672602 | 3, 3, 1, 0, 0, 3 |
| 672624 | 3, 0, 0, 7, 3, 3, 3 |
| 672636 | 5, 5, 5, 5 |
| 672637 | 1, 1, 2, 1 |
| 672640 | 6, 6, 5, 1, 6, 0 |
| 672642 | 6, 7, 0, 7, 6, 6 |
| 672651 | 6, 1, 1, 6, 3, 2, 3 |
| 672652 | 6, 1, 1, 5, 4, 4 |

Study 4 with 5-8-5 MOE Oligonucleotides at 3,000 μg

The oligonucleotides tested in this study are presented in the Table below. The FOB scores are given below.

TABLE 86

Antisense oligonucleotides targeted to SEQ ID NO: 2

| ISIS No | Start Site of SEQ ID NO: 2 |
|---|---|
| 672664 | 1427 |
| 672665 | 1428 |
| 672670 | 1433 |
| 672671 | 1434 |

TABLE 86-continued

Antisense oligonucleotides targeted to SEQ ID NO: 2

| ISIS No | Start Site of SEQ ID NO: 2 |
|---|---|
| 672675 | 1438 |
| 672676 | 1439 |
| 672678 | 1441 |
| 672679 | 1442 |
| 672681 | 1444 |
| 672683 | 1446 |
| 672693 | 1464 |
| 672697 | 1468 |
| 672699 | 1470 |
| 672700 | 1471 |
| 672723 | 1512 |
| 672730 | 1519 |

TABLE 87

FOB scores in Sprague-Dawley rats

| ISIS No | 3 hr |
|---|---|
| PBS | 1, 1, 1, 0 |
| 672664 | 6, 6, 6, 5 |
| 672665 | 4, 0, 4, 0, 4, 1 |
| 672670 | 4, 2, 4, 4 |
| 672671 | 4, 0, 0, 2, 5, 3 |
| 672675 | 3, 3, 0, 2, 1, 1 |
| 672676 | 1, 5, 0, 1, 1, 4 |
| 672678 | 0, 6, 6, 4, 6, 6 |
| 672679 | 3, 0, 0, 2, 3, 4 |
| 672681 | 1, 2, 2, 2 |
| 672683 | 0, 2, 5, 5, 0, 4 |
| 672693 | ND |
| 672697 | 6, 6, 6, 6 |
| 672699 | 0, 0, 3, 4, 4, 1 |
| 672700 | 4, 7, 4, 4 |
| 672723 | 4, 4, 4, 4 |
| 672730 | 2, 2, 3, 3 |

Study 5 with 5-10-5 MOE Oligonucleotides at 3,000 µg

The oligonucleotides tested in this study are presented in the Table below. The FOB scores are given below and indicate that several oligonucleotides were tolerable in this model.

TABLE 88

Antisense oligonucleotides targeted to SEQ ID NO: 2

| ISIS No | Start Site of SEQ ID NO: 2 |
|---|---|
| 619411 | 8004 |
| 619412 | 8012 |
| 627833 | 8001 |
| 655153 | 7916 |
| 655173 | 7992 |
| 655178 | 8014 |
| 655179 | 8016 |
| 655202 | 8098 |
| 655231 | 8183 |
| 655232 | 8186 |
| 655233 | 8189 |
| 655417 | 14089 |
| 655420 | 14331 |
| 671081 | 8110 |
| 671082 | 8140 |

TABLE 88-continued

Antisense oligonucleotides targeted to SEQ ID NO: 2

| ISIS No | Start Site of SEQ ID NO: 2 |
|---|---|
| 671083 | 8230 |
| 671084 | 14316 |
| 672561 | mRNA |

TABLE 89

FOB scores in Sprague-Dawley rats

| | 3 hr |
|---|---|
| PBS | 0,0,0,0 |
| 619411 | 6,6,6,6 |
| 619412 | 4,6,6,0 |
| 627833 | 6,6,6,1 |
| 655153 | 6,6,6,1 |
| 655173 | 6,6,6,0 |
| 655178 | 5,5,6,6 |
| 655179 | 6,6,6,6 |
| 655202 | 6,0,6,6 |
| 655231 | 4,4,4,4 |
| 655232 | 0,0,0,0 |
| 655233 | 6,6,6,6 |
| 655417 | 1,6,6,7 |
| 655420 | 5,7,5,5 |
| 671081 | 5,5,5,5 |
| 671082 | 5,6,5,7 |
| 671083 | 7,6,7,6 |
| 671084 | 6,0,4,3 |
| 672561 | 4,4,4,1 |

Study 6 with 5-8-5 MOE Oligonucleotides at 2,000 µg

The oligonucleotides tested in this study are presented in the Table below. The FOB scores are given below and indicate that several oligonucleotides were tolerable in this model.

TABLE 90

Antisense oligonucleotides targeted to SEQ ID NO: 2

| ISIS No | Start Site of SEQ ID NO: 2 |
|---|---|
| 687978 | 14315 |
| 688022 | 7918 |
| 688077 | 7992 |
| 688088 | 8003 |
| 688089 | 8004 |
| 688099 | 8014 |
| 688100 | 8015 |

TABLE 91

FOB scores in Sprague-Dawley rats

| | 3 hr |
|---|---|
| PBS | 0, 0, 0, 0 |
| 687978 | 3, 3, 3, 3 |
| 688022 | 3, 3, 3, 3 |
| 688077 | 0, 3, 1, 3, 3, 3 |
| 688088 | 3, 0, 3, 3, 3 |

TABLE 91-continued

FOB scores in Sprague-Dawley rats

| | 3 hr |
|---|---|
| 688089 | 1, 3, 3, 3, 3 |
| 688099 | 3, 4, 0, 3, 3 |
| 688100 | 0, 3, 4, 4 |

Study 7 with 5-8-5 and 5-10-5 MOE Oligonucleotides at 2,000 µg

The oligonucleotides tested in this study are presented in the Table below. The FOB scores are given below and indicate that several oligonucleotides were tolerable in this model.

TABLE 92

Antisense oligonucleotides targeted to SEQ ID NO: 2

| ISIS No | Start Site of SEQ ID NO: 2 |
|---|---|
| 688101 | 8016 |
| 688348 | 7993 |
| 688356 | 8015 |
| 688380 | 8184 |
| 688382 | 8187 |
| 688400 | 14090 |
| 688407 | 14304 |
| 688415 | 14312 |
| 688416 | 14313 |
| 688417 | 14314 |

TABLE 93

FOB scores in Sprague-Dawley rats

| | 3 hr |
|---|---|
| PBS | 0, 0, 0, 0 |
| 688101 | 3, 2, 2, 2 |
| 688348 | 2, 1, 2, 2 |
| 688356 | 3, 3, 3, 3 |
| 688380 | 0, 0, 1, 0 |
| 688382 | 2, 2, 2, 2 |
| 688400 | 0, 3, 3, 3 |
| 688407 | 2, 2, 2, 2 |
| 688415 | 3, 0, 3, 3 |
| 688416 | 3, 3, 3, 3 |
| 688417 | 4, 4, 3, 3 |

Example 16: Acute Tolerability of Oligonucleotides from WO 2014/062691

Oligonucleotides described in WO 2014/062691 were tested in an acute tolerability study in mice. The tested oligonucleotides include ISIS 576816, ISIS 576974, ISIS 577061, ISIS 577065, and ISIS 577083, which are 5-10-5 MOE gapmers with a full phosphorothioate backbone and each cytosine is a 5-methylcytosine. The sequences are provided in the Table below. Mice were separated into groups of 3 or 4 mice. Each mouse in each group of mice was administered a single ICV dose of either 700 ug of the oligonucleotides in the table below. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the ICV dose, and met all other criteria, it would get a summed score of 0. If another mouse was not bright, alert, and responsive 3 hours after the dose but met all other criteria, it would receive a score of 1. Saline treated mice generally receive a score of 0. Results are presented as the average score for each treatment group in the Table below. These results demonstrate that ISIS 576816, ISIS 576974, ISIS 577061, ISIS 577065, and ISIS 577083 were poorly tolerated.

TABLE 94

Antisense oligonucleotides from WO 2014/062691

| ISIS No | Sequence | SEQ ID NO |
|---|---|---|
| 576816 | GCCTTACTCTAGGACCAAGA | 20 |
| 576974 | GGGACACTACAAGGTAGTAT | 401 |
| 577061 | TACAGGCTGCGGTTGTTTCC | 97 |
| 577065 | CCCGGCCCCTAGCGCGCGAC | 98 |
| 577083 | GGTAACTTCAAACTCTTGGG | 382 |

TABLE 95

FOB scores in mice

| | 3 hrs | 5 hrs |
|---|---|---|
| 576816 | 7,7,7 | 7,7,7 |
| 576974 | 6,5,6 | 7,5,7 |
| 577061 | 7,7,7 | 7,7,7 |
| 577065 | 6,6,6 | 7,7,7 |
| 577083 | 7,7,7 | 7,7,7 |

Gapmers from the studies described above, including compounds ISIS 576816, ISIS 576974, ISIS 577061, ISIS 577065, and ISIS 577083 which were previously disclosed in WO 2014/062691, are tested for tolerability in Sprague-Dawley rats. Rats are injected intrathecally with 3 mg of a single dose of ISIS oligonucleotide. A control group of rats is injected intrathecally with PBS. Acute tolerability is assessed 3 hours post-dose using a functional observational battery (FOB). This score is used to evaluate the acute tolerability of a compound with lower scores denoting better tolerated compounds. Control animals usually have a score of '0' or '1'. At 3 hours post injection, the rats are observed by placing each rat on the cage top and evaluating certain functions, assigning a number of '0' or '1' depending on whether the rat exhibits normal function in the region of interest (0) or does not (1) for each function, and then adding the total scores. Seven regions are assessed, including tail, hind paws, hind legs, hind end, front posture, fore paws, and head.

Poor acute tolerability in mice is generally predictive of poor acute tolerability in rats. For example, ISIS 619185 (see Example 14 hereinabove) had an acute tolerability score of 7,6,6,6 (4 animals) in mouse, and an acute tolerability score of 7,7,6 (3 animals) in rats (See Example 15 hereinabove). ISIS 619342 (see Example 14 hereinabove) had an acute tolerability score of 6,6,6,6 (4 animals) in mouse, and an acute tolerability score of 6,6,6 (3 animals) in rats (see Example 15 hereinabove). Both compounds were deemed to be poorly tolerated acutely. It is therefore expected that the compounds ISIS 576816, ISIS 576974, ISIS 577061, ISIS 577065, and ISIS 577083, which were previously disclosed in WO 2014/062691, will show similarly high FOB scores in rats as they did in mice.

What is claimed is:

1. A compound comprising a modified oligonucleotide consisting of 12 to 30 linked nucleosides and having a nucleobase sequence comprising at least 12 consecutive nucleobases of a nucleobase sequence selected from SEQ ID NOs: 442-467.

2. A compound comprising a modified oligonucleotide consisting of 12 to 30 linked nucleosides and having a nucleobase sequence comprising at least 8 consecutive nucleobases complementary to an equal length portion of nucleobases 7860-7906 or 7907-7944 of SEQ ID NO: 2.

3. The compound of claim 2, wherein the modified oligonucleotide is a single-stranded modified oligonucleotide.

4. The compound of claim 3, wherein at least one internucleoside linkage of the modified oligonucleotide is a modified internucleoside linkage.

5. The compound of claim 4, wherein the modified internucleoside linkage is a phosphorothioate internucleoside linkage.

6. The compound of claim 4, wherein each internucleoside linkage of the modified oligonucleotide is a modified internucleoside linkage.

7. The compound of claim 6, wherein the modified internucleoside linkage is a phosphorothioate linkage.

8. The compound of claim 5, wherein at least one internucleoside linkage of the modified oligonucleotide is a phosphodiester internucleoside linkage.

9. The compound of claim 2, wherein at least one nucleobase of the modified oligonucleotide comprises a modified nucleobase.

10. The compound of claim 9, wherein the modified nucleobase is a 5-methylcytosine.

11. The compound of claim 2, wherein at least one nucleoside of the modified oligonucleotide comprises a modified sugar.

12. The compound of claim 11, wherein each nucleoside of the modified oligonucleotide comprises a modified sugar.

13. The compound of claim 11, wherein the modified sugar is a bicyclic sugar.

14. The compound of claim 13, wherein each bicyclic sugar comprises a chemical bridge between the 4' and 2' positions of the sugar, wherein each chemical bridge is independently selected from: 4'-CH(R)—O-2' and 4'-(CH$_2$)$_2$—O-2', wherein R is independently selected from H, C$_1$-C$_6$ alkyl, and C$_1$-C$_6$ alkoxy.

15. The compound of claim 14, wherein at least one chemical bridge is 4'-CH(R)—O-2' and wherein R is methyl.

16. The compound of claim 14, wherein at least one chemical bridge is 4'-CH(R)—O-2' and wherein R is H.

17. The compound of claim 14, wherein at least one chemical bridge is 4'-CH(R)—O-2' and wherein R is CH$_2$—O—CH$_3$.

18. The compound of claim 11, wherein at least one modified sugar comprises a 2'-O-methoxyethyl group.

19. The compound of claim 11, wherein at least one modified sugar comprises a 2'-O-methyl group.

20. The compound of claim 12, wherein each modified sugar comprises a 2'-O-methoxyethyl group or a 2'-O-methyl group.

21. The compound of claim 2, wherein the modified oligonucleotide is a gapmer.

22. The compound of claim 2, wherein the modified oligonucleotide comprises:
   a gap segment consisting of 10 linked deoxynucleosides;
   a 5' wing segment consisting of 5 linked nucleosides; and
   a 3' wing segment consisting of 5 linked nucleosides;
   wherein the gap segment is positioned between the 5' wing segment and the 3' wing segment and wherein each nucleoside of each wing segment comprises a modified sugar.

23. The compound of claim 2, wherein the modified oligonucleotide comprises:
a gap segment consisting of 8 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

24. The compound of claim 2, wherein the modified oligonucleotide comprises sugar modified nucleosides in any of the following patterns: eeekkddddddddkkeee, eekkddddddddkkeee, ekddddddddekekeee, kekeddddddddekeke, and ekekddddddddkekee; wherein,
e=a 2'-O-methoxyethyl modified nucleoside,
d=a 2'-deoxynucleoside, and
k=a cEt nucleoside.

25. The compound of claim 2, wherein the modified oligonucleotide comprises internucleoside linkages in any of the following patterns: soooossssssssssooss, sooossssssss-sooss, soossssssssssooss, and sossssssssssoooss; wherein,
s=a phosphorothioate linkage, and
o=a phosphodiester linkage.

26. The compound of claim 2, wherein the modified oligonucleotide consists of 17, 18, 19, or 20 linked nucleosides.

27. The compound of claim 2, wherein the modified oligonucleotide has a nucleobase sequence complementary to a region of C9ORF72 other than a hexanucleotide repeat expansion, wherein the hexanucleotide repeat expansion comprises any of GGGCC, GGGGGG, GGGGCG, and GGGGGC.

28. A conjugated antisense compound comprising the compound of claim 2.

29. The compound of claim 2, consisting of the modified oligonucleotide.

30. A double-stranded compound comprising the compound of claim 2.

31. A conjugated antisense compound comprising the double-stranded compound of claim 30.

32. A composition comprising a compound according to claim 2 and at least one of a pharmaceutically acceptable carrier or diluent, wherein optionally the pharmaceutically acceptable diluent is phosphate-buffered saline (PBS).

33. The composition according to claim 32, wherein the compound is a salt, wherein optionally the salt is a sodium salt.

* * * * *